United States Patent
Wang et al.

(10) Patent No.: US 12,139,492 B2
(45) Date of Patent: Nov. 12, 2024

(54) SUBSTITUTED PYRIMIDINES FOR THE TARGETED DEGRADATION OF BRUTON'S TYROSINE KINASE

(71) Applicants: Endotarget Inc., New Orleans, LA (US); EnhancedBio Inc., Seoul (KR)

(72) Inventors: Guangdi Wang, New Orleans, LA (US); Xianyou Peng, New Orleans, LA (US); Borui Kang, New Orleans, LA (US); HongJoong Kim, Seoul (KR)

(73) Assignee: Endotarget Inc.

( * ) Notice: Subject to any disclaimer, the term of this patent is extended or adjusted under 35 U.S.C. 154(b) by 0 days.

(21) Appl. No.: 17/820,312

(22) Filed: Aug. 17, 2022

(65) Prior Publication Data

US 2023/0137175 A1 May 4, 2023

Related U.S. Application Data

(60) Provisional application No. 63/301,207, filed on Jan. 20, 2022, provisional application No. 63/233,984, filed on Aug. 17, 2021.

(51) Int. Cl.
*A61K 31/519* (2006.01)
*C07D 487/04* (2006.01)

(52) U.S. Cl.
CPC .................. *C07D 487/04* (2013.01)

(58) Field of Classification Search
CPC ................. A61K 31/519; C07D 487/04
USPC ....................... 514/262.1; 544/262
See application file for complete search history.

(56) References Cited

FOREIGN PATENT DOCUMENTS

| | | |
|---|---|---|
| CN | 108191871 | 6/2018 |
| WO | 2017134685 | 8/2017 |
| WO | 2020051235 | 3/2020 |
| WO | 2020239103 | 12/2020 |
| WO | WO-2023072270 A1 * | 5/2023 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Byrd, J. C. et al. Targeting BTK with ibrutinib in relapsed chronic lymphocytic leukemia. N. Engl. J. Med. 369, 32-42 (2013).
De Claro, R.A., et al., FDA Approval: Ibrutinib for Patients with Previously Treated Mantle Cell Lymphoma and Previously Treated Chronic Lymphocytic Leukemia. Clin. Cancer Res. 2015, 21, 3586-3590.
Emerich DF, Tracy MA, Ward KL, Figueiredo M, Qian R, Henschel C, Bartus RT. Biocompatibility of poly (DL-lactide-co-glycolide) microspheres implanted into the brain. Cell Transplant. Jan.-Feb. 1999;8(1):47-58.
International Search Report and Written Opinion for corresponding PCT/US22/75050.
Jolliet-Riant P, Tillement JP. Drug transfer across the blood-brain barrier and improvement of brain delivery. Fundam Clin Pharmacol. 1999;13(1):16-26.
Pal Singh, S.; Dammeijer, F.; Hendriks, R.W. Role of Bruton's tyrosine kinase in B cells and malignancies. Mol. Cancer Ther. 2018, 17, 57.
Pubchem CID 155345449.
Schroeder U, Sabel BA, Schroeder H. Diffusion enhancement of drugs by loaded nanoparticles in vitro. Prog Neuropsychopharmacol Biol Psychiatry. Jul. 1999;23(5):941-9. doi: 10.1016/s0278-5846(99)00037-8.
Wang, M. L. et al. Targeting BTK with ibrutinib in relapsed or refractory mantle-cell lymphoma. N. Engl. J. Med. 369, 507-516 (2013).

* cited by examiner

*Primary Examiner* — Douglas M Willis
(74) *Attorney, Agent, or Firm* — Riverside Law LLP

(57) ABSTRACT

The present disclosure relates to compounds having the structure of Formula (I) that serve as degraders (and/or inhibitors) of Bruton's tyrosine kinase (BTK). In the present disclosure, the said compounds, which contain a target protein (BTK) binding moiety and a E3 ubiquitin ligase (CRBN) binding moiety, are directed to bind to both the BTK and CRBN, such that the BTK is placed in close proximity to the E3 ligase to mediate ubiquitylation of the target protein followed by degradation of the target protein by the proteasome. The present disclosure provides methods for synthesizing the herein disclosed said compounds, and their pharmacological activities associated with degradation or inhibition of the target protein. Further, the present disclosure teaches the utilization of such compounds in a treatment for proliferative diseases and autoimmune disorders, including hematological cancers and rheumatoid arthritis, particularly non-Hodgkin lymphoma, and especially chronic lymphocytic leukemia (CLL) and mantle cell lymphoma.

15 Claims, 15 Drawing Sheets

SUBSTITUTED PYRIMIDINES FOR THE TARGETED DEGRADATION OF BRUTON'S TYROSINE KINASE

CROSS-REFERENCE TO RELATED APPLICATIONS

This application claims priority to and the benefit of U.S. Provisional Application No. 63/233,984, filed Aug. 17, 2021, and U.S. Provisional Application No. 63/301,207, filed Jan. 20, 2022, the disclosures of which are hereby incorporated by reference herein in their entireties.

FIELD OF THE INVENTION

The present disclosure relates to bifunctional compounds that modulate the target protein, Bruton's tyrosine kinase (BTK), by eliminating the kinase protein via ubiquitination and subsequent proteasomal degradation to block BTK signaling. The bifunctional compounds contain one ligand that binds BTK and another ligand that binds to a specific E3 ubiquitin ligase, which are linked via a linker molecule. In the present disclosure the bifunctional compounds can simultaneously bind BTK (target protein) and a CRBN E3 ligase, which promotes ubiquitination of BTK and leads to degradation of BTK by the proteasome. The disclosure also relates to pharmaceutical compositions comprising these BTK degrading compounds, and methods for using the same for treatment of diseases and conditions mediated by the BTK, including cancer and autoimmune diseases.

BACKGROUND OF THE INVENTION

The B cell receptor (BCR) signaling pathway plays a fundamental role in determining B cell fate and function by regulating cellular selection, maturation, proliferation, and antibody production. Constitutive or aberrant BCR signaling cascade has been implicated in the propagation and maintenance of a variety of B cell malignancies. Bruton's tyrosine kinase (BTK), a non-receptor tyrosine kinase expressed in all hematopoietic cells except T cells and terminally differentiated plasma cells, is a crucial signaling hub in the BCR pathway. BTK is implicated in pathogenesis of B-cell malignancies including chronic lymphocytic leukemia (CLL), mantle cell lymphoma (MCL), diffuse large B cell lymphoma (DLBCL), follicular lymphoma (FL) and Waldenstrom's macroglobulinemia (WM). Therapies targeting BTK have proven their potential in both pre-clinical and clinical settings (Byrd et al 2013, Wang et al 2013). Ibrutinib (Imbruvica, Pharmacyclics, LLC) is the first BTK inhibitor to receive FDA approval as a single-agent frontline therapy for the B cell malignancies MCL, WM and CLL (de Claro et al 2015). Despite the promising activity of ibrutinib across multiple B-cell lymphoma subtypes, almost one third of patients have primary intrinsic resistance, while many others develop acquired resistance (Pal Singh et al 2018). In primary drug resistance, patients do not respond to initial therapy, whereas in secondary drug resistance, patients have an initial response that is subsequently lost due to acquired resistance or clonal evolution. In autoimmune diseases, such as rheumatoid arthritis (RA) and lupus, the pathophysiology relies on many of the pathways regulated by BTK, including B cell and myeloid cellular functions. Inhibition of BTK may be effective for the treatment of immunological disorders in which B cells and/or myeloid cells foster an excessive autoimmune response.

Thus, there is a need in the art for compositions and methods for modulating specific target proteins (e.g., BTK), which is degraded or eliminated as a result of ubiquitination and subsequent degradation of the ubiquitinated targeted protein by the proteasome. The present invention addresses this unmet need in the art.

SUMMARY OF THE INVENTION

The present disclosure relates to novel bifunctional compounds and compositions useful for the degradation of a target protein by recruiting the target protein to an E3 ubiquitin ligase for degradation by the endogenous cellular ubiquitin proteasome system (UPS). In particular, the present disclosure furnishes bifunctional compounds, which facilitates targeted ubiquitination of Bruton's tyrosine kinase (BTK) (target protein), and then undergo degradation and/or exhibit inhibition of the target protein by the bifunctional compounds disclosed herein. In addition, the description provides the methods of making such compounds and compositions; methods of using such compounds and compositions; pharmaceutical compositions comprising such compounds and compositions; and methods of using such pharmaceutical compositions, for the treatment or amelioration of a disease condition, such as cancer, especially breast cancer.

In an additional aspect, the present disclosure provides a method of ubiquitinating followed by degrading a target protein by bifunctional compounds attached by a chemical linker; therapeutic compositions comprising an effective amount of a compound disclosed herein or salt/solvate form thereof, and its delivery using a pharmaceutically acceptable carrier. In yet another aspect, the therapeutic compositions of a compound or multiple compounds that degrade and/or inhibit the target protein in a patient or subject, such as a human or animal, can be used for treating or ameliorating disease conditions/states, e.g., non-Hodgins lymphoma, through modulation of wild-type BTK or mutant BTK or other variants of BTK.

In one aspect, the present invention provides a compound of having the structure of Formula (I), or a tautomer, stereoisomer or a mixture of stereoisomers, pharmaceutically acceptable salt, or solvate thereof:

Formula (I)

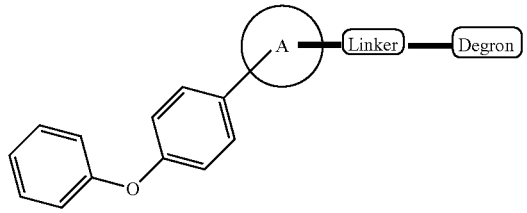

In some embodiments, Ring A is selected from the group consisting of

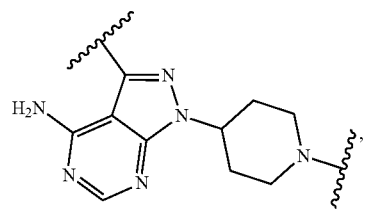

-continued
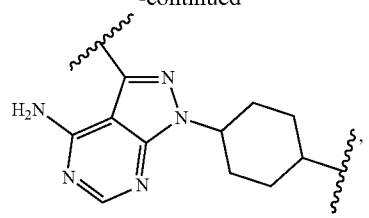
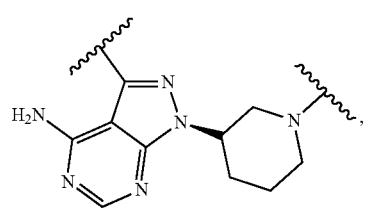
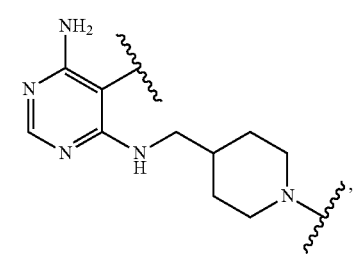
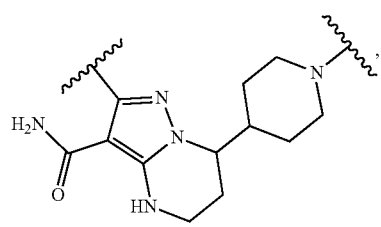
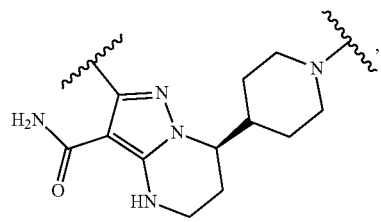
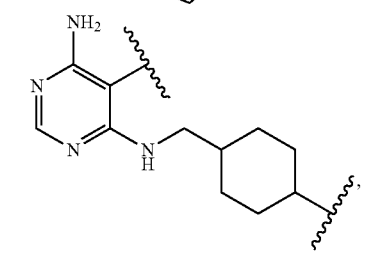
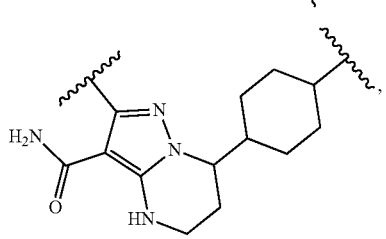
-continued
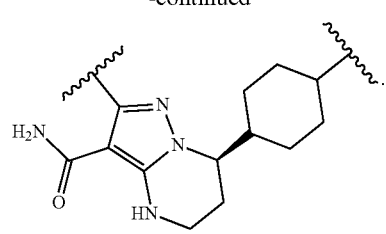
The Degron is capable of binding to a ubiquitin ligase, such as an E3 ubiquitin ligase (e.g., CRBN). The Degron is selected from the following structures:
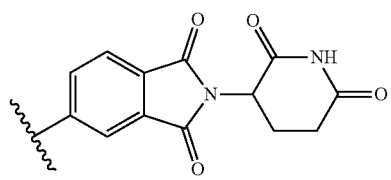
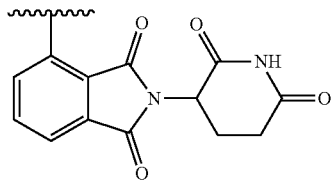
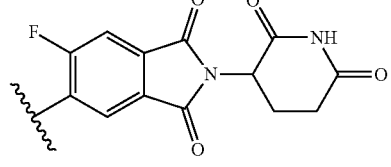
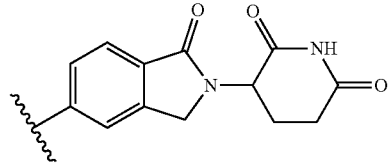
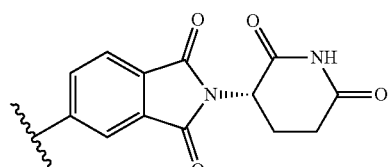
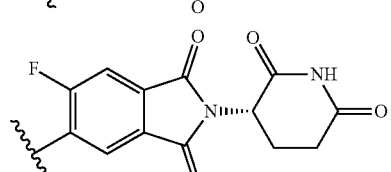
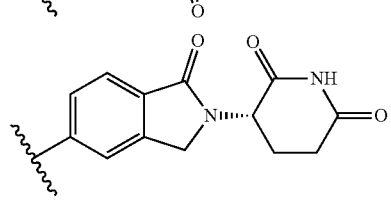

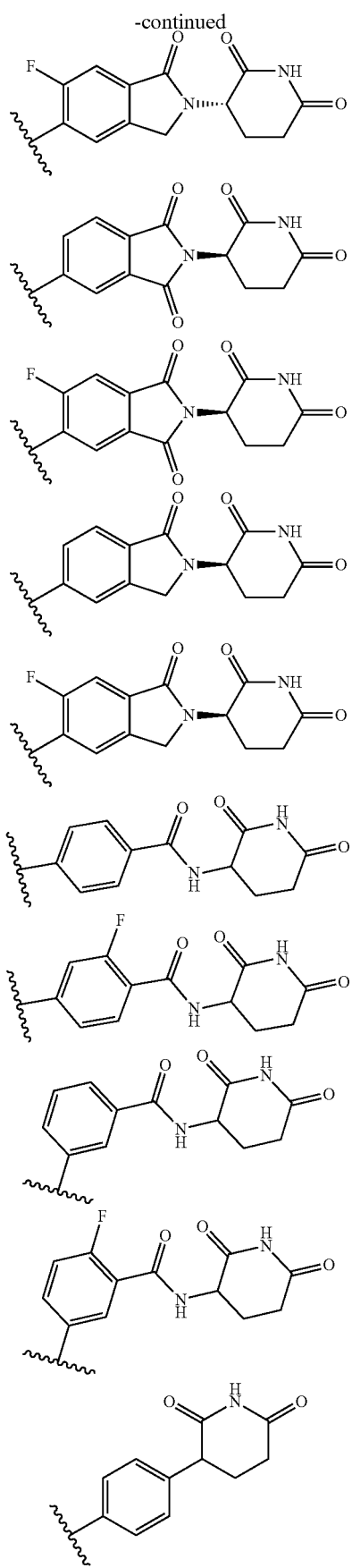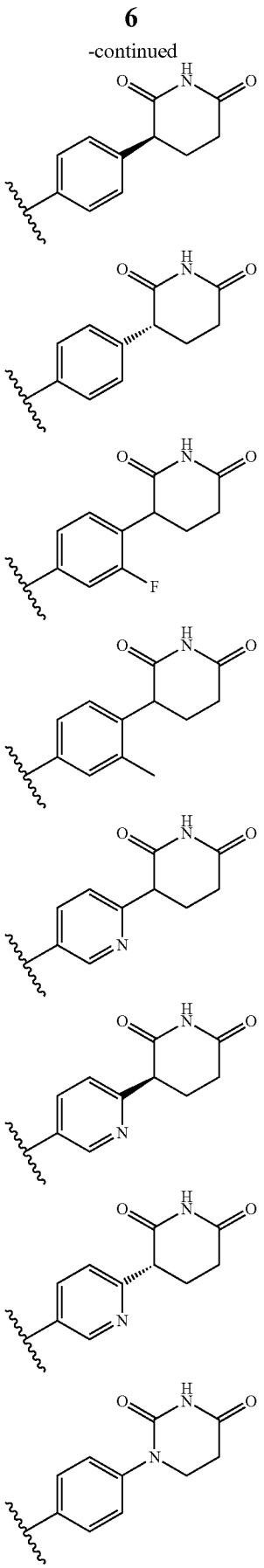

-continued

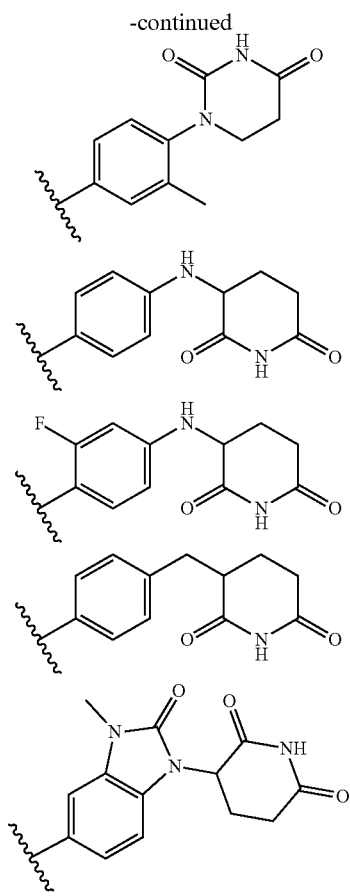

In some embodiments, the linker is an optionally substituted linking moiety comprising a branched or unbranched, cyclized or uncyclized, saturated or unsaturated chain of 5 to 16 carbon atoms in length, wherein 1 to 6 of the carbon atoms are optionally replaced with a heteroatom independently selected from O, N and S.

In one embodiment, the linker is an optionally substituted linking moiety. In some embodiments, the linking moiety comprises a branched or linear $C_5$-$C_{16}$ alkyl, branched or linear amino-$C_5$-$C_{16}$ alkyl, branched or linear $C_5$-$C_{16}$ alkoxy, branched or linear thio-$C_5$-$C_{16}$ alkyl, $C_5$-$C_{16}$ cycloalkyl, amino-$C_5$-$C_{16}$ cycloalkyl, hydroxy-$C_5$-$C_{16}$ cycloalkyl, or thio-$C_5$-$C_{16}$ cycloalkyl. In some embodiments, the linking moiety comprises 1 to 6 of the carbon atoms that are optionally replaced with a heteroatom. In some embodiments, the heteroatom is independently O, N and S.

In one aspect, the present invention relates, in part, to a composition comprising at least one compound of the present invention. In various embodiments, the composition is a pharmaceutical composition. In one embodiment, the pharmaceutical composition comprises at least one compound of the present invention and a pharmaceutically acceptable carrier.

In one embodiment, the pharmaceutical composition is suitable for oral administration. In one embodiment, the pharmaceutical composition is suitable for parenteral administration.

In one aspect, the present invention relates, in part, to a method of preparing at least one compound of the present invention or composition or pharmaceutical composition thereof.

In one aspect, the present invention relates, in part, to a method of treating a disease or disorder in a subject in need thereof, the method comprising administering at least one compound of the present invention or composition or pharmaceutical composition thereof to the subject.

In one aspect, the present invention relates, in part, to a method for treating B-cell malignancies in a subject in need thereof, the method comprising administering an effective amount of a compound of the present invention or composition or pharmaceutical composition thereof to the subject. In one embodiment, the B-cell malignancy is a chronic lymphocytic leukemia. In one embodiment, the B-cell malignancy is a mantle cell lymphoma. In one embodiment, the B-cell malignancy is a Diffuse large B-cell lymphoma. In one embodiment, the B-cell malignancy is a Waldenstrom's macroglobulinemia.

In one aspect, the present invention relates, in part, to a method for treating an autoimmune disease in a subject in need thereof, the method comprising administering an effective amount of a compound of the present invention or composition or pharmaceutical composition thereof to the subject. In one embodiment, the autoimmune disease is rheumatoid arthritis. In one embodiment, the autoimmune disease is systemic lupus erythematosus. In one embodiment, the autoimmune disease is anaphylaxis.

In one aspect, the present invention relates, in part, to a method of reducing the level or activity of a target protein, the method comprising administering at least one compound of the present invention or composition or pharmaceutical composition thereof.

In another aspect, the present invention relates, in part, to a method of inhibiting a target protein, the method comprising administering at least one compound of the present invention or composition or pharmaceutical composition thereof.

In one embodiment, the target protein is Bruton's tyrosine kinase.

BRIEF DESCRIPTION OF THE DRAWINGS

For a further understanding of the nature, objects, and advantages of the present disclosure, reference should be had to the following detailed description, read in conjunction with the following drawings, wherein like reference numerals denote like elements.

The following detailed description of preferred embodiments of the invention will be better understood when read in conjunction with the appended drawings. It should be understood, however, that the invention is not limited to the precise arrangements and instrumentalities of the embodiments shown in the drawings.

DETAILED DESCRIPTION OF THE DISCLOSURE

Figure 1:
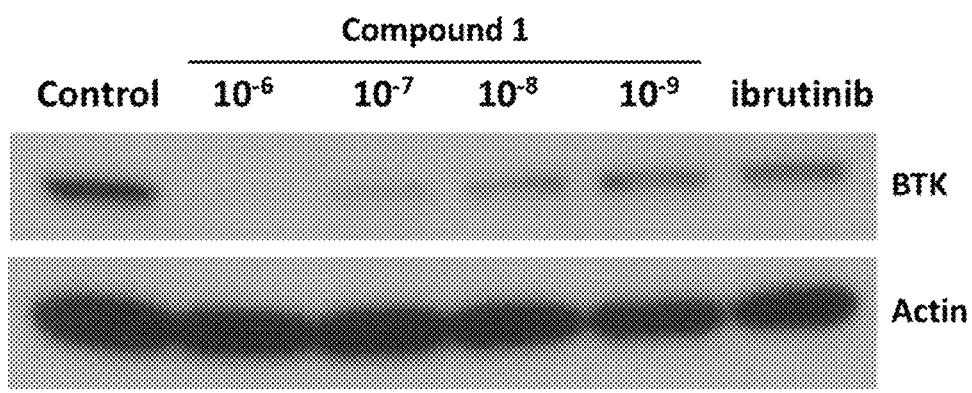
FIG. 1 shows the dose-dependent degradation of BTK protein by exemplary compound 1 of the present disclosure in Namalwa B lymphocyte cells.
Figure 2:
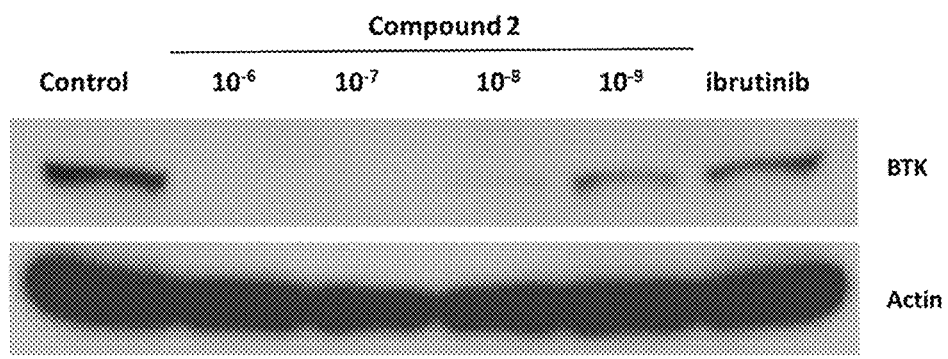
FIG. 2 shows the dose-dependent degradation of BTK protein by exemplary compound 2 of the present disclosure in Namalwa B lymphocyte cells.
Figure 3:
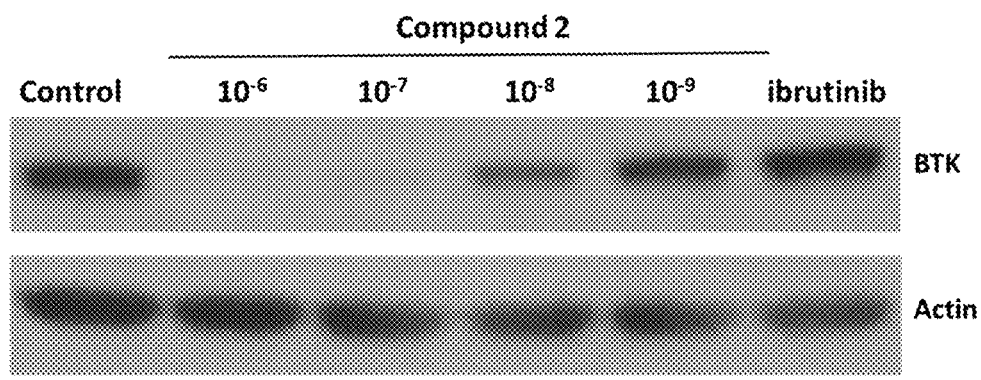
FIG. 3 shows the dose-dependent degradation of BTK protein by exemplary compound 2 of the present disclosure in JeKo-1 mantle cell lymphoma cells.
Figure 4:
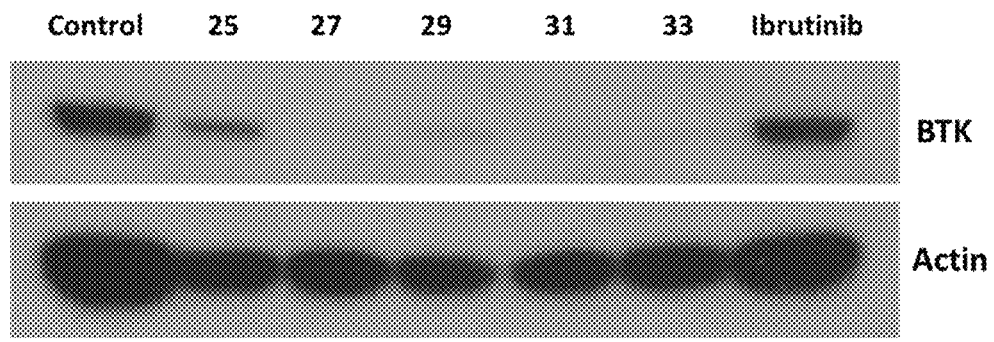
FIG. 4 shows the degradation of BTK protein by exemplary compounds 25, 27, 29, 31, and 33 of the present disclosure at $10^{-6}$ M in Namalwa B lymphocyte cells.
Figure 5:
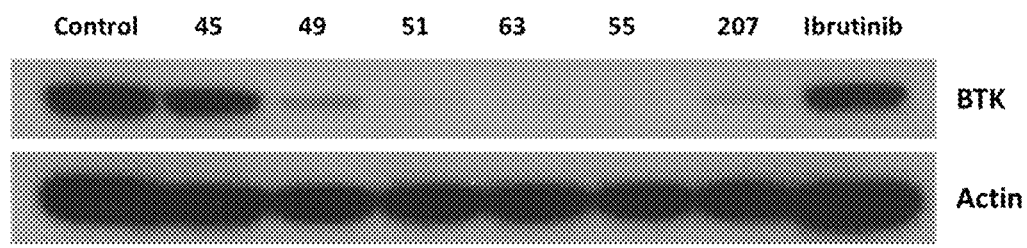
FIG. 5 shows the degradation of BTK protein by exemplary compounds 45, 49, 51, 63, 55, and 207 of the present disclosure at $10^{-6}$ M in Namalwa B lymphocyte cells.
Figure 6:
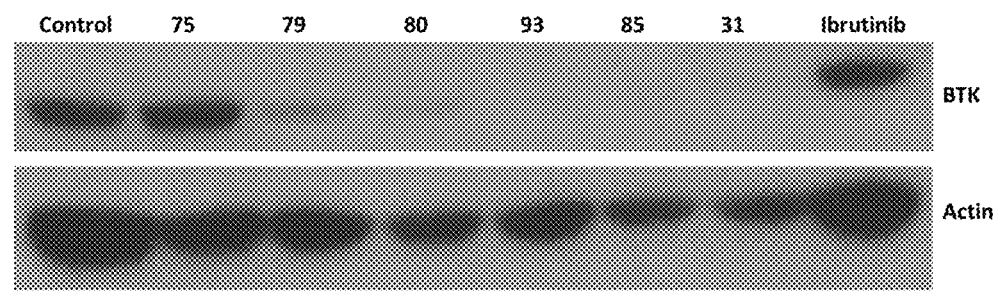
FIG. 6 shows the degradation of BTK protein by exemplary compounds 75, 79, 80, 93, 85, and 31 of the present disclosure at $10^{-6}$ M in Namalwa B lymphocyte cells.
Figure 7:
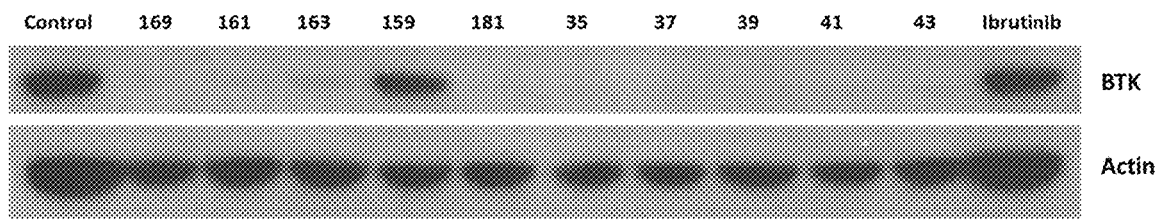
FIG. 7 shows the degradation of BTK protein by exemplary compounds 169, 161, 163, 159, 181, 35, 37, 39, 41, and 43 of the present disclosure at $10^{-6}$ M in Namalwa B lymphocyte cells.
Figure 8:
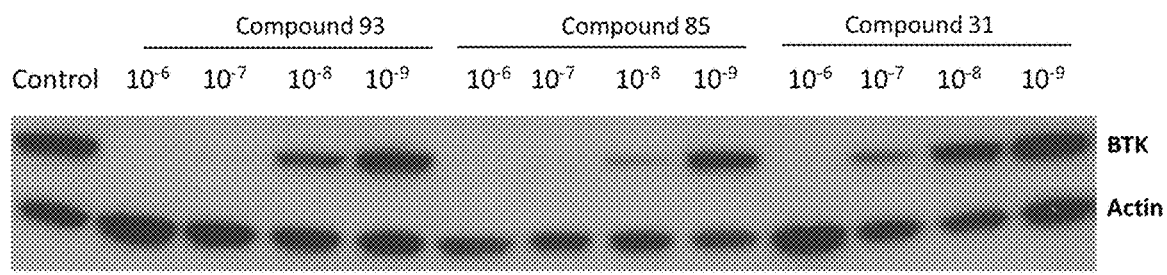
FIG. 8 shows the dose-dependent degradation of BTK protein by exemplary compounds 93, 85, and 31 of the present disclosure in Namalwa B lymphocyte cells.
Figure 9:
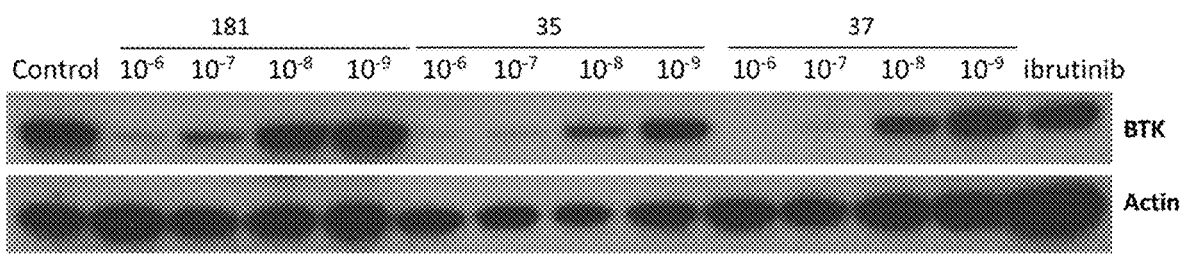
FIG. 9 shows the dose-dependent degradation of BTK protein by exemplary compounds 181, 35, and 37 of the present disclosure in Namalwa B lymphocyte cells.
Figure 10:
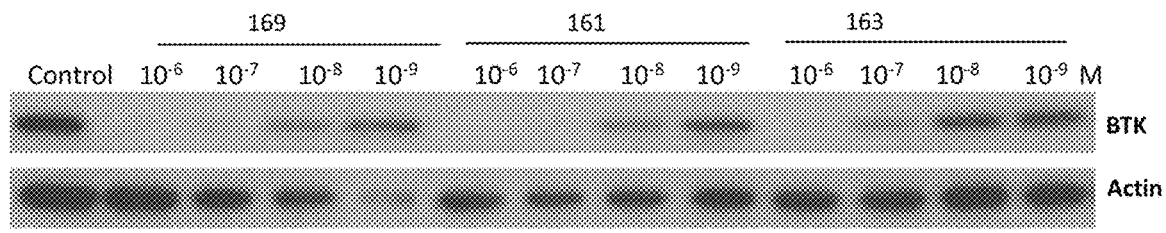
FIG. 10 shows the dose-dependent degradation of BTK protein by exemplary compounds 169, 161, and 163 of the present disclosure in Namalwa B lymphocyte cells.
Figure 11:
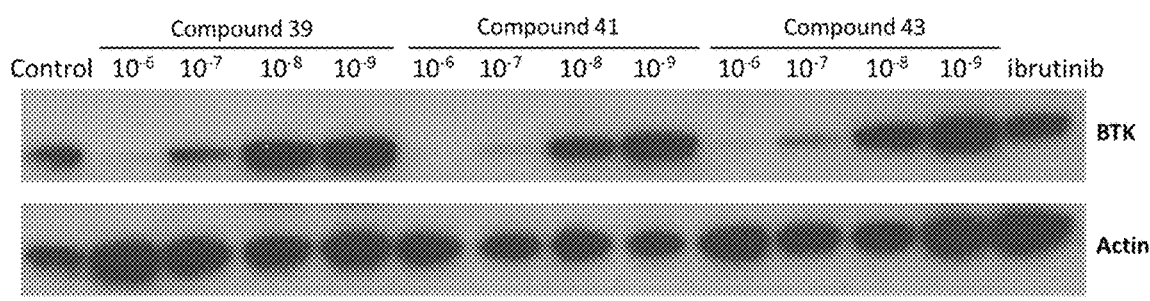
FIG. 11 shows the dose-dependent degradation of BTK protein by exemplary compounds 39, 41, and 43 of the present disclosure in Namalwa B lymphocyte cells.
Figure 12:
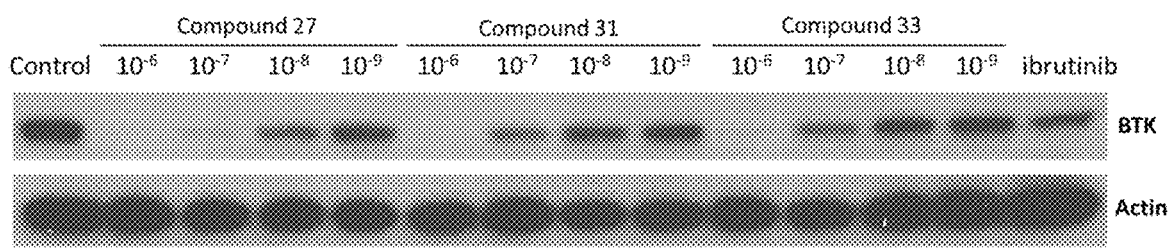
FIG. 12 shows the dose-dependent degradation of BTK protein by exemplary compounds 27, 31, and 33 of the present disclosure in Namalwa B lymphocyte cells.
Figure 13:
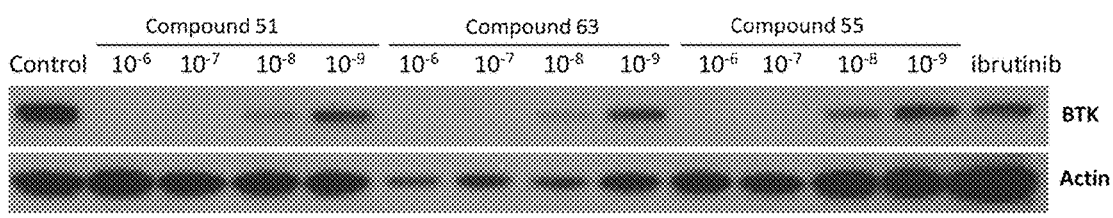
FIG. 13 shows the dose-dependent degradation of BTK protein by exemplary compounds 51, 63, and 55 of the present disclosure in Namalwa B lymphocyte cells.
Figure 14:
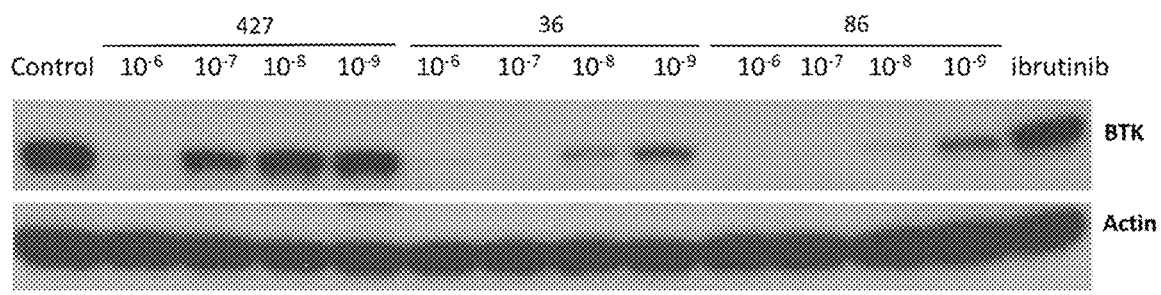
FIG. 14 shows the dose-dependent degradation of BTK protein by exemplary compounds 427, 36, and 86 of the present disclosure in Namalwa B lymphocyte cells.
Figure 15:
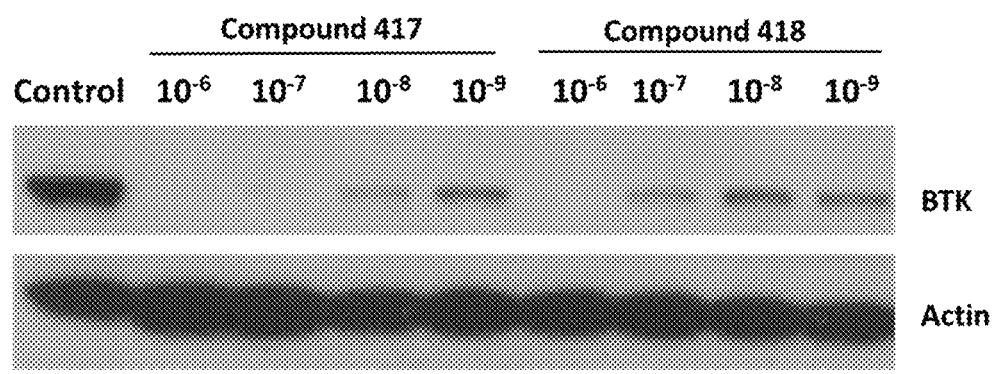
FIG. 15 shows the dose-dependent degradation of BTK protein by exemplary compound 417 and 418 of the present disclosure in Namalwa B lymphocyte cells.
Figure 16:
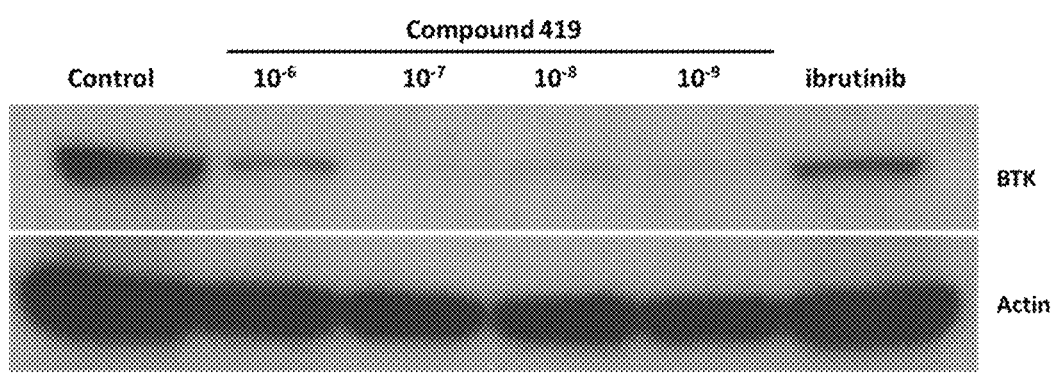
FIG. 16 shows the dose-dependent degradation of BTK protein by exemplary compound 419 of the present disclosure in Namalwa B lymphocyte cells.
Figure 17:
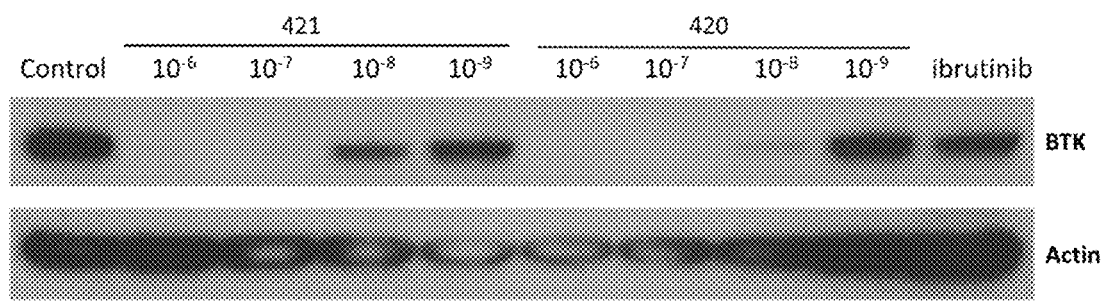
FIG. 17 shows the dose-dependent degradation of BTK protein by exemplary compound 421 and 420 of the present disclosure in Namalwa B lymphocyte cells.
Figure 18:
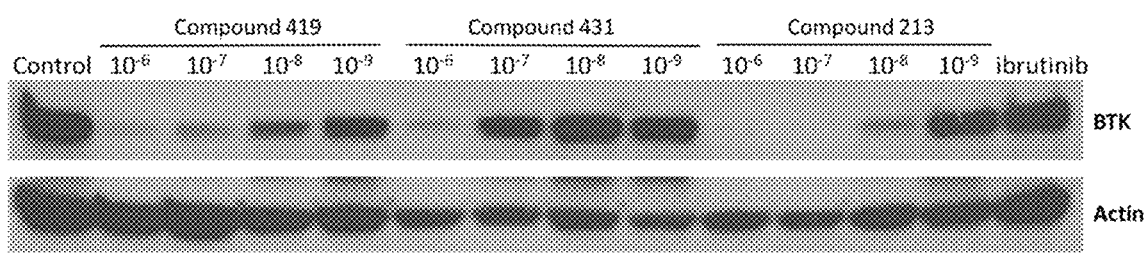
FIG. 18 shows the dose-dependent degradation of BTK protein by exemplary compound 419, 431, and 213 of the present disclosure in Namalwa B lymphocyte cells.
Figure 19:
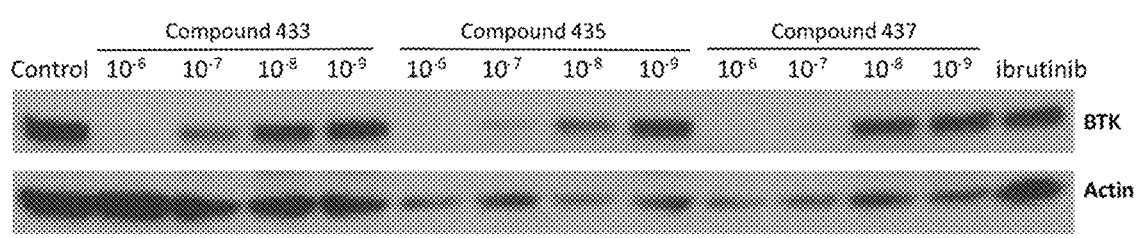
FIG. 19 shows the dose-dependent degradation of BTK protein by exemplary compound 433, 435, and 437 of the present disclosure in Namalwa B lymphocyte cells.
Figure 20:
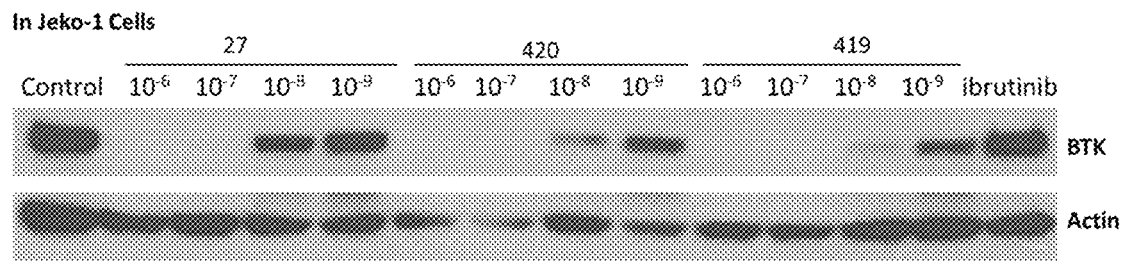
FIG. 20 shows the dose-dependent degradation of BTK protein by exemplary compound 27, 420, and 419 of the present disclosure in Jeko-1 mantle cell lymphoma cells.
Figure 21:
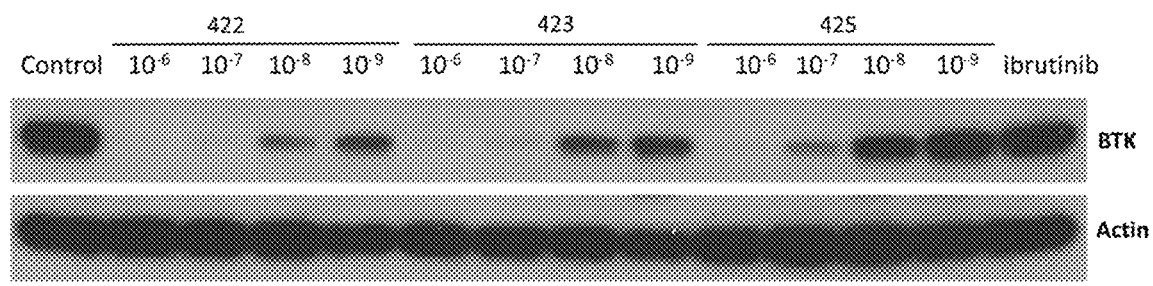
FIG. 21 shows the dose-dependent degradation of BTK protein by exemplary compound 422, 423, and 425 of the present disclosure in Namalwa B lymphocyte cells.
Figure 22:
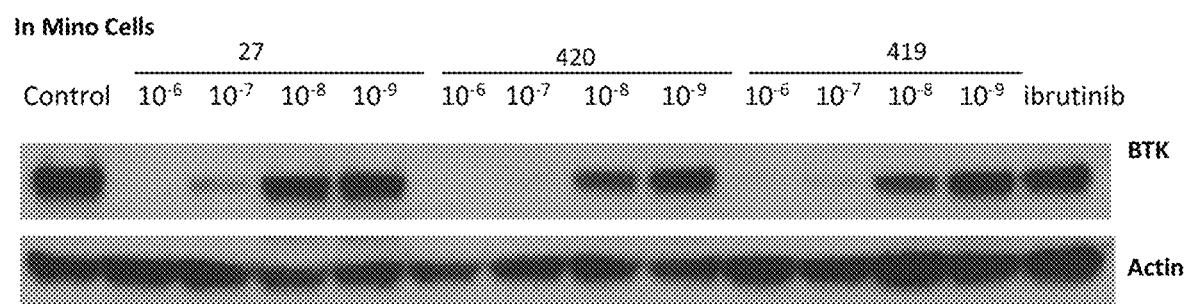
FIG. 22 shows the dose-dependent degradation of BTK protein by exemplary compound 27, 420, and 419 of the present disclosure in Mino mantle cell lymphoma cells.
Figure 23:
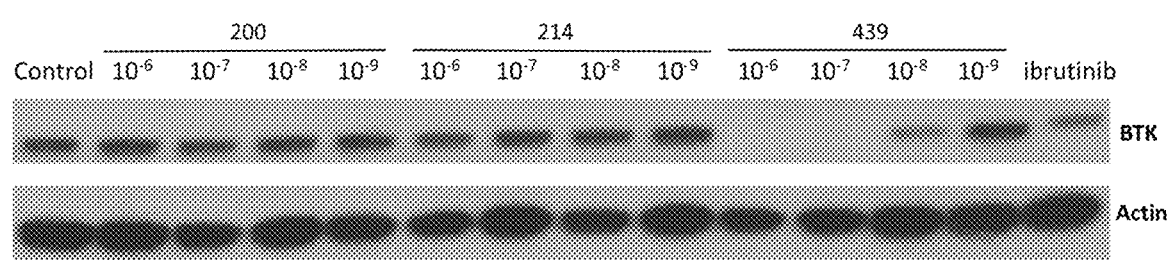
FIG. 23 shows the dose-dependent degradation of BTK protein by exemplary compound 200, 214, and 439 of the present disclosure in Namalwa B lymphocyte cells.
Figure 24:
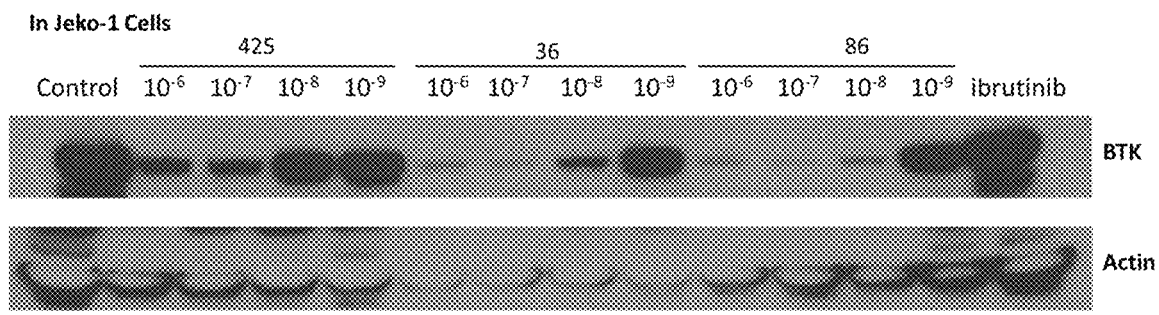
FIG. 24 shows the dose-dependent degradation of BTK protein by exemplary compound 425, 36, and 86 of the present disclosure in Jeko-1 mantle cell lymphoma cells.
Figure 25:
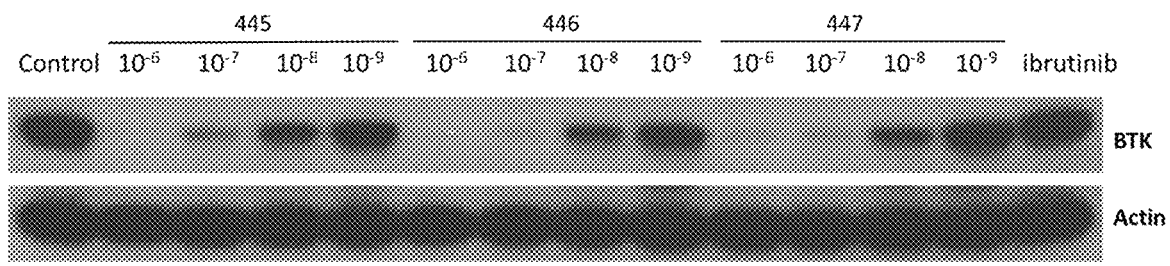
FIG. 25 shows the dose-dependent degradation of BTK protein by exemplary compound 445, 446, and 447 of the present disclosure in Namalwa B lymphocyte cells.
Figure 26:
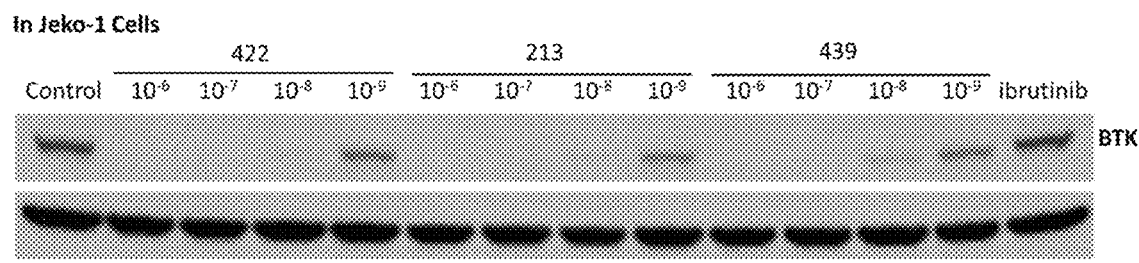
FIG. 26 shows the dose-dependent degradation of BTK protein by exemplary compound 422, 213, and 439 of the present disclosure in Jeko-1 mantle cell lymphoma cells.
Figure 27:
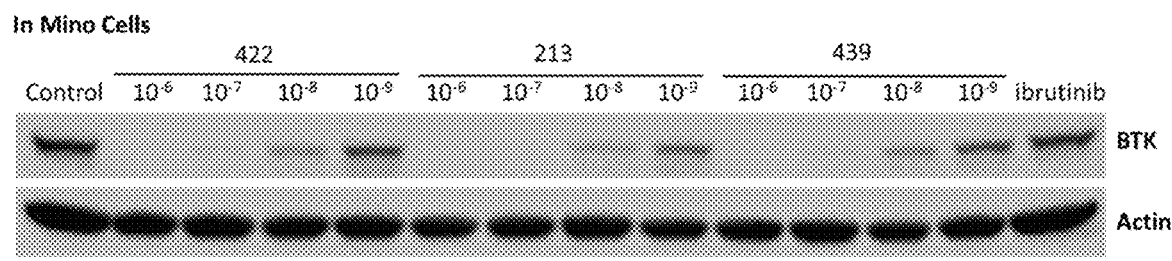
FIG. 27 shows the dose-dependent degradation of BTK protein by exemplary compound 422, 213, and 439 of the present disclosure in Mino mantle cell lymphoma cells.
Figure 28:
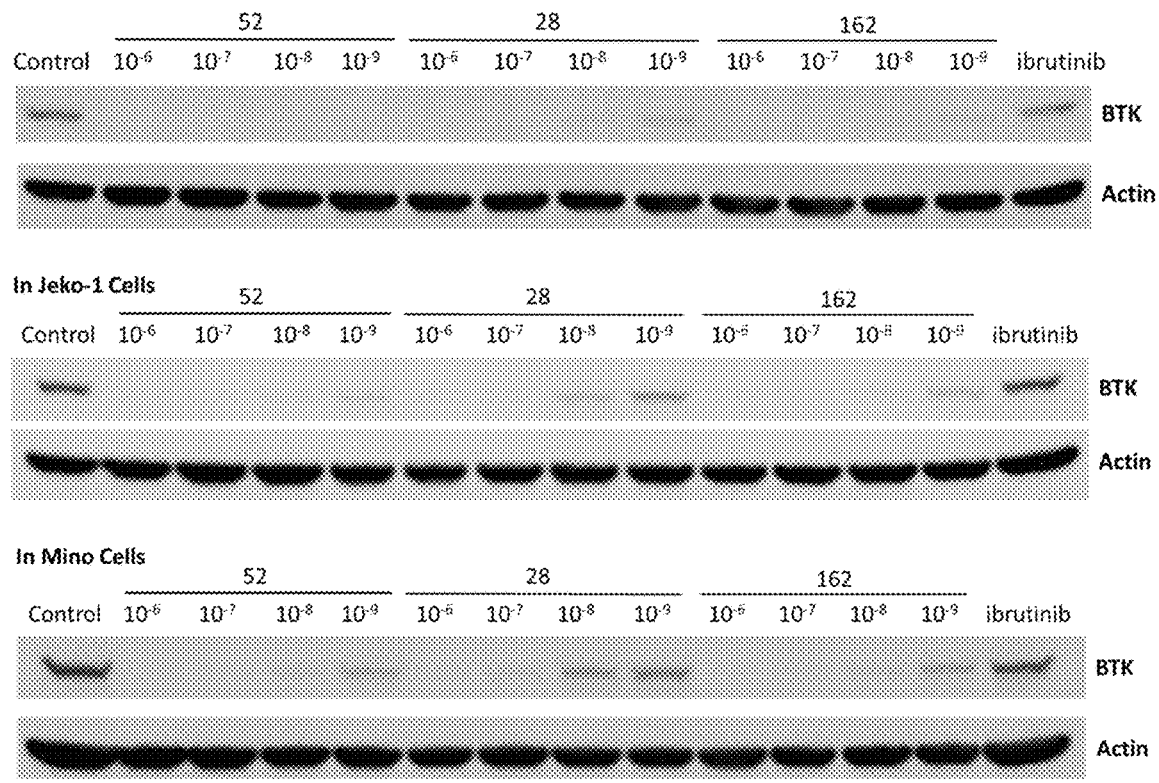
FIG. 28 shows the dose-dependent degradation of BTK protein by exemplary compound 52, 28, and 162 of the present disclosure in Namalwa B lymphocyte cells, Jeko-1 cells, and Mino cells.
Figure 29:
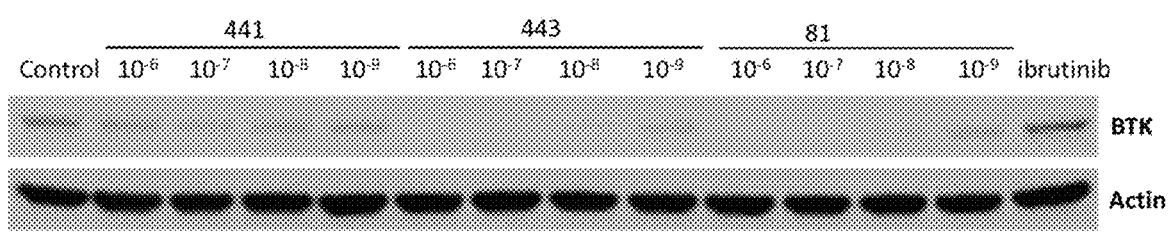
FIG. 29 shows the dose-dependent degradation of BTK protein by exemplary compound 441, 443, and 81 of the present disclosure in Namalwa B lymphocyte cells.
Figure 30:
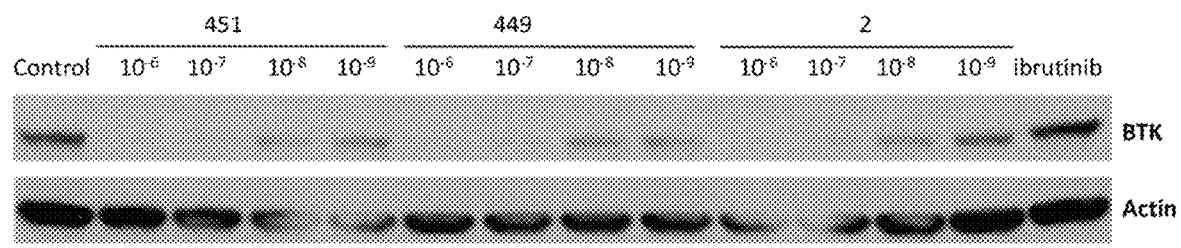
FIG. 30 shows the dose-dependent degradation of BTK protein by exemplary compound 451, 449, and 2 of the present disclosure in Namalwa B lymphocyte cells.
Figure 31:
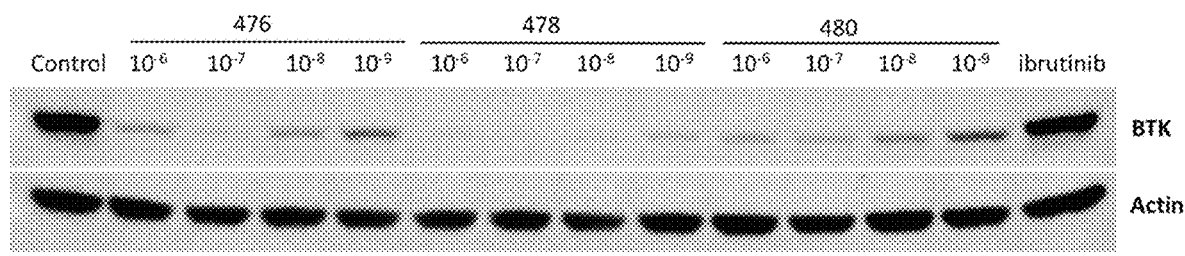
FIG. 31 shows the dose-dependent degradation of BTK protein by exemplary compound 476, 478, and 480 of the present disclosure in Namalwa B lymphocyte cells.
Figure 32:
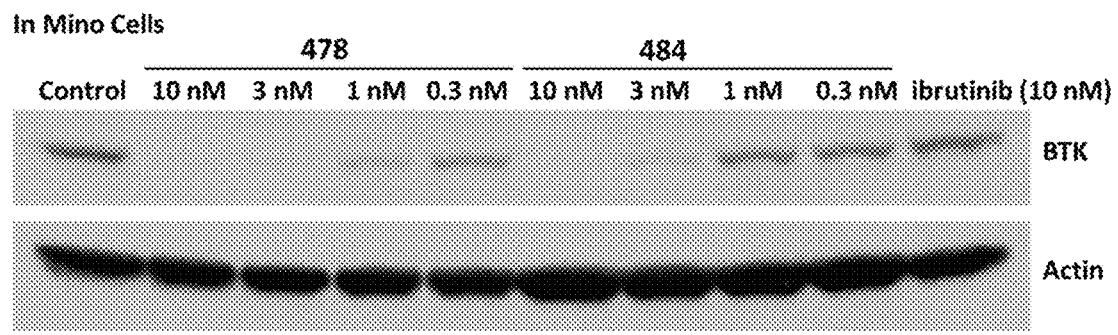
FIG. 32 shows the dose-dependent degradation of BTK protein by exemplary compound 478 and 484 of the present disclosure in Mino cells.
Figure 33:
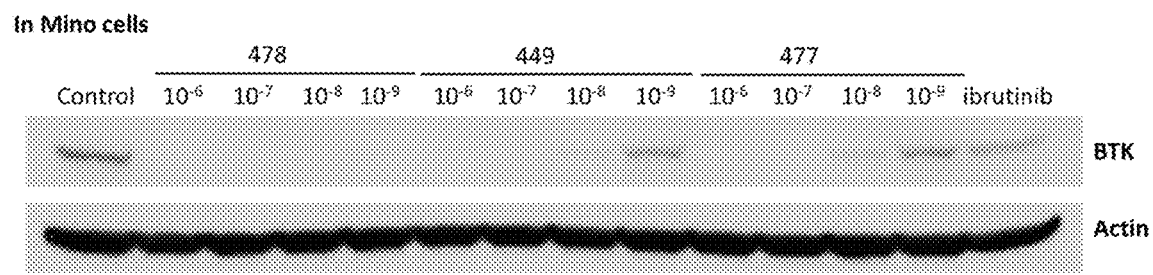
FIG. 33 shows the dose-dependent degradation of BTK protein by exemplary compound 478, 449, and 477 of the present disclosure in Mino cells.
Figure 34:
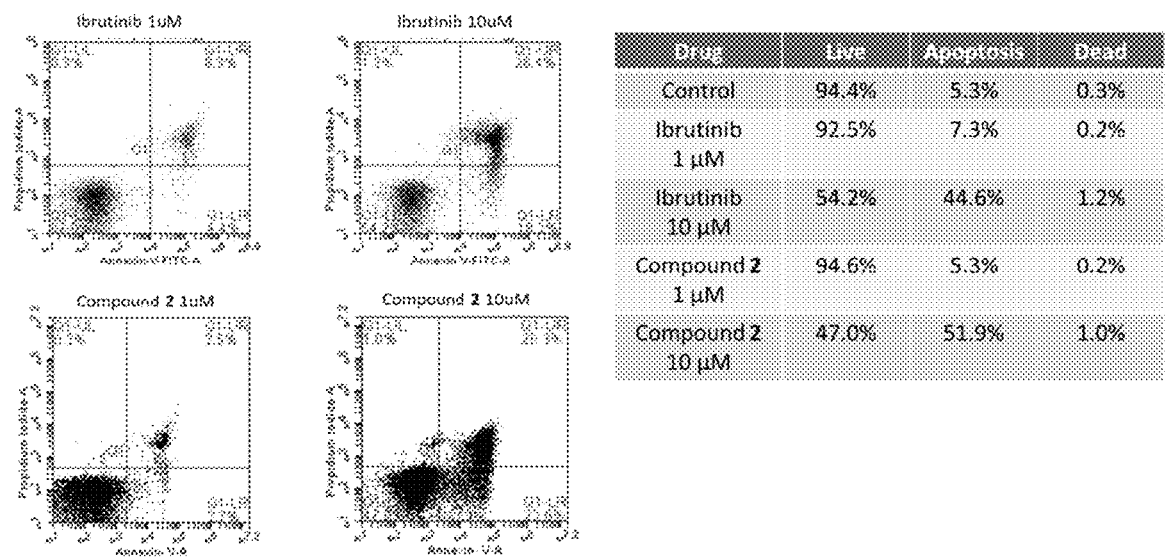
FIG. 34 shows the induction of MOLT-4 cell apoptosis by compound 2 in vitro. The cells were incubated at the concentration of 1 and 10 µM for 72 hours.
Figure 35:
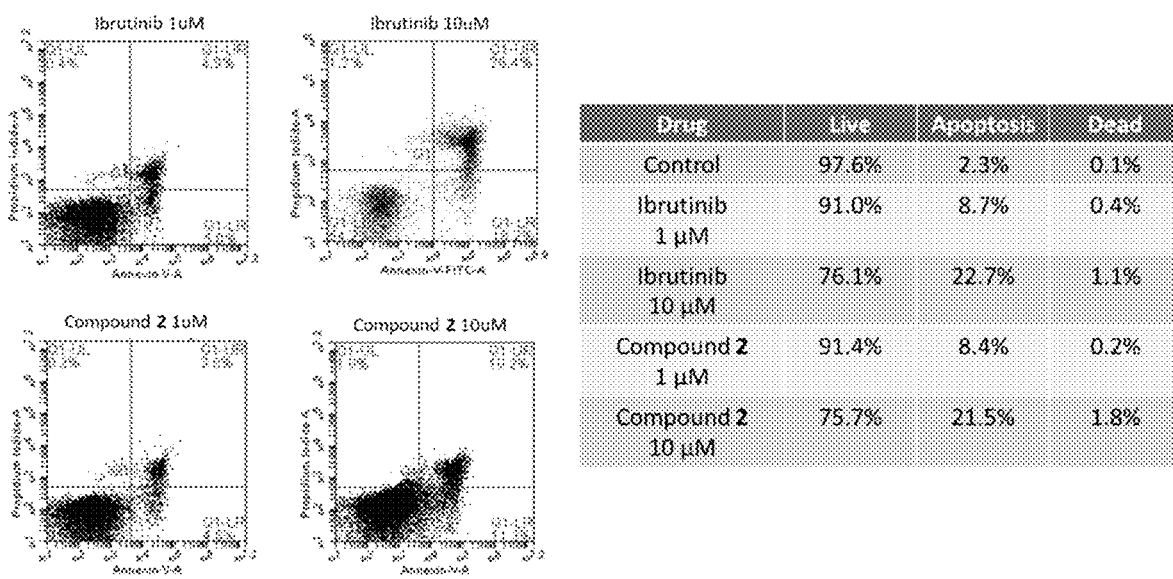
FIG. 35 shows the induction of Namalwa cell apoptosis by compound 2 in vitro. The cells were incubated at the concentration of 1 and 10 µM for 72 hours.
Figure 36:
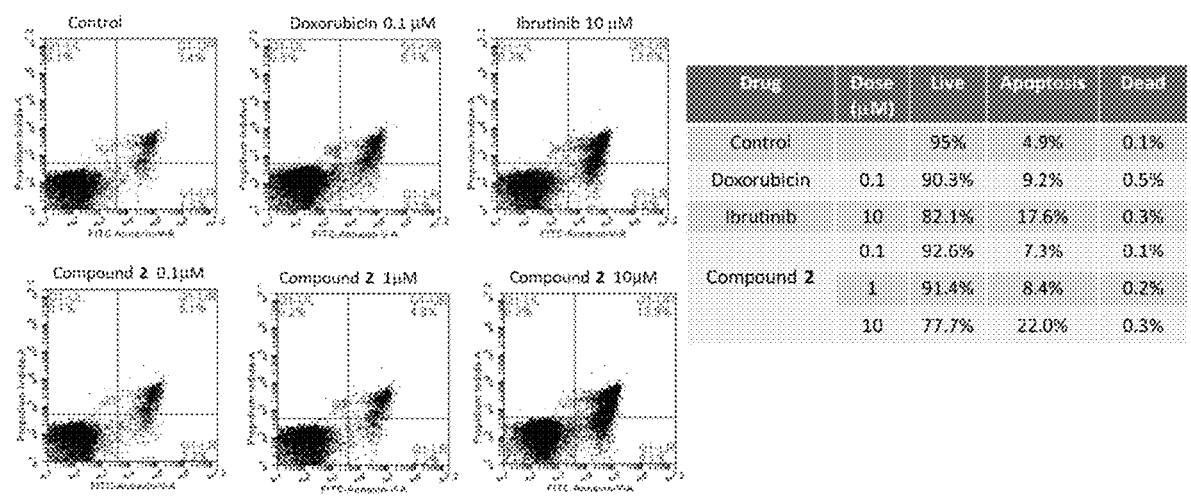
FIG. 36 shows the induction of JeKo-1 cell apoptosis by compound 2 in vitro. The cells were incubated at the concentration of 0.1, 1, and 10 µM for 72 hours.
Figure 37:
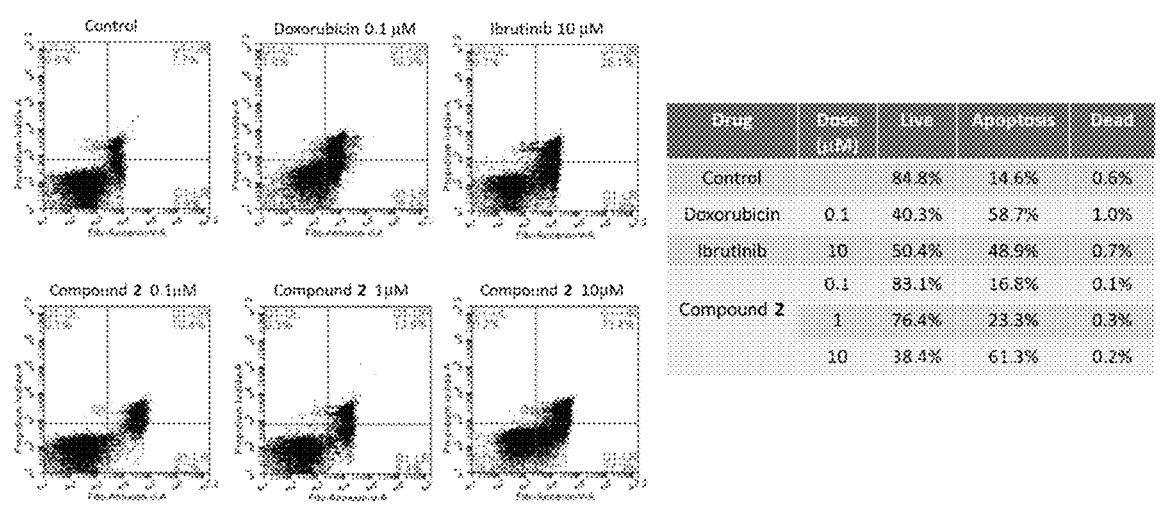
FIG. 37 shows the induction of Mino cell apoptosis by compound 2 in vitro. The cells were incubated at the concentration of 1 and 10 µM for 72 hours.

The present disclosure relates to compounds that bind competitively and/or non-competitively to the Bruton's tyrosine kinase (BTK), and the E3 ubiquitin ligase, cereblon (CRBN) to effect ubiquitination and subsequent degradation of the BTK protein, thereby blocking the BCR signaling pathways and inhibiting the growth of BTK dependent cells. The disclosure also relates to pharmaceutical compositions comprising these BTK degrading compounds, and methods for using the same for treatment of diseases and conditions mediated by the Bruton's tyrosine kinase, including B cell malignancies.

Based on the ideas of the invention described above, the disclosed bifunctional compounds can be applied for targeted degradation of BTK and be used to treat or prevent diseases where BTK is dysregulated. The following detailed description is furnished to assist those skilled in the art in joining the present disclosure.

Before the subject disclosure is further described, it is to be understood that the disclosure is not limited to the particular embodiments of the disclosure described below, as variations of the particular embodiments may be made by those of ordinary skill in the art and still maintain the spirit and scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

In this specification and the claims reported herein, the phrase "and/or," as used is construed to mean "either or both" of the elements, i.e., either the elements can be conjunctively present in some cases or the elements can be disjunctively present in other cases.

"About" as used herein when referring to a measurable value such as an amount, a temporal duration, and the like, is meant to encompass variations of ±20%, 10%, 5%, 1%, or ±0.1% from the specified value, as such variations are appropriate to perform the disclosed methods.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "cancer" refers to any of various types of malignant neoplasms, most of which invade surrounding tissues, may metastasize to several sites and are likely to recur after attempted removal and to cause death of the patient unless adequately treated. As used herein, neoplasia comprises cancer. Representative cancers include, for example, squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias, including non-acute and acute leukemias, such as acute myelogenous leukemia, acute lymphocytic leukemia, acute promyelocytic leukemia (APL), acute T-cell lymphoblastic leukemia, T-lineage acute lymphoblastic leukemia (T-ALL), adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, glioblastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas, among others, which may be treated by one or more compounds of the present invention.

A disease or disorder is "alleviated" if the severity of a sign or symptom of the disease or disorder, the frequency with which such a sign or symptom is experienced by a patient, or both, is reduced.

As used herein, the term "minimize" or "reduce", or derivatives thereof, include a complete or partial degradation of a target protein (BTK) and/or inhibition of a specified biological effect and/or reduction of BTK expression at the transcript or protein level. (which is apparent from the context in which the terms "minimize" or "reduce" are used).

The term "inhibit," as used herein, means to suppress or block an activity or function by at least about ten percent relative to a control value. Preferably, the activity is suppressed or blocked by 50% compared to a control value, more preferably by 75%, and even more preferably by 95% or more.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell from a patient (e.g., for diagnosis or ex vivo applications), who has a disease or disorder contemplated herein, a sign or symptom of a disease or disorder contemplated herein or the potential to develop a disease or disorder contemplated herein, with the purpose to cure, heal, alleviate, relieve, alter, remedy, ameliorate, improve or affect a disease or disorder contemplated herein, the signs or symptoms of a disease or disorder contemplated herein or the potential to develop a disease or disorder contemplated herein. Such treatments may be specifically tailored or modified, based on knowledge obtained from the field of pharmacogenomics. To "treat" a disease as the term is used herein, means to reduce the frequency or severity of at least one sign or symptom of a disease or disorder experienced by a subject.

"Parenteral" administration of a composition includes, e.g., subcutaneous (s.c.), intravenous (i.v.), intramuscular (i.m.), or intrasternal injection, or infusion techniques.

The compounds according to the disclosure are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present disclosure which possess a sufficiently basic or acidic functionality, may result in the formation of a salt, such as, in the case of a compound of the present disclosure which is sufficiently basic, a trifluoroacetate or formate salt for example, or, in the case of a compound of the present disclosure which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present disclosure may not fully remove traces of cosolvents, especially such as formic acid or trifluoroacetic acid, to give solvates or inclusion complexes. The person skilled in the art will recognize which solvates or inclusion complexes are acceptable to be used in subsequent biological assays. It is to be understood that the specific form (e.g., salt, free base, solvate, inclusion complex) of a compound of the present disclosure as isolated as described herein is not necessarily the only form in which said compound can be applied to a biological assay in order to quantify the specific biological activity.

One aspect of the disclosure is salts of the compounds according to the disclosure including all inorganic and organic salts, especially all pharmaceutically acceptable inorganic and organic salts, particularly all pharmaceutically acceptable inorganic and organic salts customarily used in pharmacy.

Examples of salts include, but are not limited to, lithium, sodium, potassium, calcium, aluminum, magnesium, titanium, meglumine, ammonium, salts optionally derived from $NH_3$ or organic amines having from 1 to 16 C-atoms such as, e.g., ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, ethylendiamine, N-methylpiperidine, arginine, lysine, and guanidinium salts.

The salts of the disclosed compounds include pharmaceutically acceptable water-insoluble and, particularly, water-soluble salts.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, "pharmaceutically acceptable salts" refer to derivatives of the compounds disclosed herein wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycoloylarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-(2.2.2)-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt may be 1:1, or any ratio other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

Salts of the compounds of Formula (I) according to the disclosure can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

According to the person skilled in the art the compounds of Formula (I) according to this disclosure as well as their salts may contain, e.g., when isolated in crystalline form, varying amounts of solvents. Included within the scope of the disclosure are therefore all solvates and in particular all hydrates of the compounds of Formula (I) according to this disclosure as well as all solvates and in particular all hydrates of the salts of the compounds of Formula (I) according to this disclosure.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The compounds according to the disclosure and their salts can exist in the form of tautomers which are included in the embodiments of the disclosure.

The term "tautomer" refers to one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH conditions. The concept of tautomers that are interconvertible by tautomerizations is called tautomerism.

Where the present specification depicts a compound prone to tautomerization, but only depicts one of the tautomers, it is understood that all tautomers are included as part of the meaning of the chemical depicted. It is to be understood that the compounds disclosed herein may be depicted as different tautomers. It should also be understood that when compounds have tautomeric forms, all tautomeric forms are intended to be included, and the naming of the compounds does not exclude any tautomer form.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

The compounds of the disclosure may, depending on their structure, exist in different stereoisomeric forms. These forms include configurational isomers or optically conformational isomers (enantiomers and/or diastereoisomers including those of atropisomers). The present disclosure therefore includes enantiomers, diastereoisomers as well as mixtures thereof. From those mixtures of enantiomers and/or diastereoisomers pure stereoisomeric forms can be isolated with methods known in the art, preferably methods of chromatography, especially high performance liquid chromatography (HPLC) using achiral or chiral phase. The disclosure further includes all mixtures of the stereoisomers mentioned above independent of the ratio, including the racemates.

The compounds of the disclosure may, depending on their structure, exist in various stable isotopic forms. These forms include those in which one or more hydrogen atoms have been replaced with deuterium atoms, those in which one or more nitrogen atoms have been replaced with $^{15}N$ atoms, or those in which one or more atoms of carbon, fluorine, chlorine, bromine, sulfur, or oxygen have been replaced by the stable isotope of the respective, original atoms.

Some of the compounds and salts according to the disclosure may exist in different crystalline forms (polymorphs) which are within the scope of the disclosure.

It is a further object of the disclosure to provide BTK degrading compounds, methods of synthesizing the BTK degrading bifunctional compounds, methods of manufacturing the BTK degrading compounds, and methods of using the BTK degrading compounds.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration. The term "pharmacological composition," "therapeutic composition," "therapeutic formulation" or "pharmaceutically acceptable formulation" can mean, but is in no way limited to, a composition or formulation that allows for the effective distribution of an agent provided by the invention, which is in a form suitable for administration to the physical location most suitable for their desired activity, e.g., systemic administration.

Non-limiting examples of agents suitable for formulation with the, e.g., compounds provided by the instant invention include: cinnamoyl, PEG, phospholipids or lipophilic moieties, phosphorothioates, P-glycoprotein inhibitors (such as Pluronic P85) which can enhance entry of drugs into various tissues, for example the CNS (Jolliet-Riant and Tillement, 1999, Fundam. Clin. Pharmacol., 13, 16-26); biodegradable polymers, such as poly (DL-lactide-coglycolide) microspheres for sustained release delivery after implantation (Emerich D F et al, 1999, Cell Transplant, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (Schroeder U et al, 1999, Prog Neuropsychopharmacol Biol Psychiatry, 23, 941-949).

A "therapeutic" treatment is a treatment administered to a subject who exhibits signs or symptoms of pathology disease or disorder, for the purpose of diminishing or eliminating those signs or symptoms.

As used herein, the terms "effective amount," "pharmaceutically effective amount" and "therapeutically effective amount" refer to a sufficient amount of an agent to provide the desired biological or physiologic result. That result may be reduction and/or alleviation of a sign, a symptom, or a cause of a disease or disorder, or any other desired alteration of a biological system. An appropriate effective amount in any individual case may be determined by one of ordinary skill in the art using routine experimentation.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention.

As used herein, the term "halo" or "halogen" alone or as part of another substituent means, unless otherwise stated, a fluorine, chlorine, bromine, or iodine atom.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and includes straight, branched chain, or cyclic substituent groups. Examples include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. The term "alkyl," unless otherwise noted, is also meant to include those derivatives of alkyl defined in more detail below, such as "heteroalkyl", "haloalkyl" and "homoalkyl".

As used herein, the term "substituted alkyl" means alkyl, as defined above, substituted by one, two or three substituents selected from the group consisting of halogen, —OH, alkoxy, —NH$_2$, —N(CH$_3$)$_2$, —C(=O)OH, trifluoromethyl, —C≡N, —C(=O)O(C$_1$-C$_4$)alkyl, —C(=O)NH$_2$, —SO$_2$NH$_2$, —C(=NH)NH$_2$, and —NO$_2$, preferably containing one or two substituents selected from halogen, —OH, alkoxy, —NH$_2$, trifluoromethyl, —N(CH$_3$)$_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

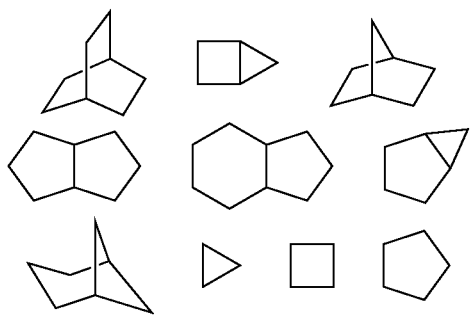

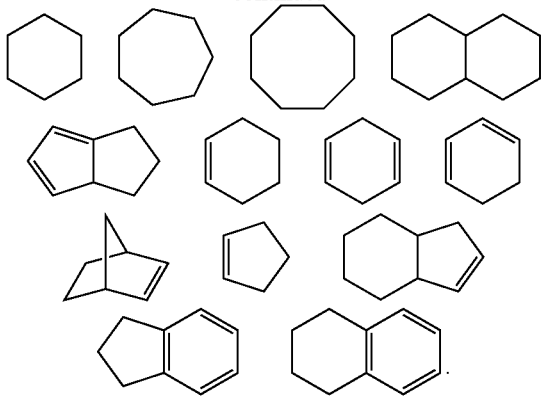

Monocyclic cycloalkyls include, but are no limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$. As used herein, the terms "heteroalkyl" refers to "alkoxy," "alkylamino" and "alkylthio" that are used in their conventional sense, and refer to alkyl groups linked to molecules via an oxygen atom, an amino group, a sulfur atom, respectively.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

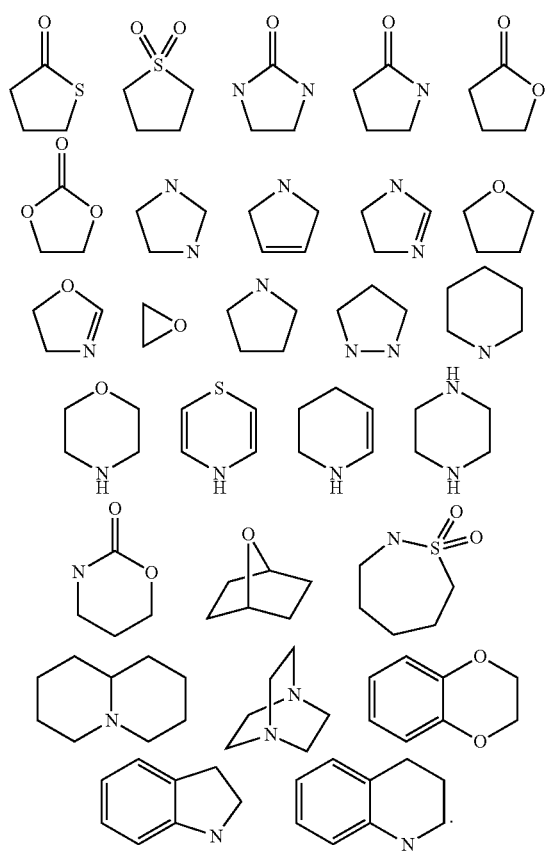

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "heteroaryl" or "heteroaromatic" refers to a heterocycle having aromatic character. A polycyclic heteroaryl may include one or more rings that are partially saturated. Examples include the following moieties:

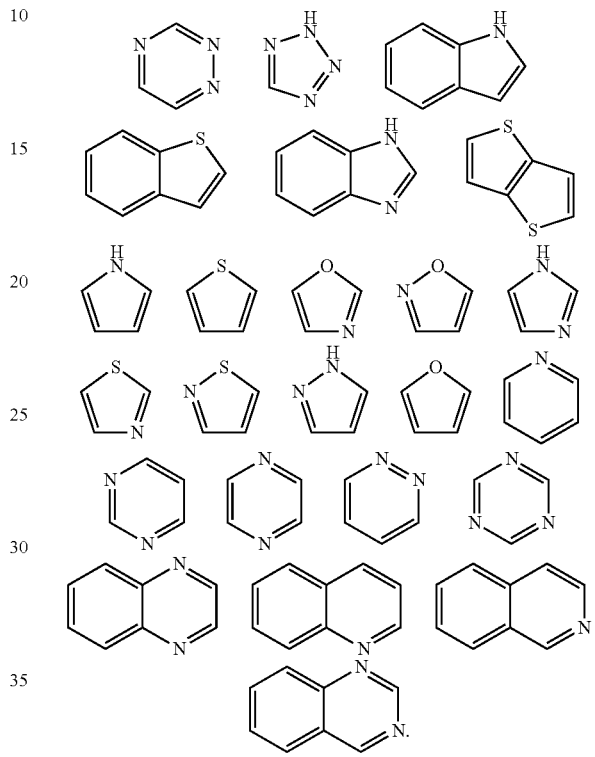

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two. The substituents are independently selected, and substitution may be at any chemically accessible position. In one embodiment, the substituents vary in number between one and four. In another embodiment, the substituents vary in number between one and three. In yet another embodiment, the substituents vary in number between one and two. In yet another embodiment, the substituents are independently selected from the group consisting of $C_{1-6}$ alkyl, —OH, $C_{1-6}$ alkoxy, halo, amino, acetamido and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic, with straight being preferred.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$ alkyl, —C(=O)NH (substituted or unsubstituted alkyl, or substituted or unsubstituted phenyl), —C(=O)N(H or alkyl)$_2$, —OC(=O)N(substituted or unsubstituted alkyl)$_2$, —NHC(=O)NH (substituted or unsubstituted alkyl, or substituted or unsubstituted phenyl), —NHC(=O)alkyl, —N(substituted or unsubstituted alkyl)C(=O)(substituted or unsubstituted alkyl), —NHC(=O)(substituted or unsubstituted alkyl), —C(OH)(substituted or unsubstituted alkyl)$_2$, —C(NH$_2$)(substituted or unsubstituted alkyl)$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of $C_{1-6}$ alkyl, —OH, $C_{1-6}$ alkoxy, halo, amino, acetamido, oxo and nitro. In yet another embodiment, the substituents are independently selected from the group consisting of $C_{1-6}$ alkyl, $C_{1-6}$ alkoxy, halo, acetamido, and nitro. As used herein, where a substituent is an alkyl or alkoxy group, the carbon chain may be branched, straight or cyclic.

As used herein, the term "analog," "analogue," or "derivative" is meant to refer to a chemical compound or molecule made from a parent compound or molecule by one or more chemical reactions. As such, an analog can be a structure having a structure similar to that of the small molecule therapeutic agents described herein or can be based on a scaffold of a small molecule therapeutic agents described herein, but differing from it in respect to certain components or structural makeup, which may have a similar or opposite action metabolically. An analog or derivative can also be a small molecule that differs in structure from the reference molecule, but retains the essential properties of the reference molecule. An analog or derivative may change its interaction with certain other molecules relative to the reference molecule. An analog or derivative molecule may also include a salt, an adduct, tautomer, isomer, or other variant of the reference molecule.

As used herein, the term "potency" refers to the dose needed to produce half the maximal response (ED$_{50}$).

As used herein, the term "efficacy" refers to the maximal effect (E$_{max}$) achieved within an assay.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

In some embodiments, provided herein are compounds of Formula I, or a tautomer, stereoisomer or a mixture of stereoisomers, pharmaceutically acceptable salt, or solvate thereof:

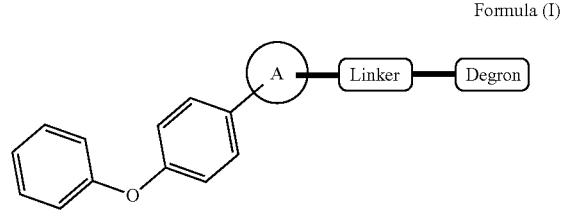

Formula (I)

In some embodiments, X is CH$_2$ or C=O.

In some embodiments, Ring A is selected from the group consisting of

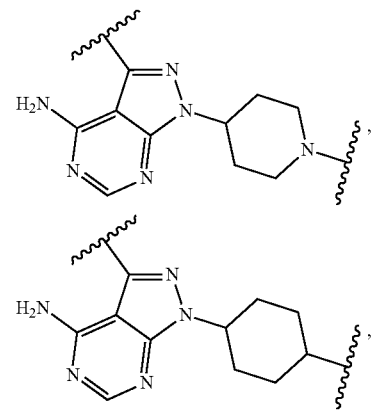

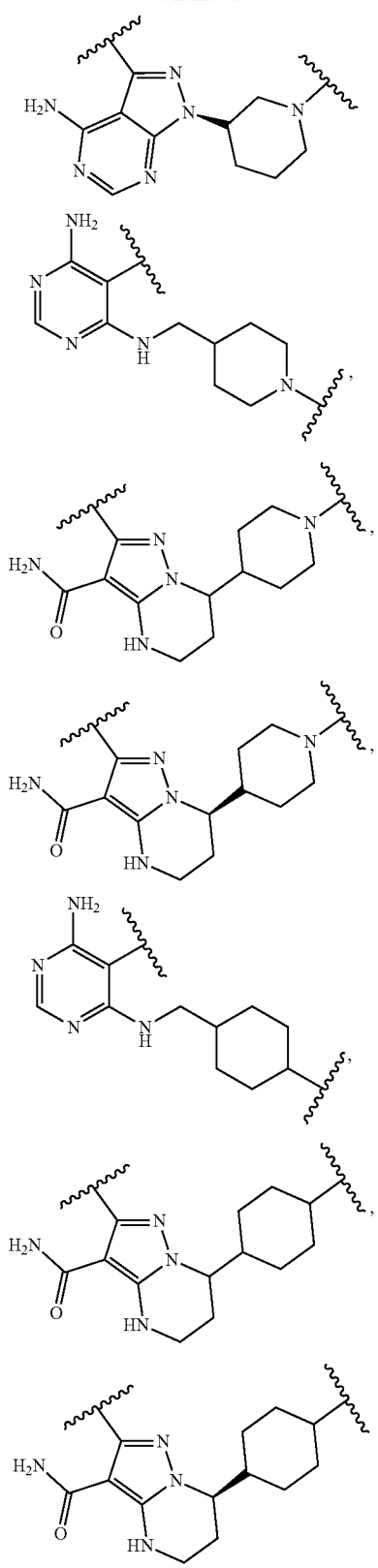
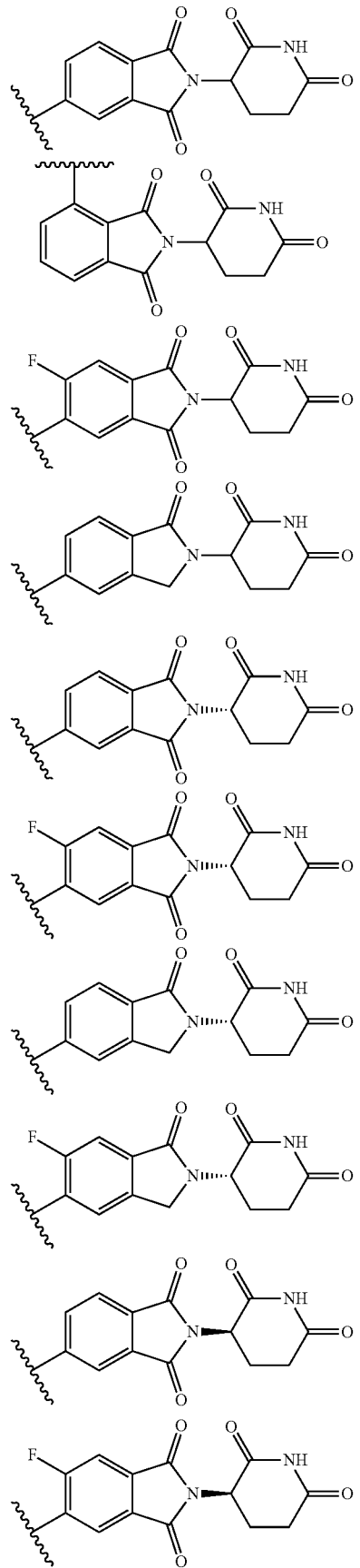
The Degron is capable of binding to a ubiquitin ligase, such as an E3 ubiquitin ligase (e.g., CRBN). The Degron is selected from the following structures:

-continued
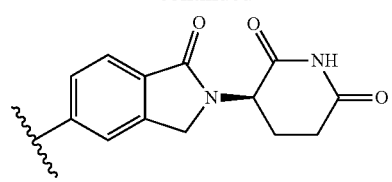
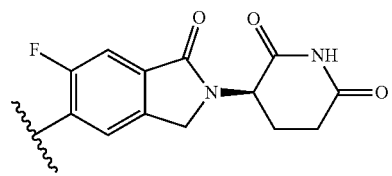
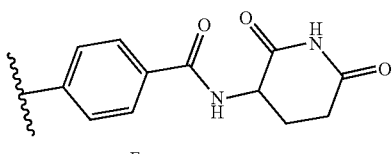
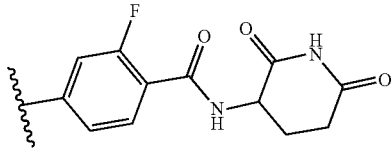
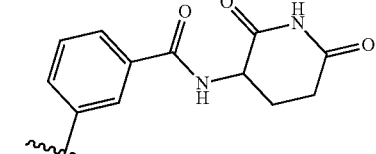
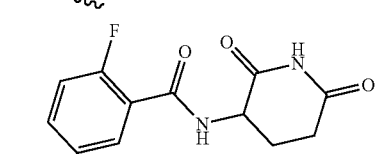
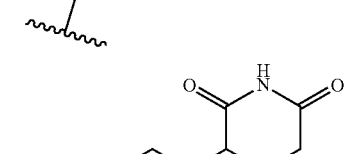
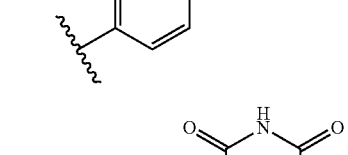
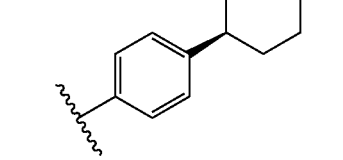
-continued
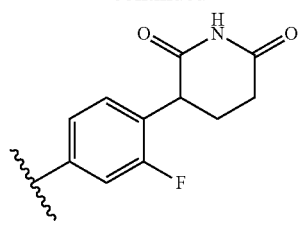
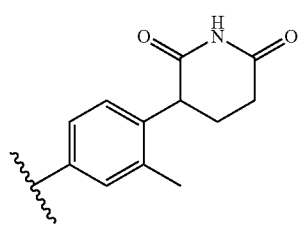
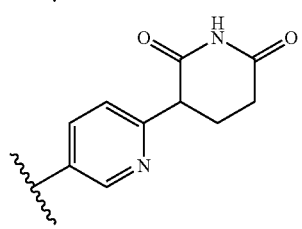
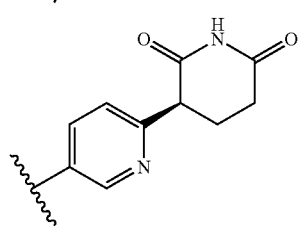
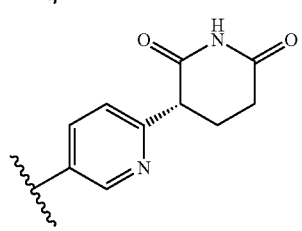
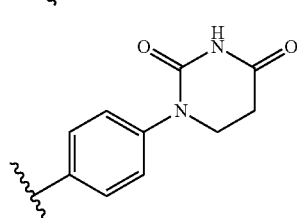
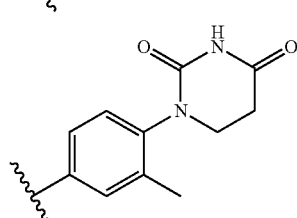
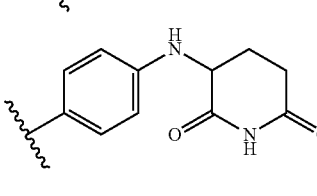

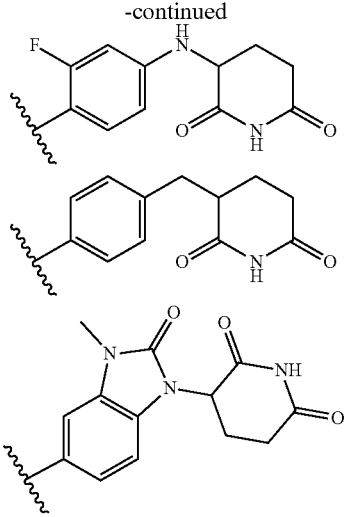

In some embodiments, the linker is an optionally substituted linking moiety comprising a branched or unbranched, cyclized or uncyclized, saturated or unsaturated chain of 5 to 22 carbon atoms in length, wherein 1 to 6 of the carbon atoms are optionally replaced with a heteroatom independently selected from O, N and S. For example, in some embodiments, the linker is an optionally substituted linking moiety comprising a branched or unbranched, cyclized or uncyclized, saturated or unsaturated chain of 5 to 18 carbon atoms in length, wherein 1 to 6 of the carbon atoms are optionally replaced with a heteroatom independently selected from O, N and S. In some embodiments, the linker is an optionally substituted linking moiety comprising a branched or unbranched, cyclized or uncyclized, saturated or unsaturated chain of 5 to 16 carbon atoms in length, wherein 1 to 6 of the carbon atoms are optionally replaced with a heteroatom independently selected from O, N and S.

In some embodiments, the linker is selected from the group consisting of

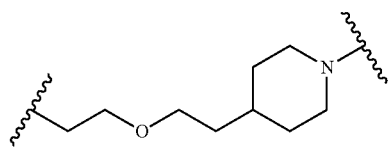
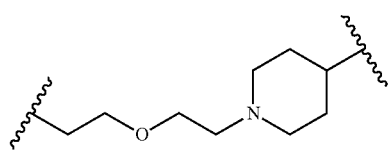
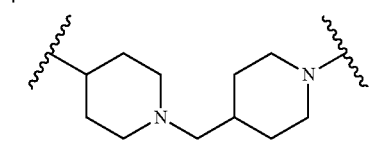
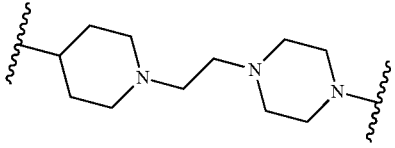
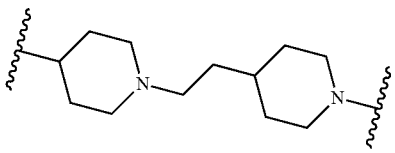
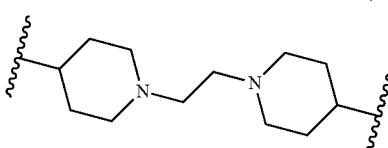
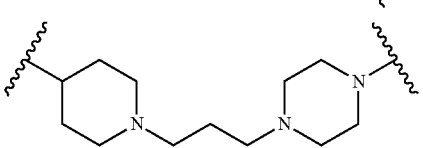
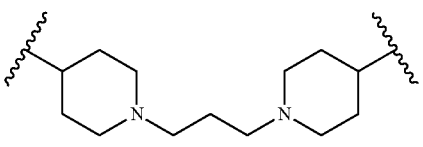
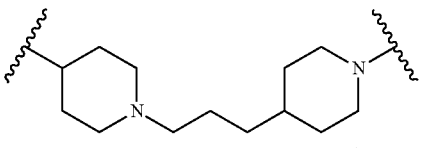
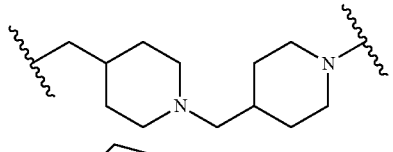
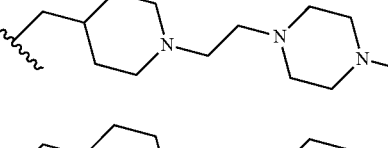

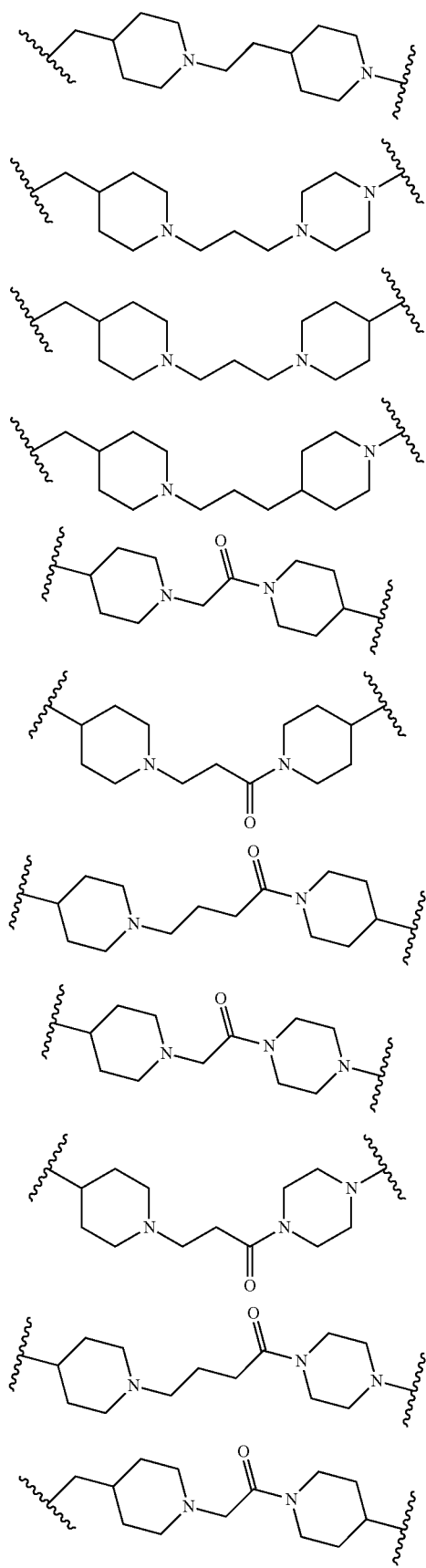
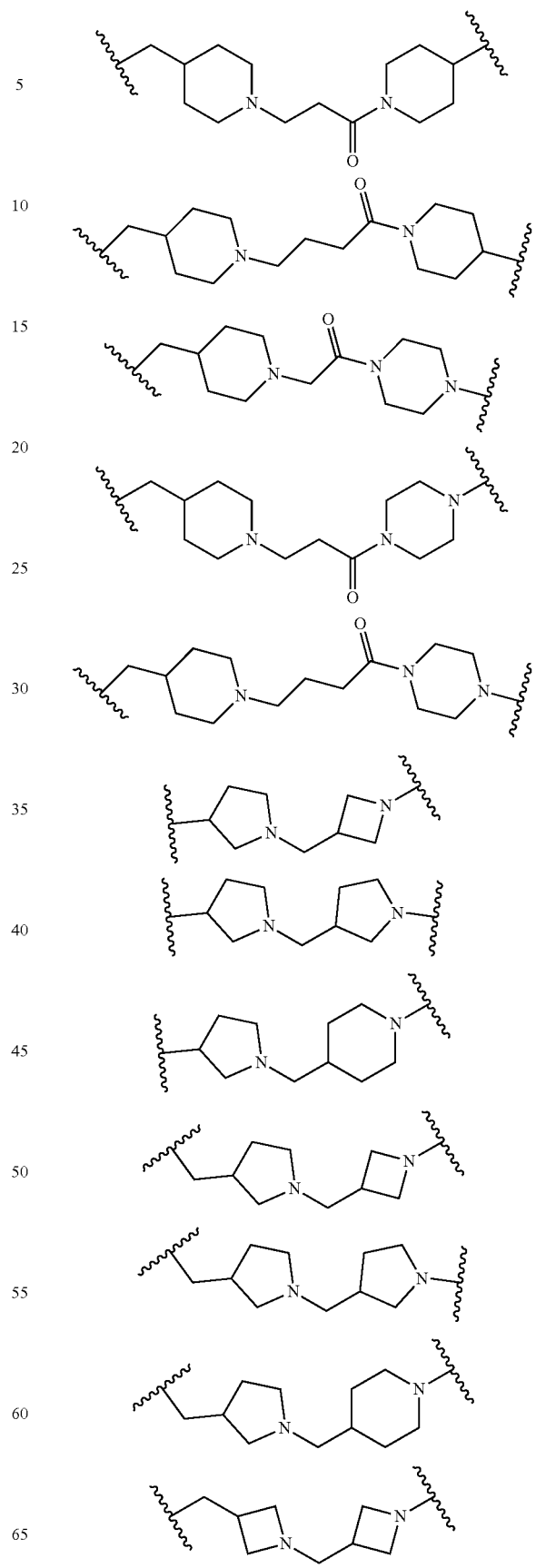

31
-continued
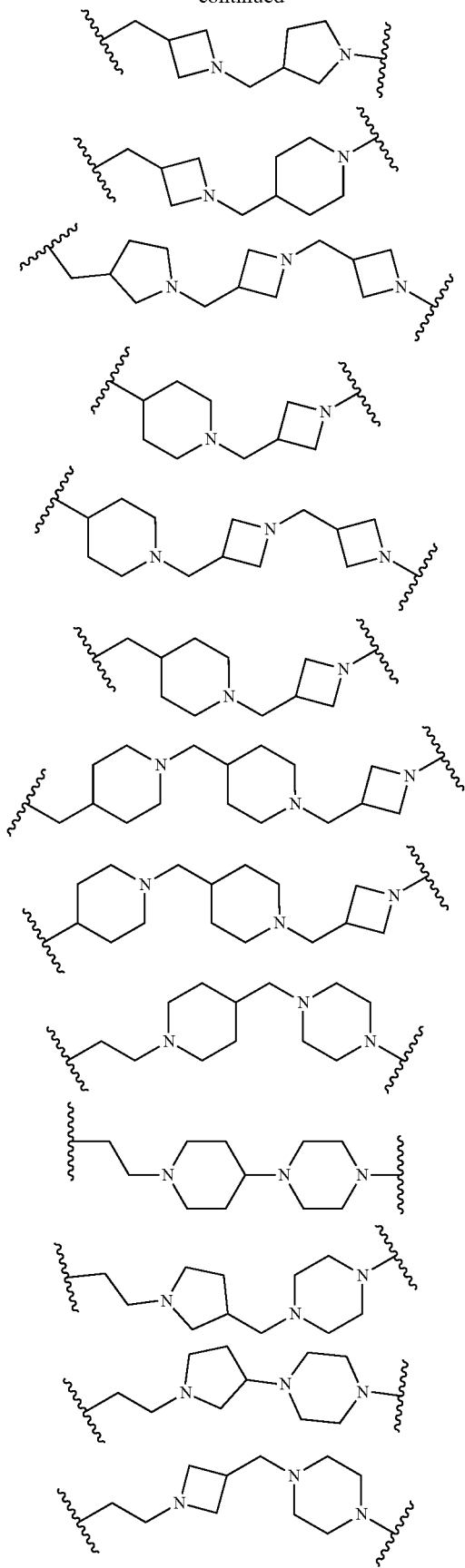
32
-continued
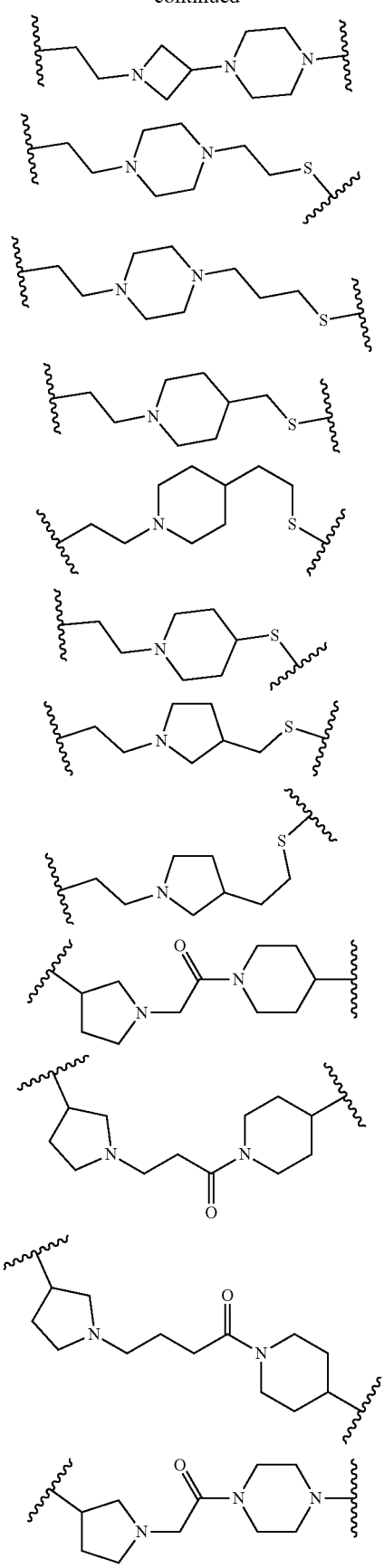

33
-continued
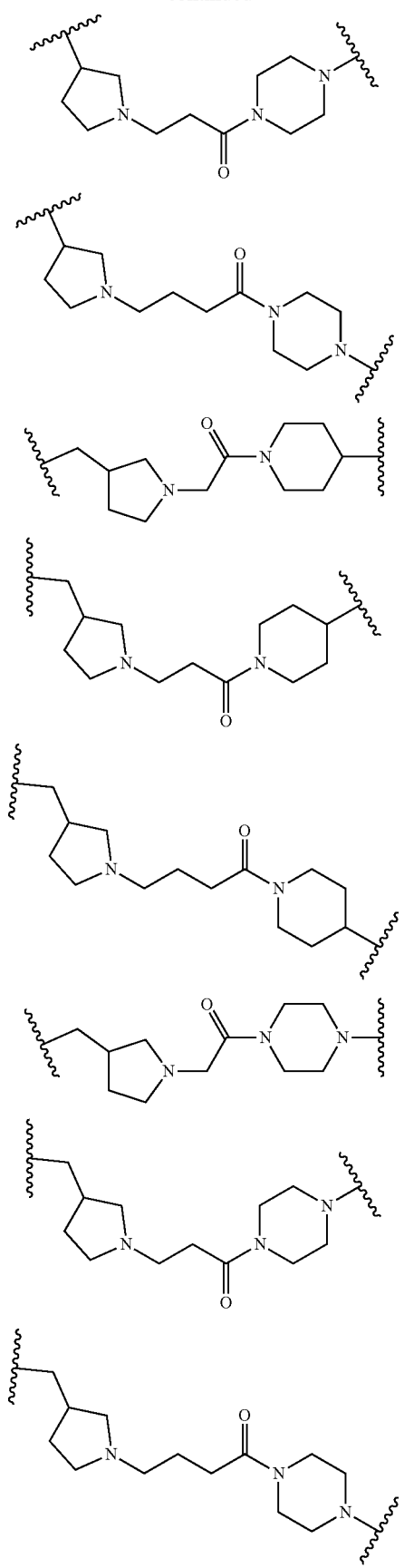
34
-continued
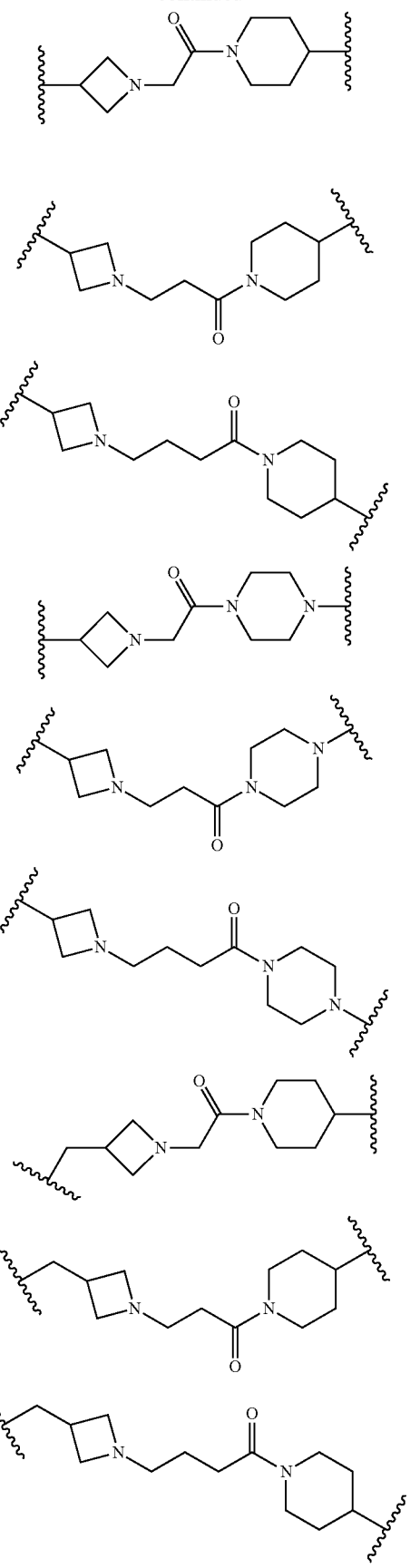

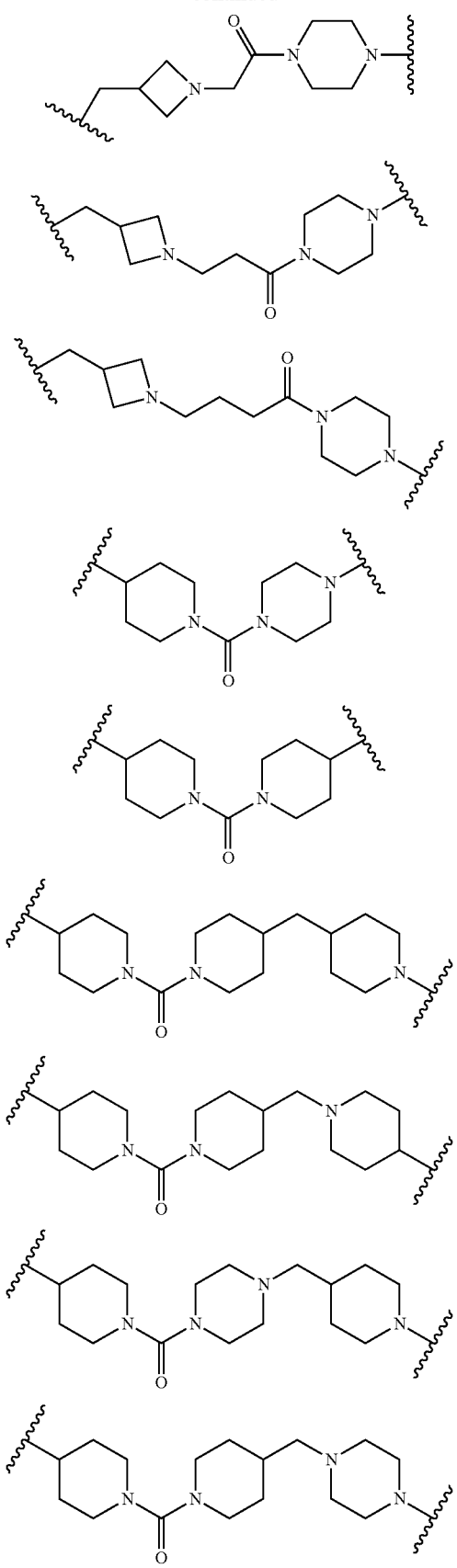
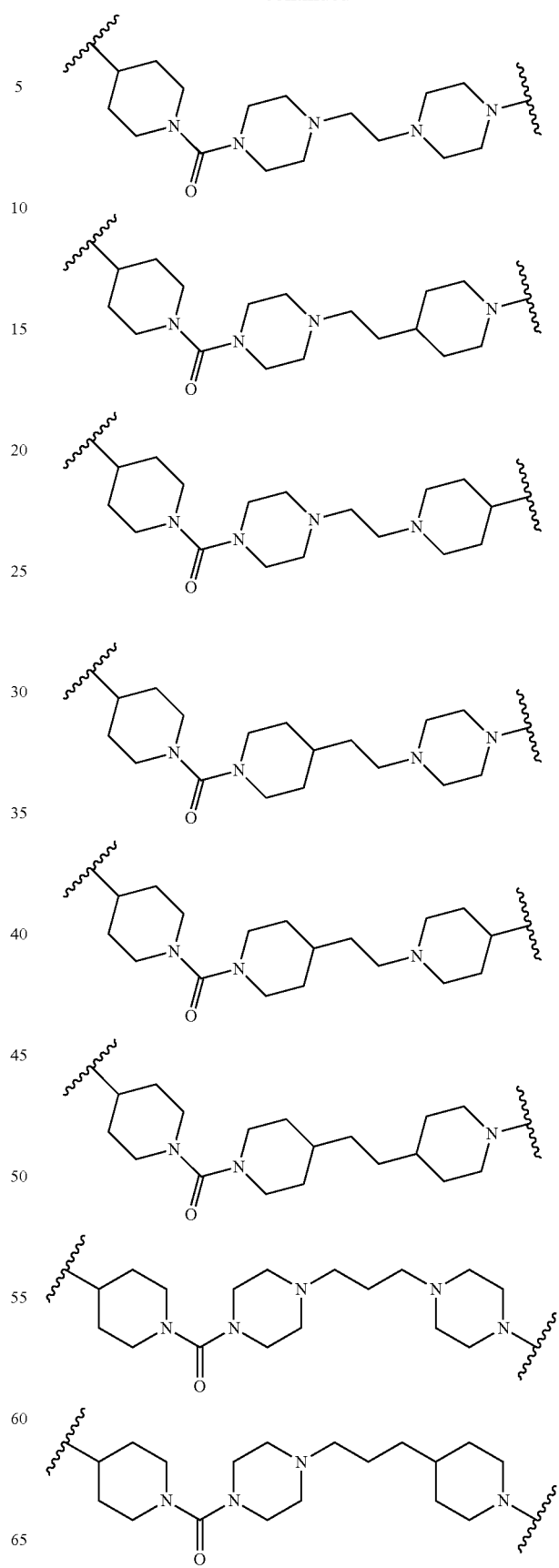

-continued

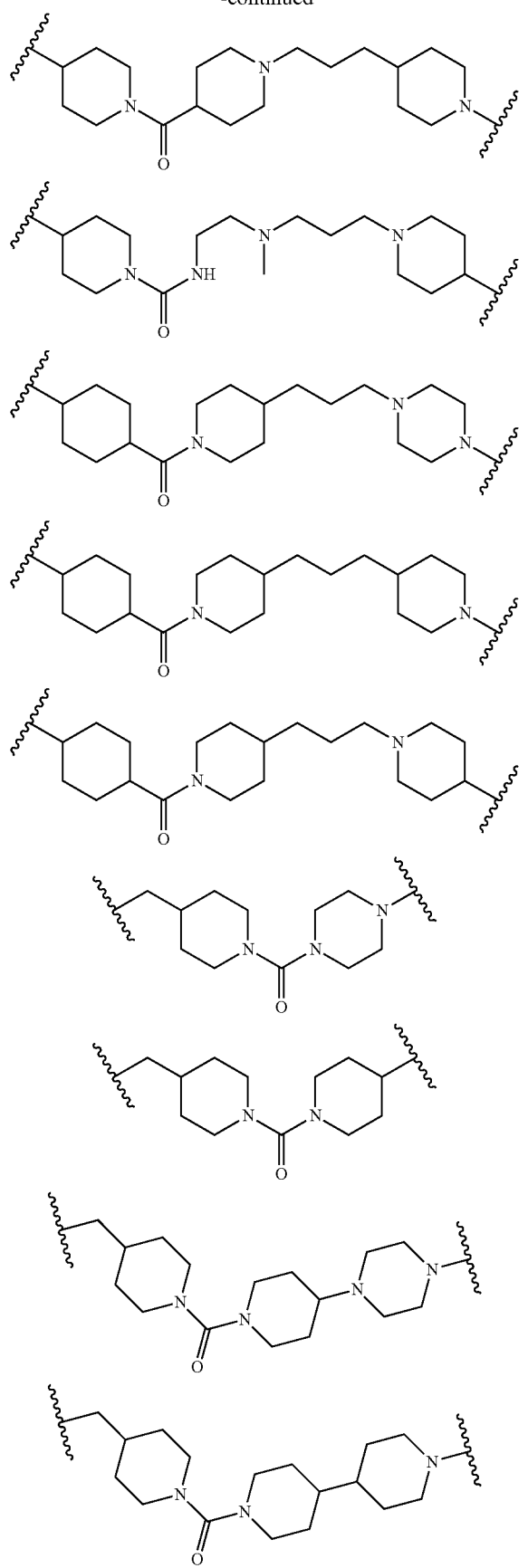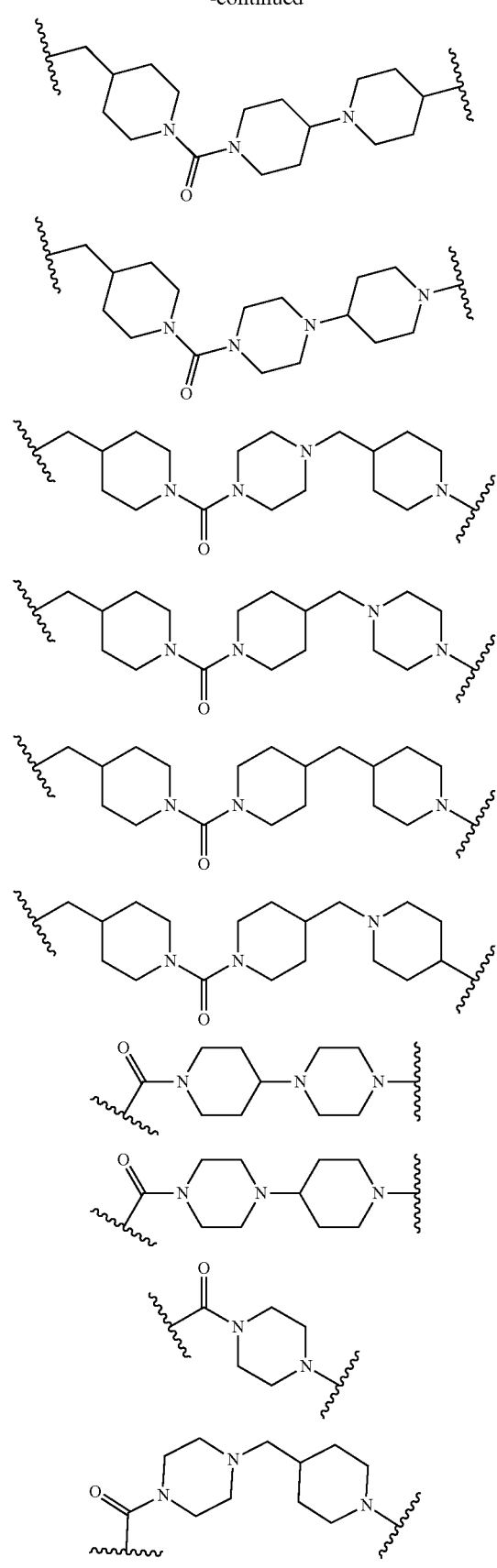

-continued
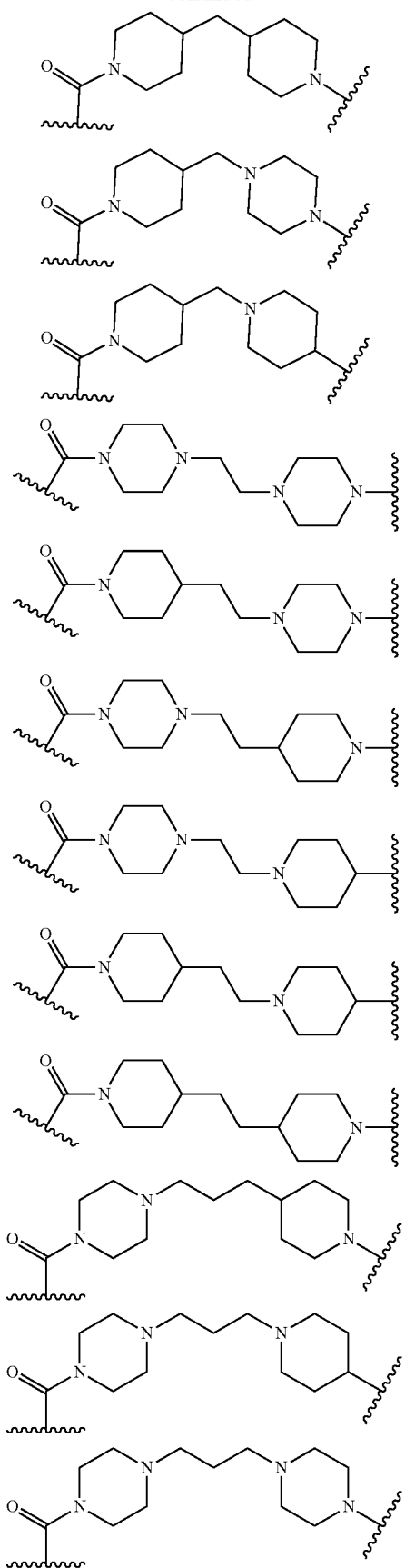
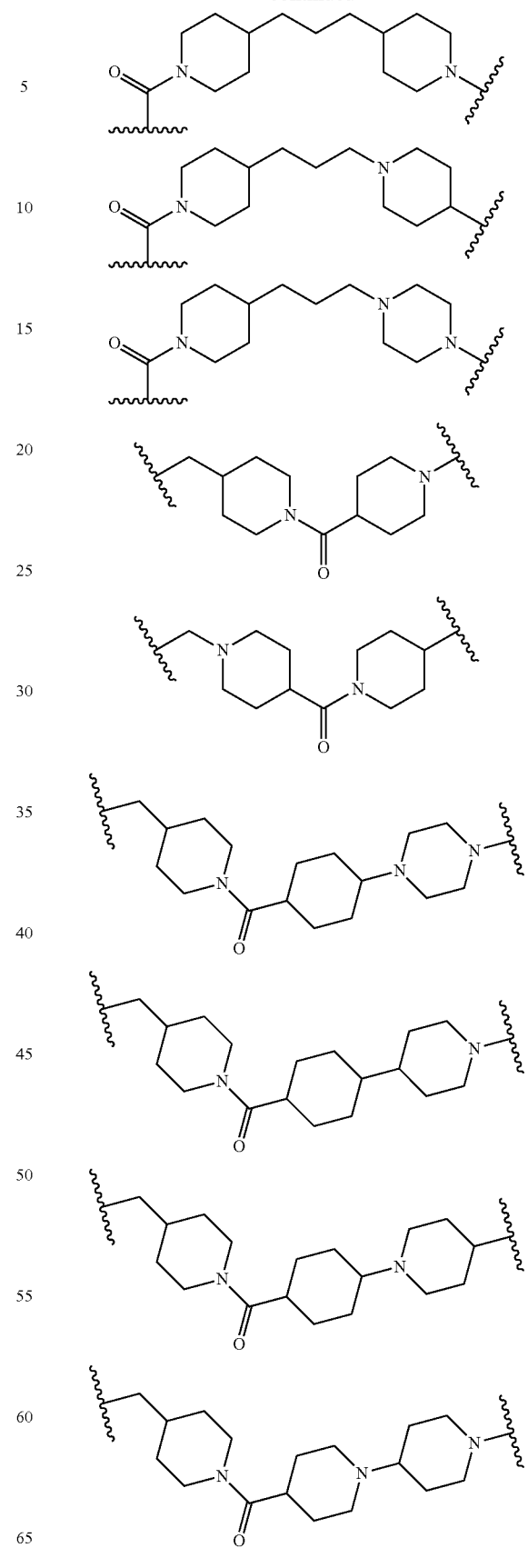

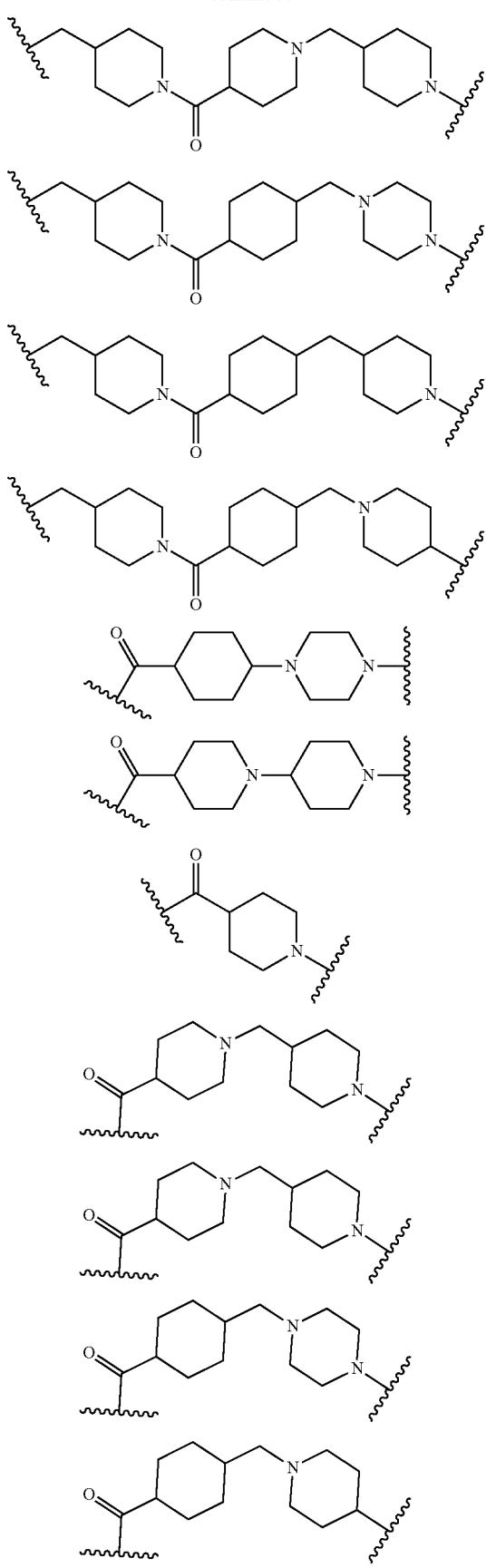
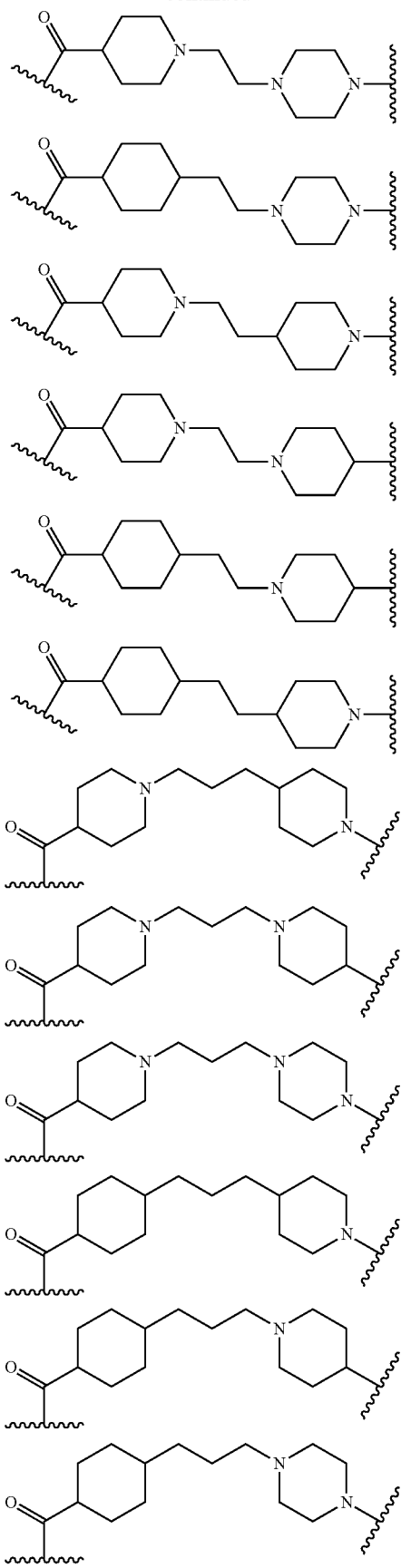

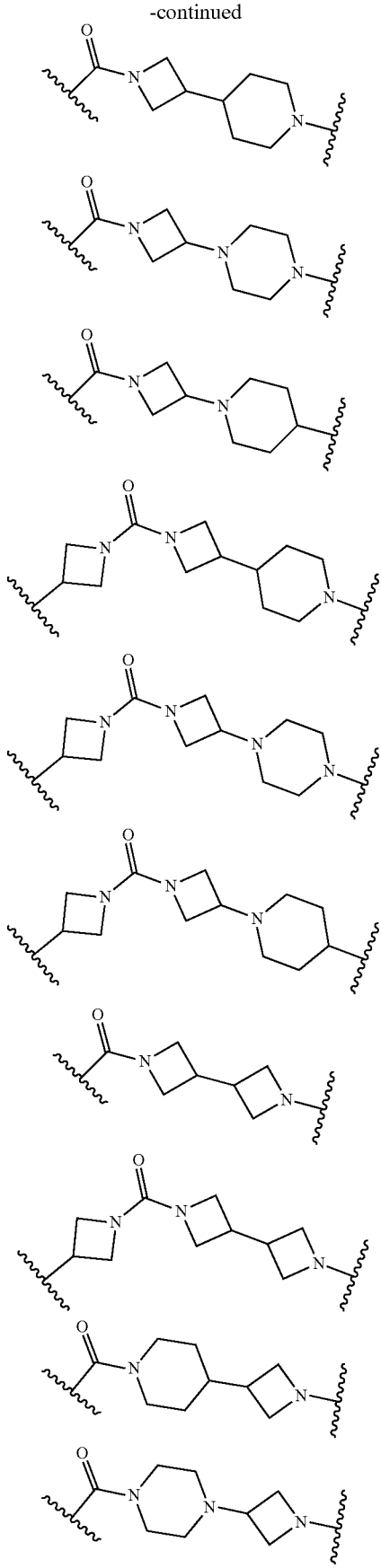
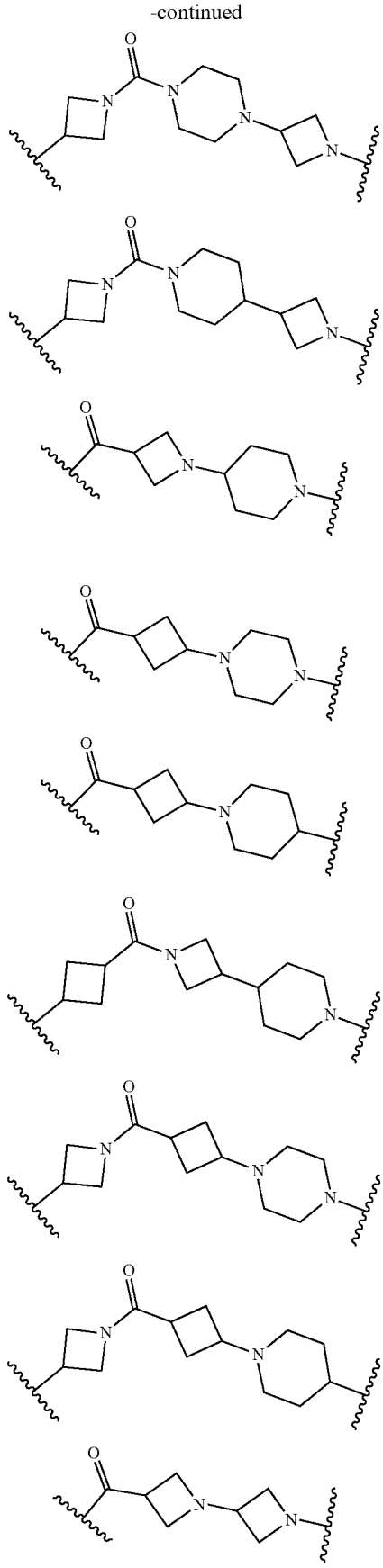

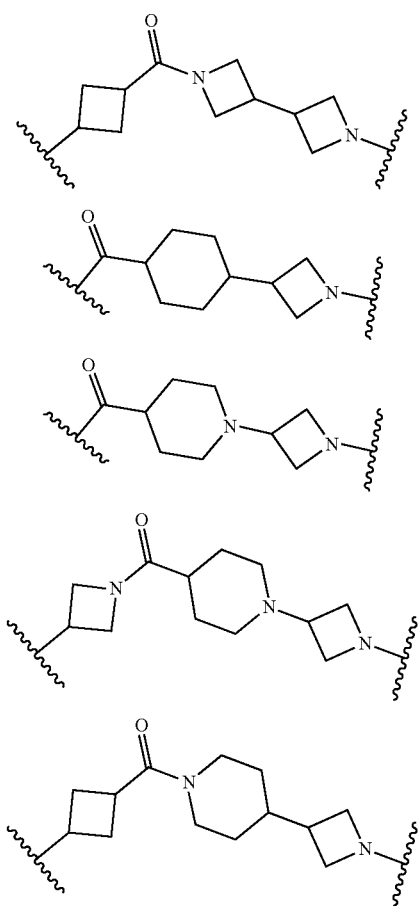
In some embodiments, the linker comprises at least one stereocenter. For example, in some embodiments, the linker is selected from the group consisting of
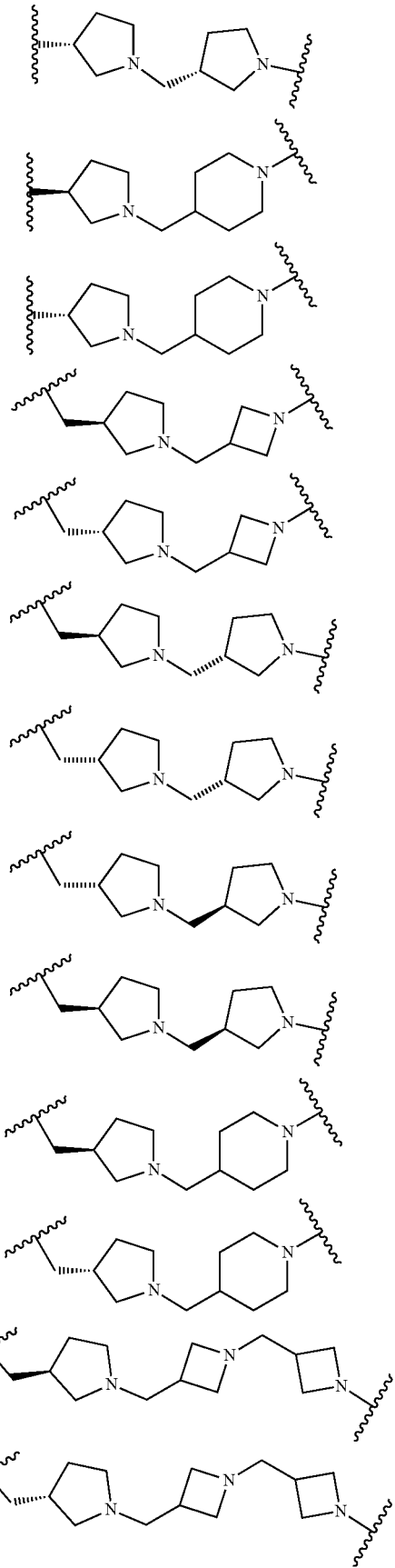

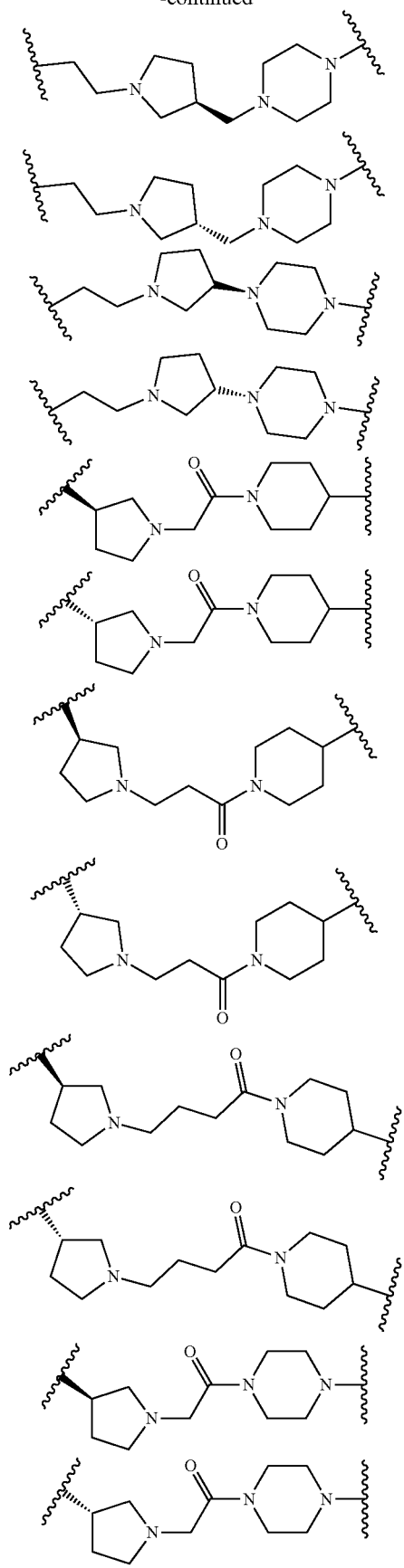
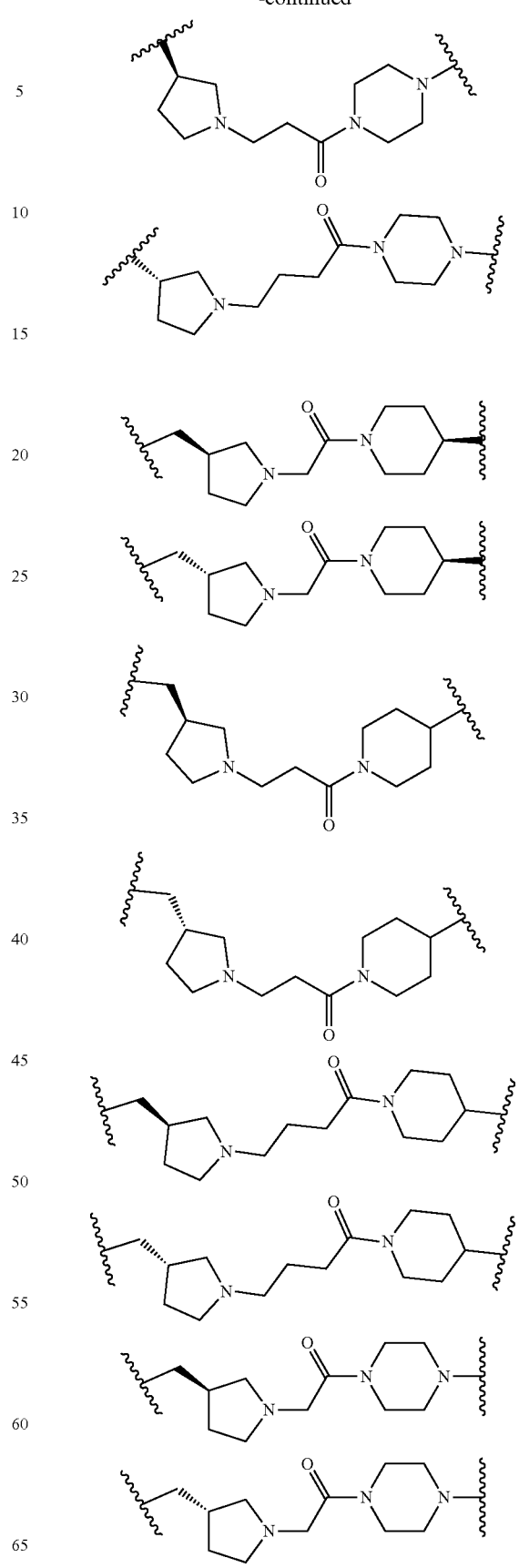

51
-continued

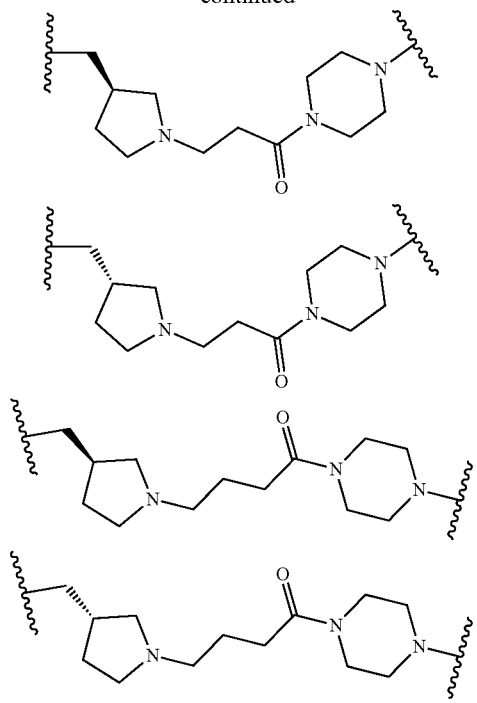

52
-continued

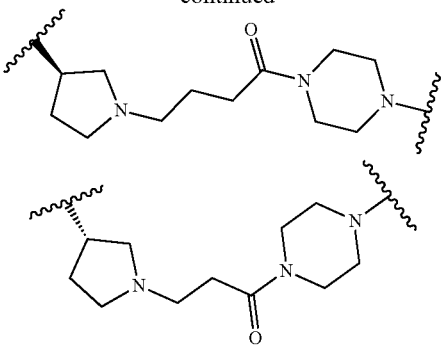

In some embodiments, the compound of Formula (I) may encompass both the E and Z isomers. In some embodiments, the compound of Formula (I) may be a mixture of trans- and -cis olefin.

In some embodiments, the compound of the present invention, or tautomer, stereoisomer, pharmaceutically acceptable salt, or hydrate thereof is selected from the group consisting of compounds presented in Table 1 and any combination thereof. For example, in some embodiments, the compound of the present invention or pharmaceutically acceptable salt thereof is selected from the group consisting of compounds presented in Table 1 and any combination thereof.

TABLE 1

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 1 | Exact Mass: 842.39 | 5-(4-(2-(2-(2-(4-amino-3-(4-phenoxyphenyl)-1H-pyrazolo[3,4-d]pyrimidin-1-yl)piperidin-1-yl)ethoxy)ethoxy)ethyl)piperazin-1-yl)-2-(2,6-dioxopiperidin-3-yl)isoindoline-1,3-dione | 842.39 | B | B | B | A |
| 2 | 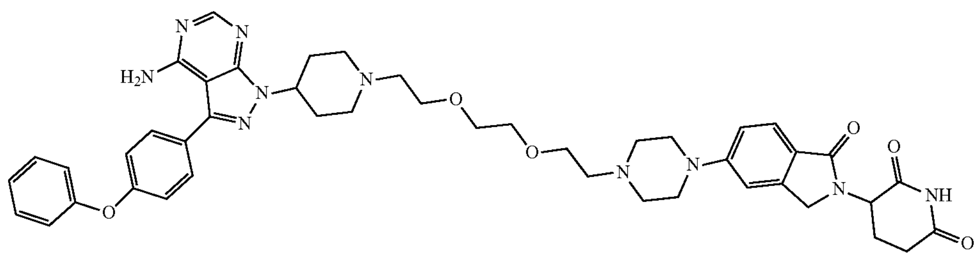 [SMILES: Nc1ncnc2c1c(-c1ccc(Oc3ccccc3)cc1)nn2C1CCN(CCOCCOCCN2CCN(c3ccc4c(c3)CN(C3CCC(=O)NC3=O)C4=O)CC2)CC1] | 3-(5-(4-(2-(2-(2-(4-amino-3-(4-phenoxyphenyl)-1H-pyrazolo[3,4-d]pyrimidin-1-yl)piperidin-1-yl)ethoxy)ethoxy)ethyl)piperazin-1-yl)-1-oxoisoindolin-2-yl)piperidine-2,6-dione | 828.41 | A | A | A | A |
| 3 | 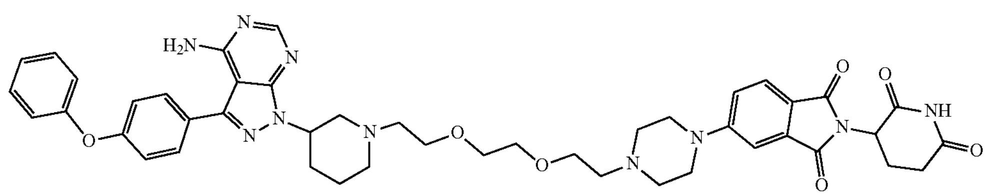 [SMILES: Nc1ncnc2c1c(-c1ccc(Oc3ccccc3)cc1)nn2C1CCCN(CCOCCOCCN2CCN(c3ccc4c(c3)C(=O)N(C3CCC(=O)NC3=O)C4=O)CC2)C1] | 5-(4-(2-(2-(2-(3-(4-amino-3-(4-phenoxyphenyl)-1H-pyrazolo[3,4-d]pyrimidin-1-yl)piperidin-1-yl)ethoxy)ethoxy)ethyl)piperazin-1-yl)-2-(2,6-dioxopiperidin-3-yl)isoindoline-1,3-dione | 842.39 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 4 | 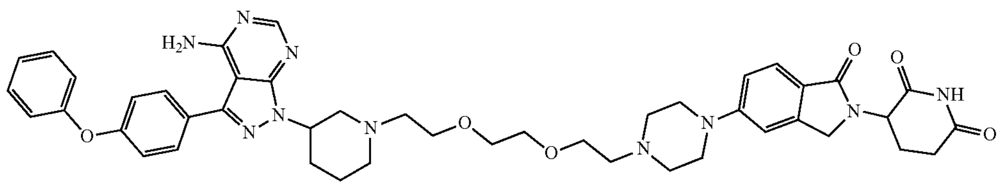 [SMILES: Nc1ncnc2c1c(-c1ccc(Oc3ccccc3)cc1)nn2C1CCCN(CCOCCOCCN2CCN(c3ccc4c(c3)CN(C3CCC(=O)NC3=O)C4=O)CC2)C1] | 3-(5-(4-(2-(2-(2-(3-(4-amino-3-(4-phenoxyphenyl)-1H-pyrazolo[3,4-d]pyrimidin-1-yl)piperidin-1-yl)ethoxy)ethoxy)ethyl)piperazin-1-yl)-1-oxoisoindolin-2-yl)piperidine-2,6-dione | 828.41 | B | B | A | A |
| 5 | 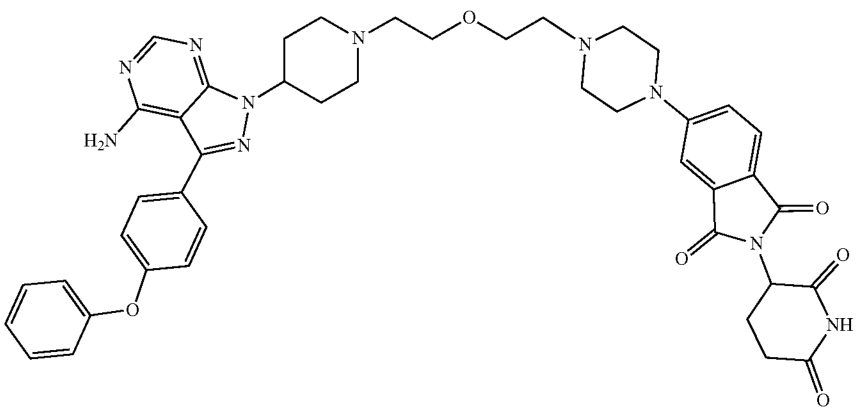 [SMILES: Nc1ncnc2c1c(-c1ccc(Oc3ccccc3)cc1)nn2C1CCN(CCOCCN2CCN(c3ccc4c(c3)C(=O)N(C3CCC(=O)NC3=O)C4=O)CC2)CC1] | 5-(4-(2-(2-(2-(4-(4-amino-3-(4-phenoxyphenyl)-1H-pyrazolo[3,4-d]pyrimidin-1-yl)piperidin-1-yl)ethoxy)ethyl)piperazin-1-yl)-2-(2,6-dioxopiperidin-3-yl)isoindoline-1,3-dione | 798.36 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 6 | Exact Mass: 784.38 | 3-(5-(4-(2-(2-(4-(4-amino-3-(4-phenoxyphenyl)-1H-pyrazolo[3,4-d]pyrimidin-1-yl)piperidin-1-yl)ethoxy)ethyl)piperazin-1-yl)-1-oxoisoindolin-2-yl)piperidine-2,6-dione | 784.38 | A | A | B | A |
| 7 | 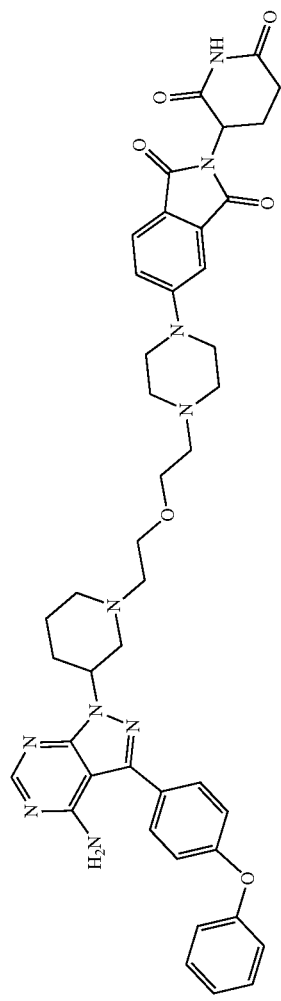 | 5-(4-(2-(2-(3-(4-amino-3-(4-phenoxyphenyl)-1H-pyrazolo[3,4-d]pyrimidin-1-yl)piperidin-1-yl)ethoxy)ethyl)piperazin-1-yl)-2-(2,6-dioxopiperidin-3-yl)isoindoline-1,3-dione | 798.36 | B | B | B | B |

TABLE 1-continued

Exemplary compounds of the present invention. Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 8 | 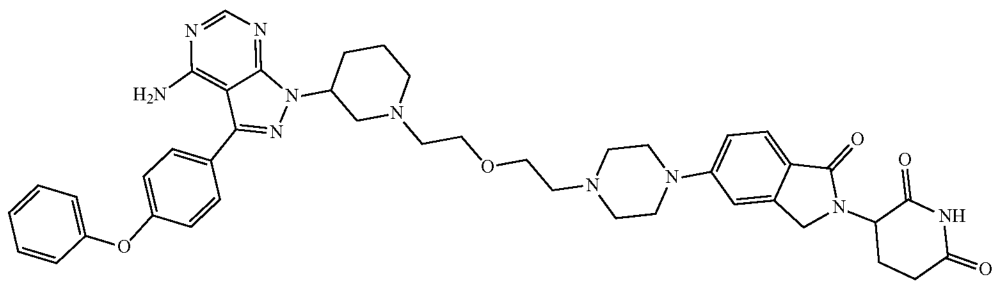 [SMILES: Nc1ncnc2c1c(-c1ccc(Oc3ccccc3)cc1)nn2C1CCCN(CCOCCN2CCN(c3ccc4c(c3)CN(C3CCC(=O)NC3=O)C4=O)CC2)C1] | 3-(5-(4-(2-(3-(4-amino-3-(4-phenoxyphenyl)-1H-pyrazolo[3,4-d]pyrimidin-1-yl)piperidin-1-yl)ethoxy)ethyl)piperazin-1-yl)-1-oxoisoindolin-2-yl)piperidine-2,6-dione | 784.38 | B | B | B | A |
| 9 | 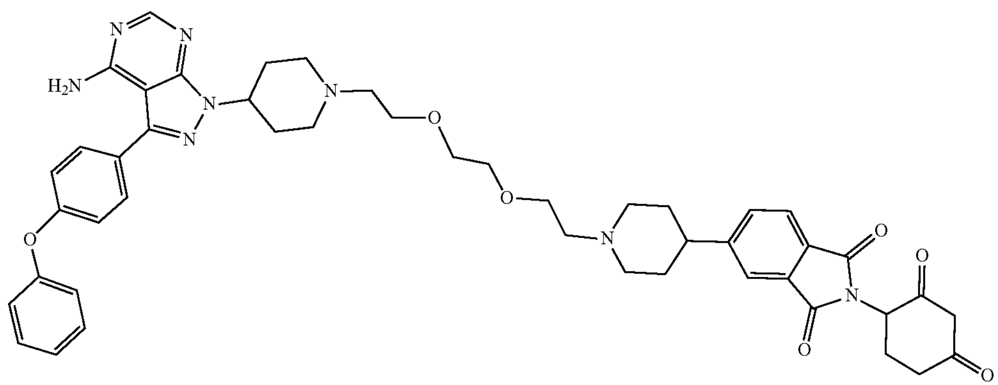 [SMILES: Nc1ncnc2c1c(-c1ccc(Oc3ccccc3)cc1)nn2C1CCN(CCOCCOCCN2CCC(c3ccc4c(c3)C(=O)N(C3CCC(=O)CC3=O)C4=O)CC2)CC1] | 5-(1-(2-(2-(4-(4-amino-3-(4-phenoxyphenyl)-1H-pyrazolo[3,4-d]pyrimidin-1-yl)piperidin-1-yl)ethoxy)ethyl)piperidin-4-yl)-2-(2,6-dioxopiperidin-3-yl)isoindoline-1,3-dione | 841.39 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 10 | 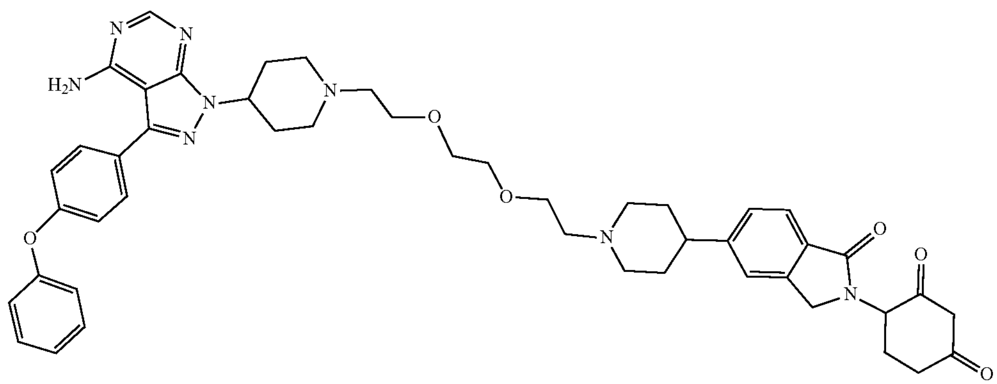 [SMILES: Nc1ncnc2c1c(-c1ccc(Oc3ccccc3)cc1)nn2C1CCN(CCOCCOCCN2CCC(c3ccc4c(c3)CN(C3CCC(=O)CC3=O)C4=O)CC2)CC1] | 3-(5-(1-(2-(2-(2-(4-(4-amino-3-(4-phenoxyphenyl)-1H-pyrazolo[3,4-d]pyrimidin-1-yl)piperidin-1-yl)ethoxy)ethoxy)ethyl)piperidin-4-yl)-1-oxoisoindolin-2-yl)piperidine-2,6-dione | 827.4 | B | A | A | A |
| 11 | 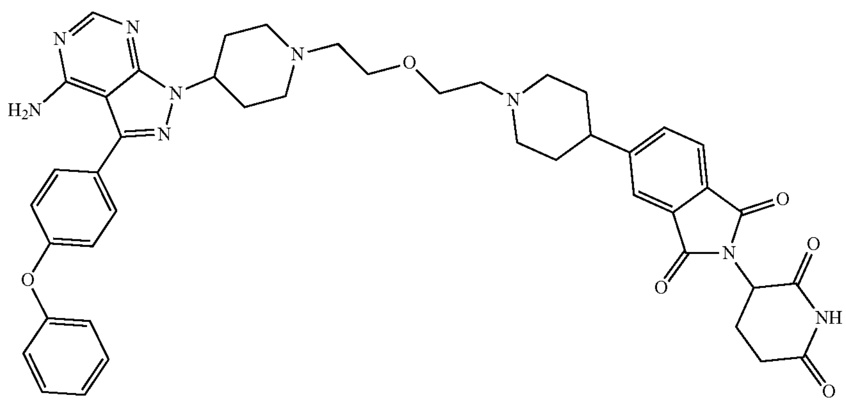 [SMILES: Nc1ncnc2c1c(-c1ccc(Oc3ccccc3)cc1)nn2C1CCN(CCOCCN2CCC(c3ccc4c(c3)C(=O)N(C3CCC(=O)NC3=O)C4=O)CC2)CC1] | 5-(1-(2-(2-(4-(4-amino-3-(4-phenoxyphenyl)-1H-pyrazolo[3,4-d]pyrimidin-1-yl)piperidin-1-yl)ethoxy)ethyl)piperidin-4-yl)-2-(2,6-dioxopiperidin-3-yl)isoindoline-1,3-dione | 797.36 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 12 | 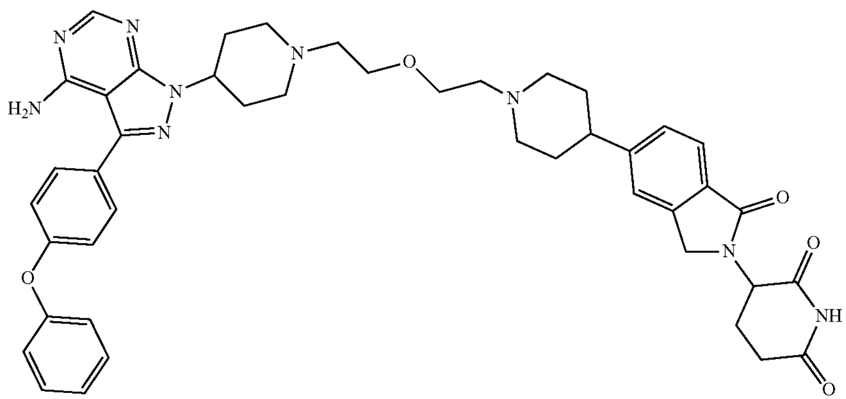 [SMILES: Nc1ncnc2c1c(-c1ccc(Oc3ccccc3)cc1)nn2C1CCN(CCOCCN2CCC(c3ccc4c(c3)CN(C3CCC(=O)NC3=O)C4=O)CC2)CC1] | 3-(5-(1-(2-(2-(4-(4-amino-3-(4-phenoxyphenyl)-1H-pyrazolo[3,4-d]pyrimidin-1-yl)piperidin-1-yl)ethoxy)ethyl)piperidin-4-yl)-1-oxoisoindolin-2-yl)piperidine-2,6-dione | 783.39 | A | A | B | A |
| 13 | 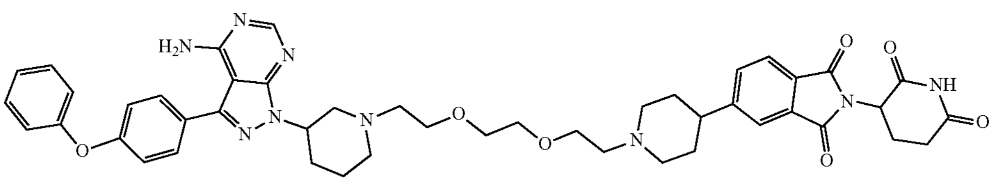 [SMILES: Nc1ncnc2c1c(-c1ccc(Oc3ccccc3)cc1)nn2C1CCCN(CCOCCOCCN2CCC(c3ccc4c(c3)C(=O)N(C3CCC(=O)NC3=O)C4=O)CC2)C1] | 5-(1-(2-(2-(3-(4-amino-3-(4-phenoxyphenyl)-1H-pyrazolo[3,4-d]pyrimidin-1-yl)piperidin-1-yl)ethoxy)ethyl)piperidin-4-yl)-2-(2,6-dioxopiperidin-3-yl)isoindoline-1,3-dione | 841.39 | B | B | B | B |
| 14 | 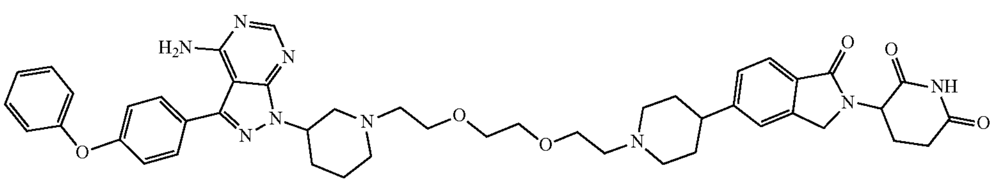 [SMILES: Nc1ncnc2c1c(-c1ccc(Oc3ccccc3)cc1)nn2C1CCCN(CCOCCOCCN2CCC(c3ccc4c(c3)CN(C3CCC(=O)NC3=O)C4=O)CC2)C1] | 3-(5-(1-(2-(2-(3-(4-amino-3-(4-phenoxyphenyl)-1H-pyrazolo[3,4-d]pyrimidin-1-yl)piperidin-1-yl)ethoxy)ethyl)piperidin-4-yl)-1-oxoisoindolin-2-yl)piperidine-2,6-dione | 827.41 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 15 | 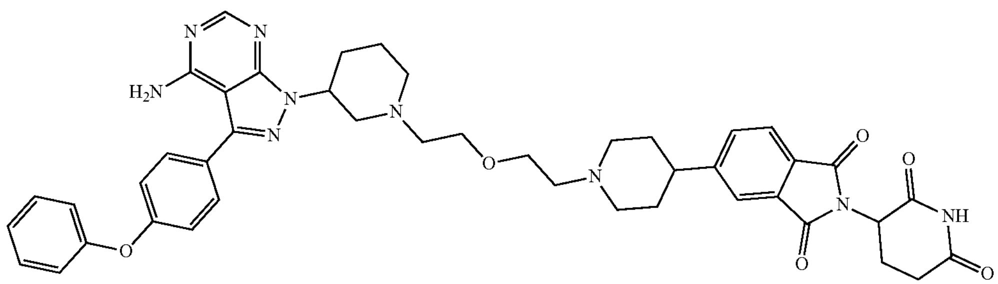 [SMILES: Nc1ncnc2c1c(-c1ccc(Oc3ccccc3)cc1)nn2C1CCCN(CCOCCN2CCC(c3ccc4c(c3)C(=O)N(C3CCC(=O)NC3=O)C4=O)CC2)C1] | 5-(1-(2-(2-(3-(4-amino-3-(4-phenoxyphenyl)-1H-pyrazolo[3,4-d]pyrimidin-1-yl)piperidin-1-yl)ethoxy)ethyl)piperidin-4-yl)-2-(2,6-dioxopiperidin-3-yl)isoindoline-1,3-dione | 796.36 | B | B | B | B |
| 16 | 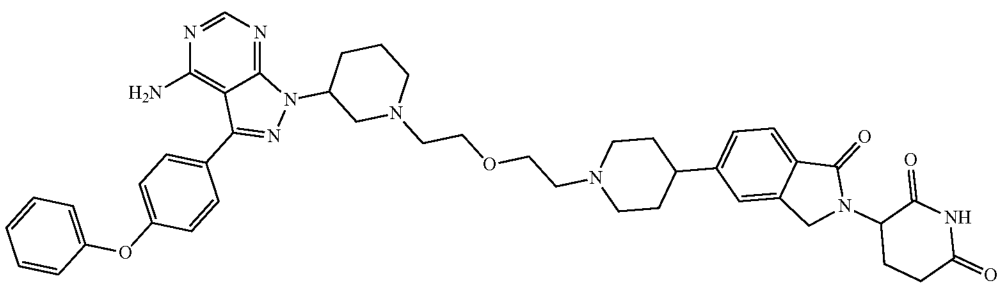 [SMILES: Nc1ncnc2c1c(-c1ccc(Oc3ccccc3)cc1)nn2C1CCCN(CCOCCN2CCC(c3ccc4c(c3)CN(C3CCC(=O)NC3=O)C4=O)CC2)C1] | 3-(5-(1-(2-(2-(3-(4-amino-3-(4-phenoxyphenyl)-1H-pyrazolo[3,4-d]pyrimidin-1-yl)piperidin-1-yl)ethoxy)ethyl)piperidin-4-yl)-1-oxoisoindolin-2-yl)piperidine-2,6-dione | 783.39 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 17 | 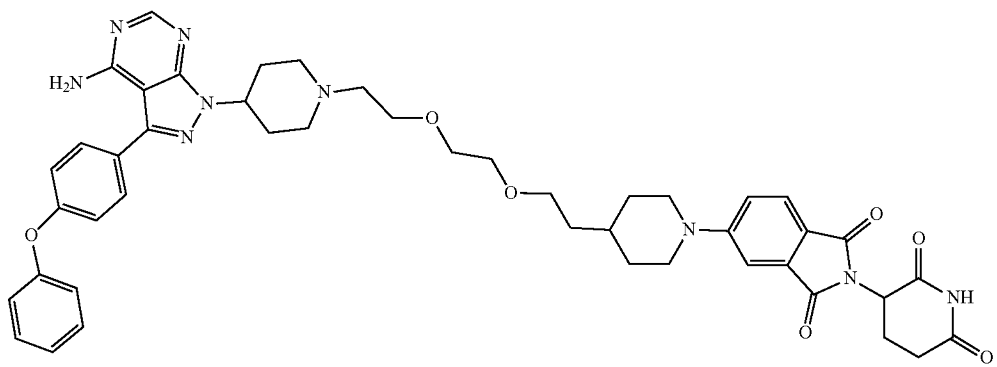 [SMILES: Nc1ncnc2c1c(-c1ccc(Oc3ccccc3)cc1)nn2C1CCN(CCOCCOCCC2CCN(c3ccc4c(c3)C(=O)N(C3CCC(=O)NC3=O)C4=O)CC2)CC1] | 5-(4-(2-(2-(2-(4-(4-amino-3-(4-phenoxyphenyl)-1H-pyrazolo[3,4-d]pyrimidin-1-yl)piperidin-1-yl)ethoxy)ethoxy)ethyl)piperidin-1-yl)-2-(2,6-dioxopiperidin-3-yl)isoindoline-1,3-dione | 841.3 | B | B | A | A |
| 18 | 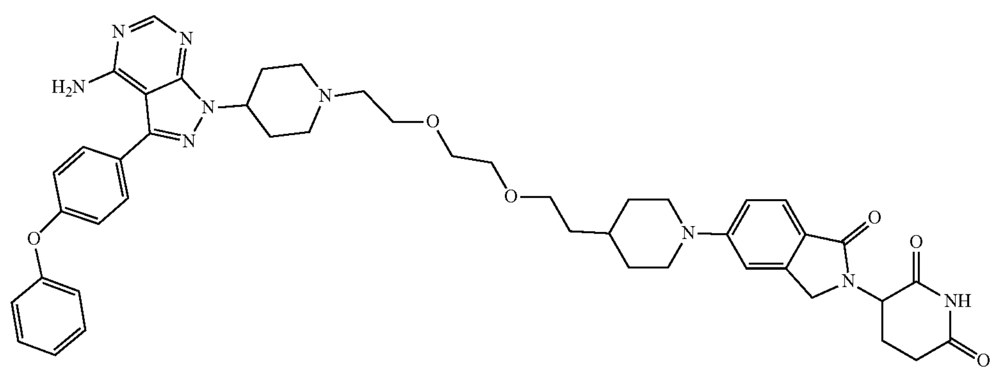 [SMILES: Nc1ncnc2c1c(-c1ccc(Oc3ccccc3)cc1)nn2C1CCN(CCOCCOCCC2CCN(c3ccc4c(c3)CN(C3CCC(=O)NC3=O)C4=O)CC2)CC1] | 3-(5-(4-(2-(2-(2-(4-(4-amino-3-(4-phenoxyphenyl)-1H-pyrazolo[3,4-d]pyrimidin-1-yl)piperidin-1-yl)ethoxy)ethyl)piperidin-1-yl)-1-oxoisoindolin-2-yl)piperidine-2,6-dione | 827.4 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 19 | 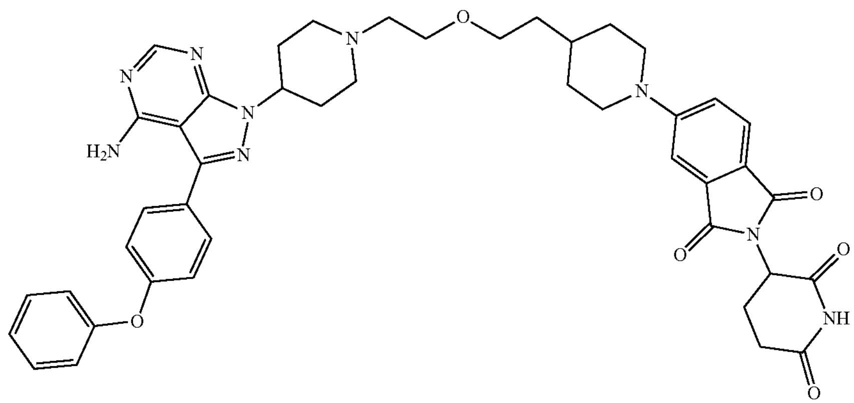 [SMILES: Nc1ncnc2c1c(-c1ccc(Oc3ccccc3)cc1)nn2C1CCN(CCOCCC2CCN(c3ccc4c(c3)C(=O)N(C3CCC(=O)NC3=O)C4=O)CC2)CC1] | 5-(4-(2-(2-(4-(4-amino-3-(4-phenoxyphenyl)-1H-pyrazolo[3,4-d]pyrimidin-1-yl)piperidin-1-yl)ethoxy)ethyl)piperidin-1-yl)-2-(2,6-dioxopiperidin-3-yl)isoindoline-1,3-dione | 797.36 | B | B | B | A |
| 20 | 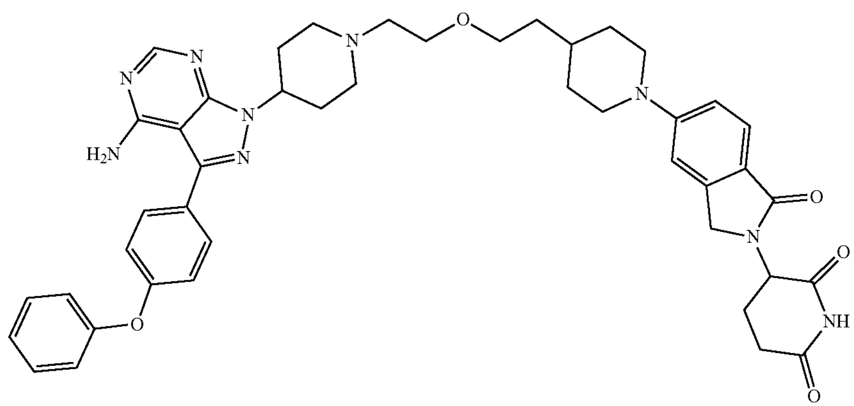 [SMILES: Nc1ncnc2c1c(-c1ccc(Oc3ccccc3)cc1)nn2C1CCN(CCOCCC2CCN(c3ccc4c(c3)CN(C3CCC(=O)NC3=O)C4=O)CC2)CC1] | 3-(5-(4-(2-(2-(4-(4-amino-3-(4-phenoxyphenyl)-1H-pyrazolo[3,4-d]pyrimidin-1-yl)piperidin-1-yl)ethoxy)ethyl)piperidin-1-yl)-1-oxoisoindolin-2-yl)piperidine-2,6-dione | 783.39 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 21 | 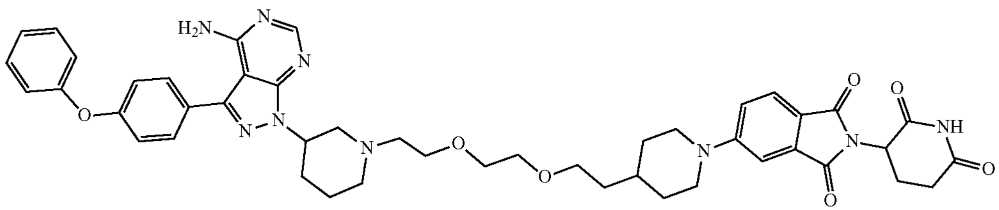 [SMILES: Nc1ncnc2c1c(-c1ccc(Oc3ccccc3)cc1)nn2C1CCCN(CCOCCOCCC2CCN(c3ccc4c(c3)C(=O)N(C3CCC(=O)NC3=O)C4=O)CC2)C1] | 5-(4-(2-(2-(2-(3-(4-amino-3-(4-phenoxyphenyl)-1H-pyrazolo[3,4-d]pyrimidin-1-yl)piperidin-1-yl)ethoxy)ethoxy)ethyl)piperidin-1-yl)-2-(2,6-dioxopiperidin-3-yl)isoindoline-1,3-dione | 841.39 | B | B | A | A |
| 22 | 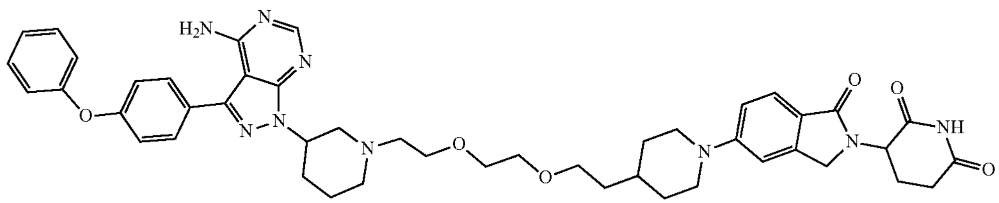 [SMILES: Nc1ncnc2c1c(-c1ccc(Oc3ccccc3)cc1)nn2C1CCCN(CCOCCOCCC2CCN(c3ccc4c(c3)CN(C3CCC(=O)NC3=O)C4=O)CC2)C1] | 3-(5-(4-(2-(2-(2-(3-(4-amino-3-(4-phenoxyphenyl)-1H-pyrazolo[3,4-d]pyrimidin-1-yl)piperidin-1-yl)ethoxy)ethoxy)ethyl)piperidin-1-yl)-1-oxoisoindolin-2-yl)piperidine-2,6-dione | 827.41 | B | A | A | A |
| 23 | 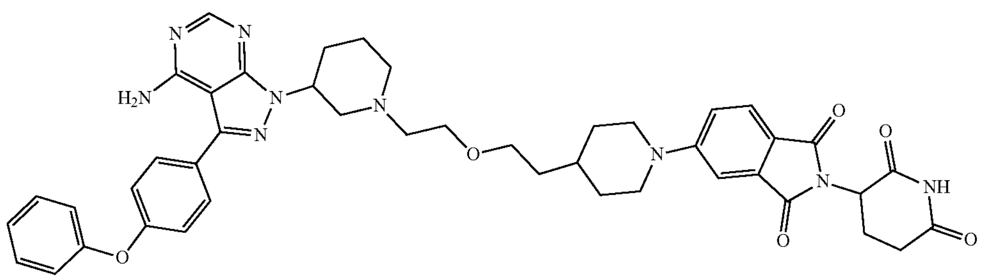 [SMILES: Nc1ncnc2c1c(-c1ccc(Oc3ccccc3)cc1)nn2C1CCCN(CCOCCC2CCN(c3ccc4c(c3)C(=O)N(C3CCC(=O)NC3=O)C4=O)CC2)C1] | 5-(4-(2-(2-(3-(4-amino-3-(4-phenoxyphenyl)-1H-pyrazolo[3,4-d]pyrimidin-1-yl)piperidin-1-yl)ethoxy)ethyl)piperidin-1-yl)-2-(2,6-dioxopiperidin-3-yl)isoindoline-1,3-dione | 797.36 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 24 | 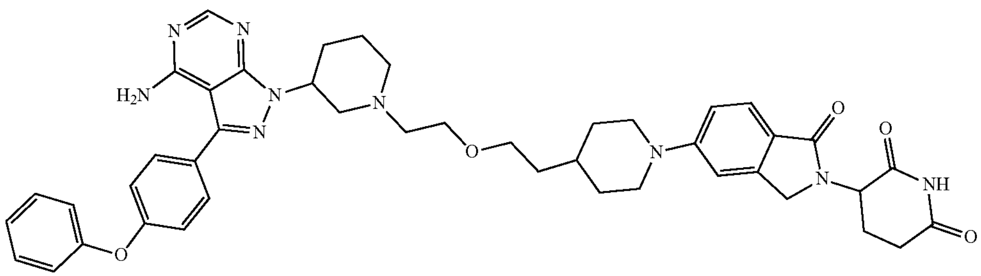 [SMILES: Nc1ncnc2c1c(-c1ccc(Oc3ccccc3)cc1)nn2C1CCCN(CCOCCC2CCN(c3ccc4c(c3)CN(C3CCC(=O)NC3=O)C4=O)CC2)C1] | 3-(5-(4-(2-(3-(4-amino-3-(4-phenoxyphenyl)-1H-pyrazolo[3,4-d]pyrimidin-1-yl)piperidin-1-yl)ethoxy)ethyl)piperidin-1-yl)-1-oxoisoindolin-2-yl)piperidine-2,6-dione | 782.39 | B | B | B | A |
| 25 | 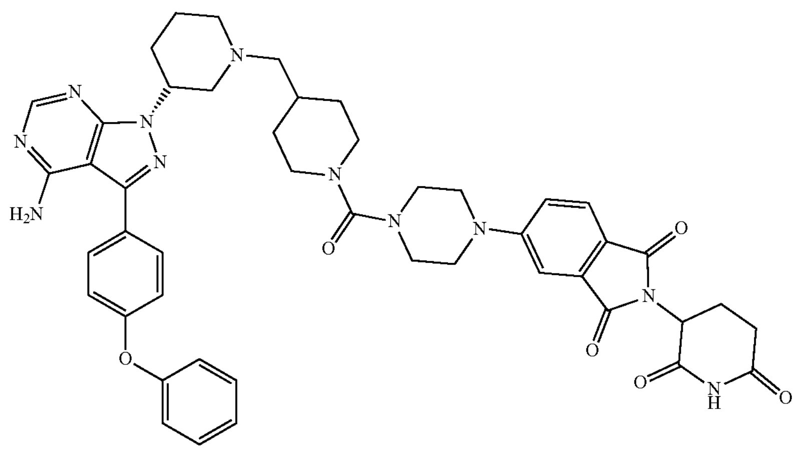 | 5-(4-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperazin-1-yl)-2-(2,6-dioxopiperidin-3-yl)isoindoline-1,3-dione | 851.39 | B | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 26 | 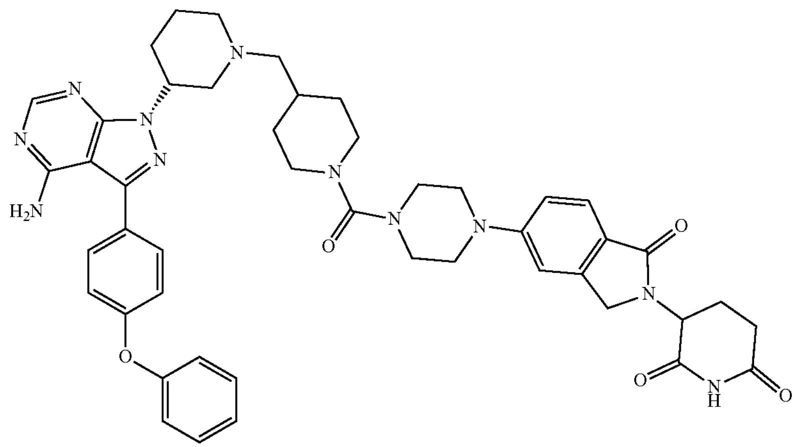 | 3-(5-(4-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperazin-1-yl)-1-oxoisoindolin-2-yl)piperidine-2,6-dione Exact Mass: 837.41 | 837.41 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 27 | 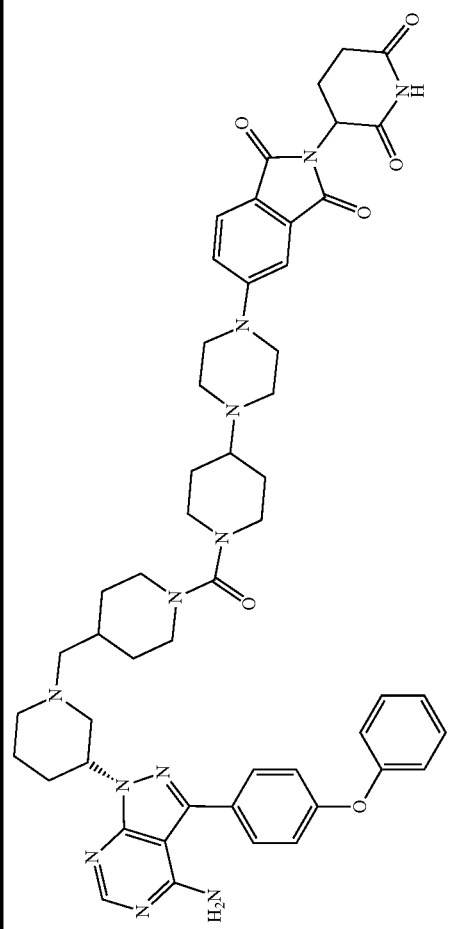 | 5-(4-(1-(4-((R)-3-(4-amino-3-(4-phenoxyphenyl)-1H-pyrazolo[3,4-d]pyrimidin-1-yl)piperidin-1-yl)methyl)piperidine-1-carbonyl)piperidin-4-yl)piperazin-1-yl)-2-(2,6-dioxopiperidin-3-yl)isoindoline-1,3-dione | 934.46 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 28 | 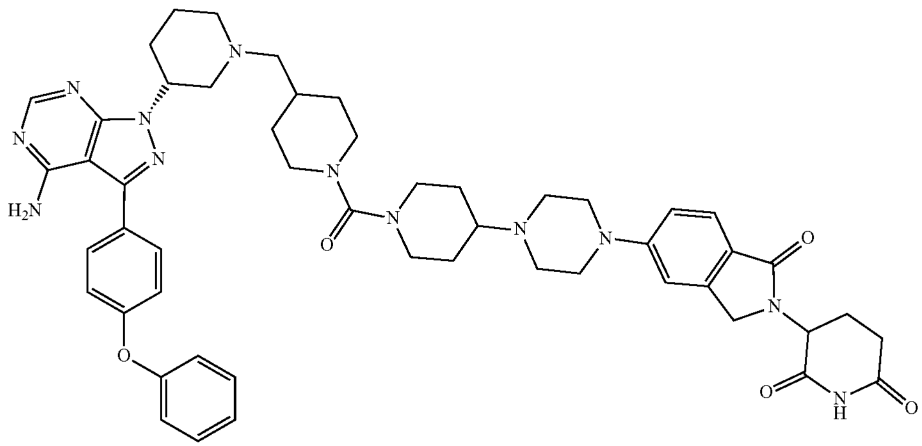 | 3-(5-(4-(1-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperidin-4-yl)piperazin-1-yl)-1-oxoisoindolin-2-yl)piperidine-2,6-dione | 920.48 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 29 | 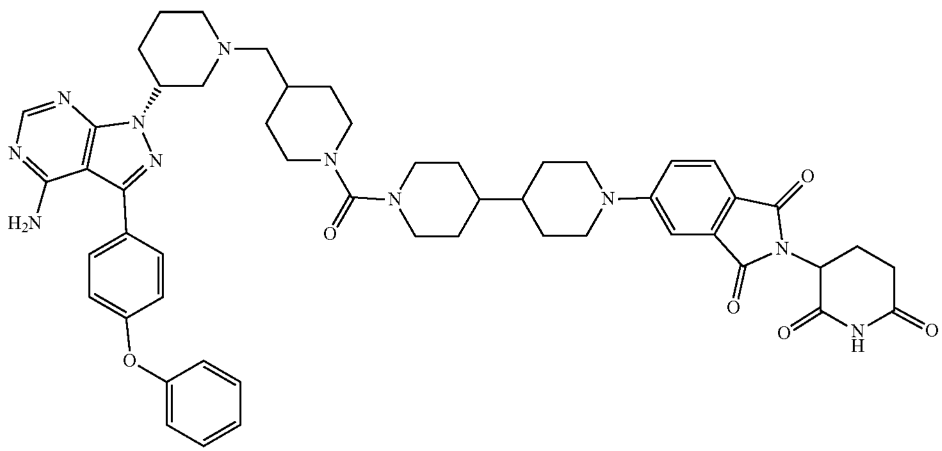 | 5-(1'-(4-(((R)-3-(4-amino-3-(4-phenoxyphenyl)-1H-pyrazolo[3,4-d]pyrimidin-1-yl)piperidin-1-yl)methyl)piperidine-1-carbonyl)-[4,4'-bipiperidin]-1-yl)-2-(2,6-dioxopiperidin-3-yl)isoindoline-1,3-dione | 933.46 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 30 | 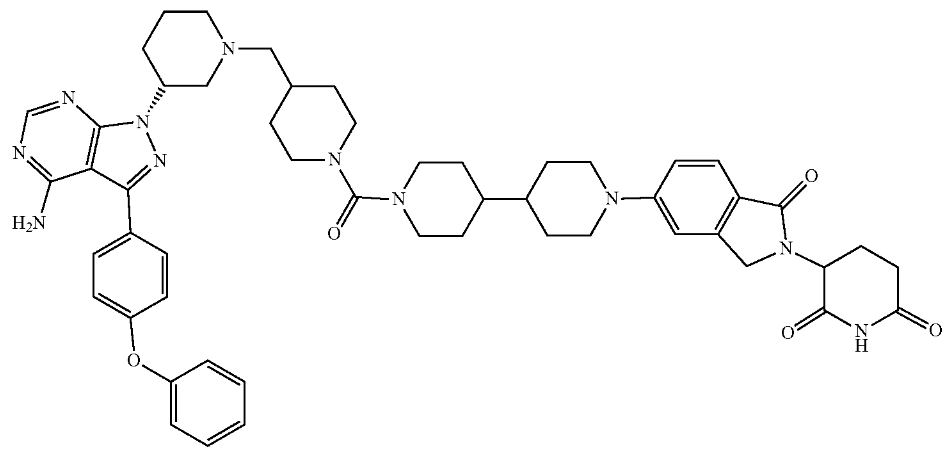 | 3-(5-(1'-(4-(((R)-3-(4-amino-3-(4-phenoxyphenyl)-1H-pyrazolo[3,4-d]pyrimidin-1-yl)piperidin-1-yl)methyl)piperidine-1-carbonyl)-[4,4'-bipiperidin]-1-yl)-1-oxoisoindolin-2-yl)piperidine-2,6-dione | 919.49 | B | B | B | A |
| 31 | 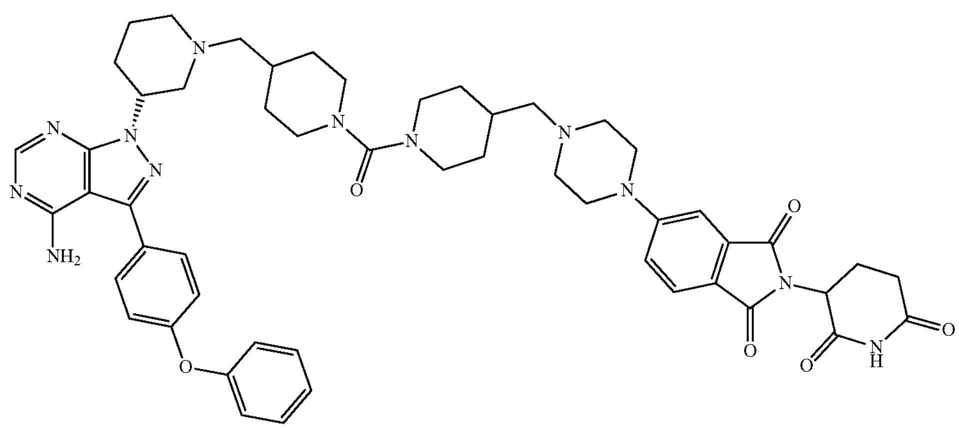 | 5-(4-((1-(4-(((R)-3-(4-amino-3-(4-phenoxyphenyl)-1H-pyrazolo[3,4-d]pyrimidin-1-yl)piperidin-4-yl)methyl)piperidine-4-carbonyl)piperazin-1-yl)-2-(2,6-dioxopiperidin-3-yl)isoindoline-1,3-dione | 948.48 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 32 | 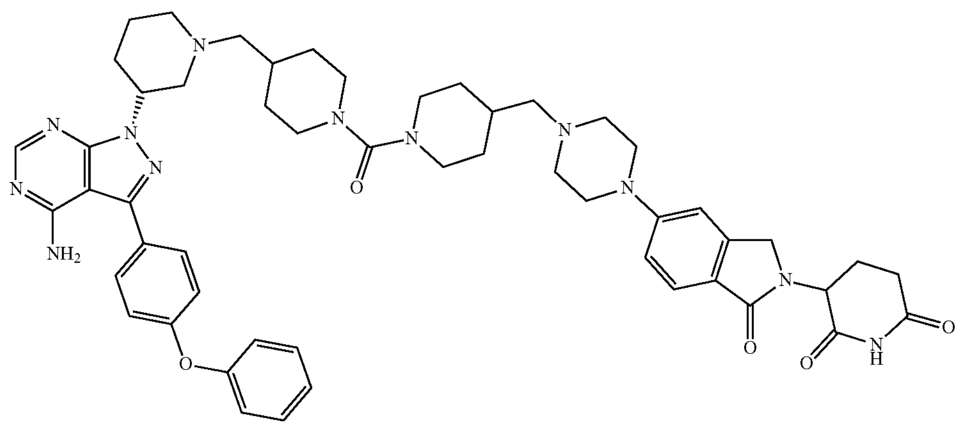 | 3-(5-(4-((1-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperidin-4-yl)methyl)piperazin-1-yl)-1-oxoisoindolin-2-yl)piperidine-2,6-dione | 934.50 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 33 | 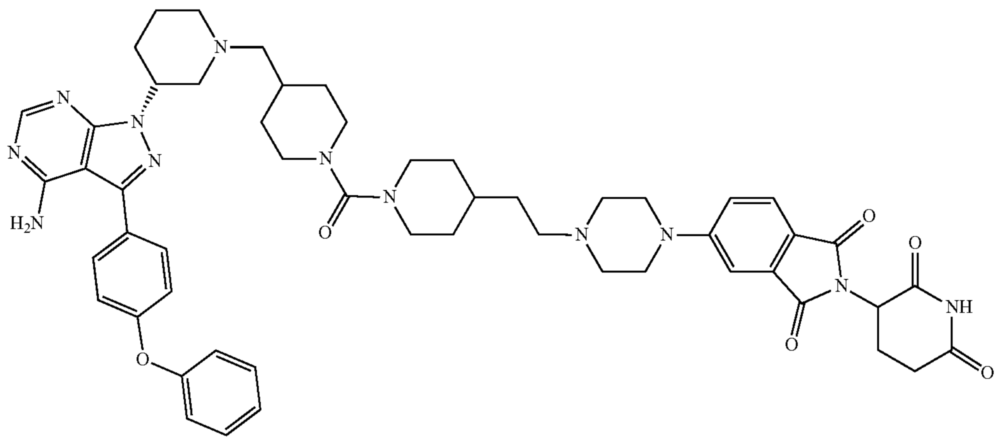 | 5-(4-(2-(1-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione | 962.49 | B | B | C | A |
| 34 | 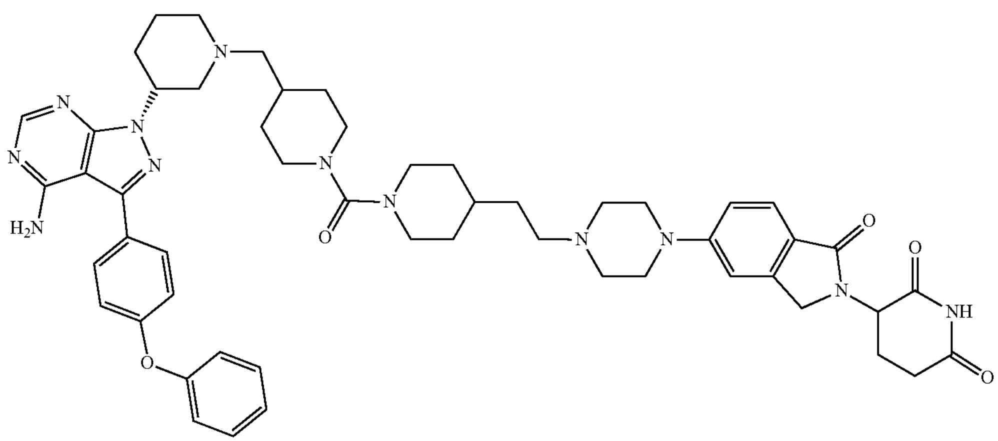 | 3-(5-(4-(2-(1-(4-(((R)-3-(4-amino-3-(4-phenoxyphenyl)-1H-pyrazolo[3,4-d]pyrimidin-1-yl)piperidin-1-yl)methyl)piperidine-1-carbonyl)piperidin-4-yl)ethyl)piperazin-1-yl)-1-oxoisoindolin-2-yl)piperidine-2,6-dione | 948.51 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 35 | 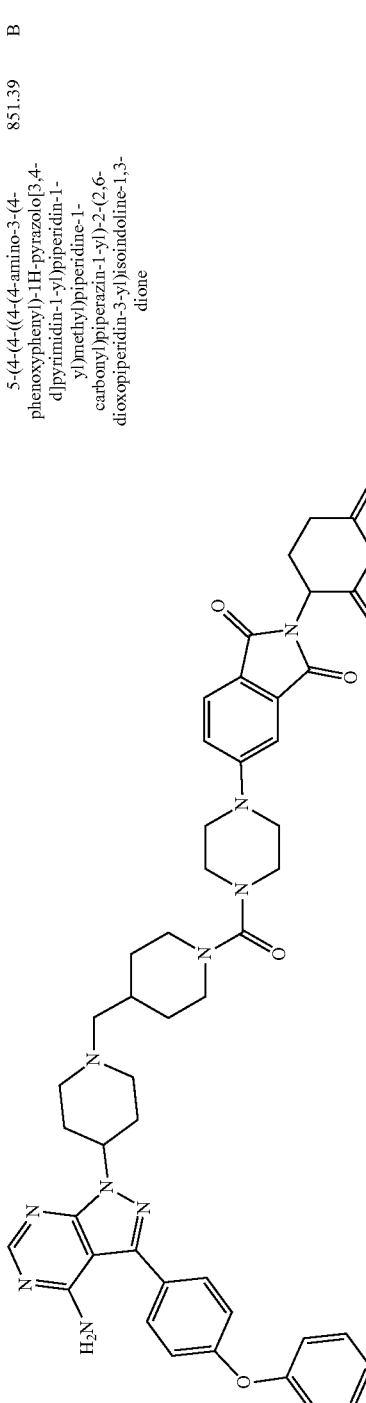 | 5-(4-(4-((4-(4-amino-3-(4-phenoxyphenyl)-1H-pyrazolo[3,4-d]pyrimidin-1-yl)piperidin-1-yl)methyl)piperidine-1-carbonyl)piperazin-1-yl)-2-(2,6-dioxopiperidin-3-yl)isoindoline-1,3-dione | 851.39 | B | A | A | A |
| 36 | 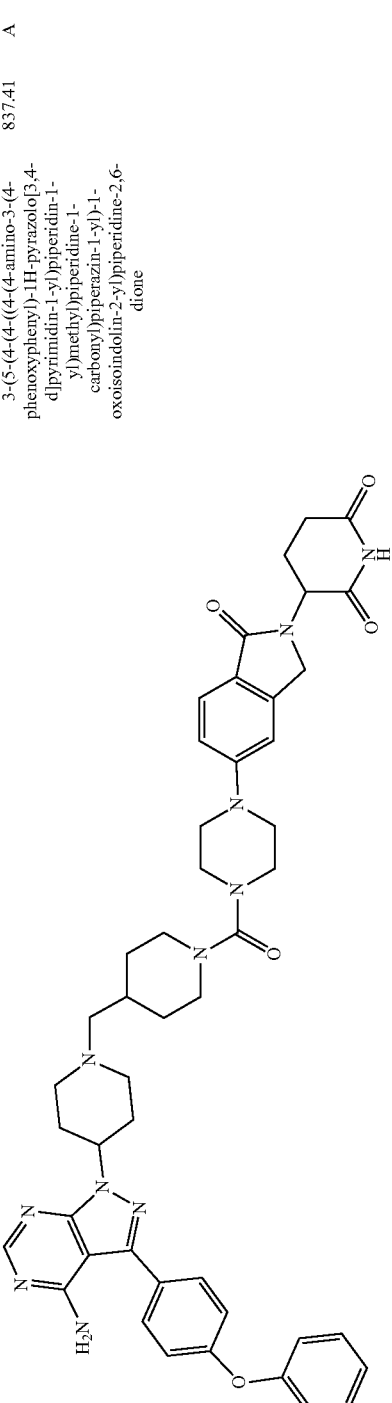 | 3-(5-(4-(4-((4-(4-amino-3-(4-phenoxyphenyl)-1H-pyrazolo[3,4-d]pyrimidin-1-yl)piperidin-1-yl)methyl)piperidine-1-carbonyl)piperazin-1-yl)-1-oxoisoindolin-2-yl)piperidine-2,6-dione | 837.41 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 37 | 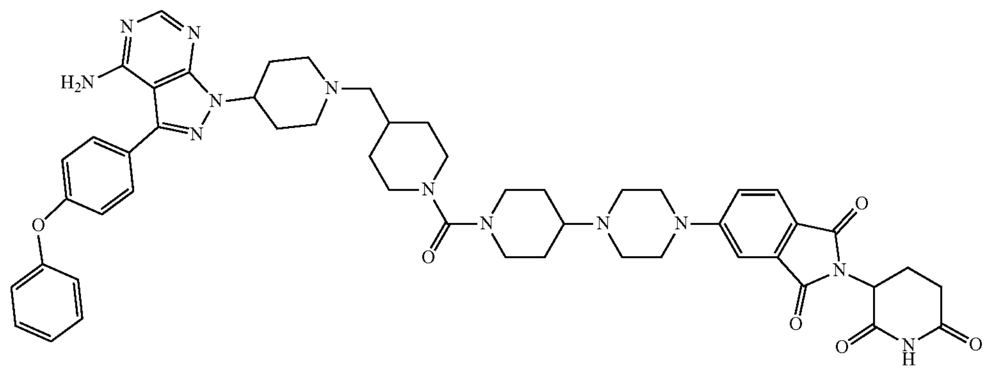 | 5-(4-(1-(4-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)piperidin-1-yl)-2-(2,6-dioxopiperidin-3-yl)isoindoline-1,3-dione | 934.46 | B | A | B | A |
| 38 | 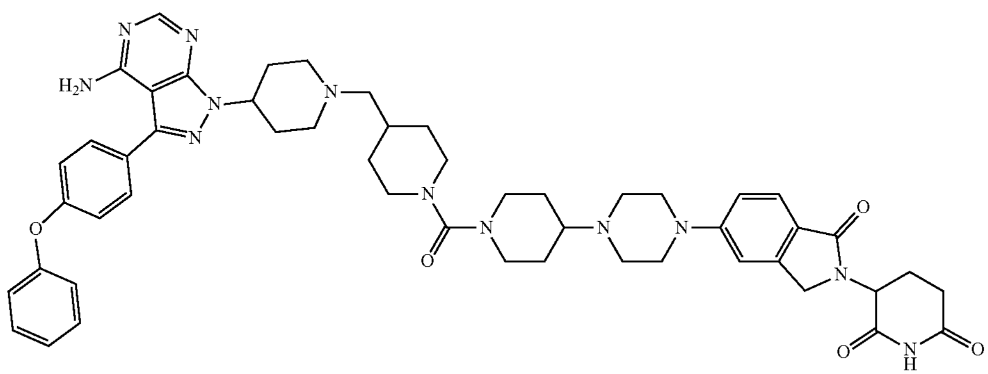 [SMILES: Nc1ncnc2c1c(-c1ccc(Oc3ccccc3)cc1)nn2C1CCN(CC2CCN(C(=O)N3CCC(N4CCN(c5ccc6c(c5)CN(C5CCC(=O)NC5=O)C6=O)CC4)CC3)CC2)CC1] | 3-(5-(4-(1-(4-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)piperazin-1-yl)-1-oxoisoindolin-2-yl)piperidine-2,6-dione | 920.48 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 39 | 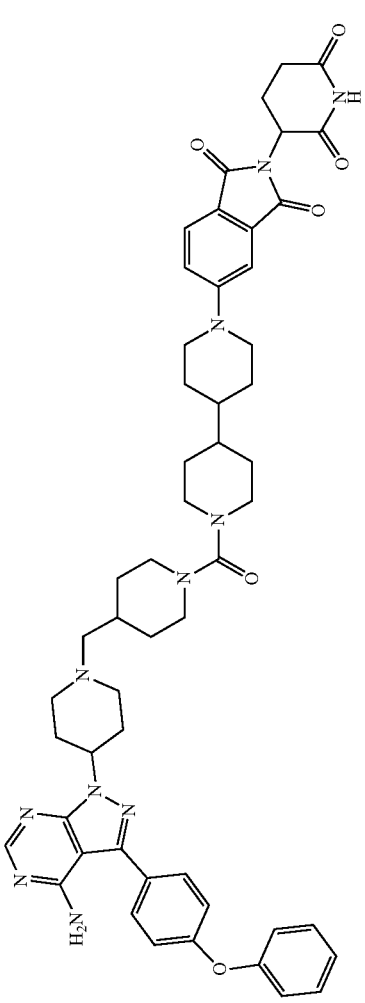 | 5-(1'-(4-((4-(4-amino-3-(4-phenoxyphenyl)-1H-pyrazolo[3,4-d]pyrimidin-1-yl)piperidin-1-yl)methyl)piperidine-1-carbonyl)-[4,4'-bipiperidin]-1-yl)-2-(2,6-dioxopiperidin-3-yl)isoindoline-1,3-dione | 933.46 | C | B | C | A |
| 40 | 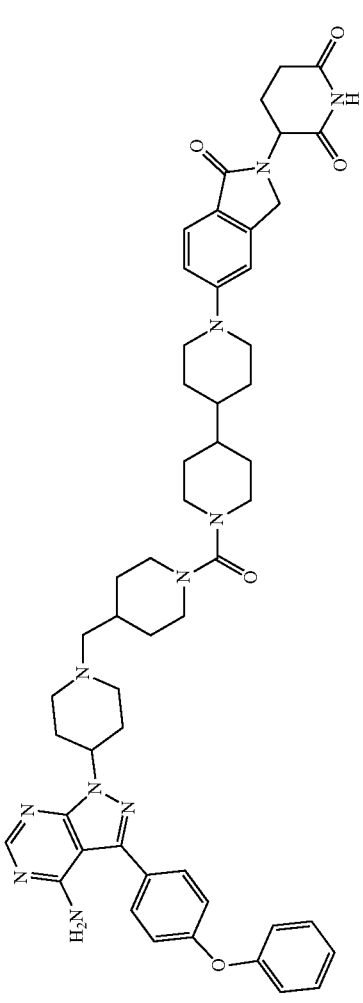 | 3-(5-(1'-(4-((4-(4-amino-3-(4-phenoxyphenyl)-1H-pyrazolo[3,4-d]pyrimidin-1-yl)piperidin-1-yl)methyl)piperidine-1-carbonyl)-[4,4'-bipiperidin]-1-yl)-1-oxoisoindolin-2-yl)piperidine-2,6-dione | 919.49 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 41 | 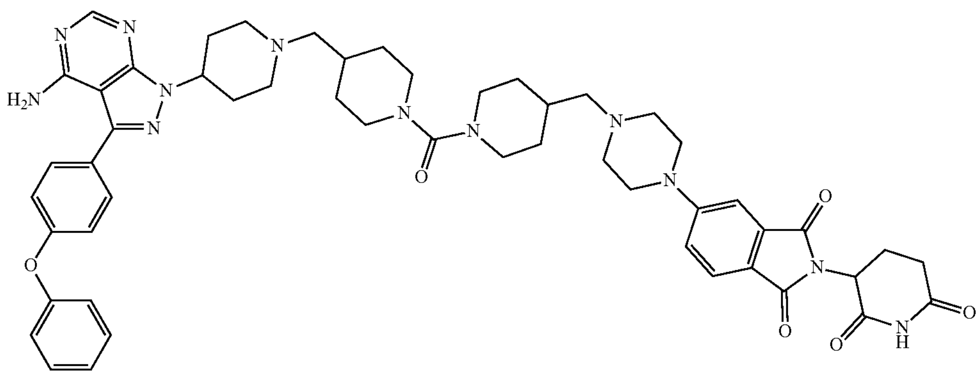 [SMILES: Nc1ncnc2c1c(-c1ccc(Oc3ccccc3)cc1)nn2C1CCN(CC2CCN(C(=O)N3CCC(CN4CCN(c5ccc6c(c5)C(=O)N(C5CCC(=O)NC5=O)C6=O)CC4)CC3)CC2)CC1] | 5-(4-((1-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)methyl)piperazin-1-yl)-2-(2,6-dioxopiperidin-3-yl)isoindoline-1,3-dione | 948.48 | B | A | B | A |
| 42 | 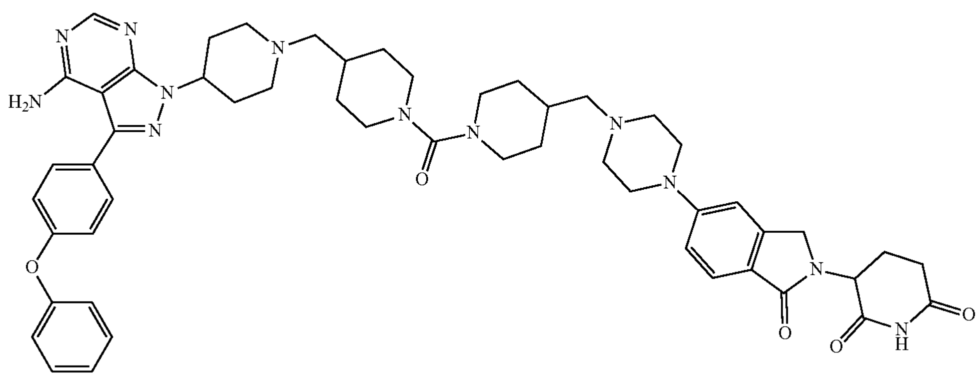 [SMILES: Nc1ncnc2c1c(-c1ccc(Oc3ccccc3)cc1)nn2C1CCN(CC2CCN(C(=O)N3CCC(CN4CCN(c5ccc6c(c5)CN(C5CCC(=O)NC5=O)C6=O)CC4)CC3)CC2)CC1] | 3-(5-(4-((1-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)methyl)piperazin-1-yl)-1-oxoisoindolin-2-yl)piperidine-2,6-dione | 934.50 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 43 | 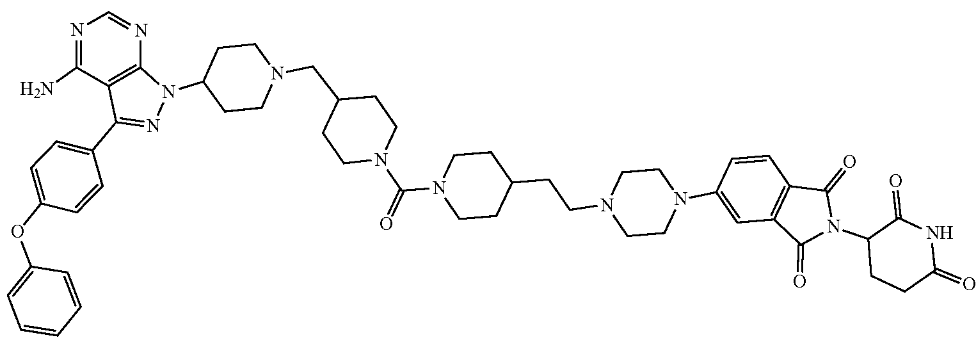 [SMILES: Nc1ncnc2c1c(-c1ccc(Oc3ccccc3)cc1)nn2C1CCN(CC2CCN(C(=O)N3CCC(CCN4CCN(c5ccc6c(c5)C(=O)N(C5CCC(=O)NC5=O)C6=O)CC4)CC3)CC2)CC1] | 5-(4-(2-(1-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione | 962.49 | B | B | B | A |
| 44 | 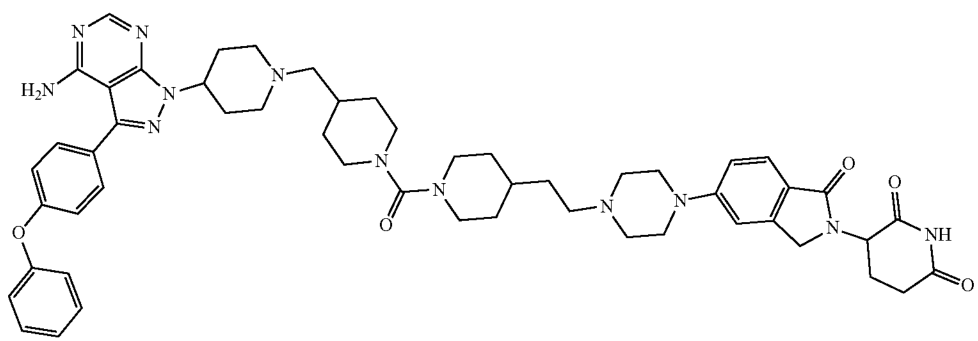 [SMILES: Nc1ncnc2c1c(-c1ccc(Oc3ccccc3)cc1)nn2C1CCN(CC2CCN(C(=O)N3CCC(CCN4CCN(c5ccc6c(c5)CN(C5CCC(=O)NC5=O)C6=O)CC4)CC3)CC2)CC1] | 3-(5-(4-(2-(1-(4-((4-(4-amino-3-(4-phenoxyphenyl)-1H-pyrazolo[3,4-d]pyrimidin-1-yl)piperidin-1-yl)methyl)piperidine-1-carbonyl)piperidin-4-yl)ethyl)piperazin-1-yl)-1-oxoisoindolin-2-yl)piperidine-2,6-dione | 948.51 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 45 | 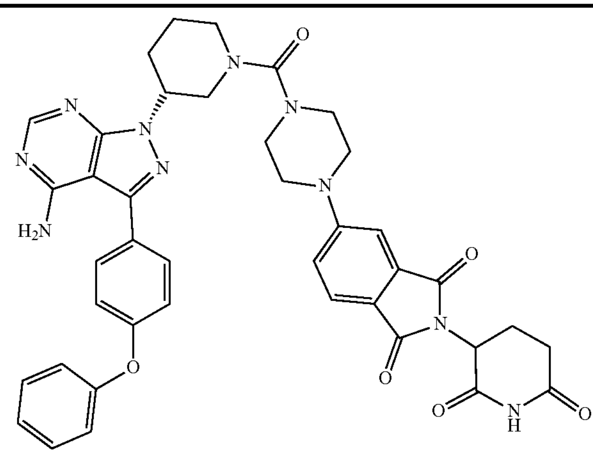 | 5-(4-((R)-3-(4-amino-3-(4-phenoxyphenyl)-1H-pyrazolo[3,4-d]pyrimidin-1-yl)piperidine-1-carbonyl)piperazin-1-yl)-2-(2,6-dioxopiperidin-3-yl)isoindoline-1,3-dione | 754.30 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 46 | 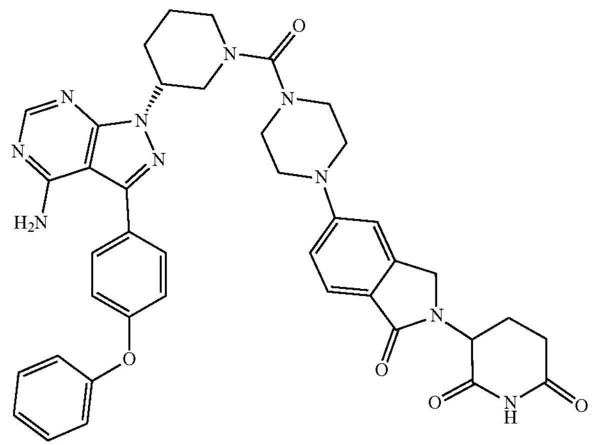 | 3-(5-(4-((R)-3-(4-amino-3-(4-phenoxyphenyl)-1H-pyrazolo[3,4-d]pyrimidin-1-yl)piperidine-1-carbonyl)piperazin-1-yl)-1-oxoisoindolin-2-yl)piperidine-2,6-dione | 740.32 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 47 | 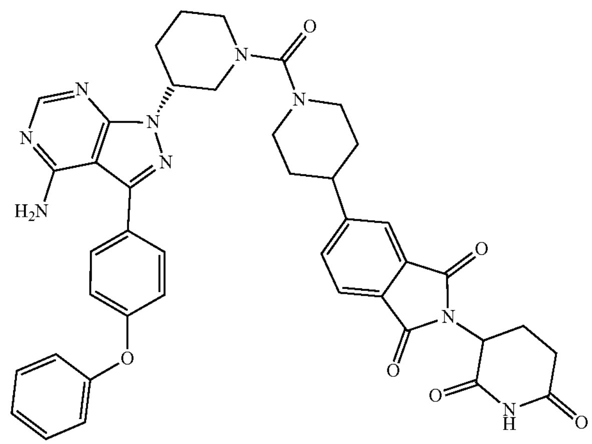 | 5-(1-((R)-3-(4-amino-3-(4-phenoxyphenyl)-1H-pyrazolo[3,4-d]pyrimidin-1-yl)piperidine-1-carbonyl)piperidin-4-yl)-2-(2,6-dioxopiperidin-3-yl)isoindoline-1,3-dione | 753.30 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 48 | 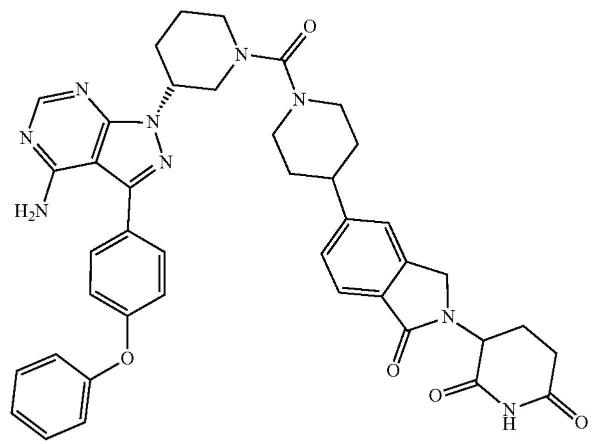 | 3-(5-(1-((R)-3-(4-amino-3-(4-phenoxyphenyl)-1H-pyrazolo[3,4-d]pyrimidin-1-yl)piperidine-1-carbonyl)piperidin-4-yl)-1-oxoisoindolin-2-yl)piperidine-2,6-dione | 739.32 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 49 | 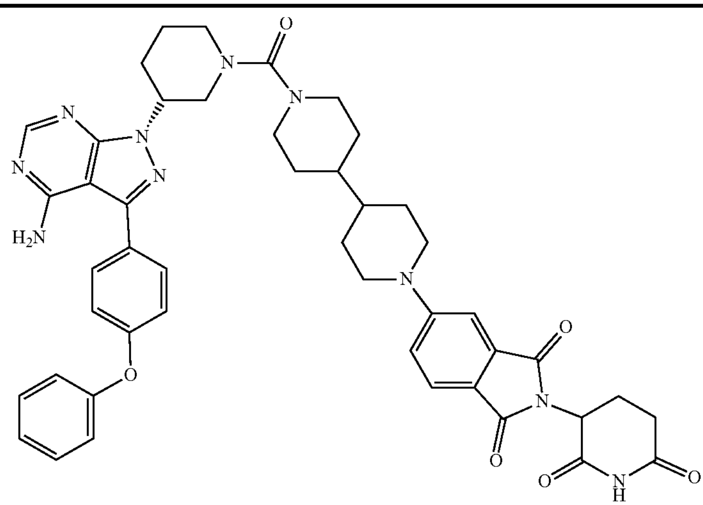 | 5-(1'-((R)-3-(4-amino-3-(4-phenoxyphenyl)-1H-pyrazolo[3,4-d]pyrimidin-1-yl)piperidine-1-carbonyl)-[4,4'-bipiperidin]-1-yl)-2-(2,6-dioxopiperidin-3-yl)isoindoline-1,3-dione | 836.38 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 50 | 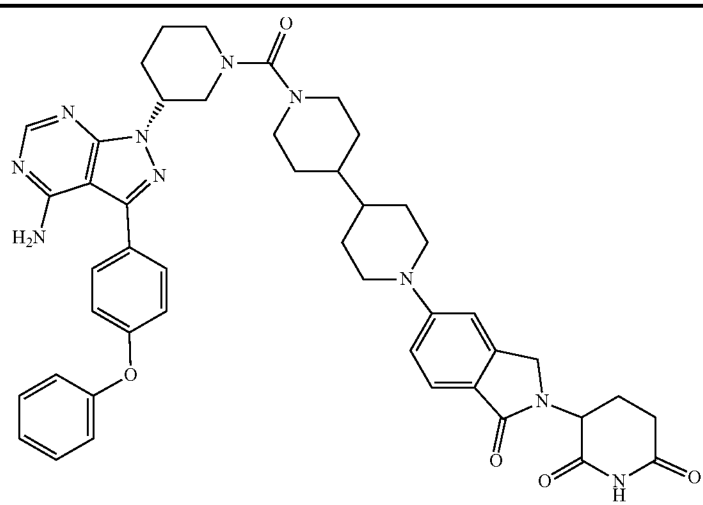 | 3-(5-(1'-((R)-3-(4-amino-3-(4-phenoxyphenyl)-1H-pyrazolo[3,4-d]pyrimidin-1-yl)piperidine-1-carbonyl)-[4,4'-bipiperidin]-1-yl)-1-oxoisoindolin-2-yl)piperidine-2,6-dione | 822.50 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 51 | 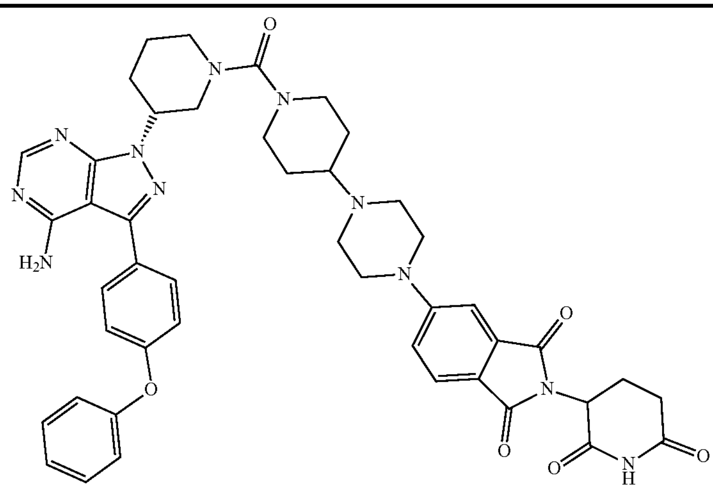 | 5-(4-(1-((R)-3-(4-amino-3-(4-phenoxyphenyl)-1H-pyrazolo[3,4-d]pyrimidin-1-yl)piperidine-1-carbonyl)piperidin-4-yl)piperazin-1-yl)-2-(2,6-dioxopiperidin-3-yl)isoindoline-1,3-dione | 837.37 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 52 | 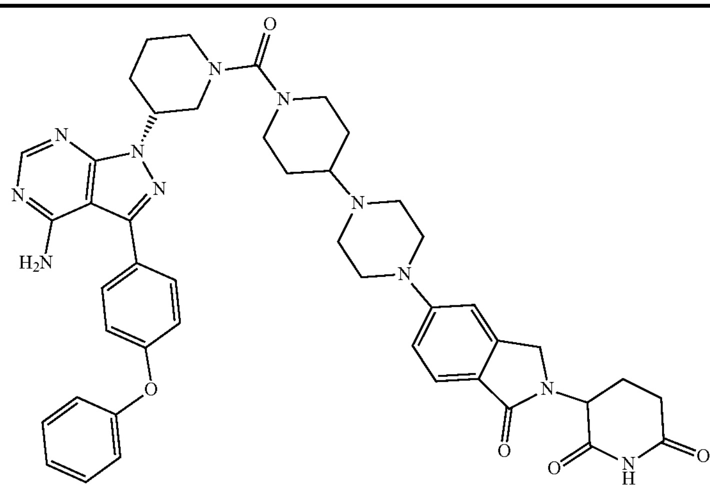 | 3-(5-(4-(1-((R)-3-(4-amino-3-(4-phenoxyphenyl)-1H-pyrazolo[3,4-d]pyrimidin-1-yl)piperidine-1-carbonyl)piperidin-4-yl)piperazin-1-yl)-1-oxoisoindolin-2-yl)piperidine-2,6-dione | 823.39 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 53 | 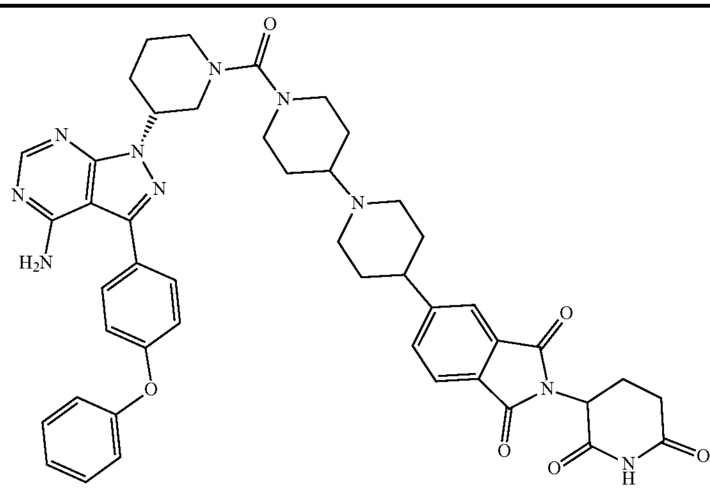 | 5-(1'-((R)-3-(4-amino-3-(4-phenoxyphenyl)-1H-pyrazolo[3,4-d]pyrimidin-1-yl)piperidine-1-carbonyl)-[1,4'-bipiperidin]-4-yl)-2-(2,6-dioxopiperidin-3-yl)isoindoline-1,3-dione | 836.38 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 54 | 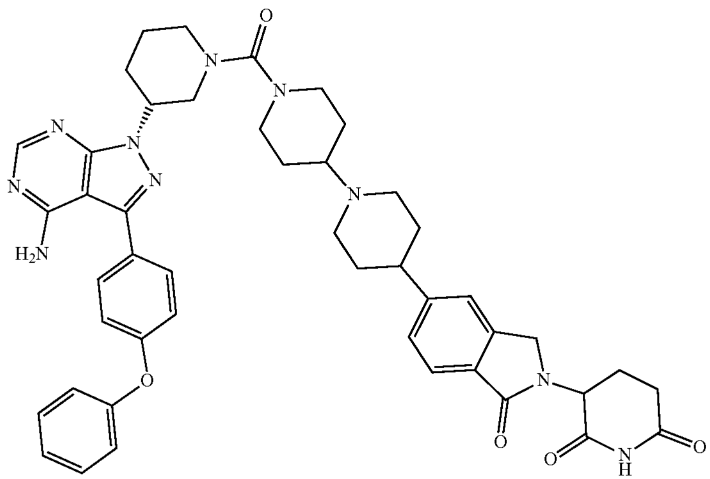 | 3-(5-(1'-((R)-3-(4-amino-3-(4-phenoxyphenyl)-1H-pyrazolo[3,4-d]pyrimidin-1-yl)piperidine-1-carbonyl)-[1,4'-bipiperidin]-4-yl)-1-oxoisoindolin-2-yl)piperidine-2,6-dione | 822.40 | A | A | A | A |
| 55 | 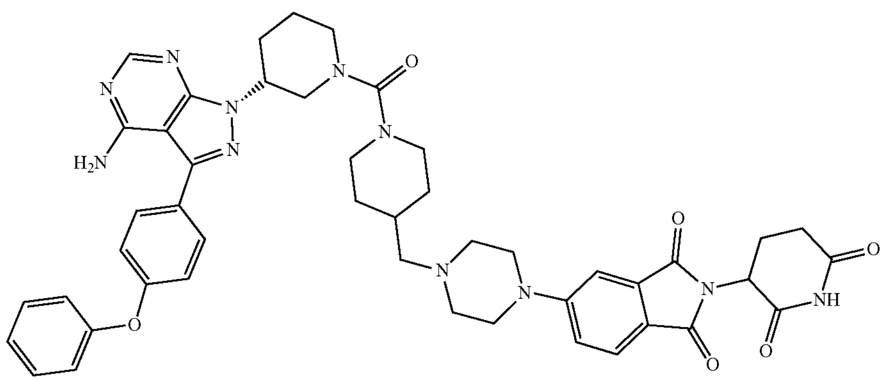 | 5-(4-((1-((R)-3-(4-amino-3-(4-phenoxyphenyl)-1H-pyrazolo[3,4-d]pyrimidin-1-yl)piperidine-4-yl)methyl)piperazin-1-yl)-2-(2,6-dioxopiperidin-3-yl)isoindoline-1,3-dione | 851.39 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 56 | 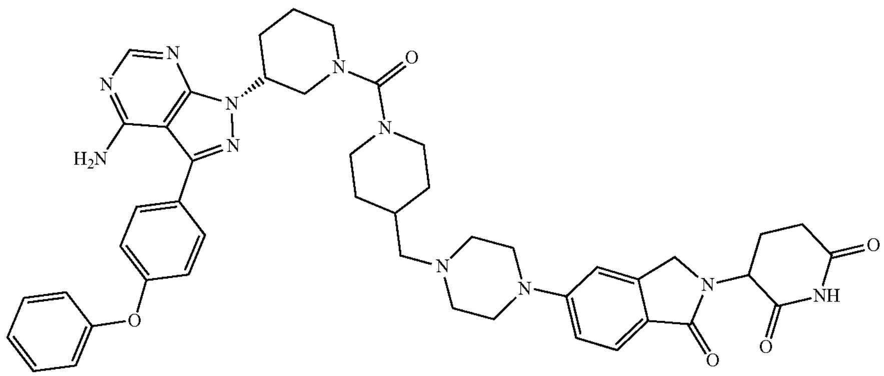 | 3-(5-(4-((1-((R)-3-(4-amino-3-(4-phenoxyphenyl)-1H-pyrazolo[3,4-d]pyrimidin-1-yl)piperidine-1-carbonyl)piperidin-4-yl)methyl)piperazin-1-yl)-1-oxoisoindolin-2-yl)piperidine-2,6-dione | 837.41 | A | A | A | A |
| 57 | 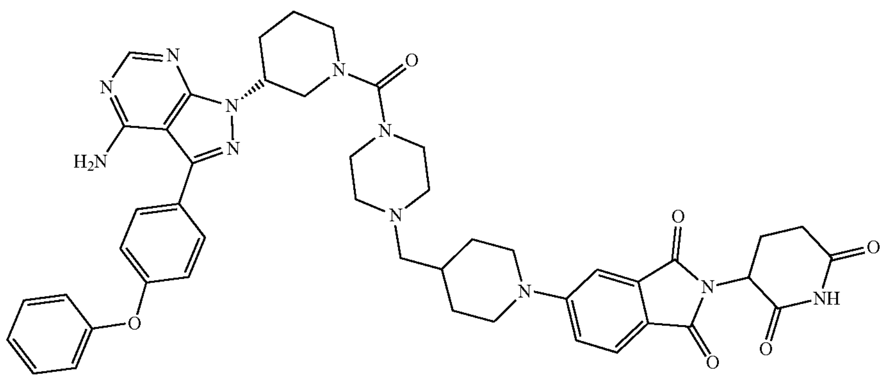 | 5-(4-((4-((R)-3-(4-amino-3-(4-phenoxyphenyl)-1H-pyrazolo[3,4-d]pyrimidin-1-yl)piperidine-1-carbonyl)piperidin-1-yl)methyl)piperidin-1-yl)-2-(2,6-dioxopiperidin-3-yl)isoindoline-1,3-dione | 851.39 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 58 | 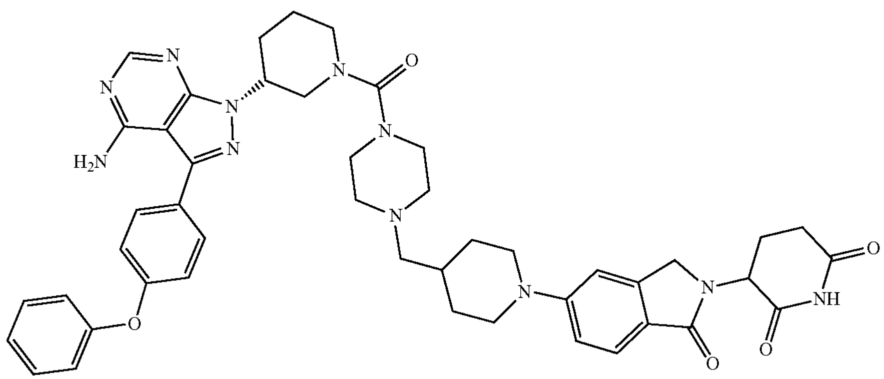 | 3-(5-(4-((R)-3-(4-amino-3-(4-phenoxyphenyl)-1H-pyrazolo[3,4-d]pyrimidin-1-yl)piperidine-1-carbonyl)piperazin-1-yl)methyl)piperidin-1-yl)-1-oxoisoindolin-2-yl)piperidine-2,6-dione | 837.41 | A | A | B | A |
| 59 | 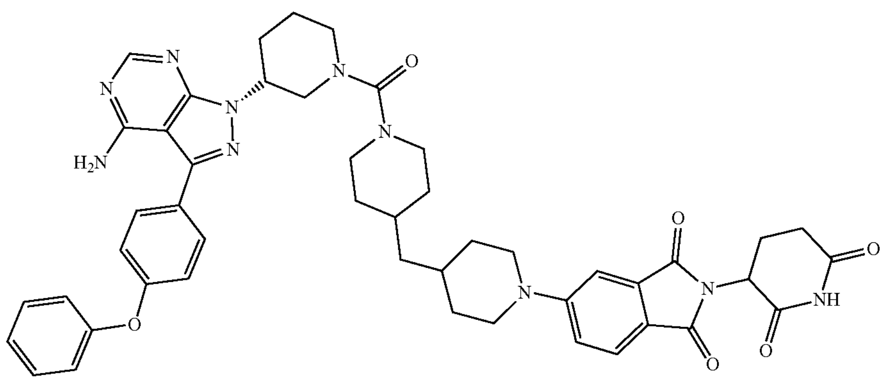 | 5-(4-((1-((R)-3-(4-amino-3-(4-phenoxyphenyl)-1H-pyrazolo[3,4-d]pyrimidin-1-yl)piperidine-1-carbonyl)piperidine-4-yl)methyl)piperidin-1-yl)-2-(2,6-dioxopiperidin-3-yl)isoindoline-1,3-dione | 850.39 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 60 | 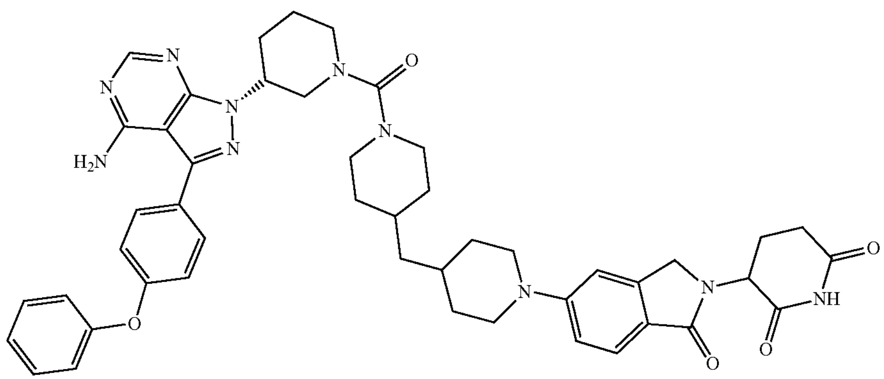 | 3-(5-(4-((1-((R)-3-(4-amino-3-(4-phenoxyphenyl)-1H-pyrazolo[3,4-d]pyrimidin-1-yl)piperidine-1-carbonyl)piperidin-4-yl)methyl)piperidin-1-yl)-1-oxoisoindolin-2-yl)piperidine-2,6-dione | 836.41 | A | A | A | A |
| 61 | 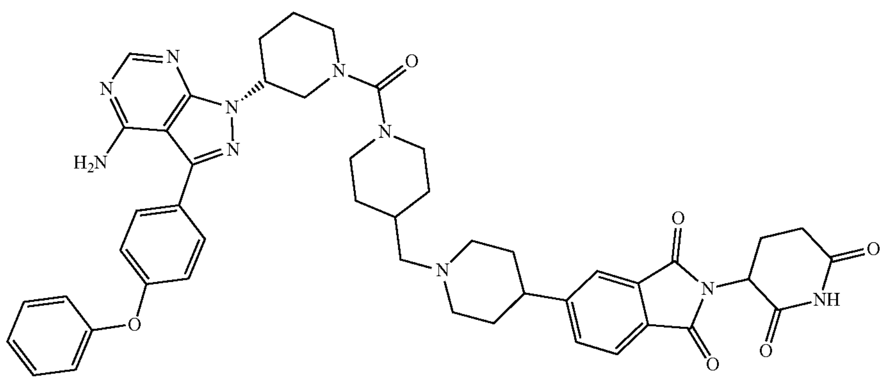 | 5-(1-((R)-3-(4-amino-3-(4-phenoxyphenyl)-1H-pyrazolo[3,4-d]pyrimidin-1-yl)piperidine-1-carbonyl)piperidin-4-yl)methyl)piperidin-4-yl)-2-(2,6-dioxopiperidin-3-yl)isoindoline-1,3-dione | 850.39 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 62 | 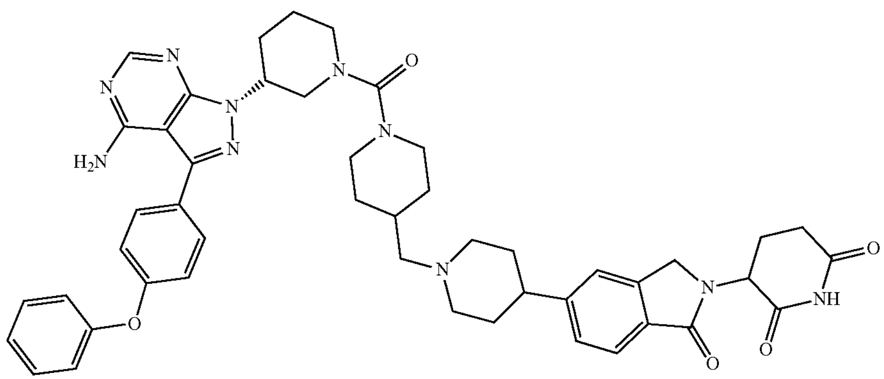 | 3-(5-(1-((R)-3-(4-amino-3-(4-phenoxyphenyl)-1H-pyrazolo[3,4-d]pyrimidin-1-yl)piperidine-1-carbonyl)piperidin-4-yl)methyl)piperidin-4-yl)-1-oxoisoindolin-2-yl)piperidine-2,6-dione | 836.41 | A | A | B | A |
| 63 | 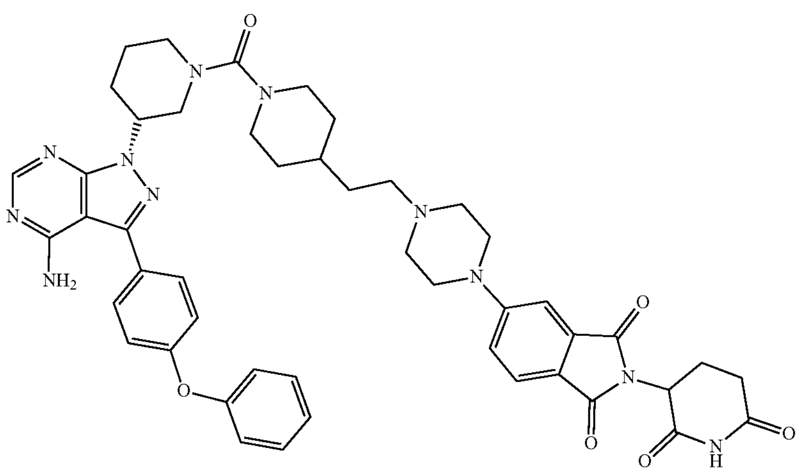 | 5-(4-(2-(1-((R)-3-(4-amino-3-(4-phenoxyphenyl)-1H-pyrazolo[3,4-d]pyrimidin-1-yl)piperidine-1-carbonyl)piperidin-4-yl)ethyl)piperazin-1-yl)-2-(2,6-dioxopiperidin-3-yl)isoindoline-1,3-dione | 865.40 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 64 | 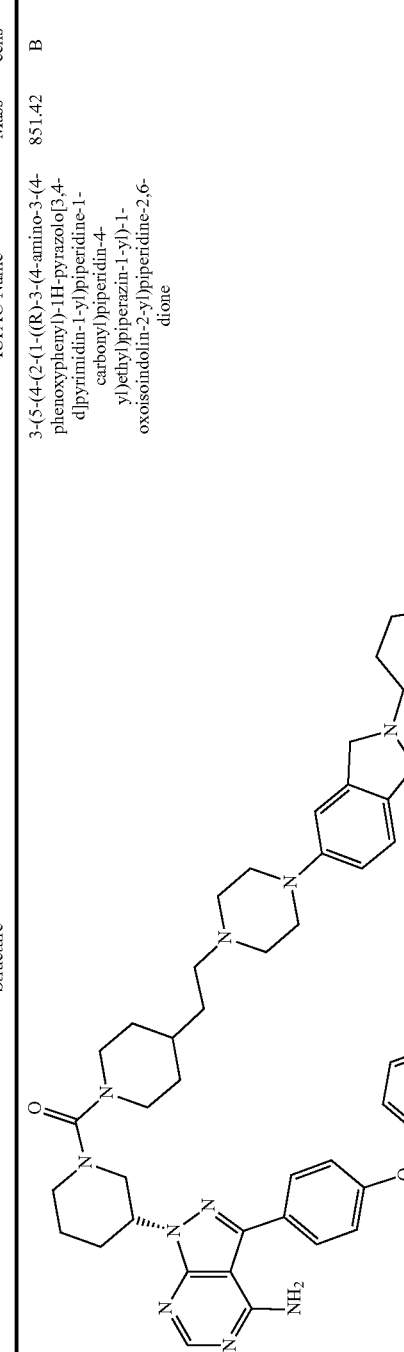 | 3-(5-(4-(2-(1-((R)-3-(4-amino-3-(4-phenoxyphenyl)-1H-pyrazolo[3,4-d]pyrimidin-1-yl)piperidine-1-carbonyl)piperidin-4-yl)ethyl)piperazin-1-yl)-1-oxoisoindolin-2-yl)piperidine-2,6-dione | 851.42 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 65 | 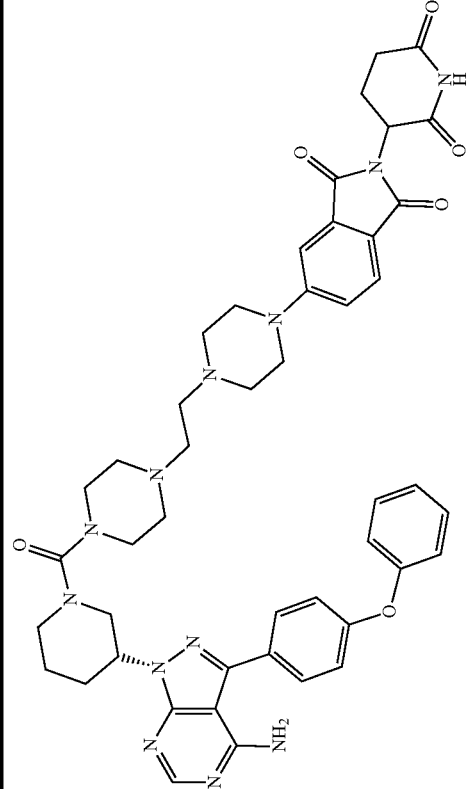 | 5-(4-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperazin-1-yl)-2-(2,6-dioxopiperidin-3-yl)isoindoline-1,3-dione | 866.40 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 66 | 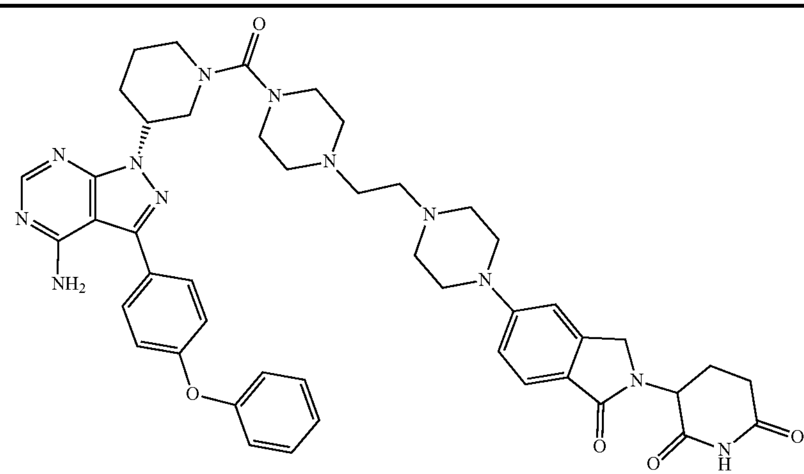 | 3-(5-(4-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperazin-1-yl)-1-oxoisoindolin-2-yl)piperidine-2,6-dione | 852.42 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 67 | 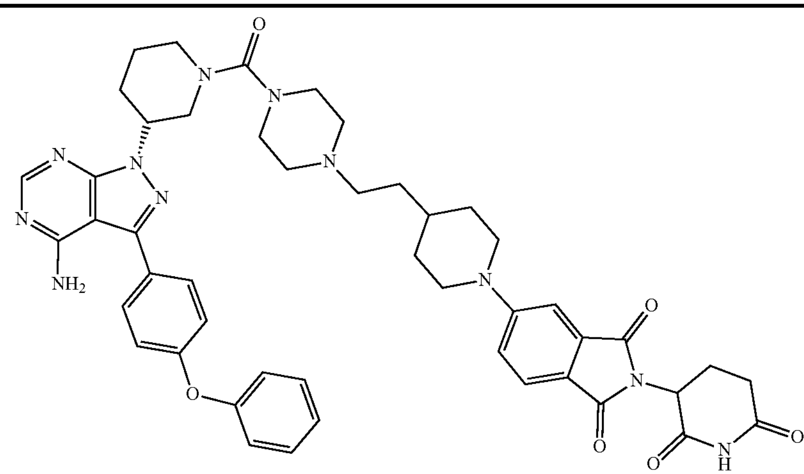 | 5-(4-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperidin-1-yl)-2-(2,6-dioxopiperidin-3-yl)isoindoline-1,3-dione | 865.40 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 68 | 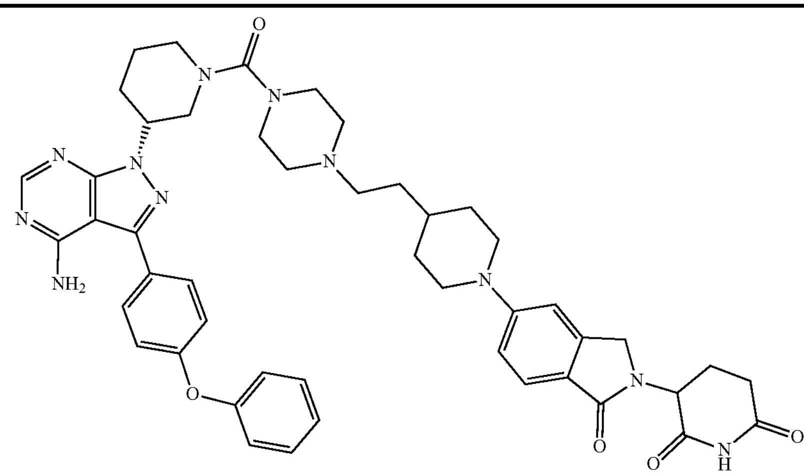 | 3-(5-(4-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperidin-1-yl)-1-oxoisoindolin-2-yl)piperidine-2,6-dione | 851.42 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 69 | 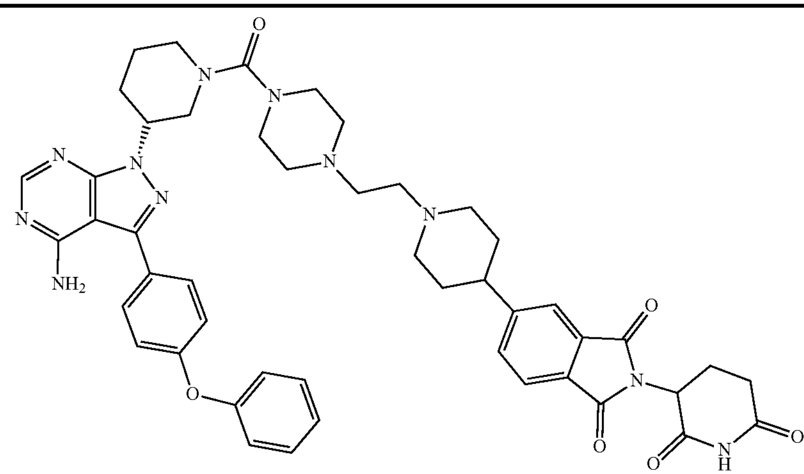 | 5-(1-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperidin-4-yl)-2-(2,6-dioxopiperidin-3-yl)isoindoline-1,3-dione | 865.40 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 70 | 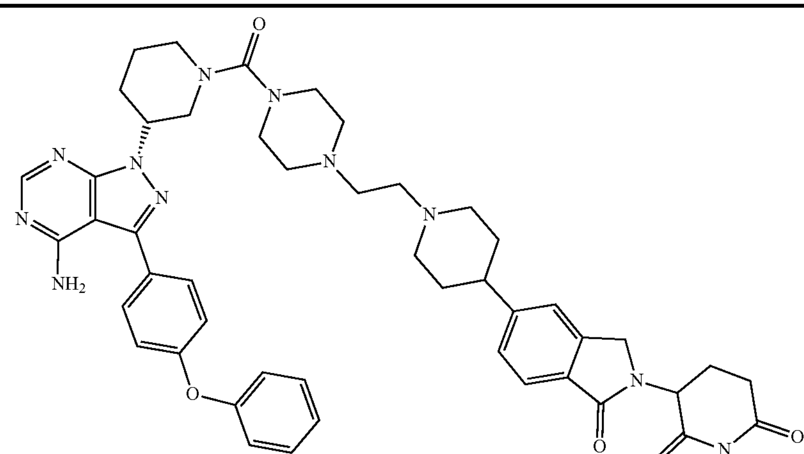 | 3-(5-(1-(2-(4-((R)-3-(4-amino-3-(4-phenoxyphenyl)-1H-pyrazolo[3,4-d]pyrimidin-1-yl)piperidine-1-carbonyl)piperazin-1-yl)ethyl)piperidin-4-yl)-1-oxoisoindolin-2-yl)piperidine-2,6-dione | 851.42 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 71 | 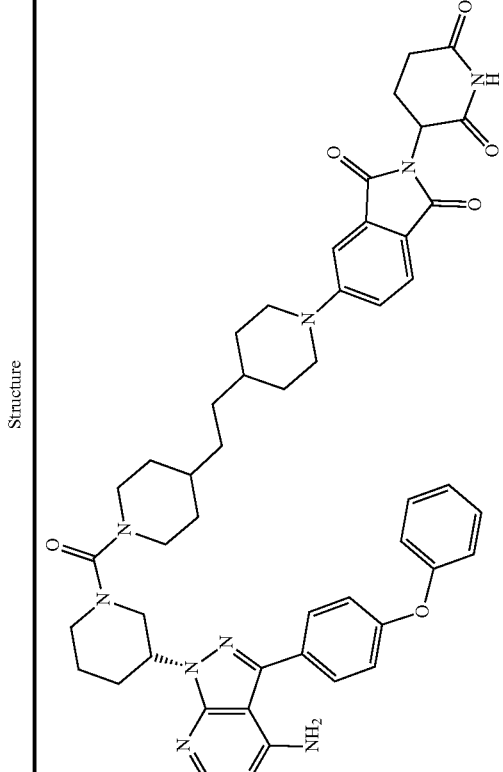 | 5-(4-(2-(1-((R)-3-(4-amino-3-(4-phenoxyphenyl)-1H-pyrazolo[3,4-d]pyrimidin-1-yl)piperidine-1-carbonyl)piperidin-4-yl)ethyl)piperidin-1-yl)-2-(2,6-dioxopiperidin-3-yl)isoindoline-1,3-dione | 864.41 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 72 | 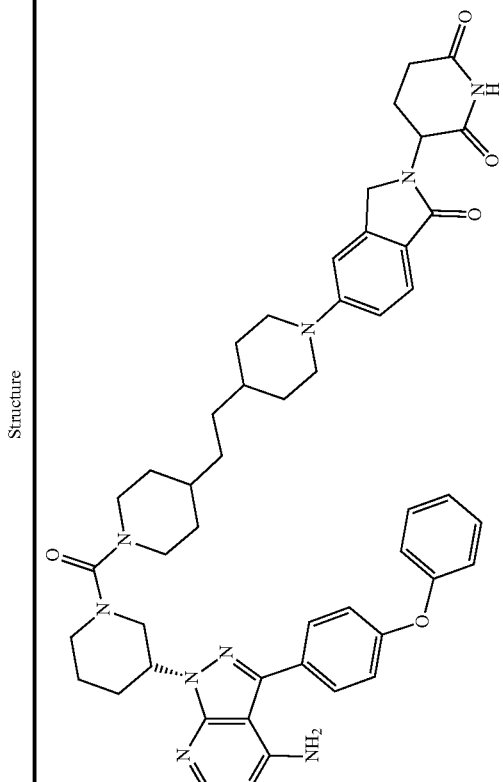 | 3-(5-(4-(2-(1-((R)-3-(4-amino-3-(4-phenoxyphenyl)-1H-pyrazolo[3,4-d]pyrimidin-1-yl)piperidine-1-carbonyl)piperidin-4-yl)ethyl)piperidin-1-yl)-1-oxoisoindolin-2-yl)piperidine-2,6-dione | 850.43 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 73 | 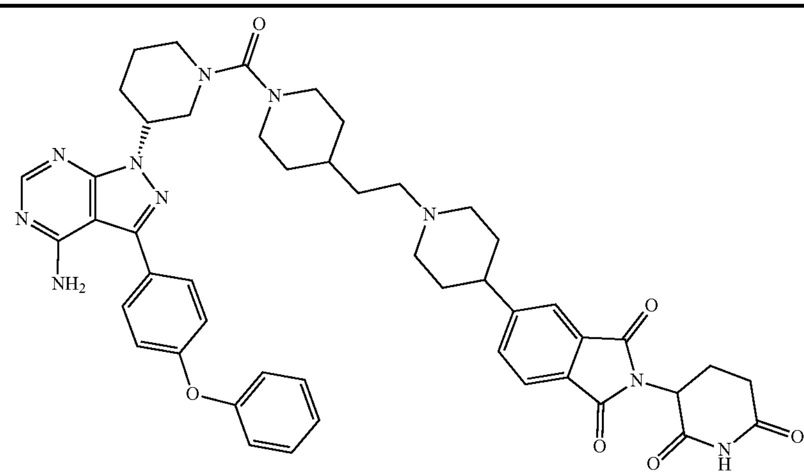 | 5-(1-(2-(1-(3-(4-amino-3-(4-phenoxyphenyl)-1H-pyrazolo[3,4-d]pyrimidin-1-yl)piperidine-1-carbonyl)piperidin-4-yl)ethyl)piperidin-4-yl)-2-(2,6-dioxopiperidin-3-yl)isoindoline-1,3-dione | 864.41 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 74 | 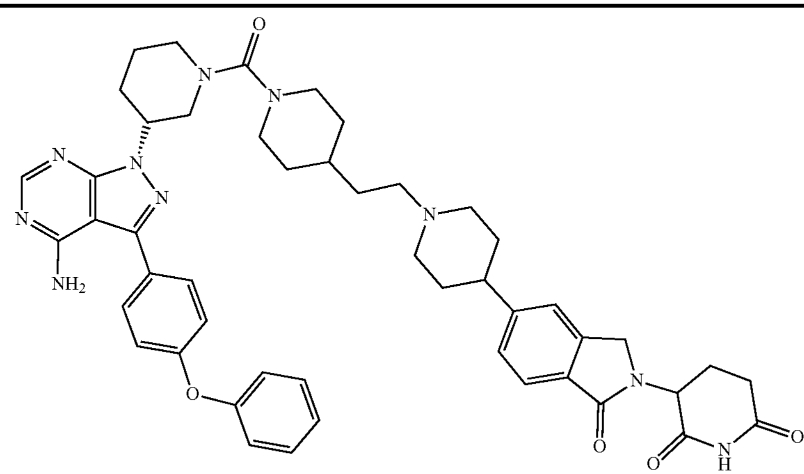 | 3-(5-(1-(2-(1-((R)-3-(4-amino-3-(4-phenoxyphenyl)-1H-pyrazolo[3,4-d]pyrimidin-1-yl)piperidine-1-carbonyl)piperidin-4-yl)ethyl)piperidin-4-yl)-1-oxoisoindolin-2-yl)piperidine-2,6-dione | 850.43 | C | C | B | A |
| 75 | 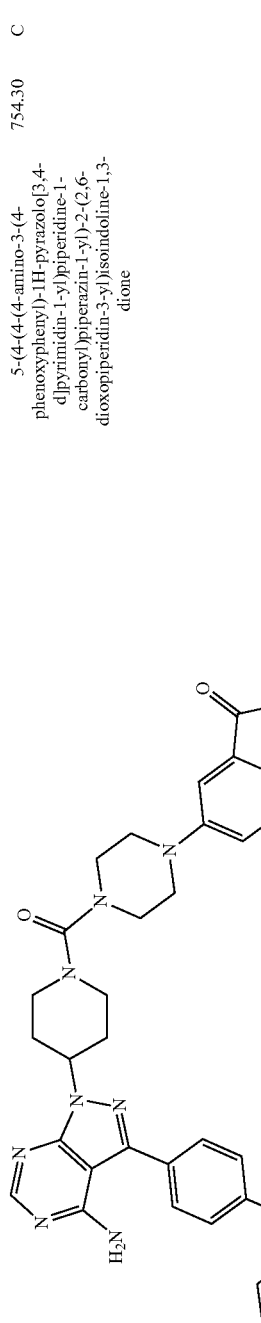 | 5-(4-(4-(4-amino-3-(4-phenoxyphenyl)-1H-pyrazolo[3,4-d]pyrimidin-1-yl)piperidine-1-carbonyl)piperazin-1-yl)-2-(2,6-dioxopiperidin-3-yl)isoindoline-1,3-dione | 754.30 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 76 | 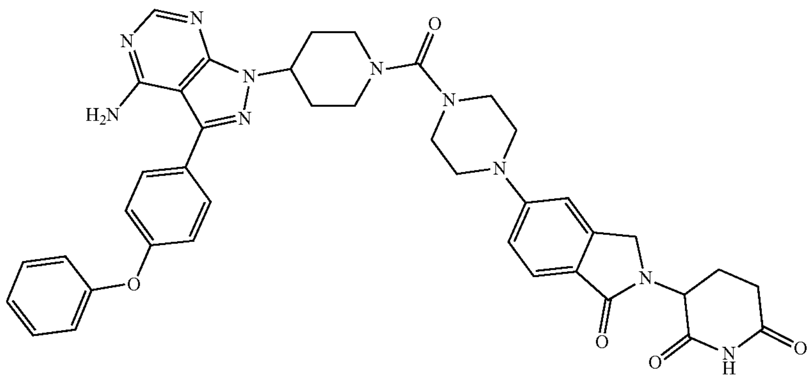 [SMILES: Nc1ncnc2c1c(-c1ccc(Oc3ccccc3)cc1)nn2C1CCN(C(=O)N2CCN(c3ccc4c(c3)CN(C3CCC(=O)NC3=O)C4=O)CC2)CC1] | 3-(5-(4-(4-(4-amino-3-(4-phenoxyphenyl)-1H-pyrazolo[3,4-d]pyrimidin-1-yl)piperidine-1-carbonyl)piperazin-1-yl)-1-oxoisoindolin-2-yl)piperidine-2,6-dione | 740.32 | C | C | C | C |
| 77 | 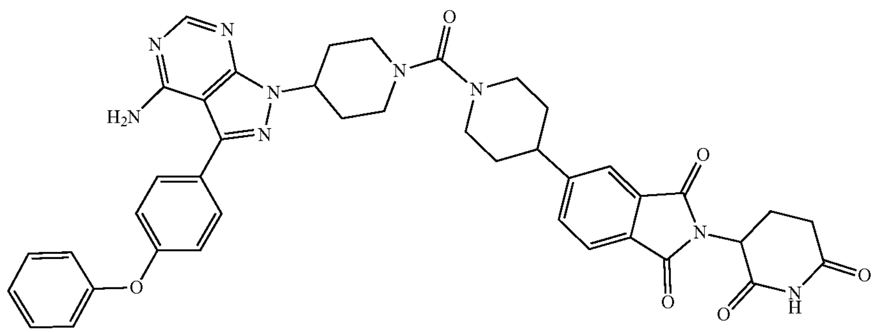 [SMILES: Nc1ncnc2c1c(-c1ccc(Oc3ccccc3)cc1)nn2C1CCN(C(=O)N2CCC(c3ccc4c(c3)C(=O)N(C3CCC(=O)NC3=O)C4=O)CC2)CC1] | 5-(1-(4-(4-(4-amino-3-(4-phenoxyphenyl)-1H-pyrazolo[3,4-d]pyrimidin-1-yl)piperidine-1-carbonyl)piperidin-4-yl)-2-(2,6-dioxopiperidin-3-yl)isoindoline-1,3-dione | 753.30 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 78 | 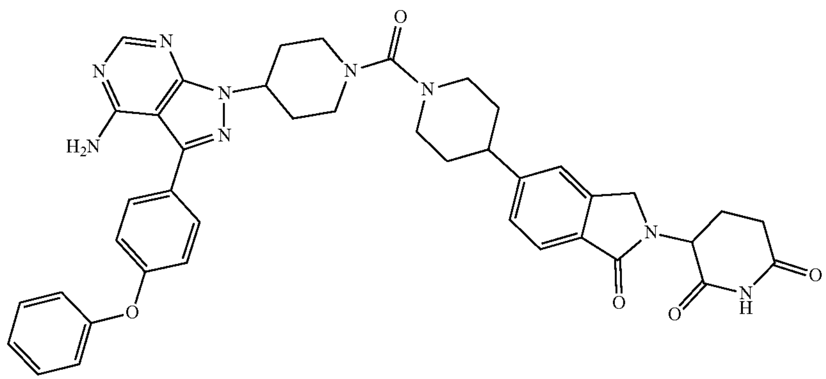 [SMILES: Nc1ncnc2c1c(-c1ccc(Oc3ccccc3)cc1)nn2C1CCN(C(=O)N2CCC(c3ccc4c(c3)CN(C3CCC(=O)NC3=O)C4=O)CC2)CC1] | 3-(5-(1-(4-(4-amino-3-(4-phenoxyphenyl)-1H-pyrazolo[3,4-d]pyrimidin-1-yl)piperidine-1-carbonyl)piperidin-4-yl)-1-oxoisoindolin-2-yl)piperidine-2,6-dione | 739.32 | C | C | C | C |
| 79 | 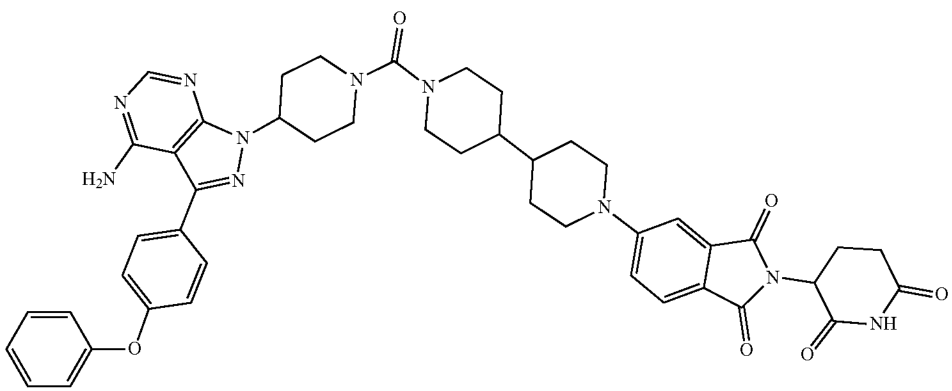 [SMILES: Nc1ncnc2c1c(-c1ccc(Oc3ccccc3)cc1)nn2C1CCN(C(=O)N2CCC(C3CCN(c4ccc5c(c4)C(=O)N(C4CCC(=O)NC4=O)C5=O)CC3)CC2)CC1] | 5-(1'-(4-(4-amino-3-(4-phenoxyphenyl)-1H-pyrazolo[3,4-d]pyrimidin-1-yl)piperidine-1-carbonyl)-[4,4'-bipiperidin]-1-yl)-2-(2,6-dioxopiperidin-3-yl)isoindoline-1,3-dione | 836.38 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 80 | 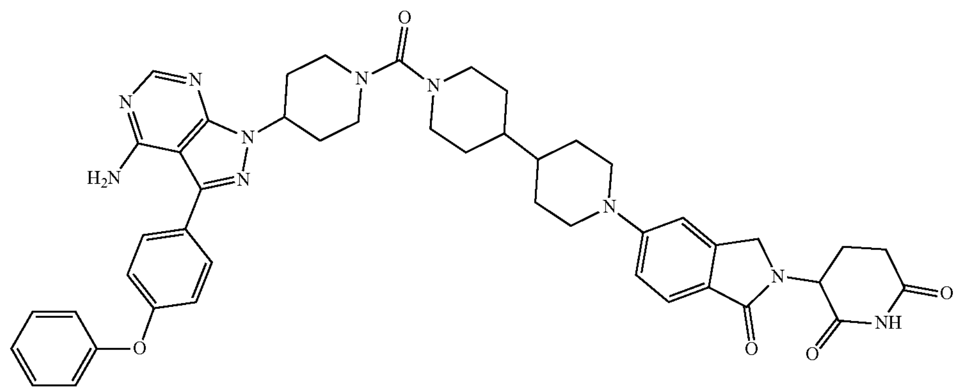 [SMILES: Nc1ncnc2c1c(-c1ccc(Oc3ccccc3)cc1)nn2C1CCN(C(=O)N2CCC(C3CCN(c4ccc5c(c4)CN(C4CCC(=O)NC4=O)C5=O)CC3)CC2)CC1] | 3-(5-(1'-(4-(4-amino-3-(4-phenoxyphenyl)-1H-pyrazolo[3,4-d]pyrimidin-1-yl)piperidine-1-carbonyl)-[4,4'-bipiperidin]-1-yl)-1-oxoisoindolin-2-yl)piperidine-2,6-dione | 822.40 | C | C | C | B |
| 81 | 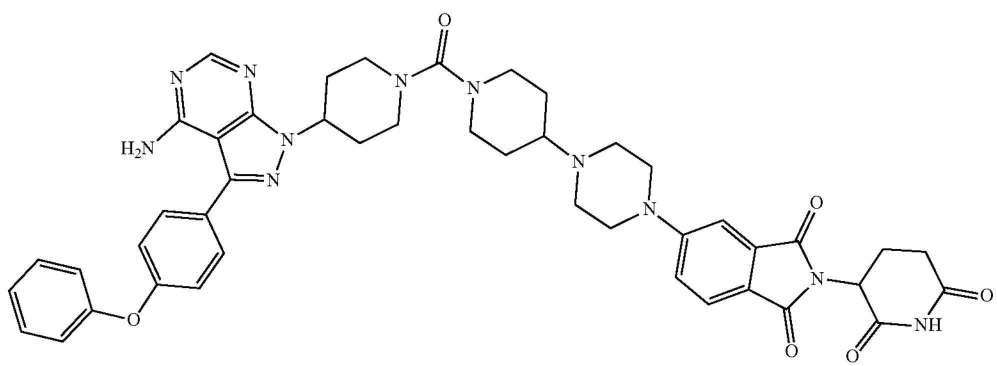 [SMILES: Nc1ncnc2c1c(-c1ccc(Oc3ccccc3)cc1)nn2C1CCN(C(=O)N2CCC(N3CCN(c4ccc5c(c4)C(=O)N(C4CCC(=O)NC4=O)C5=O)CC3)CC2)CC1] | 5-(4-(1-(4-(4-amino-3-(4-phenoxyphenyl)-1H-pyrazolo[3,4-d]pyrimidin-1-yl)piperidine-1-carbonyl)piperidin-4-yl)piperazin-1-yl)-2-(2,6-dioxopiperidin-3-yl)isoindoline-1,3-dione | 837.37 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKo-1 cells | IC$_{50}$ (antiproliferation) Mino cells | DC$_{50}$ | D$_{max}$ |
|---|---|---|---|---|---|---|---|
| 82 | 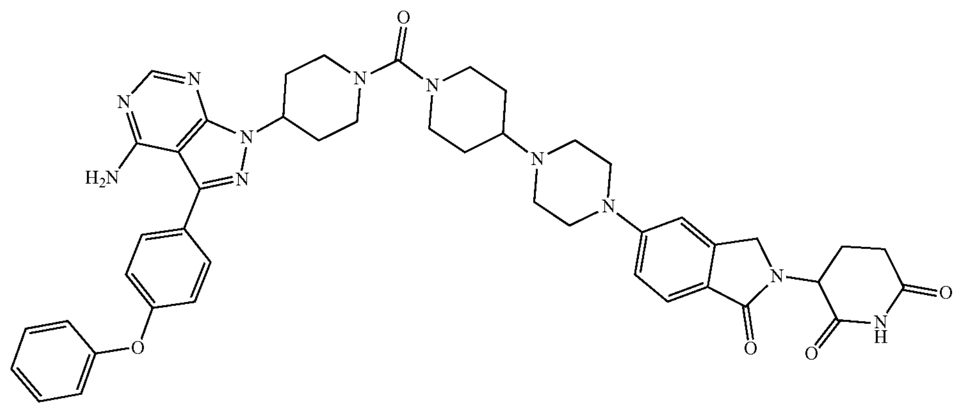 [SMILES: Nc1ncnc2c1c(-c1ccc(Oc3ccccc3)cc1)nn2C1CCN(C(=O)N2CCC(N3CCN(c4ccc5c(c4)CN(C4CCC(=O)NC4=O)C5=O)CC3)CC2)CC1] | 3-(5-(4-(1-(4-(4-amino-3-(4-phenoxyphenyl)-1H-pyrazolo[3,4-d]pyrimidin-1-yl)piperidine-1-carbonyl)piperidin-4-yl)piperazin-1-yl)-1-oxoisoindolin-2-yl)piperidine-2,6-dione | 823.39 | C | C | B | B |
| 83 | 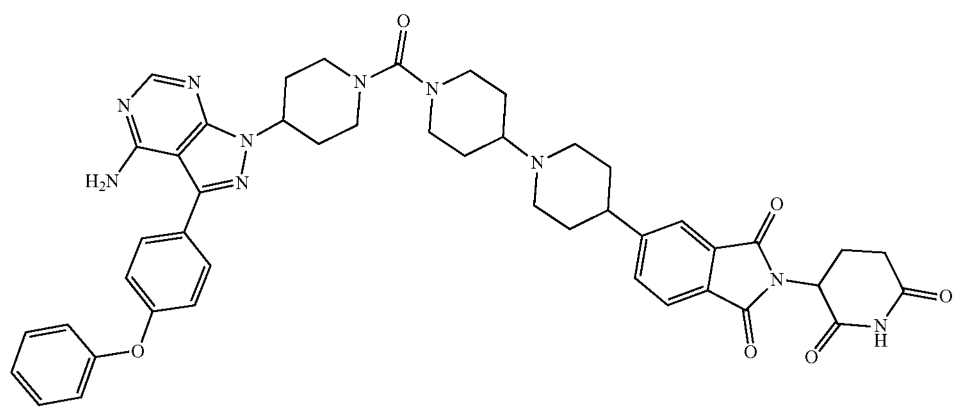 [SMILES: Nc1ncnc2c1c(-c1ccc(Oc3ccccc3)cc1)nn2C1CCN(C(=O)N2CCC(N3CCC(c4ccc5c(c4)C(=O)N(C4CCC(=O)NC4=O)C5=O)CC3)CC2)CC1] | 5-(1'-(4-(4-amino-3-(4-phenoxyphenyl)-1H-pyrazolo[3,4-d]pyrimidin-1-yl)piperidine-1-carbonyl)-[1,4'-bipiperidin]-4-yl)-2-(2,6-dioxopiperidin-3-yl)isoindoline-1,3-dione | 836.38 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 84 | 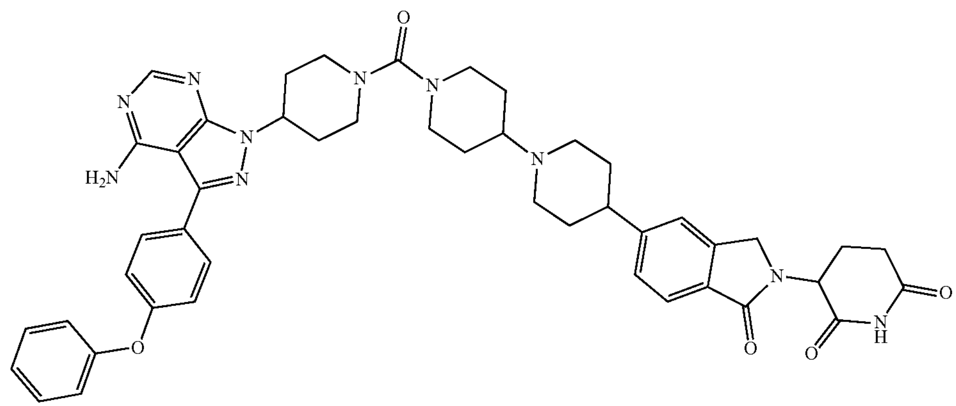 [SMILES: Nc1ncnc2c1c(-c1ccc(Oc3ccccc3)cc1)nn2C1CCN(C(=O)N2CCC(N3CCC(c4ccc5c(c4)CN(C4CCC(=O)NC4=O)C5=O)CC3)CC2)CC1] | 3-(5-(1'-(4-(4-amino-3-(4-phenoxyphenyl)-1H-pyrazolo[3,4-d]pyrimidin-1-yl)piperidine-1-carbonyl)-[1,4'-bipiperidin]-4-yl)-1-oxoisoindolin-2-yl)piperidine-2,6-dione | 822.40 | C | C | C | B |
| 85 | 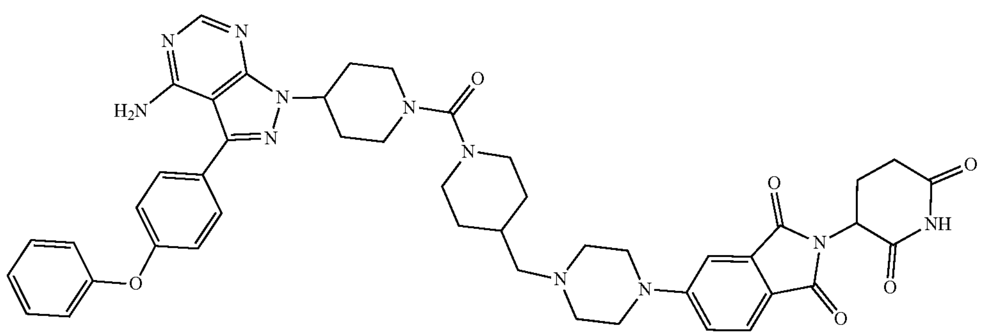 [SMILES: Nc1ncnc2c1c(-c1ccc(Oc3ccccc3)cc1)nn2C1CCN(C(=O)N2CCC(CN3CCN(c4ccc5c(c4)C(=O)N(C4CCC(=O)NC4=O)C5=O)CC3)CC2)CC1] | 5-(4-((1-(4-(4-amino-3-(4-phenoxyphenyl)-1H-pyrazolo[3,4-d]pyrimidin-1-yl)piperidine-1-carbonyl)piperidin-4-yl)methyl)piperazin-1-yl)-2-(2,6-dioxopiperidin-3-yl)isoindoline-1,3-dione | 851.39 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 86 | 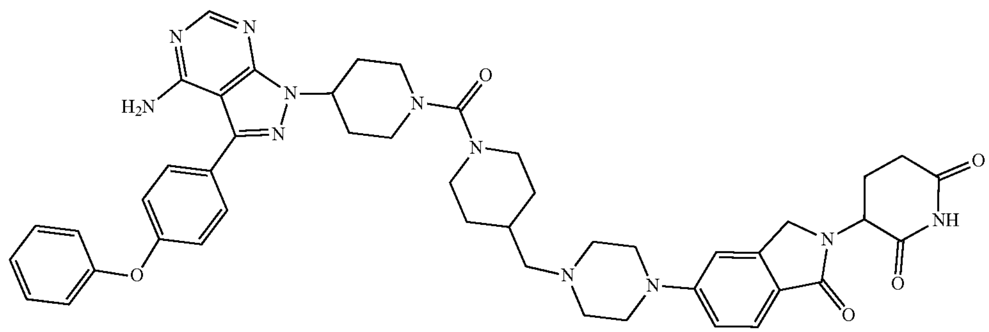 [SMILES: Nc1ncnc2c1c(-c1ccc(Oc3ccccc3)cc1)nn2C1CCN(C(=O)N2CCC(CN3CCN(c4ccc5c(c4)CN(C4CCC(=O)NC4=O)C5=O)CC3)CC2)CC1] | 3-(5-(4-((1-(4-(4-amino-3-(4-phenoxyphenyl)-1H-pyrazolo[3,4-d]pyrimidin-1-yl)piperidine-1-carbonyl)piperidin-4-yl)methyl)piperazin-1-yl)-1-oxoisoindolin-2-yl)piperidine-2,6-dione | 837.41 | A | A | A | A |
| 87 | 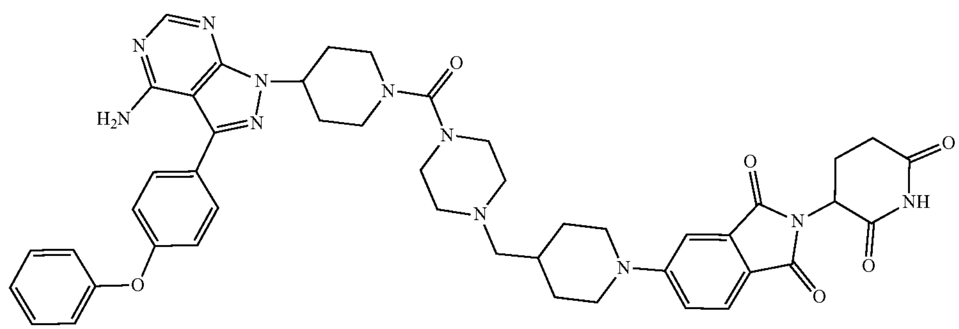 [SMILES: Nc1ncnc2c1c(-c1ccc(Oc3ccccc3)cc1)nn2C1CCN(C(=O)N2CCN(CC3CCN(c4ccc5c(c4)C(=O)N(C4CCC(=O)NC4=O)C5=O)CC3)CC2)CC1] | 5-(4-((4-(4-amino-3-(4-phenoxyphenyl)-1H-pyrazolo[3,4-d]pyrimidin-1-yl)piperidine-1-carbonyl)piperazin-1-yl)methyl)piperidin-1-yl)-2-(2,6-dioxopiperidin-3-yl)isoindoline-1,3-dione | 851.39 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 88 | 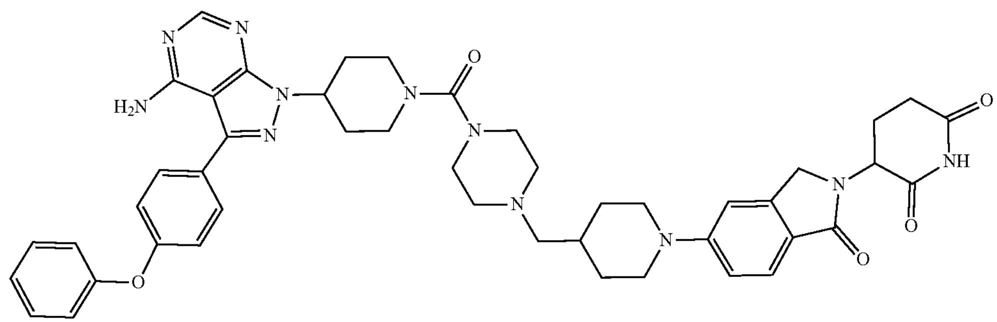 [SMILES: Nc1ncnc2c1c(-c1ccc(Oc3ccccc3)cc1)nn2C1CCN(C(=O)N2CCN(CC3CCN(c4ccc5c(c4)CN(C4CCC(=O)NC4=O)C5=O)CC3)CC2)CC1] | 3-(5-(4-((4-(4-amino-3-(4-phenoxyphenyl)-1H-pyrazolo[3,4-d]pyrimidin-1-yl)piperidine-1-carbonyl)piperazin-1-yl)methyl)piperidin-1-yl)-1-oxoisoindolin-2-yl)piperidine-2,6-dione | 837.41 | A | A | B | A |
| 89 | 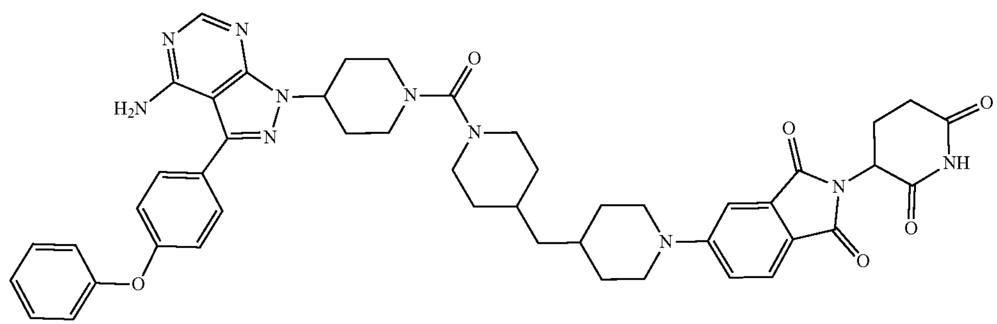 [SMILES: Nc1ncnc2c1c(-c1ccc(Oc3ccccc3)cc1)nn2C1CCN(C(=O)N2CCC(CC3CCN(c4ccc5c(c4)C(=O)N(C4CCC(=O)NC4=O)C5=O)CC3)CC2)CC1] | 5-(4-((1-(4-(4-amino-3-(4-phenoxyphenyl)-1H-pyrazolo[3,4-d]pyrimidin-1-yl)piperidine-1-carbonyl)piperidin-4-yl)methyl)piperidin-1-yl)-2-(2,6-dioxopiperidin-3-yl)isoindoline-1,3-dione | 850.39 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 90 | 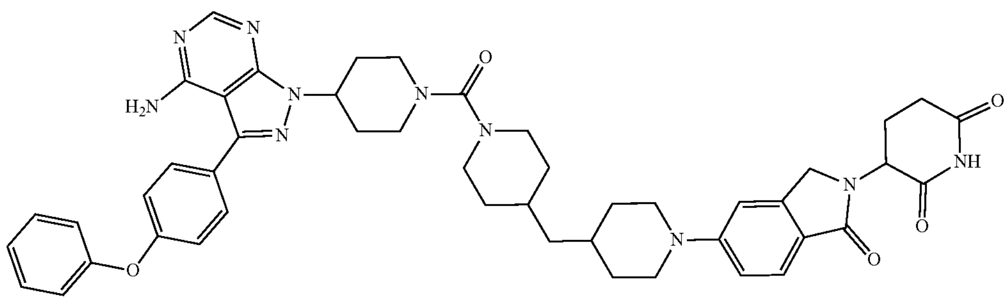 [SMILES: Nc1ncnc2c1c(-c1ccc(Oc3ccccc3)cc1)nn2C1CCN(C(=O)N2CCC(CC3CCN(c4ccc5c(c4)CN(C4CCC(=O)NC4=O)C5=O)CC3)CC2)CC1] | 3-(5-(4-((1-(4-(4-amino-3-(4-phenoxyphenyl)-1H-pyrazolo[3,4-d]pyrimidin-1-yl)piperidine-1-carbonyl)piperidin-4-yl)methyl)piperidin-1-yl)-1-oxoisoindolin-2-yl)piperidine-2,6-dione | 836.41 | B | B | A | A |
| 91 | 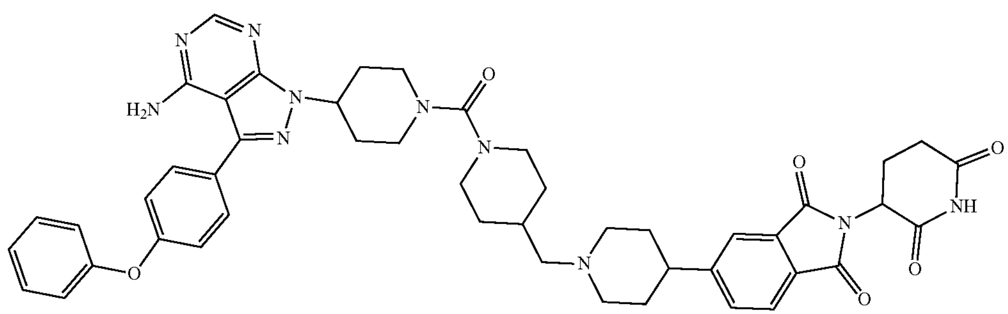 [SMILES: Nc1ncnc2c1c(-c1ccc(Oc3ccccc3)cc1)nn2C1CCN(C(=O)N2CCC(CN3CCC(c4ccc5c(c4)C(=O)N(C4CCC(=O)NC4=O)C5=O)CC3)CC2)CC1] | 5-(1-((1-(4-(4-amino-3-(4-phenoxyphenyl)-1H-pyrazolo[3,4-d]pyrimidin-1-yl)piperidine-1-carbonyl)piperidin-4-yl)methyl)piperidin-4-yl)-2-(2,6-dioxopiperidin-3-yl)isoindoline-1,3-dione | 850.39 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 92 | 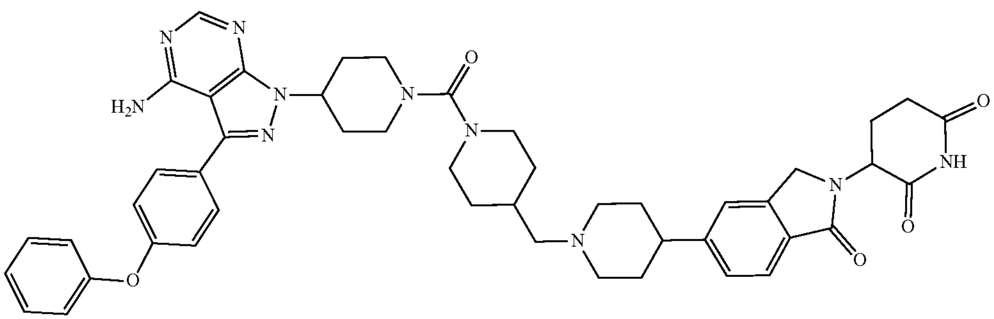 [SMILES: Nc1ncnc2c1c(-c1ccc(Oc3ccccc3)cc1)nn2C1CCN(C(=O)N2CCC(CN3CCC(c4ccc5c(c4)CN(C4CCC(=O)NC4=O)C5=O)CC3)CC2)CC1] | 3-(5-(1-((4-(4-amino-3-(4-phenoxyphenyl)-1H-pyrazolo[3,4-d]pyrimidin-1-yl)piperidine-1-carbonyl)piperidin-4-yl)methyl)piperidin-4-yl)-1-oxoisoindolin-2-yl)piperidine-2,6-dione | 836.41 | B | A | A | A |
| 93 | 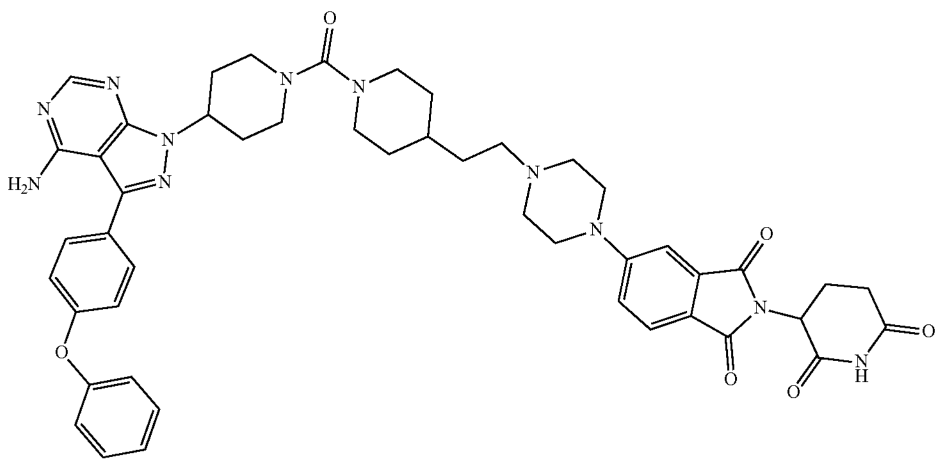 [SMILES: Nc1ncnc2c1c(-c1ccc(Oc3ccccc3)cc1)nn2C1CCN(C(=O)N2CCC(CCN3CCN(c4ccc5c(c4)C(=O)N(C4CCC(=O)NC4=O)C5=O)CC3)CC2)CC1] | 5-(4-(2-(1-(4-(4-amino-3-(4-phenoxyphenyl)-1H-pyrazolo[3,4-d]pyrimidin-1-yl)piperidine-1-carbonyl)piperidin-4-yl)ethyl)piperazin-1-yl)-2-(2,6-dioxopiperidin-3-yl)isoindoline-1,3-dione | 865.40 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 94 | 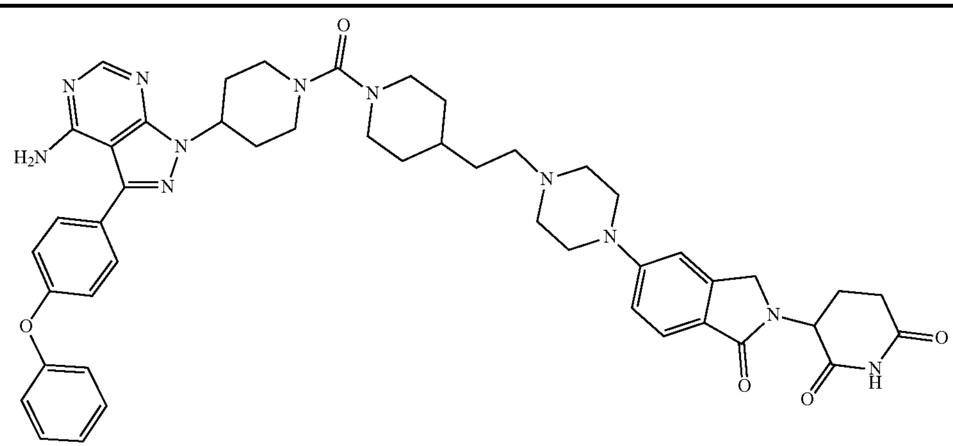 | 3-(5-(4-(2-(1-(4-(4-amino-3-(4-phenoxyphenyl)-1H-pyrazolo[3,4-d]pyrimidin-1-yl)piperidine-1-carbonyl)piperidin-4-yl)ethyl)piperazin-1-yl)-1-oxoisoindolin-2-yl)piperidine-2,6-dione | 851.42 | B | A | B | A |
| 95 | 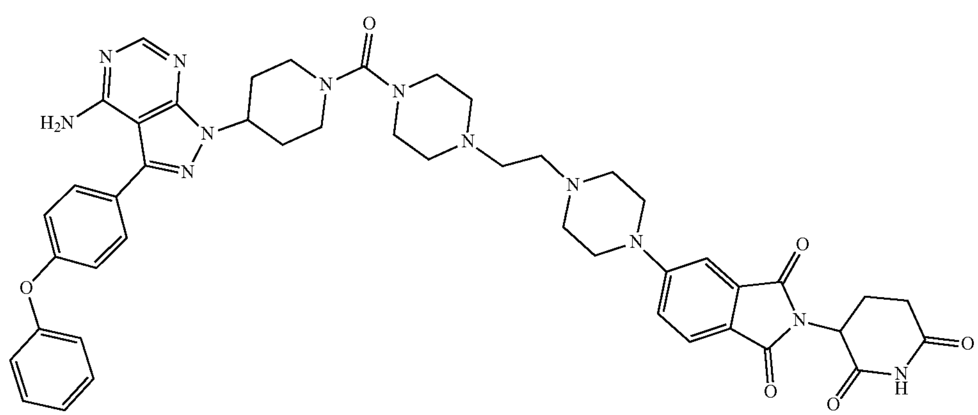 [SMILES: Nc1ncnc2c1c(-c1ccc(Oc3ccccc3)cc1)nn2C1CCN(C(=O)N2CCN(CCN3CCN(c4ccc5c(c4)C(=O)N(C4CCC(=O)NC4=O)C5=O)CC3)CC2)CC1] | 5-(4-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperazin-1-yl)-2-(2,6-dioxopiperidin-3-yl)isoindoline-1,3-dione | 866.40 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 96 | 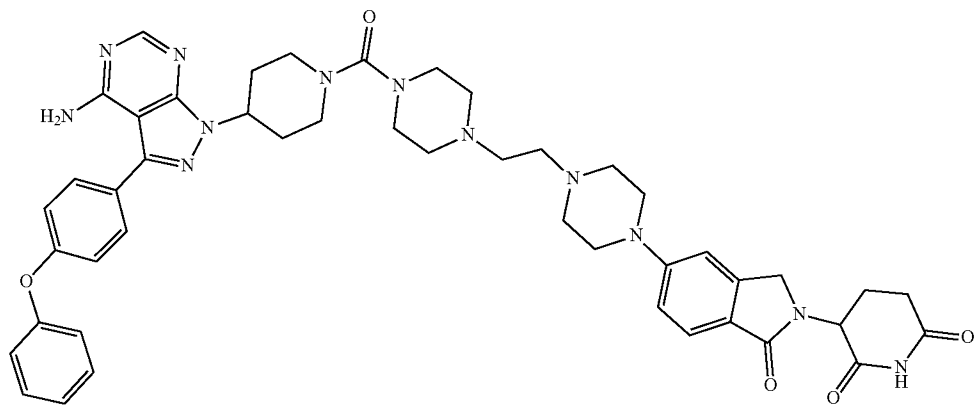 [SMILES: Nc1ncnc2c1c(-c1ccc(Oc3ccccc3)cc1)nn2C1CCN(C(=O)N2CCN(CCN3CCN(c4ccc5c(c4)CN(C4CCC(=O)NC4=O)C5=O)CC3)CC2)CC1] | 3-(5-(4-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperazin-1-yl)-1-oxoisoindolin-2-yl)piperidine-2,6-dione | 852.42 | B | B | B | A |
| 97 | 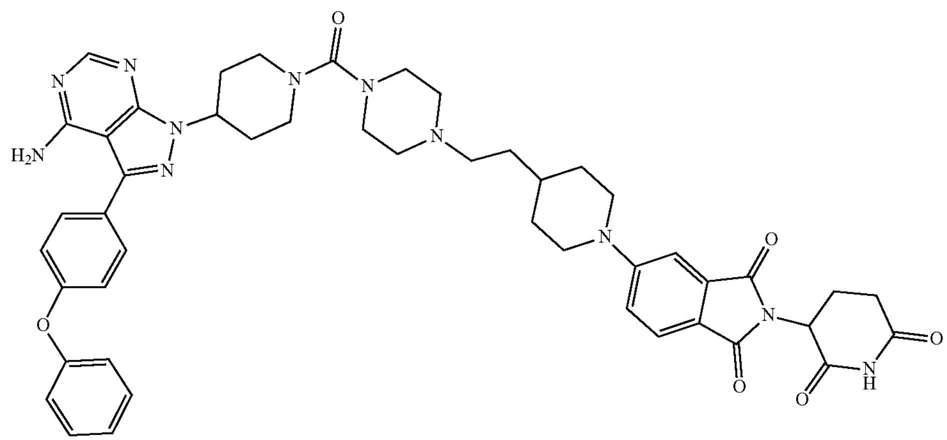 [SMILES: Nc1ncnc2c1c(-c1ccc(Oc3ccccc3)cc1)nn2C1CCN(C(=O)N2CCN(CCC3CCN(c4ccc5c(c4)C(=O)N(C4CCC(=O)NC4=O)C5=O)CC3)CC2)CC1] | 5-(4-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperidin-1-yl)-2-(2,6-dioxopiperidin-3-yl)isoindoline-1,3-dione | 865.40 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 98 | 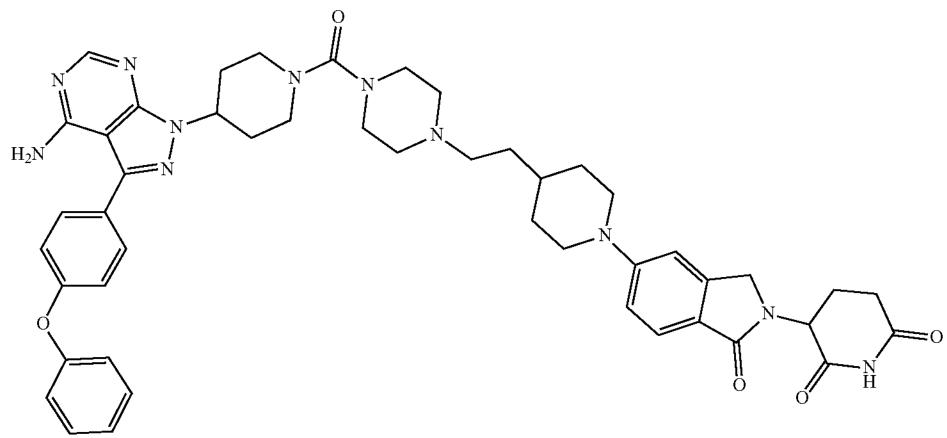 [SMILES: Nc1ncnc2c1c(-c1ccc(Oc3ccccc3)cc1)nn2C1CCN(C(=O)N2CCN(CCC3CCN(c4ccc5c(c4)CN(C4CCC(=O)NC4=O)C5=O)CC3)CC2)CC1] | 3-(5-(4-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperidin-1-yl)-1-oxoisoindolin-2-yl)piperidine-2,6-dione | 851.42 | B | B | B | A |
| 99 | 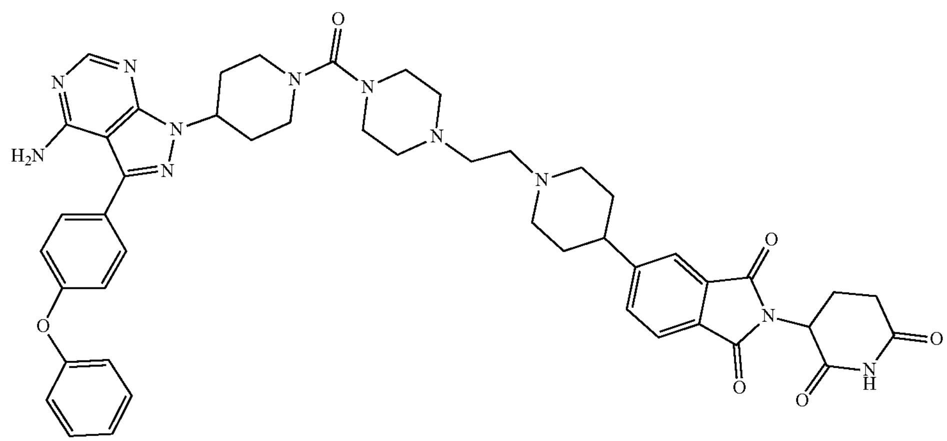 [SMILES: Nc1ncnc2c1c(-c1ccc(Oc3ccccc3)cc1)nn2C1CCN(C(=O)N2CCN(CCN3CCC(c4ccc5c(c4)C(=O)N(C4CCC(=O)NC4=O)C5=O)CC3)CC2)CC1] | 5-(1-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperidin-4-yl)-2-(2,6-dioxopiperidin-3-yl)isoindoline-1,3-dione | 865.41 | B | C | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 100 | 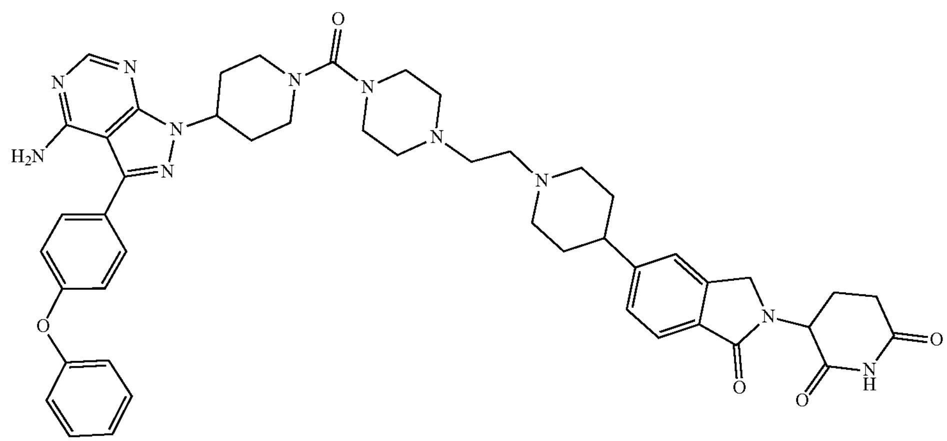 [SMILES: Nc1ncnc2c1c(-c1ccc(Oc3ccccc3)cc1)nn2C1CCN(C(=O)N2CCN(CCN3CCC(c4ccc5c(c4)CN(C4CCC(=O)NC4=O)C5=O)CC3)CC2)CC1] | 3-(5-(1-(2-(4-(4-(4-amino-3-(4-phenoxyphenyl)-1H-pyrazolo[3,4-d]pyrimidin-1-yl)piperidine-1-carbonyl)piperazin-1-yl)ethyl)piperidin-4-yl)-1-oxoisoindolin-2-yl)piperidine-2,6-dione | 851.42 | B | B | B | A |
| 101 | 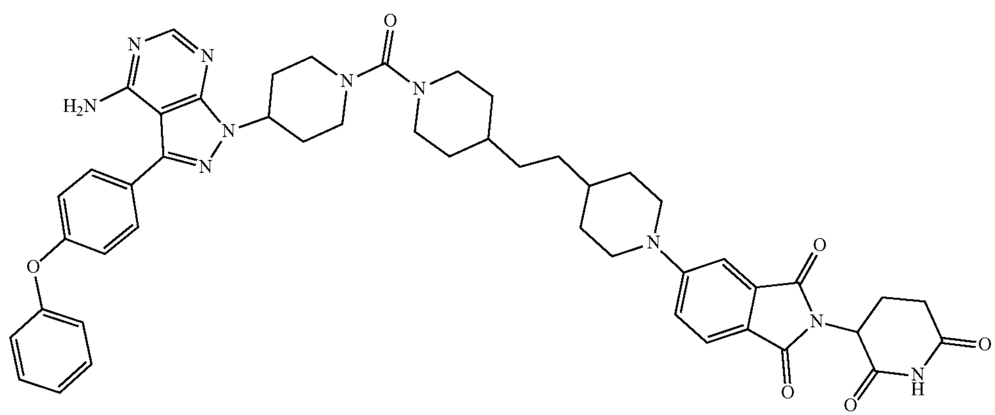 [SMILES: Nc1ncnc2c1c(-c1ccc(Oc3ccccc3)cc1)nn2C1CCN(C(=O)N2CCC(CCC3CCN(c4ccc5c(c4)C(=O)N(C4CCC(=O)NC4=O)C5=O)CC3)CC2)CC1] | 5-(4-(2-(1-(4-(4-(4-amino-3-(4-phenoxyphenyl)-1H-pyrazolo[3,4-d]pyrimidin-1-yl)piperidine-1-carbonyl)piperidin-4-yl)ethyl)piperidin-1-yl)-2-(2,6-dioxopiperidin-3-yl)isoindoline-1,3-dione | 864.41 | C | C | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 102 | 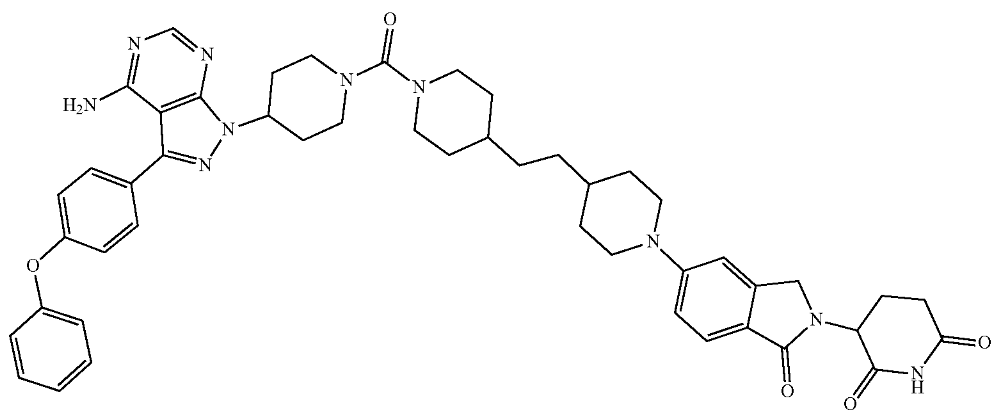 [SMILES: Nc1ncnc2c1c(-c1ccc(Oc3ccccc3)cc1)nn2C1CCN(C(=O)N2CCC(CCC3CCN(c4ccc5c(c4)CN(C4CCC(=O)NC4=O)C5=O)CC3)CC2)CC1] | 3-(5-(4-(2-(1-(4-(4-amino-3-(4-phenoxyphenyl)-1H-pyrazolo[3,4-d]pyrimidin-1-yl)piperidine-1-carbonyl)piperidin-4-yl)ethyl)piperidin-1-yl)-1-oxoisoindolin-2-yl)piperidine-2,6-dione | 850.43 | C | B | B | A |
| 103 | 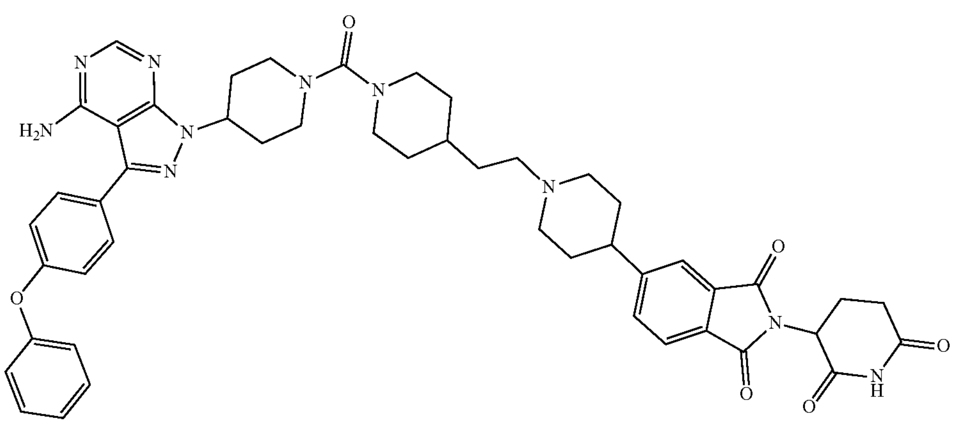 [SMILES: Nc1ncnc2c1c(-c1ccc(Oc3ccccc3)cc1)nn2C1CCN(C(=O)N2CCC(CCN3CCC(c4ccc5c(c4)C(=O)N(C4CCC(=O)NC4=O)C5=O)CC3)CC2)CC1] | 5-(1-(2-(1-(4-(4-amino-3-(4-phenoxyphenyl)-1H-pyrazolo[3,4-d]pyrimidin-1-yl)piperidine-1-carbonyl)piperidin-4-yl)ethyl)piperidin-4-yl)-2-(2,6-dioxopiperidin-3-yl)isoindoline-1,3-dione | 864.41 | B | C | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 104 | 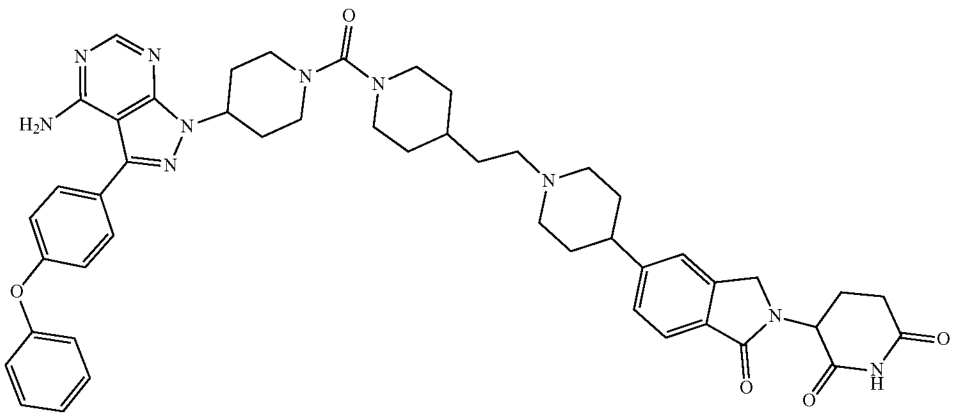 [SMILES: Nc1ncnc2c1c(-c1ccc(Oc3ccccc3)cc1)nn2C1CCN(C(=O)N2CCC(CCN3CCC(c4ccc5c(c4)CN(C4CCC(=O)NC4=O)C5=O)CC3)CC2)CC1] | 3-(5-(1-(2-(1-(4-(4-amino-3-(4-phenoxyphenyl)-1H-pyrazolo[3,4-d]pyrimidin-1-yl)piperidine-1-carbonyl)piperidin-4-yl)ethyl)piperidin-4-yl)-1-oxoisoindolin-2-yl)piperidine-2,6-dione | 850.43 | B | B | B | A |
| 105 | 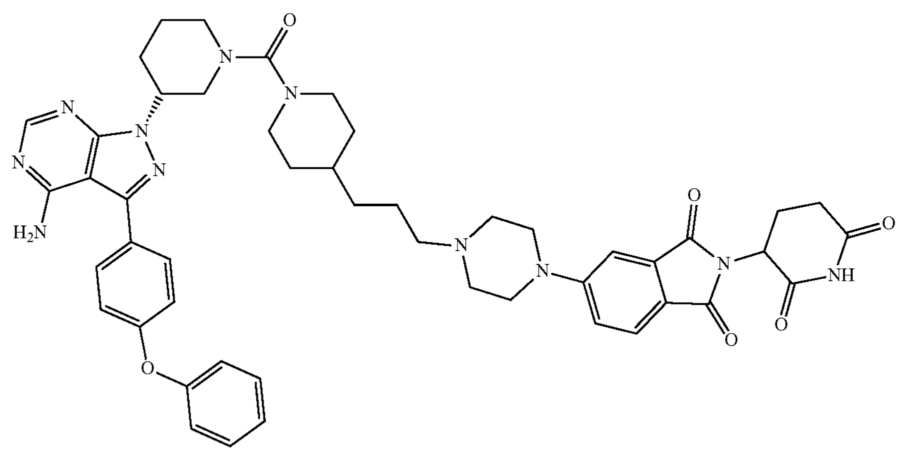 | 5-(4-(3-(1-((R)-3-(4-amino-3-(4-phenoxyphenyl)-1H-pyrazolo[3,4-d]pyrimidin-1-yl)piperidine-1-carbonyl)piperidin-4-yl)propyl)piperazin-1-yl)-2-(2,6-dioxopiperidin-3-yl)isoindoline-1,3-dione | 879.42 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 106 | 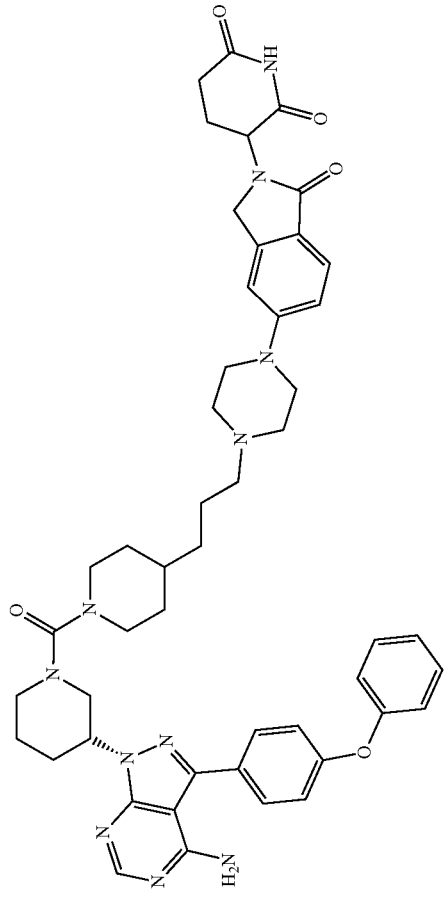 | 3-(5-(4-(3-(1-((R)-3-(4-amino-3-(4-phenoxyphenyl)-1H-pyrazolo[3,4-d]pyrimidin-1-yl)piperidin-1-carbonyl)piperidin-4-yl)propyl)piperazin-1-yl)-1-oxoisoindolin-2-yl)piperidine-2,6-dione | 865.44 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 107 | 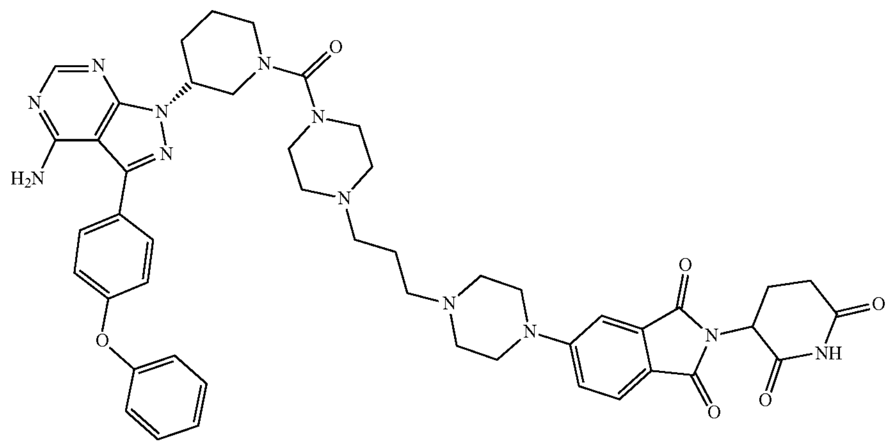 | 5-(4-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperazin-1-yl)-2-(2,6-dioxopiperidin-3-yl)isoindoline-1,3-dione | 880.41 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 108 | 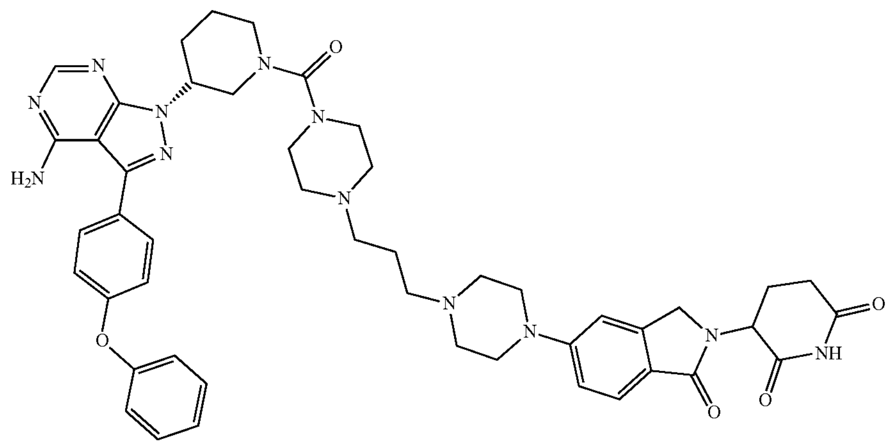 | 3-(5-(4-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperazin-1-yl)-1-oxoisoindolin-2-yl)piperidine-2,6-dione | 866.43 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 109 | 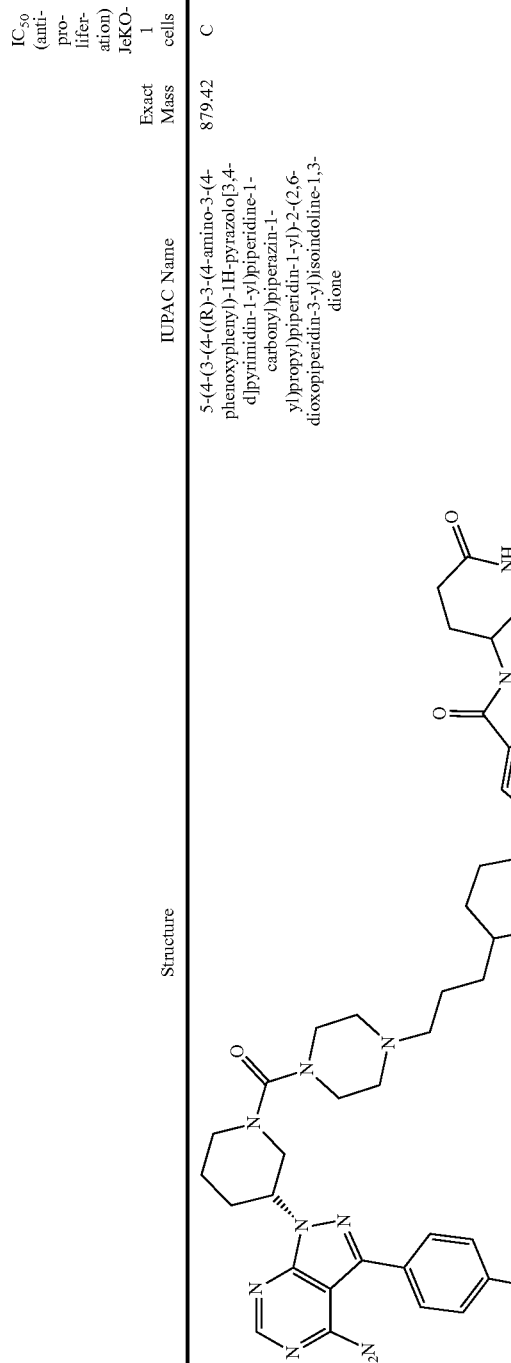 | 5-(4-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperidin-1-yl)-2-(2,6-dioxopiperidin-3-yl)isoindoline-1,3-dione | 879.42 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 110 | 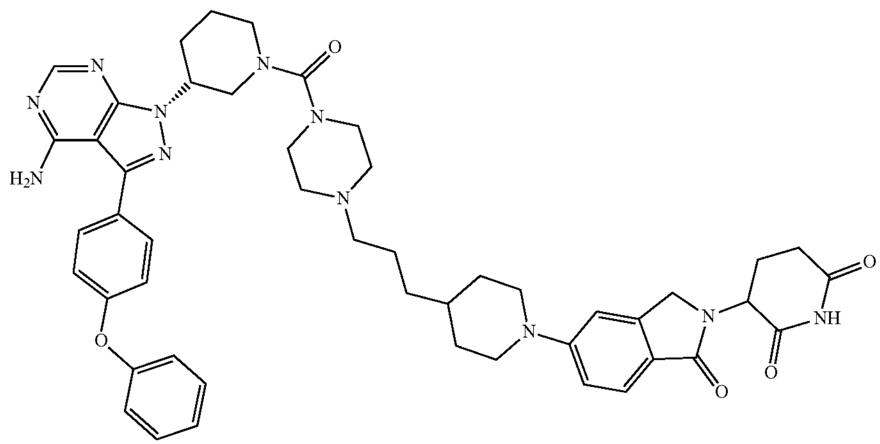 | 3-(5-(4-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperidin-1-yl)-1-oxoisoindolin-2-yl)piperidine-2,6-dione | 865.44 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 111 | 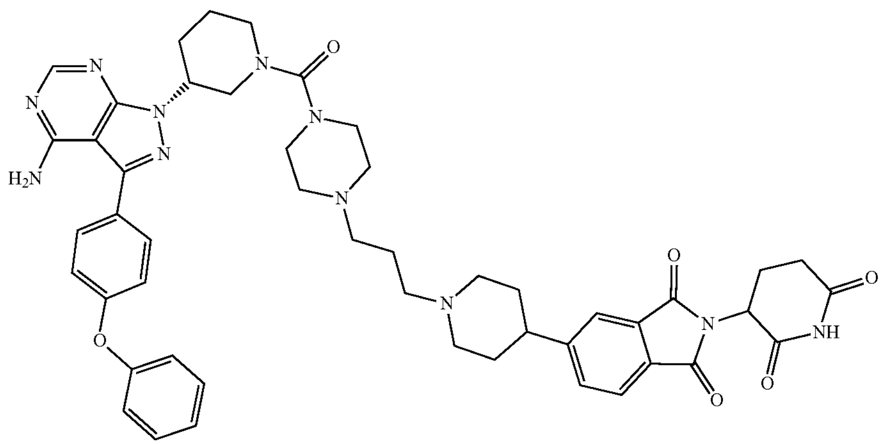 | 5-(1-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperidin-4-yl)-2-(2,6-dioxopiperidin-3-yl)isoindoline-1,3-dione | 879.42 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 112 | 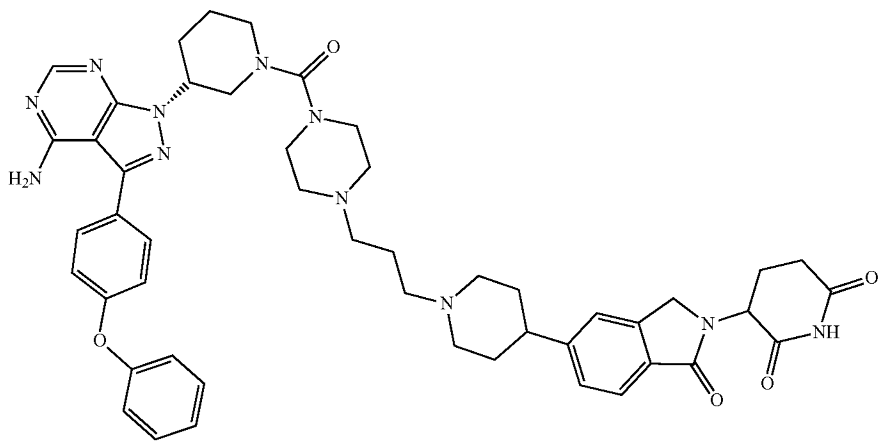 | 3-(5-(1-(3-(4-((R)-3-(4-amino-3-(4-phenoxyphenyl)-1H-pyrazolo[3,4-d]pyrimidin-1-yl)piperidine-1-carbonyl)piperazin-1-yl)propyl)piperidin-4-yl)-1-oxoisoindolin-2-yl)piperidine-2,6-dione | 865.44 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 113 | 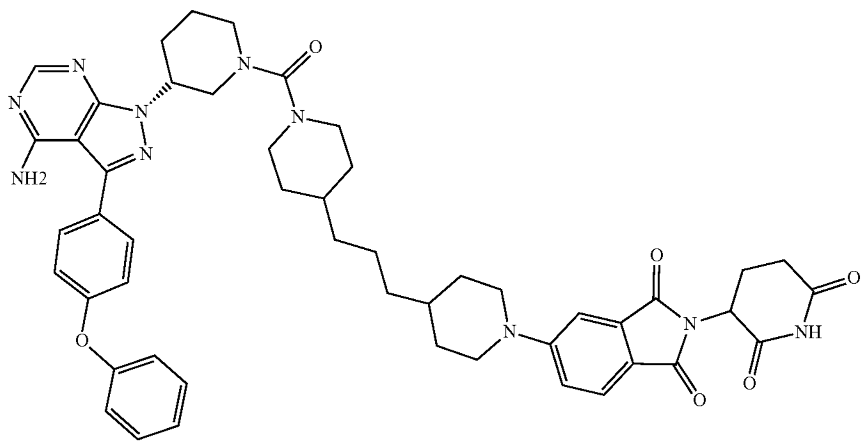 | 5-(4-(3-(1-((R)-3-(4-amino-3-(4-phenoxyphenyl)-1H-pyrazolo[3,4-d]pyrimidin-1-yl)piperidine-1-carbonyl)piperidin-4-yl)propyl)piperidin-1-yl)-2-(2,6-dioxopiperidin-3-yl)isoindoline-1,3-dione | 878.42 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 114 | 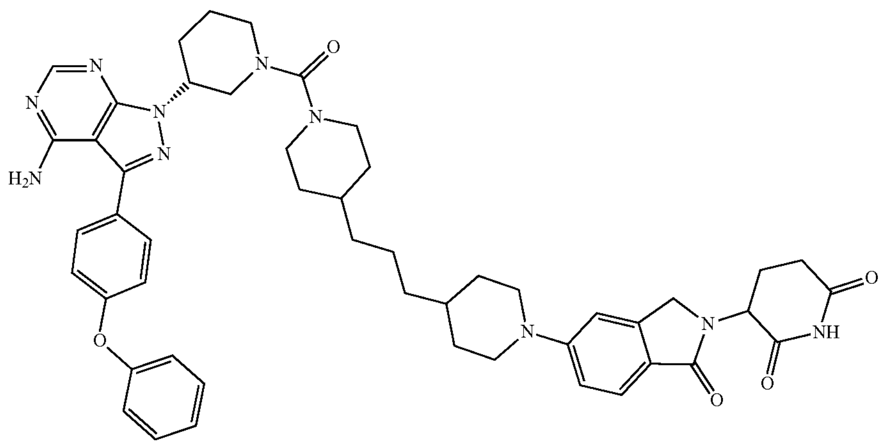 | 3-(5-(4-(3-(1-((R)-3-(4-amino-3-(4-phenoxyphenyl)-1H-pyrazolo[3,4-d]pyrimidin-1-yl)piperidine-1-carbonyl)piperidin-4-yl)propyl)piperidin-1-yl)-2-(2,6-dioxopiperidin-3-yl)isoindoline-1,3-dione | 864.44 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 115 | 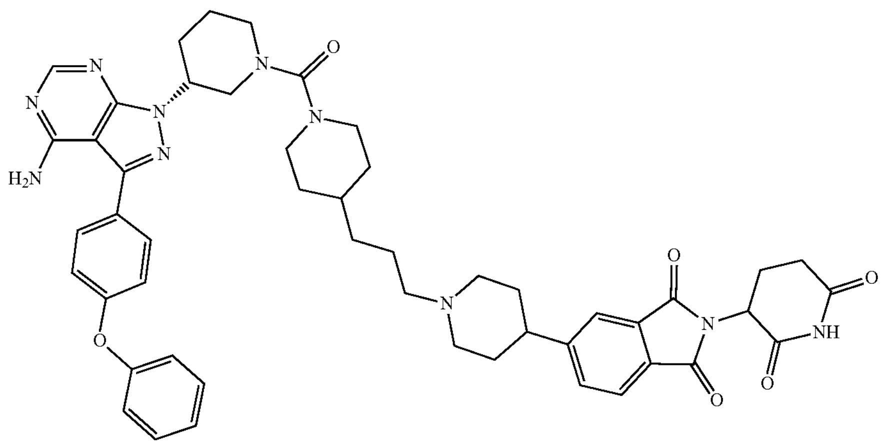 | 5-(1-(3-((1-((R)-3-(4-amino-3-(4-phenoxyphenyl)-1H-pyrazolo[3,4-d]pyrimidin-1-yl)piperidine-1-carbonyl)piperidin-4-yl)propyl)piperidin-4-yl)-2-(2,6-dioxopiperidin-3-yl)isoindoline-1,3-dione | 878.42 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | $IC_{50}$ (antiproliferation) JeKO-1 cells | $IC_{50}$ (antiproliferation) Mino cells | $DC_{50}$ | $D_{max}$ |
|---|---|---|---|---|---|---|---|
| 116 | 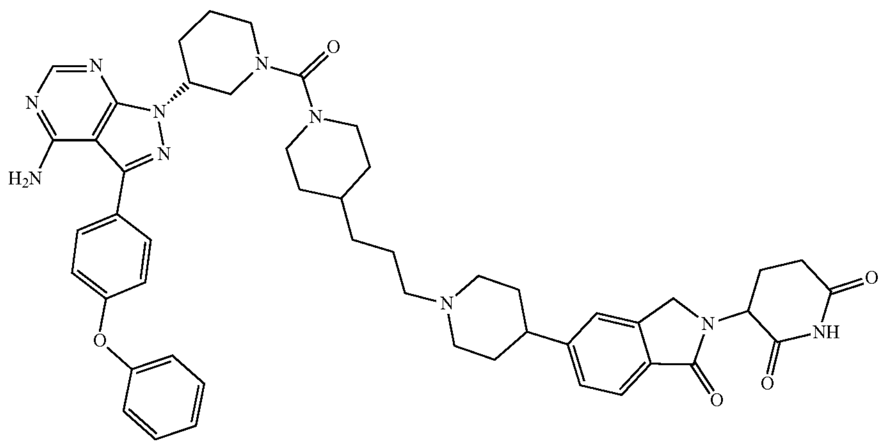 | 3-(5-(1-(3-(1-((R)-3-(4-amino-3-(4-phenoxyphenyl)-1H-pyrazolo[3,4-d]pyrimidin-1-yl)piperidine-1-carbonyl)piperidin-4-yl)propyl)piperidin-4-yl)-1-oxoisoindolin-2-yl)piperidine-2,6-dione | 864.44 | C | C | C | B |
| 117 | 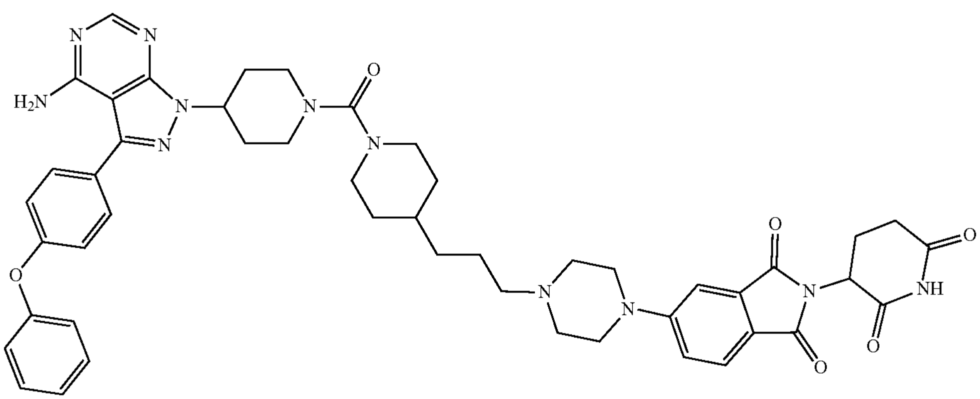 [SMILES: Nc1ncnc2c1c(-c1ccc(Oc3ccccc3)cc1)nn2C1CCN(C(=O)N2CCC(CCCN3CCN(c4ccc5c(c4)C(=O)N(C4CCC(=O)NC4=O)C5=O)CC3)CC2)CC1] | 5-(4-(3-(1-(4-(4-amino-3-(4-phenoxyphenyl)-1H-pyrazolo[3,4-d]pyrimidin-1-yl)piperidine-1-carbonyl)-piperidin-4-yl)propyl)piperazin-1-yl)-2-(2,6-dioxopiperidin-3-yl)isoindoline-1,3-dione | 879.42 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 118 | 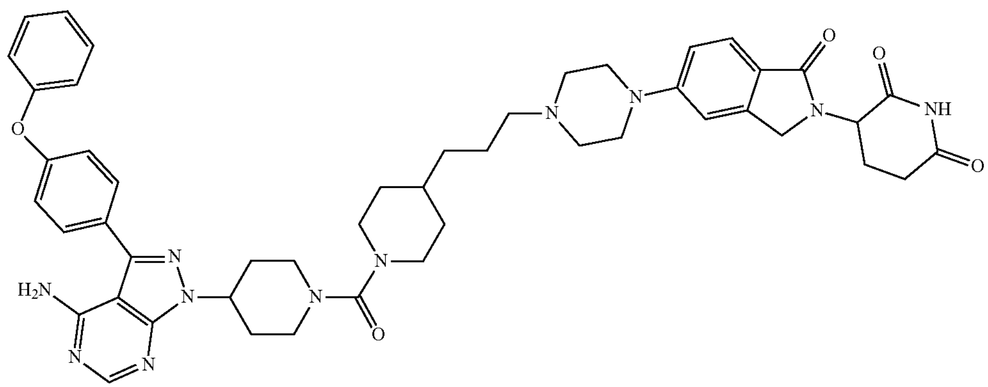 [SMILES: Nc1ncnc2c1c(-c1ccc(Oc3ccccc3)cc1)nn2C1CCN(C(=O)N2CCC(CCCN3CCN(c4ccc5c(c4)CN(C4CCC(=O)NC4=O)C5=O)CC3)CC2)CC1] | 3-(5-(4-(3-(4-(4-amino-3-(4-phenoxyphenyl)-1H-pyrazolo[3,4-d]pyrimidin-1-yl)piperidine-1-carbonyl)piperidin-4-yl)propyl)piperazin-1-yl)-1-oxoisoindolin-2-yl)piperidine-2,6-dione | 865.44 | B | C | C | B |
| 119 | 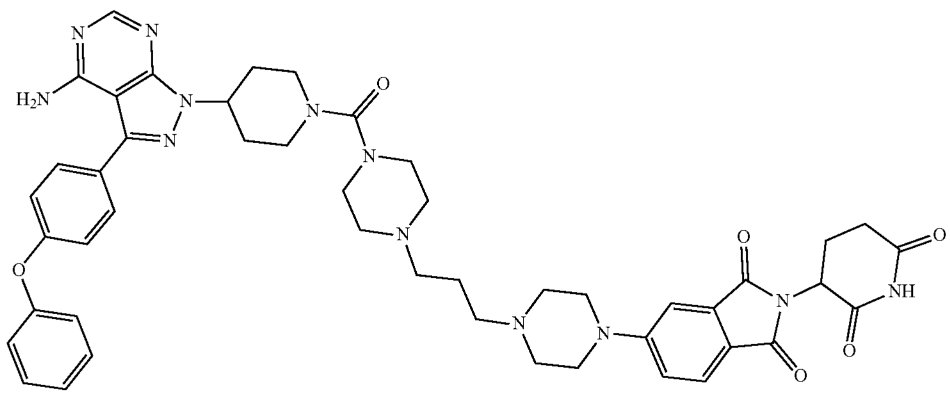 [SMILES: Nc1ncnc2c1c(-c1ccc(Oc3ccccc3)cc1)nn2C1CCN(C(=O)N2CCN(CCCN3CCN(c4ccc5c(c4)C(=O)N(C4CCC(=O)NC4=O)C5=O)CC3)CC2)CC1] | 5-(4-(3-(4-(4-(4-amino-3-(4-phenoxyphenyl)-1H-pyrazolo[3,4-d]pyrimidin-1-yl)piperidine-1-carbonyl)piperazin-1-yl)propyl)piperazin-1-yl)-2-(2,6-dioxopiperidin-3-yl)isoindoline-1,3-dione | 880.41 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 120 | 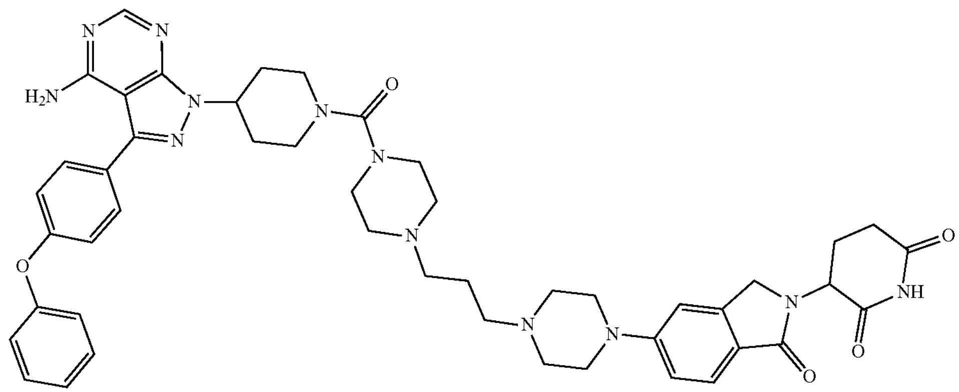 [SMILES: Nc1ncnc2c1c(-c1ccc(Oc3ccccc3)cc1)nn2C1CCN(C(=O)N2CCN(CCCN3CCN(c4ccc5c(c4)CN(C4CCC(=O)NC4=O)C5=O)CC3)CC2)CC1] | 3-(5-(4-(3-(4-(4-amino-3-(4-phenoxyphenyl)-1H-pyrazolo[3,4-d]pyrimidin-1-yl)piperidine-1-carbonyl)piperazin-1-yl)propyl)piperazin-1-yl)-1-oxoisoindolin-2-yl)piperidine-2,6-dione | 866.43 | C | C | C | B |
| 121 | 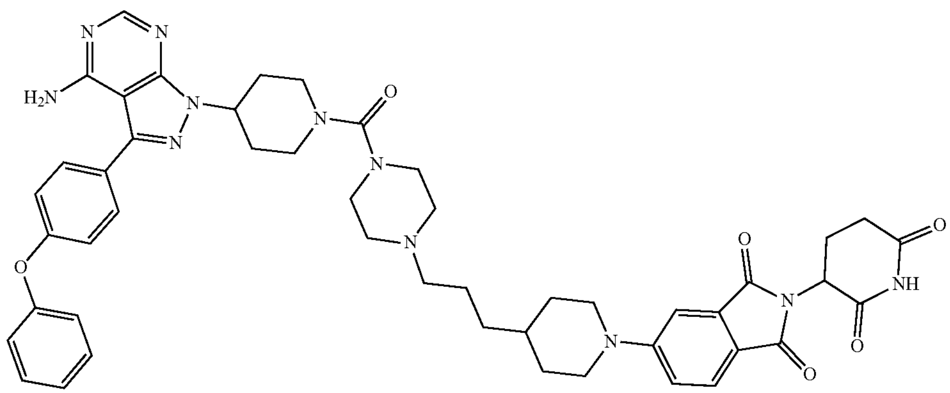 [SMILES: Nc1ncnc2c1c(-c1ccc(Oc3ccccc3)cc1)nn2C1CCN(C(=O)N2CCN(CCCC3CCN(c4ccc5c(c4)C(=O)N(C4CCC(=O)NC4=O)C5=O)CC3)CC2)CC1] | 5-(4-(3-(4-(4-amino-3-(4-phenoxyphenyl)-1H-pyrzolo[3,4-d]pyrimidin-1-yl)piperidine-1-carbonyl)piperazin-1-yl)propyl)piperidin-1-yl)-2-(2,6-dioxopiperidin-3-yl)isoindoline-1,3-dione | 879.42 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 122 | 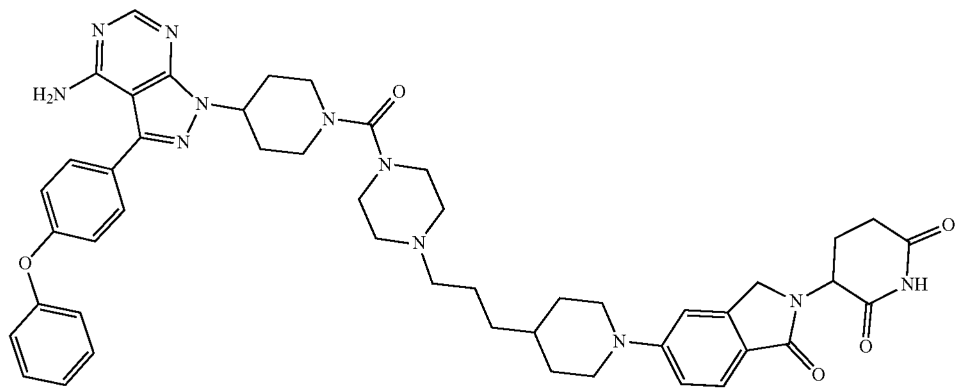 [SMILES: Nc1ncnc2c1c(-c1ccc(Oc3ccccc3)cc1)nn2C1CCN(C(=O)N2CCN(CCCC3CCN(c4ccc5c(c4)CN(C4CCC(=O)NC4=O)C5=O)CC3)CC2)CC1] | 3-(5-(4-(3-(4-(4-(4-amino-3-(4-phenoxyphenyl)-1H-pyrazolo[3,4-d]pyrimidin-1-yl)piperidine-1-carbonyl)piperazin-1-yl)propyl)piperidin-1-yl)-1-oxoisoindolin-2-yl)piperidine-2,6-dione | 865.44 | B | B | C | B |
| 123 | 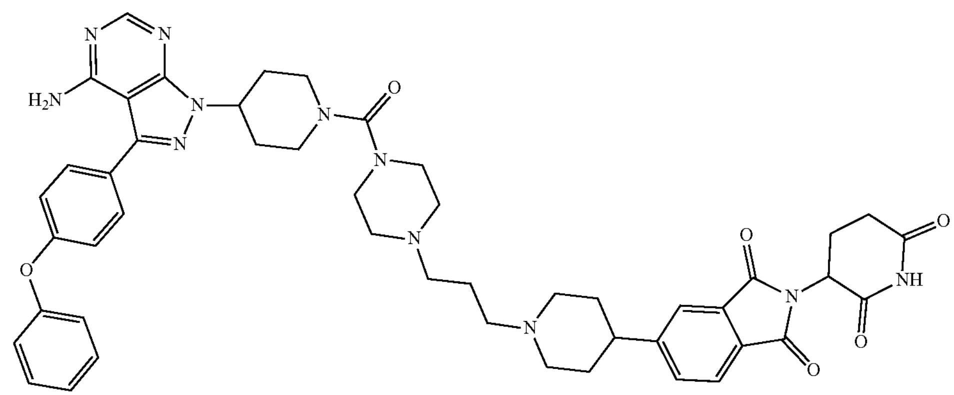 [SMILES: Nc1ncnc2c1c(-c1ccc(Oc3ccccc3)cc1)nn2C1CCN(C(=O)N2CCN(CCCN3CCC(c4ccc5c(c4)C(=O)N(C4CCC(=O)NC4=O)C5=O)CC3)CC2)CC1] | 5-(1-(3-(4-(4-(4-amino-3-(4-phenoxyphenyl)-1H-pyrazolo[3,4-d]pyrimidin-1-yl)piperidine-1-carbonyl)piperazin-1-yl)propyl)piperidin-4-yl)-2-(2,6-dioxopiperidin-3-yl)isoindoline-1,3-dione | 879.42 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 124 | 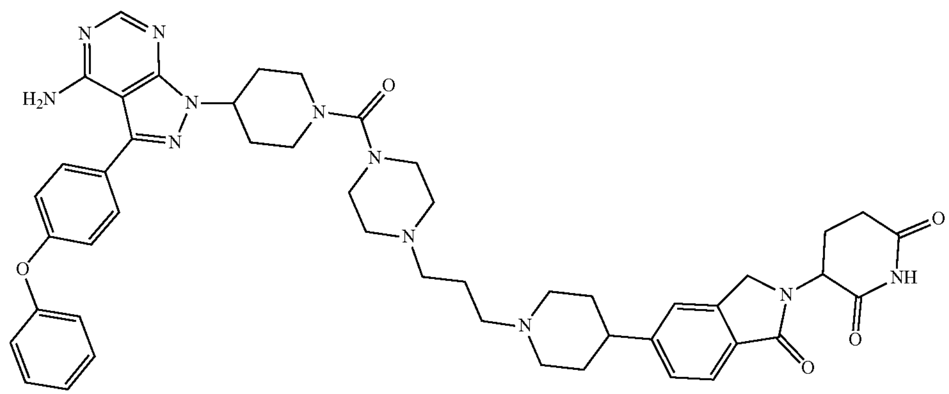 [SMILES: Nc1ncnc2c1c(-c1ccc(Oc3ccccc3)cc1)nn2C1CCN(C(=O)N2CCN(CCCN3CCC(c4ccc5c(c4)CN(C4CCC(=O)NC4=O)C5=O)CC3)CC2)CC1] | 3-(5-(1-(3-(4-(4-(4-amino-3-(4-phenoxyphenyl)-1H-pyrazolo[3,4-d]pyrimidin-1-yl)piperidine-1-carbonyl)piperazin-1-yl)propyl)piperidin-4-yl)-1-oxoisoindolin-2-yl)piperidine-2,6-dione | 865.44 | C | C | C | A |
| 125 | 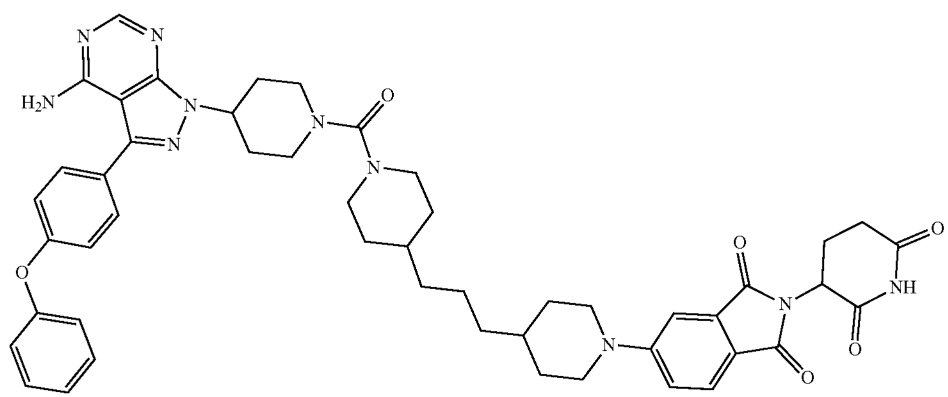 [SMILES: Nc1ncnc2c1c(-c1ccc(Oc3ccccc3)cc1)nn2C1CCN(C(=O)N2CCC(CCCC3CCN(c4ccc5c(c4)C(=O)N(C4CCC(=O)NC4=O)C5=O)CC3)CC2)CC1] | 5-(4-(3-(1-(4-(4-amino-3-(4-phenoxyphenyl)-1H-pyrazolo[3,4-d]pyrimidin-1-yl)piperidine-1-carbonyl)piperidin-4-yl)propyl)piperidin-1-yl)-2-(2,6-dioxopiperidin-3-yl)isoindoline-1,3-dione | 878.42 | B | C | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 126 | 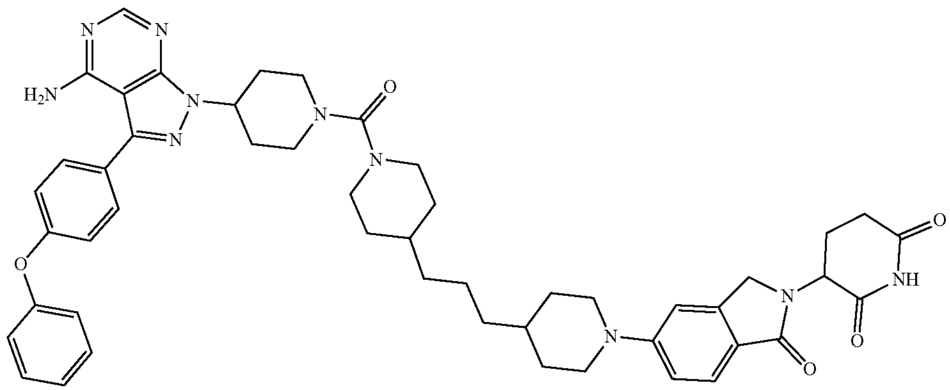 [SMILES: Nc1ncnc2c1c(-c1ccc(Oc3ccccc3)cc1)nn2C1CCN(C(=O)N2CCC(CCCC3CCN(c4ccc5c(c4)CN(C4CCC(=O)NC4=O)C5=O)CC3)CC2)CC1] | 3-(5-(4-(3-(1-(4-(4-amino-3-(4-phenoxyphenyl)-1H-pyrazolo[3,4-d]pyrimidin-1-yl)piperidine-1-carbonyl)piperidin-4-yl)propyl)piperidin-1-yl)-1-oxoisoindolin-2-yl)piperidine-2,6-dione | 864.44 | C | B | C | A |
| 127 | 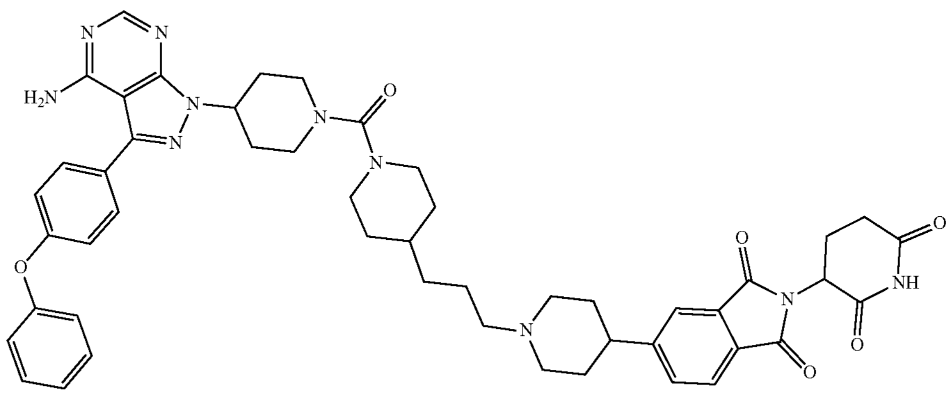 [SMILES: Nc1ncnc2c1c(-c1ccc(Oc3ccccc3)cc1)nn2C1CCN(C(=O)N2CCC(CCCN3CCC(c4ccc5c(c4)C(=O)N(C4CCC(=O)NC4=O)C5=O)CC3)CC2)CC1] | 5-(1-(3-(1-(4-(4-amino-3-(4-phenoxyphenyl)-1H-pyrazolo[3,4-d]pyrimidin-1-yl)piperidine-1-carbonyl)piperidin-4-yl)propyl)piperidin-4-yl)-2-(2,6-dioxopiperidin-3-yl)isoindoline-1,3-dione | 878.42 | C | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 128 | 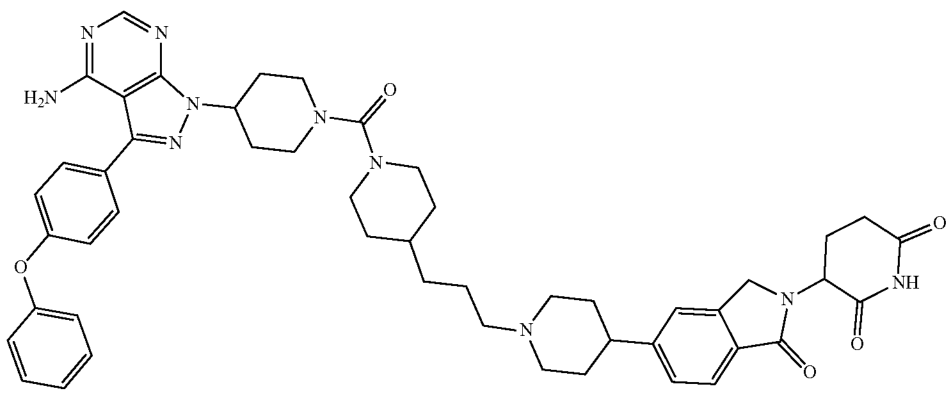 [SMILES: Nc1ncnc2c1c(-c1ccc(Oc3ccccc3)cc1)nn2C1CCN(C(=O)N2CCC(CCCN3CCC(c4ccc5c(c4)CN(C4CCC(=O)NC4=O)C5=O)CC3)CC2)CC1] | 3-(5-(1-(3-(1-(4-(4-amino-3-(4-phenoxyphenyl)-1H-pyrazolo[3,4-d]pyrimidin-1-yl)piperidine-1-carbonyl)piperidin-4-yl)propyl)piperidin-4-yl)-1-oxoisoindolin-2-yl)piperidine-2,6-dione | 864.44 | C | B | C | A |
| 129 | 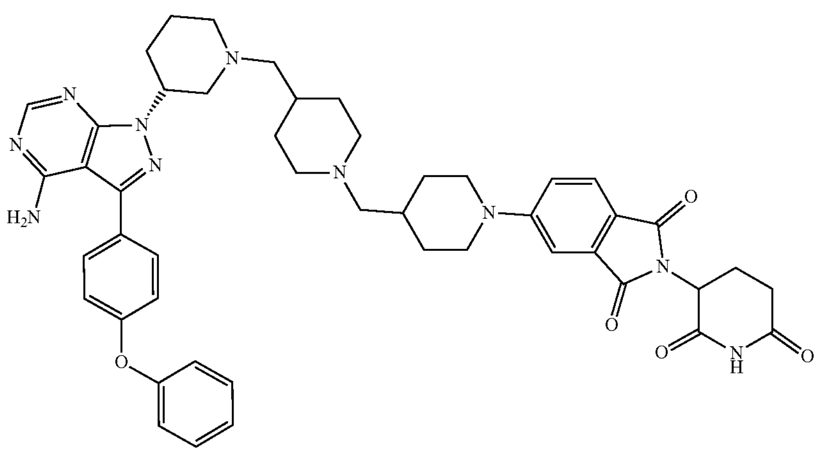 | 5-(4-(((R)-3-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-2-(2,6-dioxopiperidin-3-yl)isoindoline-1,3-dione | 836.41 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 130 | 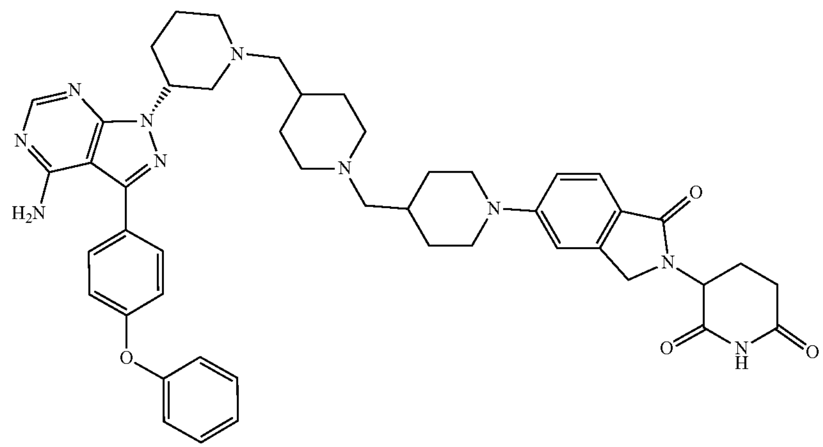 | 3-(5-(4-((4-((R)-3-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-1-oxoisoindolin-2-yl)piperidine-2,6-dione | 822.43 | B | B | B | A |
| 131 | 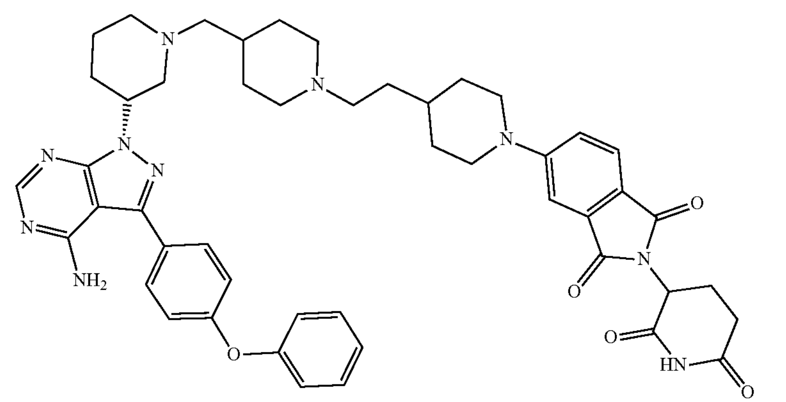 | 5-(4-(2-(4-((R)-3-(4-amino-3-(4-phenoxyphenyl)-1H-pyrazolo[3,4-d]pyrimidin-1-yl)piperidin-1-yl)ethyl)piperidin-1-yl)methyl)piperidin-1-yl)-2-(2,6-dioxopiperidin-3-yl)isoindoline-1,3-dione | 850.43 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 132 | 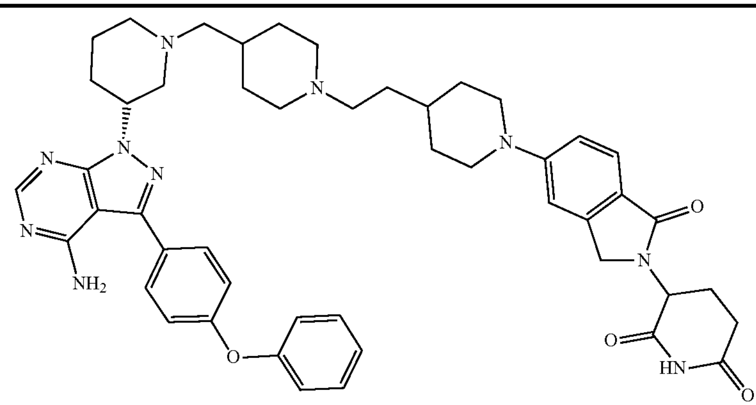 | 3-(5-(4-(2-(4-(((R)-3-(4-amino-3-(4-phenoxyphenyl)-1H-pyrazolo[3,4-d]pyrimidin-1-yl)piperidin-1-yl)methyl)piperidin-1-yl)ethyl)piperidin-1-yl)-1-oxoisoindolin-2-yl)piperidine-2,6-dione | 836.45 | B | B | B | A |
| 133 | 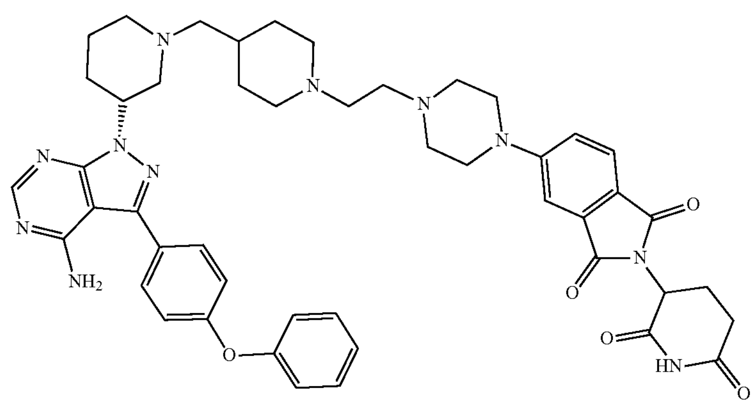 | 5-(4-(2-(4-(((R)-3-(4-amino-3-(4-phenoxyphenyl)-1H-pyrazolo[3,4-d]pyrimidin-1-yl)piperidin-1-yl)methyl)piperidin-1-yl)ethyl)piperazin-1-yl)-2-(2,6-dioxopiperidin-3-yl)isoindoline-1,3-dione | 851.42 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 134 | 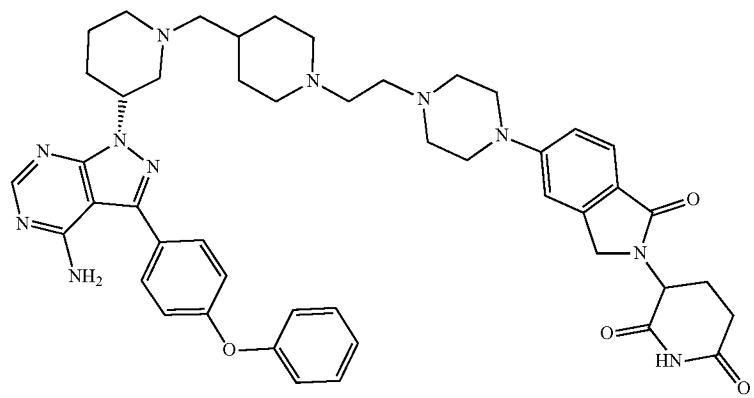 | 3-(5-(4-(2-(4-(((R)-3-(4-amino-3-(4-phenoxyphenyl)-1H-pyrazolo[3,4-d]pyrimidin-1-yl)piperidin-1-yl)methyl)piperidin-1-yl)ethyl)piperazin-1-yl)-1-oxoisoindolin-2-yl)piperidine-2,6-dione | 837.44 | B | B | B | B |
| 135 | 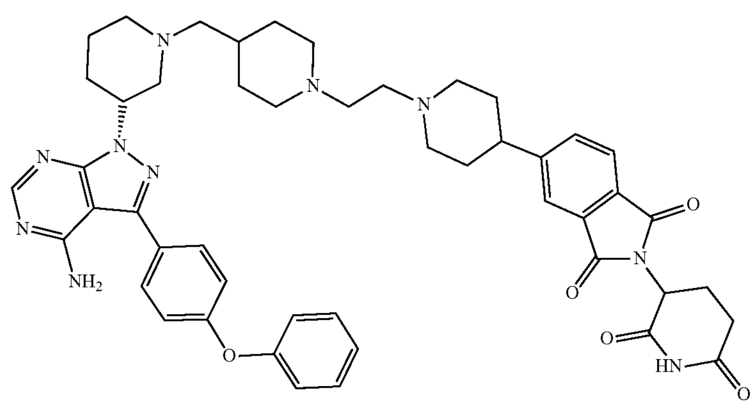 | 5-(1-(2-(4-(((R)-3-(4-amino-3-(4-phenoxyphenyl)-1H-pyrazolo[3,4-d]pyrimidin-1-yl)piperidin-1-yl)methyl)piperidin-4-yl)ethyl)piperidin-4-yl)-2-(2,6-dioxopiperidin-3-yl)isoindoline-1,3-dione | 850.43 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 136 | 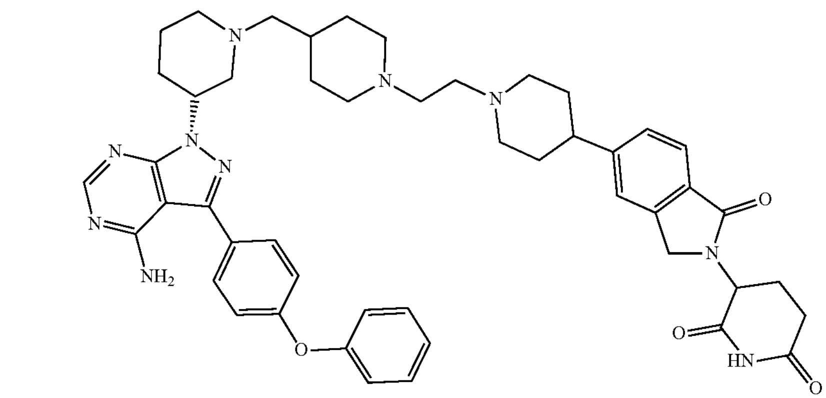 | 3-(5-(1-(2-(4-(4-(((R)-3-(4-amino-3-(4-phenoxyphenyl)-1H-pyrazolo[3,4-d]pyrimidin-1-yl)piperidin-1-yl)methyl)piperidin-1-yl)ethyl)piperidin-4-yl)-1-oxoisoindolin-2-yl)piperidine-2,6-dione | 836.45 | B | A | A | B |
| 137 | 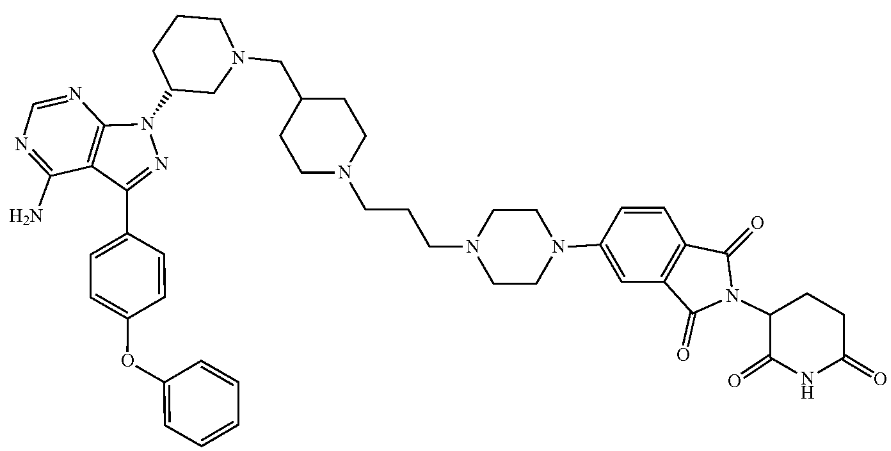 | 5-(4-(3-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperazin-1-yl)-2-(2,6-dioxopiperidin-3-yl)isoindoline-1,3-dione | 865.44 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 138 | 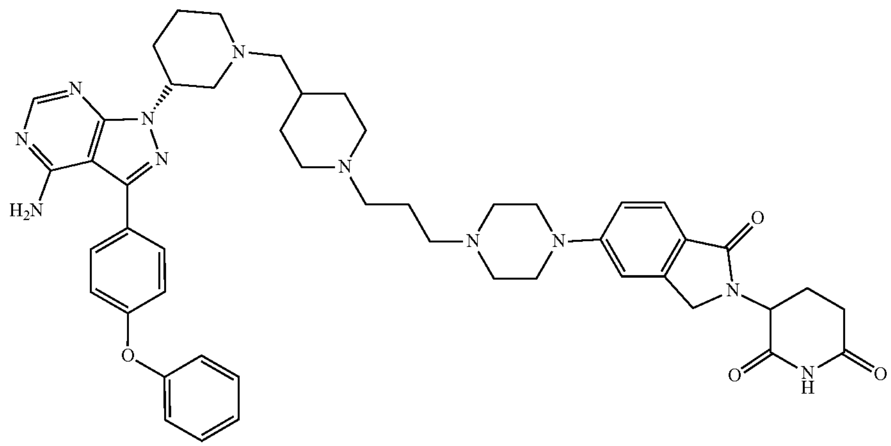 | 3-(5-(4-(3-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperazin-1-yl)-1-oxoisoindolin-2-yl)piperidine-2,6-dione | 851.46 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 139 | 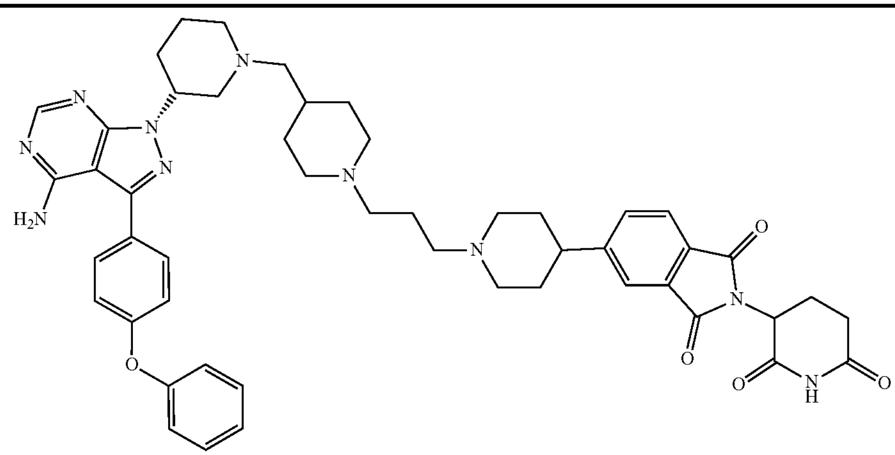 | 5-(1-(3-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperidin-4-yl)-2-(2,6-dioxopiperidin-3-yl)isoindoline-1,3-dione | 864.44 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 140 | 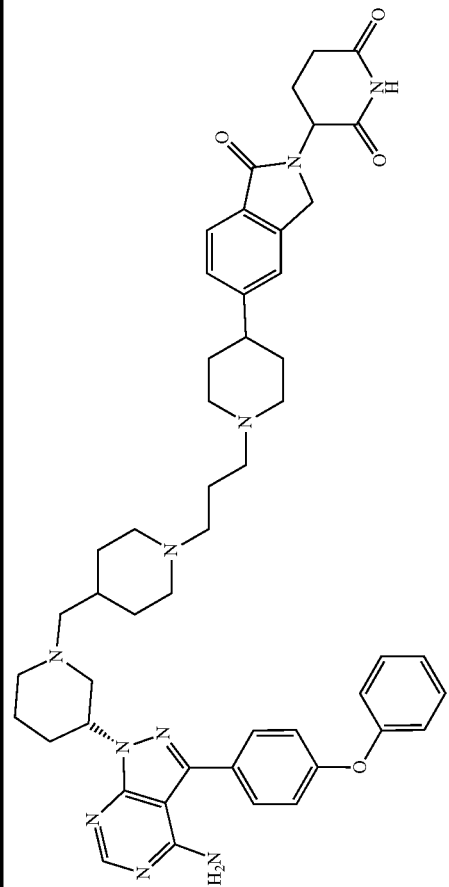 | 3-(5-(1-(3-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperidin-4-yl)-1-oxoisoindolin-2-yl)piperidine-2,6-dione | 850.46 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 141 | 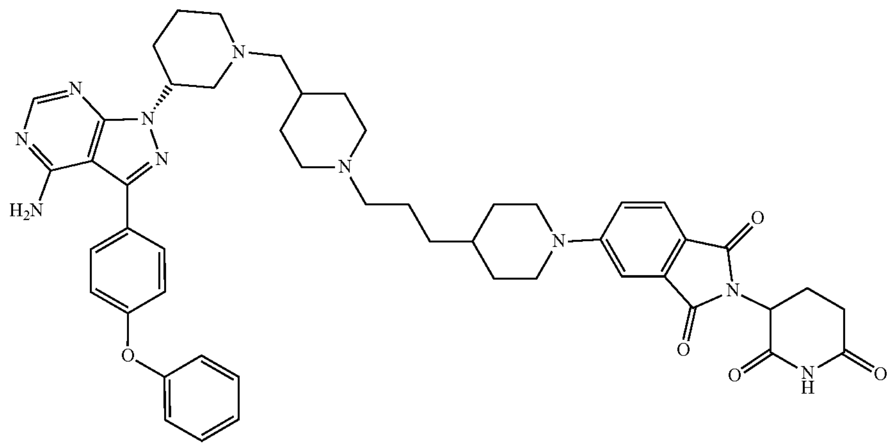 | 5-(4-(3-(4-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperidin-1-yl)-2-(2,6-dioxopiperidin-3-yl)isoindoline-1,3-dione | 864.44 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 142 | 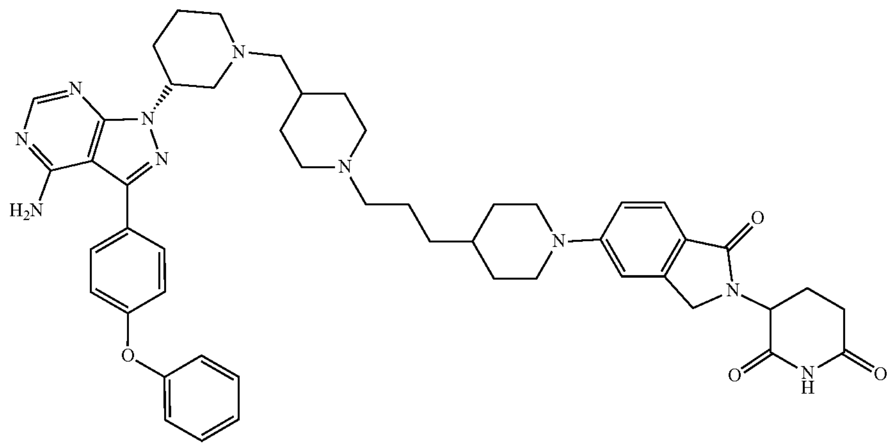 | 3-(5-(4-(3-(4-(((R)-3-(4-amino-3-(4-phenoxyphenyl)-1H-pyrazolo[3,4-d]pyrimidin-1-yl)piperidin-1-yl)methyl)piperidin-1-yl)propyl)piperidin-1-yl)-1-oxoisoindolin-2-yl)piperidine-2,6-dione | 850.46 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 143 | 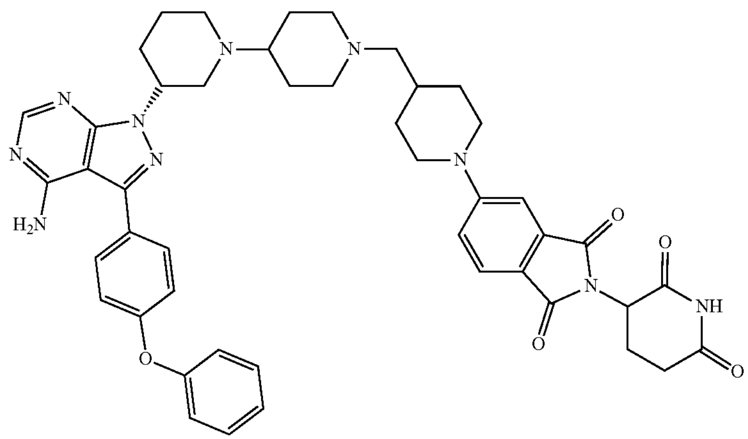 | 5-(4-((R)-3-(4-amino-3-(4-phenoxyphenyl)-1H-pyrazolo[3,4-d]pyrimidin-1-yl)-[1,4'-bipiperidin]-1'-yl)methyl)piperidin-1-yl)-2-(2,6-dioxopiperidin-3-yl)isoindoline-1,3-dione | 822.40 | C | C | B | A |
| 144 | 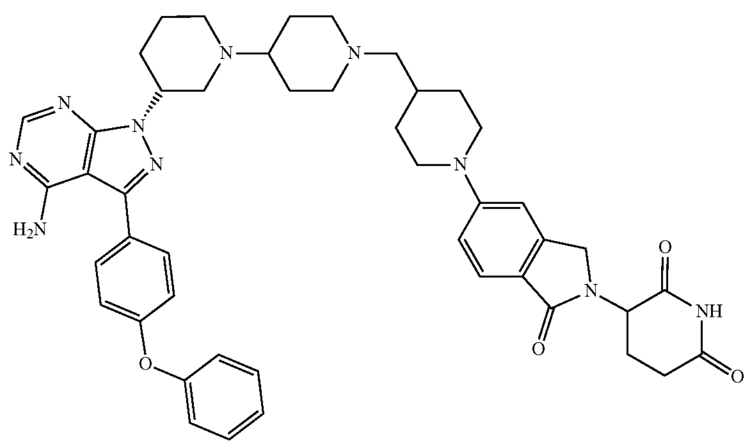 | 3-(5-(4-((R)-3-(4-amino-3-(4-phenoxyphenyl)-1H-pyrazolo[3,4-d]pyrimidin-1-yl)-[1,4'-bipiperidin]-1'-yl)methyl)piperidin-1-yl)-1-oxoisoindolin-2-yl)piperidine-2,6-dione | 808.42 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 145 | 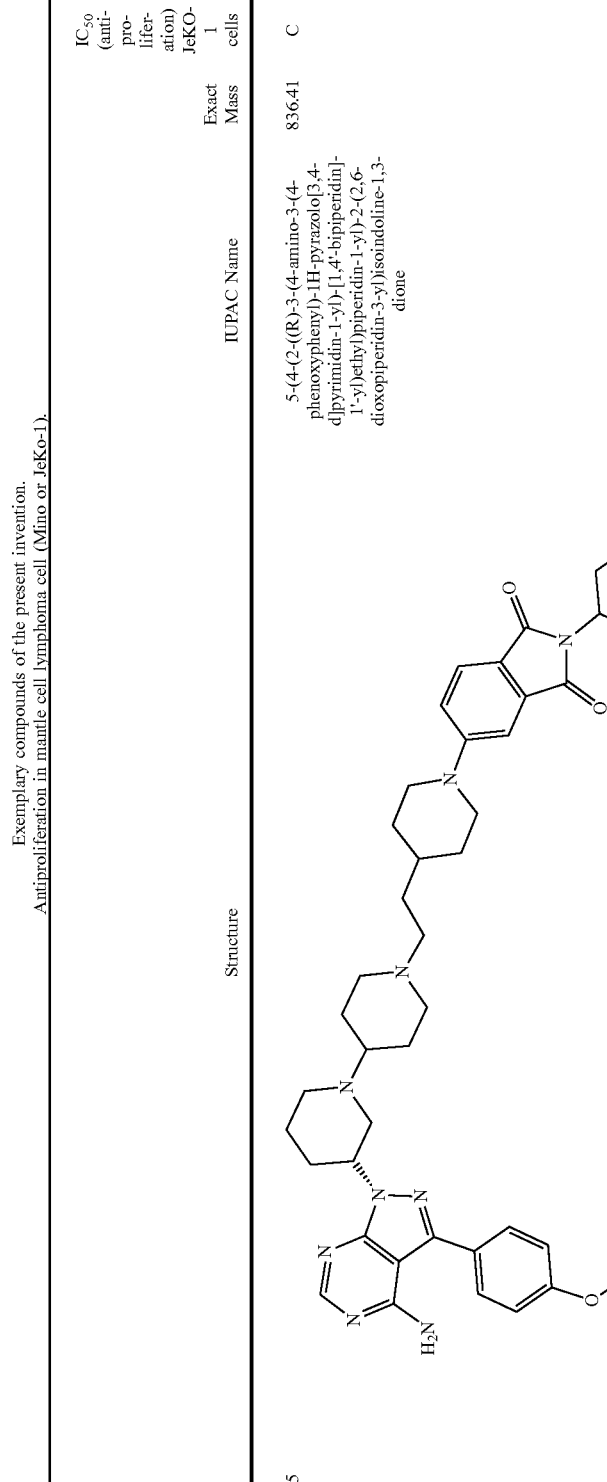 | 5-(4-(2-((R)-3-(4-amino-3-(4-phenoxyphenyl)-1H-pyrazolo[3,4-d]pyrimidin-1-yl)-[1,4'-bipiperidin]-1'-yl)ethyl)piperidin-1-yl)-2-(2,6-dioxopiperidin-3-yl)isoindoline-1,3-dione | 836.41 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 146 | 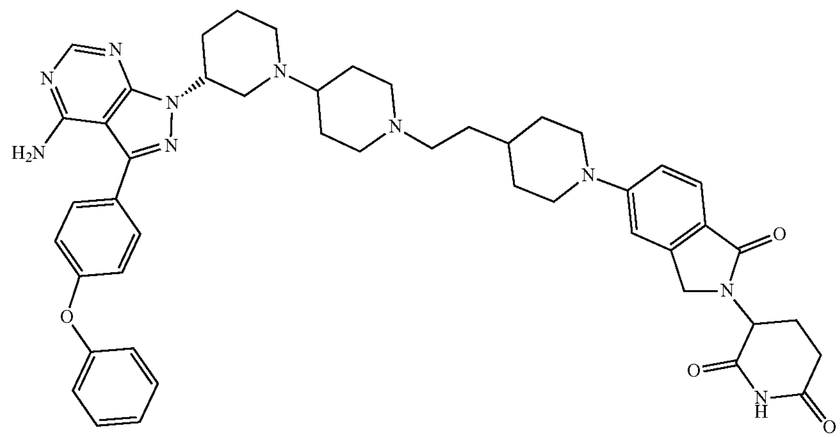 | 3-(5-(4-(2-((R)-3-(4-amino-3-(4-phenoxyphenyl)-1H-pyrazolo[3,4-d]pyrimidin-1-yl)-[1,4'-bipiperidin]-1'-yl)ethyl)piperidin-1-yl)-1-oxoisoindolin-2-yl)piperidine-2,6-dione | 822.43 | C | B | C | B |
| 147 | 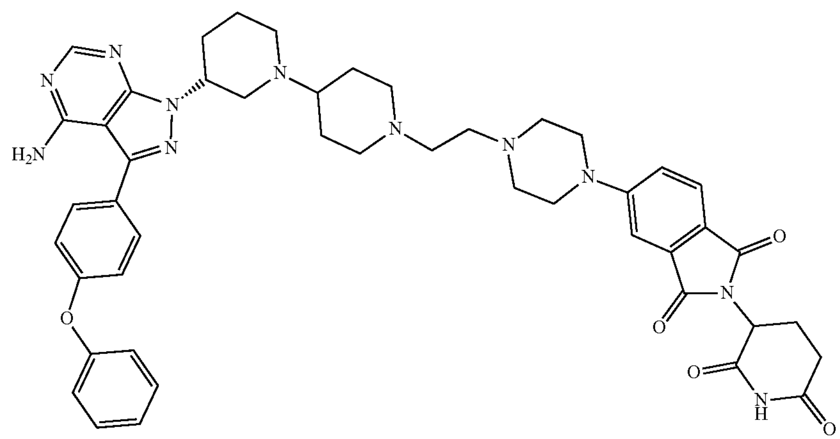 | 5-(4-(2-((R)-3-(4-amino-3-(4-phenoxyphenyl)-1H-pyrazolo[3,4-d]pyrimidin-1-yl)-[1,4'-bipiperidin]-1'-yl)ethyl)piperazin-1-yl)-2-(2,6-dioxopiperidin-3-yl)isoindoline-1,3-dione | 837.41 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 148 | 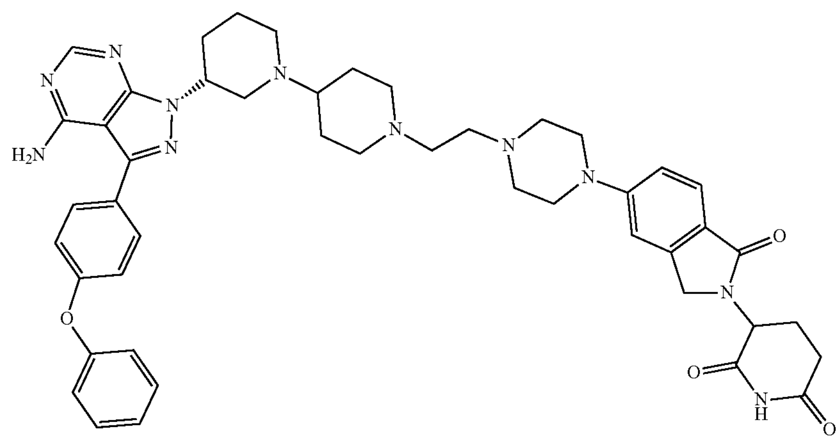 | 3-(5-(4-(2-((R)-3-(4-amino-3-(4-phenoxyphenyl)-1H-pyrazolo[3,4-d]pyrimidin-1-yl)-[1,4'-bipiperidin]-1'-yl)ethyl)piperazin-1-yl)-1-oxoisoindolin-2-yl)piperidine-2,6-dione | 823.43 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 149 | 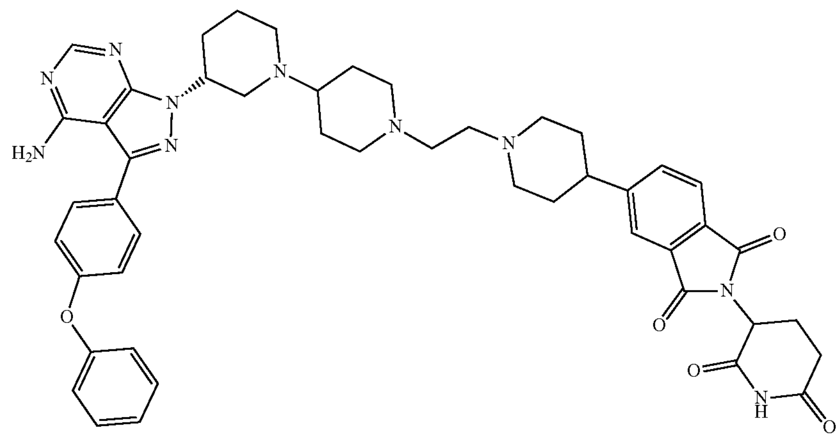 | 5-(1-(2-((R)-3-(4-amino-3-(4-phenoxyphenyl)-1H-pyrazolo[3,4-d]pyrimidin-1-yl)-[1,4'-bipiperidin]-1'-yl)ethyl)piperidin-4-yl)-2-(2,6-dioxopiperidin-3-yl)isoindoline-1,3-dione | 836.41 | C | B | B | A |
| 150 | 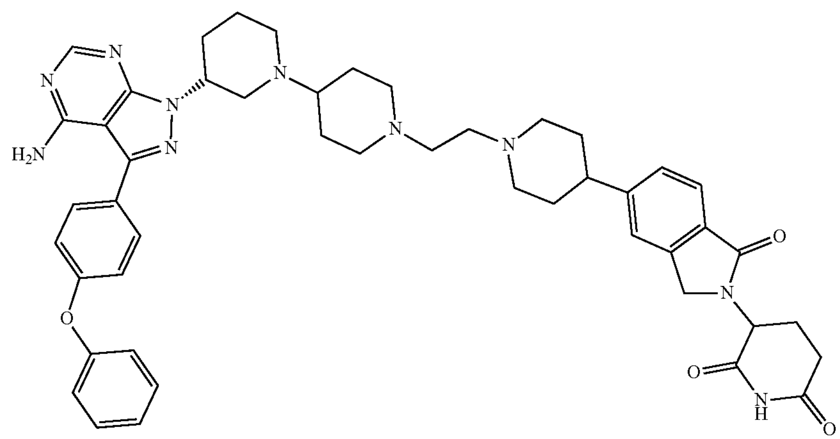 | 3-(5-(1-(2-((R)-3-(4-amino-3-(4-phenoxyphenyl)-1H-pyrazolo[3,4-d]pyrimidin-1-yl)-[1,4'-bipiperidin]-1'-yl)ethyl)piperidin-4-yl)-1-oxoisoindolin-2-yl)piperidine-2,6-dione | 822.43 | B | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 151 | 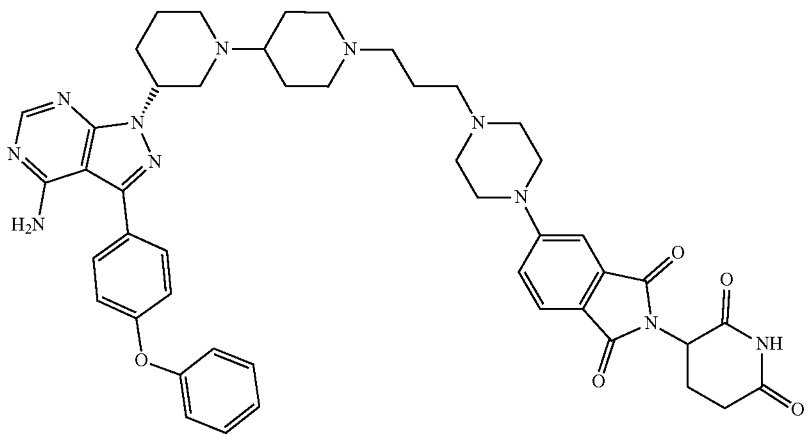 | 5-(4-(3-((R)-3-(4-amino-3-(4-phenoxyphenyl)-1H-pyrazolo[3,4-d]pyrimidin-1-yl)-[1,4'-bipiperidin]-1'-yl)propyl)piperazin-1-yl)-2-(2,6-dioxopiperidin-3-yl)isoindoline-1,3-dione | 851.42 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 152 | 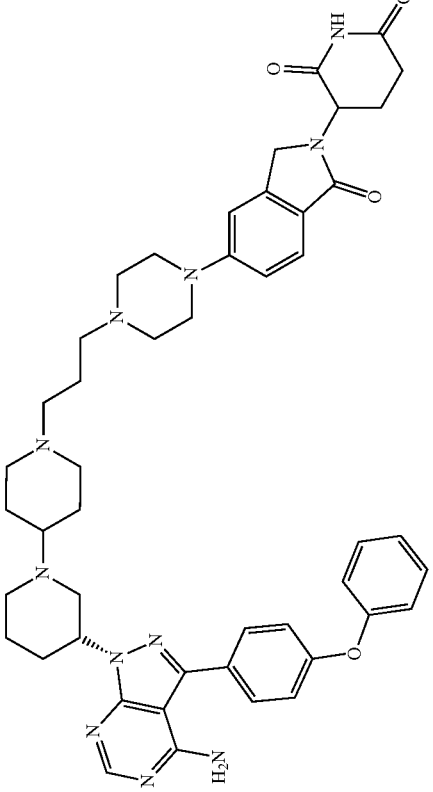 | 3-(5-(4-(3-((R)-3-(4-amino-3-(4-phenoxyphenyl)-1H-pyrazolo[3,4-d]pyrimidin-1-yl)-[1,4'-bipiperidin]-1'-yl)propyl)piperazin-1-yl)-1-oxoisoindolin-2-yl)piperidine-2,6-dione | 837.44 | C | C | C | B |
| 153 | 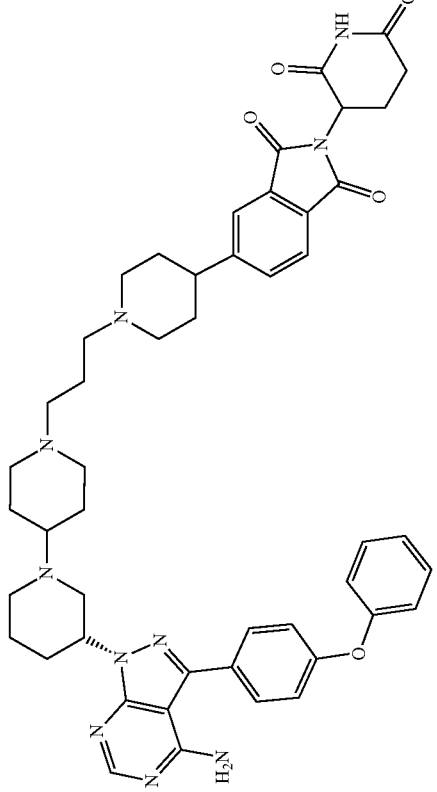 | 5-(1-(3-((R)-3-(4-amino-3-(4-phenoxyphenyl)-1H-pyrazolo[3,4-d]pyrimidin-1-yl)-[1,4'-bipiperidin]-1'-yl)propyl)piperidin-4-yl)-2-(2,6-dioxopiperidin-3-yl)isoindoline-1,3-dione | 850.43 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 154 | 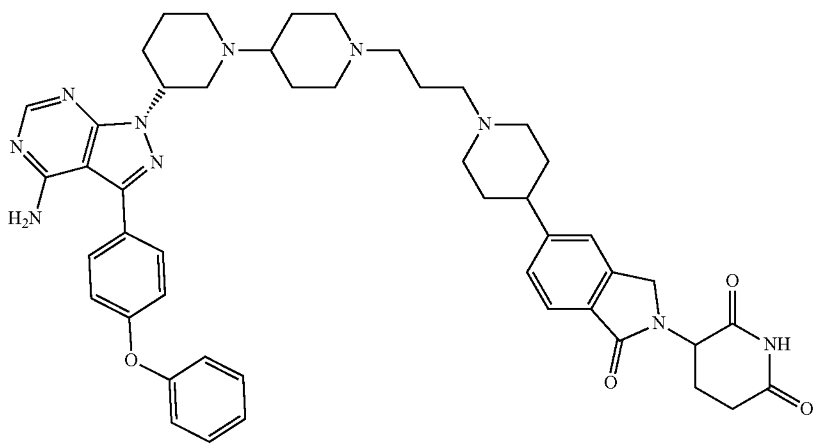 | 3-(5-(1-(3-(4-((R)-3-(4-amino-3-(4-phenoxyphenyl)-1H-pyrazolo[3,4-d]pyrimidin-1-yl)-[1,4'-bipiperidin]-1'-yl)propyl)piperidin-4-yl)-1-oxoisoindolin-2-yl)piperidine-2,6-dione | 836.45 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 155 | 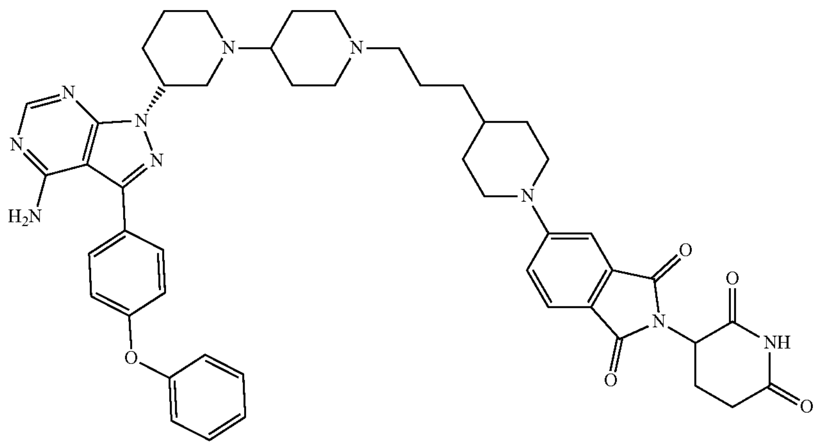 | 5-(4-(3-((R)-3-(4-amino-3-(4-phenoxyphenyl)-1H-pyrazolo[3,4-d]pyrimidin-1-yl)-[1,4'-bipiperidin]-1'-yl)propyl)piperidin-1-yl)-2-(2,6-dioxopiperidin-3-yl)isoindoline-1,3-dione | 853.43 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 156 | 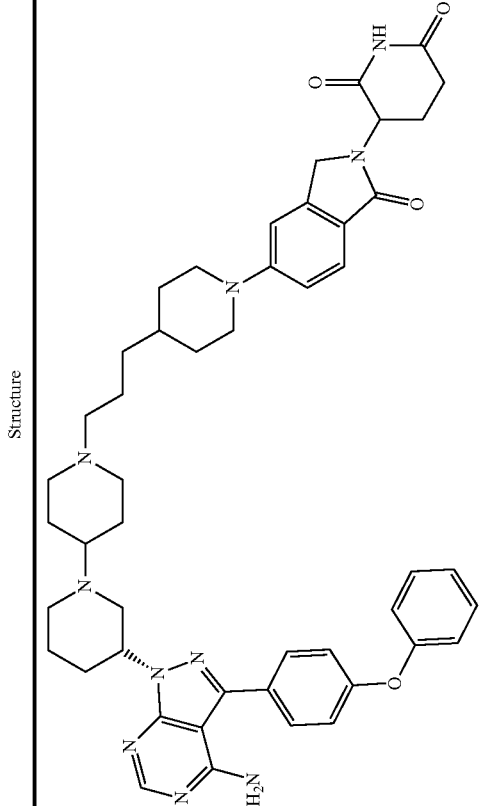 | 3-(5-(4-(3-((R)-3-(4-amino-3-(4-phenoxyphenyl)-1H-pyrazolo[3,4-d]pyrimidin-1-yl)-[1,4'-bipiperidin]-1'-yl)propyl)piperidin-1-yl)-1-oxoisoindolin-2-yl)piperidine-2,6-dione | 836.45 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 157 | 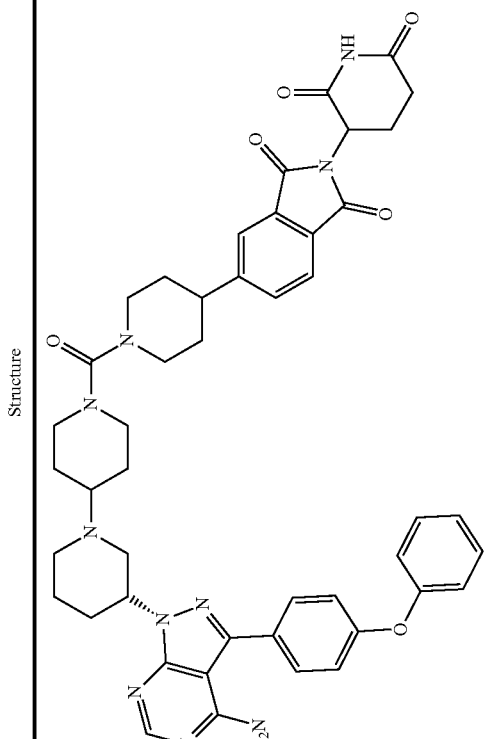 | 5-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)-2-(2,6-dioxopiperidin-3-yl)isoindoline-1,3-dione | 836.38 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 158 | 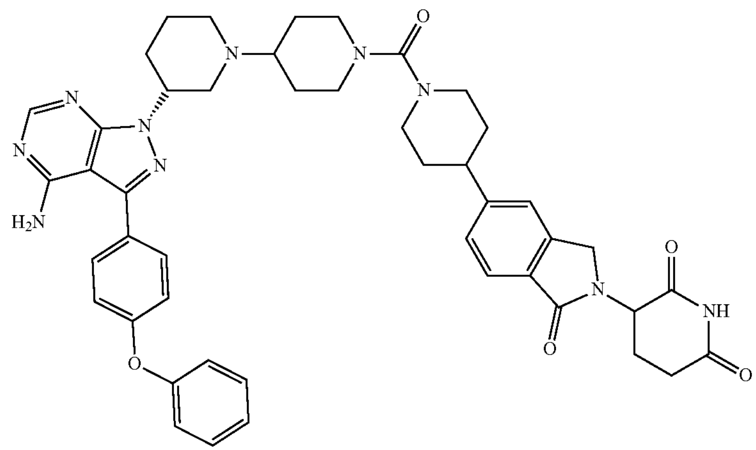 | 3-(5-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)-1-oxoisoindolin-2-yl)piperidine-2,6-dione | 822.40 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 159 | 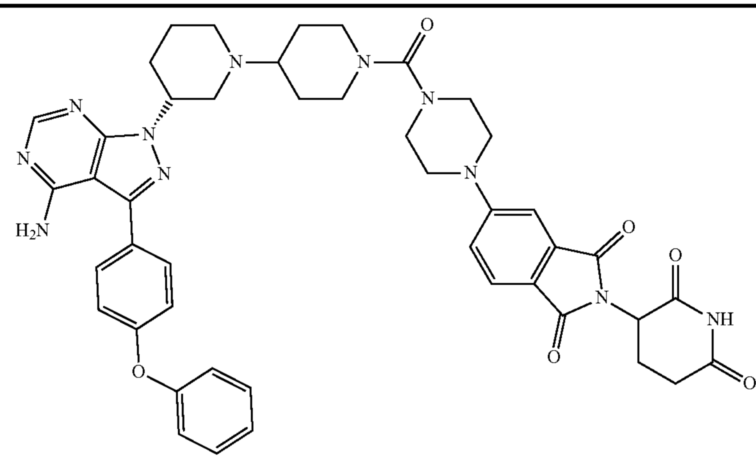 | 5-(4-((R)-3-(4-(4-amino-3-(4-phenoxyphenyl)-1H-pyrazolo[3,4-d]pyrimidin-1-yl)-[1,4'-bipiperidine]-1'-carbonyl)piperazin-1-yl)-2-(2,6-dioxopiperidin-3-yl)isoindoline-1,3-dione | 837.37 | C | B | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 160 | 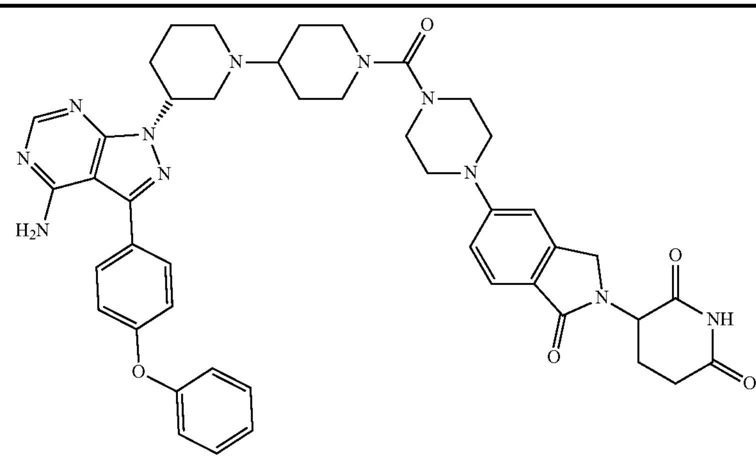 | 3-(5-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)-1-oxoisoindolin-2-yl)piperidine-2,6-dione | 823.39 | C | B | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 161 | 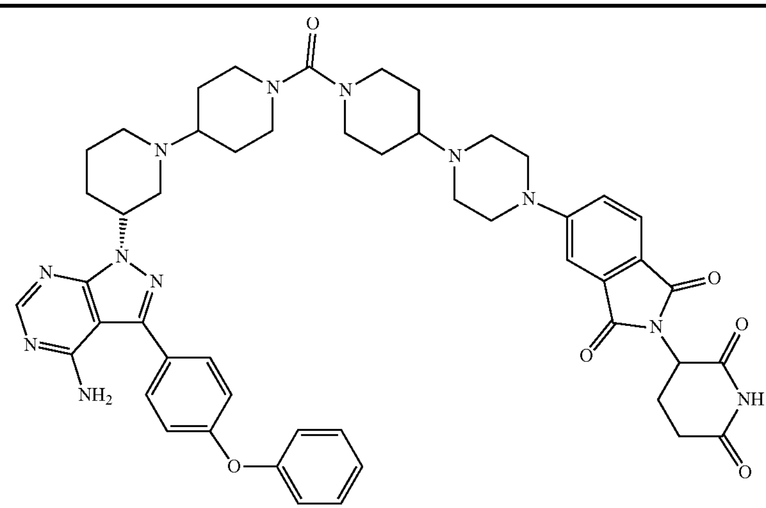 | 5-(4-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)piperazin-1-yl)-2-(2,6-dioxopiperidin-3-yl)isoindoline-1,3-dione | 920.44 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 162 | 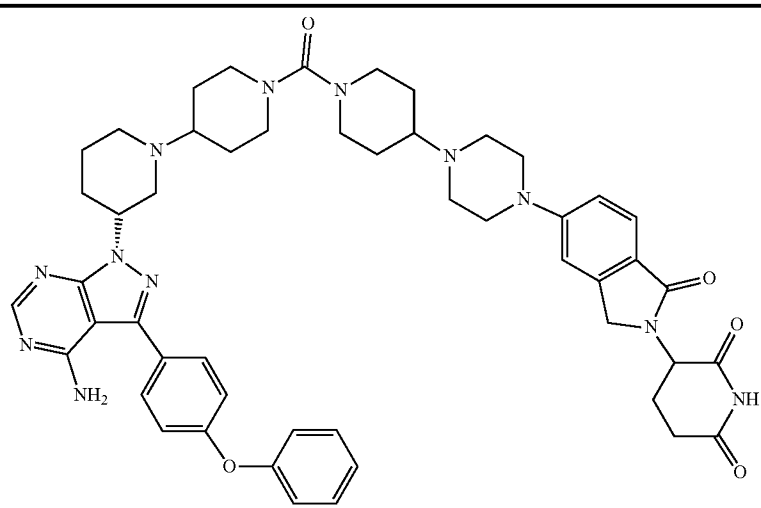 | 3-(5-(4-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)piperazin-1-yl)-1-oxoisoindolin-2-yl)piperidine-2,6-dione | 906.47 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 163 | 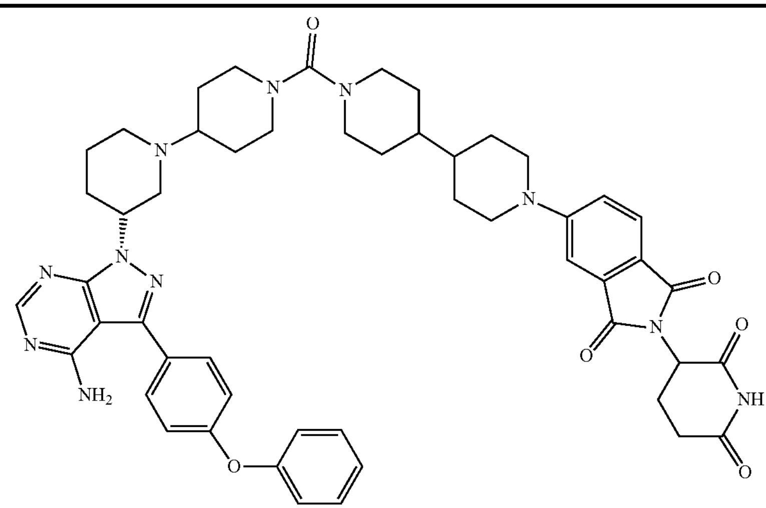 | 5-(1'-((R)-3-(4-amino-3-(4-phenoxyphenyl)-1H-pyrazolo[3,4-d]pyrimidin-1-yl)-[1,4'-bipiperidine]-1'-carbonyl)-[4,4'-bipiperidin]-1-yl)-2-(2,6-dioxopiperidin-3-yl)isoindoline-1,3-dione | 919.45 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 164 | 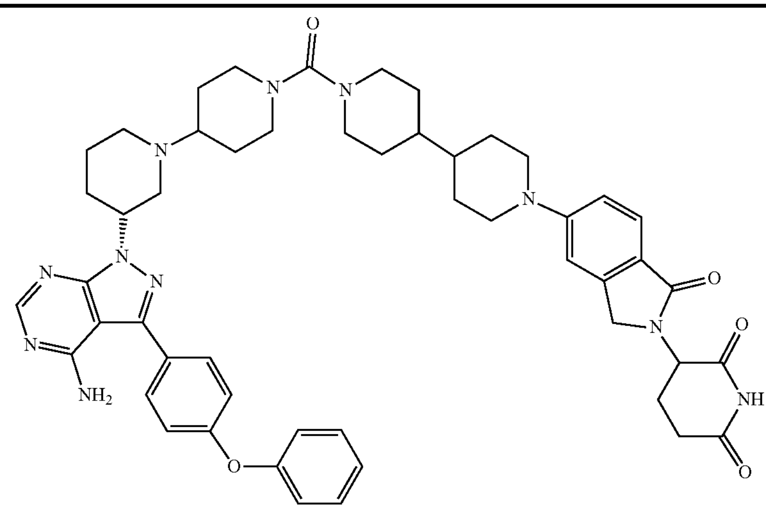 | 3-(5-(1'-((R)-3-(4-amino-3-(4-phenoxyphenyl)-1H-pyrazolo[3,4-d]pyrimidin-1-yl)-[1,4'-bipiperidine]-1'-carbonyl)-[4,4'-bipiperidin]-1-yl)-1-oxoisoindolin-2-yl)piperidine-2,6-dione | 905.47 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 165 | 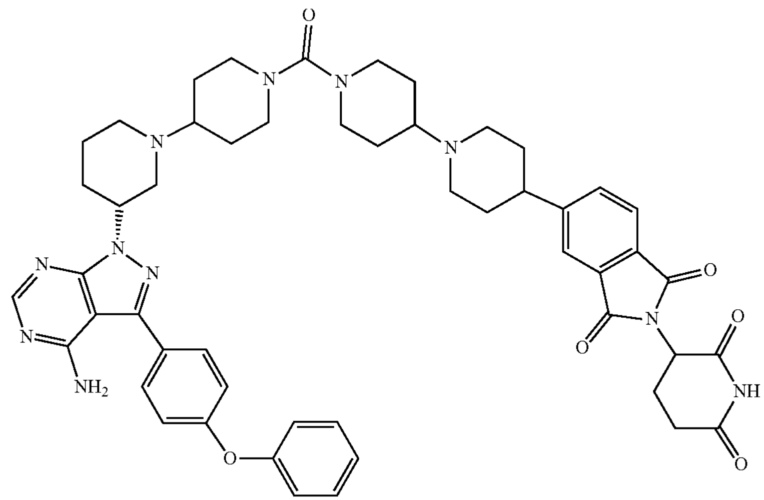 | 5-(1'-((R)-3-(4-amino-3-(4-phenoxyphenyl)-1H-pyrazolo[3,4-d]pyrimidin-1-yl)-[1,4'-bipiperidine]-1'-carbonyl)-[1,4'-bipiperidin]-4-yl)-2-(2,6-dioxopiperidin-3-yl)isoindoline-1,3-dione | 919.45 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 166 | 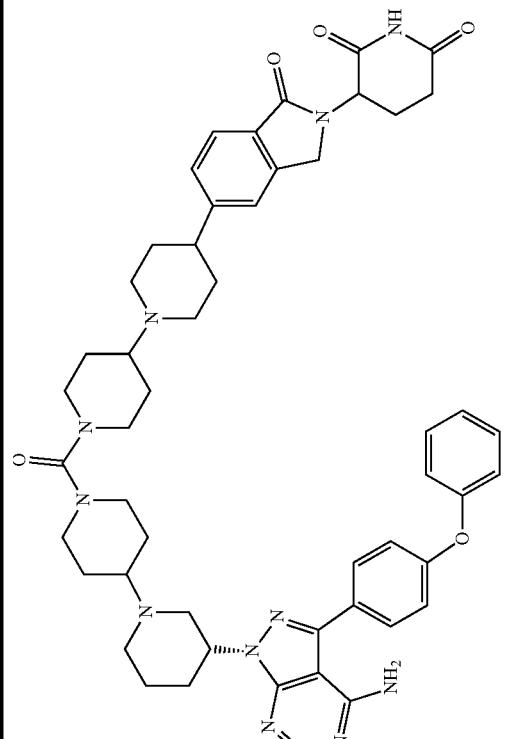 | 3-(5-(1'-((R)-3-(4-amino-3-(4-phenoxyphenyl)-1H-pyrazolo[3,4-d]pyrimidin-1-yl)-[1,4'-bipiperidine]-1'-carbonyl)-[1,4'-bipiperidin]-4-yl)-1-oxoisoindolin-2-yl)piperidine-2,6-dione | 905.47 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 167 | 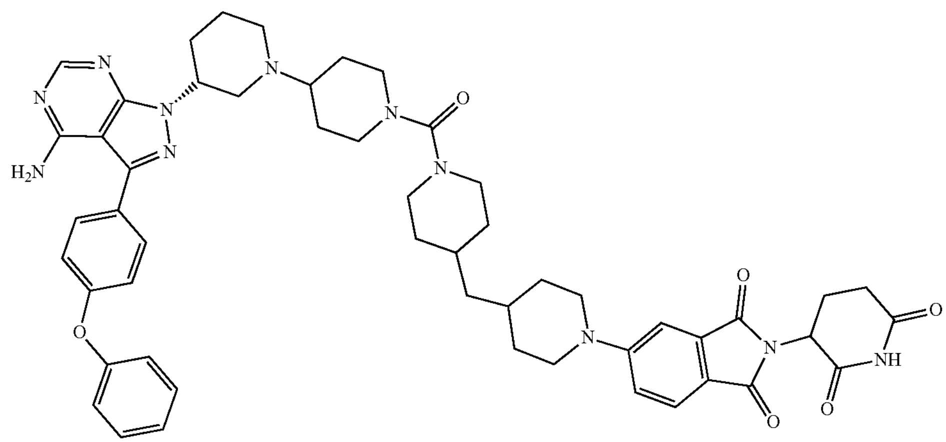 | 5-(4-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-1-yl)-2-(2,6-dioxopiperidin-3-yl)isoindoline-1,3-dione | 933.46 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 168 | 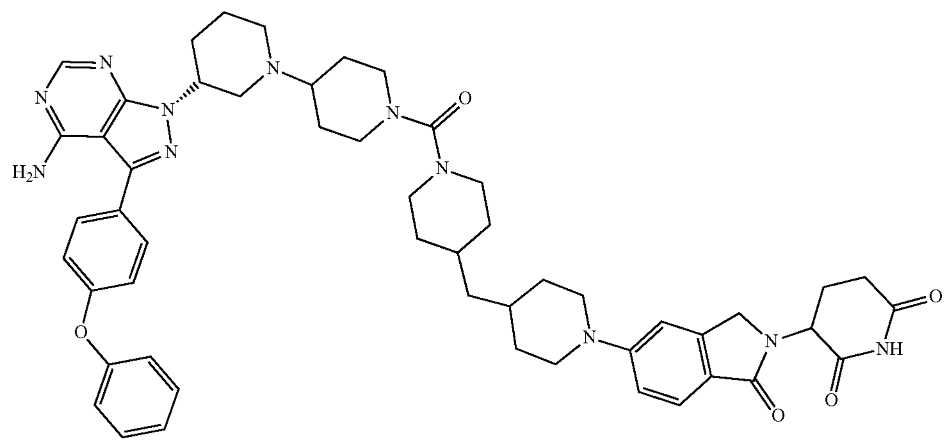 | 3-(5-(4-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-1-yl)-1-oxoisoindolin-2-yl)piperidine-2,6-dione | 919.49 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 169 | 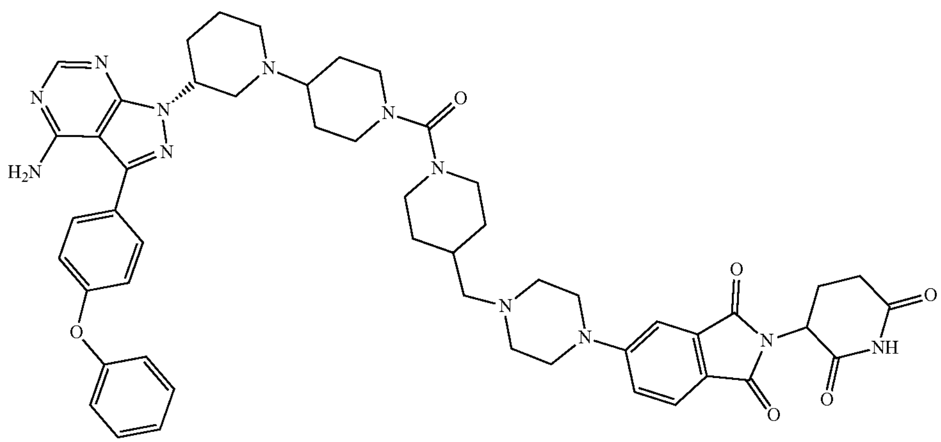 | 5-(4-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperazin-1-yl)-2-(2,6-dioxopiperidin-3-yl)isoindoline-1,3-dione | 934.46 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 170 | 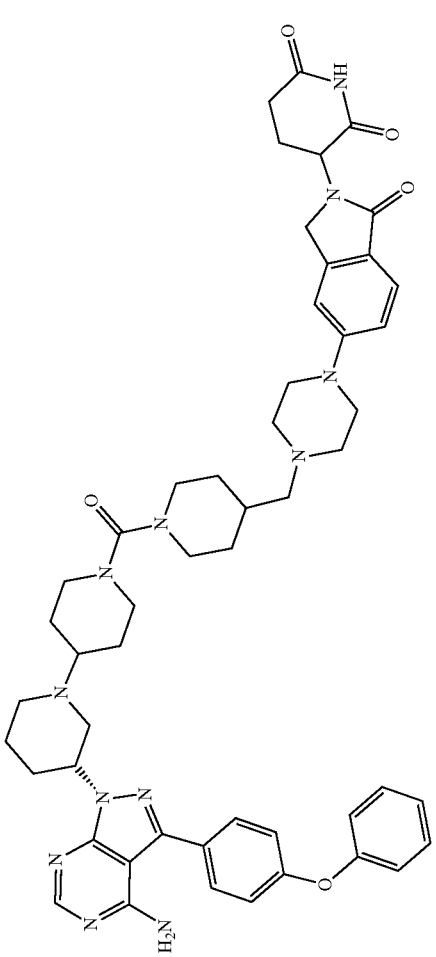 | 3-(5-(4-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperazin-1-yl)-1-oxoisoindolin-2-yl)piperidine-2,6-dione | 920.48 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 171 | 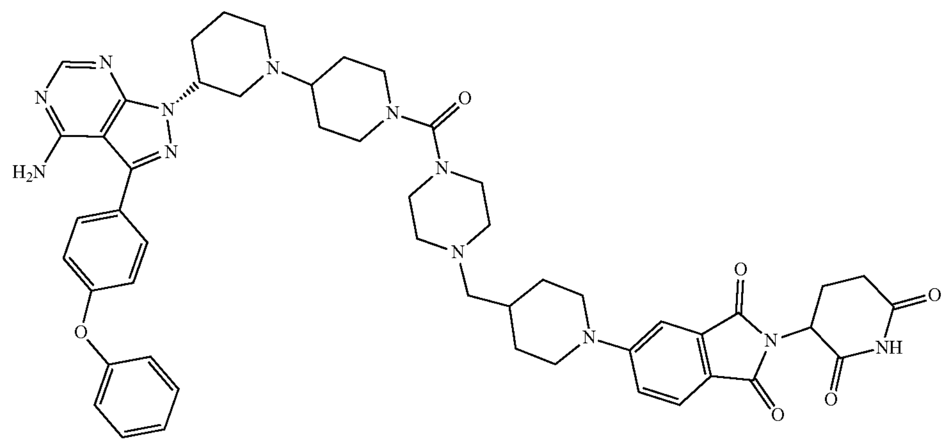 | 5-(4-((4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)methyl)piperidin-1-yl)-2-(2,6-dioxopiperidin-3-yl)isoindoline-1,3-dione | 934.46 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 172 | 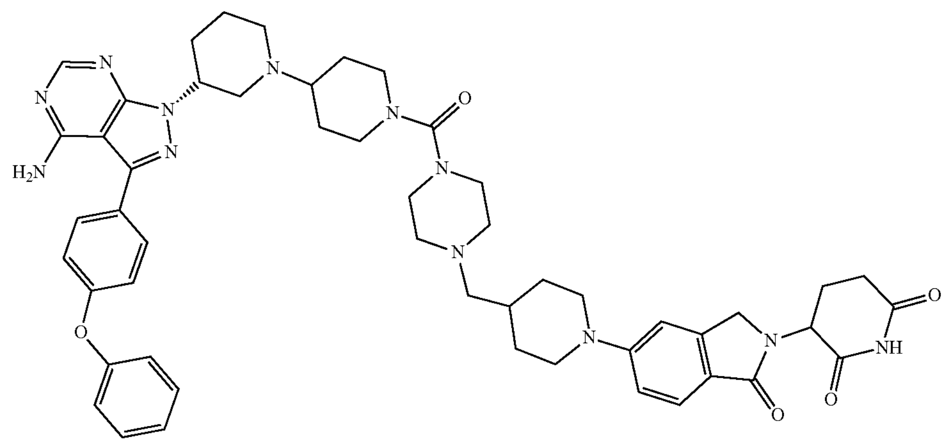 | 3-(5-(4-((4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)methyl)piperidin-1-yl)-1-oxoisoindolin-2-yl)piperidine-2,6-dione | 920.48 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 173 | 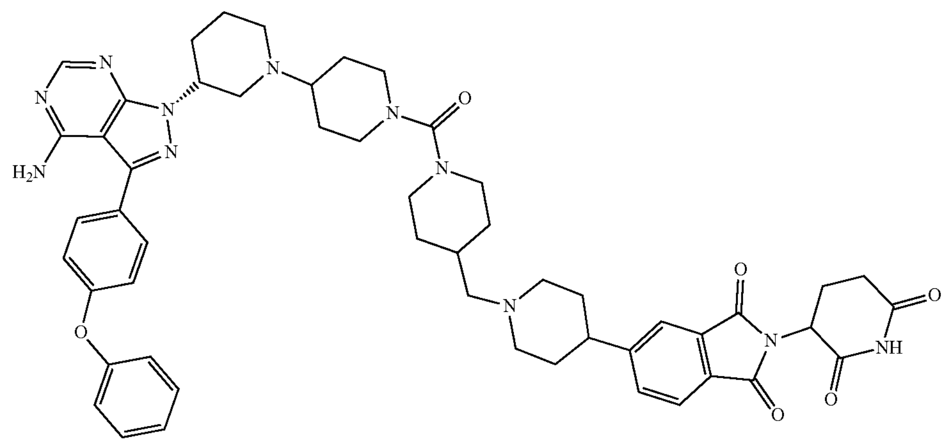 | 5-(1-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-4-yl)-2-(2,6-dioxopiperidin-3-yl)isoindoline-1,3-dione | 933.46 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 174 | 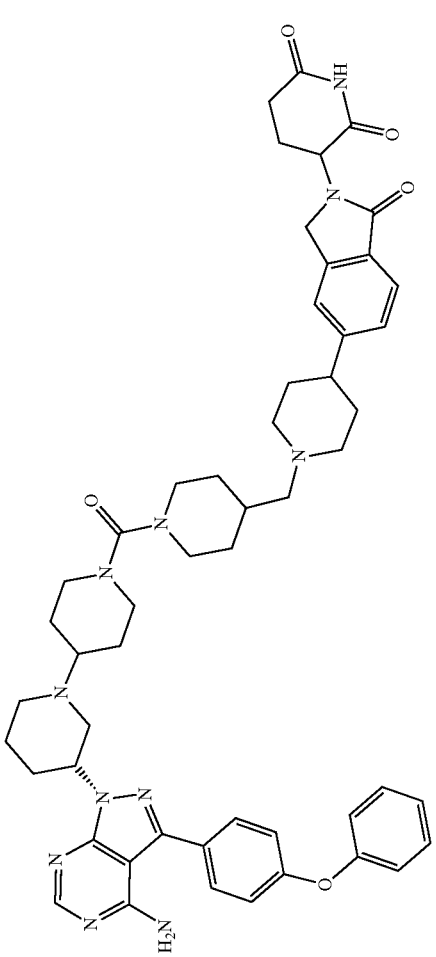 | 3-(5-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-4-yl)-1-oxoisoindolin-2-yl)piperidine-2,6-dione | 919.49 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 175 | 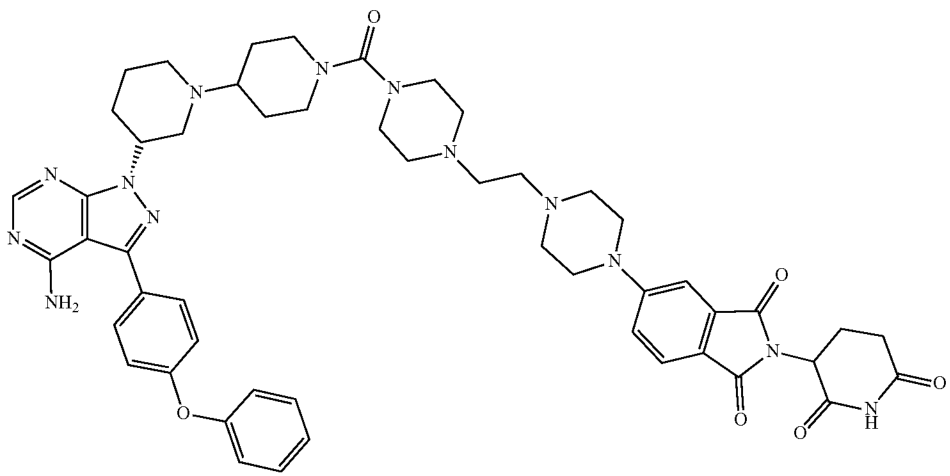 | 5-(4-(2-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperazin-1-yl)-2-(2,6-dioxopiperidin-3-yl)isoindoline-1,3-dione | 949.47 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 176 | 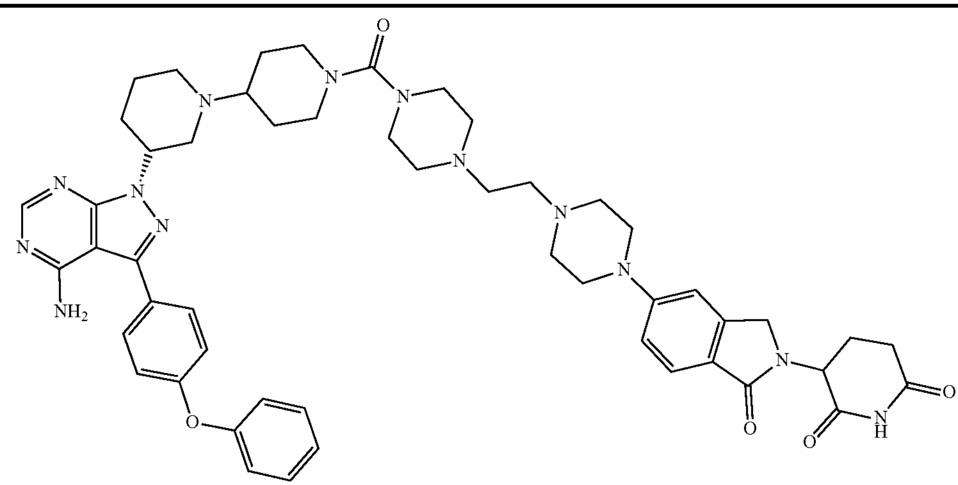 | 3-(5-(4-(2-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperazin-1-yl)-1-oxoisoindolin-2-yl)piperidine-2,6-dione | 935.49 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 177 | 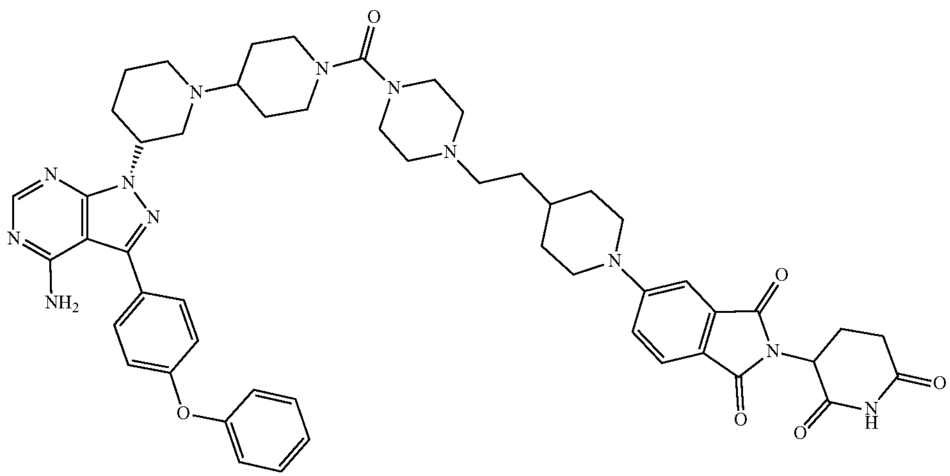 | 5-(4-(2-(4-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-1-yl)-2-(2,6-dioxopiperidin-3-yl)isoindoline-1,3-dione | 948.48 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 178 | 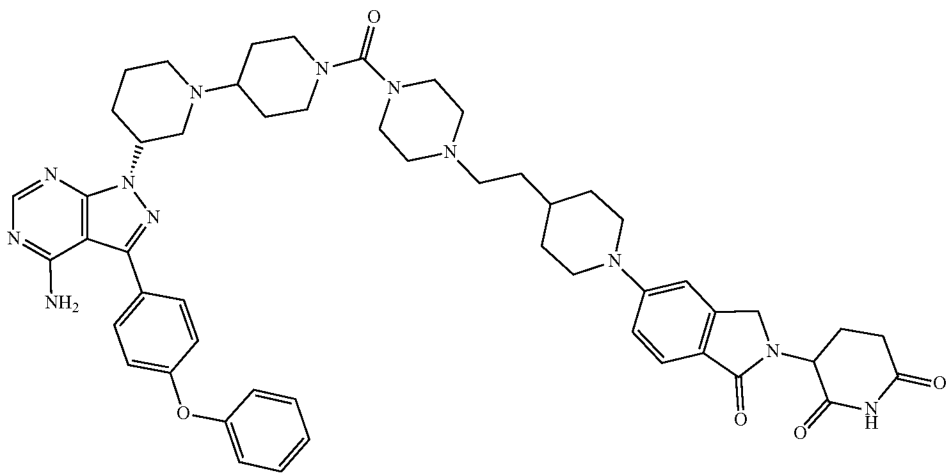 | 3-(5-(4-(2-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-1-yl)-1-oxoisoindolin-2-yl)piperidine-2,6-dione | 934.50 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 179 | 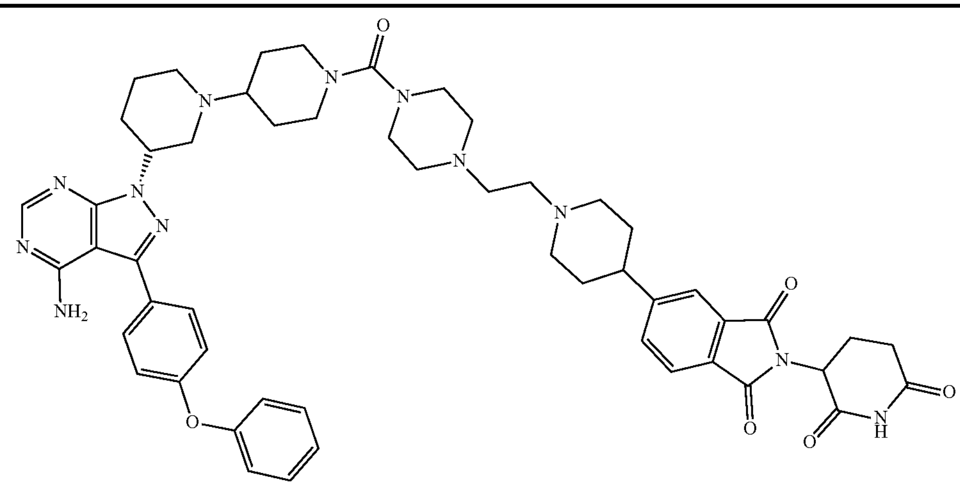 | 5-(1-(2-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-4-yl)-2-(2,6-dioxopiperidin-3-yl)isoindoline-1,3-dione | 948.48 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-pro-lifer-ation) JeKO-1 cells | IC$_{50}$ (anti-pro-lifer-ation) Mino cells | DC$_{50}$ | D$_{max}$ |
|---|---|---|---|---|---|---|---|
| 180 | 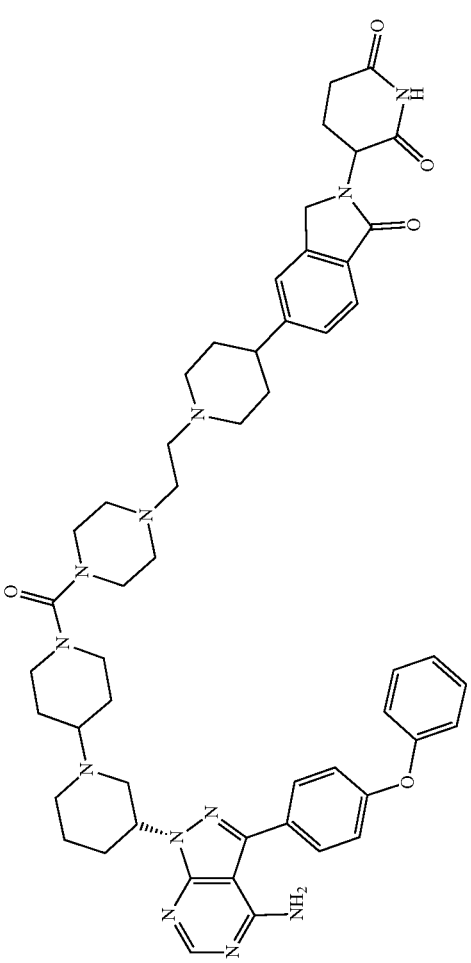 | 3-(5-(1-(2-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-4-yl)-1-oxoisoindolin-2-yl)piperidine-2,6-dione | 934.50 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 181 | 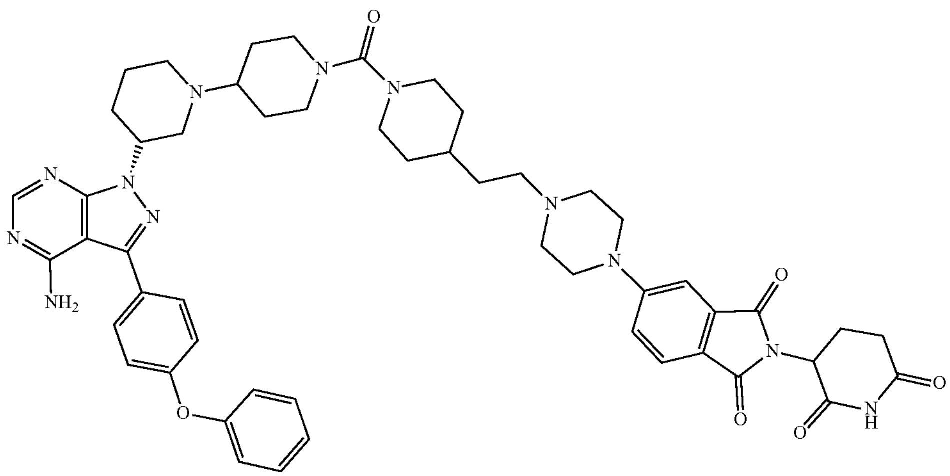 | 5-(4-(2-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperazin-1-yl)-2-(2,6-dioxopiperidin-3-yl)isoindoline-1,3-dione | 948.48 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 182 | 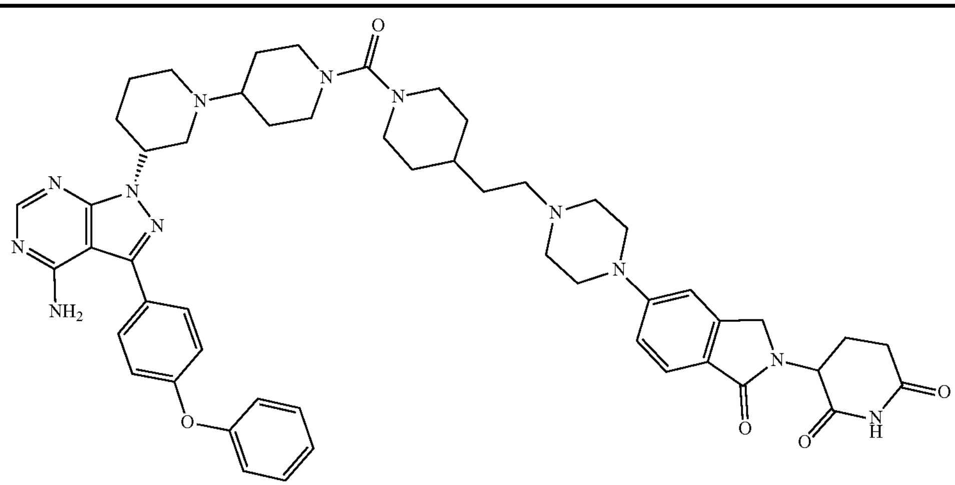 | 3-(5-(4-(2-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperazin-1-yl)-1-oxoisoindolin-2-yl)piperidine-2,6-dione | 934.50 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 183 | 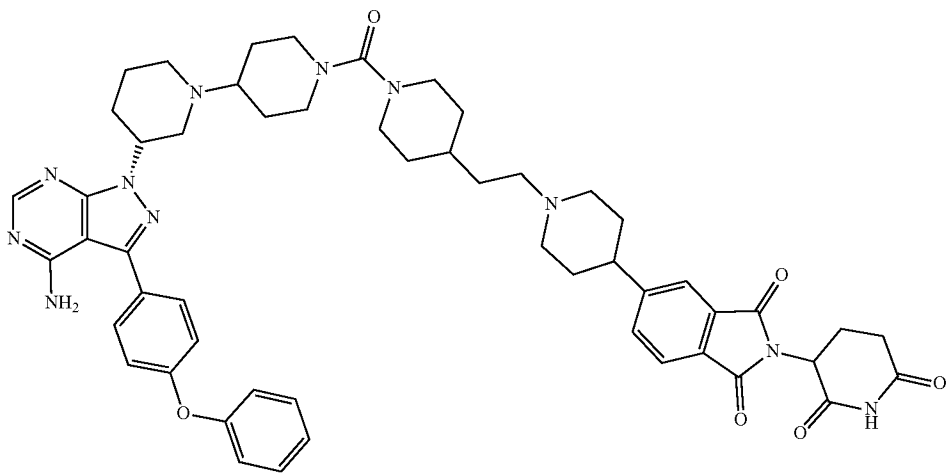 | 5-(1-(2-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-4-yl)-2-(2,6-dioxopiperidin-3-yl)isoindoline-1,3-dione | 947.48 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 184 | 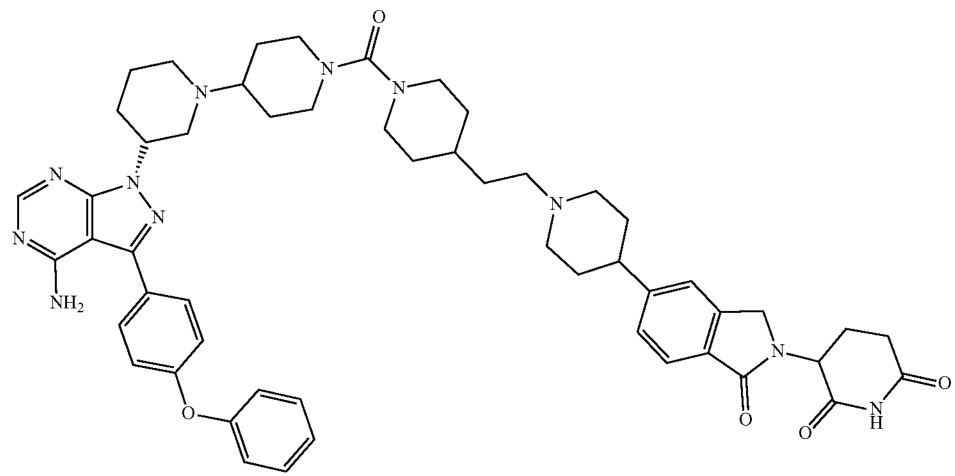 | 3-(5-(1-(2-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-4-yl)-1-oxoisoindolin-2-yl)piperidine-2,6-dione | 933.50 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 185 | 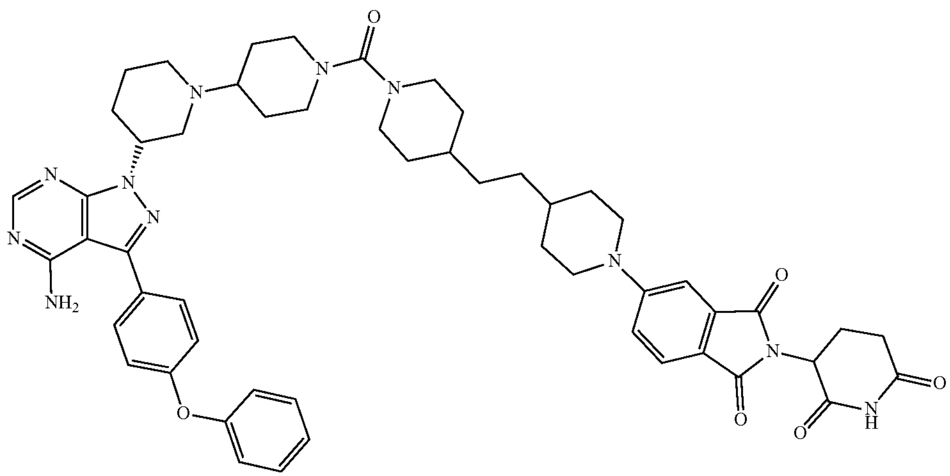 | 5-(4-(2-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-1-yl)-2-(2,6-dioxopiperidin-3-yl)isoindoline-1,3-dione | 947.48 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 186 | 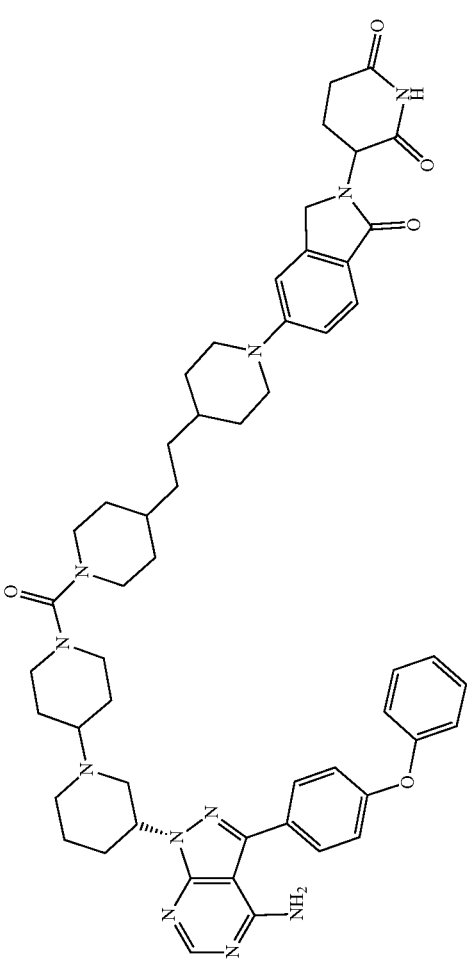 | 3-(5-(4-(2-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-1-yl)-1-oxoisoindolin-2-yl)piperidine-2,6-dione | 933.50 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 187 | | 5-(4-(3-(4-(3-(R))-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperazin-1-yl)-2-(2,6-dioxopiperidin-3-yl)isoindoline-1,3-dione | 963.49 | B | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 188 | 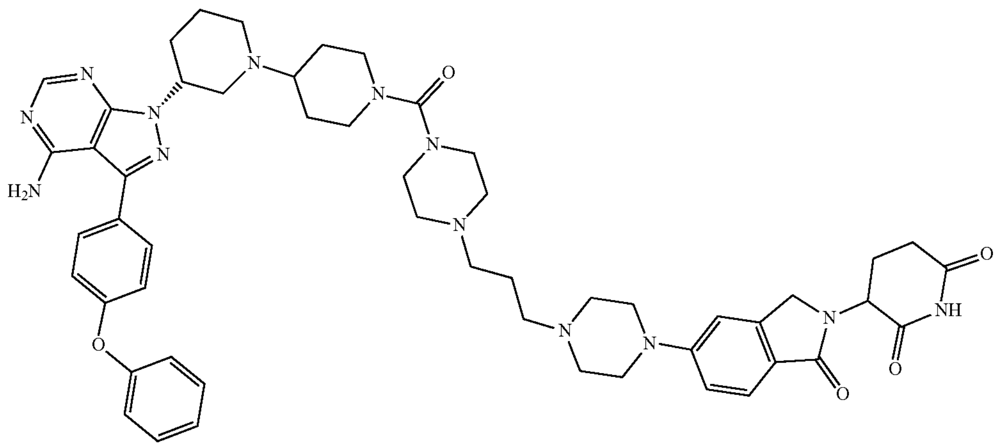 | 3-(5-(4-(3-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperazin-1-yl)-1-oxoisoindolin-2-yl)piperidine-2,6-dione | 949.51 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 189 | 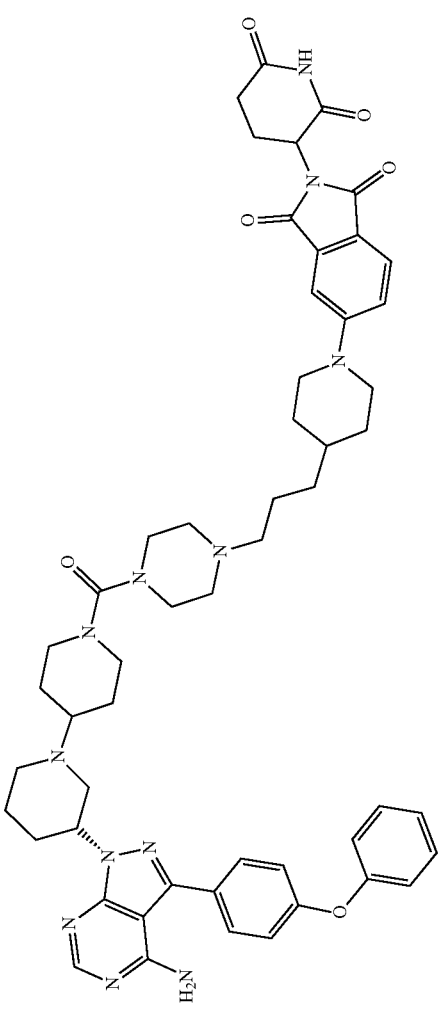 | 5-(4-(3-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-1-yl)-2-(2,6-dioxopiperidin-3-yl)isoindoline-1,3-dione | 962.49 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 190 | 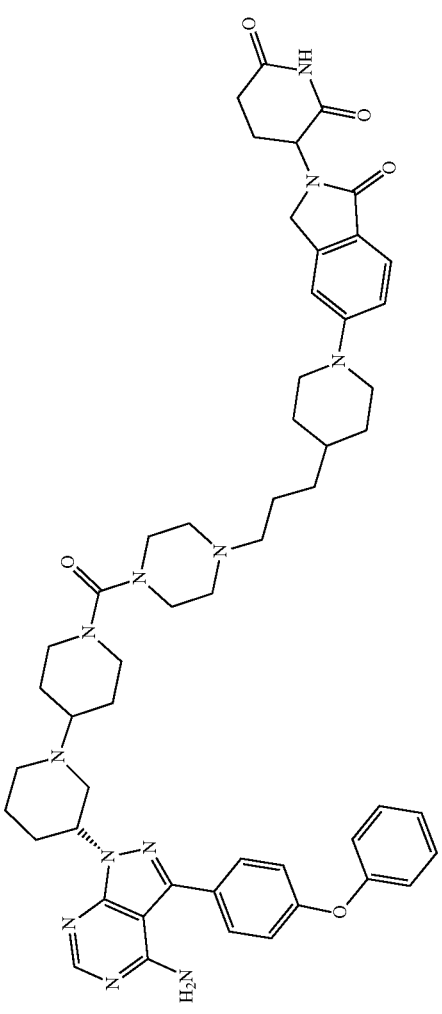 | 3-(5-(4-(3-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-1-yl)-1-oxoisoindolin-2-yl)piperidine-2,6-dione | 948.51 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 191 | 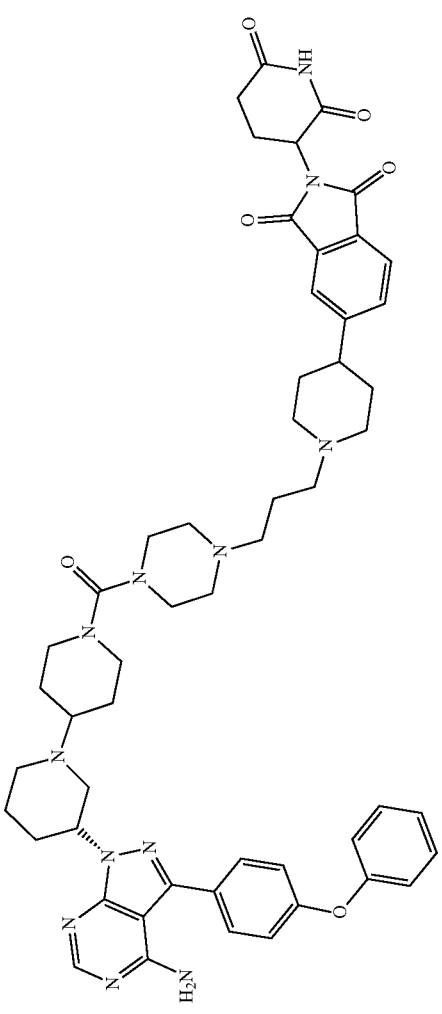 | 5-(1-(3-(4-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-4-yl)-2-(2,6-dioxopiperidin-3-yl)isoindoline-1,3-dione | 962.49 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 192 | 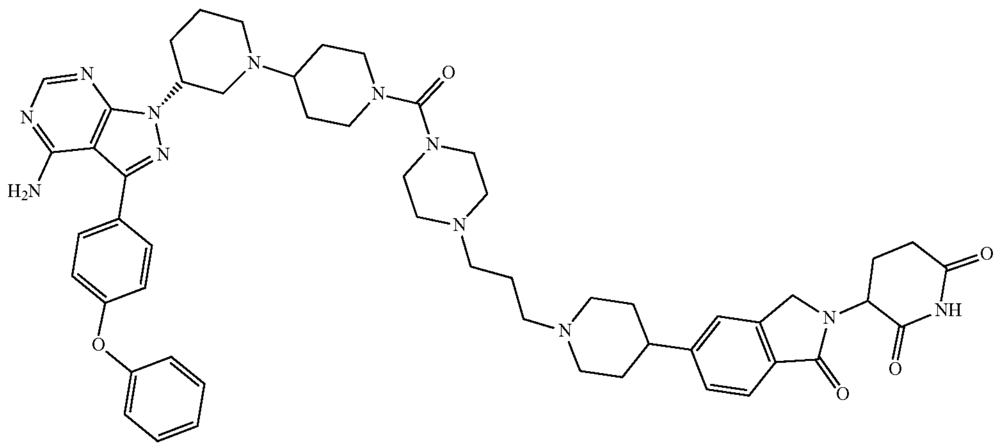 | 3-(5-(1-(3-(4-((R)-3-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-4-yl)-1-oxoisoindolin-2-yl)piperidine-2,6-dione | 948.51 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 193 | 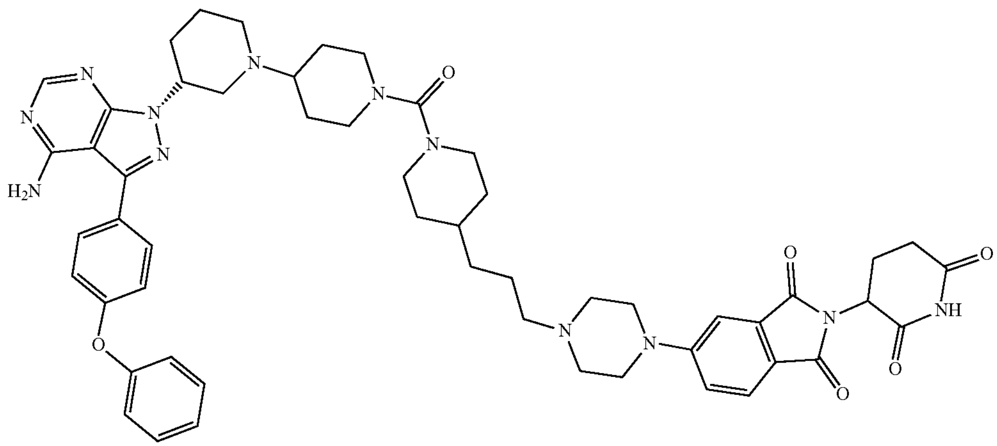 | 5-(4-(3-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperazin-1-yl)-2-(2,6-dioxopiperidin-3-yl)isoindoline-1,3-dione | 962.49 | C | B | B | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 194 | 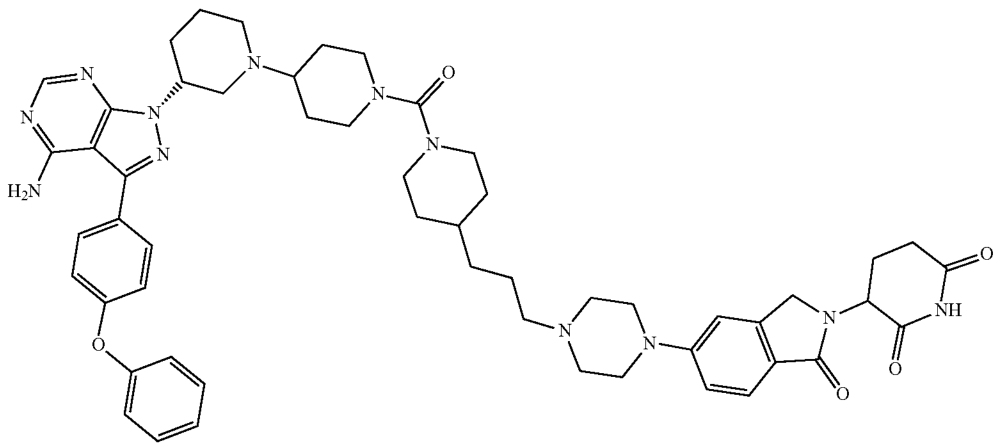 | 3-(5-(4-(3-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperazin-1-yl)-1-oxoisoindolin-2-yl)piperidine-2,6-dione | 948.51 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 195 | 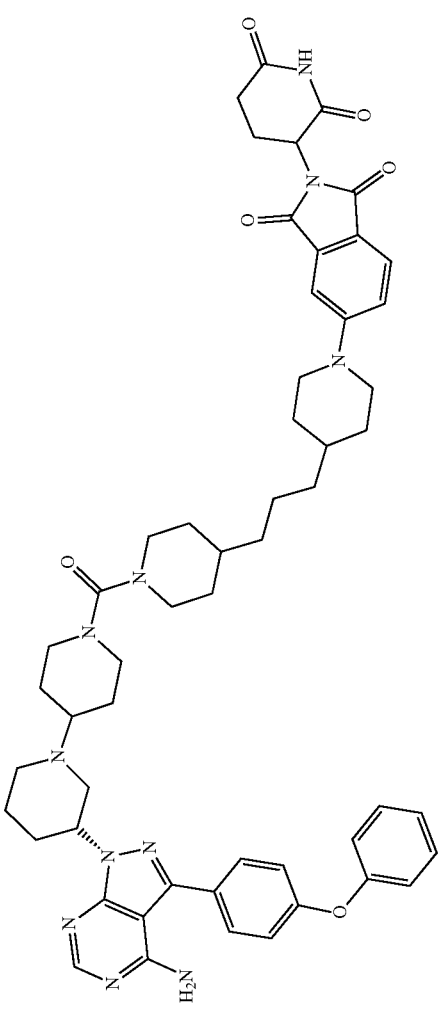 | 5-(4-(3-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-1-yl)-2-(2,6-dioxopiperidin-3-yl)isoindoline-1,3-dione | 961.50 | B | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 196 | 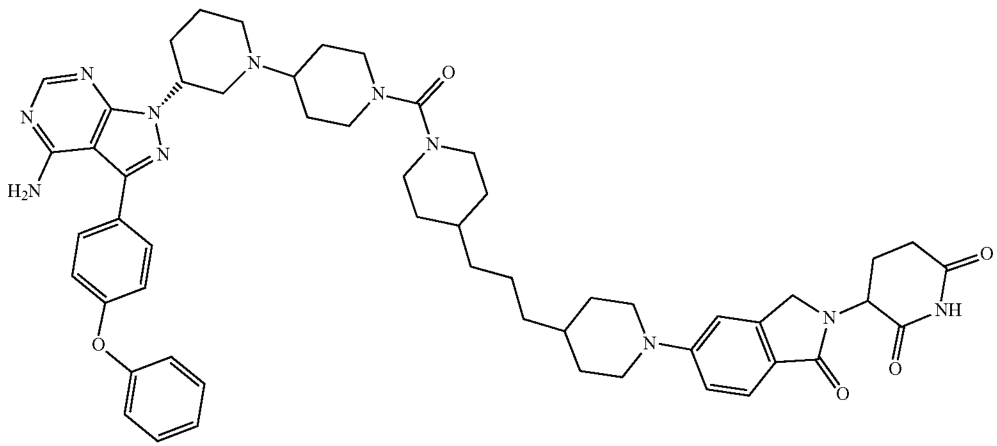 | 3-(5-(4-(3-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-1-yl)-1-oxoisoindolin-2-yl)piperidine-2,6-dione | 947.52 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 197 | 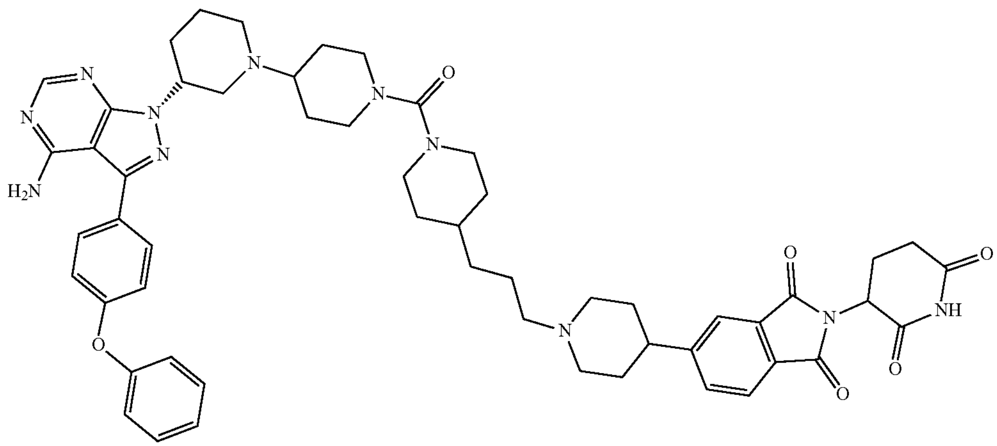 | 5-(1-(3-((1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-4-yl)-2-(2,6-dioxopiperidin-3-yl)isoindoline-1,3-dione | 961.50 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 198 | 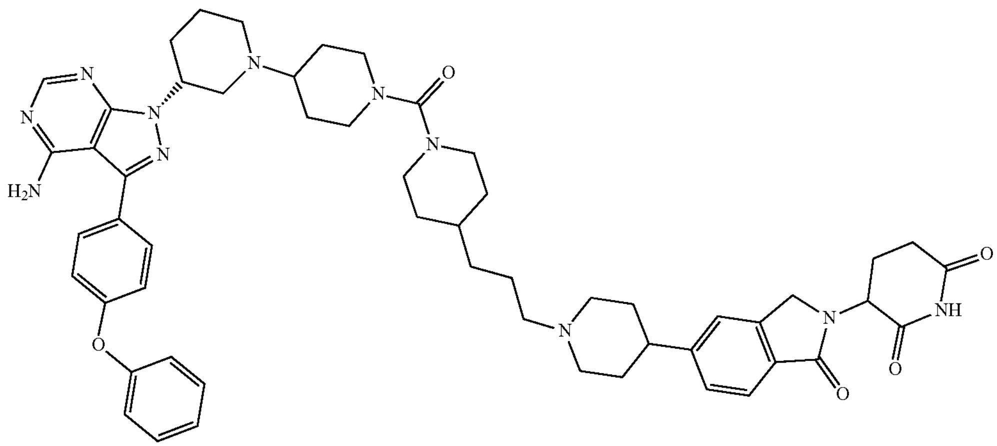 | 3-(5-(1-(3-(1-((R)-3-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-4-yl)-1-oxoisoindolin-2-yl)piperidine-2,6-dione | 947.52 | B | B | B | B |
| 199 | 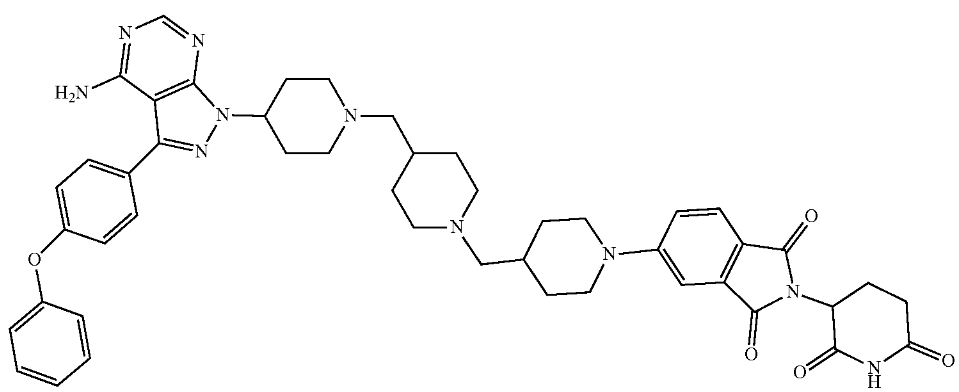 [SMILES: Nc1ncnc2c1c(-c1ccc(Oc3ccccc3)cc1)nn2C1CCN(CC2CCN(CC3CCN(c4ccc5c(c4)C(=O)N(C4CCC(=O)NC4=O)C5=O)CC3)CC2)CC1] | 5-(4-((4-((4-((R)-3-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-2-(2,6-dioxopiperidin-3-yl)isoindoline-1,3-dione | 836.41 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 200 | 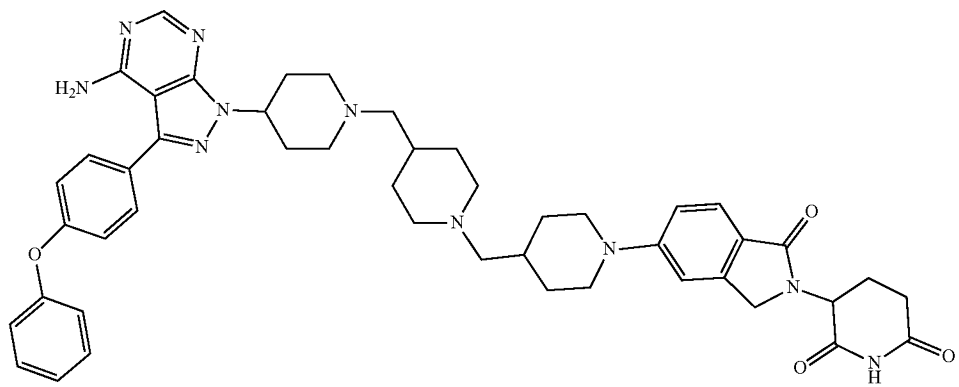 [SMILES: Nc1ncnc2c1c(-c1ccc(Oc3ccccc3)cc1)nn2C1CCN(CC2CCN(CC3CCN(c4ccc5c(c4)CN(C4CCC(=O)NC4=O)C5=O)CC3)CC2)CC1] | 3-(5-(4-((4-((4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-1-oxoisoindolin-2-yl)piperidine-2,6-dione | 822.43 | B | B | C | D |
| 201 | 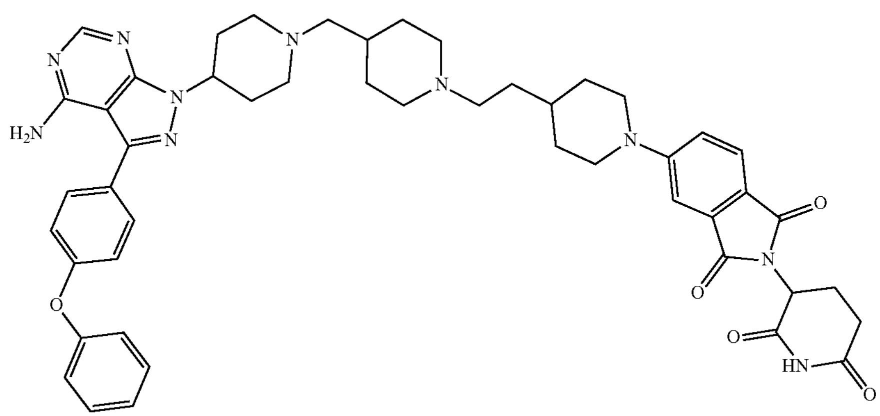 [SMILES: Nc1ncnc2c1c(-c1ccc(Oc3ccccc3)cc1)nn2C1CCN(CC2CCN(CCC3CCN(c4ccc5c(c4)C(=O)N(C4CCC(=O)NC4=O)C5=O)CC3)CC2)CC1] | 5-(4-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperidin-1-yl)-2-(2,6-dioxopiperidin-3-yl)isoindoline-1,3-dione | 850.43 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 202 | 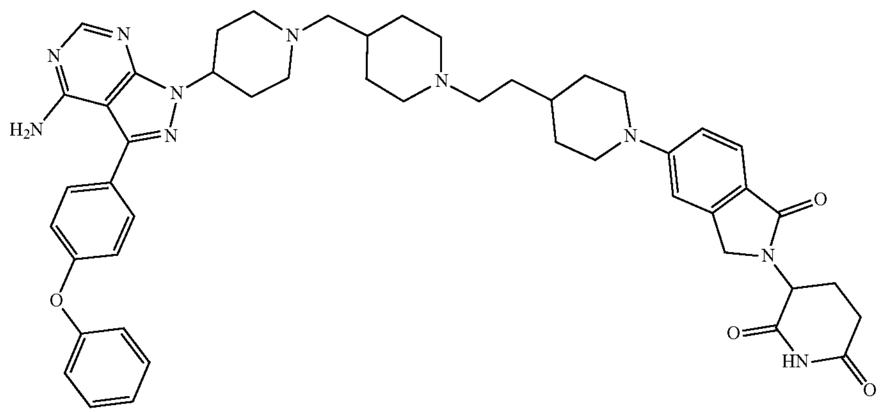 [SMILES: Nc1ncnc2c1c(-c1ccc(Oc3ccccc3)cc1)nn2C1CCN(CC2CCN(CCC3CCN(c4ccc5c(c4)CN(C4CCC(=O)NC4=O)C5=O)CC3)CC2)CC1] | 3-(5-(4-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperidin-1-yl)-1-oxoisoindolin-2-yl)piperidine-2,6-dione | 836.45 | A | B | B | A |
| 203 | 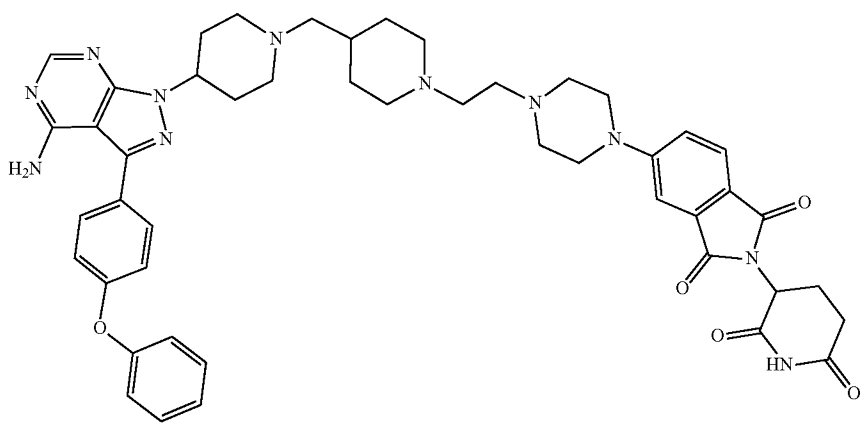 [SMILES: Nc1ncnc2c1c(-c1ccc(Oc3ccccc3)cc1)nn2C1CCN(CC2CCN(CCN3CCN(c4ccc5c(c4)C(=O)N(C4CCC(=O)NC4=O)C5=O)CC3)CC2)CC1] | 5-(4-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperazin-1-yl)-2-(2,6-dioxopiperidin-3-yl)isoindoline-1,3-dione | 851.42 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 204 | 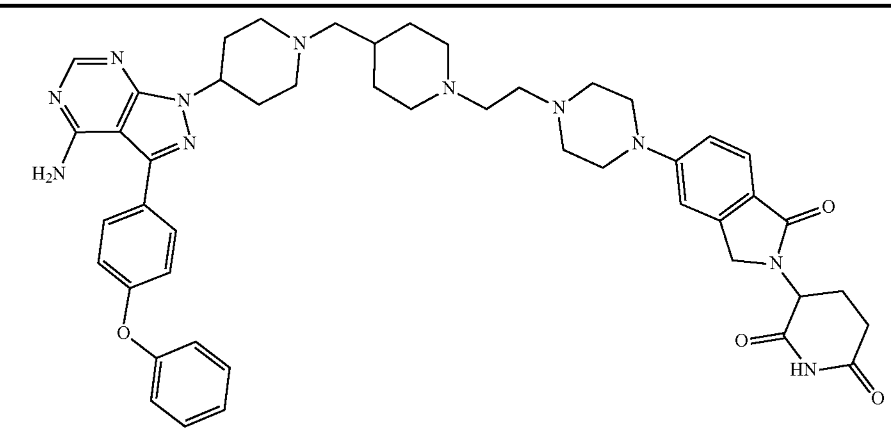 | 3-(5-(4-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperazin-1-yl)-1-oxoisoindolin-2-yl)piperidine-2,6-dione | 837.44 | B | A | B | A |
| 205 | 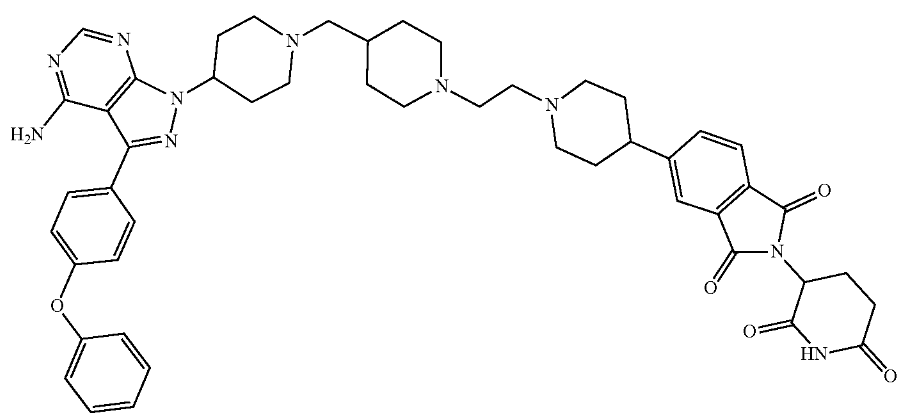 [SMILES: Nc1ncnc2c1c(-c1ccc(Oc3ccccc3)cc1)nn2C1CCN(CC2CCN(CCN3CCC(c4ccc5c(c4)C(=O)N(C4CCC(=O)NC4=O)C5=O)CC3)CC2)CC1] | 5-(1-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperidin-4-yl)-2-(2,6-dioxopiperidin-3-yl)isoindoline-1,3-dione | 850.43 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 206 | 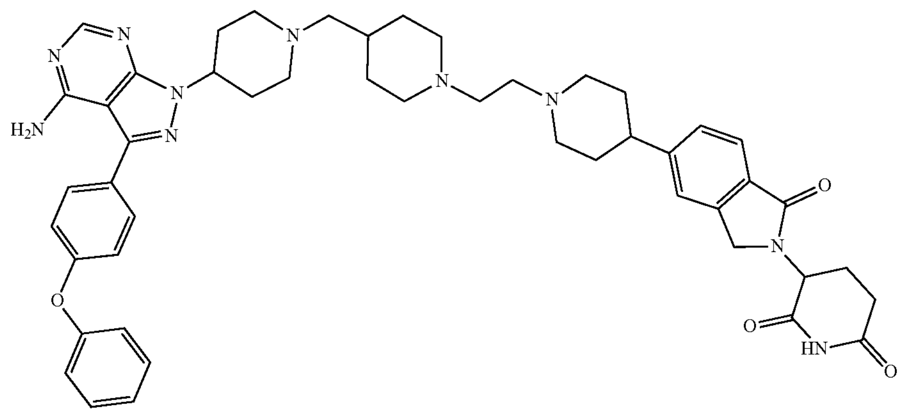 [SMILES: Nc1ncnc2c1c(-c1ccc(Oc3ccccc3)cc1)nn2C1CCN(CC2CCN(CCN3CCC(c4ccc5c(c4)CN(C4CCC(=O)NC4=O)C5=O)CC3)CC2)CC1] | 3-(5-(1-(2-(4-((4-(4-amino-3-(4-phenoxyphenyl)-1H-pyrazolo[3,4-d]pyrimidin-1-yl)piperidin-1-yl)methyl)piperidin-1-yl)ethyl)piperidin-4-yl)-1-oxoisoindolin-2-yl)piperidine-2,6-dione | 836.45 | A | A | B | A |
| 207 | 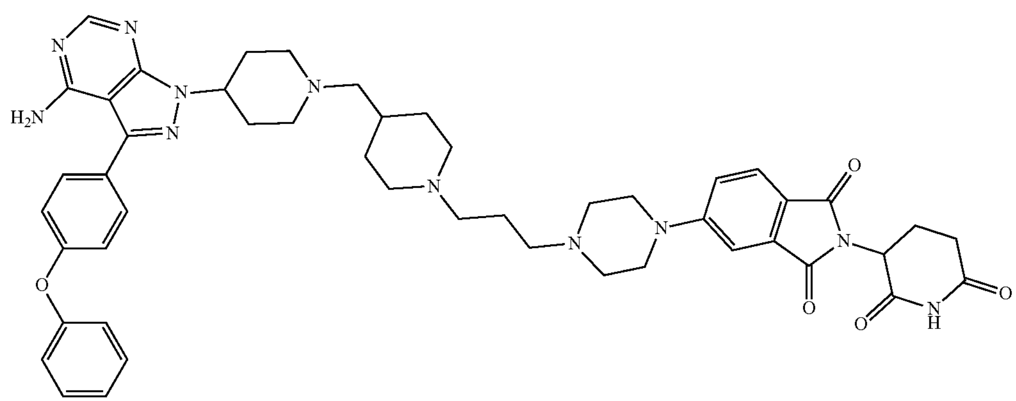 [SMILES: Nc1ncnc2c1c(-c1ccc(Oc3ccccc3)cc1)nn2C1CCN(CC2CCN(CCCN3CCN(c4ccc5c(c4)C(=O)N(C4CCC(=O)NC4=O)C5=O)CC3)CC2)CC1] | 5-(4-(3-(4-((4-(4-amino-3-(4-phenoxyphenyl)-1H-pyrazolo[3,4-d]pyrimidin-1-yl)piperidin-1-yl)methyl)piperidin-1-yl)propyl)piperazin-1-yl)-2-(2,6-dioxopiperidin-3-yl)isoindoline-1,3-dione | 865.44 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 208 | 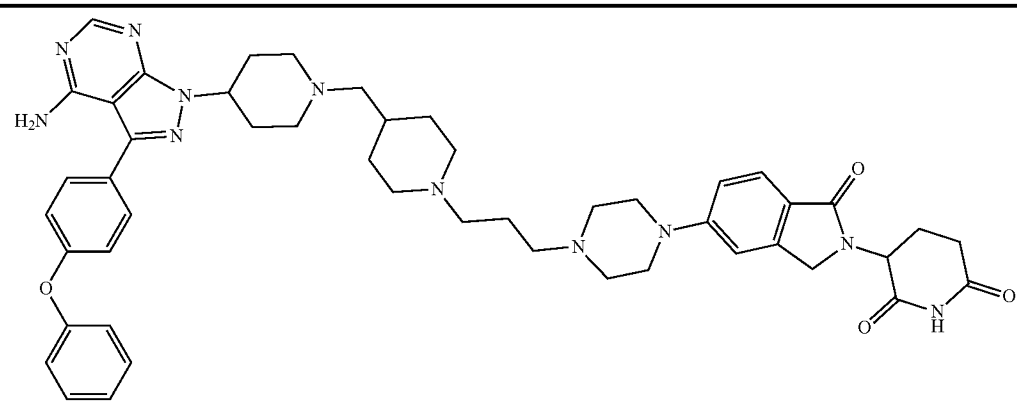 | 3-(5-(4-(3-(4-(4-((4-amino-3-(4-phenoxyphenyl)-1H-pyrazolo[3,4-d]pyrimidin-1-yl)piperidin-1-yl)methyl)piperidin-1-yl)propyl)piperazin-1-yl)-1-oxoisoindolin-2-yl)piperidine-2,6-dione | 851.42 | C | C | C | B |
| 209 | 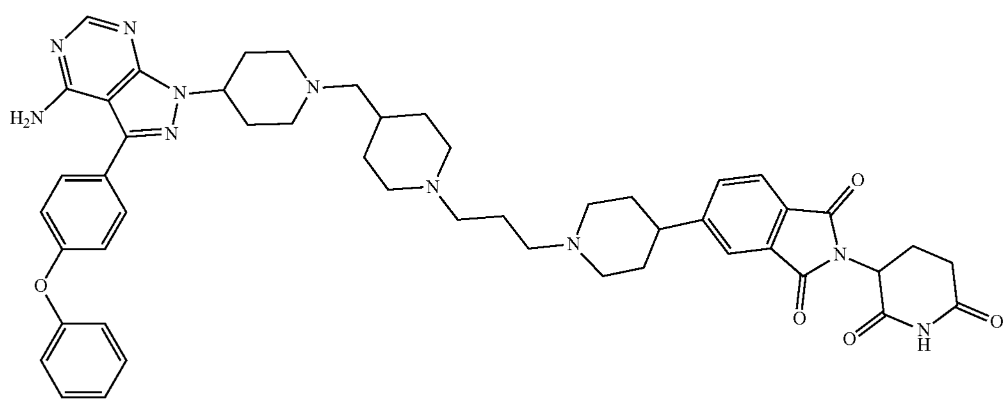 | 5-(1-(3-(4-((4-(4-amino-3-(4-phenoxyphenyl)-1H-pyrazolo[3,4-d]pyrimidin-1-yl)piperidin-1-yl)methyl)piperidin-1-yl)propyl)piperidin-4-yl)-2-(2,6-dioxopiperidin-3-yl)isoindoline-1,3-dione | 864.44 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 210 | 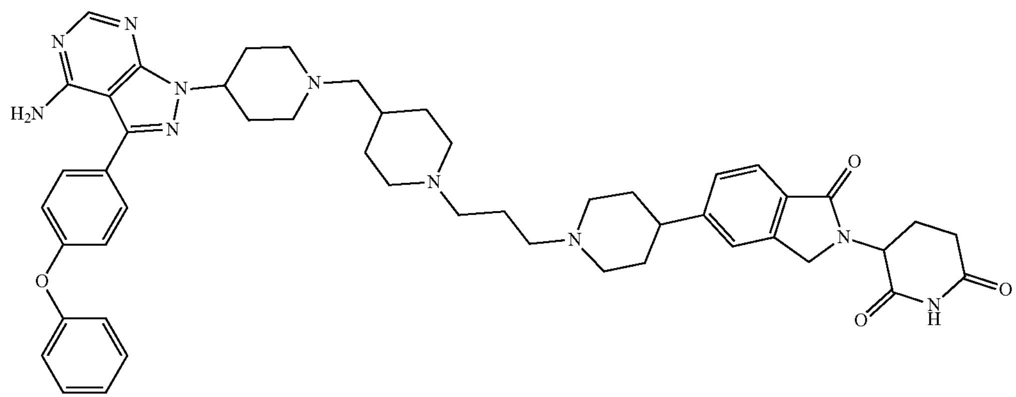 [SMILES: Nc1ncnc2c1c(-c1ccc(Oc3ccccc3)cc1)nn2C1CCN(CC2CCN(CCCN3CCN(c4ccc5c(c4)CN(C4CCC(=O)NC4=O)C5=O)CC3)CC2)CC1] | 3-(5-(1-(3-(4-(4-((4-amino-3-(4-phenoxyphenyl)-1H-pyrazolo[3,4-d]pyrimidin-1-yl)piperidin-1-yl)methyl)piperidin-1-yl)propyl)piperidin-4-yl)-1-oxoisoindolin-2-yl)piperidine-2,6-dione | 850.46 | B | B | B | B |
| 211 | 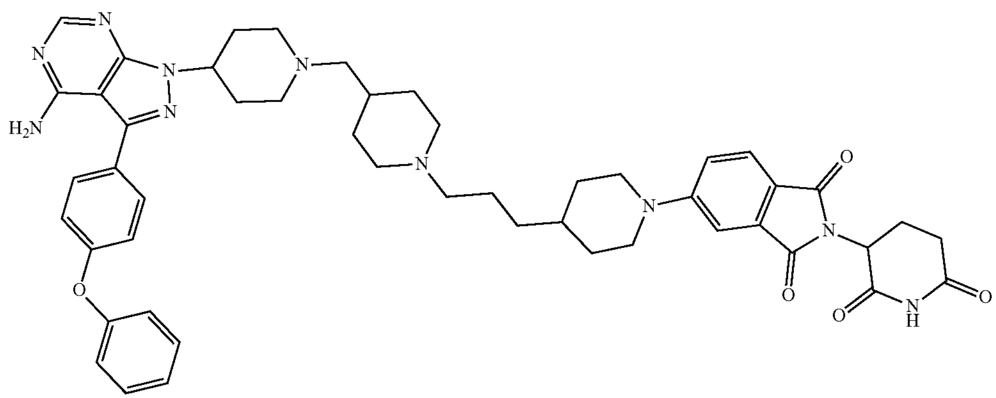 [SMILES: Nc1ncnc2c1c(-c1ccc(Oc3ccccc3)cc1)nn2C1CCN(CC2CCN(CCCC3CCN(c4ccc5c(c4)C(=O)N(C4CCC(=O)NC4=O)C5=O)CC3)CC2)CC1] | 5-(4-(3-(4-((4-(4-amino-3-(4-phenoxyphenyl)-1H-pyrazolo[3,4-d]pyrimidin-1-yl)piperidin-1-yl)methyl)piperidin-1-yl)propyl)piperidin-1-yl)-2-(2,6-dioxopiperidin-3-yl)isoindoline-1,3-dione | 864.44 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 212 | 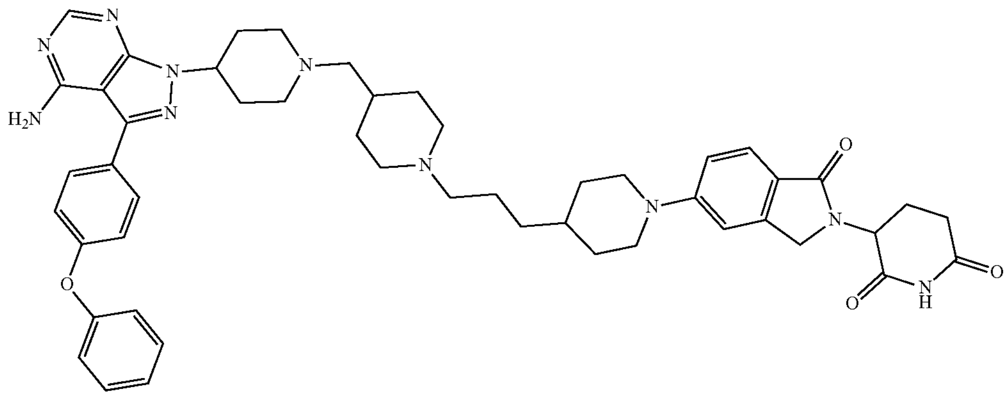 [SMILES: Nc1ncnc2c1c(-c1ccc(Oc3ccccc3)cc1)nn2C1CCN(CC2CCN(CCCC3CCN(c4ccc5c(c4)CN(C4CCC(=O)NC4=O)C5=O)CC3)CC2)CC1] | 3-(5-(4-(3-(4-((4-amino-3-(4-phenoxyphenyl)-1H-pyrazolo[3,4-d]pyrimidin-1-yl)piperidin-1-yl)methyl)piperidin-1-yl)propyl)piperidin-1-yl)-1-oxoisoindolin-2-yl)piperidine-2,6-dione | 850.46 | C | B | B | A |
| 213 | 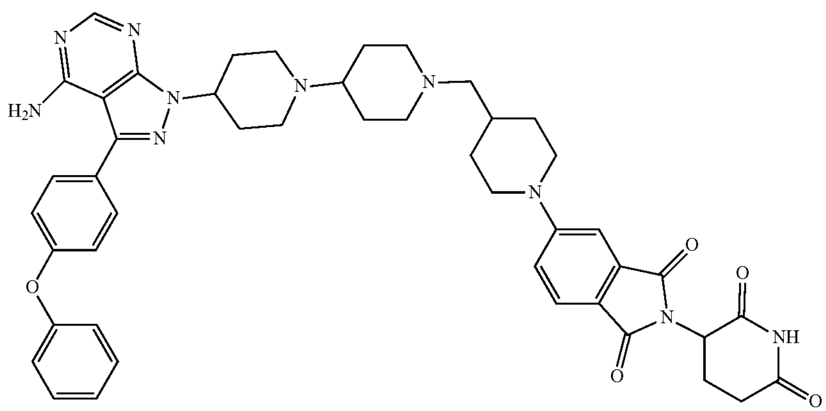 [SMILES: Nc1ncnc2c1c(-c1ccc(Oc3ccccc3)cc1)nn2C1CCN(C2CCN(CC3CCN(c4ccc5c(c4)C(=O)N(C4CCC(=O)NC4=O)C5=O)CC3)CC2)CC1] | 5-(4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)-2-(2,6-dioxopiperidin-3-yl)isoindoline-1,3-dione | 822.40 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 213a | 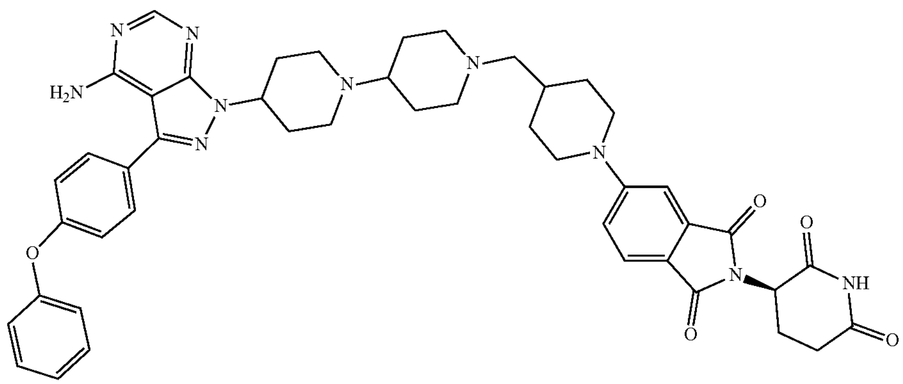 [SMILES: Nc1ncnc2c1c(-c1ccc(Oc3ccccc3)cc1)nn2C1CCN(C2CCN(CC3CCN(c4ccc5c(c4)C(=O)N([C@@H]4CCC(=O)NC4=O)C5=O)CC3)CC2)CC1] | (R)-5-(4-((4-(4-amino-3-(4-phenoxyphenyl)-1H-pyrazolo[3,4-d]pyrimidin-1-yl)[1,4'-bipiperidin]-1'-yl)methyl)piperidin-1-yl)-2-(2,6-dioxopiperidin-3-yl)isoindoline-1,3-dione | 822.40 | A | A | A | A |
| 213b | 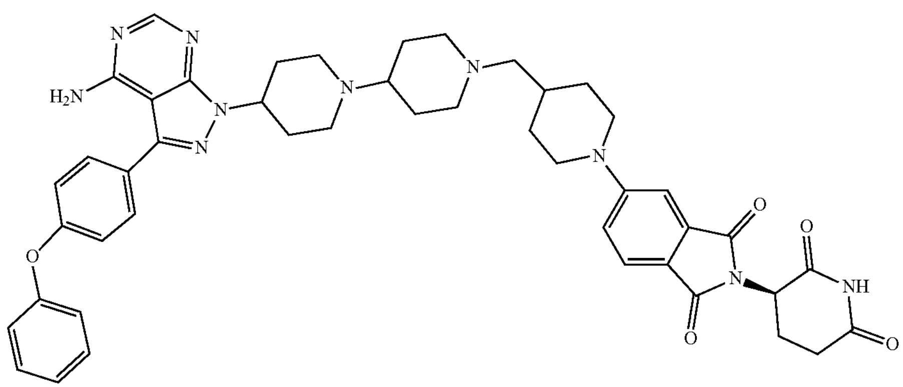 [SMILES: Nc1ncnc2c1c(-c1ccc(Oc3ccccc3)cc1)nn2C1CCN(C2CCN(CC3CCN(c4ccc5c(c4)C(=O)N([C@@H]4CCC(=O)NC4=O)C5=O)CC3)CC2)CC1] | (S)-5-(4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)-2-(2,6-dioxopiperidin-3-yl)isoindoline-1,3-dione | 822.40 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 214 | 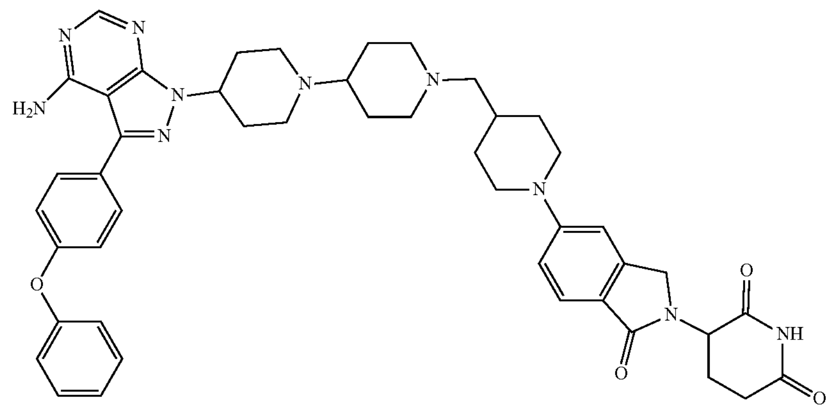 [SMILES: Nc1ncnc2c1c(-c1ccc(Oc3ccccc3)cc1)nn2C1CCN(C2CCN(CC3CCN(c4ccc5c(c4)CN(C4CCC(=O)NC4=O)C5=O)CC3)CC2)CC1] | 3-(5-(4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)-1-oxoisoindolin-2-yl)piperidine-2,6-dione | 808.42 | B | B | C | D |
| 215 | 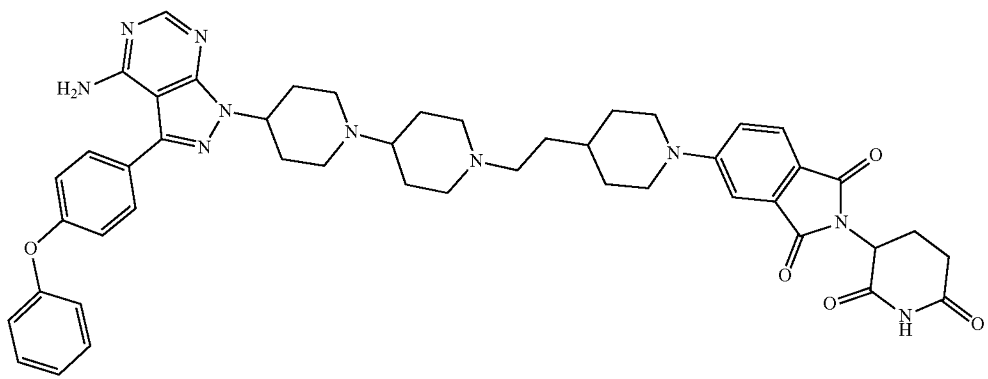 [SMILES: Nc1ncnc2c1c(-c1ccc(Oc3ccccc3)cc1)nn2C1CCN(C2CCN(CCC3CCN(c4ccc5c(c4)C(=O)N(C4CCC(=O)NC4=O)C5=O)CC3)CC2)CC1] | 5-(4-(2-(4-(4-amino-3-(4-phenoxyphenyl)-1H-pyrazolo[3,4-d]pyrimidin-1-yl)-[1,4'-bipiperidin]-1'-yl)ethyl)piperidin-3-yl)isoindoline-1,3-dione | 836.41 | A | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 216 | 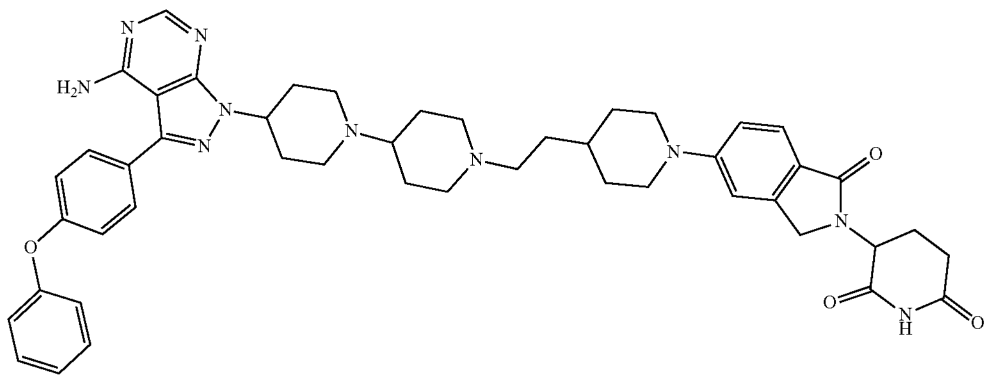 [SMILES: Nc1ncnc2c1c(-c1ccc(Oc3ccccc3)cc1)nn2C1CCN(C2CCN(CCC3CCN(c4ccc5c(c4)CN(C4CCC(=O)NC4=O)C5=O)CC3)CC2)CC1] | 3-(5-(4-(2-(4-(4-amino-3-(4-phenoxyphenyl)-1H-pyrazolo[3,4-d]pyrimidin-1-yl)-[1,4'-bipiperidin]-1'-yl)ethyl)piperidin-1-yl)-1-oxoisoindolin-2-yl)piperidine-2,6-dione | 822.42 | A | A | B | B |
| 217 | 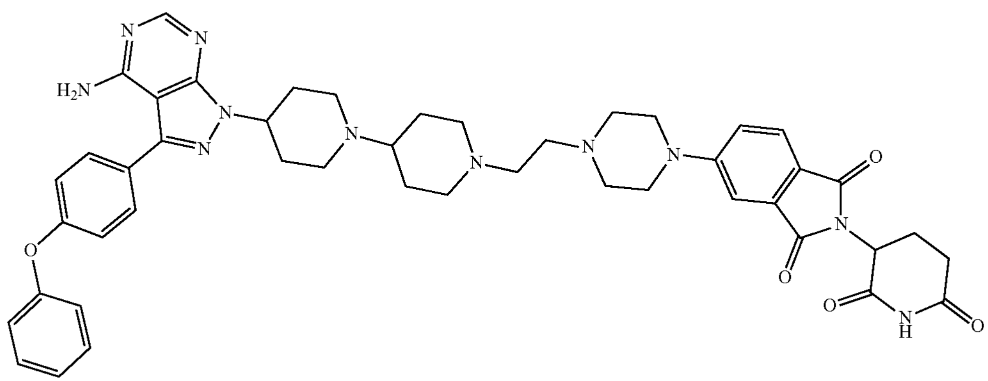 [SMILES: Nc1ncnc2c1c(-c1ccc(Oc3ccccc3)cc1)nn2C1CCN(C2CCN(CCN3CCN(c4ccc5c(c4)C(=O)N(C4CCC(=O)NC4=O)C5=O)CC3)CC2)CC1] | 5-(4-(2-(4-(4-amino-3-(4-phenoxyphenyl)-1H-pyrazolo[3,4-d]pyrimidin-1-yl)-[1,4'-bipiperidin]-1'-yl)ethyl)piperazin-1-yl)-2-(2,6-dioxopiperidin-3-yl)isoindoline-1,3-dione | 837.41 | A | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 218 | 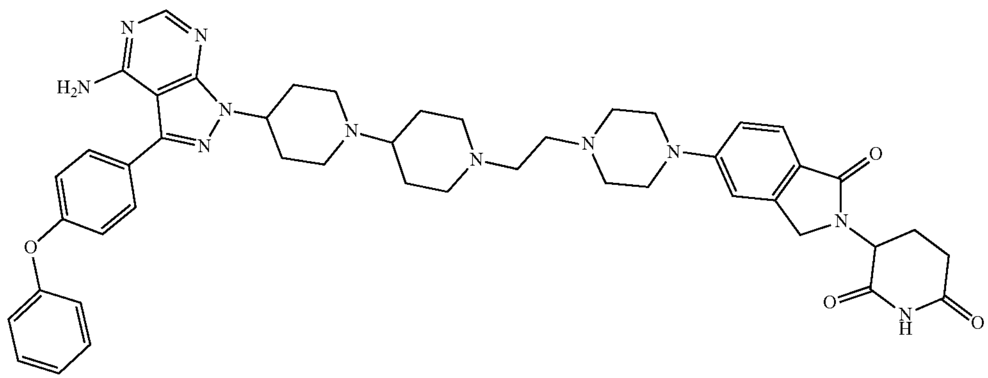 [SMILES: Nc1ncnc2c1c(-c1ccc(Oc3ccccc3)cc1)nn2C1CCN(C2CCN(CCN3CCN(c4ccc5c(c4)CN(C4CCC(=O)NC4=O)C5=O)CC3)CC2)CC1] | 3-(5-(4-(2-(4-(4-amino-3-(4-phenoxyphenyl)-1H-pyrazolo[3,4-d]pyrimidin-1-yl)-[1,4'-bipiperidin]-1'-yl)ethyl)piperazin-1-yl)-1-oxoisoindolin-2-yl)piperidine-2,6-dione | 823.43 | A | B | B | B |
| 219 | 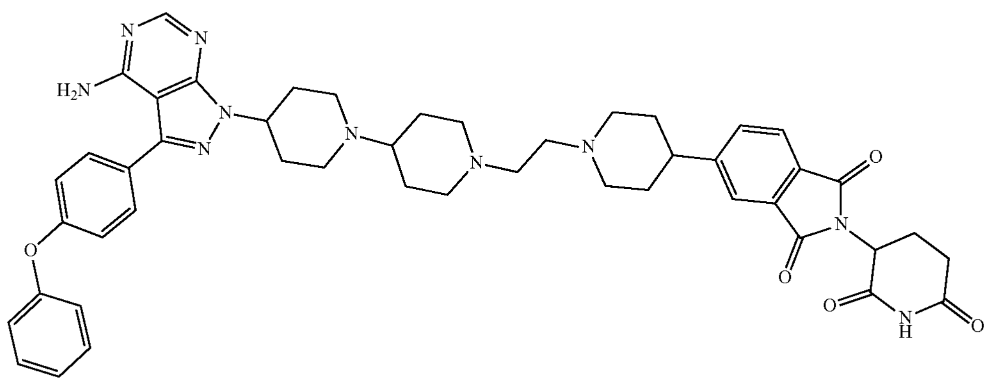 [SMILES: Nc1ncnc2c1c(-c1ccc(Oc3ccccc3)cc1)nn2C1CCN(C2CCN(CCN3CCC(c4ccc5c(c4)C(=O)N(C4CCC(=O)NC4=O)C5=O)CC3)CC2)CC1] | 5-(1-(2-(4-(4-amino-3-(4-phenoxyphenyl)-1H-pyrazolo[3,4-d]pyrimidin-1-yl)-[1,4'-bipiperidin]-1'-yl)ethyl)piperidin-4-yl)-2-(2,6-dioxopiperidin-3-yl)isoindoline-1,3-dione | 836.41 | B | B | B | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 220 | 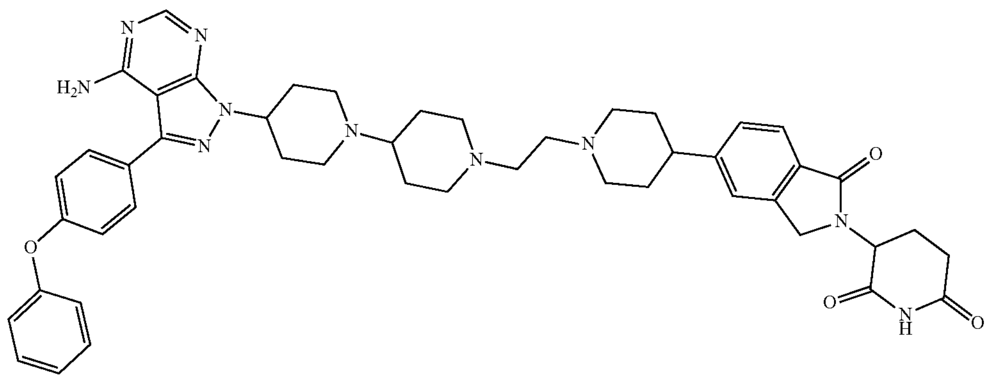 [SMILES: Nc1ncnc2c1c(-c1ccc(Oc3ccccc3)cc1)nn2C1CCN(C2CCN(CCN3CCC(c4ccc5c(c4)CN(C4CCC(=O)NC4=O)C5=O)CC3)CC2)CC1] | 3-(5-(1-(2-(4-(4-amino-3-(4-phenoxyphenyl)-1H-pyrazolo[3,4-d]pyrimidin-1-yl)-[1,4'-bipiperidin]-1'-yl)ethyl)piperidin-4-yl)-1-oxoisoindolin-2-yl)piperidine-2,6-dione | 822.43 | B | B | B | B |
| 221 | 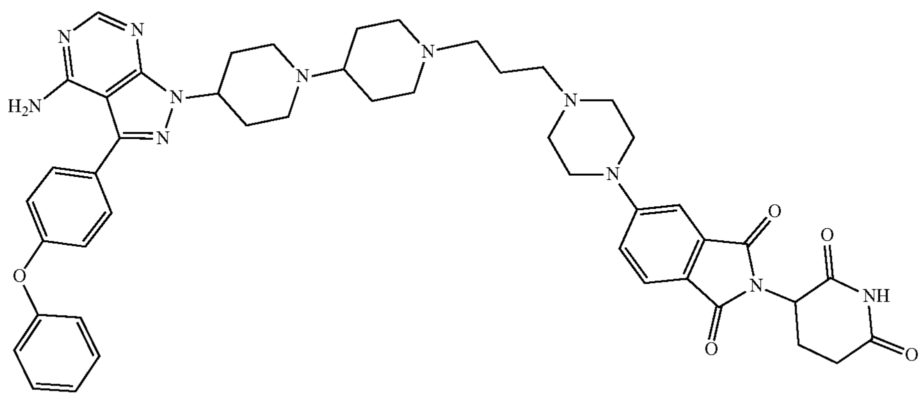 [SMILES: Nc1ncnc2c1c(-c1ccc(Oc3ccccc3)cc1)nn2C1CCN(C2CCN(CCCN3CCN(c4ccc5c(c4)C(=O)N(C4CCC(=O)NC4=O)C5=O)CC3)CC2)CC1] | 5-(4-(3-(4-(4-amino-3-(4-phenoxyphenyl)-1H-pyrazolo[3,4-d]pyrimidin-1-yl)-[1,4'-bipiperidin]-1'-yl)propyl)piperazin-1-yl)-2-(2,6-dioxopiperidin-3-yl)isoindoline-1,3-dione | 851.42 | B | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 222 | 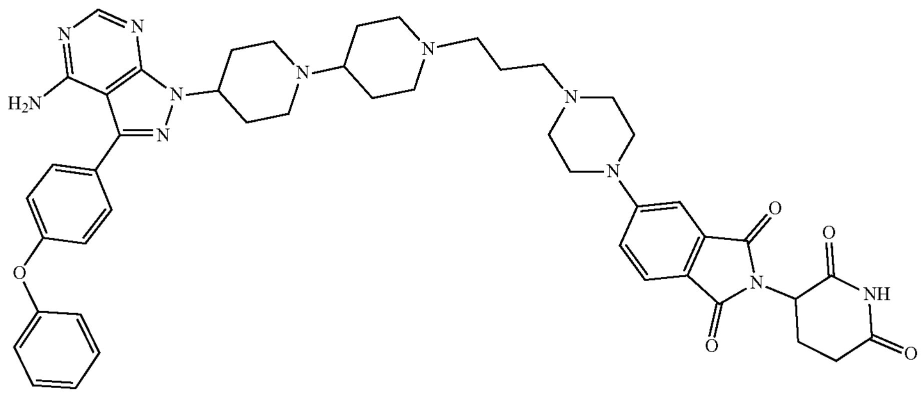 [SMILES: Nc1ncnc2c1c(-c1ccc(Oc3ccccc3)cc1)nn2C1CCN(C2CCN(CCCN3CCN(c4ccc5c(c4)C(=O)N(C4CCC(=O)NC4=O)C5=O)CC3)CC2)CC1] | 3-(5-(4-(3-(4-(4-amino-3-(4-phenoxyphenyl)-1H-pyrazolo[3,4-d]pyrimidin-1-yl)-[1,4'-bipiperidin]-1'-yl)propyl)piperazin-1-yl)-1-oxoisoindolin-2-yl)piperidine-2,6-dione | 837.44 | B | B | B | A |
| 223 | 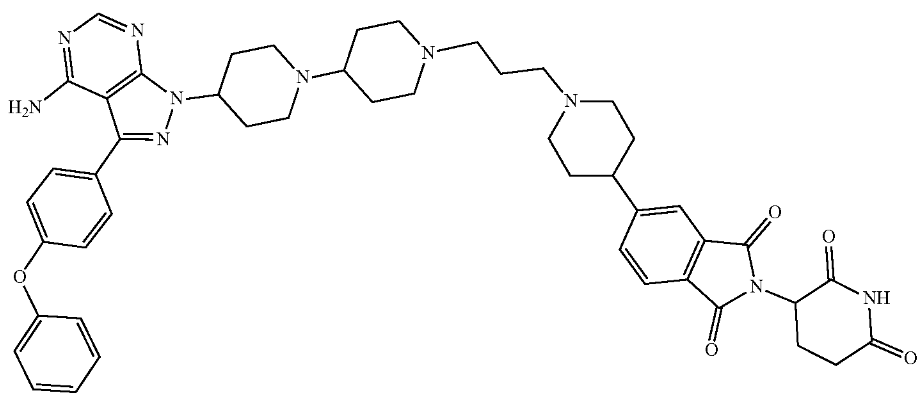 [SMILES: Nc1ncnc2c1c(-c1ccc(Oc3ccccc3)cc1)nn2C1CCN(C2CCN(CCCN3CCC(c4ccc5c(c4)C(=O)N(C4CCC(=O)NC4=O)C5=O)CC3)CC2)CC1] | 5-(1-(3-(4-(4-amino-3-(4-phenoxyphenyl)-1H-pyrazolo[3,4-d]pyrimidin-1-yl)-[1,4'-bipiperidin]-1'-yl)propyl)piperidin-4-yl)-2-(2,6-dioxopiperidin-3-yl)isoindoline-1,3-dione | 850.43 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 224 | 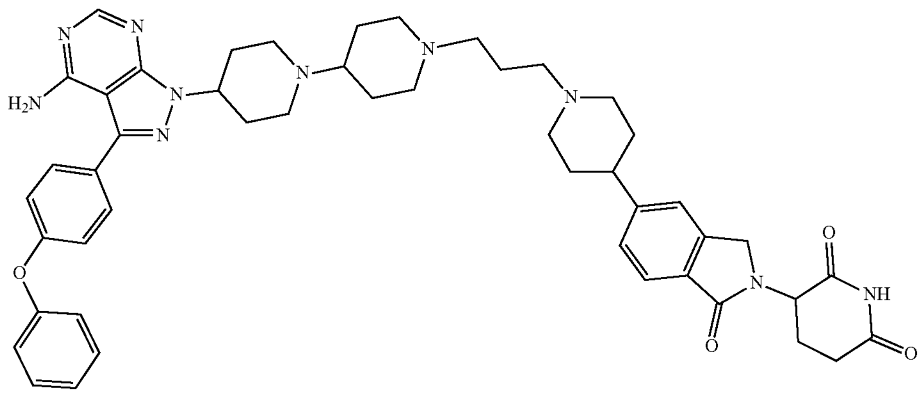 [SMILES: Nc1ncnc2c1c(-c1ccc(Oc3ccccc3)cc1)nn2C1CCN(C2CCN(CCCN3CCC(c4ccc5c(c4)CN(C4CCC(=O)NC4=O)C5=O)CC3)CC2)CC1] | 3-(5-(1-(3-(4-(4-amino-3-(4-phenoxyphenyl)-1H-pyrazolo[3,4-d]pyrimidin-1-yl)-[1,4'-bipiperidin]-1'-yl)propyl)piperidin-4-yl)-1-oxoisoindolin-2-yl)piperidine-2,6-dione | 836.45 | B | B | B | B |
| 225 | 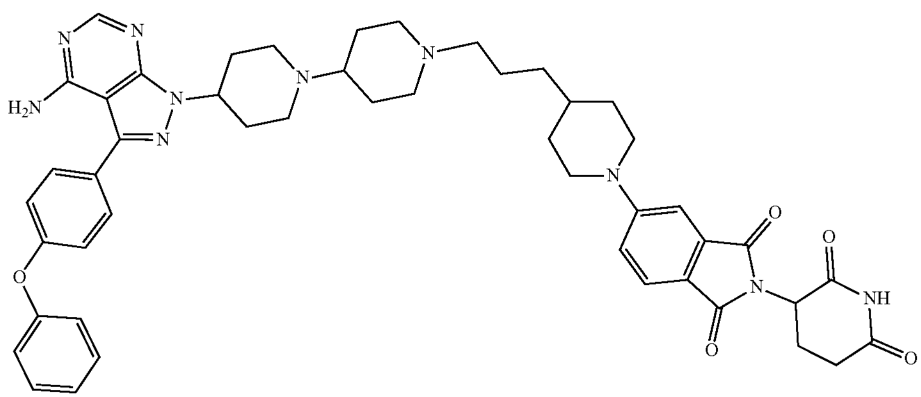 [SMILES: Nc1ncnc2c1c(-c1ccc(Oc3ccccc3)cc1)nn2C1CCN(C2CCN(CCCC3CCN(c4ccc5c(c4)C(=O)N(C4CCC(=O)NC4=O)C5=O)CC3)CC2)CC1] | 5-(4-(3-(4-(4-amino-3-(4-phenoxyphenyl)-1H-pyrazolo[3,4-d]pyrimidin-1-yl)-[1,4'-bipiperidin]-1'-yl)propyl)piperidin-1-yl)-2-(2,6-dioxopiperidin-3-yl)isoindoline-1,3-dione | 850.43 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 226 | 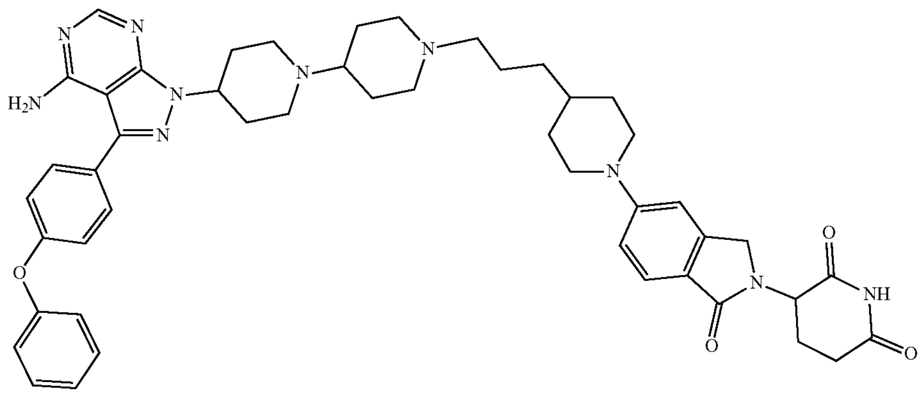 [SMILES: Nc1ncnc2c1c(-c1ccc(Oc3ccccc3)cc1)nn2C1CCN(C2CCN(CCCC3CCN(c4ccc5c(c4)CN(C4CCC(=O)NC4=O)C5=O)CC3)CC2)CC1] | 3-(5-(4-(3-(4-(4-amino-3-(4-phenoxyphenyl)-1H-pyrazolo[3,4-d]pyrimidin-1-yl)-[1,4'-bipiperidin]-1'-yl)propyl)piperidin-1-yl)-1-oxoisoindolin-2-yl)piperidine-2,6-dione | 835.45 | C | B | B | B |
| 227 | 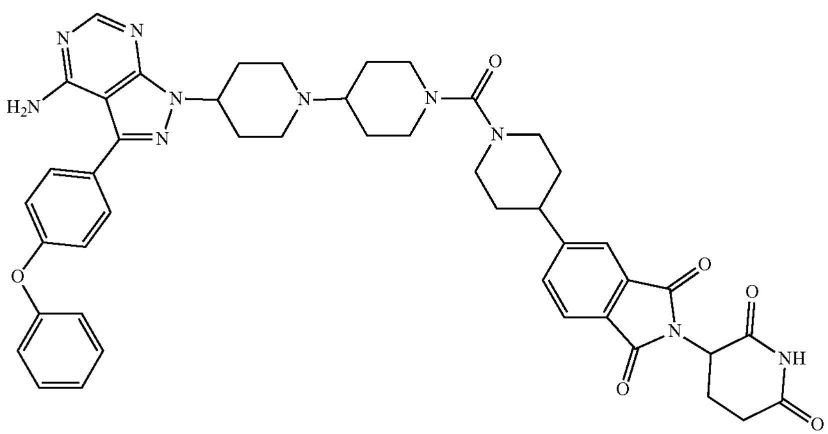 [SMILES: Nc1ncnc2c1c(-c1ccc(Oc3ccccc3)cc1)nn2C1CCN(C2CCN(C(=O)N3CCC(c4ccc5c(c4)C(=O)N(C4CCC(=O)NC4=O)C5=O)CC3)CC2)CC1] | 5-(1-(4-(4-(4-amino-3-(4-phenoxyphenyl)-1H-pyrazolo[3,4-d]pyrimidin-1-yl)-[1,4'-bipiperidine]-1'-carbonyl)piperidin-4-yl)-2-(2,6-dioxopiperidin-3-yl)isoindoline-1,3-dione | 836.38 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 228 | 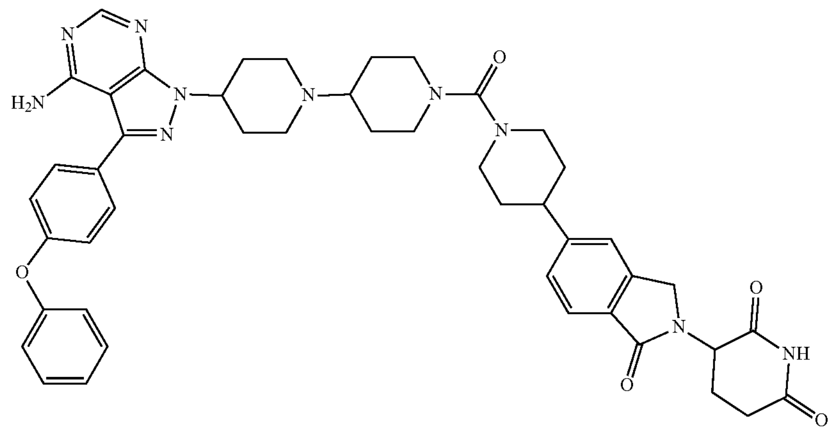 [SMILES: Nc1ncnc2c1c(-c1ccc(Oc3ccccc3)cc1)nn2C1CCN(C2CCN(C(=O)N3CCC(c4ccc5c(c4)CN(C4CCC(=O)NC4=O)C5=O)CC3)CC2)CC1] | 3-(5-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)-1-oxoisoindolin-2-yl)piperidine-2,6-dione | 822.40 | C | C | C | C |
| 229 | 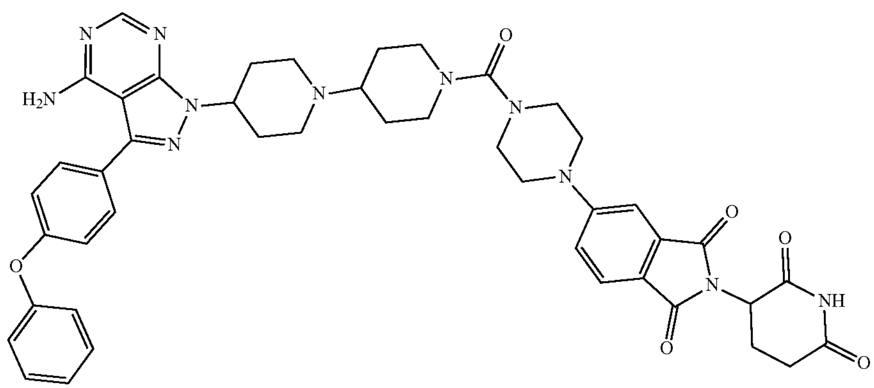 [SMILES: Nc1ncnc2c1c(-c1ccc(Oc3ccccc3)cc1)nn2C1CCN(C2CCN(C(=O)N3CCN(c4ccc5c(c4)C(=O)N(C4CCC(=O)NC4=O)C5=O)CC3)CC2)CC1] | 5-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)-2-(2,6-dioxopiperidin-3-yl)isoindoline-1,3-dione | 837.37 | B | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 230 | 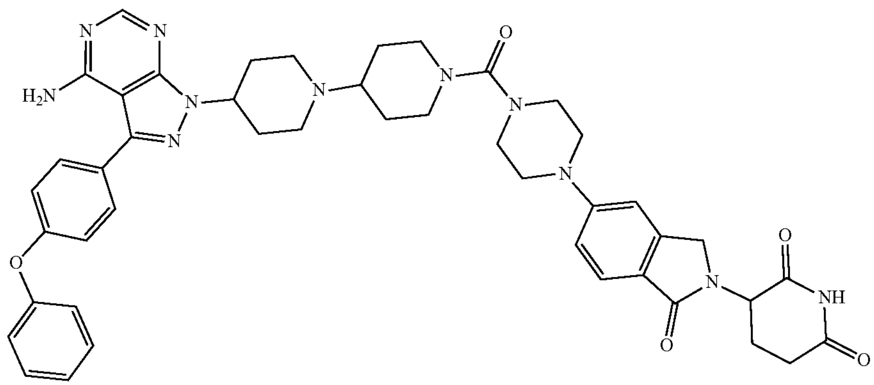 [SMILES: Nc1ncnc2c1c(-c1ccc(Oc3ccccc3)cc1)nn2C1CCN(C2CCN(C(=O)N3CCN(c4ccc5c(c4)CN(C4CCC(=O)NC4=O)C5=O)CC3)CC2)CC1] | 3-(5-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)-1-oxoisoindolin-2-yl)piperidine-2,6-dione | 823.39 | B | B | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 231 | 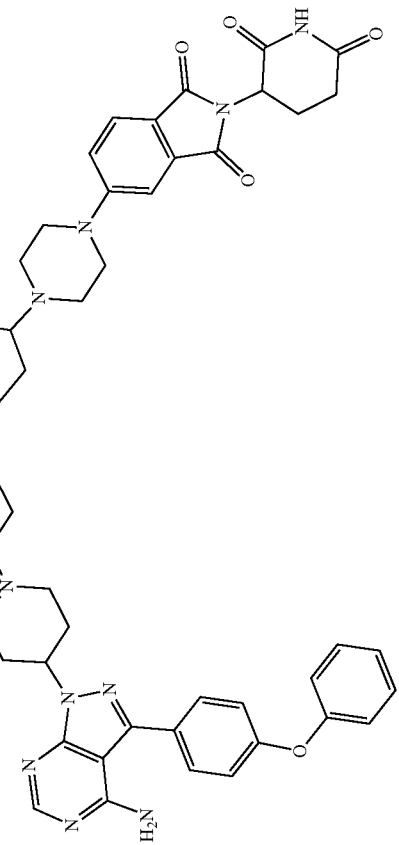 | 5-(4-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)piperazin-1-yl)-2-(2,6-dioxopiperidin-3-yl)isoindoline-1,3-dione | 920.44 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 232 | 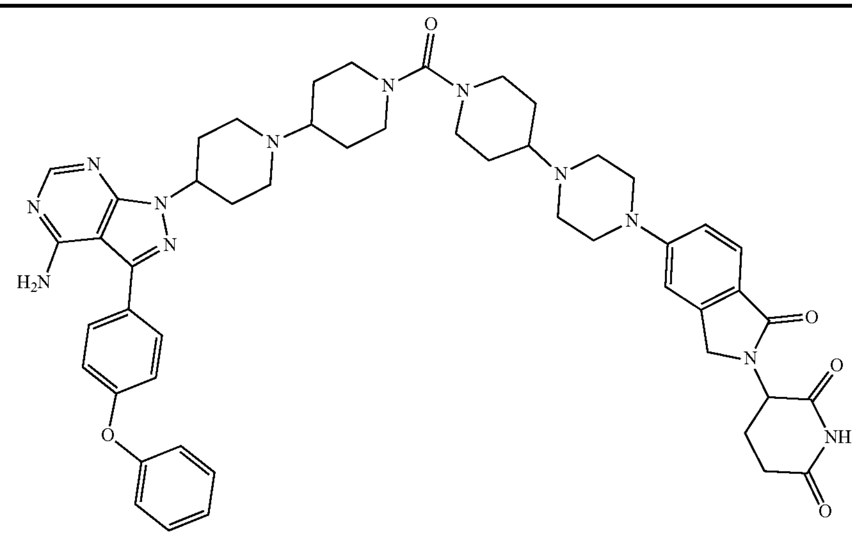 | 3-(5-(4-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)piperazin-1-yl)-1-oxoisoindolin-2-yl)piperidine-2,6-dione | 906.47 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 233 | 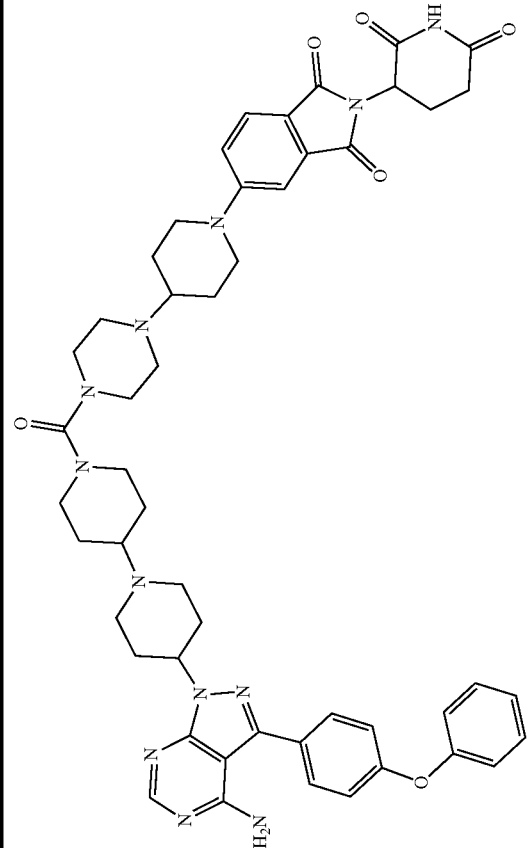 | 5-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)piperidin-1-yl)-2-(2,6-dioxopiperidin-3-yl)isoindoline-1,3-dione | 920.44 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 234 | 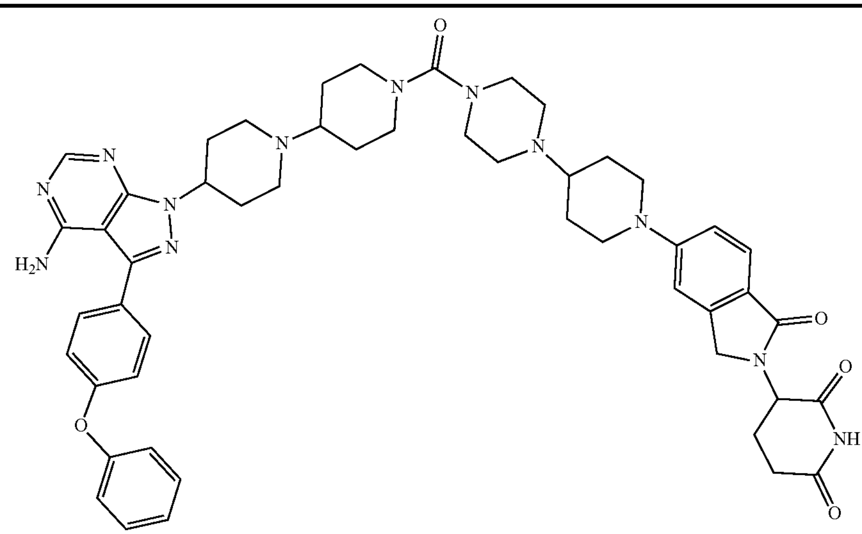 | 3-(5-(4-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)piperidin-1-yl)-1-oxoisoindolin-2-yl)piperidine-2,6-dione | 906.47 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 235 | 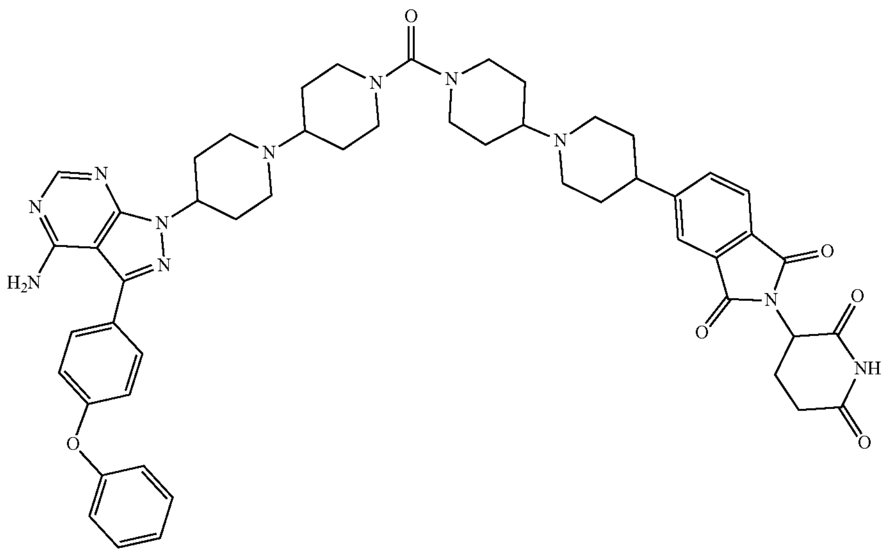 [SMILES: Nc1ncnc2c1c(-c1ccc(Oc3ccccc3)cc1)nn2C1CCN(C2CCN(C(=O)N3CCC(N4CCC(c5ccc6c(c5)C(=O)N(C5CCC(=O)NC5=O)C6=O)CC4)CC3)CC2)CC1] | 5-(1'-(4-(4-amino-3-(4-phenoxyphenyl)-1H-pyrazolo[3,4-d]pyrimidin-1-yl)-[1,4'-bipiperidine]-1'-carbonyl)-[1,4'-bipiperidin]-4-yl)-2-(2,6-dioxopiperidin-3-yl)isoindoline-1,3-dione | 919.45 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 236 | 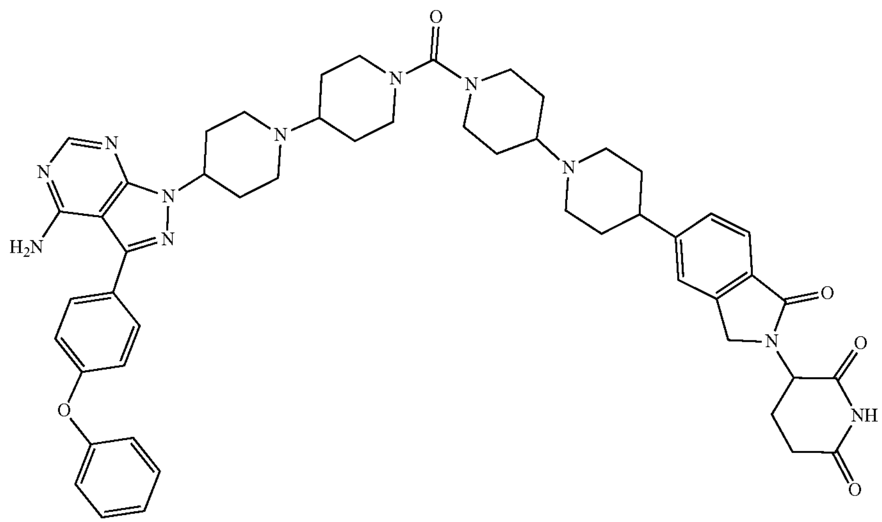 [SMILES: Nc1ncnc2c1c(-c1ccc(Oc3ccccc3)cc1)nn2C1CCN(C2CCN(C(=O)N3CCC(N4CCC(c5ccc6c(c5)CN(C5CCC(=O)NC5=O)C6=O)CC4)CC3)CC2)CC1] | 3-(5-(1'-(4-(4-amino-3-(4-phenoxyphenyl)-1H-pyrazolo[3,4-d]pyrimidin-1-yl)-[1,4'-bipiperidine]-1'-carbonyl)-[1,4'-bipiperidin]-4-yl)-1-oxoisoindolin-2-yl)piperidine-2,6-dione | 905.47 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 237 | 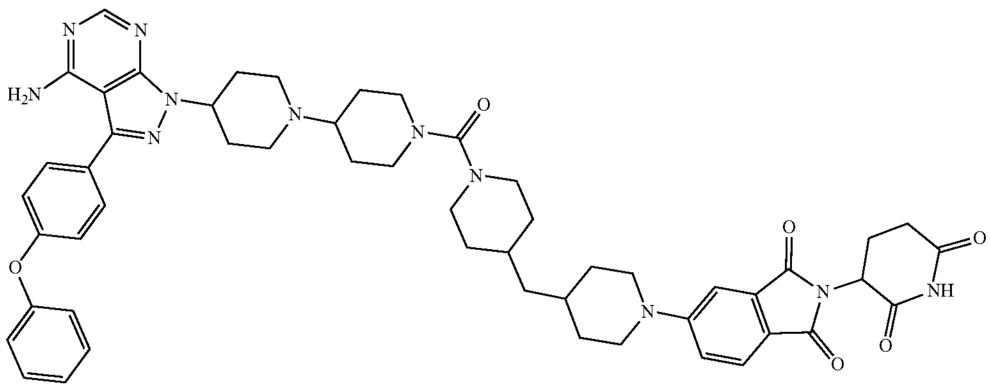 [SMILES: Nc1ncnc2c1c(-c1ccc(Oc3ccccc3)cc1)nn2C1CCN(C2CCN(C(=O)N3CCC(CC4CCN(c5ccc6c(c5)C(=O)N(C5CCC(=O)NC5=O)C6=O)CC4)CC3)CC2)CC1] | 5-(4-((1-(4-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-1-yl)-2-(2,6-dioxopiperidin-3-yl)isoindoline-1,3-dione | 933.46 | B | A | B | A |
| 238 | 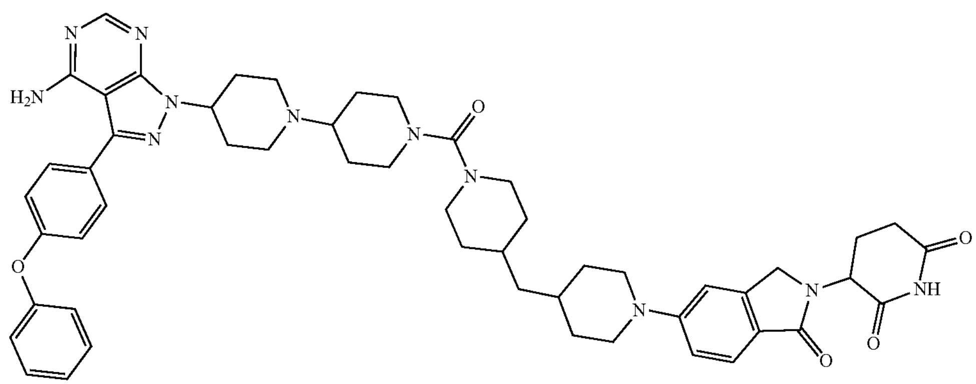 | 3-(5-(4-((1-(4-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-1-yl)-1-oxoisoindolin-2-yl)piperidine-2,6-dione | 919.49 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 239 | 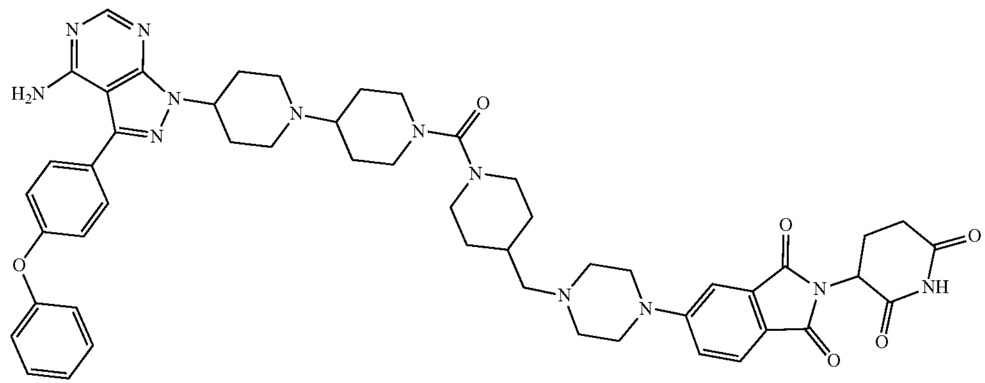 [SMILES: Nc1ncnc2c1c(-c1ccc(Oc3ccccc3)cc1)nn2C1CCN(C2CCN(C(=O)N3CCC(CN4CCN(c5ccc6c(c5)C(=O)N(C5CCC(=O)NC5=O)C6=O)CC4)CC3)CC2)CC1] | 5-(4-((1-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperazin-1-yl)-2-(2,6-dioxopiperidin-3-yl)isoindoline-1,3-dione | 934.46 | A | B | B | A |
| 240 | 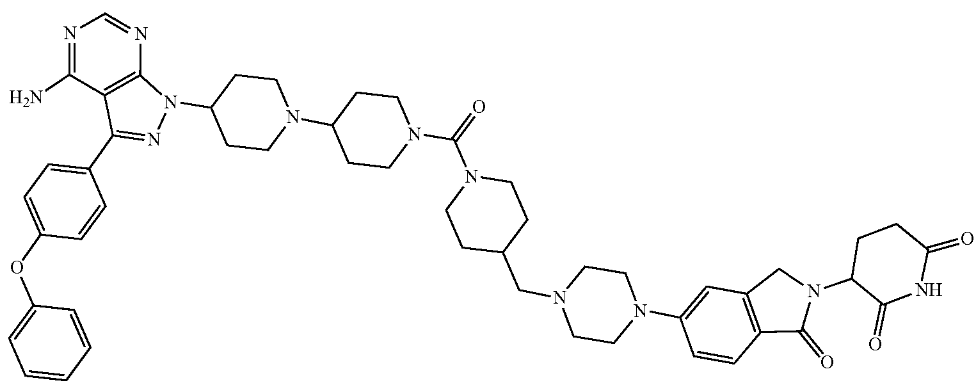 [SMILES: Nc1ncnc2c1c(-c1ccc(Oc3ccccc3)cc1)nn2C1CCN(C2CCN(C(=O)N3CCC(CN4CCN(c5ccc6c(c5)CN(C5CCC(=O)NC5=O)C6=O)CC4)CC3)CC2)CC1] | 3-(5-(4-((1-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperazin-1-yl)-1-oxoisoindolin-2-yl)piperidine-2,6-dione | 920.48 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 241 | 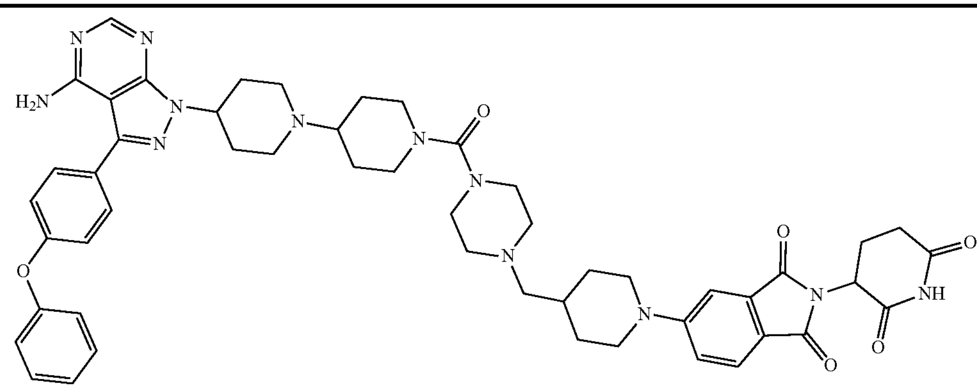 | 5-(4-((4-(4-(4-amino-3-(4-phenoxyphenyl)-1H-pyrazolo[3,4-d]pyrimidin-1-yl)-[1,4'-bipiperidine]-1'-carbonyl)piperazin-1-yl)methyl)piperidin-1-yl)-2-(2,6-dioxopiperidin-3-yl)isoindoline-1,3-dione | 934.46 | B | B | B | A |
| 242 | 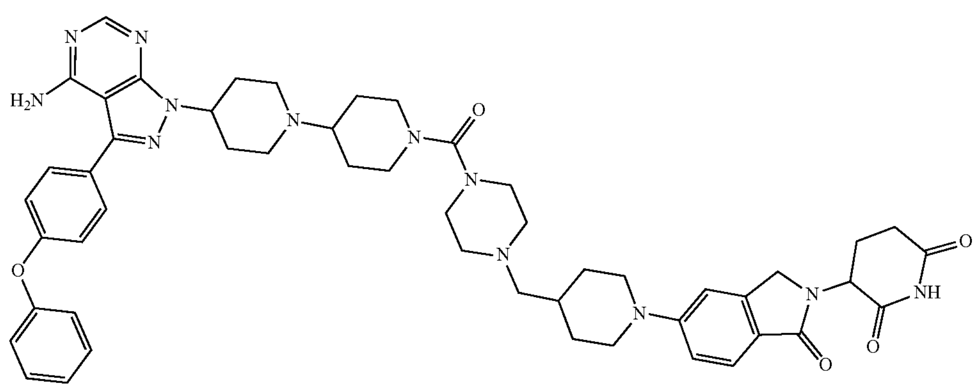 [SMILES: Nc1ncnc2c1c(-c1ccc(Oc3ccccc3)cc1)nn2C1CCN(C2CCN(C(=O)N3CCN(CC4CCN(c5ccc6c(c5)CN(C5CCC(=O)NC5=O)C6=O)CC4)CC3)CC2)CC1] | 3-(5-(4-((4-(4-(4-amino-3-(4-phenoxyphenyl)-1H-pyrazolo[3,4-d]pyrimidin-1-yl)-[1,4'-bipiperidine]-1'-carbonyl)piperazin-1-yl)methyl)piperidin-1-yl)-1-oxoisoindolin-2-yl)piperidine-2,6-dione | 920.48 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 243 | 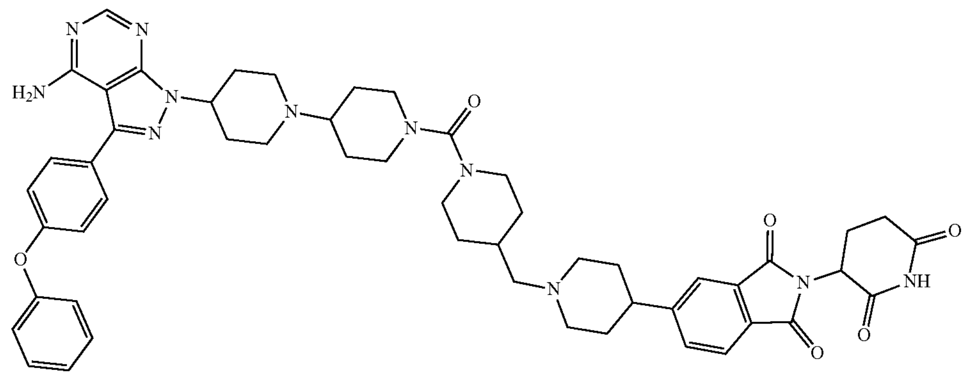 [SMILES: Nc1ncnc2c1c(-c1ccc(Oc3ccccc3)cc1)nn2C1CCN(C2CCN(C(=O)N3CCC(CN4CCC(c5ccc6c(c5)C(=O)N(C5CCC(=O)NC5=O)C6=O)CC4)CC3)CC2)CC1] | 5-(1-(1-(4-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-4-yl)-2-(2,6-dioxopiperidin-3-yl)isoindoline-1,3-dione | 933.46 | B | B | A | A |
| 244 | 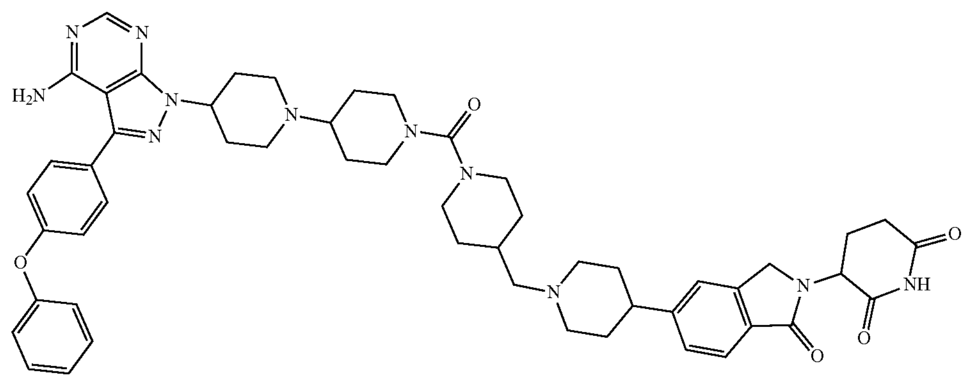 | 3-(5-(1-((1-(4-(4-(4-amino-3-(4-phenoxyphenyl)-1H-pyrazolo[3,4-d]pyrimidin-1-yl)-[1,4'-bipiperidine]-1'-carbonyl)piperidin-4-yl)methyl)piperidin-4-yl)-1-oxoisoindolin-2-yl)piperidine-2,6-dione | 919.49 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 245 | 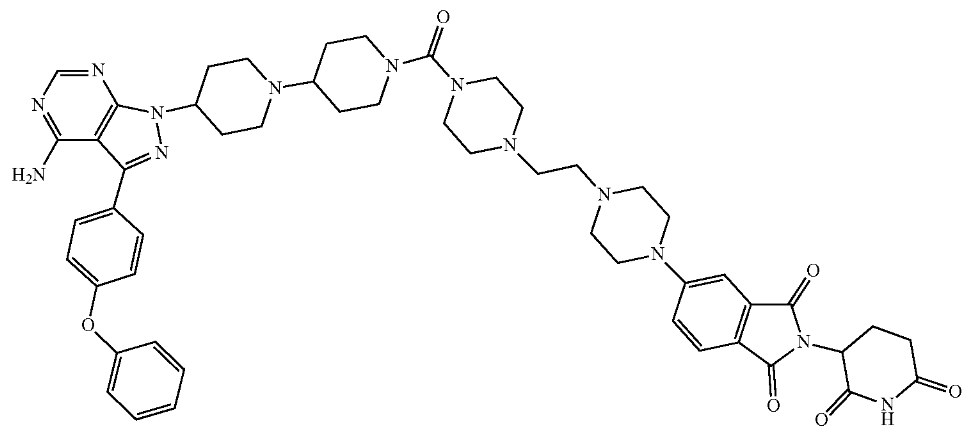 [SMILES: Nc1ncnc2c1c(-c1ccc(Oc3ccccc3)cc1)nn2C1CCN(C2CCN(C(=O)N3CCN(CCN4CCN(c5ccc6c(c5)C(=O)N(C5CCC(=O)NC5=O)C6=O)CC4)CC3)CC2)CC1] | 5-(4-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperazin-1-yl)-2-(2,6-dioxopiperidin-3-yl)isoindoline-1,3-dione | 949.47 | B | B | B | B |
| 246 | 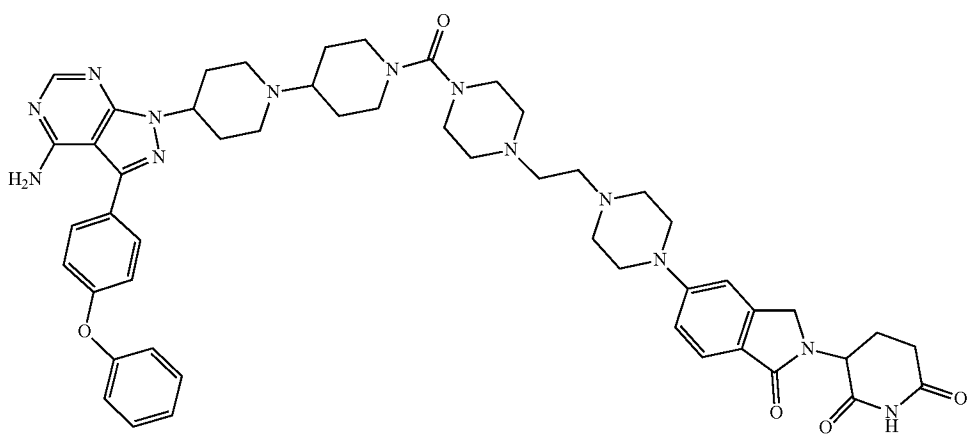 [SMILES: Nc1ncnc2c1c(-c1ccc(Oc3ccccc3)cc1)nn2C1CCN(C2CCN(C(=O)N3CCN(CCN4CCN(c5ccc6c(c5)CN(C5CCC(=O)NC5=O)C6=O)CC4)CC3)CC2)CC1] | 3-(5-(4-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperazin-1-yl)-1-oxoisoindolin-2-yl)piperidine-2,6-dione | 935.49 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 247 | 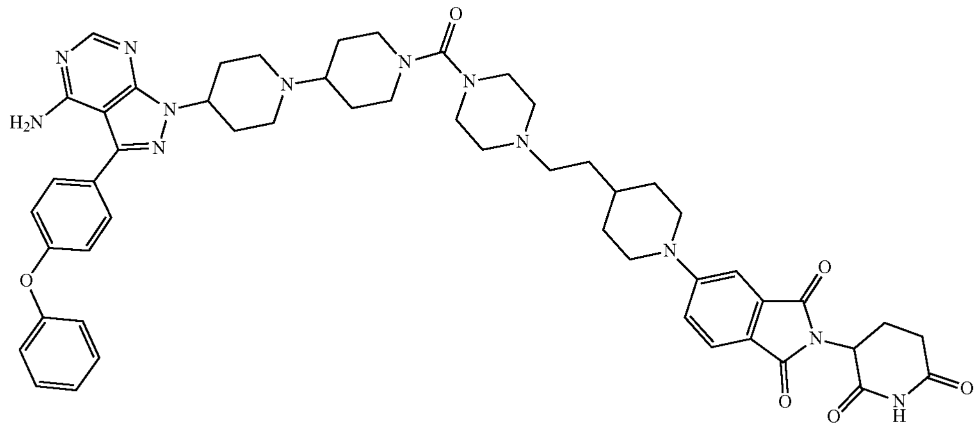 [SMILES: Nc1ncnc2c1c(-c1ccc(Oc3ccccc3)cc1)nn2C1CCN(C2CCN(C(=O)N3CCN(CCN4CCC(c5ccc6c(c5)C(=O)N(C5CCC(=O)NC5=O)C6=O)CC4)CC3)CC2)CC1] | 5-(4-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-1-yl)-2-(2,6-dioxopiperidin-3-yl)isoindoline-1,3-dione | 948.48 | B | B | B | B |
| 248 | 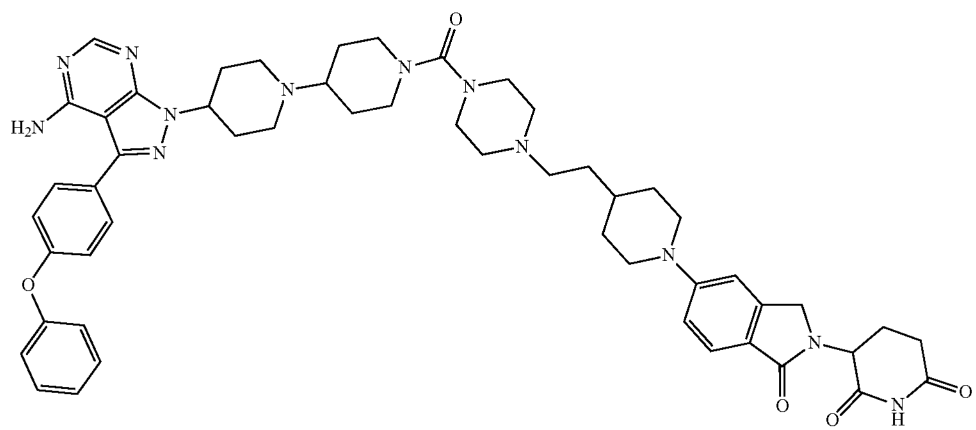 | 3-(5-(4-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-1-yl)-1-oxoisoindolin-2-yl)piperidine-2,6-dione | 934.50 | B | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 249 | 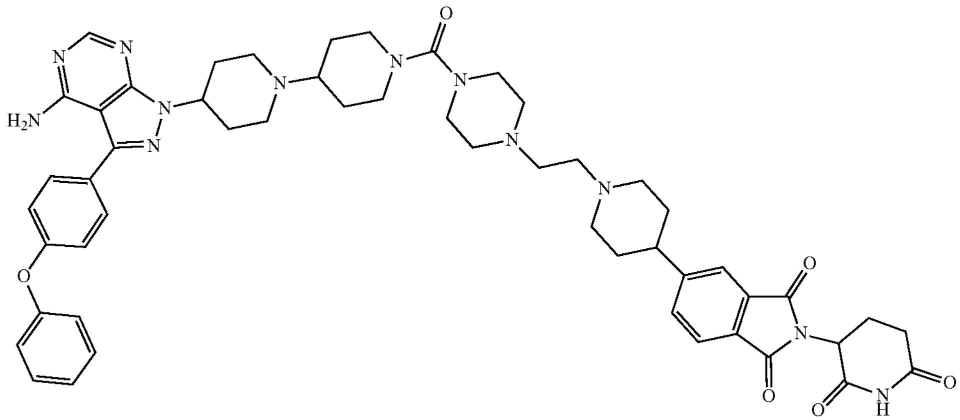 | 5-(1-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-4-yl)-2-(2,6-dioxopiperidin-3-yl)isoindoline-1,3-dione | 948.48 | B | A | B | B |
| 250 | 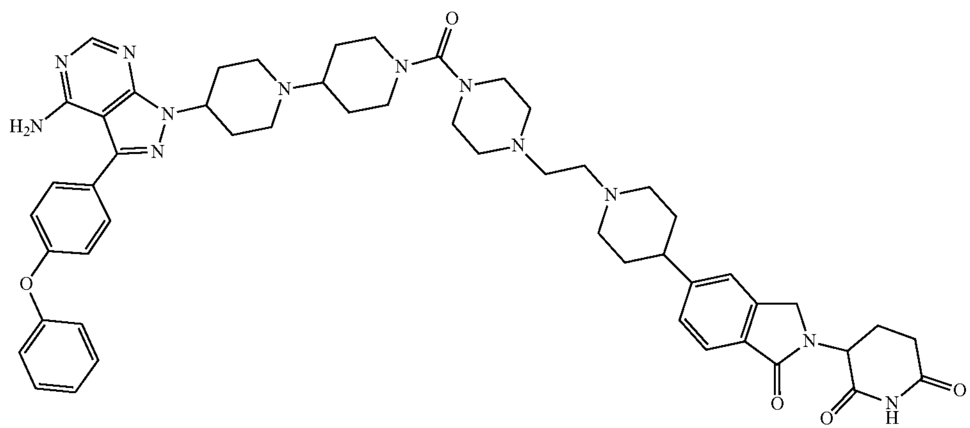 | 3-(5-(1-(2-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)ethyl)piperidin-4-yl)-1-oxoisoindolin-2-yl)piperidine-2,6-dione | 934.50 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 251 | 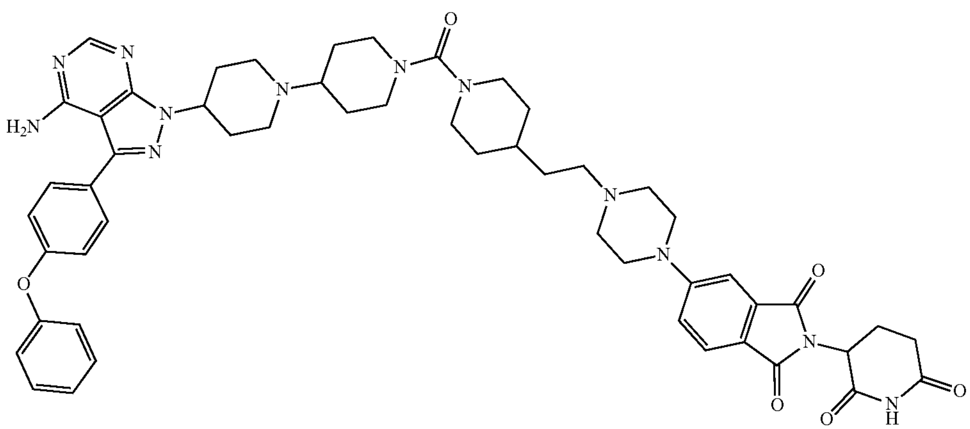 | 5-(4-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperazin-1-yl)-2-(2,6-dioxopiperidin-3-yl)isoindoline-1,3-dione | 948.48 | B | A | B | A |
| 252 | 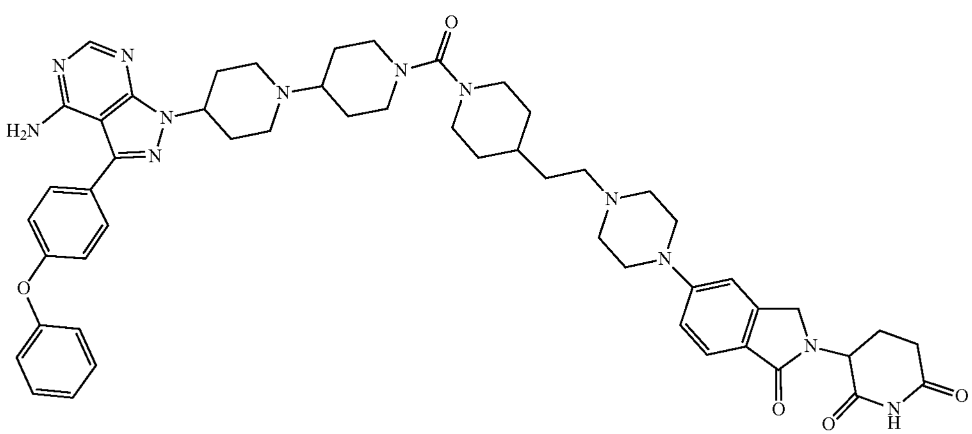 | 3-(5-(4-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperazin-1-yl)-1-oxoisoindolin-2-yl)piperidine-2,6-dione | 934.50 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 253 | 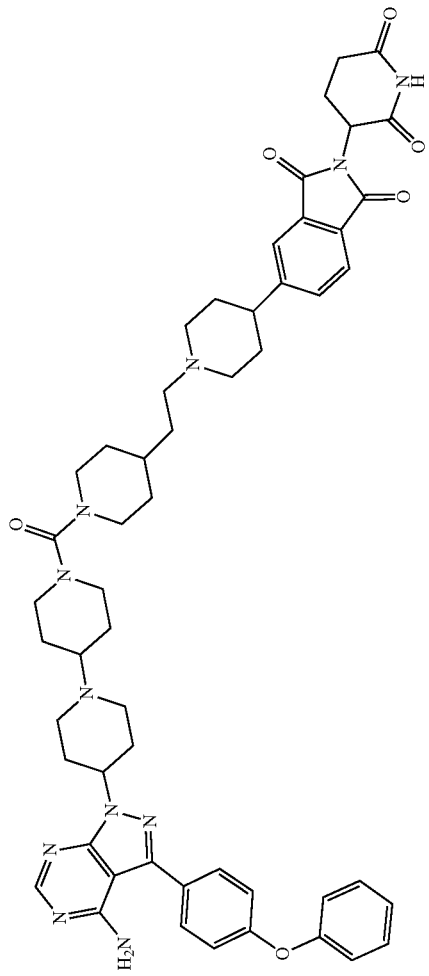 | 5-(1-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-4-yl)-2-(2,6-dioxopiperidin-3-yl)isoindoline-1,3-dione | 947.48 | B | B | B | A |
| 254 | 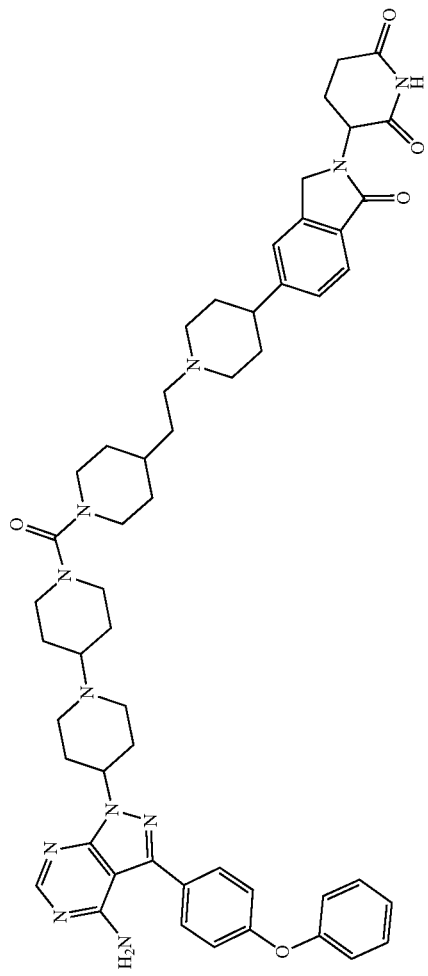 | 3-(5-(1-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-4-yl)-1-oxoisoindolin-2-yl)piperidine-2,6-dione | 933.50 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 255 | 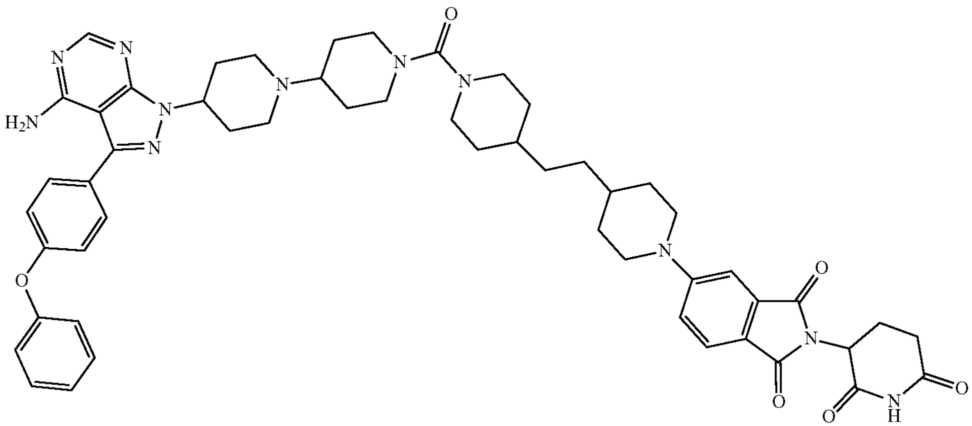 | 5-(4-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-1-yl)-2-(2,6-dioxopiperidin-3-yl)isoindoline-1,3-dione | 947.48 | B | A | B | A |
| 256 | 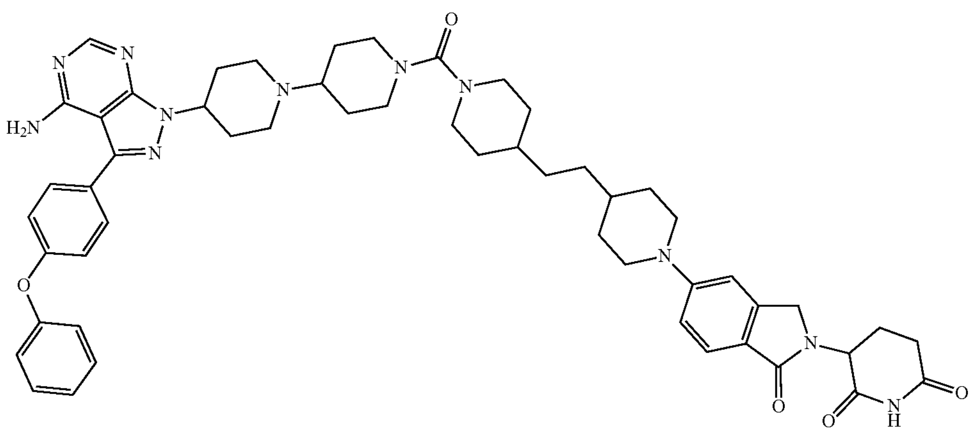 [SMILES: Nc1ncnc2c1c(-c1ccc(Oc3ccccc3)cc1)nn2C1CCN(C2CCN(C(=O)N3CCN(CCN4CCC(c5ccc6c(c5)CN(C5CCC(=O)NC5=O)C6=O)CC4)CC3)CC2)CC1] | 3-(5-(4-(2-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)ethyl)piperidin-1-yl)-1-oxoisoindolin-2-yl)piperidine-2,6-dione | 933.50 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 257 | 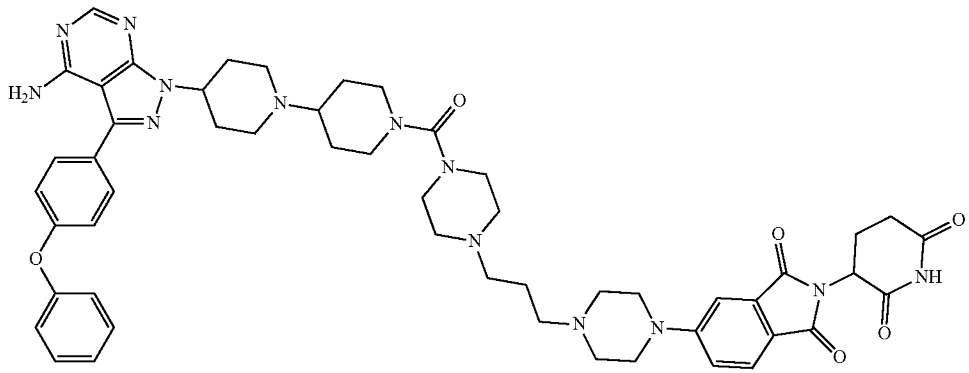 [SMILES: Nc1ncnc2c1c(-c1ccc(Oc3ccccc3)cc1)nn2C1CCN(C2CCN(C(=O)N3CCN(CCCN4CCN(c5ccc6c(c5)C(=O)N(C5CCC(=O)NC5=O)C6=O)CC4)CC3)CC2)CC1] | 5-(4-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperazin-1-yl)-2-(2,6-dioxopiperidin-3-yl)isoindoline-1,3-dione | 963.49 | C | C | C | B |
| 258 | 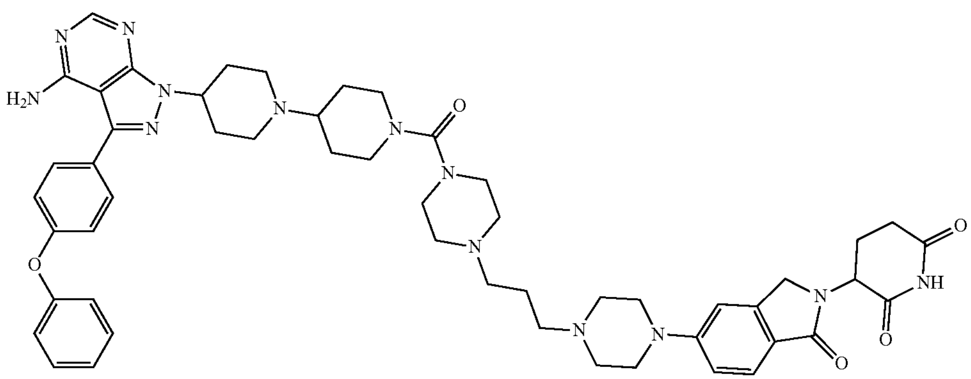 [SMILES: Nc1ncnc2c1c(-c1ccc(Oc3ccccc3)cc1)nn2C1CCN(C2CCN(C(=O)N3CCN(CCCN4CCN(c5ccc6c(c5)CN(C5CCC(=O)NC5=O)C6=O)CC4)CC3)CC2)CC1] | 3-(5-(4-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperazin-1-yl)-1-oxoisoindolin-2-yl)piperidine-2,6-dione | 948.51 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 259 | 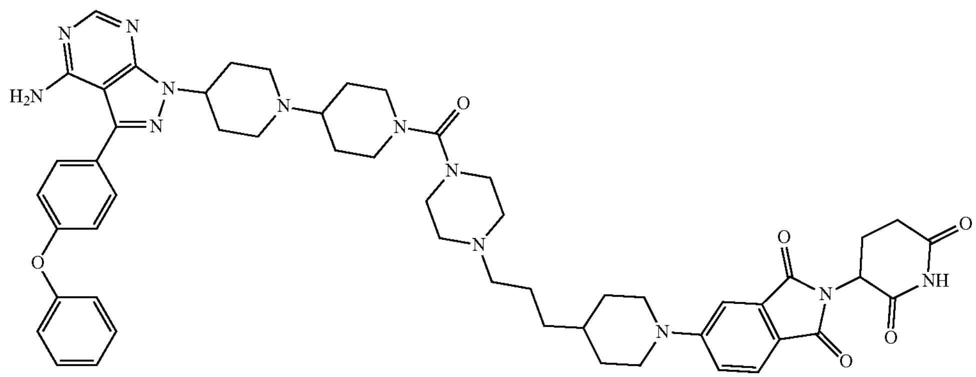 | 5-(4-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-1-yl)-2-(2,6-dioxopiperidin-3-yl)isoindoline-1,3-dione | 962.49 | B | C | C | B |
| 260 | 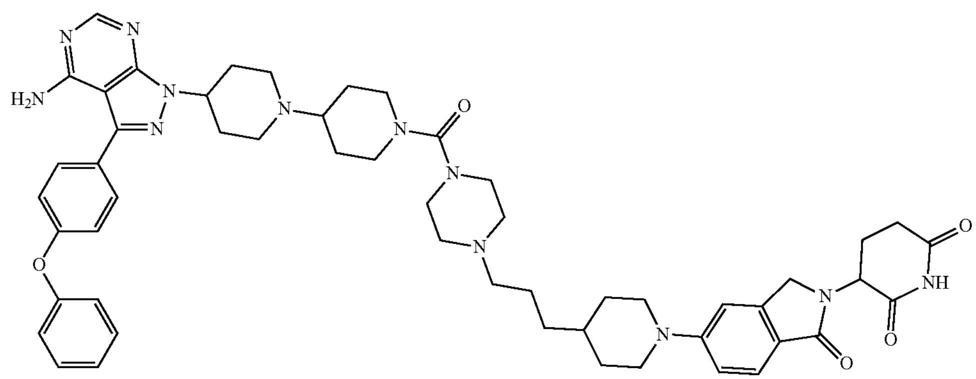 [SMILES: Nc1ncnc2c1c(-c1ccc(Oc3ccccc3)cc1)nn2C1CCN(C2CCN(C(=O)N3CCN(CCCC4CCN(c5ccc6c(c5)CN(C5CCC(=O)NC5=O)C6=O)CC4)CC3)CC2)CC1] | 3-(5-(4-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-1-yl)-1-oxoisoindolin-2-yl)piperidine-2,6-dione | 948.51 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 261 | 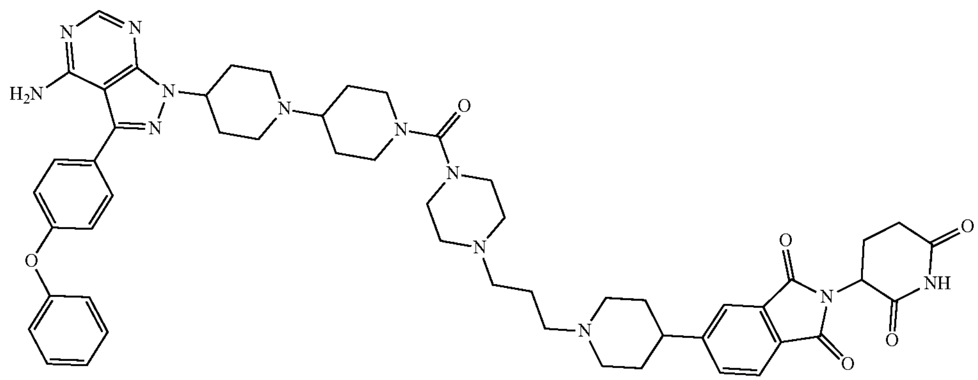 [SMILES: Nc1ncnc2c1c(-c1ccc(Oc3ccccc3)cc1)nn2C1CCN(C2CCN(C(=O)N3CCN(CCCN4CCC(c5ccc6c(c5)C(=O)N(C5CCC(=O)NC5=O)C6=O)CC4)CC3)CC2)CC1] | 5-(1-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-4-yl)-2-(2,6-dioxopiperidin-3-yl)isoindoline-1,3-dione | 962.49 | B | C | B | A |
| 262 | 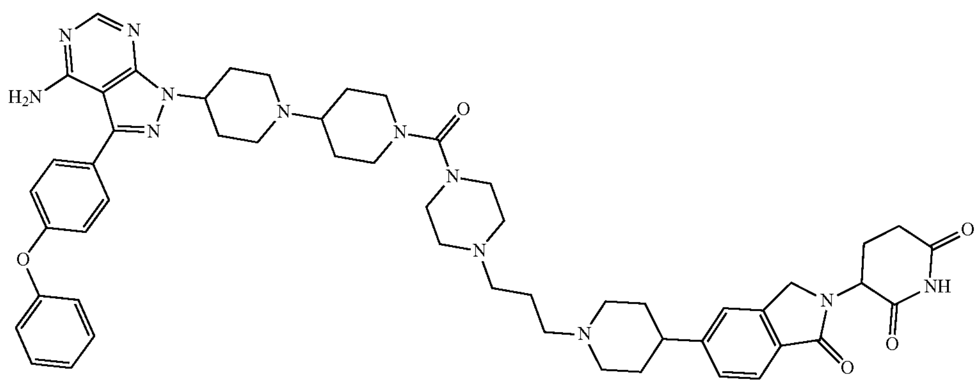 | 3-(5-(1-(3-(4-(4-(4-amino-3-(4-phenoxyphenyl)-1H-pyrazolo[3,4-d]pyrimidin-1-yl)-[1,4'-bipiperidine]-1'-carbonyl)piperazin-1-yl)propyl)piperidin-4-yl)-1-oxoisoindolin-2-yl)piperidine-2,6-dione | 948.51 | B | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 263 | 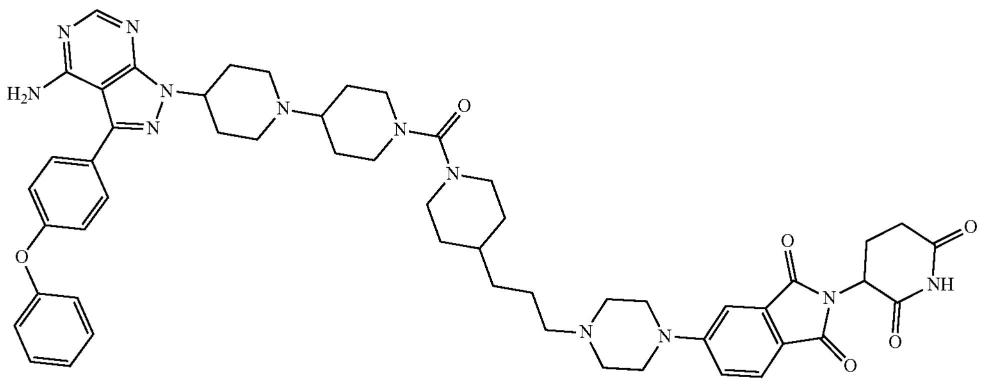 [SMILES: Nc1ncnc2c1c(-c1ccc(Oc3ccccc3)cc1)nn2C1CCN(C2CCN(C(=O)N3CCC(CCCN4CCN(c5ccc6c(c5)C(=O)N(C5CCC(=O)NC5=O)C6=O)CC4)CC3)CC2)CC1] | 5-(4-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperazin-1-yl)-2-(2,6-dioxopiperidin-3-yl)isoindoline-1,3-dione | 962.49 | C | B | B | A |
| 264 | 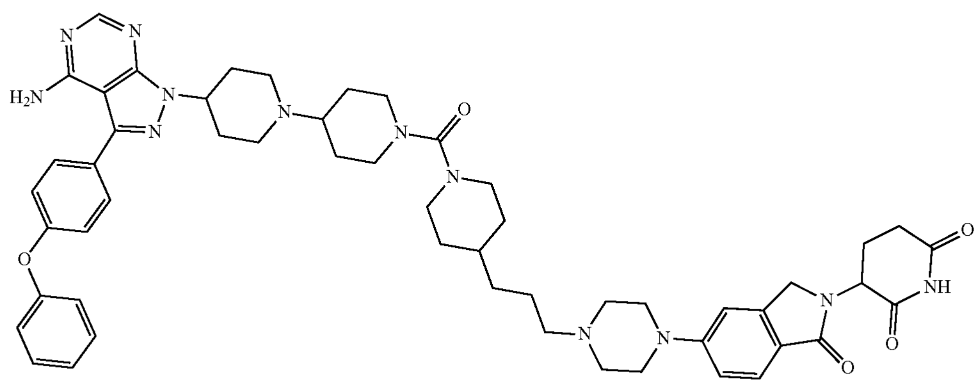 [SMILES: Nc1ncnc2c1c(-c1ccc(Oc3ccccc3)cc1)nn2C1CCN(C2CCN(C(=O)N3CCC(CCCN4CCN(c5ccc6c(c5)CN(C5CCC(=O)NC5=O)C6=O)CC4)CC3)CC2)CC1] | 3-(5-(4-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperazin-1-yl)-1-oxoisoindolin-2-yl)piperidine-2,6-dione | 948.51 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 265 | 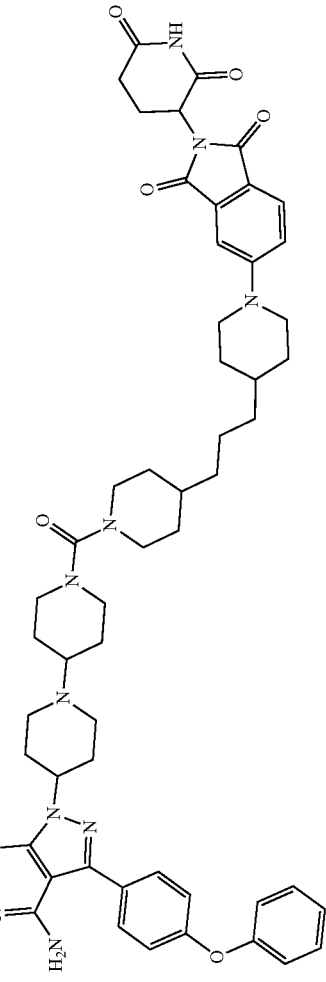 | 5-(4-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-1-yl)-2-(2,6-dioxopiperidin-3-yl)isoindoline-1,3-dione | 961.50 | B | B | B | B |
| 266 | 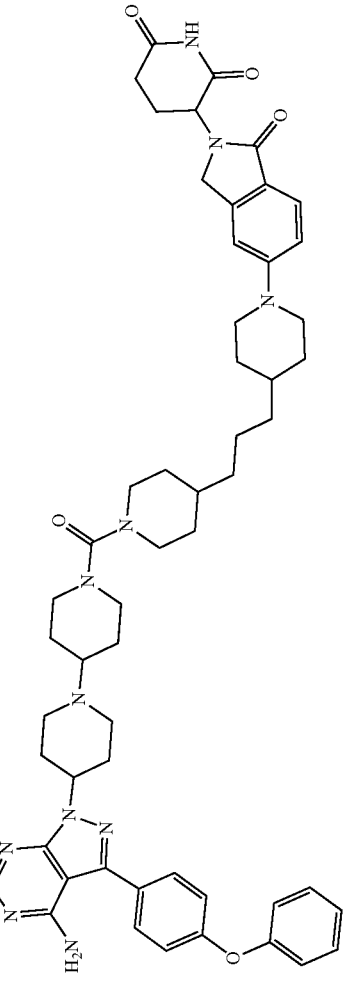 | 3-(5-(4-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-1-yl)-1-oxoisoindolin-2-yl)piperidine-2,6-dione | 947.52 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 267 | 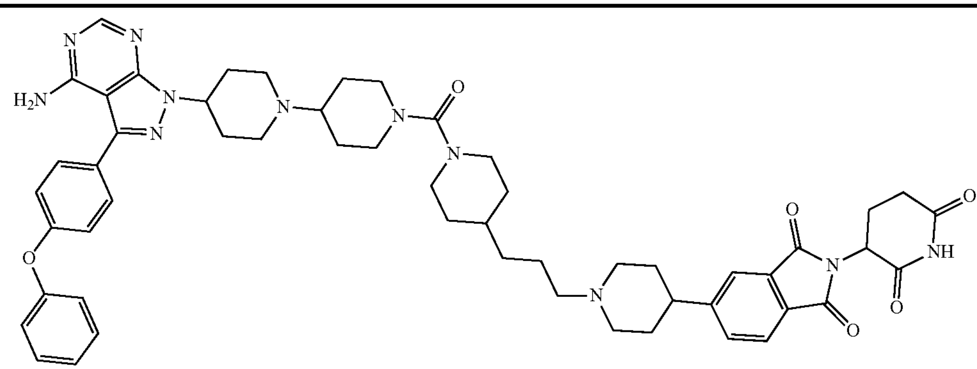 | 5-(1-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-4-yl)-2-(2,6-dioxopiperidin-3-yl)isoindoline-1,3-dione | 961.50 | B | B | B | A |
| 268 | 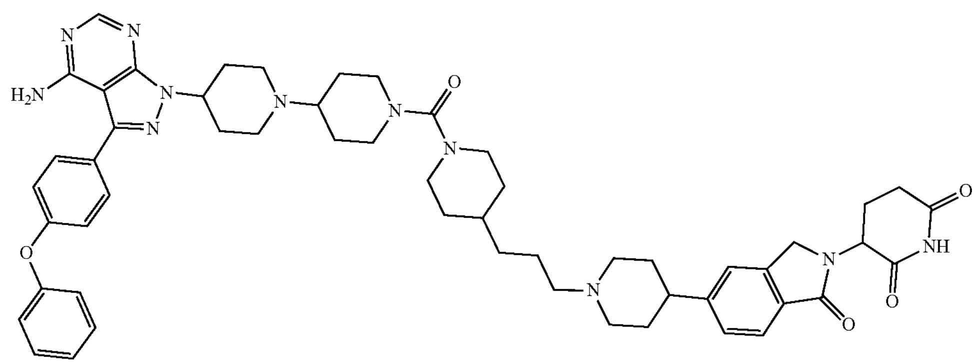 [SMILES: Nc1ncnc2c1c(-c1ccc(Oc3ccccc3)cc1)nn2C1CCN(C2CCN(C(=O)N3CCC(CCCN4CCC(c5ccc6c(c5)CN(C5CCC(=O)NC5=O)C6=O)CC4)CC3)CC2)CC1] | 3-(5-(1-(3-(1-(4-(4-amino-3-(4-phenoxyphenyl)-1H-pyrazolo[3,4-d]pyrimidin-1-yl)-[1,4'-bipiperidine]-1'-carbonyl)piperidin-4-yl)propyl)piperidin-4-yl)-1-oxoisoindolin-2-yl)piperidine-2,6-dione | 947.52 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 269 | 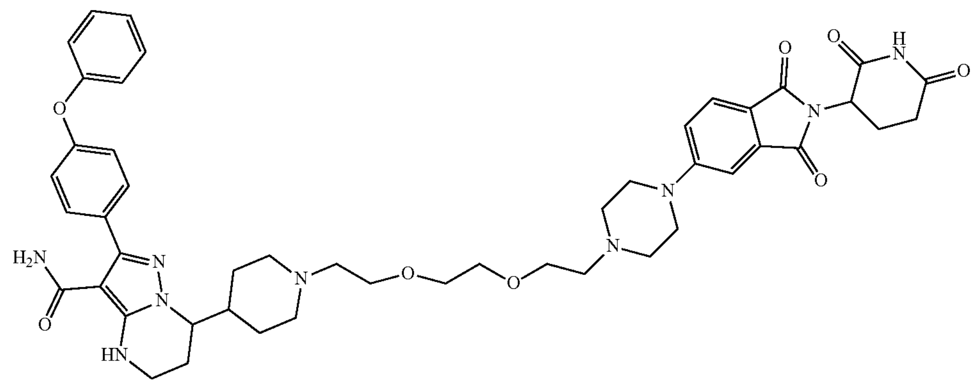 | 7-(1-(2-(2-(4-(2-(2,6-dioxopiperidin-3-yl)-1,3-dioxoisoindolin-5-yl)piperazin-1-yl)ethoxy)ethyl)piperidin-4-yl)-2-(4-phenoxyphenyl)-4,5,6,7-tetrahydropyrazolo[1,5-a]pyrimidine-3-carboxamide | 873.42 | C | C | B | A |
| 270 | 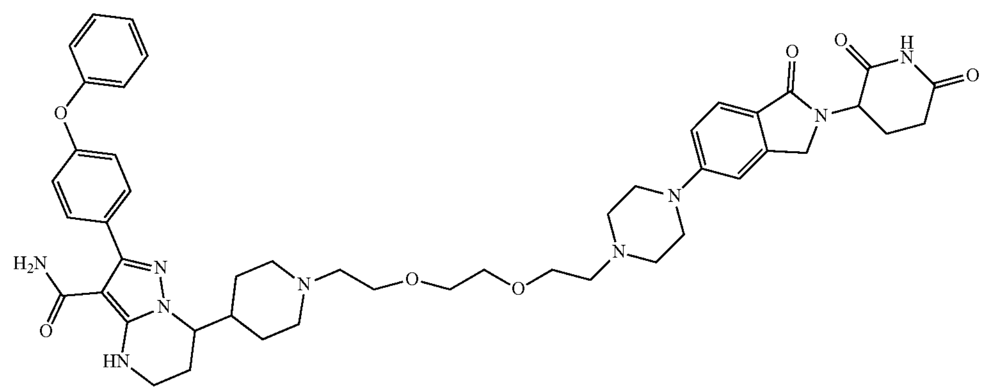 [SMILES: NC(=O)c1c(-c2ccc(Oc3ccccc3)cc2)nn2c1NCCC2C1CCN(CCOCCOCCN2CCN(c3ccc4c(c3)CN(C3CCC(=O)NC3=O)C4=O)CC2)CC1] | 7-(1-(2-(2-(4-(2-(2,6-dioxopiperidin-3-yl)-1-oxoisoindolin-5-yl)piperazin-1-yl)ethoxy)ethyl)piperidin-4-yl)-2-(4-phenoxyphenyl)-4,5,6,7-tetrahydropyrazolo[1,5-a]pyrimidine-3-carboxamide | 859.44 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 271 | 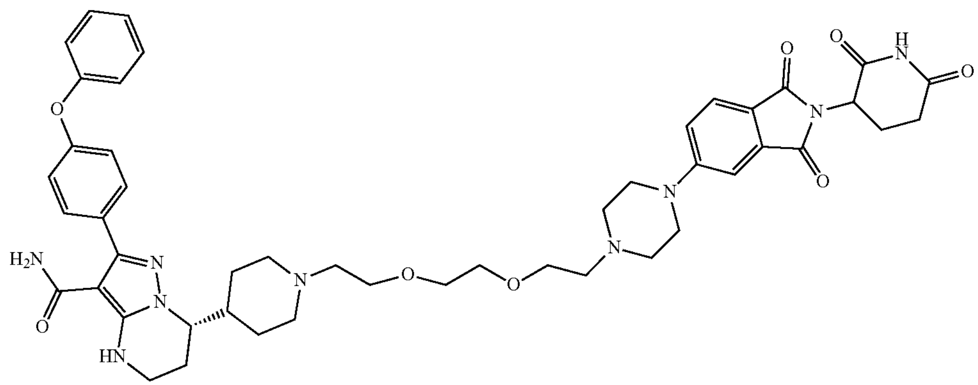 [SMILES: NC(=O)c1c(-c2ccc(Oc3ccccc3)cc2)nn2c1NCC[C@H]2C1CCN(CCOCCOCCN2CCN(c3ccc4c(c3)C(=O)N(C3CCC(=O)NC3=O)C4=O)CC2)CC1] | (7S)-7-(1-(2-(2-(4-(2-(2,6-dioxopiperidin-3-yl)-1,3-dioxoisoindolin-5-yl)piperazin-1-yl)ethoxy)ethoxy)piperidin-4-yl)-2-(4-phenoxyphenyl)-4,5,6,7-tetrahydropyrazolo[1,5-a]pyrimidine-3-carboxamide | 873.42 | C | B | B | A |
| 272 | 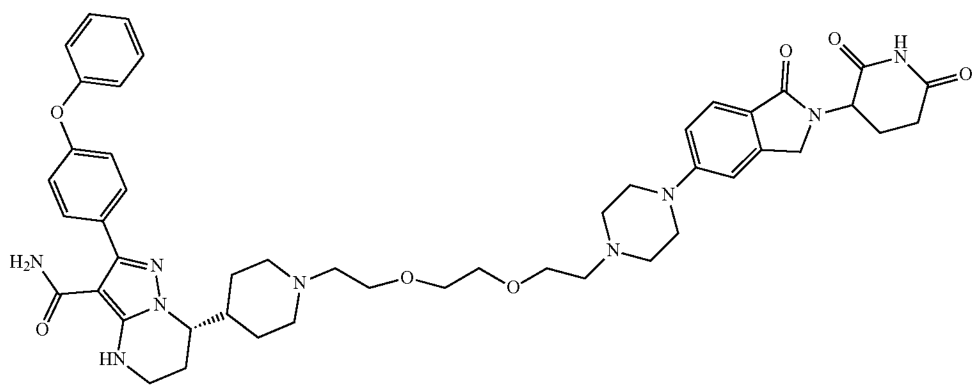 | (7S)-7-(1-(2-(2-(4-(2-(2,6-dioxopiperidin-3-yl)-1-oxoisoindolin-5-yl)piperazin-1-yl)ethoxy)ethoxy)piperidin-4-yl)-2-(4-phenoxyphenyl)-4,5,6,7-tetrahydropyrazolo[1,5-a]pyrimidine-3-carboxamide | 859.44 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 273 | 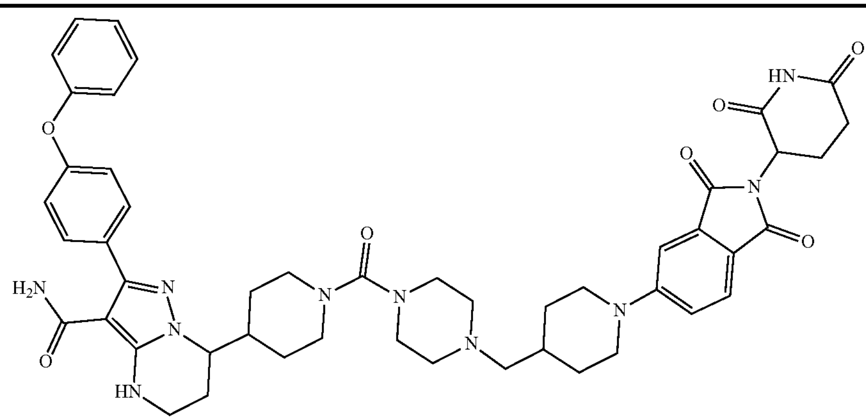 | 7-(1-(4-((1-(2-(2,6-dioxopiperidin-3-yl)-1,3-dioxoisoindolin-5-yl)piperidin-4-yl)methyl)piperazine-1-carbonyl)piperidin-4-yl)-2-(4-phenoxyphenyl)-4,5,6,7-tetrahydropyrazolo[1,5-a]pyrimidine-3-carboxamide | 882.42 | B | A | B | A |
| 274 | 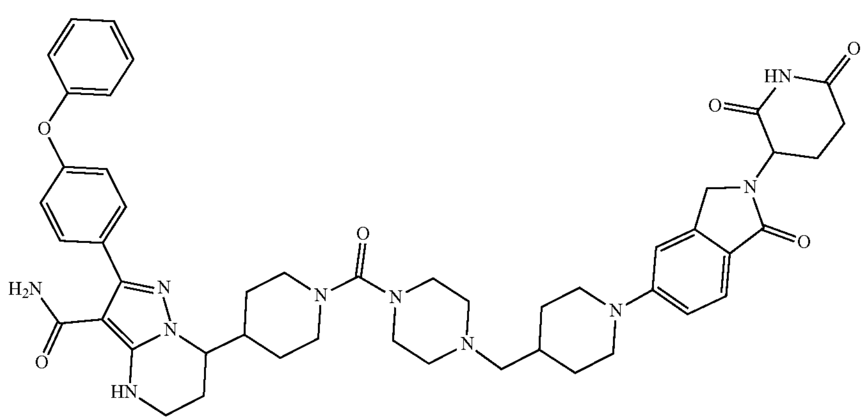 [SMILES: NC(=O)c1c(-c2ccc(Oc3ccccc3)cc2)nn2c1NCCC2C1CCN(C(=O)N2CCN(CC3CCN(c4ccc5c(c4)CN(C4CCC(=O)NC4=O)C5=O)CC3)CC2)CC1] | 7-(1-(4-((1-(2-(2,6-dioxopiperidin-3-yl)-1-oxoisoindolin-5-yl)piperidin-4-yl)methyl)piperazine-1-carbonyl)piperidin-4-yl)-2-(4-phenoxyphenyl)-4,5,6,7-tetrahydropyrazolo[1,5-a]pyrimidine-3-carboxamide | 868.44 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 275 | 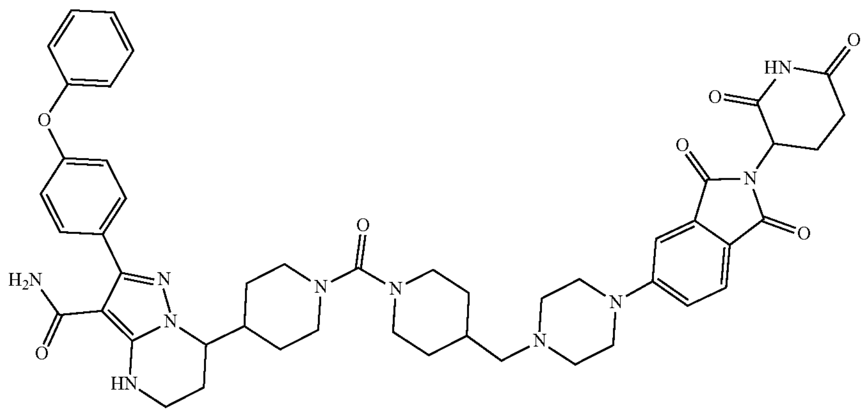 [SMILES: NC(=O)c1c(-c2ccc(Oc3ccccc3)cc2)nn2c1NCCC2C1CCN(C(=O)N2CCC(CN3CCN(c4ccc5c(c4)C(=O)N(C4CCC(=O)NC4=O)C5=O)CC3)CC2)CC1] | 7-(1-(4-((4-(2-(2,6-dioxopiperidin-3-yl)-1,3-dioxoisoindolin-5-yl)piperazin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 882.42 | B | B | A | A |
| 276 | 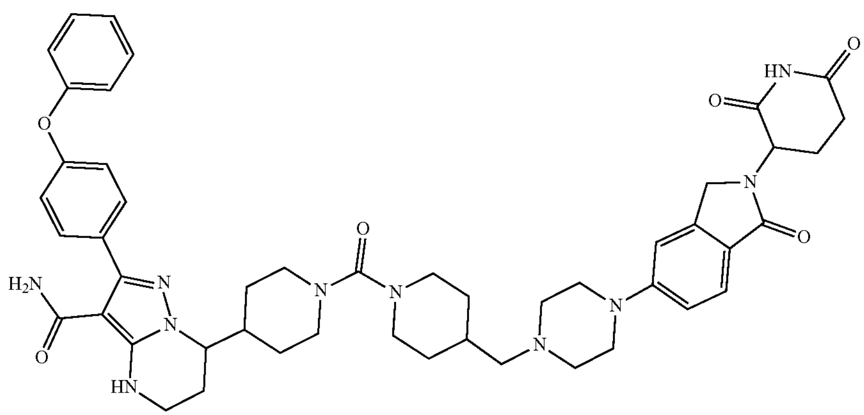 [SMILES: NC(=O)c1c(-c2ccc(Oc3ccccc3)cc2)nn2c1NCCC2C1CCN(C(=O)N2CCC(CN3CCN(c4ccc5c(c4)CN(C4CCC(=O)NC4=O)C5=O)CC3)CC2)CC1] | 7-(1-(4-((4-(2-(2,6-dioxopiperidin-3-yl)-1-oxoisoindolin-5-yl)piperazin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 868.44 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 277 | 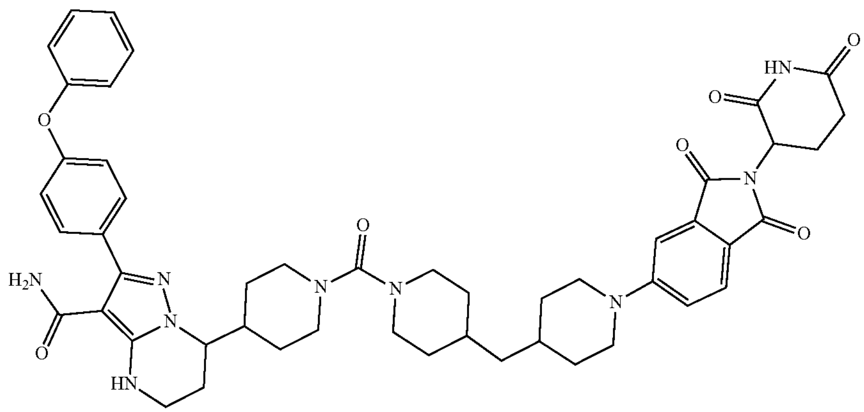 [SMILES: NC(=O)c1c(-c2ccc(Oc3ccccc3)cc2)nn2c1NCCC2C1CCN(C(=O)N2CCC(CC3CCN(c4ccc5c(c4)C(=O)N(C4CCC(=O)NC4=O)C5=O)CC3)CC2)CC1] | 7-(1-(4-((1-(2-(2,6-dioxopiperidin-3-yl)-1,3-dioxoisoindolin-5-yl)piperidin-4-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 881.42 | B | A | A | A |
| 278 | 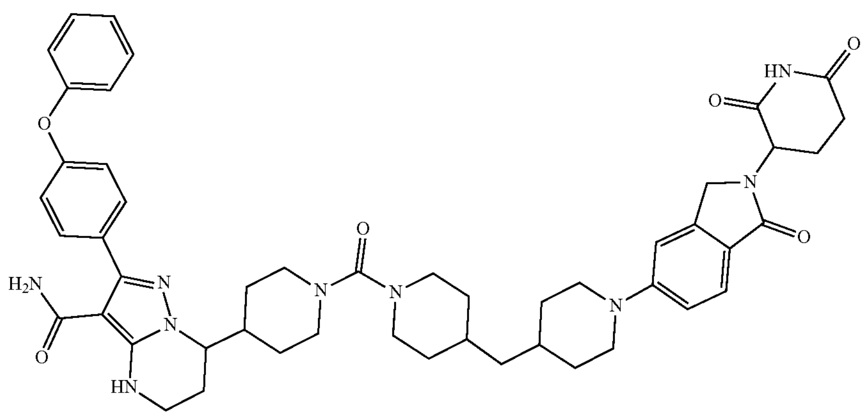 [SMILES: NC(=O)c1c(-c2ccc(Oc3ccccc3)cc2)nn2c1NCCC2C1CCN(C(=O)N2CCC(CC3CCN(c4ccc5c(c4)CN(C4CCC(=O)NC4=O)C5=O)CC3)CC2)CC1] | 7-(1-(4-((1-(2-(2,6-dioxopiperidin-3-yl)-1-oxoisoindolin-5-yl)piperidin-4-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 867.44 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 279 | 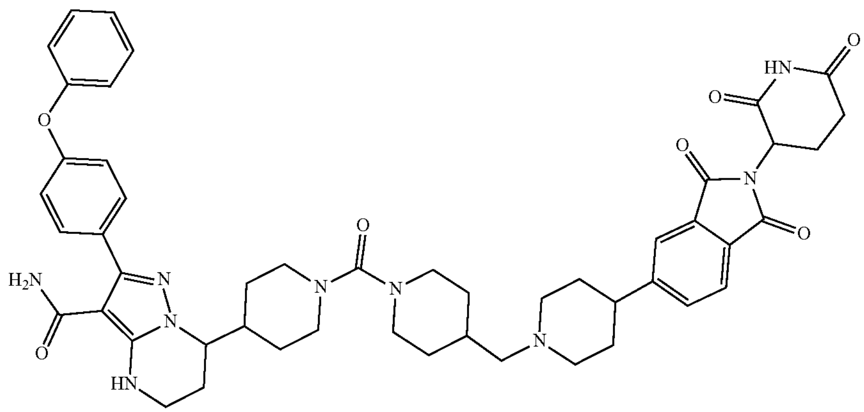 [SMILES: NC(=O)c1c(-c2ccc(Oc3ccccc3)cc2)nn2c1NCCC2C1CCN(C(=O)N2CCC(CN3CCC(c4ccc5c(c4)C(=O)N(C4CCC(=O)NC4=O)C5=O)CC3)CC2)CC1] | 7-(1-(4-((4-(2-(2,6-dioxopiperidin-3-yl)-1,3-dioxoisoindolin-5-yl)piperidin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 881.42 | B | B | B | A |
| 280 | 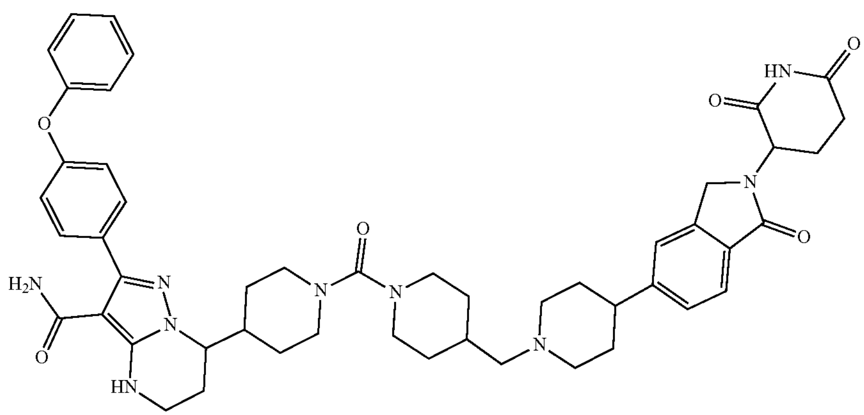 [SMILES: NC(=O)c1c(-c2ccc(Oc3ccccc3)cc2)nn2c1NCCC2C1CCN(C(=O)N2CCC(CN3CCC(c4ccc5c(c4)CN(C4CCC(=O)NC4=O)C5=O)CC3)CC2)CC1] | 7-(1-(4-((4-(2-(2,6-dioxopiperidin-3-yl)-1-oxoisoindolin-5-yl)piperidin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 867.44 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 281 | 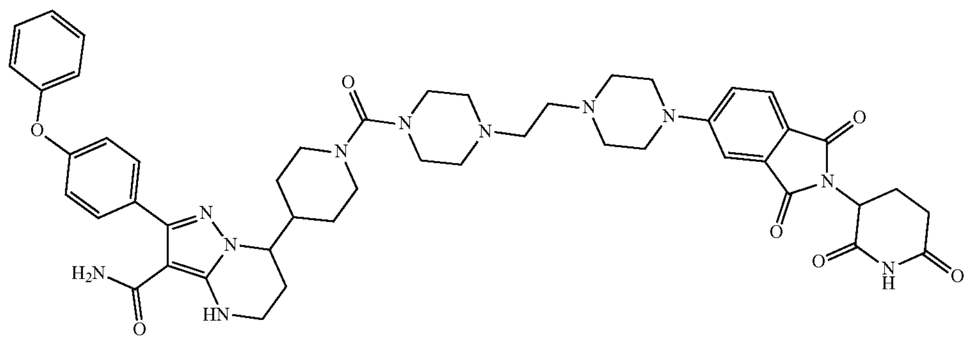 | 7-(1-(4-(2-(4-(2-(2,6-dioxopiperidin-3-yl)-1,3-dioxoisoindolin-5-yl)piperazin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 897.43 | B | B | B | A |
| 282 | 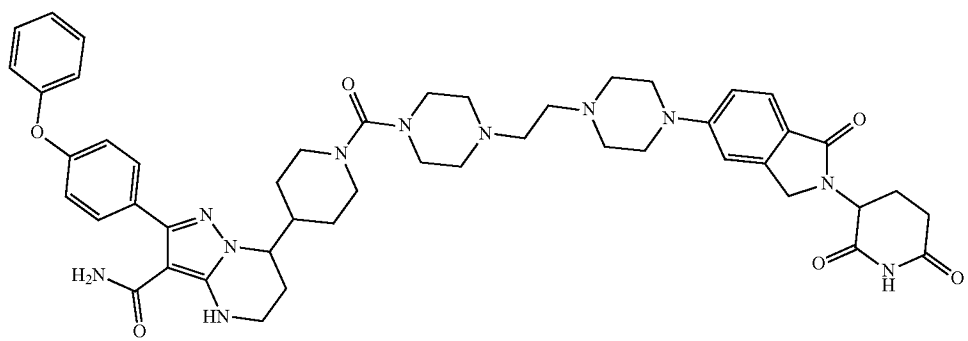 | 7-(1-(4-(2-(4-(2-(2,6-dioxopiperidin-3-yl)-1-oxoisoindolin-5-yl)piperazin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 883.45 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 283 | 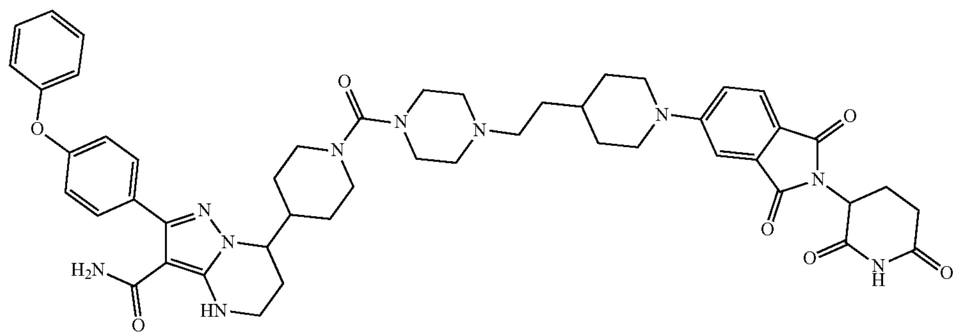 [SMILES: NC(=O)c1c(-c2ccc(Oc3ccccc3)cc2)nn2c1NCCC2C1CCN(C(=O)N2CCN(CCC3CCN(c4ccc5c(c4)C(=O)N(C4CCC(=O)NC4=O)C5=O)CC3)CC2)CC1] | 7-(1-(4-(2-(1-(2-(2,6-dioxopiperidin-3-yl)-1,3-dioxoisoindolin-5-yl)piperidin-4-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 896.43 | C | B | B | B |
| 284 | 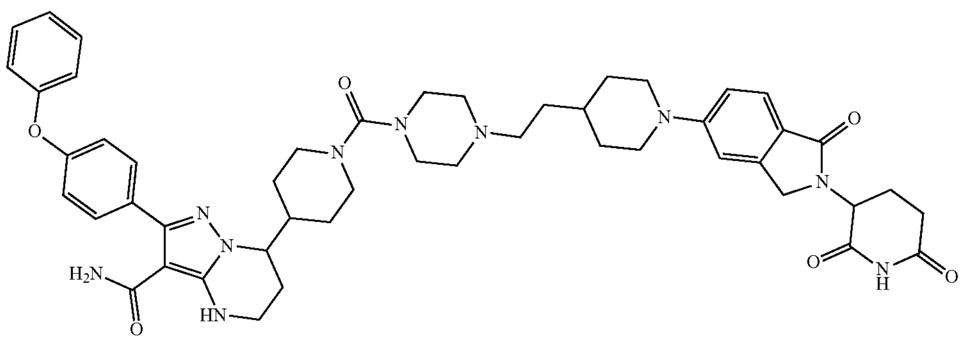 [SMILES: NC(=O)c1c(-c2ccc(Oc3ccccc3)cc2)nn2c1NCCC2C1CCN(C(=O)N2CCN(CCC3CCN(c4ccc5c(c4)CN(C4CCC(=O)NC4=O)C5=O)CC3)CC2)CC1] | 7-(1-(4-(2-(1-(2-(2,6-dioxopiperidin-3-yl)-1-oxoisoindolin-5-yl)piperidin-4-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 882.45 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 285 | Exact Mass: 895.44 | 7-(1-(4-(2-(4-(2-(2,6-dioxopiperidin-3-yl)-1,3-dioxoisoindolin-5-yl)piperidin-1-yl)ethyl)piperidine-1-carbonyl)piperidin-4-yl)-2-(4-phenoxyphenyl)-4,5,6,7-tetrahydropyrazolo[1,5-a]pyrimidine-3-carboxamide | 895.44 | B | B | C | B |
| 286 | Exact Mass: 881.46 | 7-(1-(4-(2-(4-(2-(2,6-dioxopiperidin-3-yl)-1-oxoisoindolin-5-yl)piperidin-1-yl)ethyl)piperidine-1-carbonyl)piperidin-4-yl)-2-(4-phenoxyphenyl)-4,5,6,7-tetrahydropyrazolo[1,5-a]pyrimidine-3-carboxamide | 881.46 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 287 | 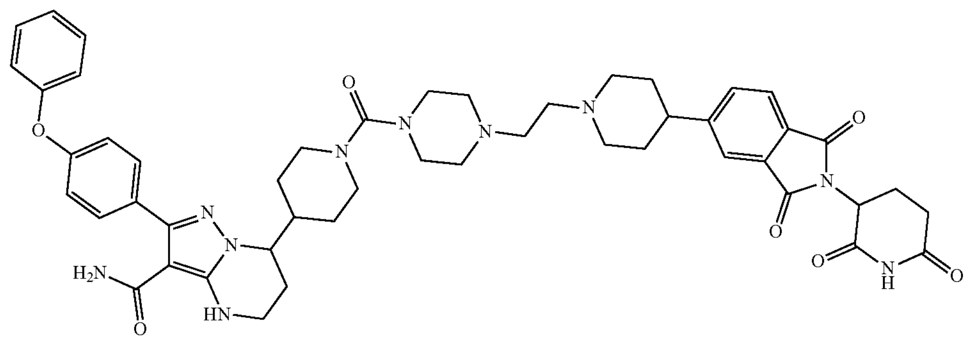 [SMILES: NC(=O)c1c(-c2ccc(Oc3ccccc3)cc2)nn2c1NCCC2C1CCN(C(=O)N2CCN(CCN3CCC(c4ccc5c(c4)C(=O)N(C4CCC(=O)NC4=O)C5=O)CC3)CC2)CC1] | 7-(1-(4-(2-(4-(2,6-dioxopiperidin-3-yl)-1,3-dioxoisoindolin-5-yl)piperidin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 896.43 | C | B | B | B |
| 288 | 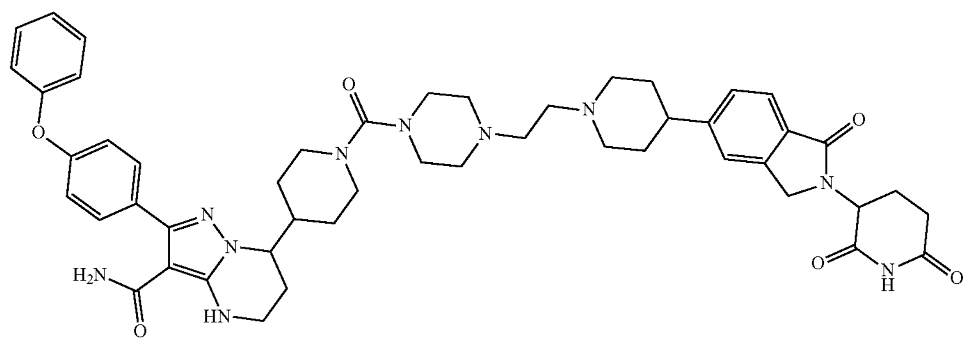 [SMILES: NC(=O)c1c(-c2ccc(Oc3ccccc3)cc2)nn2c1NCCC2C1CCN(C(=O)N2CCN(CCN3CCC(c4ccc5c(c4)CN(C4CCC(=O)NC4=O)C5=O)CC3)CC2)CC1] | 7-(1-(4-(2-(4-(2-(2,6-dioxopiperidin-3-yl)-1-oxoisoindolin-5-yl)piperidin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 882.45 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 289 | Exact Mass: 882.42 | (7S)-7-(1-(4-((1-(2-(2,6-dioxopiperidin-3-yl)-1,3-dioxoisoindolin-5-yl)piperidin-4-yl)methyl)piperazine-1-carbonyl)piperidin-4-yl)-2-(4-phenoxyphenyl)-4,5,6,7-tetrahydropyrazolo[1,5-a]pyrimidine-3-carboxamide | 882.42 | A | B | B | A |
| 290 | 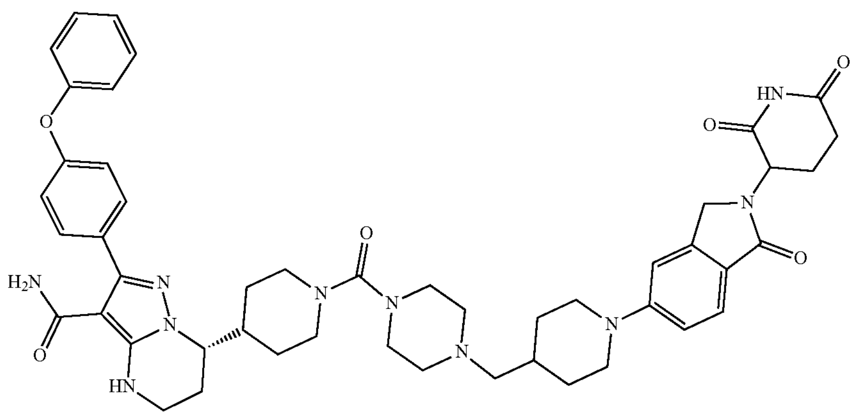 [SMILES: NC(=O)c1c(-c2ccc(Oc3ccccc3)cc2)nn2c1NCC[C@H]2C1CCN(C(=O)N2CCN(CC3CCN(c4ccc5c(c4)CN(C4CCC(=O)NC4=O)C5=O)CC3)CC2)CC1] | (7S)-7-(1-(4-((1-(2-(2,6-dioxopiperidin-3-yl)-1-oxoisoindolin-5-yl)piperidin-4-yl)methyl)piperazine-1-carbonyl)piperidin-4-yl)-2-(4-phenoxyphenyl)-4,5,6,7-tetrahydropyrazolo[1,5-a]pyrimidine-3-carboxamide | 868.44 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 291 | 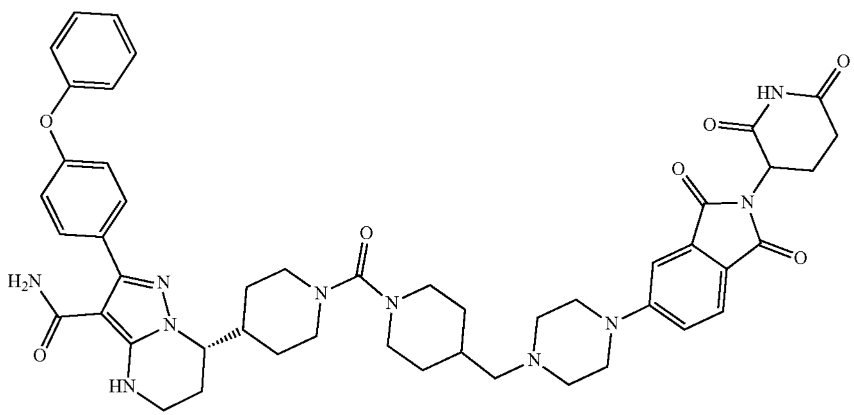 [SMILES: NC(=O)c1c(-c2ccc(Oc3ccccc3)cc2)nn2c1NCC[C@H]2C1CCN(C(=O)N2CCC(CN3CCN(c4ccc5c(c4)C(=O)N(C4CCC(=O)NC4=O)C5=O)CC3)CC2)CC1] | (7S)-7-(1-(4-((4-(2-(2,6-dioxopiperidin-3-yl)-1,3-dioxoisoindolin-5-yl)piperazin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 882.42 | A | A | B | A |
| 292 | 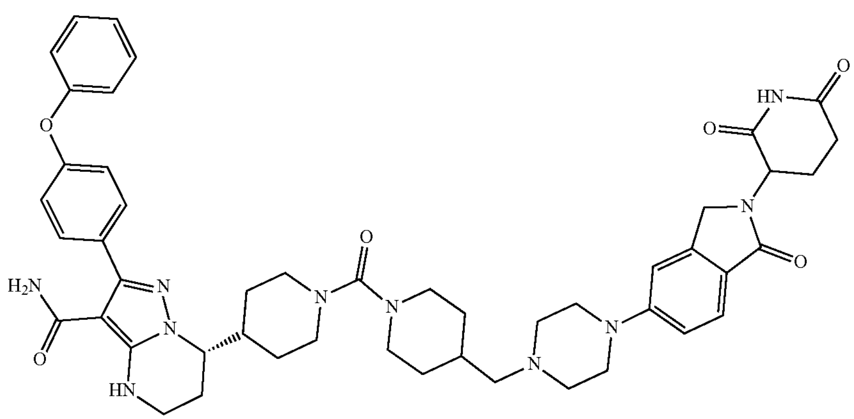 [SMILES: NC(=O)c1c(-c2ccc(Oc3ccccc3)cc2)nn2c1NCC[C@H]2C1CCN(C(=O)N2CCC(CN3CCN(c4ccc5c(c4)CN(C4CCC(=O)NC4=O)C5=O)CC3)CC2)CC1] | (7S)-7-(1-(4-((4-(2-(2,6-dioxopiperidin-3-yl)-1-oxoisoindolin-5-yl)piperazin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 868.44 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 293 | 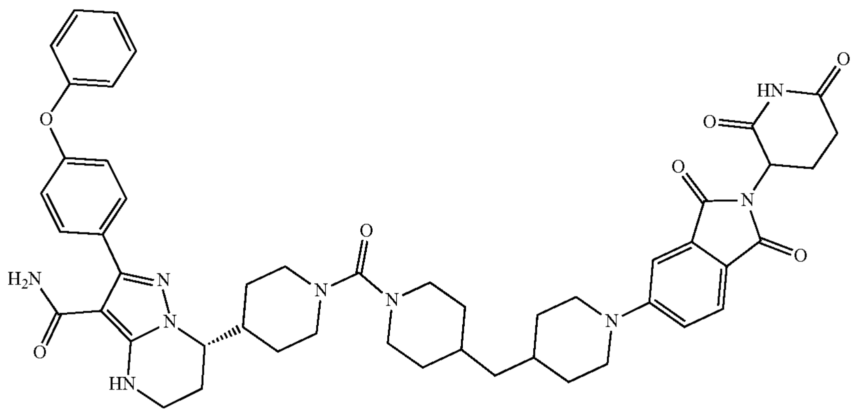 [SMILES: NC(=O)c1c(-c2ccc(Oc3ccccc3)cc2)nn2c1NCC[C@H]2C1CCN(C(=O)N2CCC(CC3CCN(c4ccc5c(c4)C(=O)N(C4CCC(=O)NC4=O)C5=O)CC3)CC2)CC1] | (7S)-7-(1-(4-((1-(2-(2,6-dioxopiperidin-3-yl)-1,3-dioxoisoindolin-5-yl)piperidin-4-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 881.42 | B | A | B | A |
| 294 | 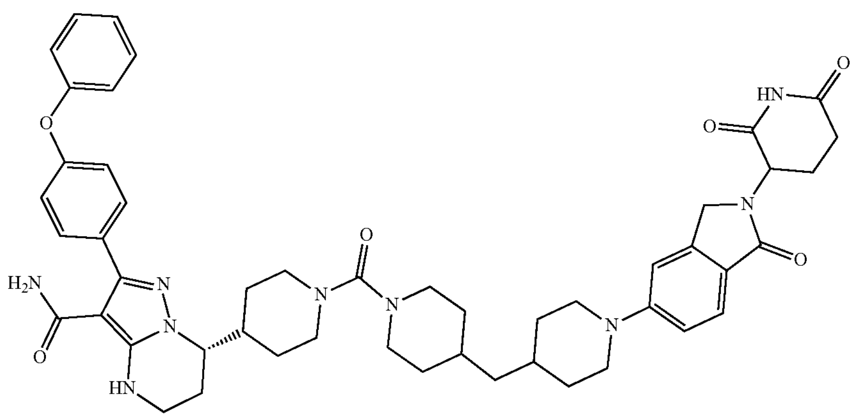 [SMILES: NC(=O)c1c(-c2ccc(Oc3ccccc3)cc2)nn2c1NCC[C@H]2C1CCN(C(=O)N2CCC(CC3CCN(c4ccc5c(c4)CN(C4CCC(=O)NC4=O)C5=O)CC3)CC2)CC1] | (7S)-7-(1-(4-((1-(2-(2,6-dioxopiperidin-3-yl)-1-oxoisoindolin-5-yl)piperidin-4-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 867.44 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 295 | 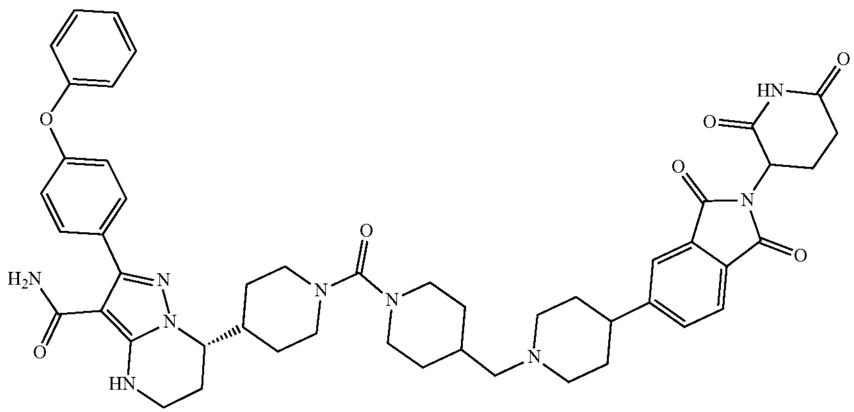 [SMILES: NC(=O)c1c(-c2ccc(Oc3ccccc3)cc2)nn2c1NCC[C@H]2C1CCN(C(=O)N2CCC(CN3CCC(c4ccc5c(c4)C(=O)N(C4CCC(=O)NC4=O)C5=O)CC3)CC2)CC1] | (7S)-7-(1-(4-((4-(2-(2,6-dioxopiperidin-3-yl)-1,3-dioxoisoindolin-5-yl)piperidin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 881.42 | B | A | B | A |
| 296 | 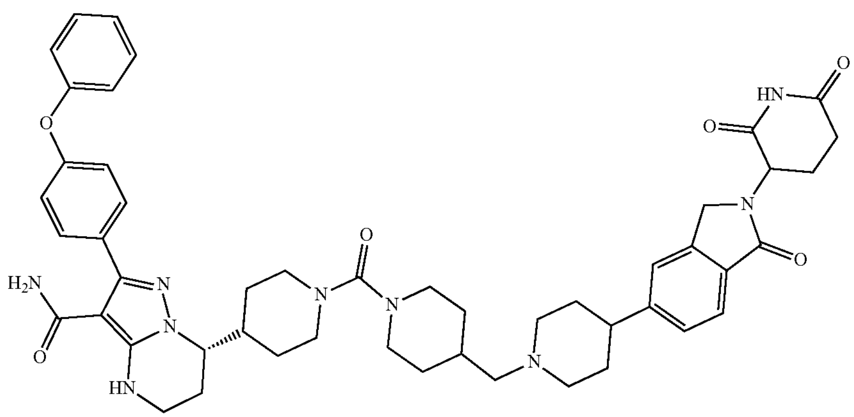 [SMILES: NC(=O)c1c(-c2ccc(Oc3ccccc3)cc2)nn2c1NCC[C@H]2C1CCN(C(=O)N2CCC(CN3CCC(c4ccc5c(c4)CN(C4CCC(=O)NC4=O)C5=O)CC3)CC2)CC1] | (7S)-7-(1-(4-((4-(2-(2,6-dioxopiperidin-3-yl)-1-oxoisoindolin-5-yl)piperidin-1-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 867.44 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | $IC_{50}$ (antiproliferation) JeKO-1 cells | $IC_{50}$ (antiproliferation) Mino cells | $DC_{50}$ | $D_{max}$ |
|---|---|---|---|---|---|---|---|
| 297 | 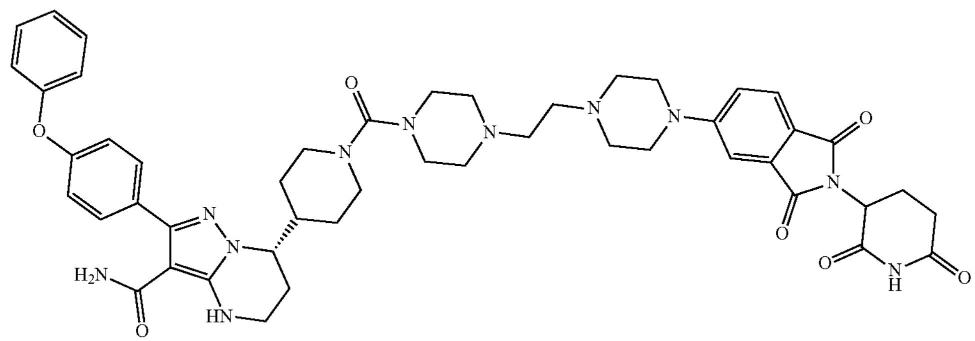 | (7S)-7-(1-(4-(2-(4-(2-(2,6-dioxopiperidin-3-yl)-1,3-dioxoisoindolin-5-yl)piperazin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 897.43 | B | B | B | A |
| 298 | 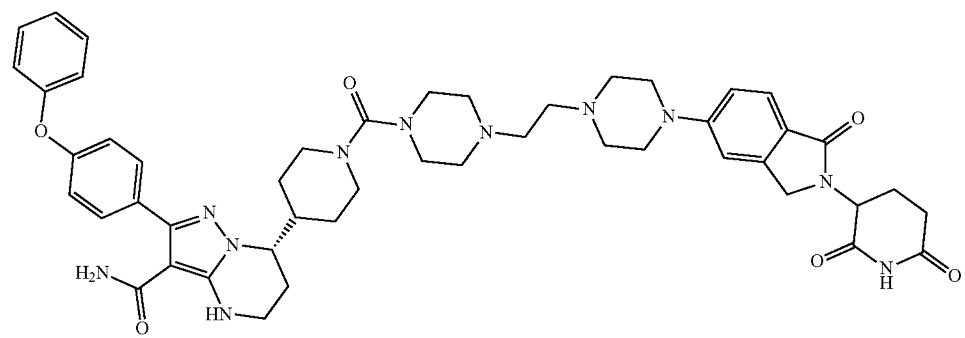 | (7S)-7-(1-(4-(2-(4-(2-(2,6-dioxopiperidin-3-yl)-1-oxoisoindolin-5-yl)piperazin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 883.45 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 299 | 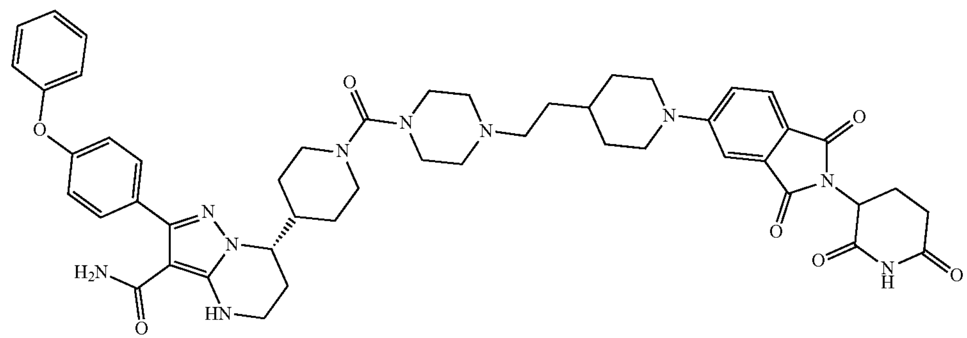 [SMILES: NC(=O)c1c(-c2ccc(Oc3ccccc3)cc2)nn2c1NCC[C@H]2C1CCN(C(=O)N2CCN(CCC3CCN(c4ccc5c(c4)C(=O)N(C4CCC(=O)NC4=O)C5=O)CC3)CC2)CC1] | (7S)-7-(1-(4-(2-(1-(2-(2,6-dioxopiperidin-3-yl)-1,3-dioxoisoindolin-5-yl)piperidin-4-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 896.43 | B | B | B | B |
| 300 | 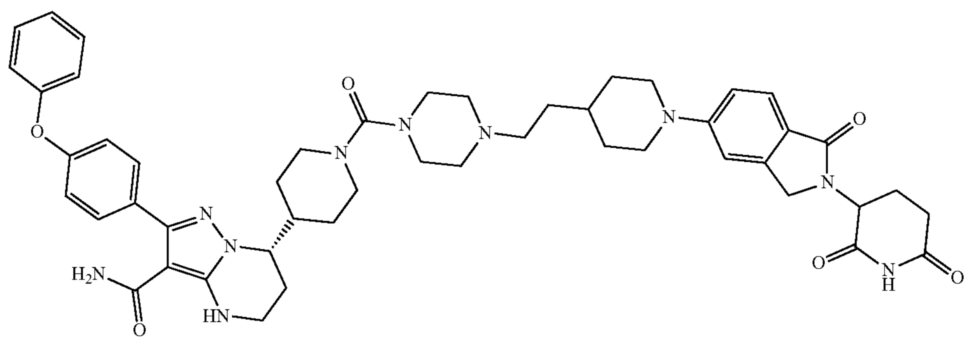 | (7S)-7-(1-(4-(2-(1-(2-(2,6-dioxopiperidin-3-yl)-1-oxoisoindolin-5-yl)piperazine-1-carbonyl)piperidin-4-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 882.45 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 301 | 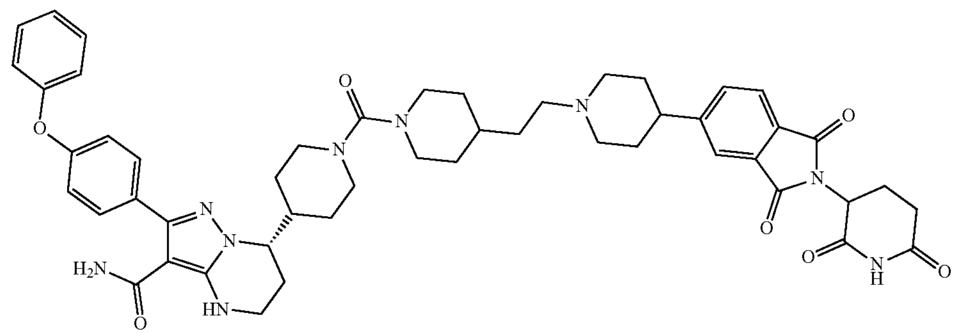 | (7S)-7-(1-(4-(2-(4-(2-(2,6-dioxopiperidin-3-yl)-1,3-dioxoisoindolin-5-yl)piperidin-1-yl)ethyl)piperidine-1-carbonyl)piperidin-4-yl)-2-(4-phenoxyphenyl)-4,5,6,7-tetrahydropyrazolo[1,5-a]pyrimidine-3-carboxamide | 895.44 | B | B | B | B |
| 302 | 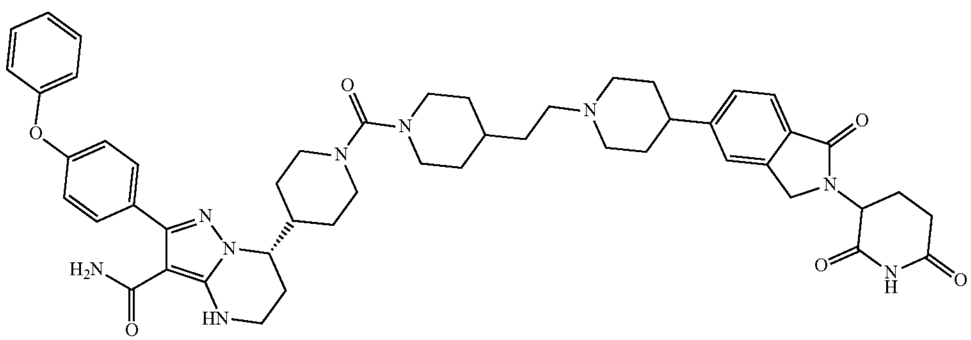 | (7S)-7-(1-(4-(2-(4-(2-(2,6-dioxopiperidin-3-yl)-1-oxoisoindolin-5-yl)piperidin-1-yl)ethyl)piperidine-1-carbonyl)piperidin-4-yl)-2-(4-phenoxyphenyl)-4,5,6,7-tetrahydropyrazolo[1,5-a]pyrimidine-3-carboxamide | 881.46 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 303 | 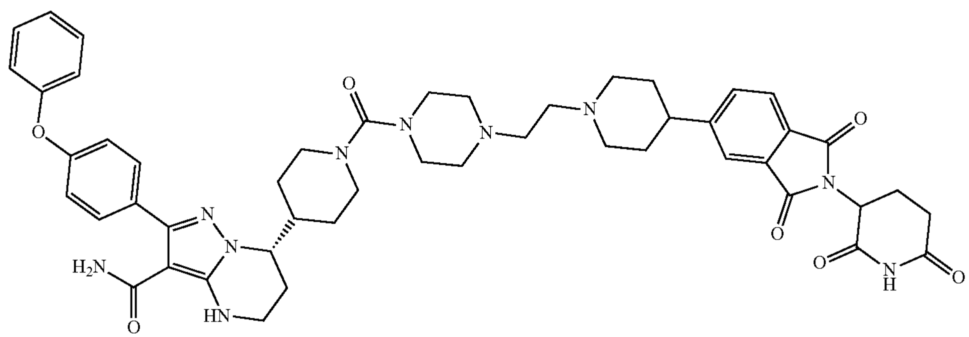 [SMILES: NC(=O)c1c(-c2ccc(Oc3ccccc3)cc2)nn2c1NCC[C@H]2C1CCN(C(=O)N2CCN(CCN3CCC(c4ccc5c(c4)C(=O)N(C4CCC(=O)NC4=O)C5=O)CC3)CC2)CC1] | (7S)-7-(1-(4-(2-(4-(2-(2,6-dioxopiperidin-3-yl)-1,3-dioxoisoindolin-5-yl)piperidin-1-yl)ethyl)piperazine-1-carbonyl)piperidin-4-yl)-2-(4-phenoxyphenyl)-4,5,6,7-tetrahydropyrazolo[1,5-a]pyrimidine-3-carboxamide | 896.43 | B | B | B | B |
| 304 | 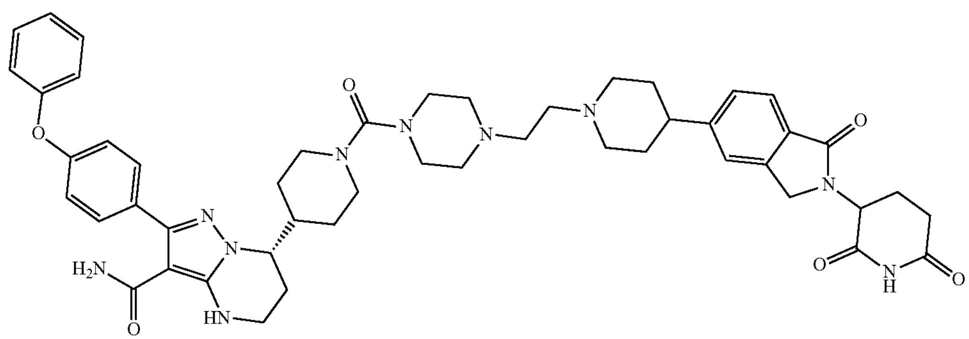 [SMILES: NC(=O)c1c(-c2ccc(Oc3ccccc3)cc2)nn2c1NCC[C@H]2C1CCN(C(=O)N2CCN(CCN3CCC(c4ccc5c(c4)CN(C4CCC(=O)NC4=O)C5=O)CC3)CC2)CC1] | (7S)-7-(1-(4-(2-(4-(2-(2,6-dioxopiperidin-3-yl)-1-oxoisoindolin-5-yl)piperazin-1-yl)ethyl)piperidin-4-yl)-1-carbonyl)piperidin-4-yl)-2-(4-phenoxyphenyl)-4,5,6,7-tetrahydropyrazolo[1,5-a]pyrimidine-3-carboxamide | 882.45 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 305 | 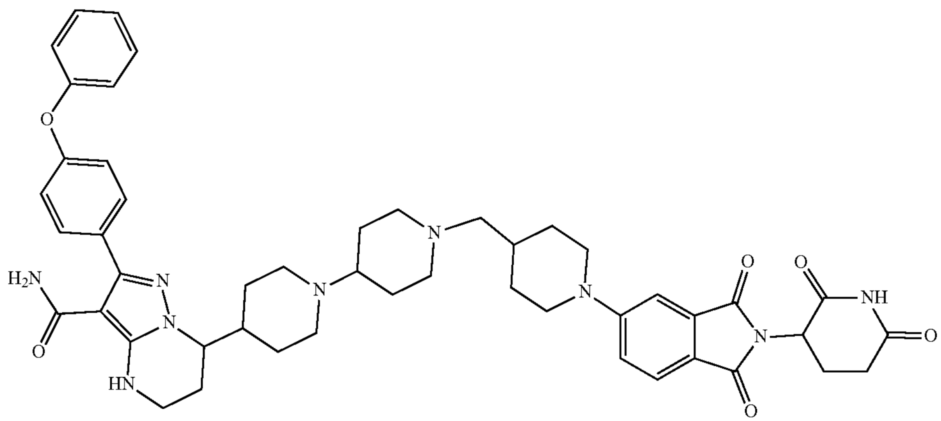 [SMILES: NC(=O)c1c(-c2ccc(Oc3ccccc3)cc2)nn2c1NCCC2C1CCN(C2CCN(CC3CCN(c4ccc5c(c4)C(=O)N(C4CCC(=O)NC4=O)C5=O)CC3)CC2)CC1] | 7-(1'-((1-(2-(2,6-dioxopiperidin-3-yl)-1,3-dioxoisoindolin-5-yl)piperidin-4-yl)methyl)-[1,4'-bipiperidin]-4-yl)-2-(4-phenoxyphenyl)-4,5,6,7-tetrahydropyrazolo[1,5-a]pyrimidine-3-carboxamide | 853.43 | B | B | B | A |
| 306 | 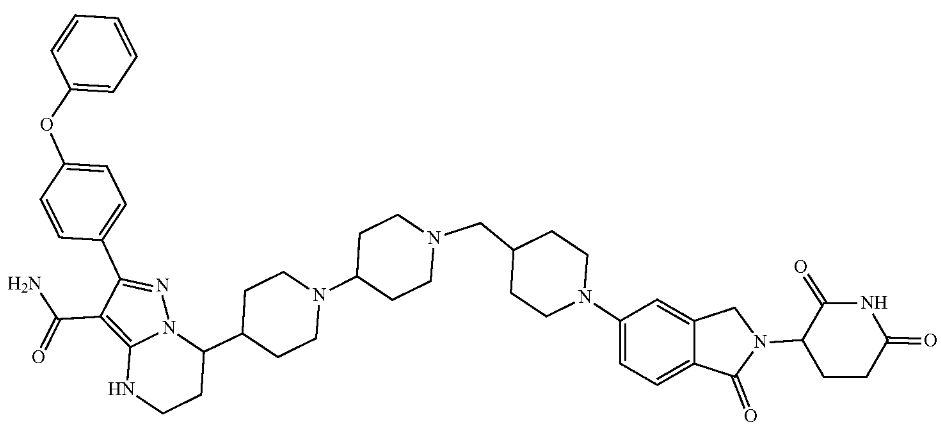 [SMILES: NC(=O)c1c(-c2ccc(Oc3ccccc3)cc2)nn2c1NCCC2C1CCN(C2CCN(CC3CCN(c4ccc5c(c4)CN(C4CCC(=O)NC4=O)C5=O)CC3)CC2)CC1] | 7-(1'-((1-(2-(2,6-dioxopiperidin-3-yl)-1-oxoisoindolin-5-yl)piperidin-4-yl)methyl)-[1,4'-bipiperidin]-4-yl)-2-(4-phenoxyphenyl)-4,5,6,7-tetrahydropyrazolo[1,5-a]pyrimidine-3-carboxamide | 839.45 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 307 | 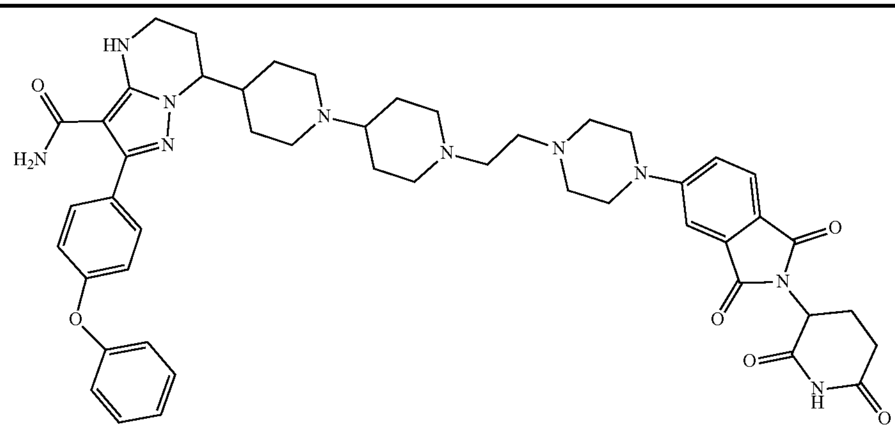 | 7-(1'-(2-(4-(2-(2,6-dioxopiperidin-3-yl)-1,3-dioxoisoindolin-5-yl)piperazin-1-yl)ethyl)-[1,4'-bipiperidin]-4-yl)-2-(4-phenoxyphenyl)-4,5,6,7-tetrahydropyrazolo[1,5-a]pyrimidine-3-carboxamide | 868.44 | C | B | C | B |
| 308 | 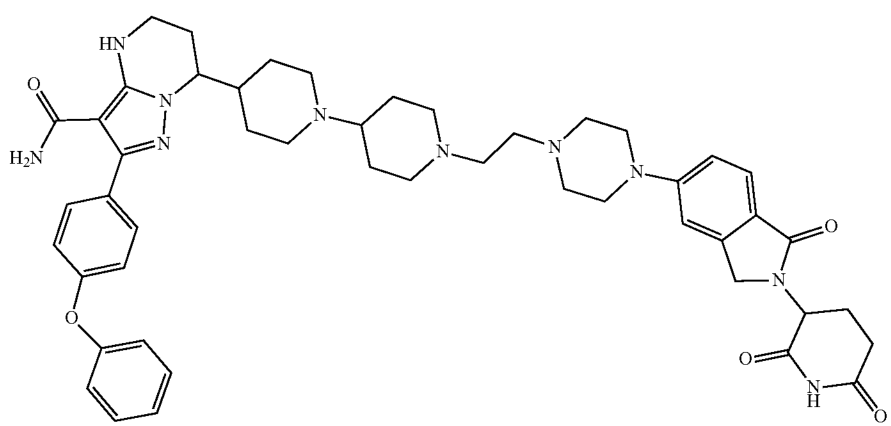 [SMILES: NC(=O)c1c(-c2ccc(Oc3ccccc3)cc2)nn2c1NCCC2C1CCN(C2CCN(CCN3CCN(c4ccc5c(c4)CN(C4CCC(=O)NC4=O)C5=O)CC3)CC2)CC1] | 7-(1'-(2-(4-(2-(2,6-dioxopiperidin-3-yl)-1-oxoisoindolin-5-yl)piperazin-1-yl)ethyl)-[1,4'-bipiperidin]-4-yl)-2-(4-phenoxyphenyl)-4,5,6,7-tetrahydropyrazolo[1,5-a]pyrimidine-3-carboxamide | 854.46 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 309 | 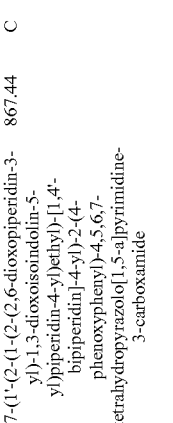 | 7-(1'-(2-(1-(2-(2,6-dioxopiperidin-3-yl)-1,3-dioxoisoindolin-5-yl)piperidin-4-yl)ethyl)-[1,4'-bipiperidin]-4-yl)-2-(4-phenoxyphenyl)-4,5,6,7-tetrahydropyrazolo[1,5-a]pyrimidine-3-carboxamide | 867.44 | C | C | B | B |
| 310 | 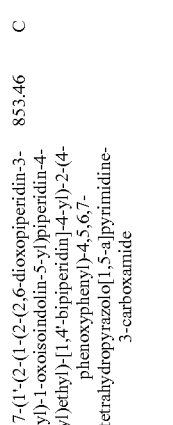 | 7-(1'-(2-(1-(2-(2,6-dioxopiperidin-3-yl)-1-oxoisoindolin-5-yl)piperidin-4-yl)ethyl)-[1,4'-bipiperidin]-4-yl)-2-(4-phenoxyphenyl)-4,5,6,7-tetrahydropyrazolo[1,5-a]pyrimidine-3-carboxamide | 853.46 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 311 | 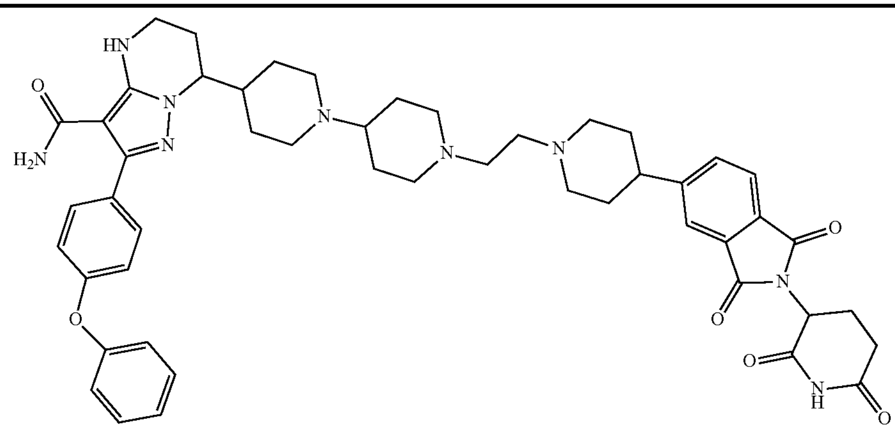 | 7-(1'-(2-(4-(2-(2,6-dioxopiperidin-3-yl)-1,3-dioxoisoindolin-5-yl)piperidin-1-yl)ethyl)-[1,4'-bipiperidin]-4-yl)-2-(4-phenoxyphenyl)-4,5,6,7-tetrahydropyrazolo[1,5-a]pyrimidine-3-carboxamide | 867.44 | C | C | C | B |
| 312 | 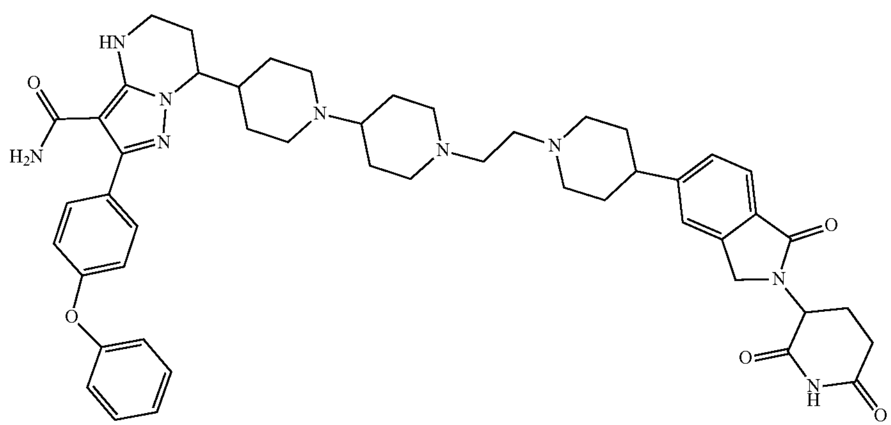 [SMILES: NC(=O)c1c(-c2ccc(Oc3ccccc3)cc2)nn2c1NCCC2C1CCN(C2CCN(CCN3CCC(c4ccc5c(c4)CN(C4CCC(=O)NC4=O)C5=O)CC3)CC2)CC1] | 7-(1'-(2-(4-(2-(2,6-dioxopiperidin-3-yl)-1-oxoisoindolin-5-yl)piperidin-1-yl)ethyl)-[1,4'-bipiperidin]-4-yl)-2-(4-phenoxyphenyl)-4,5,6,7-tetrahydropyrazolo[1,5-a]pyrimidine-3-carboxamide | 853.46 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 313 | 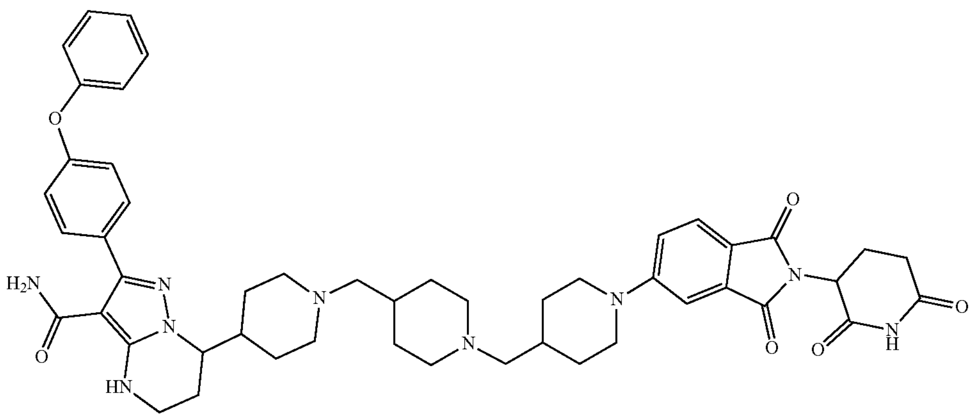 [SMILES: NC(=O)c1c(-c2ccc(Oc3ccccc3)cc2)nn2c1NCCC2C1CCN(CC2CCN(CC3CCN(c4ccc5c(c4)C(=O)N(C4CCC(=O)NC4=O)C5=O)CC3)CC2)CC1] | 7-(1-((1-(1-(2-(2,6-dioxopiperidin-3-yl)-1,3-dioxoisoindolin-5-yl)piperidin-4-yl)methyl)piperidin-4-yl)methyl)piperidin-4-yl)-2-(4-phenoxyphenyl)-4,5,6,7-tetrahydropyrazolo[1,5-a]pyrimidine-3-carboxamide | 867.44 | B | B | B | A |
| 314 | 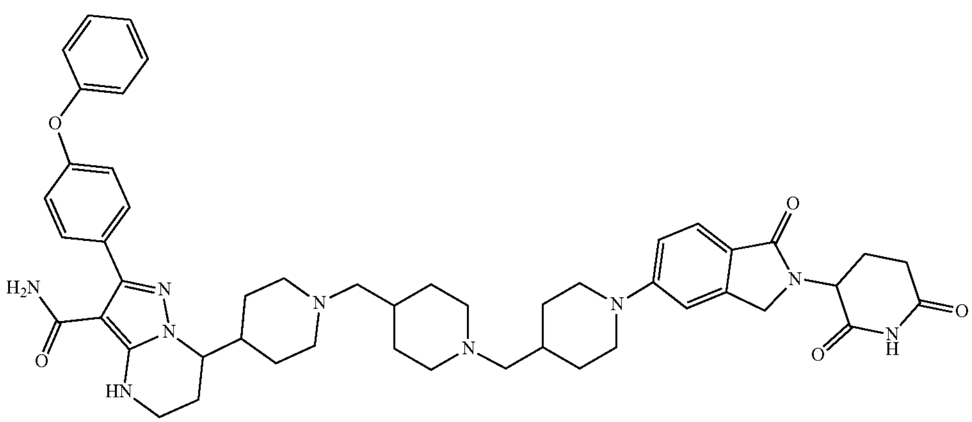 [SMILES: NC(=O)c1c(-c2ccc(Oc3ccccc3)cc2)nn2c1NCCC2C1CCN(CC2CCN(CC3CCN(c4ccc5c(c4)CN(C4CCC(=O)NC4=O)C5=O)CC3)CC2)CC1] | 7-(1-((1-(1-(2-(2,6-dioxopiperidin-3-yl)-1-oxoisoindolin-5-yl)piperidin-4-yl)methyl)piperidin-4-yl)methyl)piperidin-4-yl)-2-(4-phenoxyphenyl)-4,5,6,7-tetrahydropyrazolo[1,5-a]pyrimidine-3-carboxamide | 853.46 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 315 | 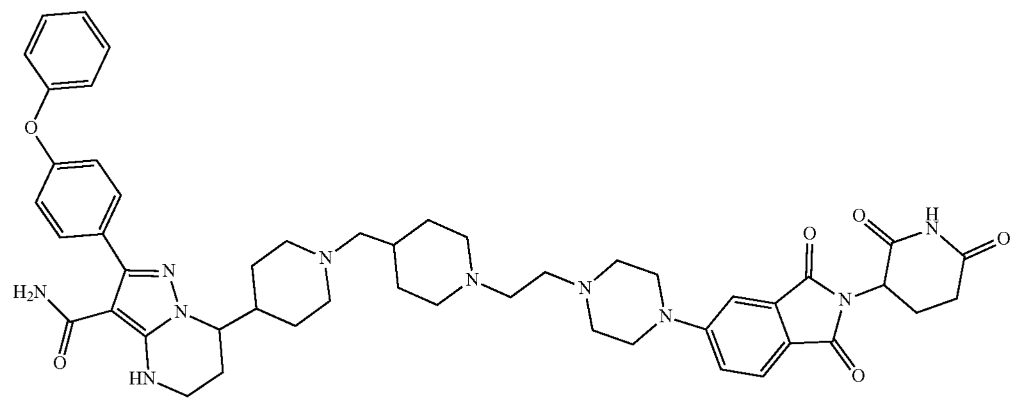 [SMILES: NC(=O)c1c(-c2ccc(Oc3ccccc3)cc2)nn2c1NCCC2C1CCN(CC2CCN(CCN3CCN(c4ccc5c(c4)C(=O)N(C4CCC(=O)NC4=O)C5=O)CC3)CC2)CC1] | 7-(1-(2-(4-(2-(2,6-dioxopiperidin-3-yl)-1,3-dioxoisoindolin-5-yl)piperazin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 882.45 | B | B | C | B |
| 316 | 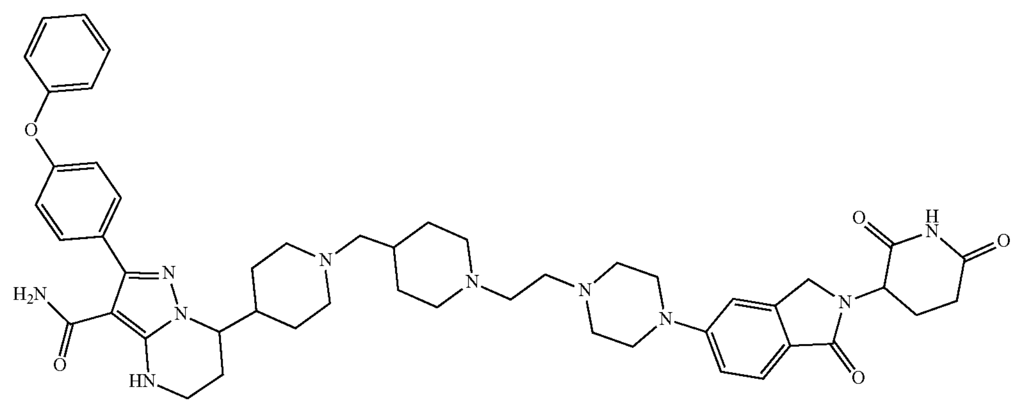 [SMILES: NC(=O)c1c(-c2ccc(Oc3ccccc3)cc2)nn2c1NCCC2C1CCN(CC2CCN(CCN3CCN(c4ccc5c(c4)CN(C4CCC(=O)NC4=O)C5=O)CC3)CC2)CC1] | 7-(1-(1-(2-(4-(2-(2,6-dioxopiperidin-3-yl)-1-oxoisoindolin-5-yl)piperazin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 868.47 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 317 | 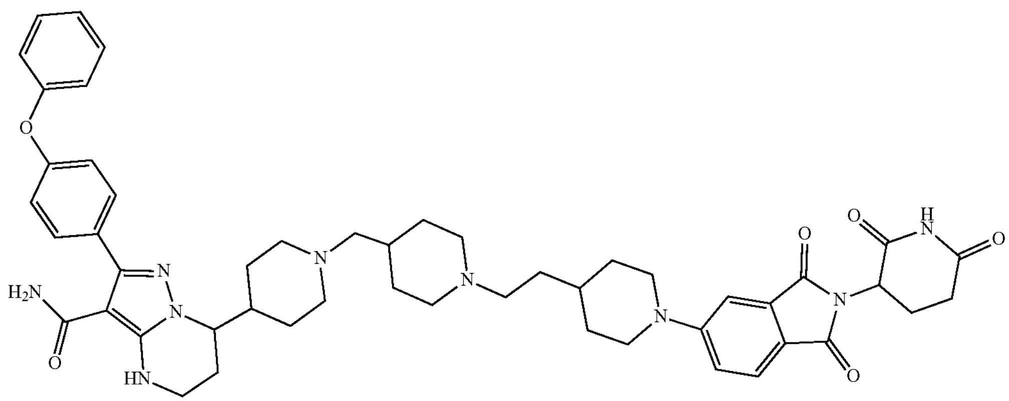 [SMILES: NC(=O)c1c(-c2ccc(Oc3ccccc3)cc2)nn2c1NCCC2C1CCN(CC2CCN(CCC3CCN(c4ccc5c(c4)C(=O)N(C4CCC(=O)NC4=O)C5=O)CC3)CC2)CC1] | 7-(1-((2-(1-(2-(2-(2,6-dioxopiperidin-3-yl)-1,3-dioxoisoindolin-5-yl)piperidin-4-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 881.46 | C | B | C | B |
| 318 | 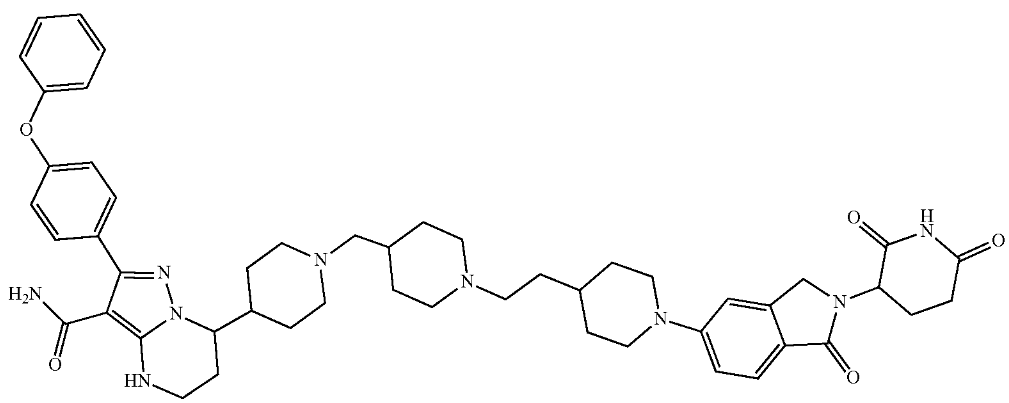 [SMILES: NC(=O)c1c(-c2ccc(Oc3ccccc3)cc2)nn2c1NCCC2C1CCN(CC2CCN(CCC3CCN(c4ccc5c(c4)CN(C4CCC(=O)NC4=O)C5=O)CC3)CC2)CC1] | 7-(1-((2-(1-(2-(2-(2,6-dioxopiperidin-3-yl)-1-oxoisoindolin-5-yl)piperidin-4-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 867.48 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 319 | 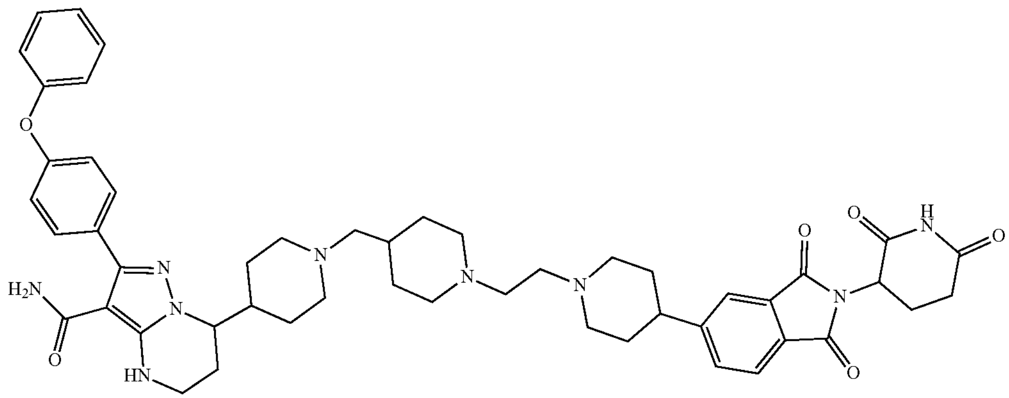 [SMILES: NC(=O)c1c(-c2ccc(Oc3ccccc3)cc2)nn2c1NCCC2C1CCN(CC2CCN(CCN3CCC(c4ccc5c(c4)C(=O)N(C4CCC(=O)NC4=O)C5=O)CC3)CC2)CC1] | 7-(1-(2-(4-(2-(2,6-dioxopiperidin-3-yl)-1,3-dioxoisoindolin-5-yl)piperidin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 881.46 | C | B | B | BB |
| 320 | 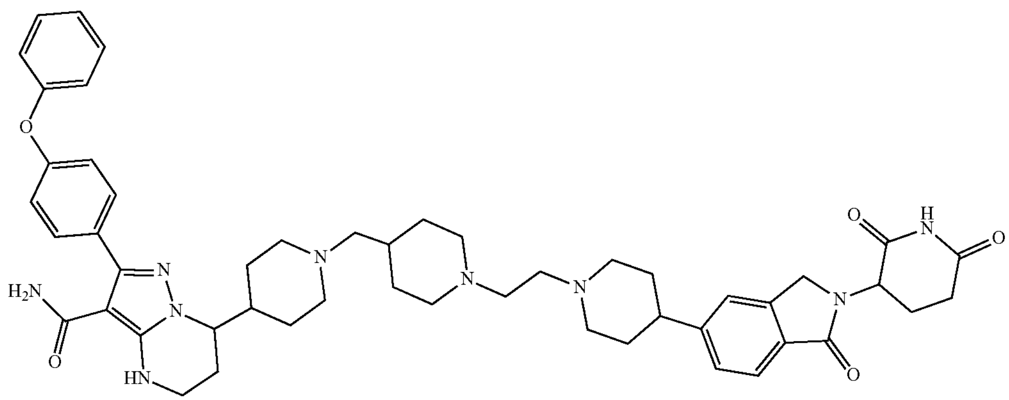 [SMILES: NC(=O)c1c(-c2ccc(Oc3ccccc3)cc2)nn2c1NCCC2C1CCN(CC2CCN(CCN3CCC(c4ccc5c(c4)CN(C4CCC(=O)NC4=O)C5=O)CC3)CC2)CC1] | 7-(1-(2-(4-(2-(2,6-dioxopiperidin-3-yl)-1-oxoisoindolin-5-yl)piperidin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 867.48 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 321 | 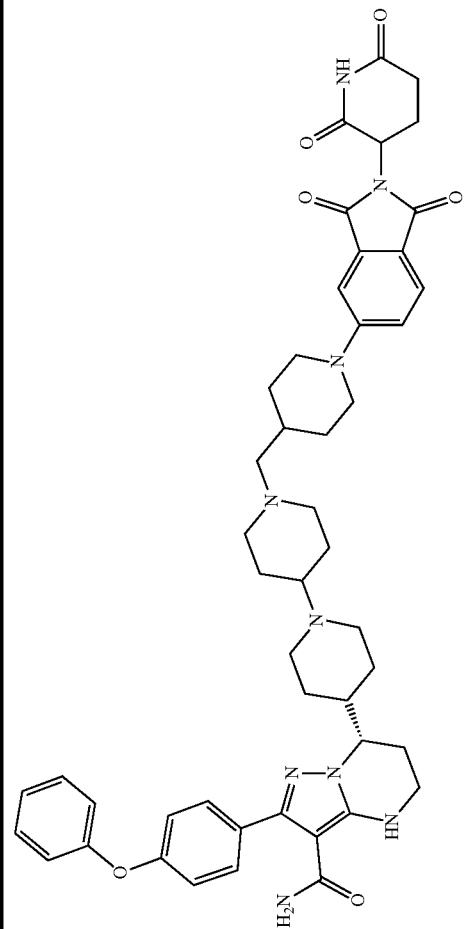 | (7S)-7-(1'-((1-(2-(2,6-dioxopiperidin-3-yl)-1,3-dioxoisoindolin-5-yl)piperidin-4-yl)methyl)-[1,4'-bipiperidin]-4-yl)-2-(4-phenoxyphenyl)-4,5,6,7-tetrahydropyrazolo[1,5-a]pyrimidine-3-carboxamide | 853.43 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 322 | 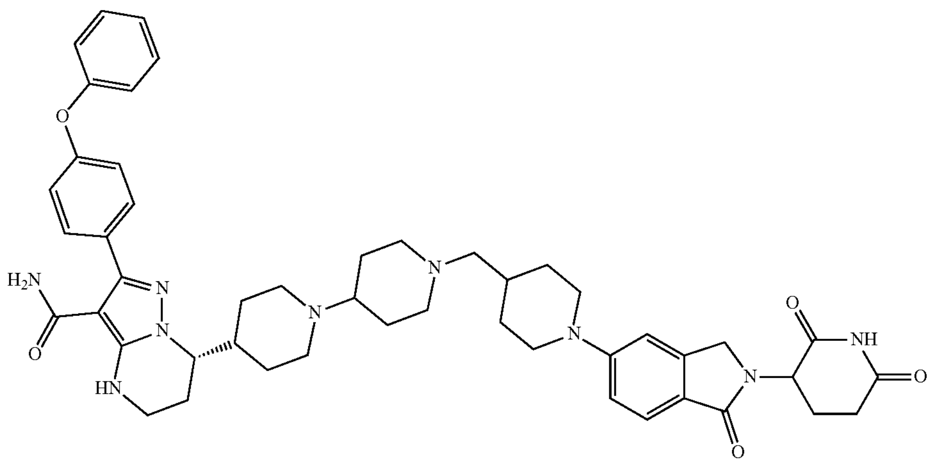 [SMILES: NC(=O)c1c(-c2ccc(Oc3ccccc3)cc2)nn2c1NCC[C@H]2C1CCN(C2CCN(CC3CCN(c4ccc5c(c4)CN(C4CCC(=O)NC4=O)C5=O)CC3)CC2)CC1] | (7S)-7-(1'-((1-(2-(2,6-dioxopiperidin-3-yl)-1-oxoisoindolin-5-yl)piperidin-4-yl)methyl)-[1,4'-bipiperidin]-4-yl)-2-(4-phenoxyphenyl)-4,5,6,7-tetrahydropyrazolo[1,5-a]pyrimidine-3-carboxamide | 839.45 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 323 | 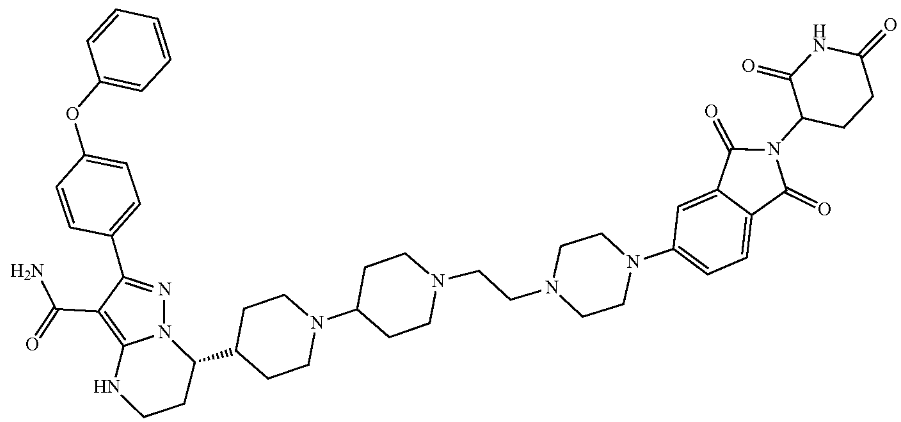 [SMILES: NC(=O)c1c(-c2ccc(Oc3ccccc3)cc2)nn2c1NCC[C@H]2C1CCN(C2CCN(CCN3CCN(c4ccc5c(c4)C(=O)N(C4CCC(=O)NC4=O)C5=O)CC3)CC2)CC1] | (7S)-7-(1'-(2-(4-(2-(2,6-dioxopiperidin-3-yl)-1,3-dioxoisoindolin-5-yl)piperazin-1-yl)ethyl)-[1,4-bipiperidin]-4-yl)-2-(4-phenoxyphenyl)-4,5,6,7-tetrahydropyrazolo[1,5-a]pyrimidine-3-carboxamide | 868.44 | B | B | B | B |
| 324 | 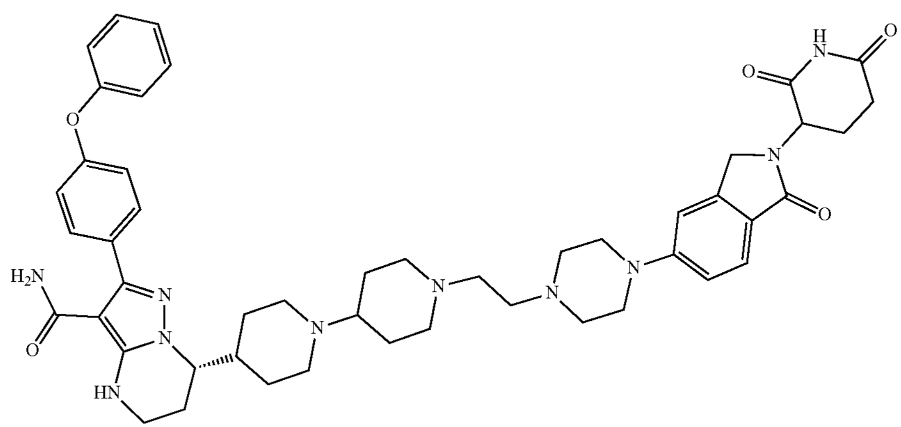 [SMILES: NC(=O)c1c(-c2ccc(Oc3ccccc3)cc2)nn2c1NCC[C@H]2C1CCN(C2CCN(CCN3CCN(c4ccc5c(c4)CN(C4CCC(=O)NC4=O)C5=O)CC3)CC2)CC1] | (7S)-7-(1'-(2-(4-(2-(2,6-dioxopiperidin-3-yl)-1-oxoisoindolin-5-yl)piperazin-1-yl)ethyl)-[1,4-bipiperidin]-4-yl)-2-(4-phenoxyphenyl)-4,5,6,7-tetrahydropyrazolo[1,5-a]pyrimidine-3-carboxamide | 854.46 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 325 | 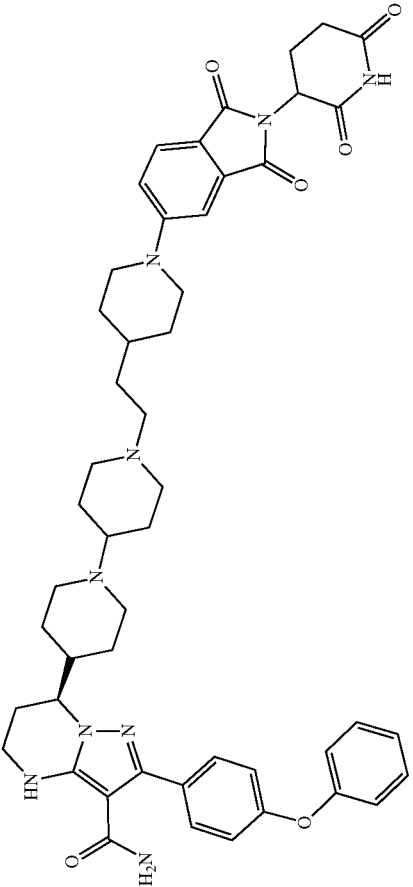  Exact Mass: 867.44 | (7S)-7-(1'-(2-(1-(2-(2,6-dioxopiperidin-3-yl)-1,3-dioxoisoindolin-5-yl)piperidin-4-yl)ethyl)-[1,4-bipiperidin]-4-yl)-2-(4-phenoxyethyl)-4,5,6,7-tetrahydropyrazolo[1,5-a]pyrimidine-3-carboxamide | 867.44 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 326 | 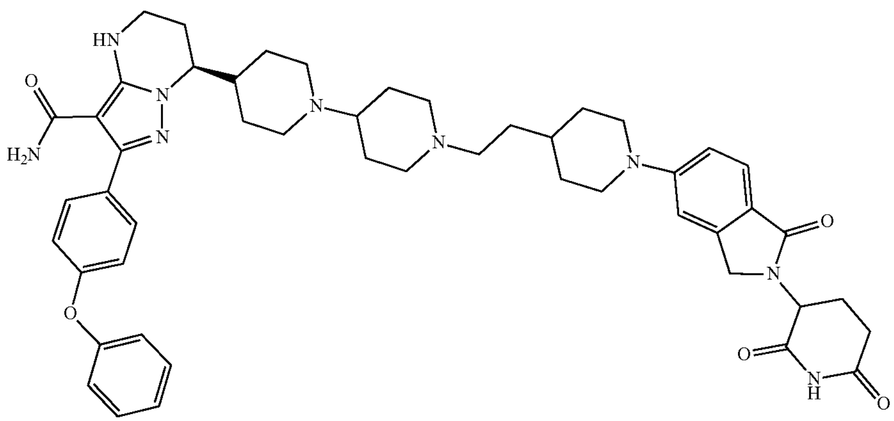 [SMILES: NC(=O)c1c(-c2ccc(Oc3ccccc3)cc2)nn2c1NCC[C@H]2C1CCN(C2CCN(CCC3CCN(c4ccc5c(c4)CN(C4CCC(=O)NC4=O)C5=O)CC3)CC2)CC1] | (7S)-7-(1'-(2-(1-(2-(2,6-dioxopiperidin-3-yl)-1-oxoisoindolin-5-yl)piperidin-4-yl)ethyl)-[1,4-bipiperidin]-4-yl)-2-(4-phenoxyphenyl)-4,5,6,7-tetrahydropyrazolo[1,5-a]pyrimidine-3-carboxamide | 853.46 | B | B | B | A |
| 327 | 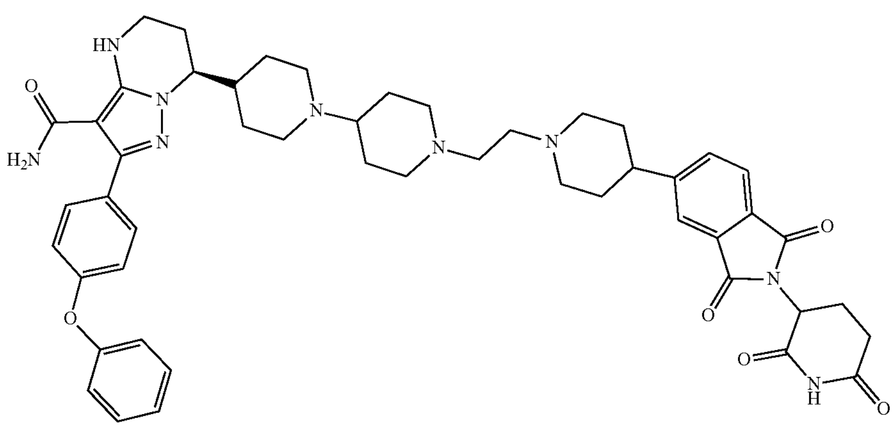 [SMILES: NC(=O)c1c(-c2ccc(Oc3ccccc3)cc2)nn2c1NCC[C@H]2C1CCN(C2CCN(CCN3CCC(c4ccc5c(c4)C(=O)N(C4CCC(=O)NC4=O)C5=O)CC3)CC2)CC1] | (7S)-7-(1'-(2-(4-(2-(2,6-dioxopiperidin-3-yl)-1,3-dioxoisoindolin-5-yl)piperidin-1-yl)ethyl)-[1,4-bipiperidin]-4-yl)-2-(4-phenoxyphenyl)-4,5,6,7-tetrahydropyrazolo[1,5-a]pyrimidine-3-carboxamide | 867.44 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 328 | 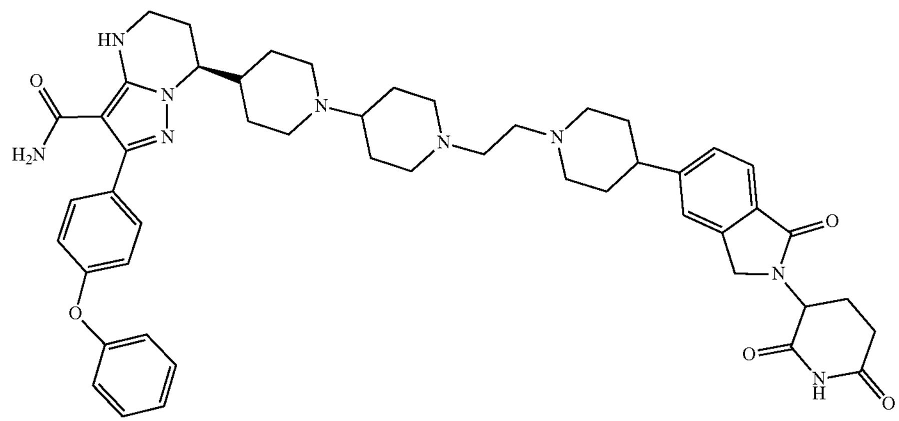 [SMILES: NC(=O)c1c(-c2ccc(Oc3ccccc3)cc2)nn2c1NCC[C@H]2C1CCN(C2CCN(CCN3CCC(c4ccc5c(c4)CN(C4CCC(=O)NC4=O)C5=O)CC3)CC2)CC1] | (7S)-7-(1'-(2-(4-(2-(2,6-dioxopiperidin-3-yl)-1-oxoisoindolin-5-yl)piperidin-1-yl)ethyl)-[1,4'-bipiperidin]-4-yl)-2-(4-phenoxyphenyl)-4,5,6,7-tetrahydropyrazolo[1,5-a]pyrimidine-3-carboxamide | 853.46 | B | B | B | B |
| 329 | 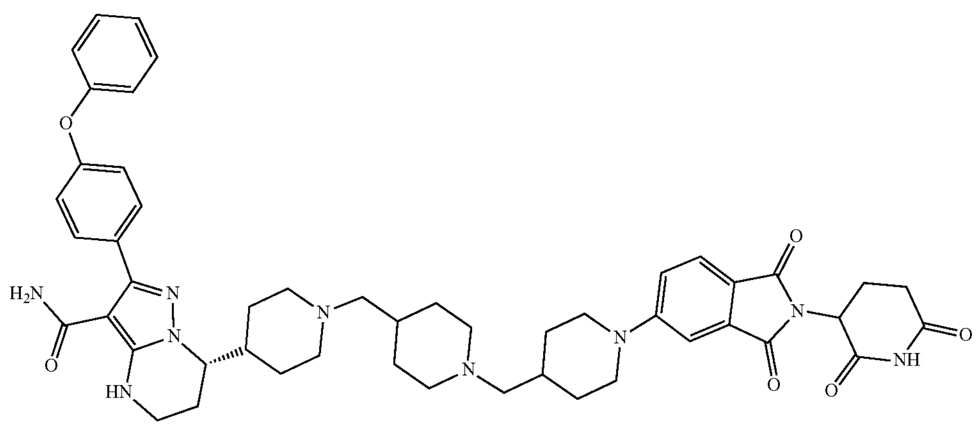 [SMILES: NC(=O)c1c(-c2ccc(Oc3ccccc3)cc2)nn2c1NCC[C@H]2C1CCN(CC2CCN(CC3CCN(c4ccc5c(c4)C(=O)N(C4CCC(=O)NC4=O)C5=O)CC3)CC2)CC1] | (7S)-7-(1'-((1-(2-(2,6-dioxopiperidin-3-yl)-1,3-dioxoisoindolin-5-yl)piperidin-4-yl)methyl)piperidin-4-yl)-2-(4-phenoxyphenyl)-4,5,6,7-tetrahydropyrazolo[1,5-a]pyrimidine-3-carboxamide | 867.44 | C | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC₅₀ (antiproliferation) JeKO-1 cells | IC₅₀ (antiproliferation) Mino cells | DC₅₀ | D$_{max}$ |
|---|---|---|---|---|---|---|---|
| 330 | 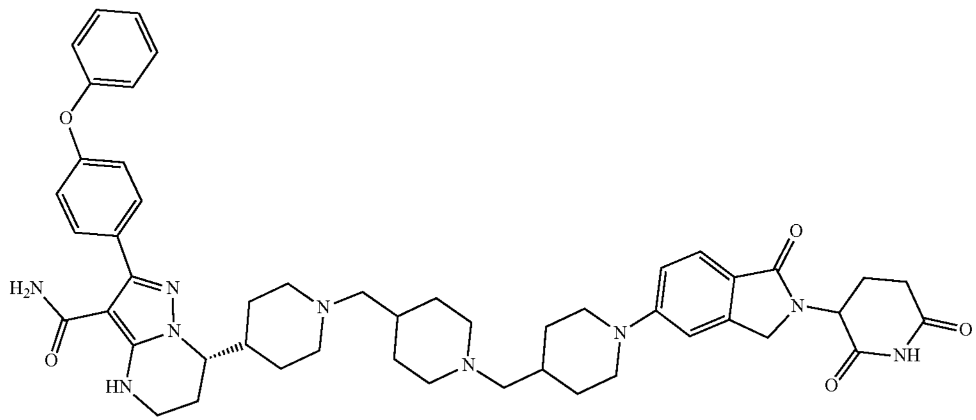 [SMILES: NC(=O)c1c(-c2ccc(Oc3ccccc3)cc2)nn2c1NCC[C@H]2C1CCN(CC2CCN(CC3CCN(c4ccc5c(c4)CN(C4CCC(=O)NC4=O)C5=O)CC3)CC2)CC1] | (7S)-7-(1-((1-(2-(2,6-dioxopiperidin-3-yl)-1-oxoisoindolin-5-yl)piperidin-4-yl)methyl)piperidin-4-yl)methyl)piperidin-4-yl)-2-(4-phenoxyphenyl)-4,5,6,7-tetrahydropyrazolo[1,5-a]pyrimidine-3-carboxamide | 853.46 | B | B | B | B |
| 331 | 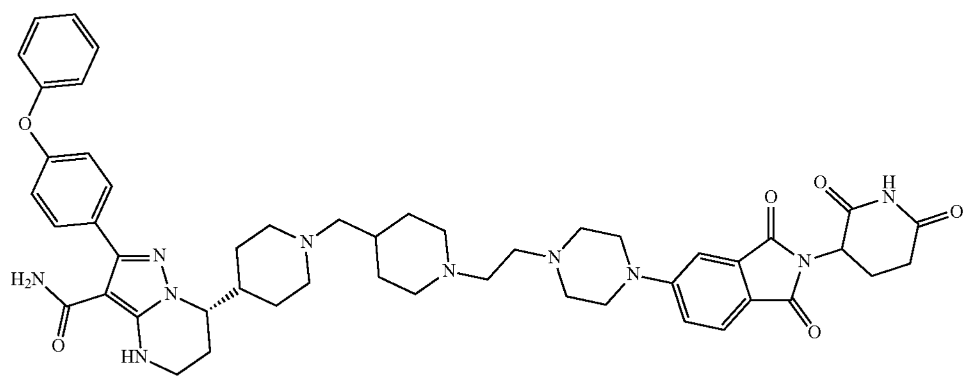 | (7S)-7-(1-((1-(2-(4-(2-(2,6-dioxopiperidin-3-yl)-1,3-dioxoisoindolin-5-yl)piperazin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 882.45 | B | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 332 | 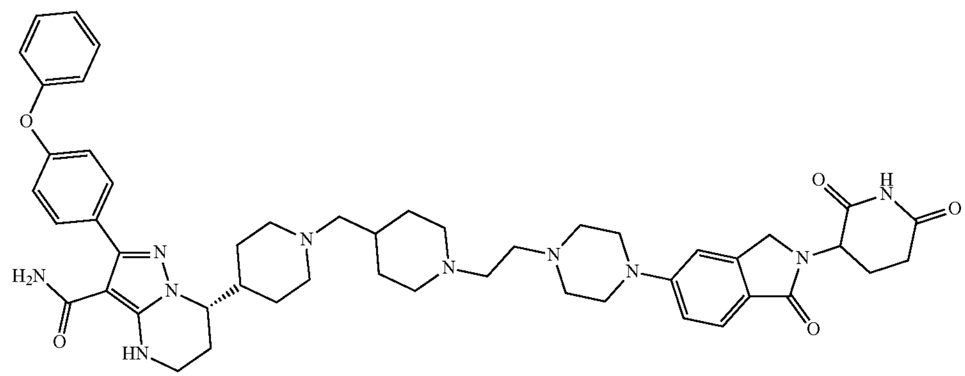 [SMILES: NC(=O)c1c(-c2ccc(Oc3ccccc3)cc2)nn2c1NCC[C@H]2C1CCN(CC2CCN(CCN3CCN(c4ccc5c(c4)CN(C4CCC(=O)NC4=O)C5=O)CC3)CC2)CC1] | (7S)-7-((1-((1-(2-(4-(2-(2,6-dioxopiperidin-3-yl)-1-oxoisoindolin-5-yl)piperazin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 868.47 | B | B | C | B |
| 333 | 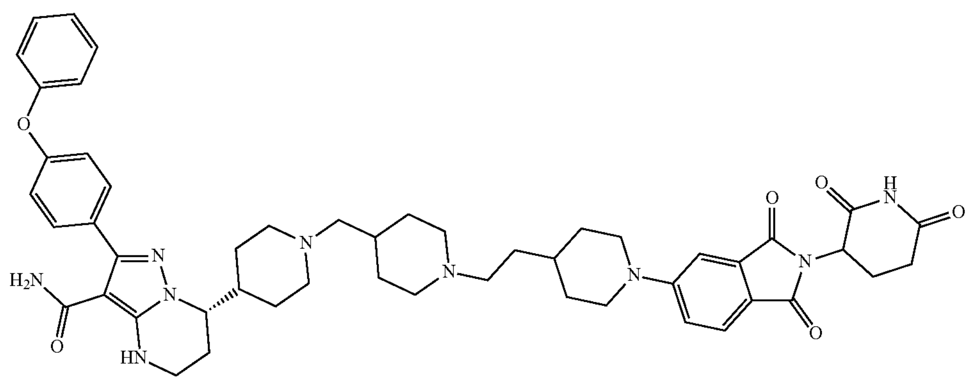 [SMILES: NC(=O)c1c(-c2ccc(Oc3ccccc3)cc2)nn2c1NCC[C@H]2C1CCN(CC2CCN(CCC3CCN(c4ccc5c(c4)C(=O)N(C4CCC(=O)NC4=O)C5=O)CC3)CC2)CC1] | (7S)-7-(1-((1-(2-(1-(2-(2,6-dioxopiperidin-3-yl)-1,3-dioxoisoindolin-5-yl)piperidin-4-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 881.46 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 334 | 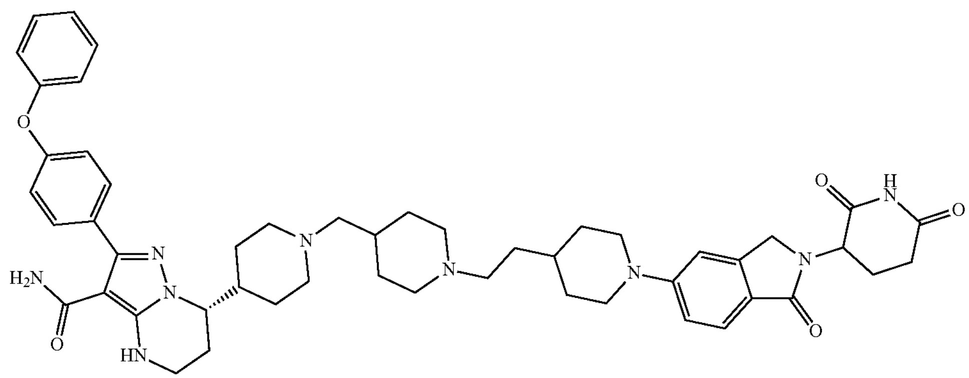 [SMILES: NC(=O)c1c(-c2ccc(Oc3ccccc3)cc2)nn2c1NCC[C@H]2C1CCN(CC2CCN(CCC3CCN(c4ccc5c(c4)CN(C4CCC(=O)NC4=O)C5=O)CC3)CC2)CC1] | (7S)-7-(1-((1-(2-(1-(2-(2,6-dioxopiperidin-3-yl)-1-oxoisoindolin-5-yl)piperidin-4-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 866.48 | C | C | B | B |
| 335 | 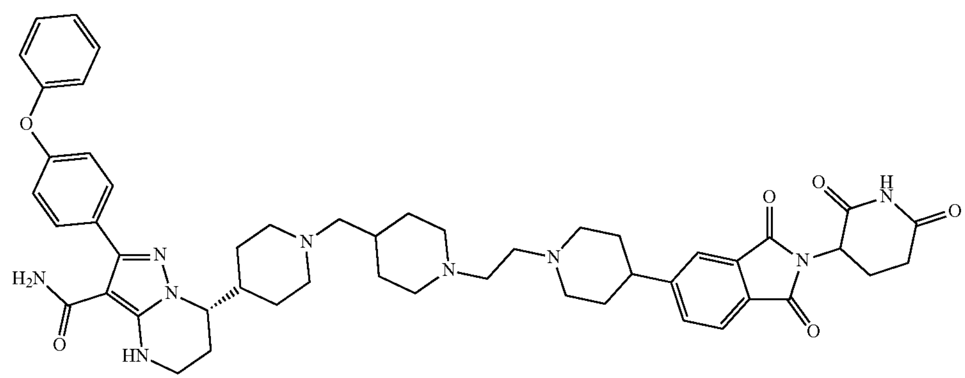 [SMILES: NC(=O)c1c(-c2ccc(Oc3ccccc3)cc2)nn2c1NCC[C@H]2C1CCN(CC2CCN(CCN3CCC(c4ccc5c(c4)C(=O)N(C4CCC(=O)NC4=O)C5=O)CC3)CC2)CC1] | (7S)-7-(1-((1-(2-(4-(2-(2,6-dioxopiperidin-3-yl)-1,3-dioxoisoindolin-5-yl)piperidin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 881.46 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 336 | 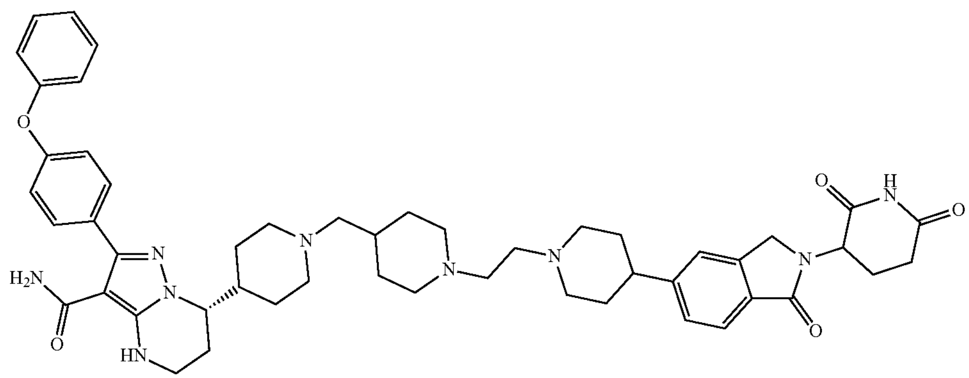 [SMILES: NC(=O)c1c(-c2ccc(Oc3ccccc3)cc2)nn2c1NCC[C@H]2C1CCN(CC2CCN(CCN3CCC(c4ccc5c(c4)CN(C4CCC(=O)NC4=O)C5=O)CC3)CC2)CC1] | (7S)-7-(1-((1-(2-(4-(2-(2,6-dioxopiperidin-3-yl)-1-oxoisoindolin-5-yl)piperidin-1-yl)ethyl)piperidin-4-yl)methyl)piperidin-4-yl)-2-(4-phenoxyphenyl)-4,5,6,7-tetrahydropyrazolo[1,5-a]pyrimidine-3-carboxamide | 867.48 | B | B | B | B |
| 337 | 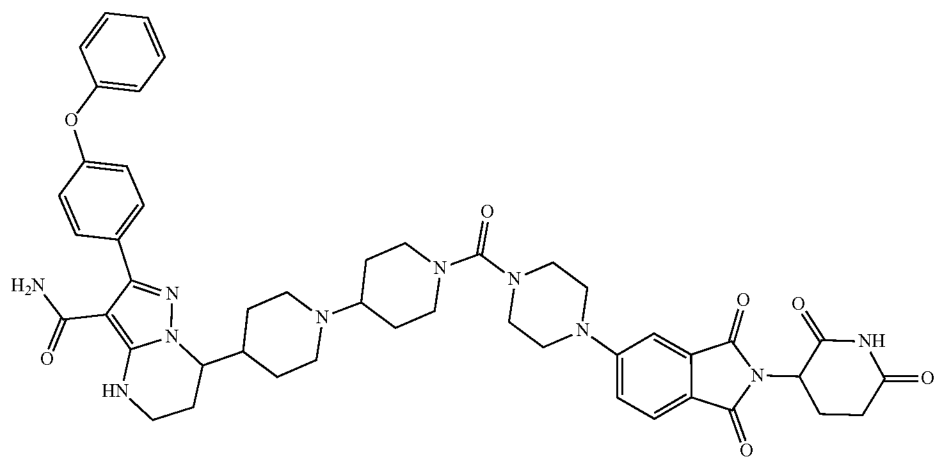 [SMILES: NC(=O)c1c(-c2ccc(Oc3ccccc3)cc2)nn2c1NCCC2C1CCN(C2CCN(C(=O)N3CCN(c4ccc5c(c4)C(=O)N(C4CCC(=O)NC4=O)C5=O)CC3)CC2)CC1] | 7-(1'-(4-(2-(2,6-dioxopiperidin-3-yl)-1,3-dioxoisoindolin-5-yl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 868.40 | B | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 338 | 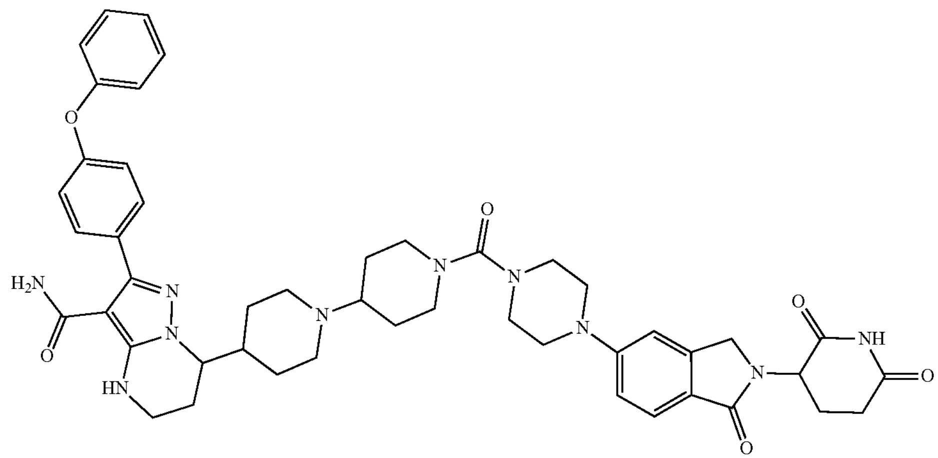 [SMILES: NC(=O)c1c(-c2ccc(Oc3ccccc3)cc2)nn2c1NCCC2C1CCN(C2CCN(C(=O)N3CCN(c4ccc5c(c4)CN(C4CCC(=O)NC4=O)C5=O)CC3)CC2)CC1] | 7-(1'-(4-(2-(2,6-dioxopiperidin-3-yl)-1-oxoisoindolin-5-yl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 854.42 | C | B | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 339 | 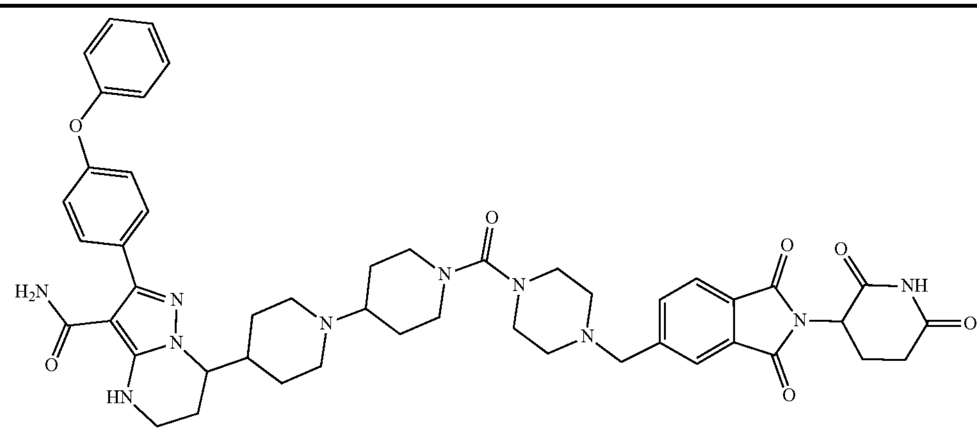 | 7-(1'-(4-((2-(2,6-dioxopiperidin-3-yl)-1,3-dioxoisoindolin-5-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 882.42 | C | C | C | C |
| 340 | 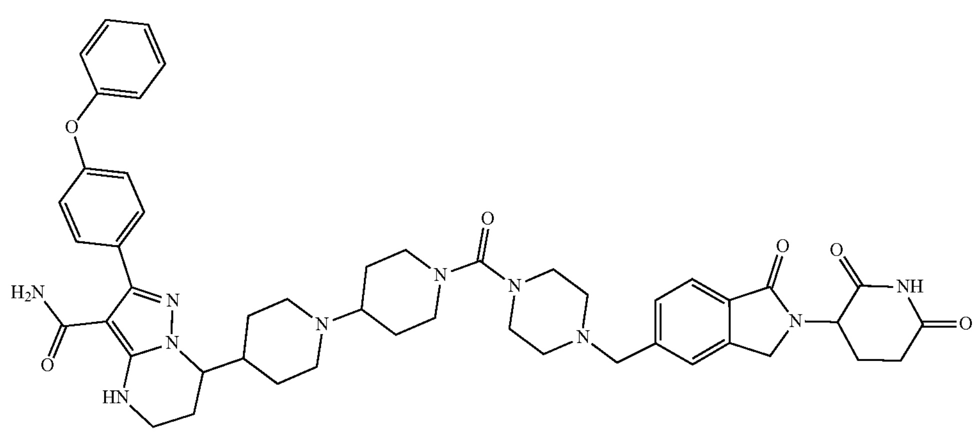 [SMILES: NC(=O)c1c(-c2ccc(Oc3ccccc3)cc2)nn2c1NCCC2C1CCN(C2CCN(C(=O)N3CCN(Cc4ccc5c(c4)CN(C4CCC(=O)NC4=O)C5=O)CC3)CC2)CC1] | 7-(1'-(4-((2-(2,6-dioxopiperidin-3-yl)-1-oxoisoindolin-5-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 868.44 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 341 | 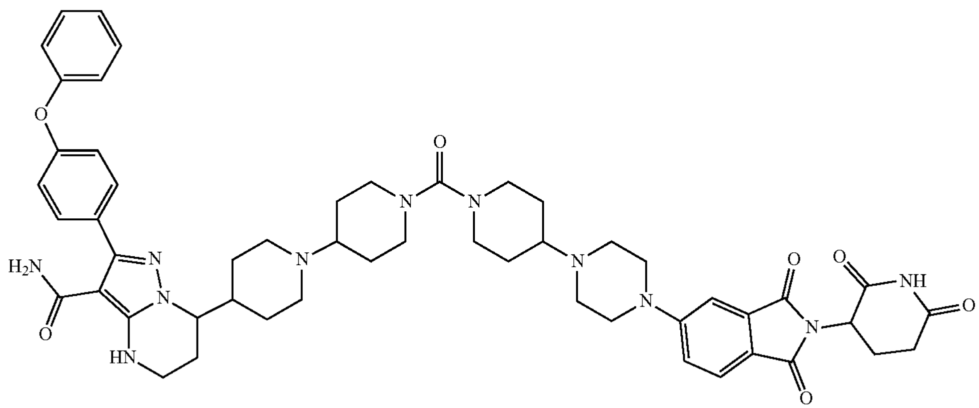 [SMILES: NC(=O)c1c(-c2ccc(Oc3ccccc3)cc2)nn2c1NCCC2C1CCN(C2CCN(C(=O)N3CCN(C4CCN(c5ccc6c(c5)C(=O)N(C5CCC(=O)NC5=O)C6=O)CC4)CC3)CC2)CC1] | 7-(1'-(4-(4-(2-(2,6-dioxopiperidin-3-yl)-1,3-dioxoisoindolin-5-yl)piperazin-1-yl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.48 | A | B | B | A |
| 342 | 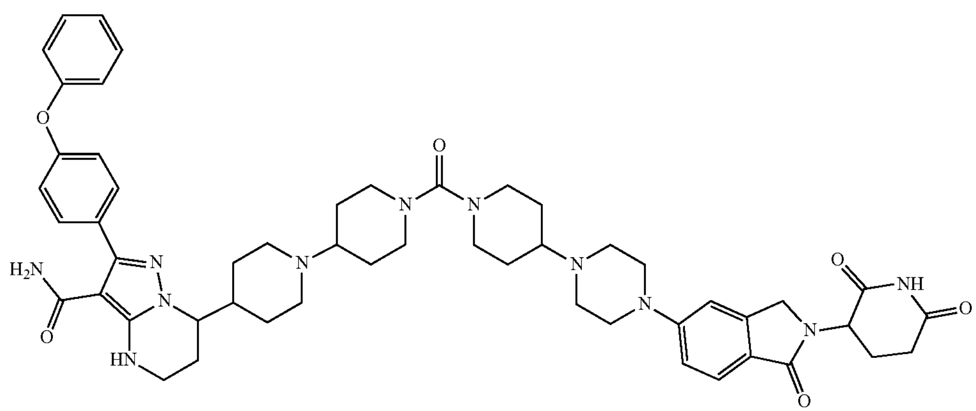 [SMILES: NC(=O)c1c(-c2ccc(Oc3ccccc3)cc2)nn2c1NCCC2C1CCN(C2CCN(C(=O)N3CCN(C4CCN(c5ccc6c(c5)CN(C5CCC(=O)NC5=O)C6=O)CC4)CC3)CC2)CC1] | 7-(1'-(4-(4-(2-(2,6-dioxopiperidin-3-yl)-1-oxoisoindolin-5-yl)piperazin-1-yl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 936.50 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 343 | 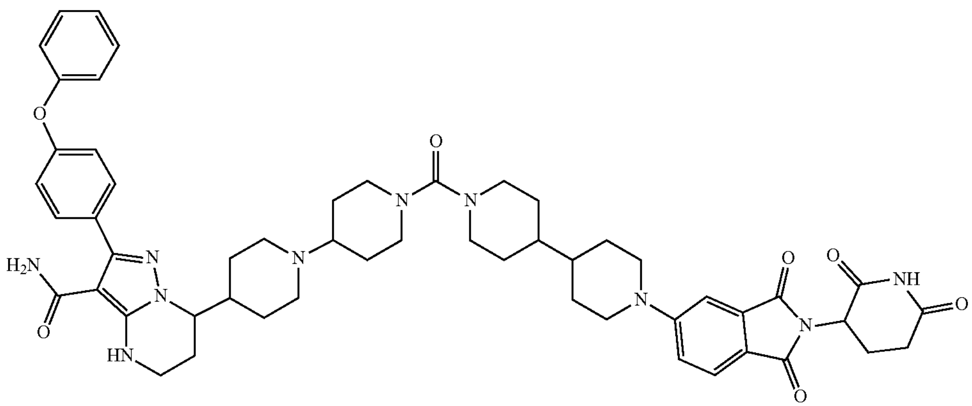 | 7-(1'-(2-(2,6-dioxopiperidin-3-yl)-1,3-dioxoisoindolin-5-yl)-[4,4'-bipiperidine]-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.48 | A | B | A | A |
| 344 | 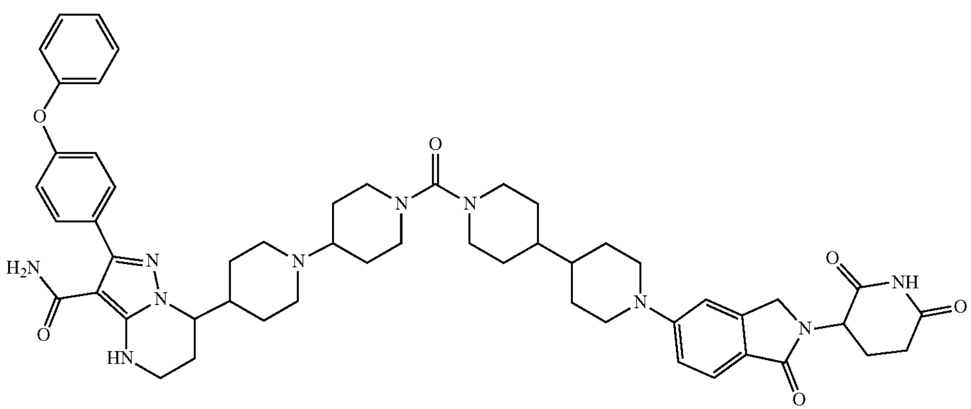 | 7-(1'-(2-(2,6-dioxopiperidin-3-yl)-1-oxoisoindolin-5-yl)-[4,4'-bipiperidine]-1-carbonyl)-[1,4'-bipiperidin]-4-yl)-2-(4-phenoxyphenyl)-4,5,6,7-tetrahydropyrazolo[1,5-a]pyrimidine-3-carboxamide | 936.50 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 345 | 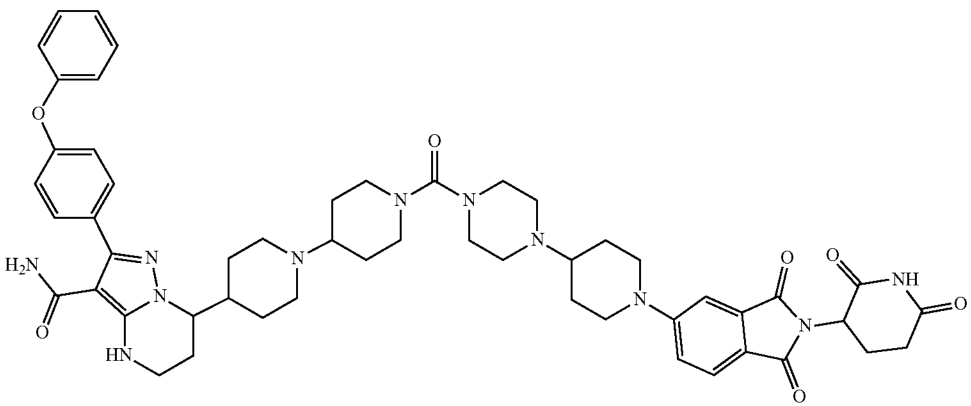 | 7-(1'-(4-(4-(2-(2,6-dioxopiperidin-3-yl)-1,3-dioxoisoindolin-5-yl)piperidin-4-yl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.48 | B | B | A | A |
| 346 | 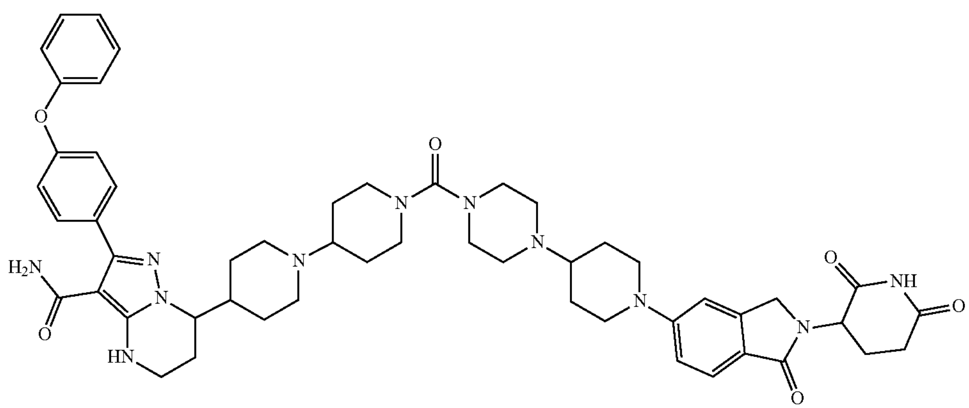 | 7-(1'-(4-(4-(2-(2,6-dioxopiperidin-3-yl)-1-oxoisoindolin-5-yl)piperidin-4-yl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 937.50 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 347 | 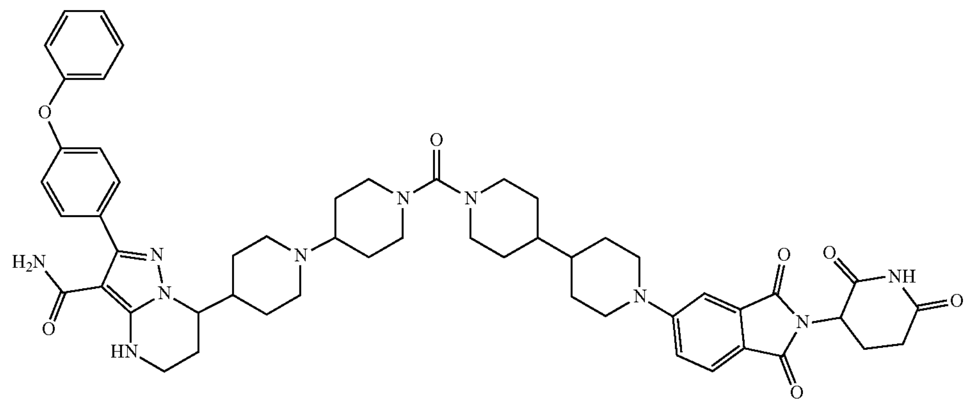 | 7-(1'-(4-(2-(2,6-dioxopiperidin-3-yl)-1,3-dioxoisoindolin-5-yl)-[1,4-bipiperidine]-1'-carbonyl)-[1,4-bipiperidin]-4-yl)-2-(4-phenoxyphenyl)-4,5,6,7-tetrahydropyrazolo[1,5-a]pyrimidine-3-carboxamide | 950.48 | A | A | A | A |
| 348 | 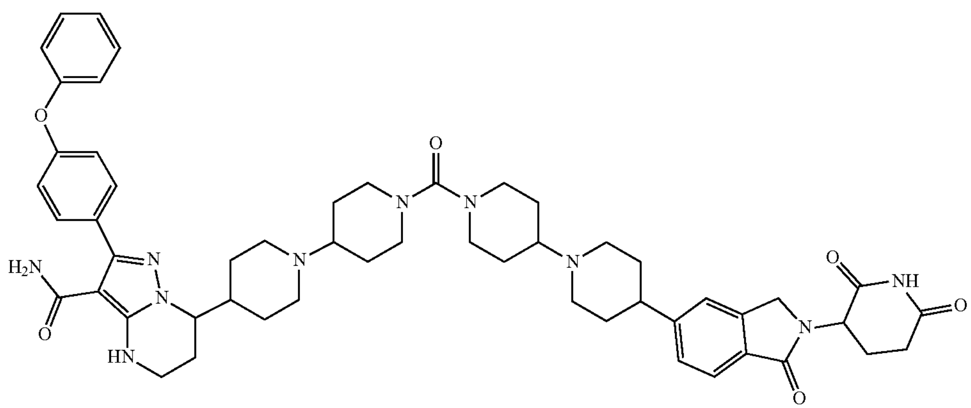 | 7-(1'-(4-(2-(2,6-dioxopiperidin-3-yl)-1-oxoisoindolin-5-yl)-[1,4-bipiperidine]-1'-carbonyl)-[1,4-bipiperidin]-4-yl)-2-(4-phenoxyphenyl)-4,5,6,7-tetrahydropyrazolo[1,5-a]pyrimidine-3-carboxamide | 936.50 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 349 | 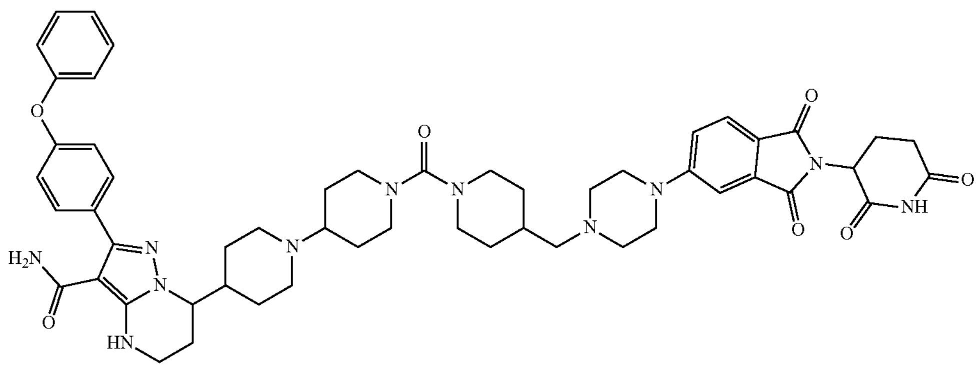 [SMILES: NC(=O)c1c(-c2ccc(Oc3ccccc3)cc2)nn2c1NCCC2C1CCN(C2CCN(C(=O)N3CCC(CN4CCN(c5ccc6c(c5)C(=O)N(C5CCC(=O)NC5=O)C6=O)CC4)CC3)CC2)CC1] | 7-(1'-(4-((4-(2-(2,6-dioxopiperidin-3-yl)-1,3-dioxoisoindolin-5-yl)piperazin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 965.49 | B | B | B | A |
| 350 | 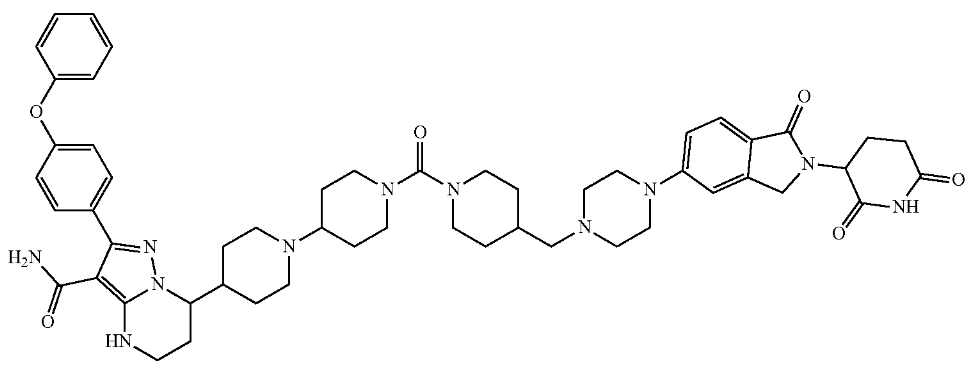 [SMILES: NC(=O)c1c(-c2ccc(Oc3ccccc3)cc2)nn2c1NCCC2C1CCN(C2CCN(C(=O)N3CCC(CN4CCN(c5ccc6c(c5)CN(C5CCC(=O)NC5=O)C6=O)CC4)CC3)CC2)CC1] | 7-(1'-(4-((4-(2-(2,6-dioxopiperidin-3-yl)-1-oxoisoindolin-5-yl)piperazin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 951.51 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 351 | 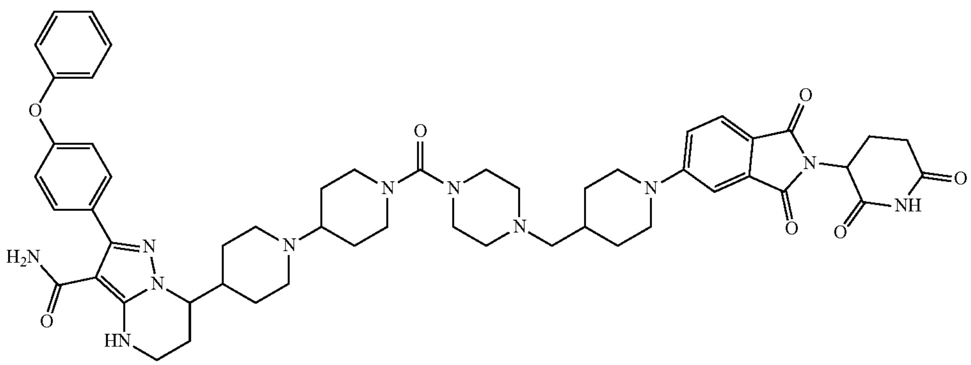 [SMILES: NC(=O)c1c(-c2ccc(Oc3ccccc3)cc2)nn2c1NCCC2C1CCN(C2CCN(C(=O)N3CCN(CC4CCN(c5ccc6c(c5)C(=O)N(C5CCC(=O)NC5=O)C6=O)CC4)CC3)CC2)CC1] | 7-(1'-(4-((1-(2-(2,6-dioxopiperidin-3-yl)-1,3-dioxoisoindolin-5-yl)piperidin-4-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 965.49 | B | A | B | A |
| 352 | 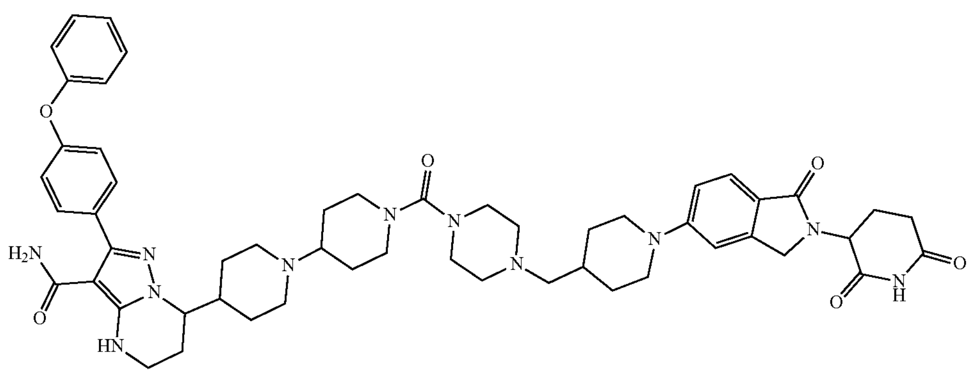 | 7-(1'-(4-((1-(2-(2,6-dioxopiperidin-3-yl)-1-oxoisoindolin-5-yl)piperidin-4-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 951.51 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 353 | 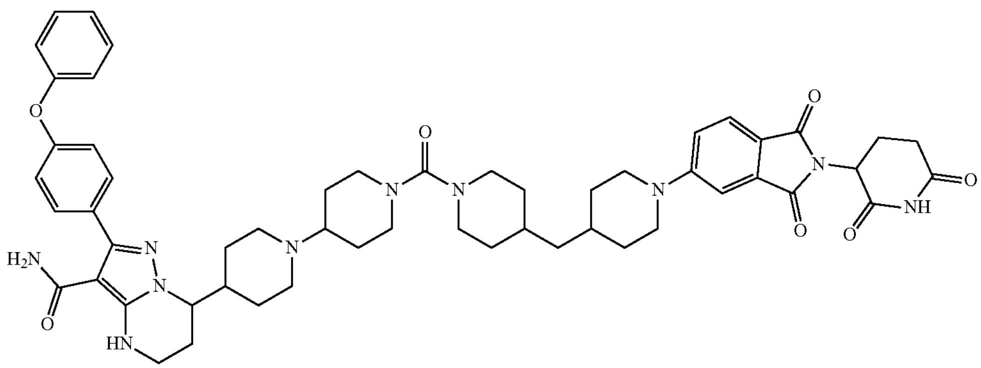 [SMILES: NC(=O)c1c(-c2ccc(Oc3ccccc3)cc2)nn2c1NCCC2C1CCN(C2CCN(C(=O)N3CCC(CC4CCN(c5ccc6c(c5)C(=O)N(C5CCC(=O)NC5=O)C6=O)CC4)CC3)CC2)CC1] | 7-(1'-(4-((1-(2-(2,6-dioxopiperidin-3-yl)-1,3-dioxoisoindolin-5-yl)piperidin-4-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 964.50 | B | A | B | A |
| 354 | 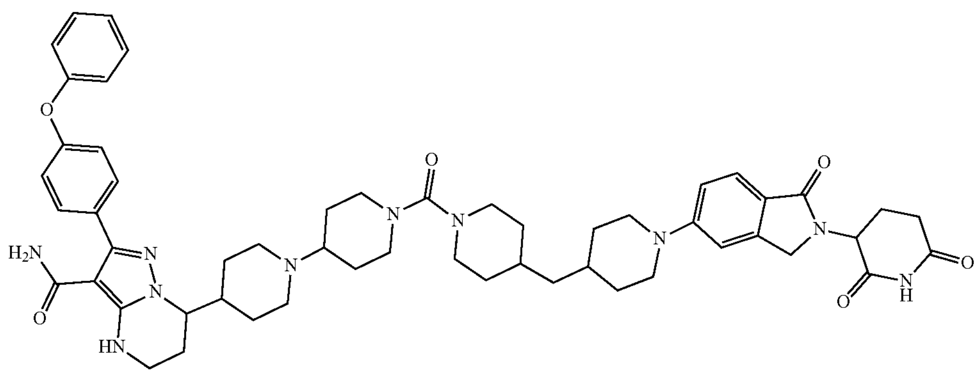 [SMILES: NC(=O)c1c(-c2ccc(Oc3ccccc3)cc2)nn2c1NCCC2C1CCN(C2CCN(C(=O)N3CCC(CC4CCN(c5ccc6c(c5)CN(C5CCC(=O)NC5=O)C6=O)CC4)CC3)CC2)CC1] | 7-(1'-(4-((1-(2-(2,6-dioxopiperidin-3-yl)-1-oxoisoindolin-5-yl)piperidin-4-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.52 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 355 | 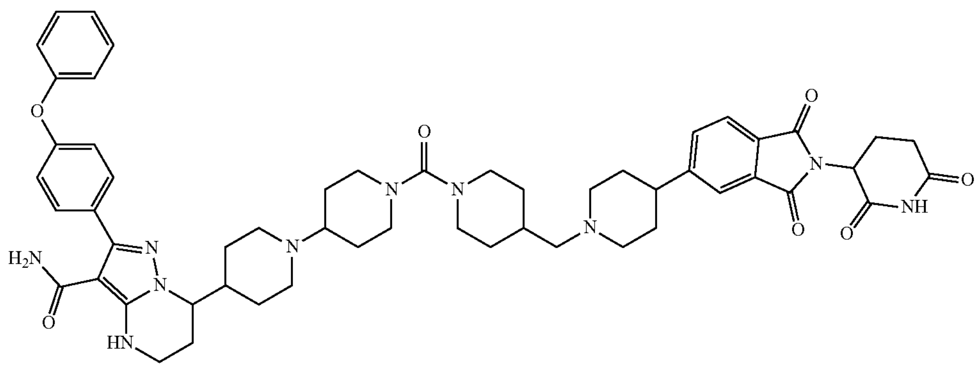 [SMILES: NC(=O)c1c(-c2ccc(Oc3ccccc3)cc2)nn2c1NCCC2C1CCN(C2CCN(C(=O)N3CCC(CN4CCC(c5ccc6c(c5)C(=O)N(C5CCC(=O)NC5=O)C6=O)CC4)CC3)CC2)CC1] | 7-(1'-(4-((4-(2-(2,6-dioxopiperidin-3-yl)-1,3-dioxoisoindolin-5-yl)piperidin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 964.50 | B | B | A | A |
| 356 | 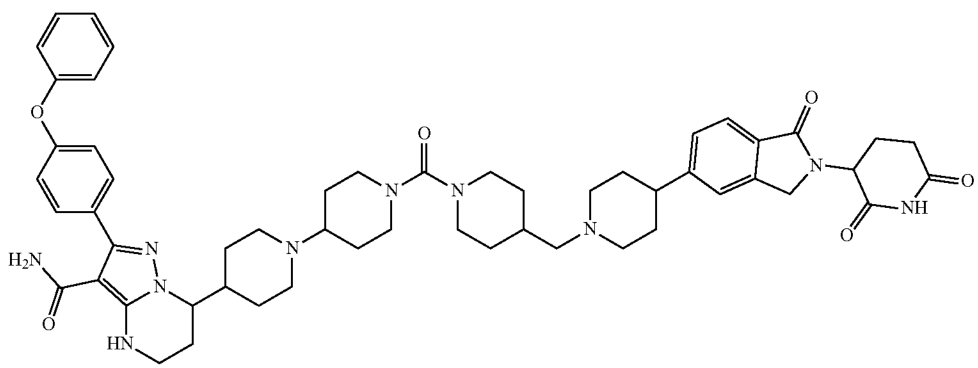 | 7-(1'-(4-((4-(2-(2,6-dioxopiperidin-3-yl)-1-oxoisoindolin-5-yl)piperidin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.52 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 357 | 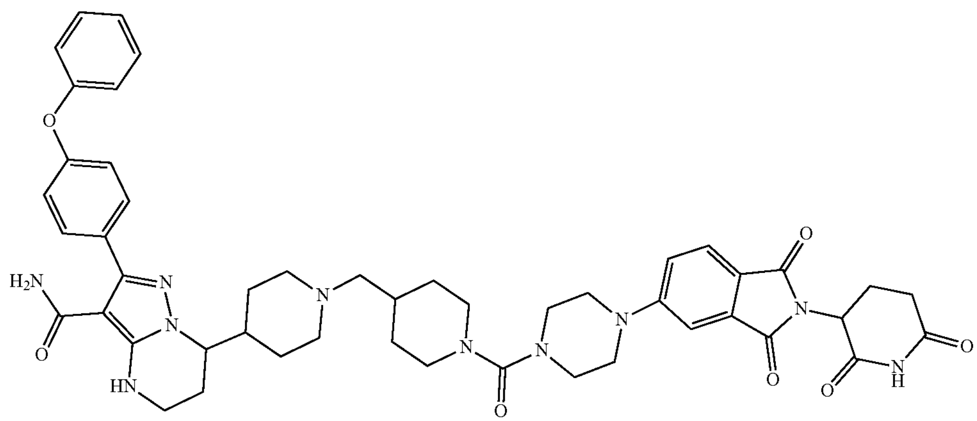 [SMILES: NC(=O)c1c(-c2ccc(Oc3ccccc3)cc2)nn2c1NCCC2C1CCN(CC2CCN(C(=O)N3CCN(c4ccc5c(c4)C(=O)N(C4CCC(=O)NC4=O)C5=O)CC3)CC2)CC1] | 7-(1-((1-(4-(2-(2,6-dioxopiperidin-3-yl)-1,3-dioxoisoindolin-5-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 882.42 | C | C | C | C |
| 358 | 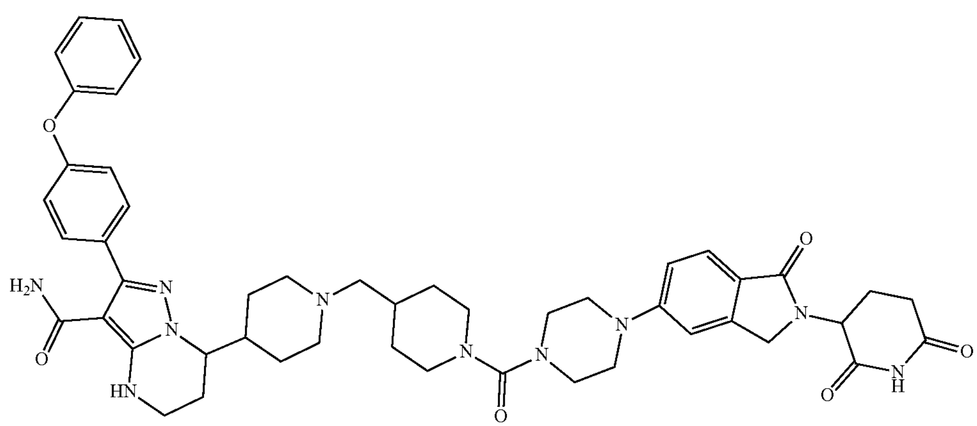 [SMILES: NC(=O)c1c(-c2ccc(Oc3ccccc3)cc2)nn2c1NCCC2C1CCN(CC2CCN(C(=O)N3CCN(c4ccc5c(c4)CN(C4CCC(=O)NC4=O)C5=O)CC3)CC2)CC1] | 7-(1-((1-(4-(2-(2,6-dioxopiperidin-3-yl)-1-oxoisoindolin-5-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 868.44 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 359 | 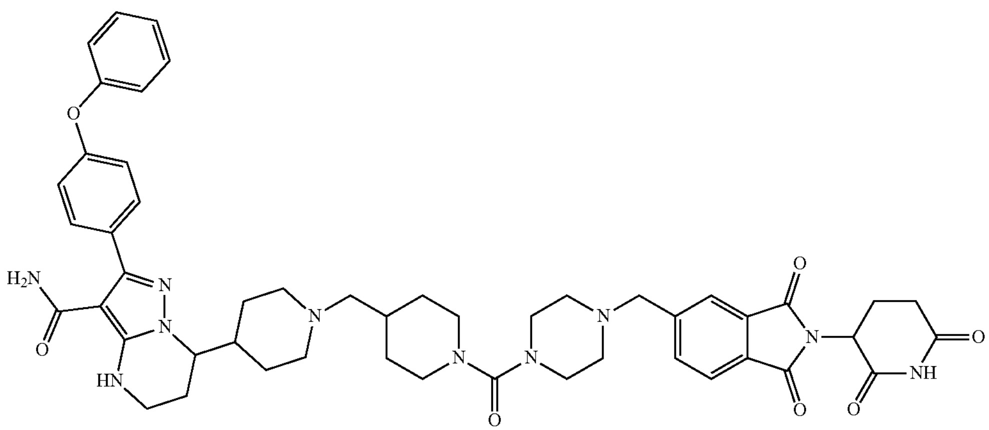 [SMILES: NC(=O)c1c(-c2ccc(Oc3ccccc3)cc2)nn2c1NCCC2C1CCN(CC2CCN(C(=O)N3CCN(Cc4ccc5c(c4)C(=O)N(C4CCC(=O)NC4=O)C5=O)CC3)CC2)CC1] | 7-(1-((4-((2-(2,6-dioxopiperidin-3-yl)-1,3-dioxoisoindolin-5-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 896.43 | C | C | C | C |
| 360 | 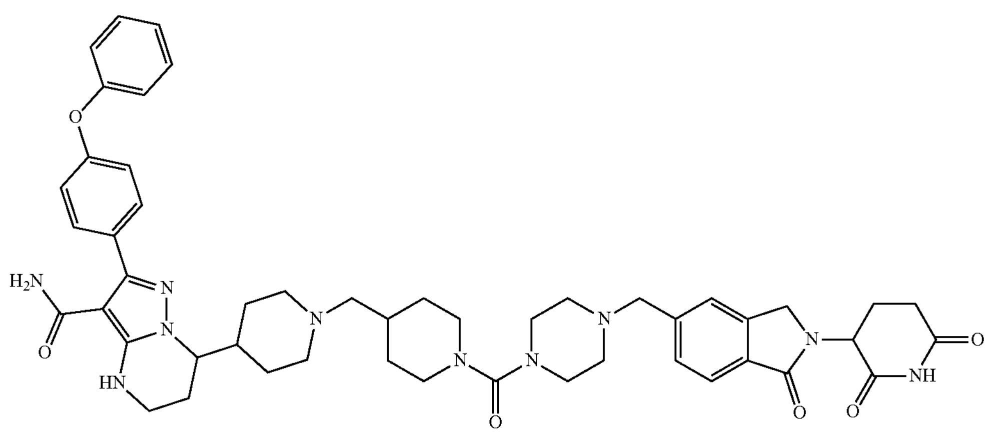 [SMILES: NC(=O)c1c(-c2ccc(Oc3ccccc3)cc2)nn2c1NCCC2C1CCN(CC2CCN(C(=O)N3CCN(Cc4ccc5c(c4)CN(C4CCC(=O)NC4=O)C5=O)CC3)CC2)CC1] | 7-(1-((4-((2-(2,6-dioxopiperidin-3-yl)-1-oxoisoindolin-5-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 882.45 | C | C | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 361 | 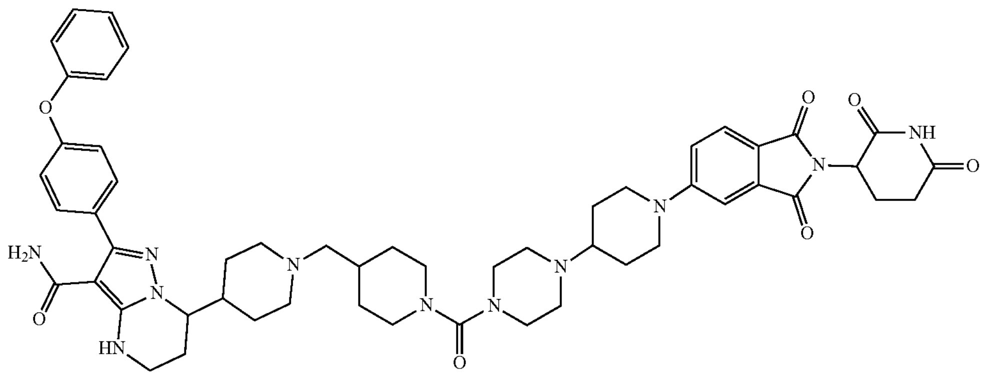 [SMILES: NC(=O)c1c(-c2ccc(Oc3ccccc3)cc2)nn2c1NCCC2C1CCN(CC2CCN(C(=O)N3CCN(C4CCN(c5ccc6c(c5)C(=O)N(C5CCC(=O)NC5=O)C6=O)CC4)CC3)CC2)CC1] | 7-(1-((1-(4-(1-(2-(2,6-dioxopiperidin-3-yl)-1,3-dioxoisoindolin-5-yl)piperidin-4-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.49 | B | B | B | A |
| 362 | 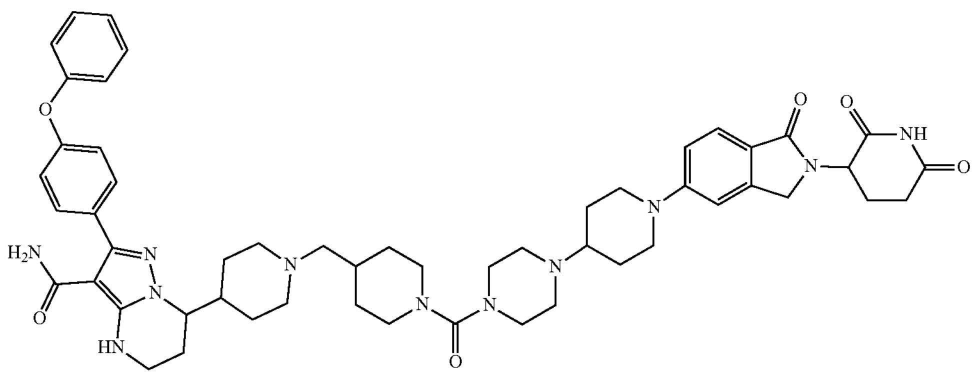 [SMILES: NC(=O)c1c(-c2ccc(Oc3ccccc3)cc2)nn2c1NCCC2C1CCN(CC2CCN(C(=O)N3CCN(C4CCN(c5ccc6c(c5)CN(C5CCC(=O)NC5=O)C6=O)CC4)CC3)CC2)CC1] | 7-(1-((1-(4-(1-(2-(2,6-dioxopiperidin-3-yl)-1-oxoisoindolin-5-yl)piperidin-4-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 951.51 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 363 | 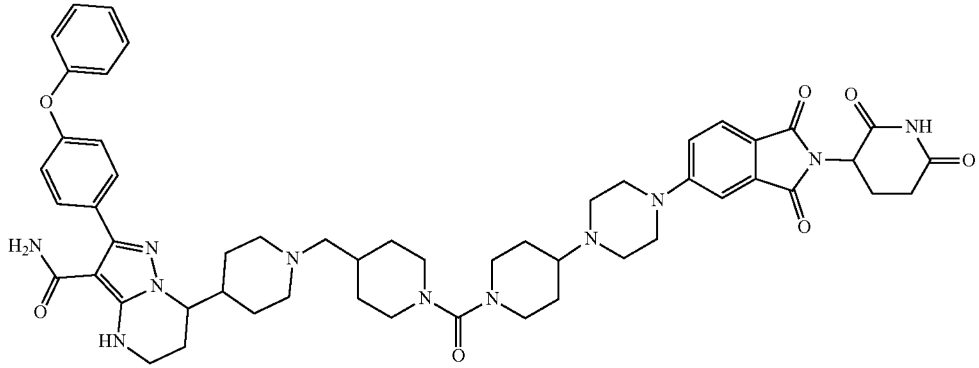 | 7-(1-((4-(4-(2-(2,6-dioxopiperidin-3-yl)-1,3-dioxoisoindolin-5-yl)piperazin-1-yl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.49 | B | A | B | A |
| 364 | 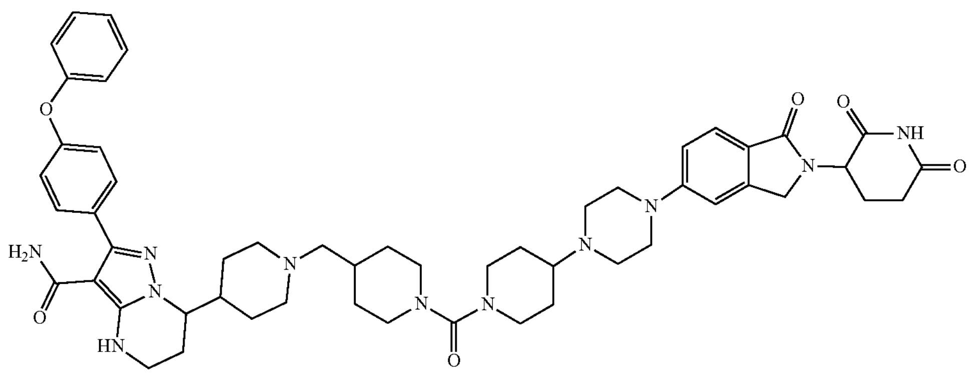 | 7-(1-((4-(4-(2-(2,6-dioxopiperidin-3-yl)-1-oxoisoindolin-5-yl)piperazin-1-yl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 951.51 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 365 | 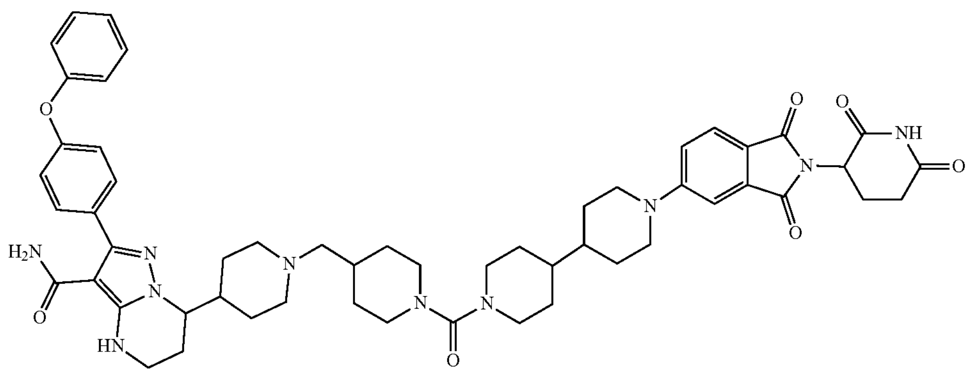 | 7-(1-((1-(1'-(2-(2,6-dioxopiperidin-3-yl)-1,3-dioxoisoindolin-5-yl)-[4,4'-bipiperidine]-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.50 | A | A | B | A |
| 366 | 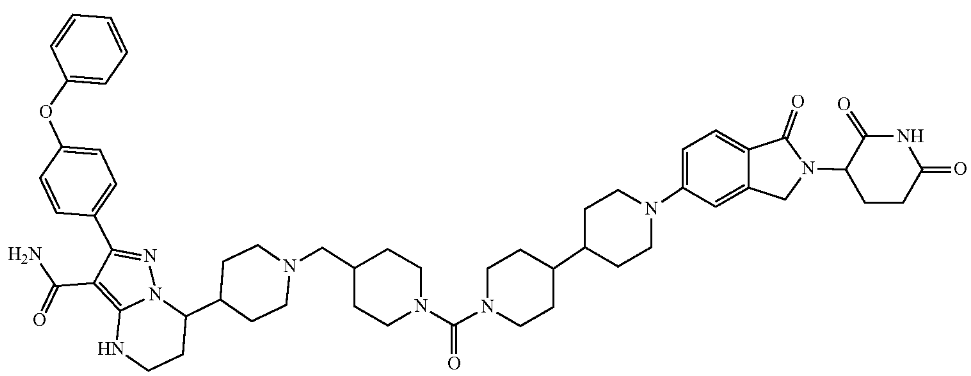 | 7-(1-((1-(1'-(2-(2,6-dioxopiperidin-3-yl)-1-oxoisoindolin-5-yl)-[4,4'-bipiperidine]-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 950.52 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 367 | 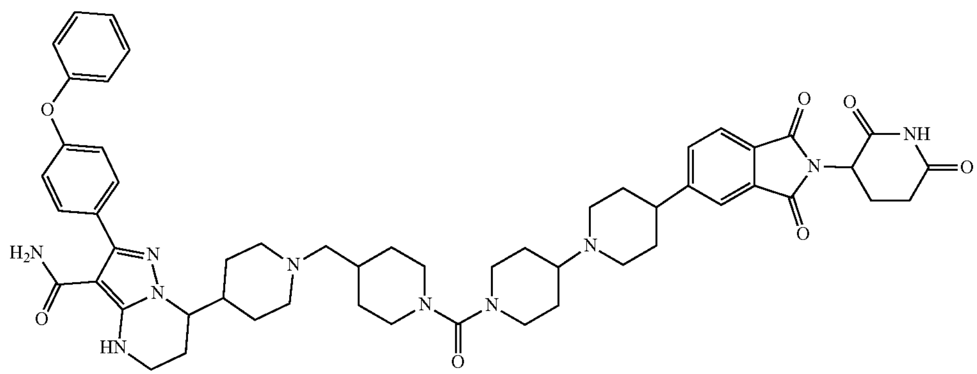 [SMILES: NC(=O)c1c(-c2ccc(Oc3ccccc3)cc2)nn2c1NCCC2C1CCN(CC2CCN(C(=O)N3CCC(N4CCN(c5ccc6c(c5)C(=O)N(C5CCC(=O)NC5=O)C6=O)CC4)CC3)CC2)CC1] | 7-(1-((1-(4-(2-(2,6-dioxopiperidin-3-yl)-1,3-dioxoisoindolin-5-yl)-[1,4-bipiperidine]-1'-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.50 | B | A | B | A |
| 368 | 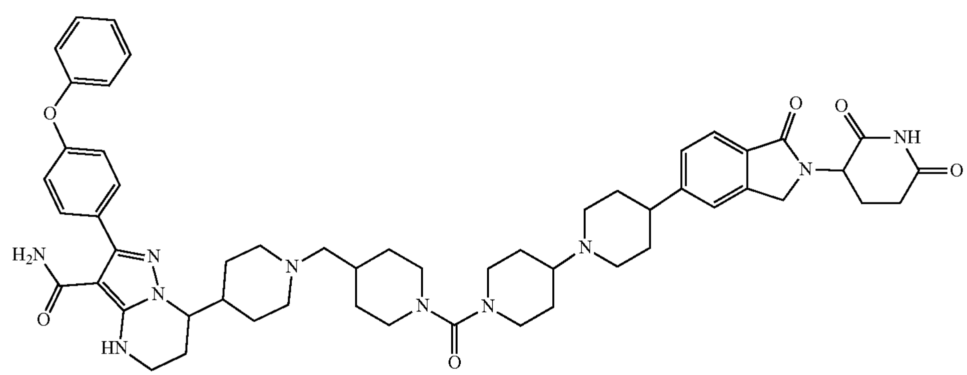 [SMILES: NC(=O)c1c(-c2ccc(Oc3ccccc3)cc2)nn2c1NCCC2C1CCN(CC2CCN(C(=O)N3CCC(C4CCN(c5ccc6c(c5)CN(C5CCC(=O)NC5=O)C6=O)CC4)CC3)CC2)CC1] | 7-(1-((1-(4-(2-(2,6-dioxopiperidin-3-yl)-1-oxoisoindolin-5-yl)-[1,4-bipiperidine]-1'-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 950.52 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 369 | 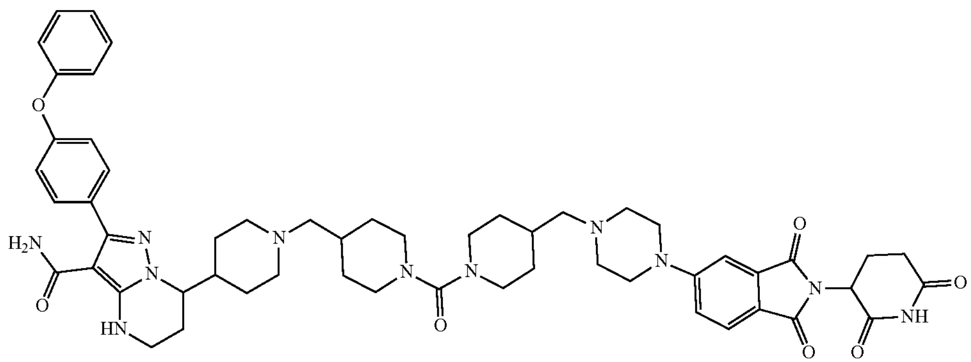 [SMILES: NC(=O)c1c(-c2ccc(Oc3ccccc3)cc2)nn2c1NCCC2C1CCN(CC2CCN(C(=O)N3CCC(CN4CCN(c5ccc6c(c5)C(=O)N(C5CCC(=O)NC5=O)C6=O)CC4)CC3)CC2)CC1] | 7-(1-(4-((4-(2-(2,6-dioxopiperidin-3-yl)-1,3-dioxoisoindolin-5-yl)piperazin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 979.51 | B | A | A | A |
| 370 | 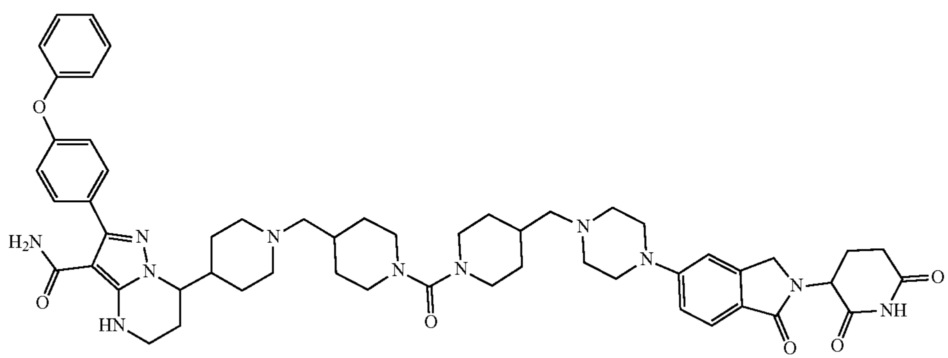 [SMILES: NC(=O)c1c(-c2ccc(Oc3ccccc3)cc2)nn2c1NCCC2C1CCN(CC2CCN(C(=O)N3CCC(CN4CCN(c5ccc6c(c5)CN(C5CCC(=O)NC5=O)C6=O)CC4)CC3)CC2)CC1] | 7-(1-(4-((4-(2-(2,6-dioxopiperidin-3-yl)-1-oxoisoindolin-5-yl)piperazin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.53 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 371 | 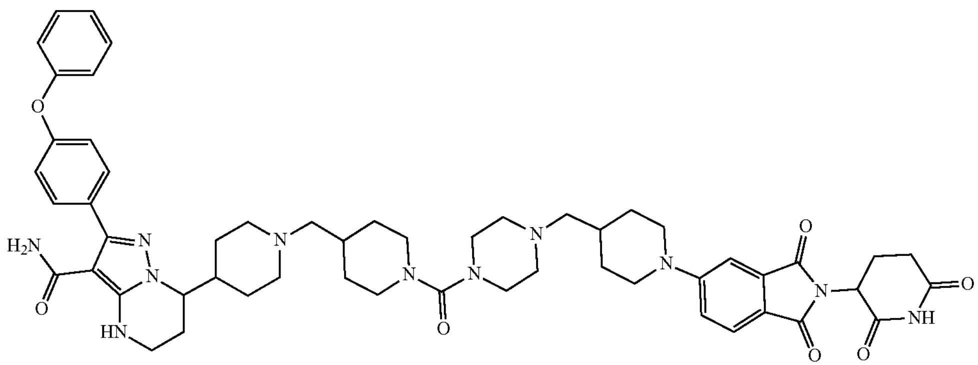 [SMILES: NC(=O)c1c(-c2ccc(Oc3ccccc3)cc2)nn2c1NCCC2C1CCN(CC2CCN(C(=O)N3CCN(CC4CCN(c5ccc6c(c5)C(=O)N(C5CCC(=O)NC5=O)C6=O)CC4)CC3)CC2)CC1] | 7-(1-(4-((1-(4-(2-(2,6-dioxopiperidin-3-yl)-1,3-dioxoisoindolin-5-yl)piperidin-4-yl)methyl)piperazine-1-carbonyl)piperidin-4-yl)methyl)piperidin-4-yl)-2-(4-phenoxyethyl)-4,5,6,7-tetrahydropyrazolo[1,5-a]pyrimidine-3-carboxamide | 979.51 | A | A | B | A |
| 372 | 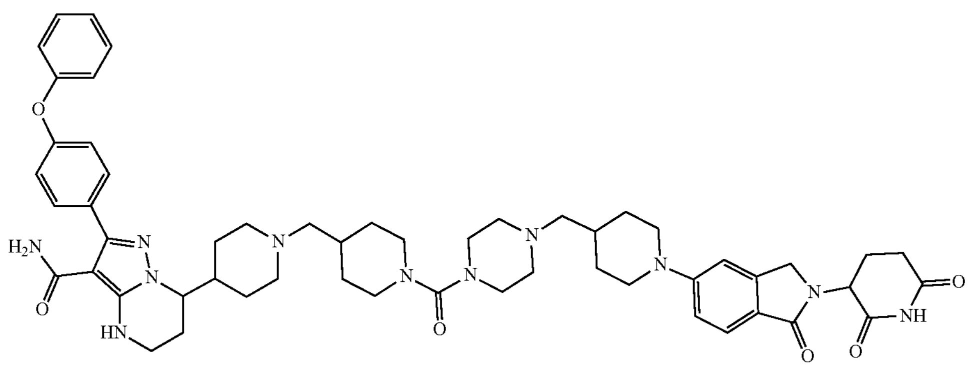 [SMILES: NC(=O)c1c(-c2ccc(Oc3ccccc3)cc2)nn2c1NCCC2C1CCN(CC2CCN(C(=O)N3CCN(CC4CCN(c5ccc6c(c5)CN(C5CCC(=O)NC5=O)C6=O)CC4)CC3)CC2)CC1] | 7-(1-(4-((1-(4-(2-(2,6-dioxopiperidin-3-yl)-1-oxoisoindolin-5-yl)piperidin-4-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.33 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 373 | 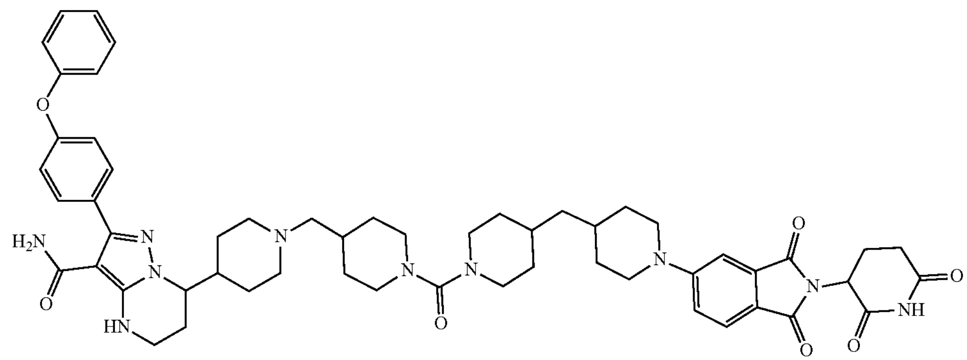 [SMILES: NC(=O)c1c(-c2ccc(Oc3ccccc3)cc2)nn2c1NCCC2C1CCN(CC2CCN(C(=O)N3CCC(CC4CCN(c5ccc6c(c5)C(=O)N(C5CCC(=O)NC5=O)C6=O)CC4)CC3)CC2)CC1] | 7-(1-((4-((1-(2-(2,6-dioxopiperidin-3-yl)-1,3-dioxoisoindolin-5-yl)piperidin-4-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 978.51 | C | B | B | B |
| 374 | 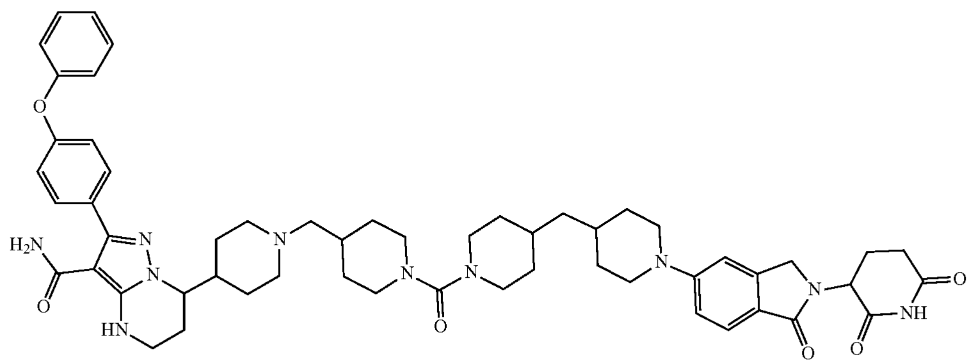 [SMILES: NC(=O)c1c(-c2ccc(Oc3ccccc3)cc2)nn2c1NCCC2C1CCN(CC2CCN(C(=O)N3CCC(CC4CCN(c5ccc6c(c5)CN(C5CCC(=O)NC5=O)C6=O)CC4)CC3)CC2)CC1] | 7-(1-((1-(4-((1-(2-(2,6-dioxopiperidin-3-yl)-1-oxoisoindolin-5-yl)piperidin-4-yl)methyl)piperidin-4-yl)methyl)piperidine-1-carbonyl)piperidin-4-yl)-2-(4-phenoxyphenyl)-4,5,6,7-tetrahydropyrazolo[1,5-a]pyrimidine-3-carboxamide | 964.53 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 375 | 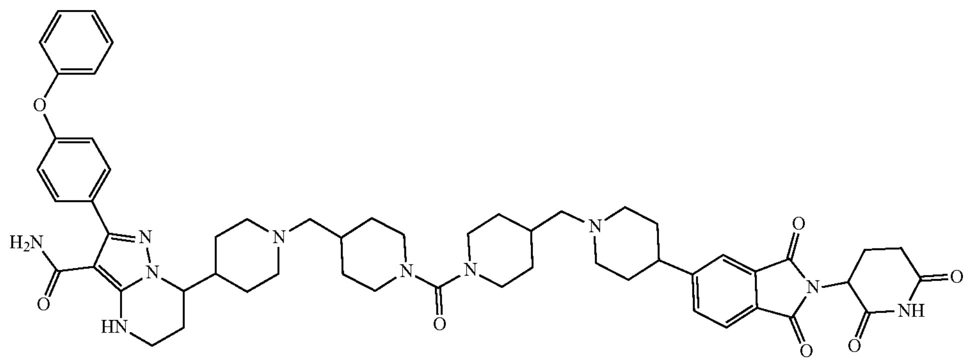 [SMILES: NC(=O)c1c(-c2ccc(Oc3ccccc3)cc2)nn2c1NCCC2C1CCN(CC2CCN(C(=O)N3CCC(CN4CCC(c5ccc6c(c5)C(=O)N(C5CCC(=O)NC5=O)C6=O)CC4)CC3)CC2)CC1] | 7-(1-(4-((4-(2-(2,6-dioxopiperidin-3-yl)-1,3-dioxoisoindolin-5-yl)piperidin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 977.51 | B | B | B | B |
| 376 | 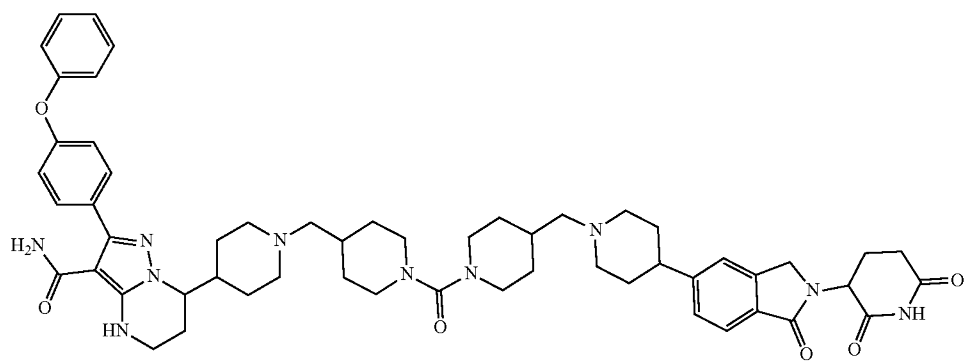 | 7-(1-((1-(4-((4-(2-(2,6-dioxopiperidin-3-yl)-1-oxoisoindolin-5-yl)piperidin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.53 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 377 | 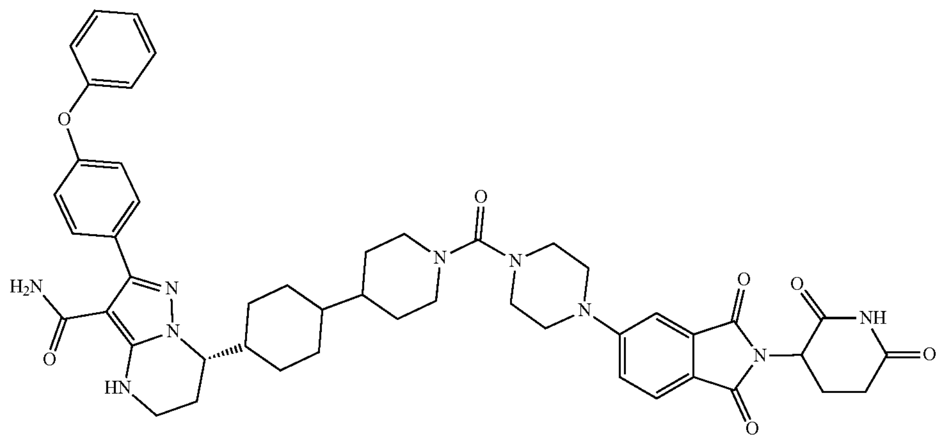 [SMILES: NC(=O)c1c(-c2ccc(Oc3ccccc3)cc2)nn2c1NCC[C@H]2C1CCC(C2CCN(C(=O)N3CCN(c4ccc5c(c4)C(=O)N(C4CCC(=O)NC4=O)C5=O)CC3)CC2)CC1] | (7S)-7-(1'-(4-(2-(2,6-dioxopiperidin-3-yl)-1,3-dioxoisoindolin-5-yl)piperazine-1-carbonyl)-[1,4'-bipiperdin]-4-yl)-2-(4-phenoxyphenyl)-4,5,6,7-tetrahydropyrazolo[1,5-a]pyrimidine-3-carboxamide | 867.41 | C | C | C | C |
| 378 | 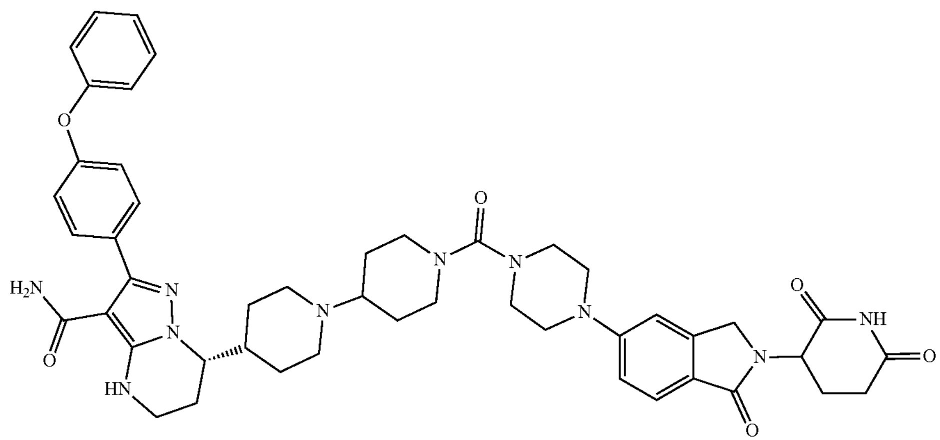 [SMILES: NC(=O)c1c(-c2ccc(Oc3ccccc3)cc2)nn2c1NCC[C@H]2C1CCN(C2CCN(C(=O)N3CCN(c4ccc5c(c4)CN(C4CCC(=O)NC4=O)C5=O)CC3)CC2)CC1] | (7S)-7-(1'-(4-(2-(2,6-dioxopiperidin-3-yl)-1-oxoisoindolin-5-yl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 854.42 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 379 | 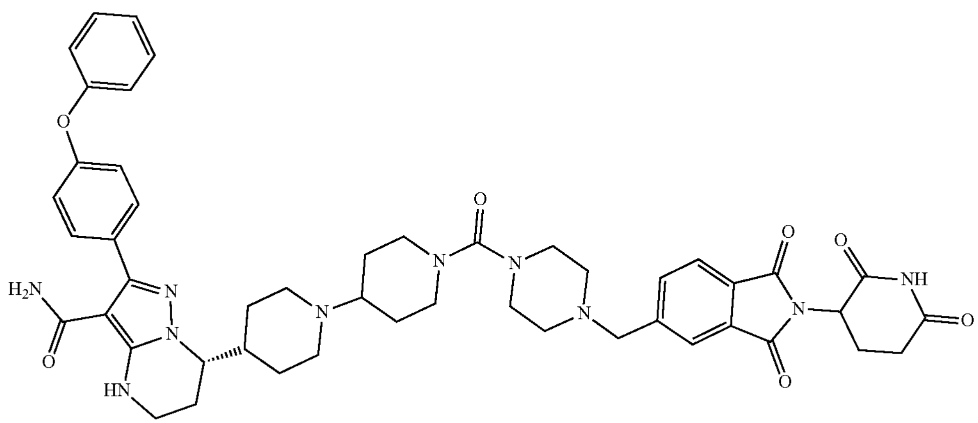 [SMILES: NC(=O)c1c(-c2ccc(Oc3ccccc3)cc2)nn2c1NCC[C@H]2C1CCN(C2CCN(C(=O)N3CCN(Cc4ccc5c(c4)C(=O)N(C4CCC(=O)NC4=O)C5=O)CC3)CC2)CC1] | (7S)-7-(1'-(4-((2-(2,6-dioxopiperidin-3-yl)-1,3-dioxoisoindolin-5-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 882.42 | C | C | C | B |
| 380 | 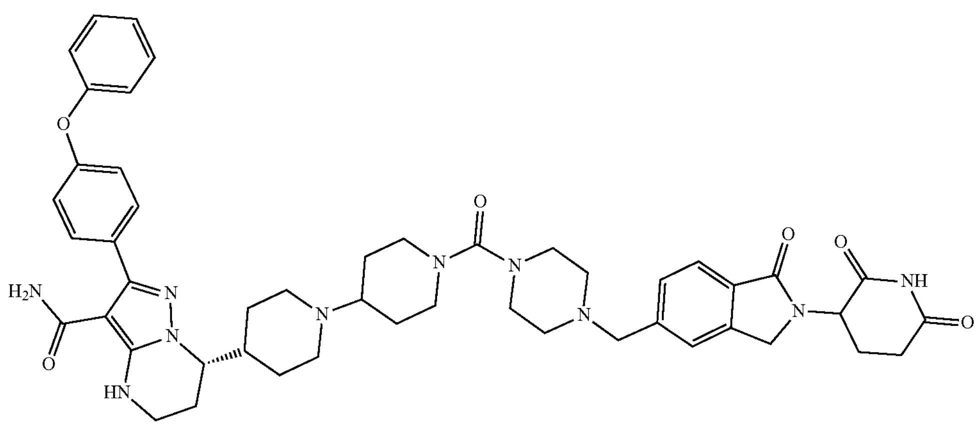 [SMILES: NC(=O)c1c(-c2ccc(Oc3ccccc3)cc2)nn2c1NCC[C@H]2C1CCN(C2CCN(C(=O)N3CCN(Cc4ccc5c(c4)CN(C4CCC(=O)NC4=O)C5=O)CC3)CC2)CC1] | (7S)-7-(1'-(4-((2-(2,6-dioxopiperidin-3-yl)-1-oxoisoindolin-5-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 868.44 | C | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 381 | 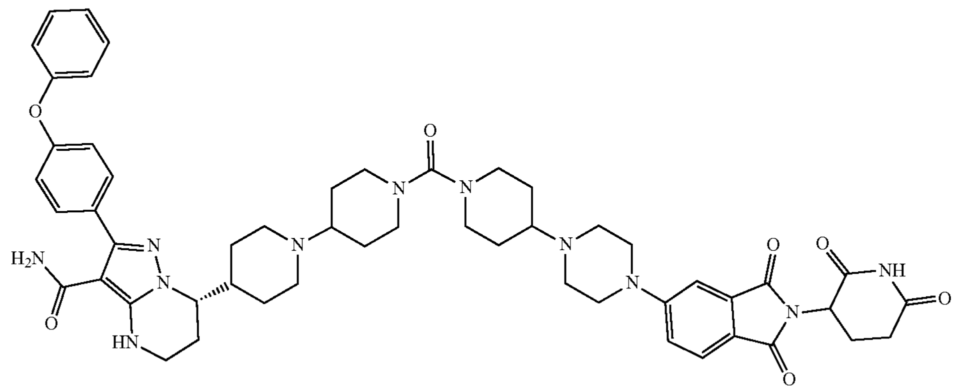 [SMILES: NC(=O)c1c(-c2ccc(Oc3ccccc3)cc2)nn2c1NCC[C@H]2C1CCN(C2CCN(C(=O)N3CCC(C4CCN(c5ccc6c(c5)C(=O)N(C5CCC(=O)NC5=O)C6=O)CC4)CC3)CC2)CC1] | (7S)-7-(1'-(4-(4-(2-(2,6-dioxopiperidin-3-yl)-1,3-dioxoisoindolin-5-yl)piperazin-1-yl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 951.48 | A | A | A | A |
| 382 | 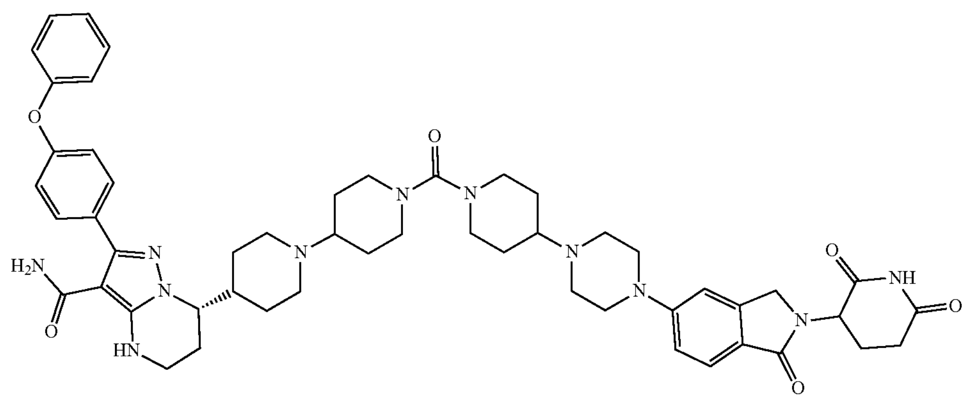 | (7S)-7-(1'-(4-(4-(2-(2,6-dioxopiperidin-3-yl)-1-oxoisoindolin-5-yl)piperazin-1-yl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 937.50 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 383 | 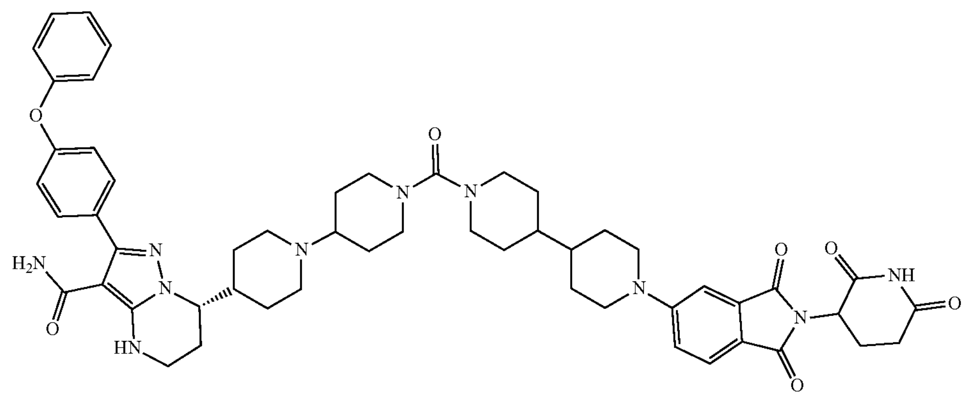 | (7S)-7-(1'-(1'-(2-(2,6-dioxopiperidin-3-yl)-1,3-dioxoisoindolin-5-yl)-[4,4'-bipiperidine]-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.48 | A | A | B | A |
| 384 | 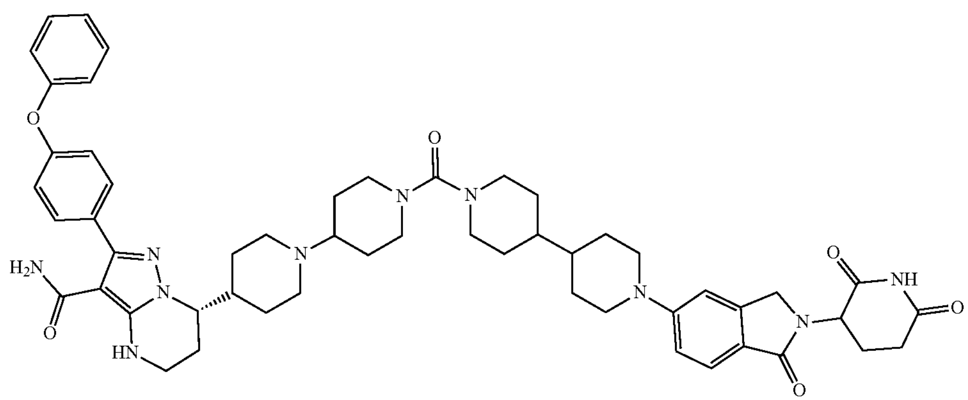 | (7S)-7-(1'-(1'-(2-(2,6-dioxopiperidin-3-yl)-1-oxoisoindolin-5-yl)-[4,4'-bipiperidine]-1-carbonyl)-[1,4'-bipiperidin]-4-yl)-2-(4-phenoxyphenyl)-4,5,6,7-tetrahydropyrazolo[1,5-a]pyrimidine-3-carboxamide | 936.50 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 385 | 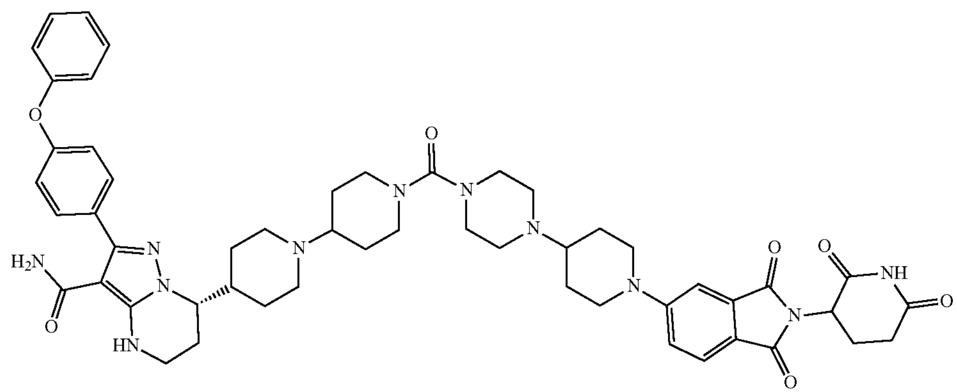 | (7S)-7-(1'-(4-(1-(2-(2,6-dioxopiperidin-3-yl)-1,3-dioxoisoindolin-5-yl)piperidin-4-yl)piperazine-1-carbonyl)-[1,4-bipiperidin]-4-yl)-2-(4-phenoxyphenyl)-4,5,6,7-tetrahydropyrazolo[1,5-a]pyrimidine-3-carboxamide | 951.48 | B | A | A | A |
| 386 | 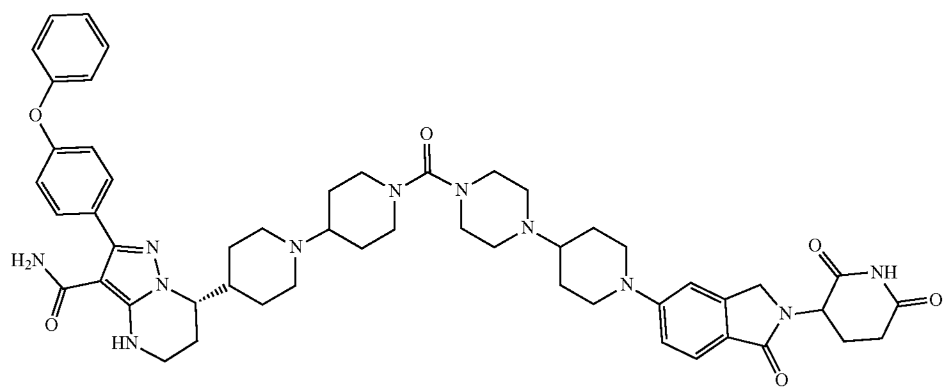 [SMILES: NC(=O)c1c(-c2ccc(Oc3ccccc3)cc2)nn2c1NCC[C@H]2C1CCN(C2CCN(C(=O)N3CCC(C4CCN(c5ccc6c(c5)CN(C5CCC(=O)NC5=O)C6=O)CC4)CC3)CC2)CC1] | (7S)-7-(1'-(4-(1-(2-(2,6-dioxopiperidin-3-yl)-1-oxoisoindolin-5-yl)piperidin-4-yl)piperazine-1-carbonyl)-[1,4-bipiperidin]-4-yl)-2-(4-phenoxyphenyl)-4,5,6,7-tetrahydropyrazolo[1,5-a]pyrimidine-3-carboxamide | 937.50 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 387 | 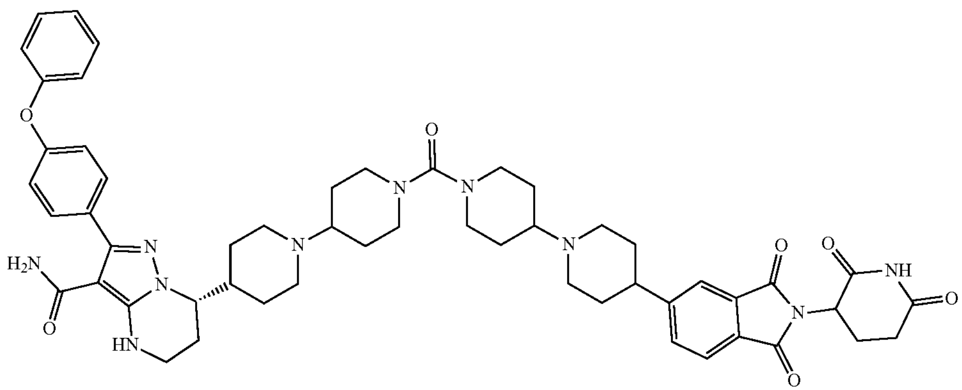 [SMILES: NC(=O)c1c(-c2ccc(Oc3ccccc3)cc2)nn2c1NCC[C@H]2C1CCN(C2CCN(C(=O)N3CCC(N4CCC(c5ccc6c(c5)C(=O)N(C5CCC(=O)NC5=O)C6=O)CC4)CC3)CC2)CC1] | (7S)-7-(1'-(4-(2-(2,6-dioxopiperidin-3-yl)-1,3-dioxoisoindolin-5-yl)-[1,4'-bipiperidine]-1'-carbonyl)-[1,4'-bipiperidin]-4-yl)-2-(4-phenoxyphenyl)-4,5,6,7-tetrahydropyrazolo[1,5-a]pyrimidine-3-carboxamide | 950.48 | B | B | B | A |
| 388 | 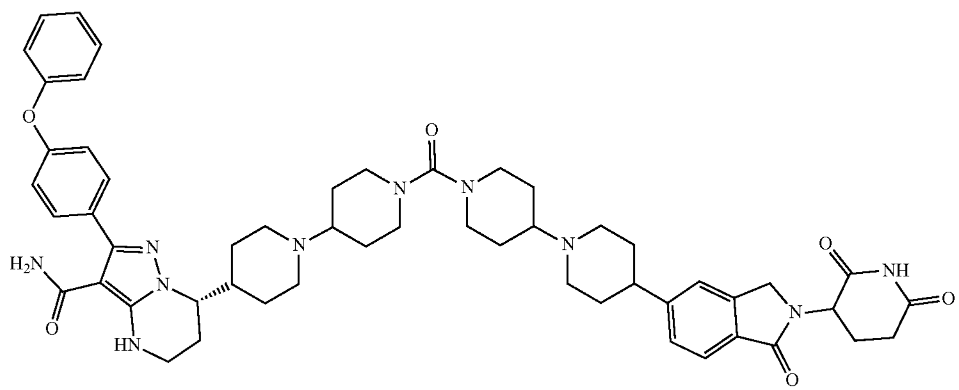 [SMILES: NC(=O)c1c(-c2ccc(Oc3ccccc3)cc2)nn2c1NCC[C@H]2C1CCN(C2CCN(C(=O)N3CCC(N4CCC(c5ccc6c(c5)CN(C5CCC(=O)NC5=O)C6=O)CC4)CC3)CC2)CC1] | (7S)-7-(1'-(4-(2-(2,6-dioxopiperidin-3-yl)-1-oxoisoindolin-5-yl)-[1,4'-bipiperidine]-1'-carbonyl)-[1,4'-bipiperidin]-4-yl)-2-(4-phenoxyphenyl)-4,5,6,7-tetrahydropyrazolo[1,5-a]pyrimidine-3-carboxamide | 936.50 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 389 | 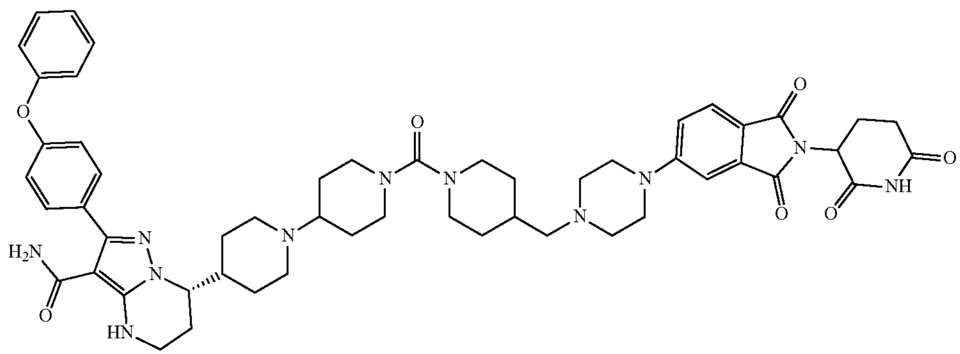 [SMILES: NC(=O)c1c(-c2ccc(Oc3ccccc3)cc2)nn2c1NCC[C@H]2C1CCN(C2CCN(C(=O)N3CCC(CN4CCN(c5ccc6c(c5)C(=O)N(C5CCC(=O)NC5=O)C6=O)CC4)CC3)CC2)CC1] | (7S)-7-(1'-(4-((4-(2-(2,6-dioxopiperidin-3-yl)-1,3-dioxoisoindolin-5-yl)piperazin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 965.49 | B | B | B | A |
| 390 | 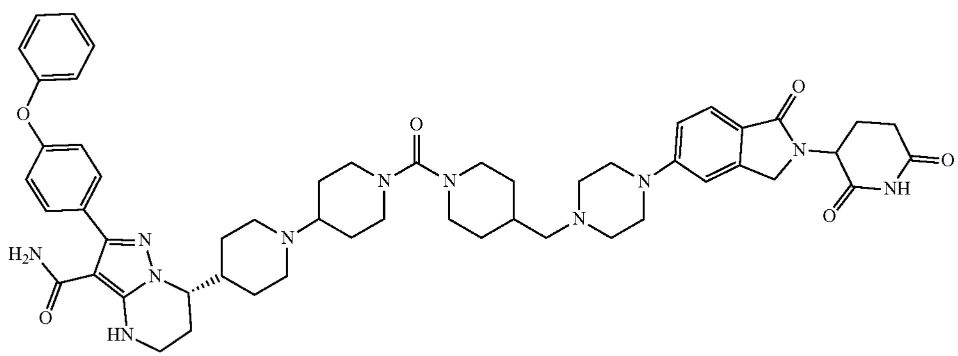 | (7S)-7-(1'-(4-((4-(2-(2,6-dioxopiperidin-3-yl)-1-oxoisoindolin-5-yl)piperazin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 951.51 | C | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 391 | 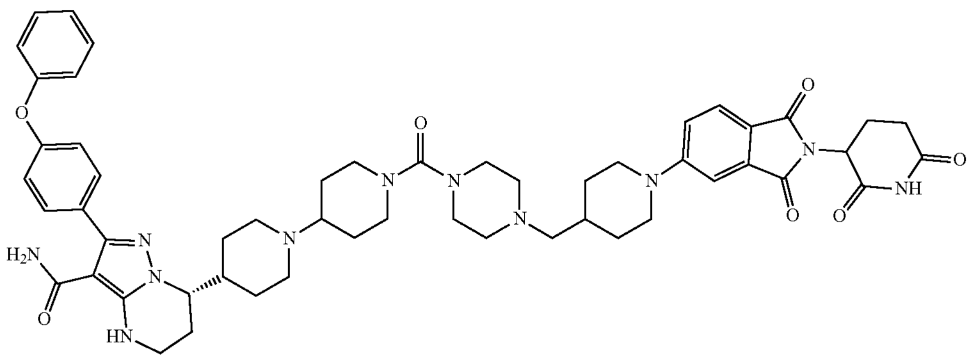 [SMILES: NC(=O)c1c(-c2ccc(Oc3ccccc3)cc2)nn2c1NCC[C@H]2C1CCN(C2CCN(C(=O)N3CCN(CC4CCN(c5ccc6c(c5)C(=O)N(C5CCC(=O)NC5=O)C6=O)CC4)CC3)CC2)CC1] | (7S)-7-(1'-(4-((1-(2-(2,6-dioxopiperidin-3-yl)-1,3-dioxoisoindolin-5-yl)piperidin-4-yl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 965.49 | C | C | B | B |
| 392 | 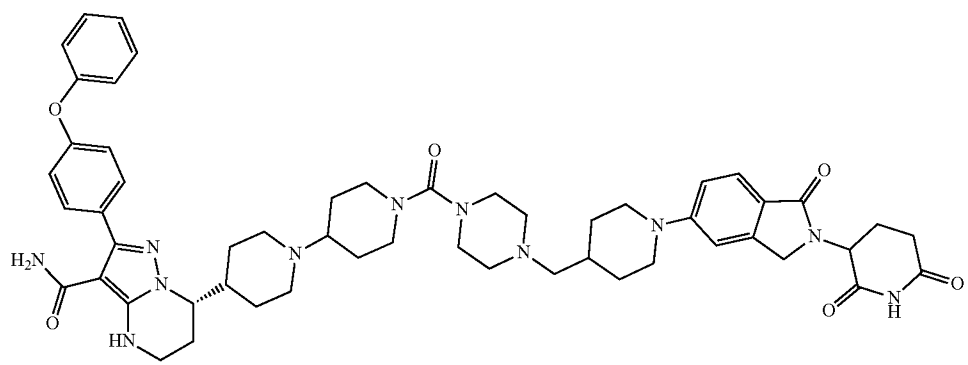 [SMILES: NC(=O)c1c(-c2ccc(Oc3ccccc3)cc2)nn2c1NCC[C@H]2C1CCN(C2CCN(C(=O)N3CCN(CC4CCN(c5ccc6c(c5)CN(C5CCC(=O)NC5=O)C6=O)CC4)CC3)CC2)CC1] | (7S)-7-(1'-(4-((1-(2-(2,6-dioxopiperidin-3-yl)-1-oxoisoindolin-5-yl)piperazine-1-carbonyl)methyl)piperazine-1-carbonyl)-[1,4'-bipiperidin]-4-yl)-2-(4-phenoxyphenyl)-4,5,6,7-tetrahydropyrazolo[1,5-a]pyrimidine-3-carboxamide | 951.51 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 393 | 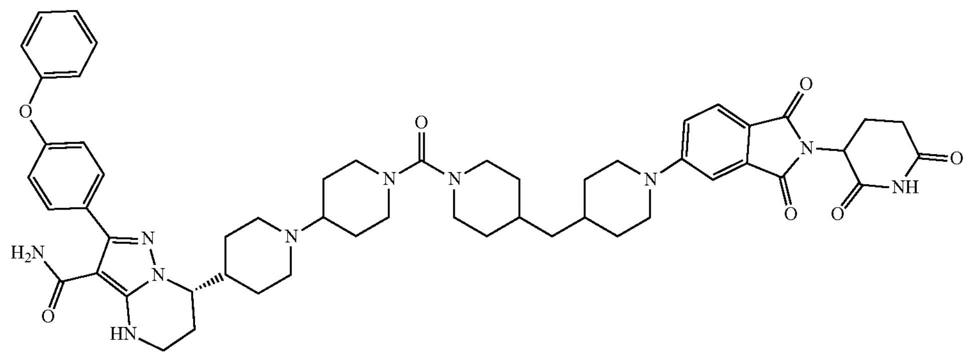 [SMILES: NC(=O)c1c(-c2ccc(Oc3ccccc3)cc2)nn2c1NCC[C@H]2C1CCN(C2CCN(C(=O)N3CCC(CC4CCN(c5ccc6c(c5)C(=O)N(C5CCC(=O)NC5=O)C6=O)CC4)CC3)CC2)CC1] | (7S)-7-(1'-(4-((1-(2-(2,6-dioxopiperidin-3-yl)-1,3-dioxoisoindolin-5-yl)piperidin-4-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 964.50 | B | B | B | B |
| 394 | 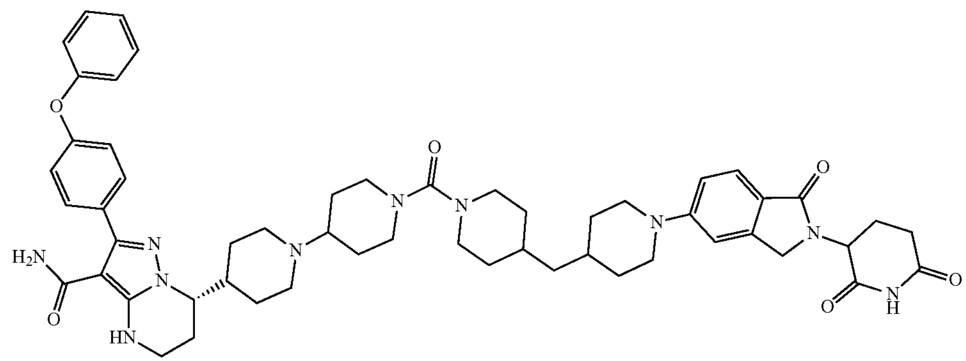 | (7S)-7-(1'-(4-((1-(2-(2,6-dioxopiperidin-3-yl)-1-oxoisoindolin-5-yl)methyl)piperidin-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.52 | B | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 395 | 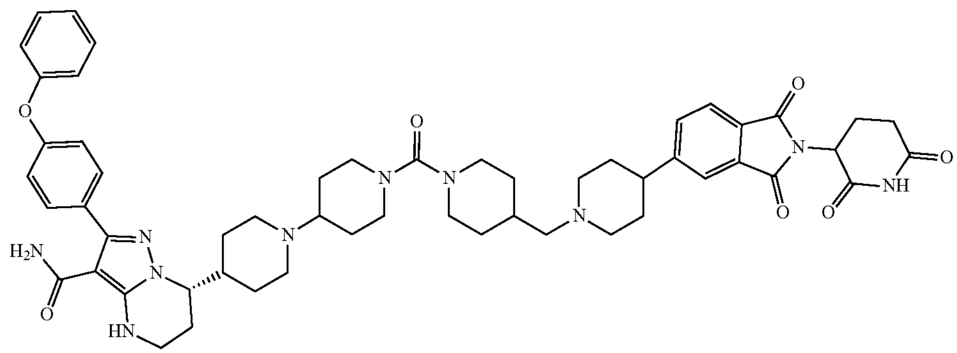 | (7S)-7-(1'-(4-(4-(2-(2,6-dioxopiperidin-3-yl)-1,3-dioxoisoindolin-5-yl)piperidin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 964.50 | B | B | B | B |
| 396 | 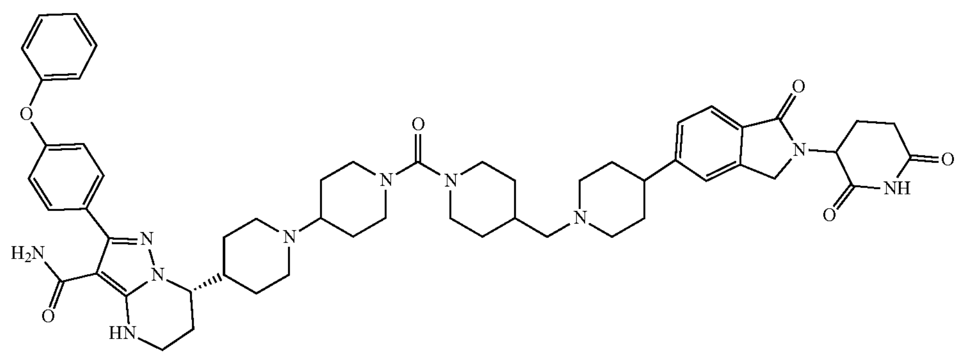 [SMILES: NC(=O)c1c(-c2ccc(Oc3ccccc3)cc2)nn2c1NCC[C@H]2C1CCN(C2CCN(C(=O)N3CCC(CN4CCC(c5ccc6c(c5)CN(C5CCC(=O)NC5=O)C6=O)CC4)CC3)CC2)CC1] | (7S)-7-(1'-(4-(4-(2-(2,6-dioxopiperidin-3-yl)-1-oxoisoindolin-5-yl)piperidin-1-yl)methyl)piperidine-1-carbonyl)-[1,4'-bipiperidin]-4-yl)-2-(4-phenoxyphenyl)-4,5,6,7-tetrahydropyrazolo[1,5-a]pyrimidine-3-carboxamide | 950.52 | C | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 397 | 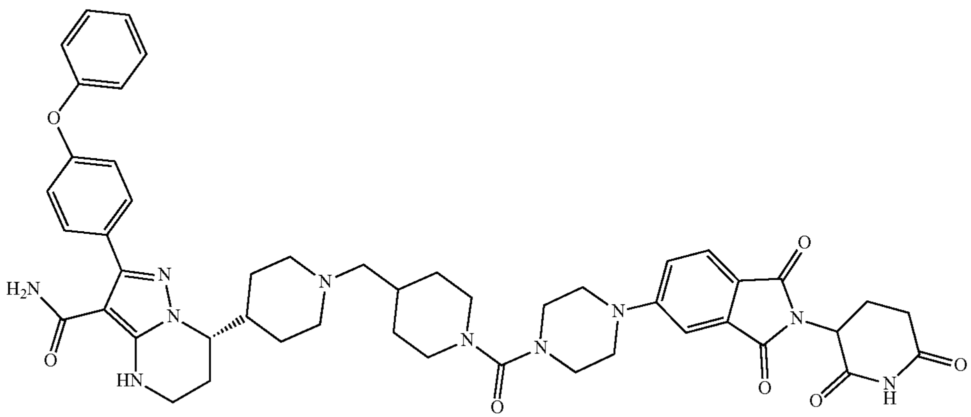 [SMILES: NC(=O)c1c(-c2ccc(Oc3ccccc3)cc2)nn2c1NCC[C@H]2C1CCN(CC2CCN(C(=O)N3CCN(c4ccc5c(c4)C(=O)N(C4CCC(=O)NC4=O)C5=O)CC3)CC2)CC1] | (7S)-7-(1-((1-(4-(2-(2,6-dioxopiperidin-3-yl)-1,3-dioxoisoindolin-5-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 881.42 | B | C | C | B |
| 398 | 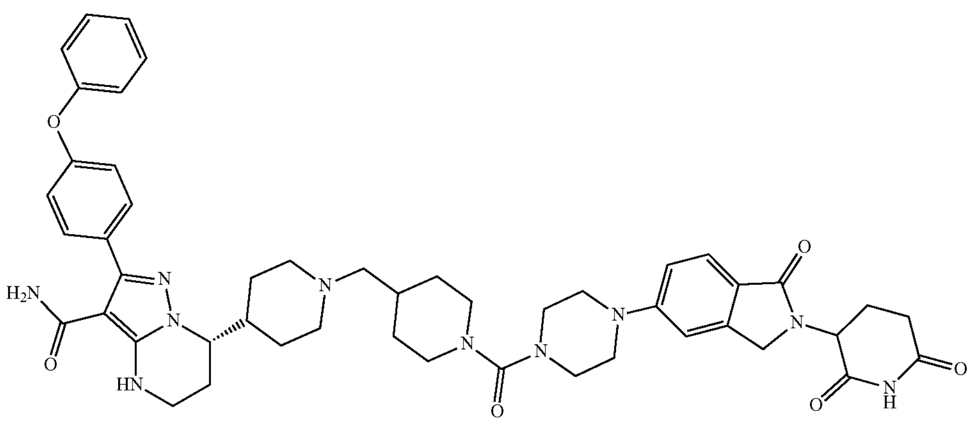 [SMILES: NC(=O)c1c(-c2ccc(Oc3ccccc3)cc2)nn2c1NCC[C@H]2C1CCN(CC2CCN(C(=O)N3CCN(c4ccc5c(c4)CN(C4CCC(=O)NC4=O)C5=O)CC3)CC2)CC1] | (7S)-7-((1-(4-(2-(2,6-dioxopiperidin-3-yl)-1-oxoisoindolin-5-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 868.44 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 399 | 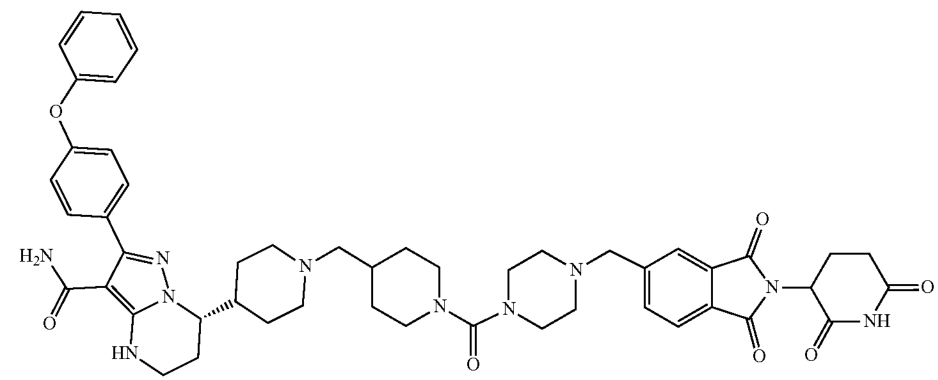 [SMILES: NC(=O)c1c(-c2ccc(Oc3ccccc3)cc2)nn2c1NCC[C@H]2C1CCN(CC2CCN(C(=O)N3CCN(Cc4ccc5c(c4)C(=O)N(C4CCC(=O)NC4=O)C5=O)CC3)CC2)CC1] | (7S)-7-(1-((4-((2-(2,6-dioxopiperidin-3-yl)-1,3-dioxoisoindolin-5-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 896.43 | C | B | C | C |
| 400 | 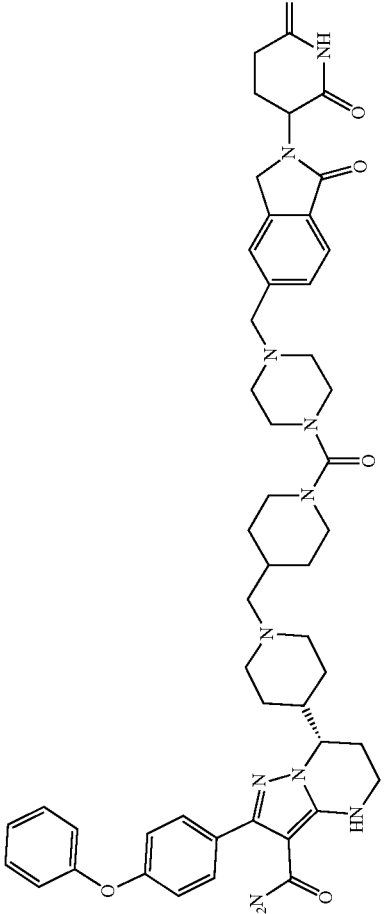 | (7S)-7-(1-((4-((2-(2,6-dioxopiperidin-3-yl)-1-oxoisoindolin-5-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 882.45 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 401 | 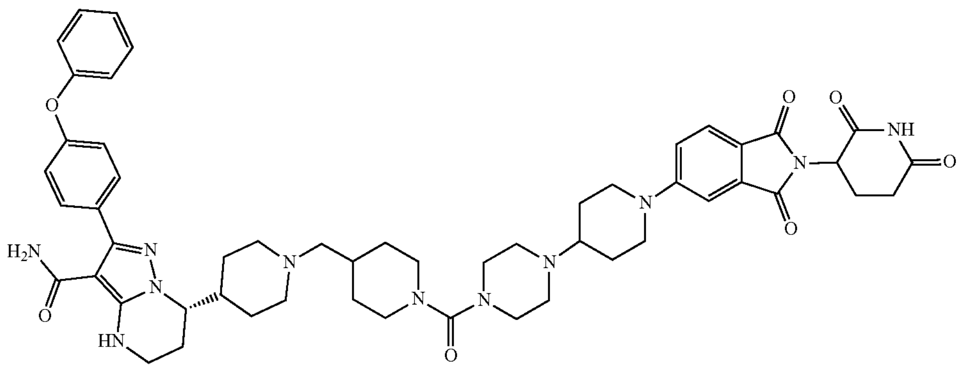 [SMILES: NC(=O)c1c(-c2ccc(Oc3ccccc3)cc2)nn2c1NCC[C@H]2C1CCN(CC2CCN(C(=O)N3CCN(C4CCN(c5ccc6c(c5)C(=O)N(C5CCC(=O)NC5=O)C6=O)CC4)CC3)CC2)CC1] | (7S)-7-(1-((1-(4-(2-(2,6-dioxopiperidin-3-yl)-1,3-dioxoisoindolin-5-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.49 | B | B | B | A |
| 402 | 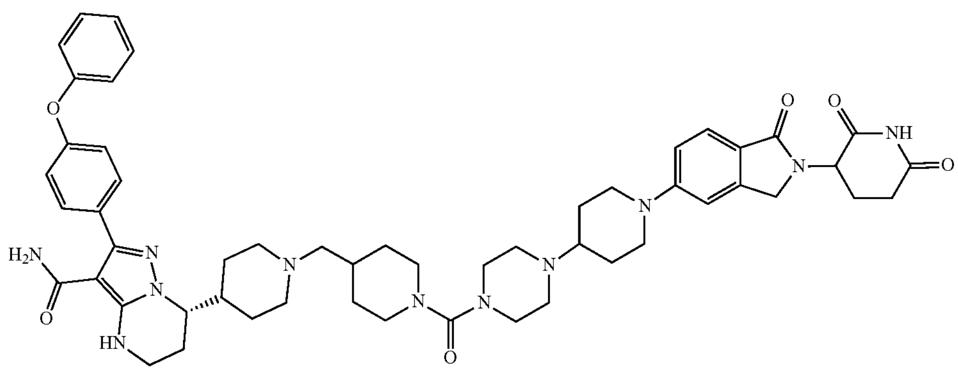 [SMILES: NC(=O)c1c(-c2ccc(Oc3ccccc3)cc2)nn2c1NCC[C@H]2C1CCN(CC2CCN(C(=O)N3CCN(C4CCN(c5ccc6c(c5)CN(C5CCC(=O)NC5=O)C6=O)CC4)CC3)CC2)CC1] | (7S)-7-(1-((1-(4-(1-(2-(2,6-dioxopiperidin-3-yl)-1-oxoisoindolin-5-yl)piperidin-4-yl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 951.51 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 403 | 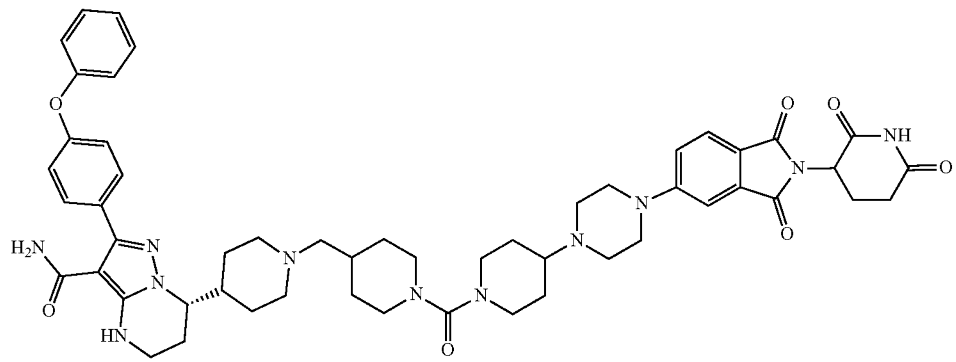 [SMILES: NC(=O)c1c(-c2ccc(Oc3ccccc3)cc2)nn2c1NCC[C@H]2C1CCN(CC2CCN(C(=O)N3CCC(N4CCN(c5ccc6c(c5)C(=O)N(C5CCC(=O)NC5=O)C6=O)CC4)CC3)CC2)CC1] | (7S)-7-(1-((1-(4-(4-(2-(2,6-dioxopiperidin-3-yl)-1,3-dioxoisoindolin-5-yl)piperazin-1-yl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.49 | A | A | B | A |
| 404 | 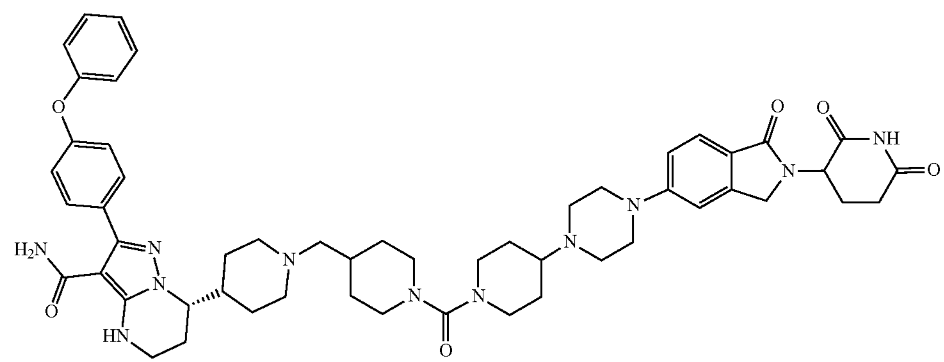 [SMILES: NC(=O)c1c(-c2ccc(Oc3ccccc3)cc2)nn2c1NCC[C@H]2C1CCN(CC2CCN(C(=O)N3CCC(N4CCN(c5ccc6c(c5)CN(C5CCC(=O)NC5=O)C6=O)CC4)CC3)CC2)CC1] | (7S)-7-(1-((1-(4-(4-(2-(2,6-dioxopiperidin-3-yl)-1-oxoisoindolin-5-yl)piperazin-1-yl)piperidine-4-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 951.51 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 405 | 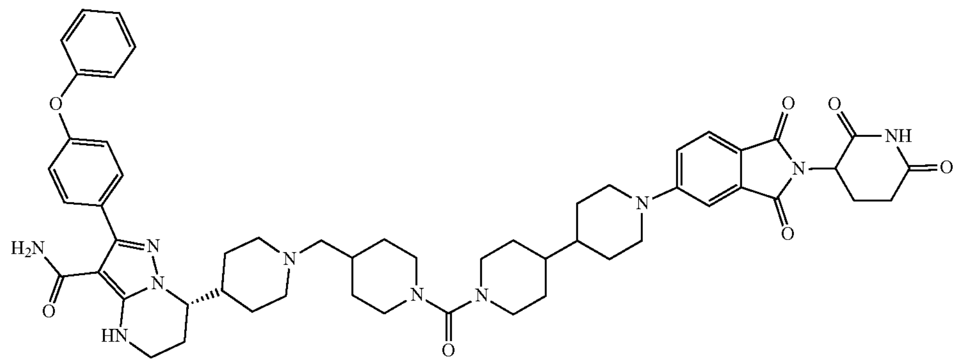 [SMILES: NC(=O)c1c(-c2ccc(Oc3ccccc3)cc2)nn2c1NCC[C@H]2C1CCN(CC2CCN(C(=O)N3CCC(C4CCN(c5ccc6c(c5)C(=O)N(C5CCC(=O)NC5=O)C6=O)CC4)CC3)CC2)CC1] | (7S)-7-(1-((1'-(2-(2,6-dioxopiperidin-3-yl)-1,3-dioxoisoindolin-5-yl)-[4,4'-bipiperidine]-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.50 | B | A | B | A |
| 406 | 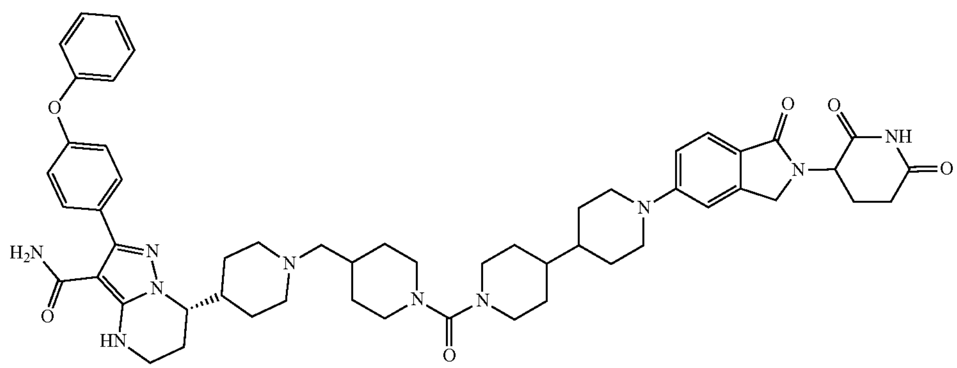 | (7S)-7-(1-((1'-(2-(2,6-dioxopiperidin-3-yl)-1-oxoisoindolin-5-yl)-[4,4'-bipiperidine]-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 950.52 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 407 | 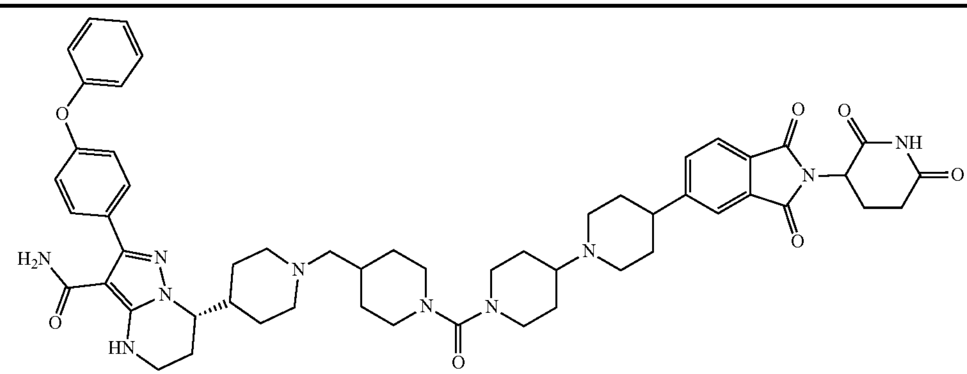 | (7S)-7-(1-((1-(4-(2-(2,6-dioxopiperidin-3-yl)-1,3-dioxoisoindolin-5-yl)-[1,4'-bipiperidine]-1'-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.50 | C | B | B | B |
| 408 | 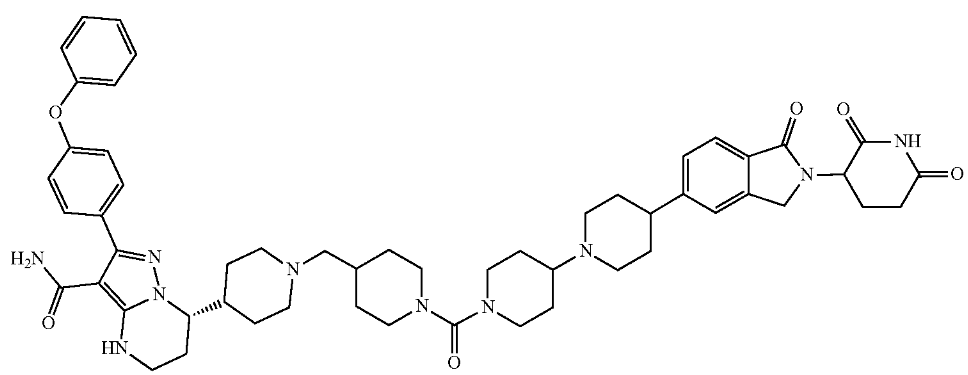 [SMILES: NC(=O)c1c(-c2ccc(Oc3ccccc3)cc2)nn2c1NCC[C@H]2C1CCN(CC2CCN(C(=O)N3CCC(N4CCC(c5ccc6c(c5)CN(C5CCC(=O)NC5=O)C6=O)CC4)CC3)CC2)CC1] | (7S)-7-(1-((1-(4-(2-(2,6-dioxopiperidin-3-yl)-1-oxoisoindolin-5-yl)-[1,4'-bipiperidin]-1'-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 950.52 | B | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 409 | 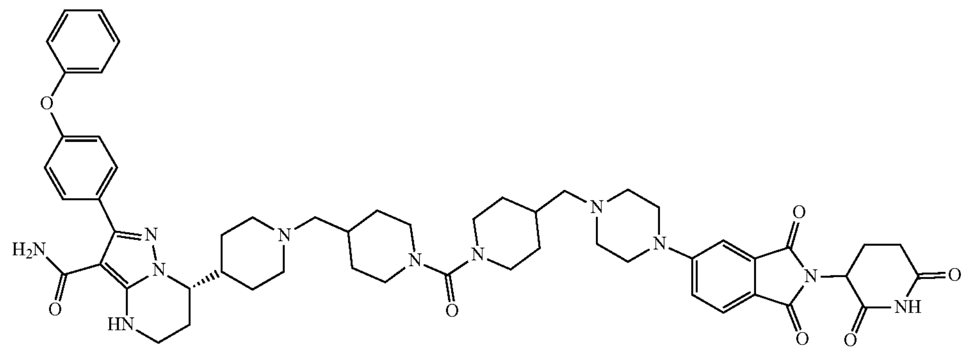 [SMILES: NC(=O)c1c(-c2ccc(Oc3ccccc3)cc2)nn2c1NCC[C@H]2C1CCN(CC2CCN(C(=O)N3CCC(CN4CCN(c5ccc6c(c5)C(=O)N(C5CCC(=O)NC5=O)C6=O)CC4)CC3)CC2)CC1] | (7S)-7-(1-((1-(4-((4-(2-(2,6-dioxopiperidin-3-yl)-1,3-dioxoisoindolin-5-yl)piperazin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 979.51 | B | A | A | A |
| 410 | 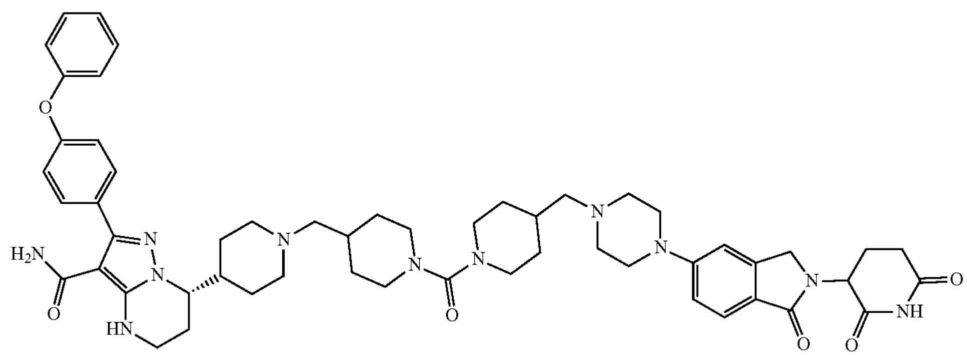 | (7S)-7-(1-((1-(4-((4-(2-(2,6-dioxopiperidin-3-yl)-1-oxoisoindolin-5-yl)piperazin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.53 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 411 | 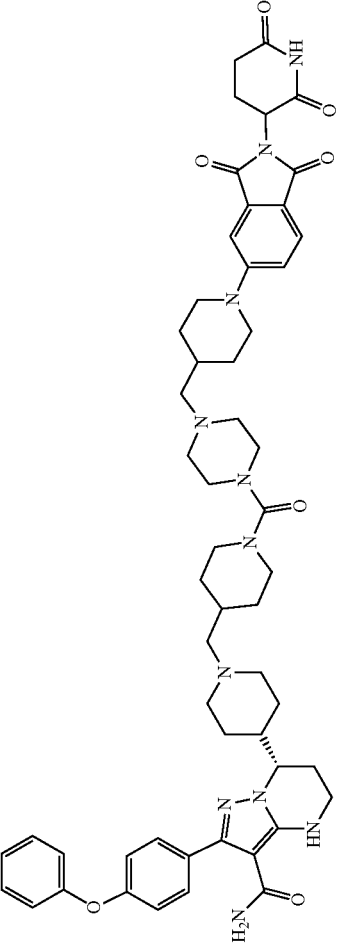 | (7S)-7-(1-(4-((1-(4-((1-(2-(2,6-dioxopiperidin-3-yl)-1,3-dioxoisoindolin-5-yl)piperidin-4-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 979.51 | B | A | B | A |
| 412 | 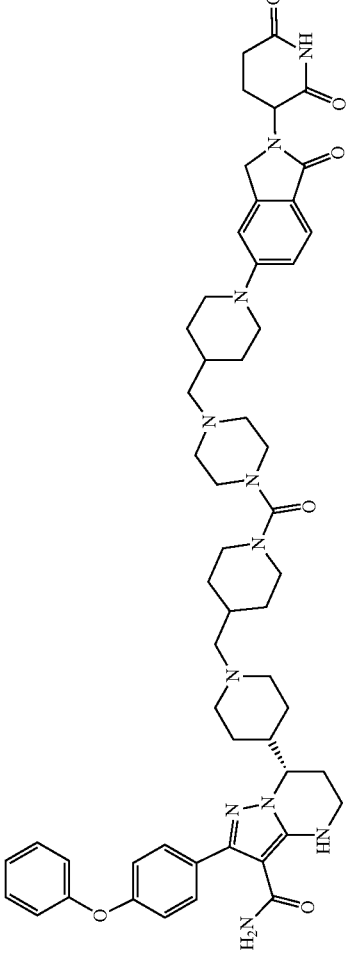 | (7S)-7-(1-(4-((1-(4-((1-(2-(2,6-dioxopiperidin-3-yl)-1-oxoisoindolin-5-yl)piperidin-4-yl)methyl)piperazine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 965.53 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 413 | 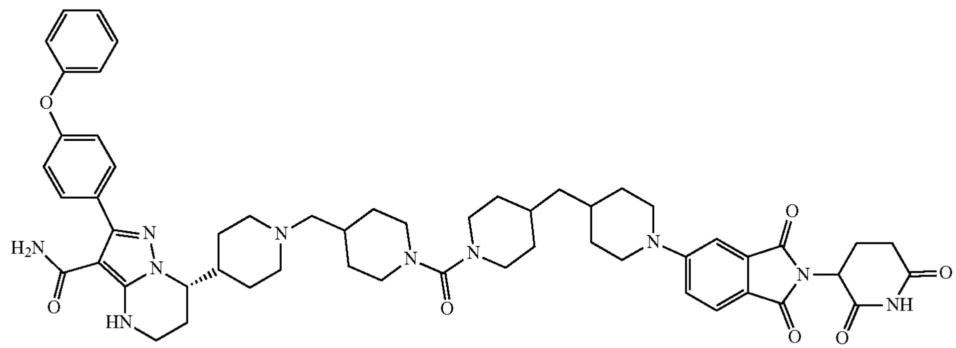 [SMILES: NC(=O)c1c(-c2ccc(Oc3ccccc3)cc2)nn2c1NCC[C@H]2C1CCN(CC2CCN(C(=O)N3CCC(CC4CCN(c5ccc6c(c5)C(=O)N(C5CCC(=O)NC5=O)C6=O)CC4)CC3)CC2)CC1] | (7S)-7-(1-(4-((1-(2-(2,6-dioxopiperidin-3-yl)-1,3-dioxoisoindolin-5-yl)piperidin-4-yl)methyl)piperidine-4-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 978.51 | A | B | B | A |
| 414 | 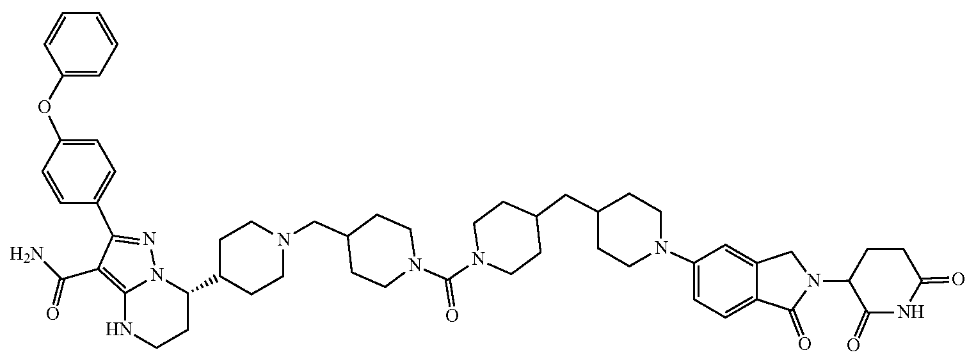 | (7S)-7-(1-((1-(4-((1-(2-(2,6-dioxopiperidin-3-yl)-1-oxoisoindolin-5-yl)piperidin-4-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.53 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 415 | 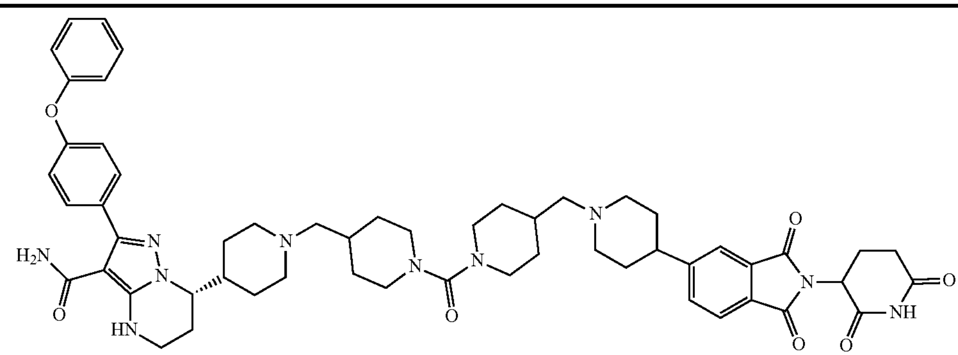 | (7S)-7-(1-((1-(4-((4-(2-(2,6-dioxopiperidin-3-yl)-1,3-dioxoisoindolin-5-yl)piperidin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 978.51 | B | A | B | B |
| 416 | 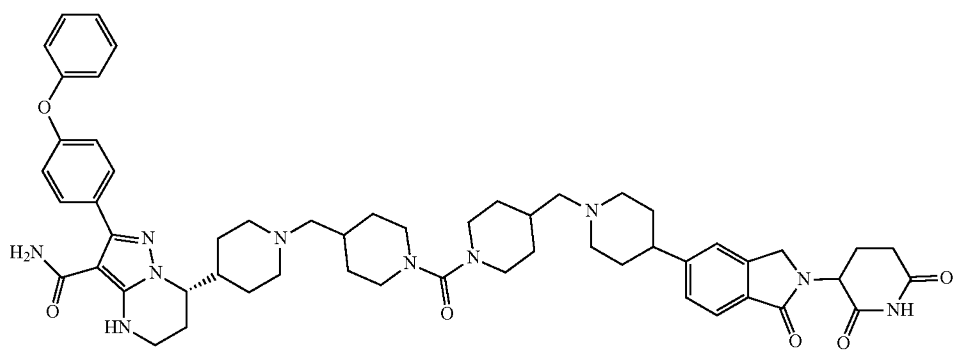 [SMILES: NC(=O)c1c(-c2ccc(Oc3ccccc3)cc2)nn2c1NCC[C@H]2C1CCN(CC2CCN(C(=O)N3CCC(CC4CCN(c5ccc6c(c5)CN(C5CCC(=O)NC5=O)C6=O)CC4)CC3)CC2)CC1] | (7S)-7-(1-((1-(4-((4-(2-(2,6-dioxopiperidin-3-yl)-1-oxoisoindolin-5-yl)piperidin-1-yl)methyl)piperidine-1-carbonyl)piperidin-4-yl)methyl)piperidin-4-yl)-2-(4-phenoxyphenyl)-4,5,6,7-tetrahydropyrazolo[1,5-a]pyrimidine-3-carboxamide | 964.53 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 417 | 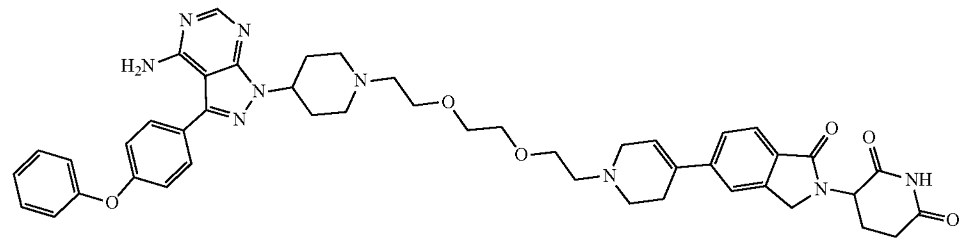 [SMILES: Nc1ncnc2c1c(-c1ccc(Oc3ccccc3)cc1)nn2C1CCN(CCOCCOCCN2CC=C(c3ccc4c(c3)CN(C3CCC(=O)NC3=O)C4=O)CC2)CC1] | 3-(5-(1-(2-(2-(2-(4-(4-amino-3-(4-phenoxyphenyl)-1H-pyrazolo[3,4-d]pyrimidin-1-yl)piperidin-1-yl)ethoxy)ethoxy)ethyl)-1,2,3,6-tetrahydropyridin-4-yl)-1-oxoisoindolin-2-yl)piperidine-2,6-dione | 825.40 | B | B | B | B |
| 418 | 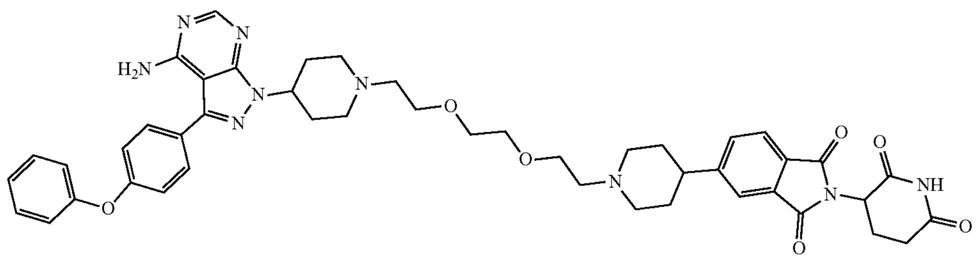 [SMILES: Nc1ncnc2c1c(-c1ccc(Oc3ccccc3)cc1)nn2C1CCN(CCOCCOCCN2CCC(c3ccc4c(c3)C(=O)N(C3CCC(=O)NC3=O)C4=O)CC2)CC1] | 5-(1-(2-(2-(2-(4-(4-amino-3-(4-phenoxyphenyl)-1H-pyrazolo[3,4-d]pyrimidin-1-yl)piperidin-1-yl)ethoxy)ethoxy)ethyl)piperidin-4-yl)-2-(2,6-dioxopiperidin-3-yl)isoindoline-1,3-dione | 841.39 | B | B | A | A |
| 419 | 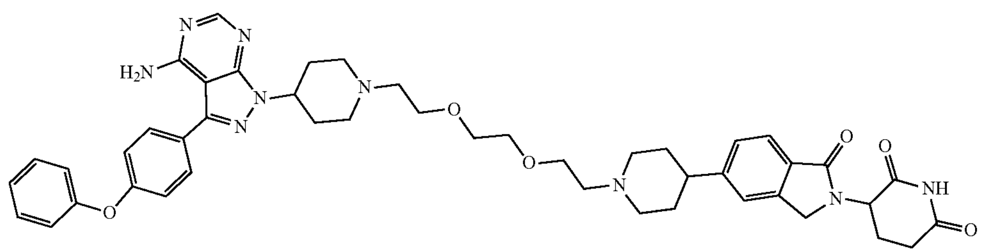 [SMILES: Nc1ncnc2c1c(-c1ccc(Oc3ccccc3)cc1)nn2C1CCN(CCOCCOCCN2CCC(c3ccc4c(c3)CN(C3CCC(=O)NC3=O)C4=O)CC2)CC1] | 3-(5-(1-(2-(2-(2-(4-(4-amino-3-(4-phenoxyphenyl)-1H-pyrazolo[3,4-d]pyrimidin-1-yl)piperidin-1-yl)ethoxy)ethoxy)ethyl)piperidin-4-yl)-1-oxoisoindolin-2-yl)piperidine-2,6-dione | 827.41 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 420 | 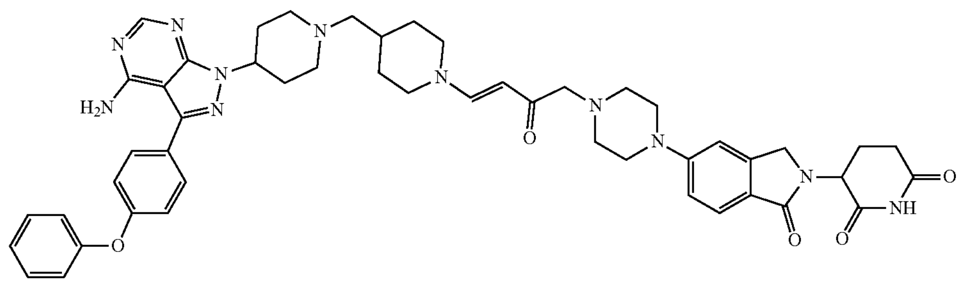 [SMILES: Nc1ncnc2c1c(-c1ccc(Oc3ccccc3)cc1)nn2C1CCN(CC2CCN(/C=C/C(=O)CN3CCN(c4ccc5c(c4)CN(C4CCC(=O)NC4=O)C5=O)CC3)CC2)CC1] | (E)-3-(5-(4-(4-(4-((4-(4-amino-3-(4-phenoxyphenyl)-1H-pyrazolo[3,4-d]pyrimidin-1-yl)piperidin-1-yl)methyl)piperidin-1-yl)piperazin-1-yl)-2-oxobut-3-en-1-yl)piperazin-1-yl)-1-oxoisoindolin-2-yl)piperidine-2,6-dione | 877.44 | B | B | A | A |
| 421 | 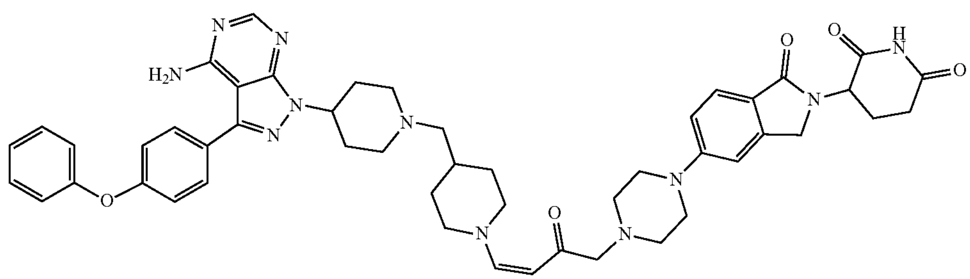 [SMILES: Nc1ncnc2c1c(-c1ccc(Oc3ccccc3)cc1)nn2C1CCN(CC2CCN(/C=C\C(=O)CN3CCN(c4ccc5c(c4)CN(C4CCC(=O)NC4=O)C5=O)CC3)CC2)CC1] | (Z)-3-(5-(4-(4-(4-((4-(4-amino-3-(4-phenoxyphenyl)-1H-pyrazolo[3,4-d]pyrimidin-1-yl)piperidin-1-yl)methyl)piperidin-1-yl)piperazin-1-yl)-2-oxobut-3-en-1-yl)piperazin-1-yl)-1-oxoisoindolin-2-yl)piperidine-2,6-dione | 877.44 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 422 | 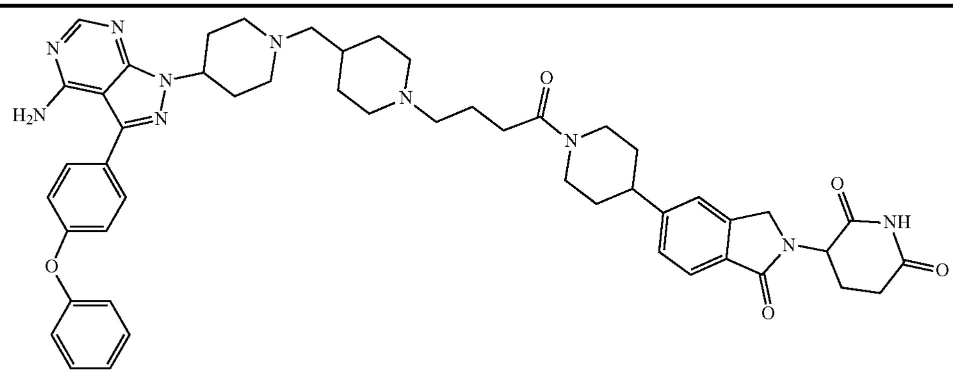 | 3-(5-(1-(4-(4-((4-(4-amino-3-(4-phenoxyphenyl)-1H-pyrazolo[3,4-d]pyrimidin-1-yl)piperidin-1-yl)methyl)piperidin-1-yl)butanoyl)piperidin-4-yl)-1-oxoisoindolin-2-yl)piperidine-2,6-dione | 877.46 | A | A | A | A |
| 423 | 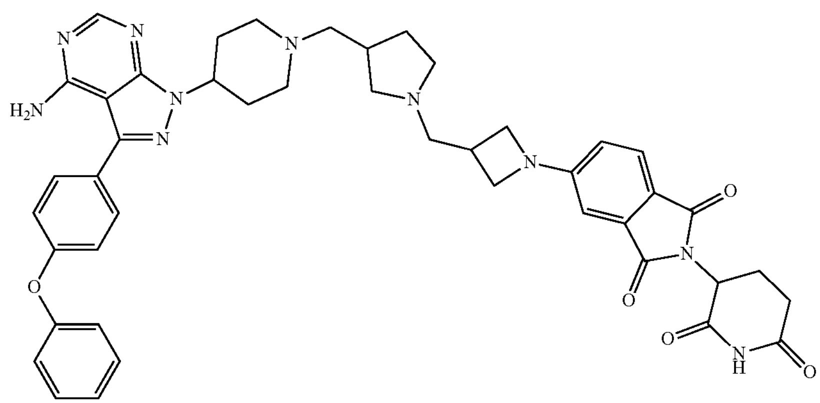 [SMILES: Nc1ncnc2c1c(-c1ccc(Oc3ccccc3)cc1)nn2C1CCN(CC2CCN(CC3CN(c4ccc5c(c4)C(=O)N(C4CCC(=O)NC4=O)C5=O)C3)C2)CC1] | 5-(3-((3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)-2-(2,6-dioxopiperidin-3-yl)isoindoline-1,3-dione | 794.37 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 423a | 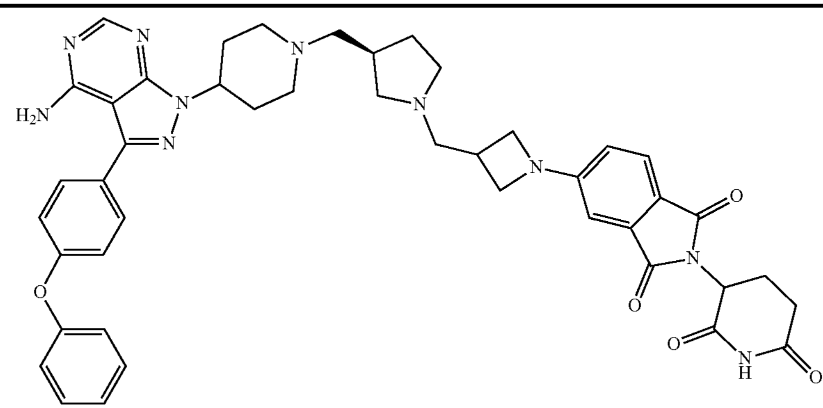 | 5-(3-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)-2-(2,6-dioxopiperidin-3-yl)isoindoline-1,3-dione | 794.34 | B | A | B | A |
| 423b | 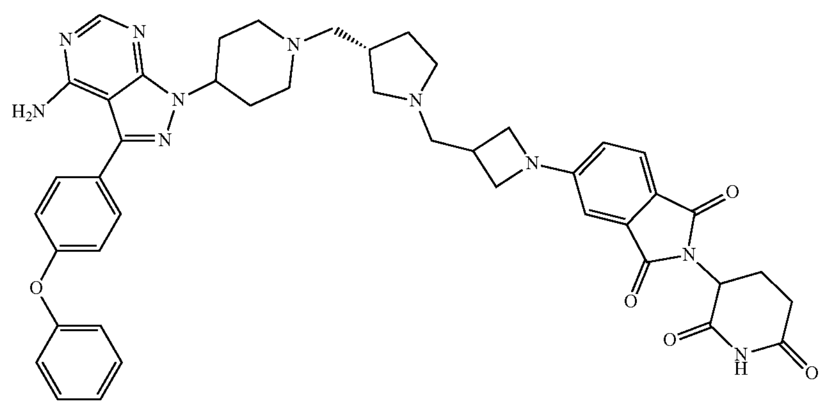 [SMILES: Nc1ncnc2c1c(-c1ccc(Oc3ccccc3)cc1)nn2C1CCN(C[C@@H]2CCN(CC3CN(c4ccc5c(c4)C(=O)N(C4CCC(=O)NC4=O)C5=O)C3)C2)CC1] | 5-(3-(((S)-3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)-2-(2,6-dioxopiperidin-3-yl)isoindoline-1,3-dione | 794.34 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 424 | 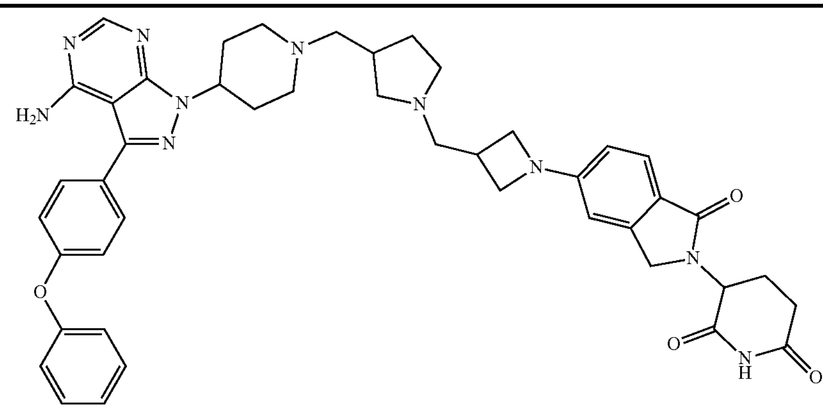 | 3-(5-((3-((3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)methyl)pyrrolidin-1-yl)-1-oxoisoindolin-2-yl)piperidine-2,6-dione | 780.39 | A | A | B | A |
| 425 | 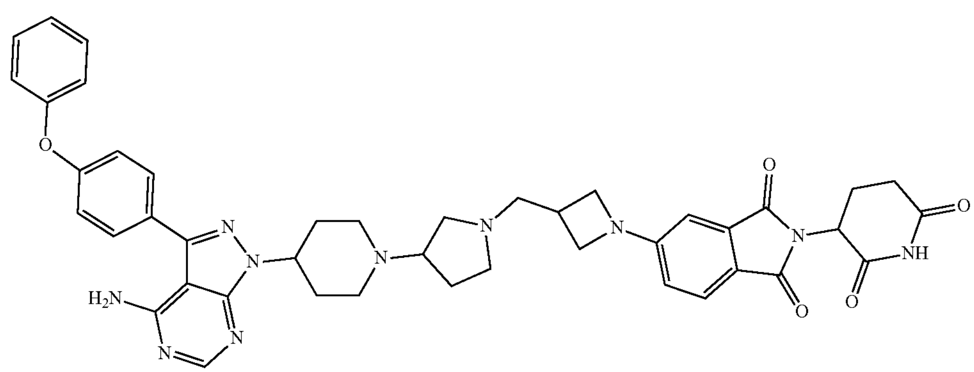 [SMILES: Nc1ncnc2c1c(-c1ccc(Oc3ccccc3)cc1)nn2C1CCN(C2CCN(CC3CN(c4ccc5c(c4)C(=O)N(C4CCC(=O)NC4=O)C5=O)C3)C2)CC1] | 5-(3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)methyl)pyrrolidin-1-yl)-2-(2,6-dioxopiperidin-3-yl)isoindoline-1,3-dione | 780.35 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 425a | 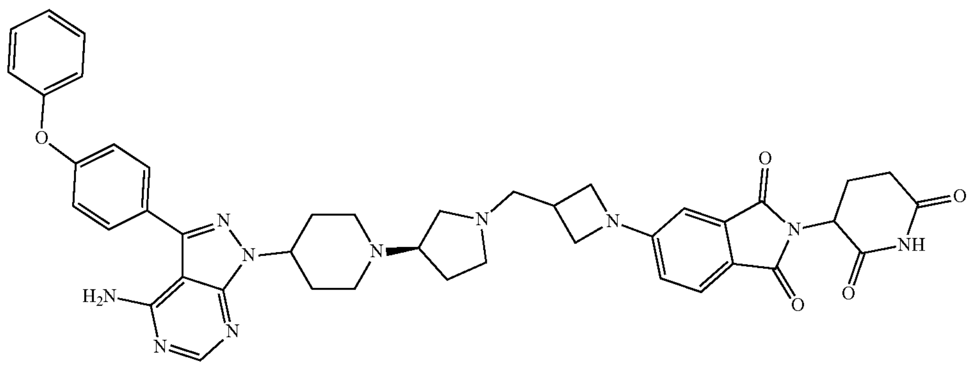 [SMILES: Nc1ncnc2c1c(-c1ccc(Oc3ccccc3)cc1)nn2C1CCN([C@@H]2CCN(CC3CN(c4ccc5c(c4)C(=O)N(C4CCC(=O)NC4=O)C5=O)C3)C2)CC1] | 5-(3-((R)-3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)-2-(2,6-dioxopiperidin-3-yl)isoindoline-1,3-dione | 780.35 | B | B | B | A |
| 425b | 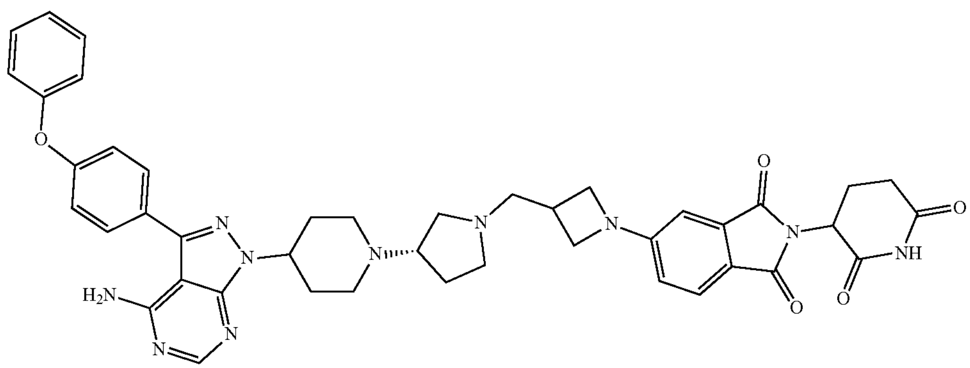 [SMILES: Nc1ncnc2c1c(-c1ccc(Oc3ccccc3)cc1)nn2C1CCN([C@H]2CCN(CC3CN(c4ccc5c(c4)C(=O)N(C4CCC(=O)NC4=O)C5=O)C3)C2)CC1] | 5-(3-((S)-3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)-2-(2,6-dioxopiperidin-3-yl)isoindoline-1,3-dione | 780.35 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 426 | 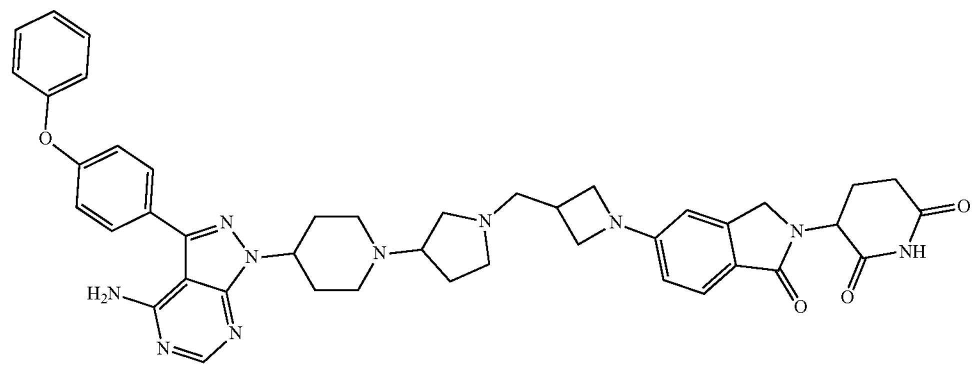 [SMILES: Nc1ncnc2c1c(-c1ccc(Oc3ccccc3)cc1)nn2C1CCN(C2CCN(CC3CN(c4ccc5c(c4)CN(C4CCC(=O)NC4=O)C5=O)C3)C2)CC1] | 3-(5-(3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)-1-oxoisoindolin-2-yl)piperidine-2,6-dione | 766.37 | A | A | B | A |
| 427 | 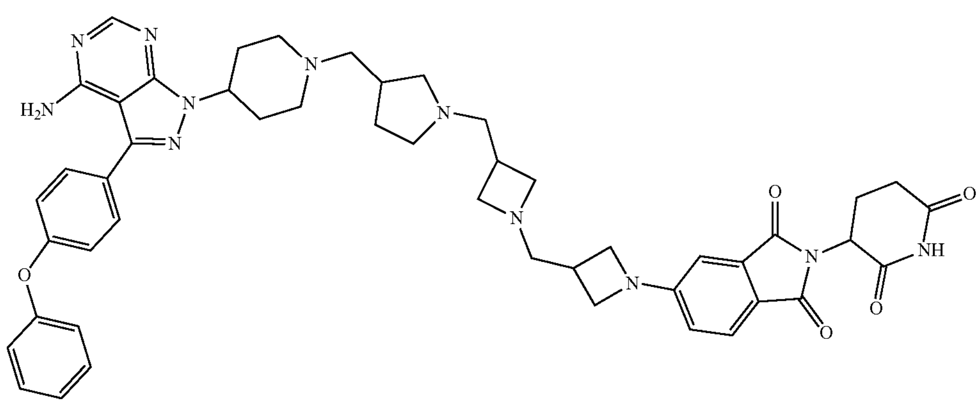 | 5-(3-((3-(((3-(4-(4-amino-3-(4-phenoxyphenyl)-1H-pyrazolo[3,4-d]pyrimidin-1-yl)piperidin-1-yl)pyrrolidin-1-yl)methyl)azetidin-1-yl)methyl)azetidin-3-yl)-2-(2,6-dioxopiperidin-3-yl)isoindoline-1,3-dione | 863.42 | B | B | C | A |

Exact Mass: 863.42

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 427a | 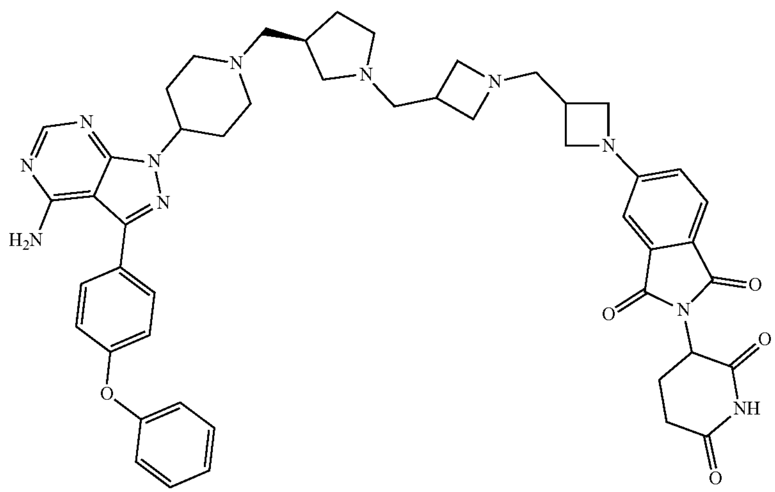 [SMILES: Nc1ncnc2c1c(-c1ccc(Oc3ccccc3)cc1)nn2C1CCN(C[C@H]2CCN(CC3CN(CC4CN(c5ccc6c(c5)C(=O)N(C5CCC(=O)NC5=O)C6=O)C4)C3)C2)CC1] | 5-(3-((3-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)methyl)azetidin-1-yl)-2-(2,6-dioxopiperidin-3-yl)isoindoline-1,3-dione | 863.42 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 427b | 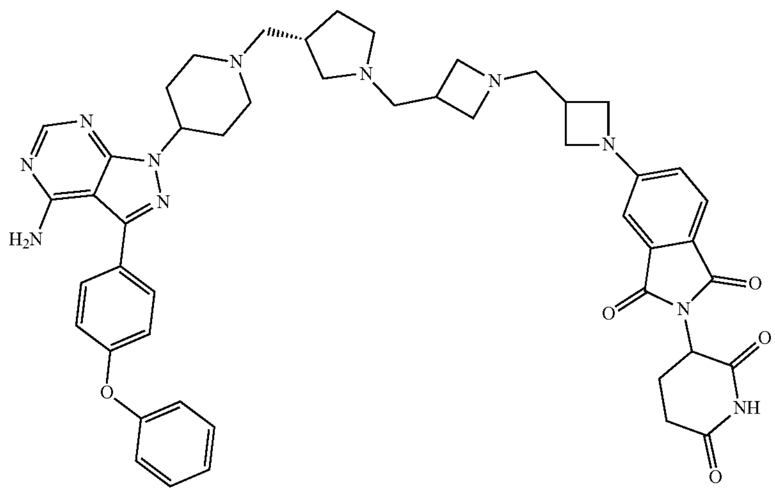 [SMILES: Nc1ncnc2c1c(-c1ccc(Oc3ccccc3)cc1)nn2C1CCN(C[C@@H]2CCN(CC3CN(CC4CN(c5ccc6c(c5)C(=O)N(C5CCC(=O)NC5=O)C6=O)C4)C3)C2)CC1] | 5-(3-((S)-3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)methyl)azetidin-3-yl)-2-(2,6-dioxopiperidin-3-yl)isoindoline-1,3-dione | 863.42 | B | B | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 428 | 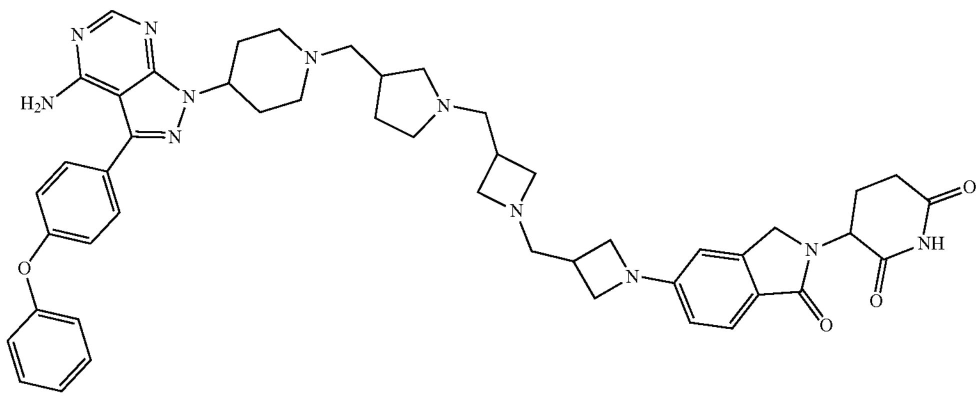 [SMILES: Nc1ncnc2c1c(-c1ccc(Oc3ccccc3)cc1)nn2C1CCN(CC2CCN(CC3CN(CC4CN(c5ccc6c(c5)CN(C5CCC(=O)NC5=O)C6=O)C4)C3)C2)CC1] | 3-(5-(3-((3-((4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)-1-oxoisoindolin-2-yl)piperidine-2,6-dione | 849.44 | B | B | B | A |
| 429 | 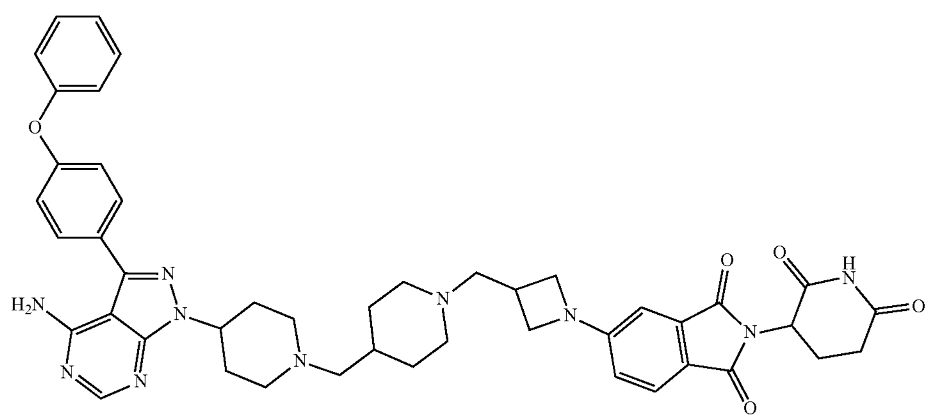 [SMILES: Nc1ncnc2c1c(-c1ccc(Oc3ccccc3)cc1)nn2C1CCN(CC2CCN(CC3CN(c4ccc5c(c4)C(=O)N(C4CCC(=O)NC4=O)C5=O)C3)CC2)CC1] | 5-(3-((4-((4-amino-3-(4-phenoxyphenyl)-1H-pyrazolo[3,4-d]pyrimidin-1-yl)piperidin-1-yl)methyl)azetidin-1-yl)-2-(2,6-dioxopiperidin-3-yl)isoindoline-1,3-dione | 808.38 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 430 | 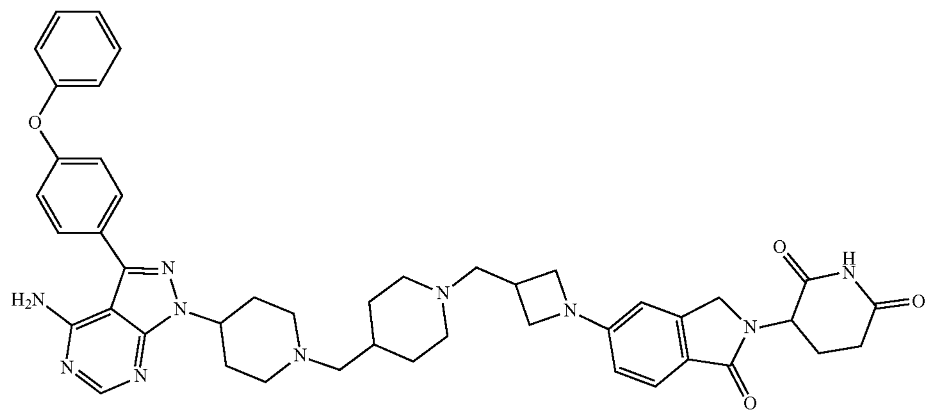 [SMILES: Nc1ncnc2c1c(-c1ccc(Oc3ccccc3)cc1)nn2C1CCN(CC2CCN(CC3CN(c4ccc5c(c4)CN(C4CCC(=O)NC4=O)C5=O)C3)CC2)CC1] | 3-(5-(3-((4-((4-(4-amino-3-(4-phenoxyphenyl)-1H-pyrazolo[3,4-d]pyrimidin-1-yl)piperidin-1-yl)methyl)piperidin-1-yl)methyl)azetidin-1-yl)-1-oxoisoindolin-2-yl)piperidine-2,6-dione | 794.40 | A | A | B | A |

TABLE 1-continued

Exemplary compounds of the present invention.
Antiproliferation in mantle cell lymphoma cell (Mino or JeKo-1).

| # | IUPAC Name | Structure | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 431 | 5-(3-((4-((4-((4-amino-3-(4-phenoxyphenyl)-1H-pyrazolo[3,4-d]pyrimidin-1-yl)piperidin-1-yl)methyl)piperidin-1-yl)methyl)piperidin-1-yl)methyl)azetidin-3-yl)-2-(2,6-dioxopiperidin-3-yl)isoindoline-1,3-dione | 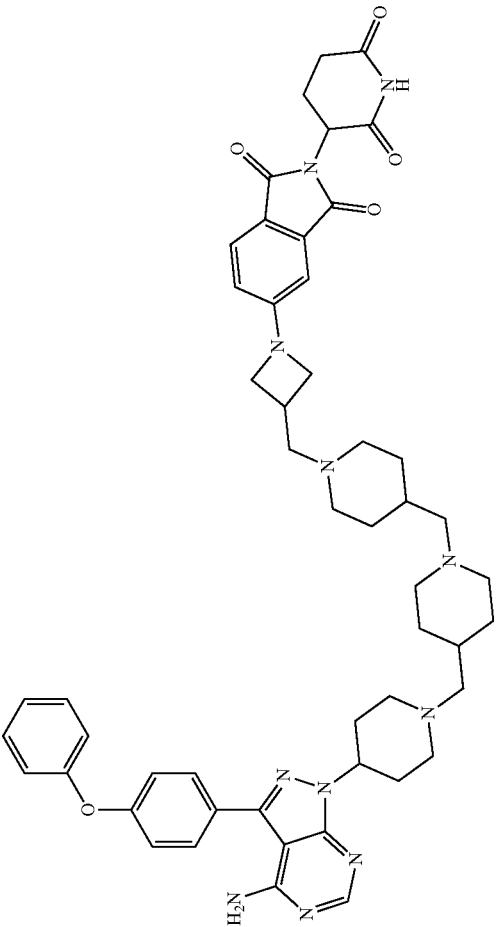 | 905.47 | A | A | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 432 | 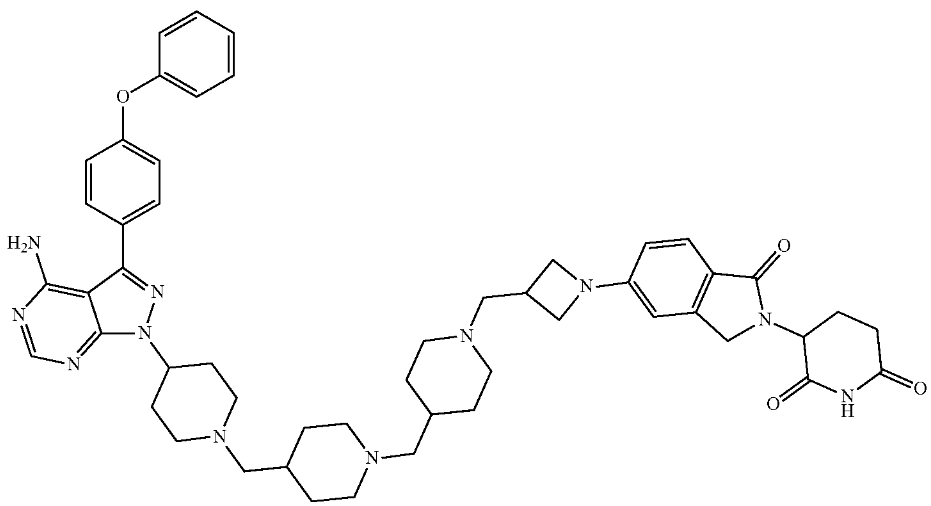 [SMILES: Nc1ncnc2c1c(-c1ccc(Oc3ccccc3)cc1)nn2C1CCN(CC2CCN(CC3CCN(CC4CN(c5ccc6c(c5)CN(C5CCC(=O)NC5=O)C6=O)C4)CC3)CC2)CC1] | 3-(5-(3-((4-((4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)methyl)azetidin-1-yl)-1-oxoisoindolin-2-yl)piperidine-2,6-dione | 891.49 | A | A | B | A |
| 433 | 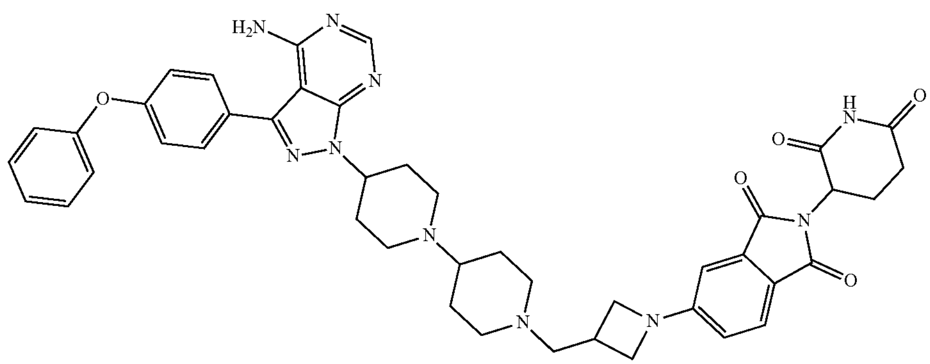 [SMILES: Nc1ncnc2c1c(-c1ccc(Oc3ccccc3)cc1)nn2C1CCN(C2CCN(CC3CN(c4ccc5c(c4)C(=O)N(C4CCC(=O)NC4=O)C5=O)C3)CC2)CC1] | 5-(3-((4-(4-amino-3-(4-phenoxyphenyl)-1H-pyrazolo[3,4-d]pyrimidin-1-yl)-[1,4'-bipiperidin]-1'-yl)methyl)azetidin-1-yl)-2-(2,6-dioxopiperidin-3-yl)isoindoline-1,3-dione | 794.37 | B | A | C | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 434 | 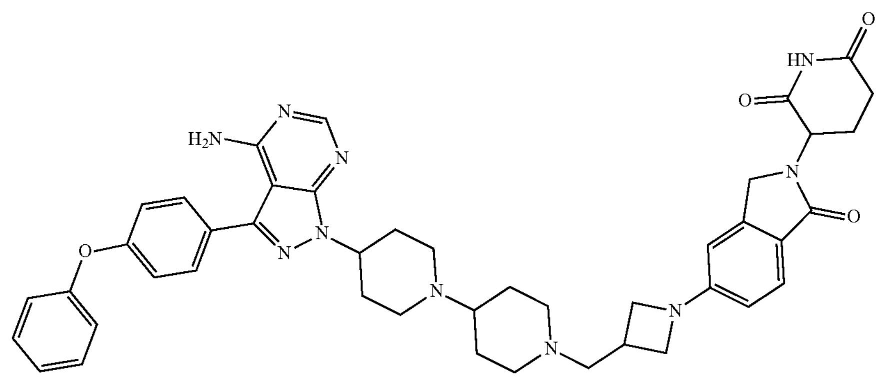 [SMILES: Nc1ncnc2c1c(-c1ccc(Oc3ccccc3)cc1)nn2C1CCN(C2CCN(CC3CN(c4ccc5c(c4)CN(C4CCC(=O)NC4=O)C5=O)C3)CC2)CC1] | 3-(5-(3-((4-(4-amino-3-(4-phenoxyphenyl)-1H-pyrazolo[3,4-d]pyrimidin-1-yl)-[1,4'-bipiperidin]-1'-yl)methyl)azetidin-1-yl)-1-oxoisoindolin-2-yl)piperidine-2,6-dione | 780.39 | B | A | B | A |
| 435 | 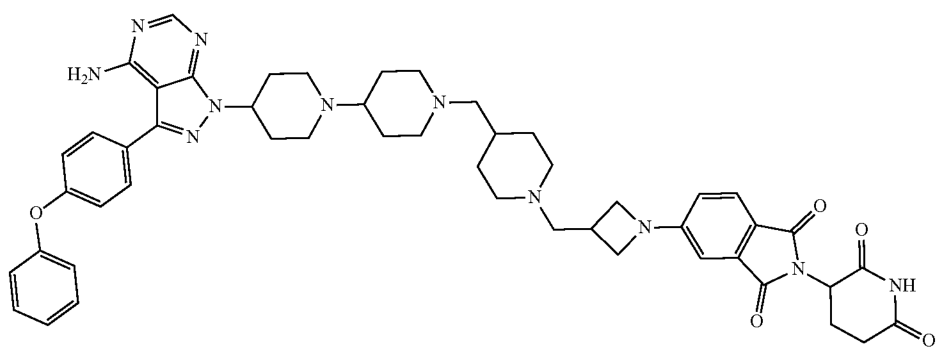 [SMILES: Nc1ncnc2c1c(-c1ccc(Oc3ccccc3)cc1)nn2C1CCN(C2CCN(CC3CCN(CC4CN(c5ccc6c(c5)C(=O)N(C5CCC(=O)NC5=O)C6=O)C4)CC3)CC2)CC1] | 5-(3-((4-(4-amino-3-(4-phenoxyphenyl)-1H-pyrazolo[3,4-d]pyrimidin-1-yl)-[1,4'-bipiperidin]-1'-yl)methyl)piperidin-1-yl)methyl)azetidin-1-yl)-2-(2,6-dioxopiperidin-3-yl)isoindoline-1,3-dione | 891.45 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 436 | 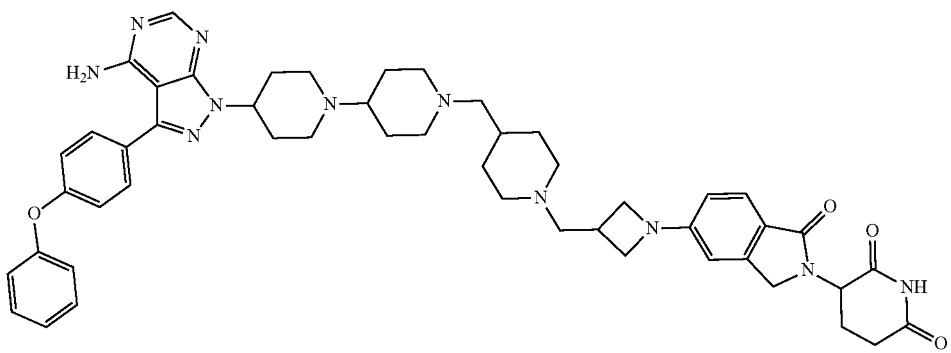 [SMILES: Nc1ncnc2c1c(-c1ccc(Oc3ccccc3)cc1)nn2C1CCN(C2CCN(CC3CCN(CC4CN(c5ccc6c(c5)CN(C5CCC(=O)NC5=O)C6=O)C4)CC3)CC2)CC1] | 3-(5-((4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)methyl)azetidin-1-yl)-1-oxoisoindolin-2-yl)piperidine-2,6-dione | 877.48 | B | A | A | A |
| 437 | 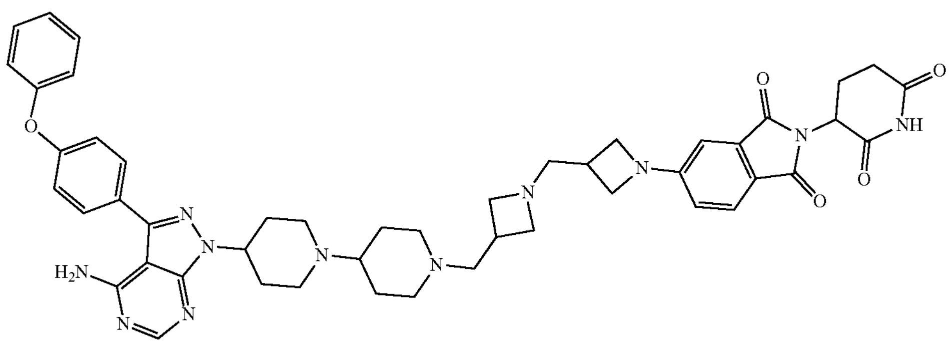 [SMILES: Nc1ncnc2c1c(-c1ccc(Oc3ccccc3)cc1)nn2C1CCN(C2CCN(CC3CN(CC4CN(c5ccc6c(c5)C(=O)N(C5CCC(=O)NC5=O)C6=O)C4)C3)CC2)CC1] | 5-(3-((4-(4-(4-amino-3-(4-phenoxyphenyl)-1H-pyrazolo[3,4-d]pyrimidin-1-yl)-[1,4'-bipiperidin]-1'-yl)methyl)azetidin-1-yl)-2-(2,6-dioxopiperidin-3-yl)isoindoline-1,3-dione | 863.42 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 438 | 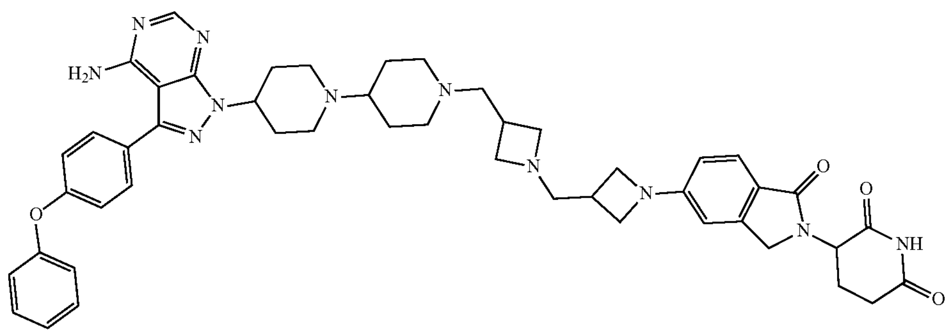 [SMILES: Nc1ncnc2c1c(-c1ccc(Oc3ccccc3)cc1)nn2C1CCN(C2CCN(CC3CN(CC4CN(c5ccc6c(c5)CN(C5CCC(=O)NC5=O)C6=O)C4)C3)CC2)CC1] | 3-(5-((3-((4-(4-amino-3-(4-phenoxyphenyl)-1H-pyrazolo[3,4-d]pyrimidin-1-yl)-[1,4'-bipiperidin]-1'-yl)methyl)azetidin-1-yl)methyl)azetidin-1-yl)-1-oxoisoindolin-2-yl)piperidin-2,6-dione | 849.44 | B | B | B | A |
| 439 | 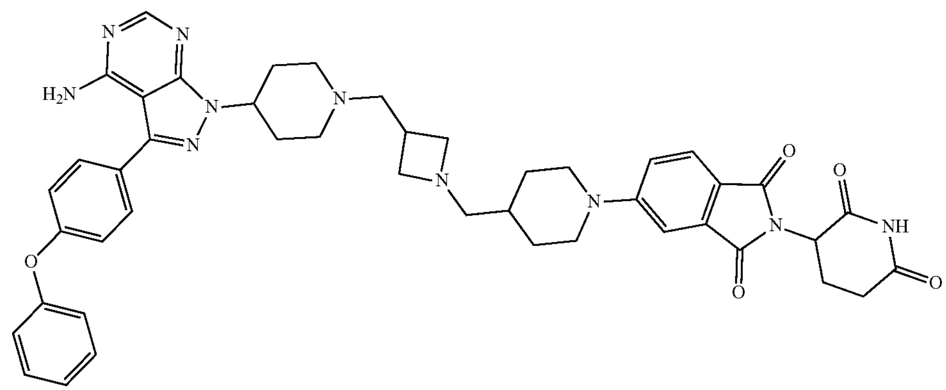 [SMILES: Nc1ncnc2c1c(-c1ccc(Oc3ccccc3)cc1)nn2C1CCN(CC2CN(CC3CCN(c4ccc5c(c4)C(=O)N(C4CCC(=O)NC4=O)C5=O)CC3)C2)CC1] | 5-(4-((3-((4-(4-amino-3-(4-phenoxyphenyl)-1H-pyrazolo[3,4-d]pyrimidin-1-yl)piperidin-1-yl)methyl)azetidin-1-yl)methyl)piperidin-1-yl)-2-(2,6-dioxopiperidin-3-yl)isoindoline-1,3-dione | 808.38 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 440 | 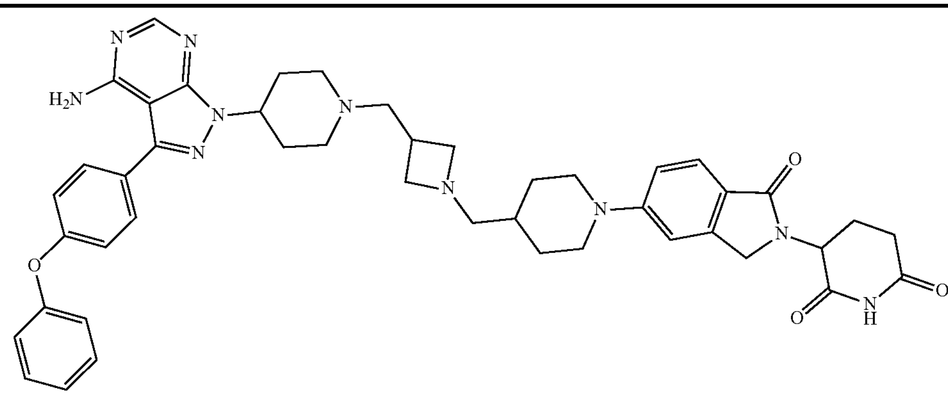 | 3-(5-(4-((3-(4-(4-amino-3-(4-phenoxyphenyl)-1H-pyrazolo[3,4-d]pyrimidin-1-yl)piperidin-1-yl)methyl)azetidin-1-yl)methyl)piperidin-1-yl)-1-oxoisoindolin-2-yl)piperidine-2,6-dione | 794.40 | B | A | A | A |
| 441 | 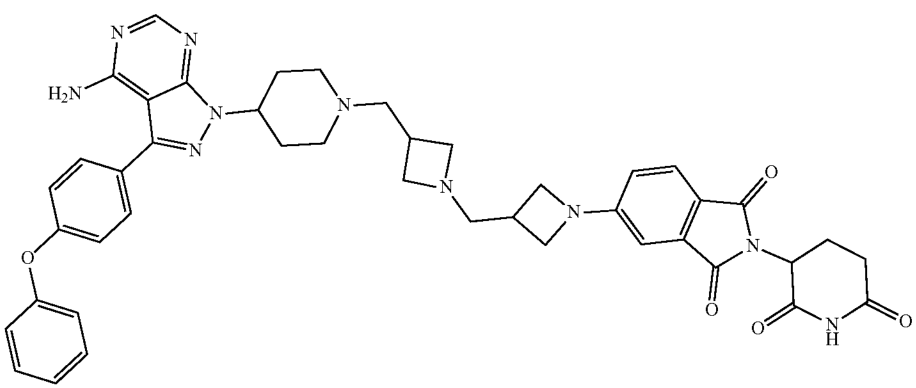 [SMILES: Nc1ncnc2c1c(-c1ccc(Oc3ccccc3)cc1)nn2C1CCN(CC2CN(CC3CN(c4ccc5c(c4)C(=O)N(C4CCC(=O)NC4=O)C5=O)C3)C2)CC1] | 5-(3-((3-(4-(4-amino-3-(4-phenoxyphenyl)-1H-pyrazolo[3,4-d]pyrimidin-1-yl)piperidin-1-yl)methyl)azetidin-1-yl)methyl)azetidin-1-yl)-2-(2,6-dioxopiperidin-3-yl)isoindoline-1,3-dione | 780.35 | C | C | D | D |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 442 | 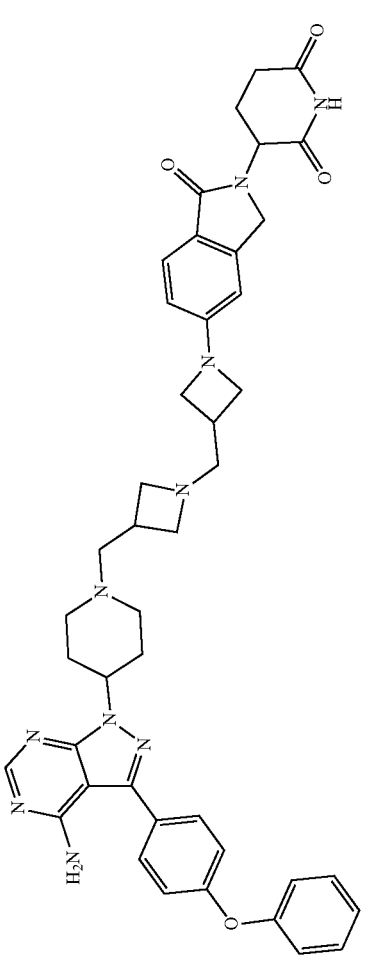 | 3-(5-((3-((4-(4-amino-3-(4-phenoxyphenyl)-1H-pyrazolo[3,4-d]pyrimidin-1-yl)piperidin-1-yl)methyl)azetidin-1-yl)methyl)azetidin-1-yl)-1-oxoisoindolin-2-yl)piperidine-2,6-dione | 766.37 | C | C | D | D |
| 443 | 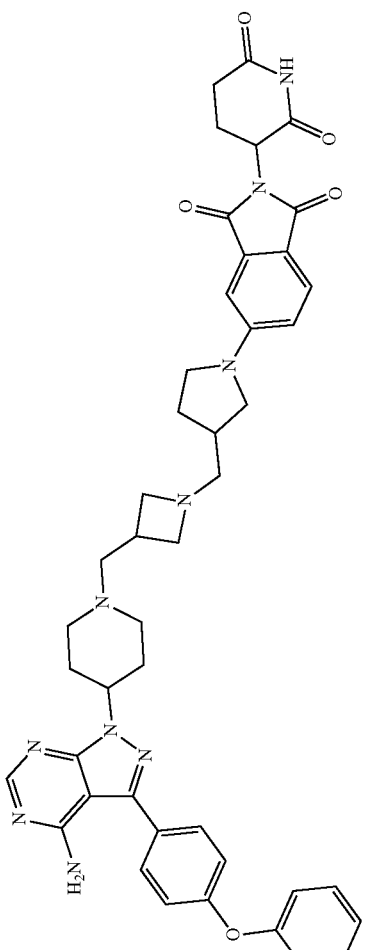 | 5-(3-((3-((4-(4-amino-3-(4-phenoxyphenyl)-1H-pyrazolo[3,4-d]pyrimidin-1-yl)piperidin-1-yl)methyl)azetidin-1-yl)methyl)pyrrolidin-1-yl)-2-(2,6-dioxopiperidin-3-yl)isoindoline-1,3-dione | 794.37 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 443a | 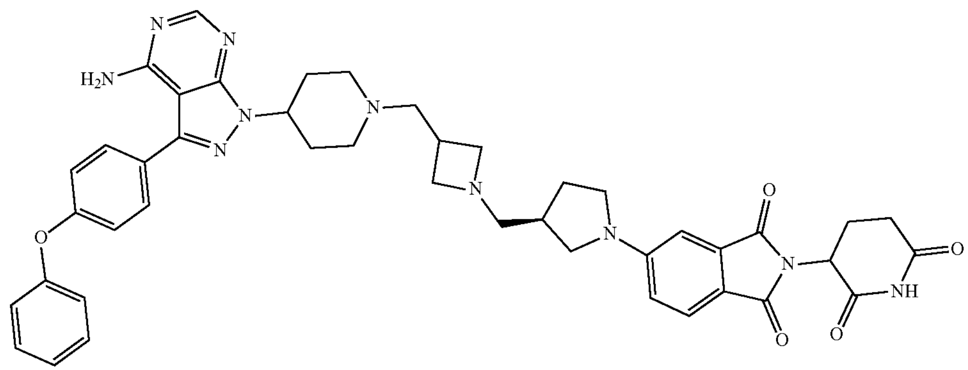 [SMILES: Nc1ncnc2c1c(-c1ccc(Oc3ccccc3)cc1)nn2C1CCN(CC2CN(C[C@H]3CCN(c4ccc5c(c4)C(=O)N(C4CCC(=O)NC4=O)C5=O)C3)C2)CC1] | 5-((R)-3-((3-(4-(4-amino-3-(4-phenoxyphenyl)-1H-pyrazolo[3,4-d]pyrimidin-1-yl)piperidin-1-yl)methyl)azetidin-1-yl)methyl)pyrrolidin-1-yl)-2-(2,6-dioxopiperidin-3-yl)isoindoline-1,3-dione | 794.37 | A | A | A | A |
| 443b | 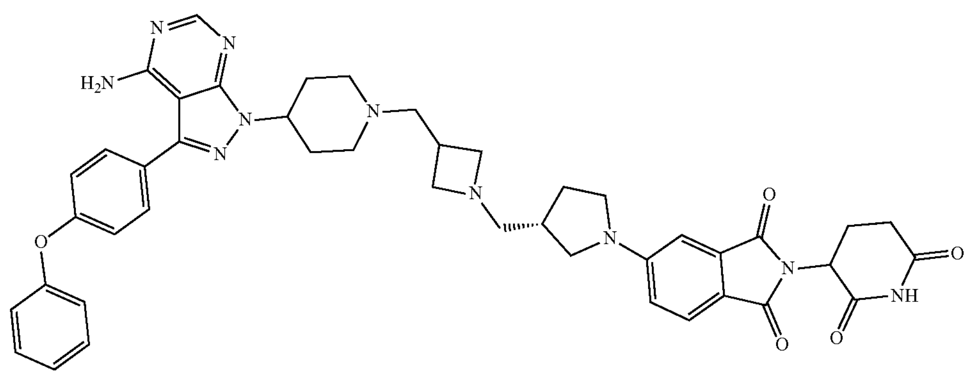 [SMILES: Nc1ncnc2c1c(-c1ccc(Oc3ccccc3)cc1)nn2C1CCN(CC2CN(C[C@@H]3CCN(c4ccc5c(c4)C(=O)N(C4CCC(=O)NC4=O)C5=O)C3)C2)CC1] | 5-((S)-3-((3-(4-(4-amino-3-(4-phenoxyphenyl)-1H-pyrazolo[3,4-d]pyrimidin-1-yl)piperidin-1-yl)methyl)azetidin-1-yl)methyl)pyrrolidin-1-yl)-2-(2,6-dioxopiperidin-3-yl)isoindoline-1,3-dione | 794.37 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 444 | 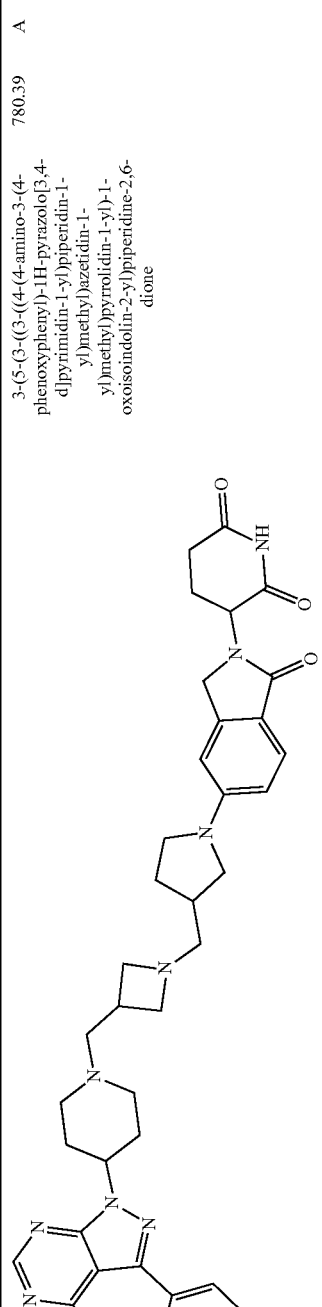 | 3-(5-((3-((3-((4-(4-amino-3-(4-phenoxyphenyl)-1H-pyrazolo[3,4-d]pyrimidin-1-yl)piperidin-1-yl)methyl)pyrrolidin-1-yl)methyl)azetidin-1-yl)methyl)pyrrolidin-1-yl)-1-oxoisoindolin-2-yl)piperidine-2,6-dione | 780.39 | A | A | A | A |
| 445 | 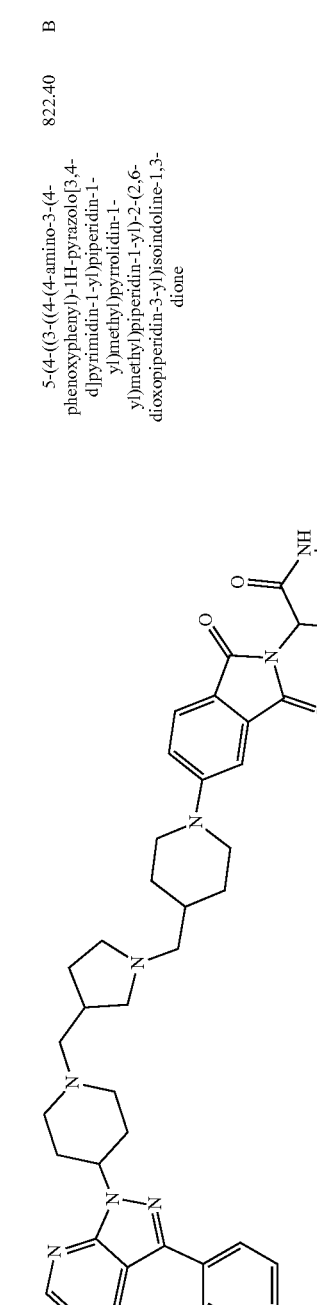 | 5-(4-(3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-2-(2,6-dioxopiperidin-3-yl)isoindoline-1,3-dione | 822.40 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 445a | 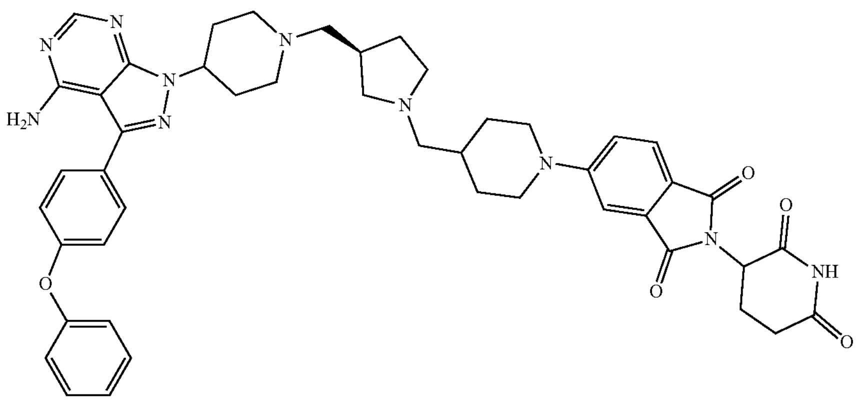 [SMILES: Nc1ncnc2c1c(-c1ccc(Oc3ccccc3)cc1)nn2C1CCN(C[C@H]2CCN(CC3CCN(c4ccc5c(c4)C(=O)N(C4CCC(=O)NC4=O)C5=O)CC3)C2)CC1] | 5-(4-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-2-(2,6-dioxopiperidin-3-yl)isoindoline-1,3-dione | 822.40 | B | B | B | A |
| 445b | 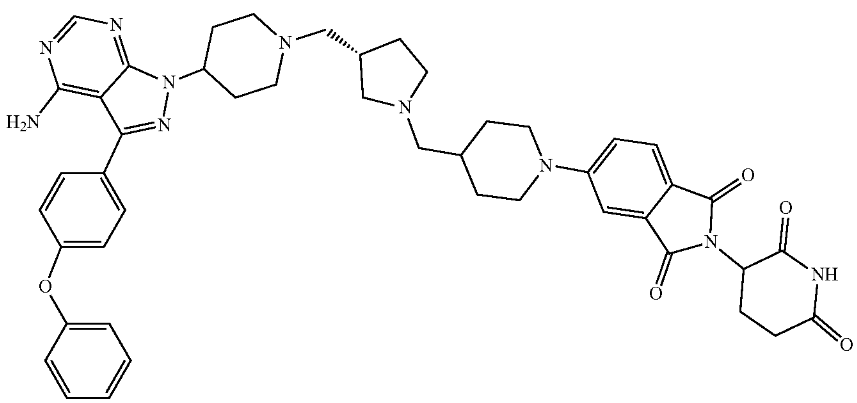 [SMILES: Nc1ncnc2c1c(-c1ccc(Oc3ccccc3)cc1)nn2C1CCN(C[C@@H]2CCN(CC3CCN(c4ccc5c(c4)C(=O)N(C4CCC(=O)NC4=O)C5=O)CC3)C2)CC1] | 5-(4-(((S)-3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-2-(2,6-dioxopiperidin-3-yl)isoindoline-1,3-dione | 822.40 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 446 | 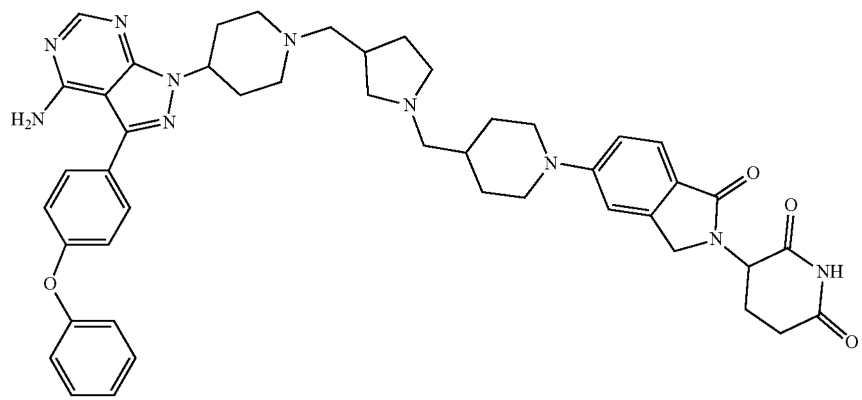 [SMILES: Nc1ncnc2c1c(-c1ccc(Oc3ccccc3)cc1)nn2C1CCN(CC2CCN(CC3CCN(c4ccc5c(c4)CN(C4CCC(=O)NC4=O)C5=O)CC3)C2)CC1] | 3-(5-(4-((3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-1-oxoisoindolin-2-yl)piperidine-2,6-dione | 808.42 | B | B | B | A |
| 446a | 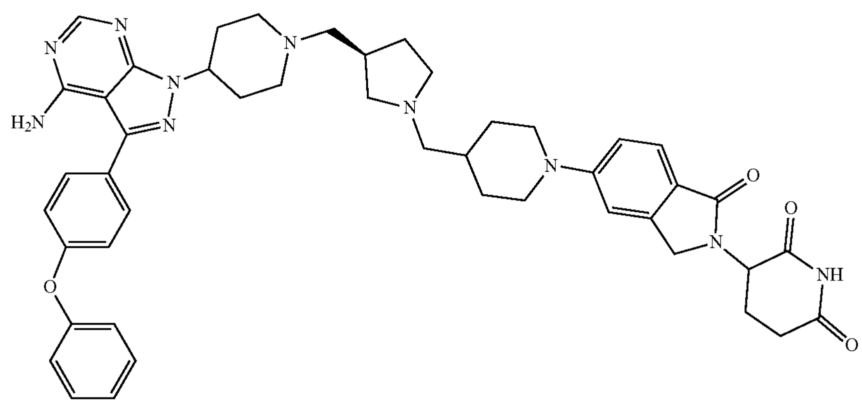 [SMILES: Nc1ncnc2c1c(-c1ccc(Oc3ccccc3)cc1)nn2C1CCN(C[C@H]2CCN(CC3CCN(c4ccc5c(c4)CN(C4CCC(=O)NC4=O)C5=O)CC3)C2)CC1] | 3-(5-(4-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-1-oxoisoindolin-2-yl)piperidine-2,6-dione | 808.42 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 446b | 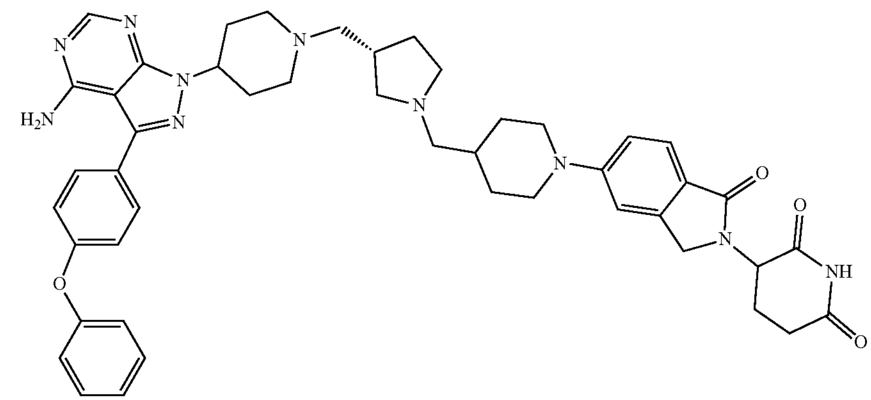 [SMILES: Nc1ncnc2c1c(-c1ccc(Oc3ccccc3)cc1)nn2C1CCN(C[C@@H]2CCN(CC3CCN(c4ccc5c(c4)CN(C4CCC(=O)NC4=O)C5=O)CC3)C2)CC1] | 3-(5-(4-(((S)-3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-1-oxoisoindolin-2-yl)piperidine-2,6-dione | 808.42 | B | A | B | A |
| 447 | 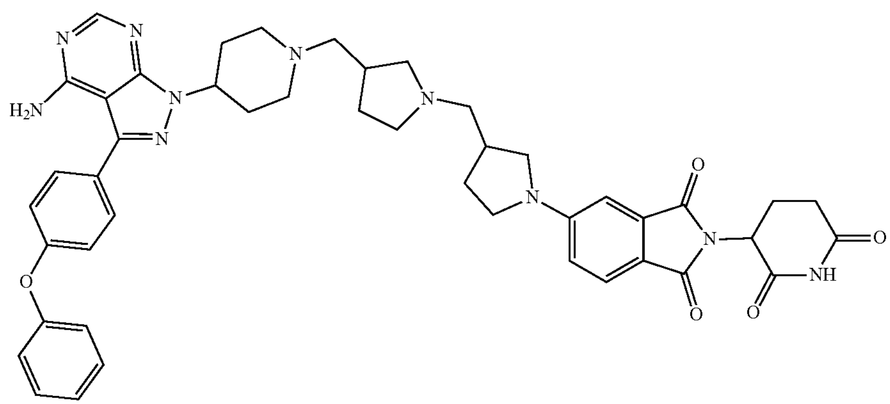 [SMILES: Nc1ncnc2c1c(-c1ccc(Oc3ccccc3)cc1)nn2C1CCN(CC2CCN(CC3CCN(c4ccc5c(c4)C(=O)N(C4CCC(=O)NC4=O)C5=O)C3)C2)CC1] | 5-(3-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione | 808.38 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 447a | 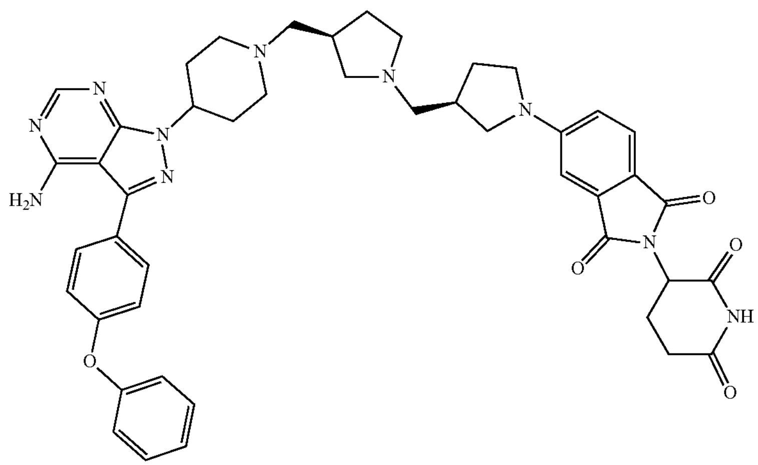 [SMILES: Nc1ncnc2c1c(-c1ccc(Oc3ccccc3)cc1)nn2C1CCN(C[C@H]2CCN(C[C@H]3CCN(c4ccc5c(c4)C(=O)N(C4CCC(=O)NC4=O)C5=O)C3)C2)CC1] | 5-((R)-3-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione | 808.38 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 447b | 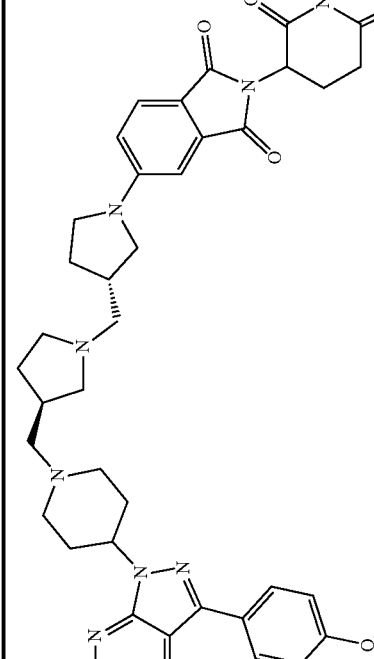 | 5-((S)-3-(((R)-3-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione | 808.38 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 447c | 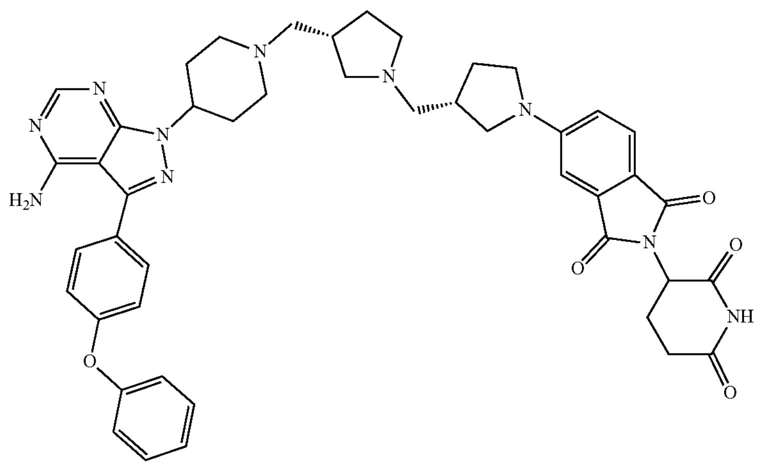 [SMILES: Nc1ncnc2c1c(-c1ccc(Oc3ccccc3)cc1)nn2C1CCN(C[C@@H]2CCN(C[C@@H]3CCN(c4ccc5c(c4)C(=O)N(C4CCC(=O)NC4=O)C5=O)C3)C2)CC1] | 5-((S)-3-(((S)-3-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione | 808.38 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 447d | 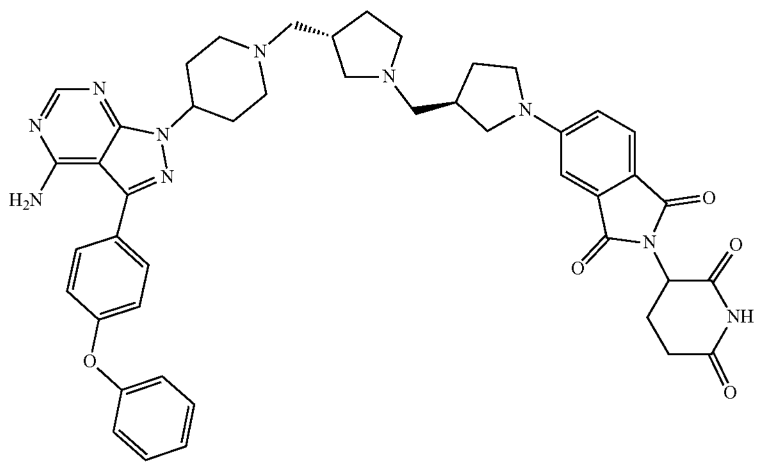 [SMILES: Nc1ncnc2c1c(-c1ccc(Oc3ccccc3)cc1)nn2C1CCN(C[C@@H]2CCN(C[C@H]3CCN(c4ccc5c(c4)C(=O)N(C4CCC(=O)NC4=O)C5=O)C3)C2)CC1] | 5-((R)-3-(((S)-1-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione | 808.38 | B | B | B | A |
| 448 | 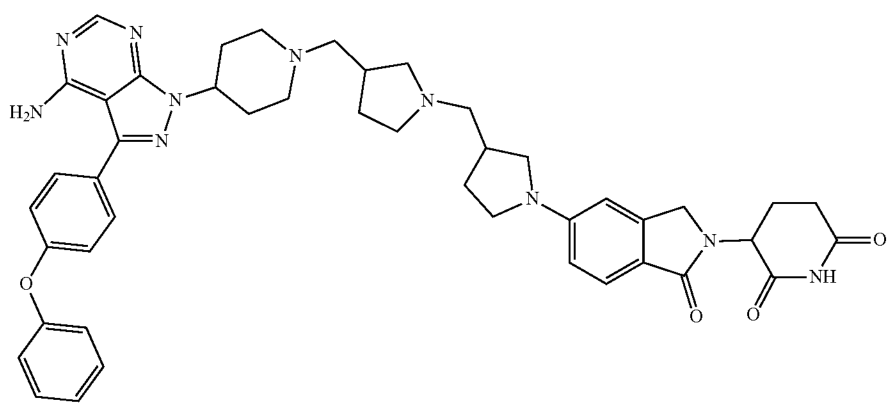 [SMILES: Nc1ncnc2c1c(-c1ccc(Oc3ccccc3)cc1)nn2C1CCN(CC2CCN(CC3CCN(c4ccc5c(c4)CN(C4CCC(=O)NC4=O)C5=O)C3)C2)CC1] | 3-(5-(3-((3-((4-(4-amino-3-(4-phenoxyphenyl)-1H-pyrazolo[3,4-d]pyrimidin-1-yl)piperidin-1-yl)methyl)pyrrolidin-1-yl)methyl)pyrrolidin-1-yl)-1-oxoisoindolin-2-yl)piperidine-2,6-dione | 794.40 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 449 | 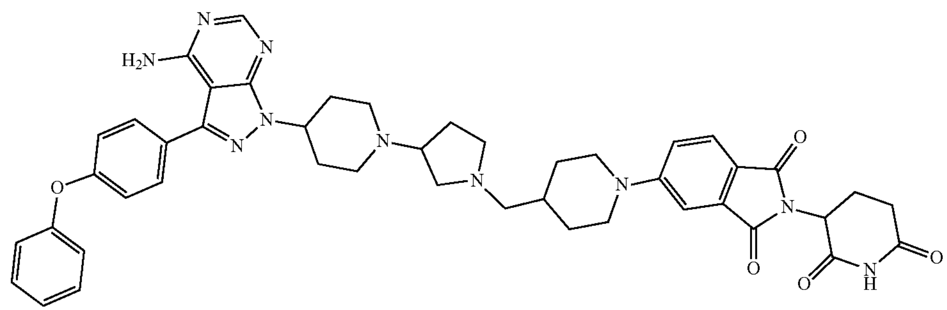 | 5-(4-(3-(4-(4-amino-3-(4-phenoxyphenyl)-1H-pyrazolo[3,4-d]pyrimidin-1-yl)piperidin-1-yl)pyrrolidin-1-yl)methyl)piperidin-1-yl)-2-(2,6-dioxopiperidin-3-yl)isoindoline-1,3-dione | 808.38 | A | A | A | A |
| 449a | 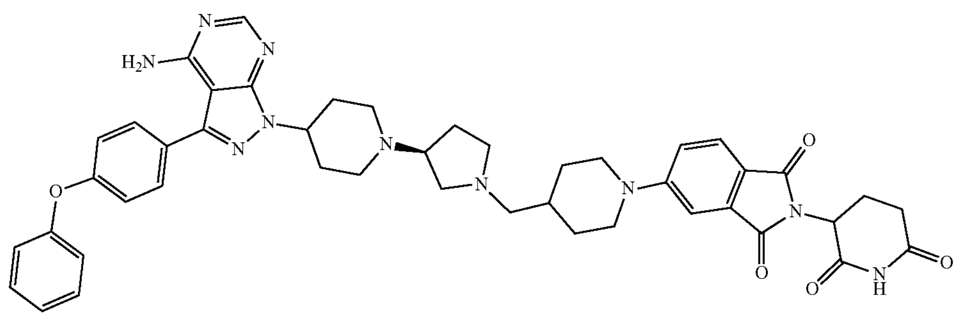 [SMILES: Nc1ncnc2c1c(-c1ccc(Oc3ccccc3)cc1)nn2C1CCN([C@H]2CCN(CC3CCN(c4ccc5c(c4)C(=O)N(C4CCC(=O)NC4=O)C5=O)CC3)C2)CC1] | 5-(4-(((S)-3-(4-(4-amino-3-(4-phenoxyphenyl)-1H-pyrazolo[3,4-d]pyrimidin-1-yl)piperidin-1-yl)pyrrolidin-1-yl)methyl)piperidin-1-yl)-2-(2,6-dioxopiperidin-3-yl)isoindoline-1,3-dione | 808.38 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 449b | 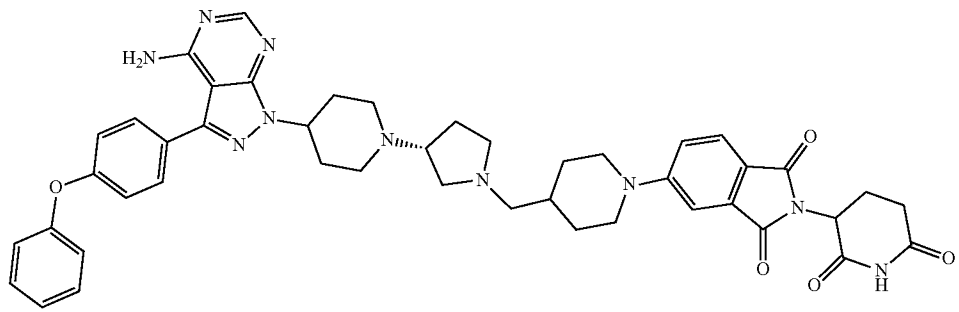 [SMILES: Nc1ncnc2c1c(-c1ccc(Oc3ccccc3)cc1)nn2C1CCN([C@@H]2CCN(CC3CCN(c4ccc5c(c4)C(=O)N(C4CCC(=O)NC4=O)C5=O)CC3)C2)CC1] | 5-(4-((R)-3-(4-(4-amino-3-(4-phenoxyphenyl)-1H-pyrazolo[3,4-d]pyrimidin-1-yl)piperidin-1-yl)pyrrolidin-1-yl)methyl)piperidin-1-yl)-2-(2,6-dioxopiperidin-3-yl)isoindoline-1,3-dione | 808.38 | A | A | A | A |
| 450 | 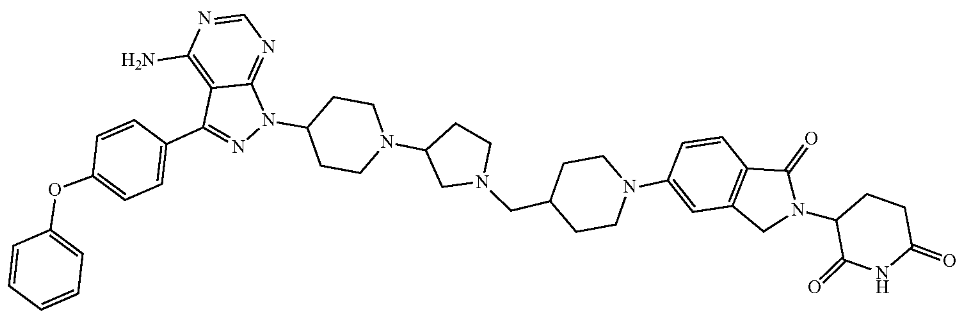 [SMILES: Nc1ncnc2c1c(-c1ccc(Oc3ccccc3)cc1)nn2C1CCN(C2CCN(CC3CCN(c4ccc5c(c4)CN(C4CCC(=O)NC4=O)C5=O)CC3)C2)CC1] | 3-(5-(4-((3-(4-(4-amino-3-(4-phenoxyphenyl)-1H-pyrazolo[3,4-d]pyrimidin-1-yl)piperidin-1-yl)pyrrolidin-1-yl)methyl)piperidin-1-yl)-1-oxoisoindolin-2-yl)piperidine-2,6-dione | 794.40 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 451 | 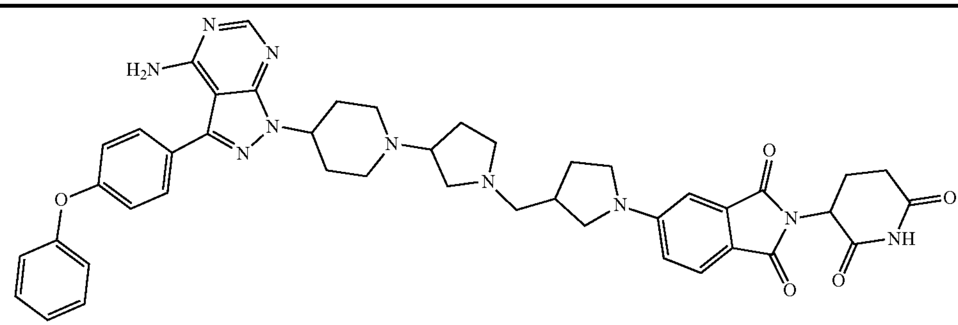 | 5-(3-((3-(4-(4-amino-3-(4-phenoxyphenyl)-1H-pyrazolo[3,4-d]pyrimidin-1-yl)piperidin-1-yl)pyrrolidin-1-yl)methyl)pyrrolidin-1-yl)-2-(2,6-dioxopiperidin-3-yl)isoindoline-1,3-dione | 794.37 | B | A | A | A |
| 452 | 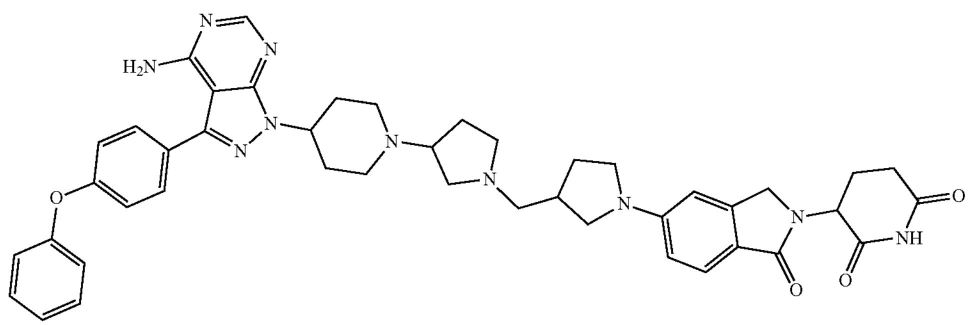 [SMILES: Nc1ncnc2c1c(-c1ccc(Oc3ccccc3)cc1)nn2C1CCN(C2CCN(CC3CCN(c4ccc5c(c4)CN(C4CCC(=O)NC4=O)C5=O)C3)C2)CC1] | 3-(5-(3-((3-(4-(4-amino-3-(4-phenoxyphenyl)-1H-pyrazolo[3,4-d]pyrimidin-1-yl)piperidin-1-yl)pyrrolidin-1-yl)methyl)pyrrolidin-1-yl)-1-oxoisoindolin-2-yl)piperidine-2,6-dione | 780.39 | B | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 453 | 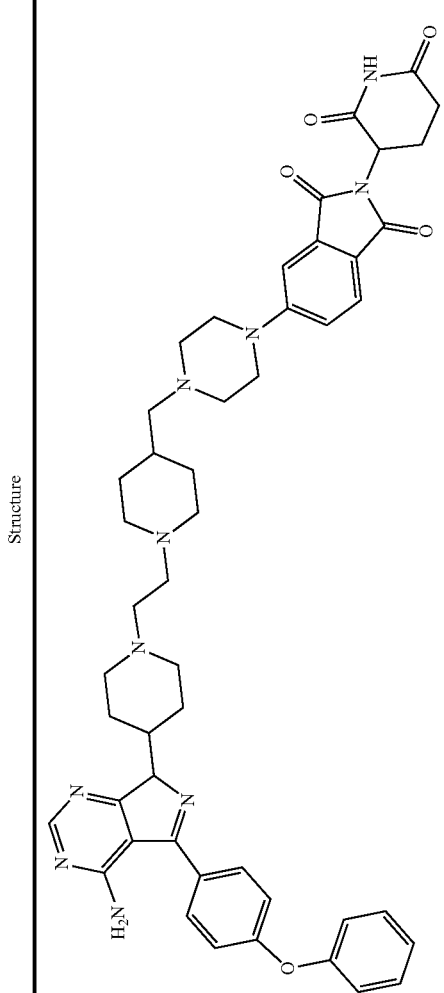 | 5-(4-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperazin-1-yl)-2-(2,6-dioxopiperidin-3-yl)isoindoline-1,3-dione | 851.42 | B | B | B | A |
| 454 | 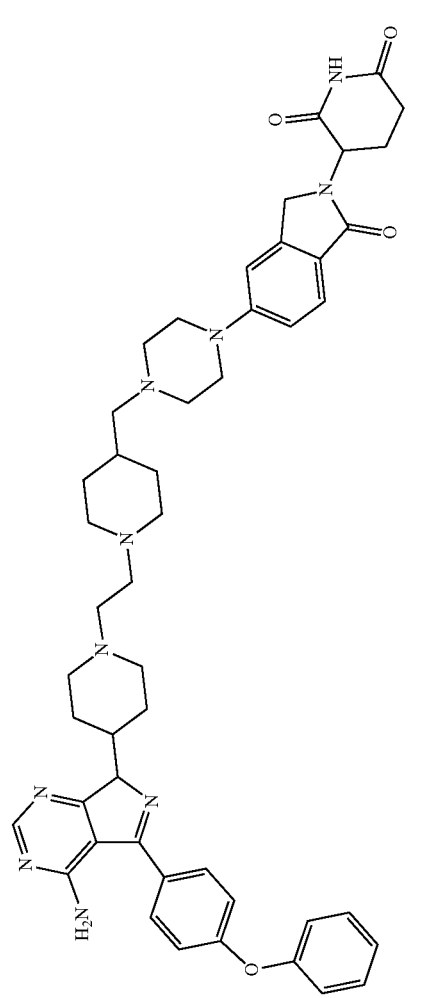 | 3-(5-(4-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperazin-1-yl)-1-oxoisoindolin-2-yl)piperidine-2,6-dione | 837.44 | B | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 455 | 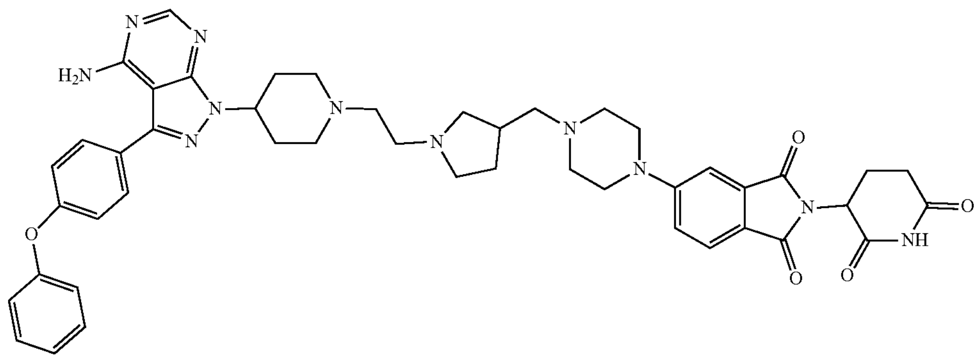 [SMILES: Nc1ncnc2c1c(-c1ccc(Oc3ccccc3)cc1)nn2C1CCN(CCN2CCC(CN3CCN(c4ccc5c(c4)C(=O)N(C4CCC(=O)NC4=O)C5=O)CC3)C2)CC1] | 5-(4-((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperazin-1-yl)-2-(2,6-dioxopiperidin-3-yl)isoindoline-1,3-dione | 837.41 | A | A | A | A |
| 456 | 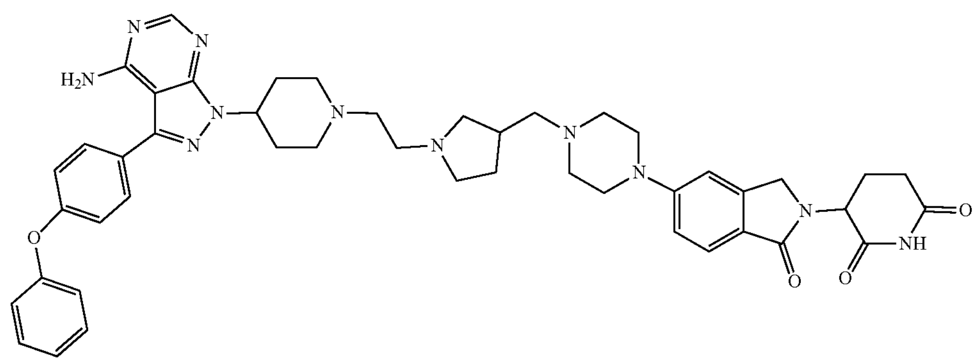 [SMILES: Nc1ncnc2c1c(-c1ccc(Oc3ccccc3)cc1)nn2C1CCN(CCN2CCC(CN3CCN(c4ccc5c(c4)CN(C4CCC(=O)NC4=O)C5=O)CC3)C2)CC1] | 3-(5-(4-((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperazin-1-yl)-1-oxoisoindolin-2-yl)piperidine-2,6-dione | 823.43 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 457 | 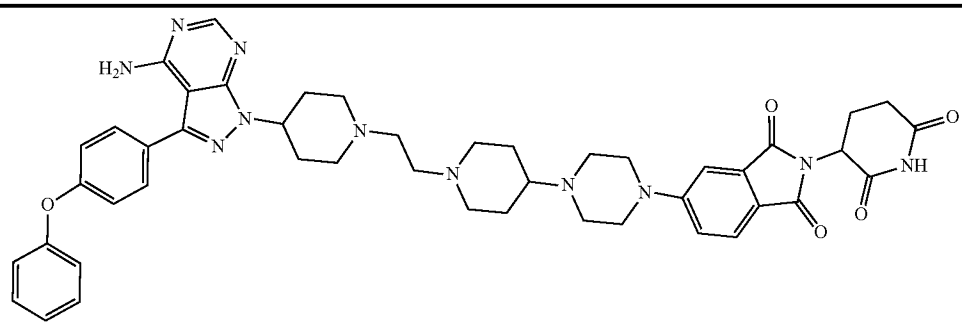 | 5-(4-(1-(2-(4-(4-amino-3-(4-phenoxyphenyl)-1H-pyrazolo[3,4-d]pyrimidin-1-yl)piperidin-1-yl)ethyl)piperidin-4-yl)piperazin-1-yl)-2-(2,6-dioxopiperidin-3-yl)isoindoline-1,3-dione | 837.41 | A | A | A | A |
| 458 | 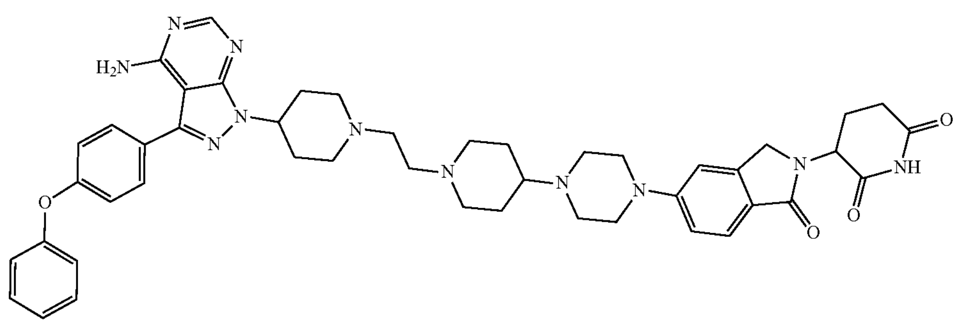 [SMILES: Nc1ncnc2c1c(-c1ccc(Oc3ccccc3)cc1)nn2C1CCN(CCN2CCC(N3CCN(c4ccc5c(c4)CN(C4CCC(=O)NC4=O)C5=O)CC3)CC2)CC1] | 3-(5-(4-(1-(2-(4-(4-amino-3-(4-phenoxyphenyl)-1H-pyrazolo[3,4-d]pyrimidin-1-yl)piperidin-1-yl)ethyl)piperidin-4-yl)piperazin-1-yl)-1-oxoisoindolin-2-yl)piperidine-2,6-dione | 823.43 | B | B | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 459 | 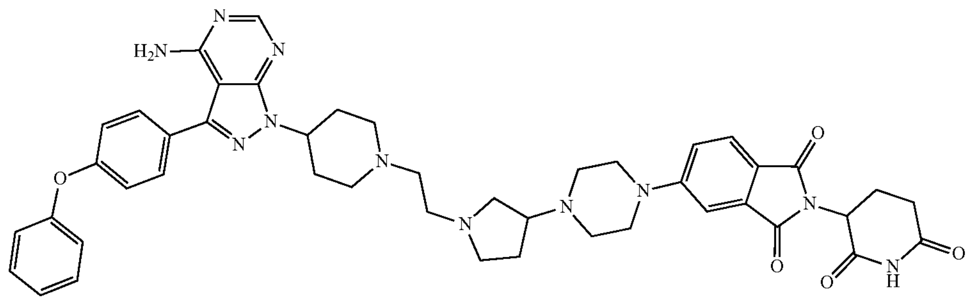 [SMILES: Nc1ncnc2c1c(-c1ccc(Oc3ccccc3)cc1)nn2C1CCN(CCN2CCC(N3CCN(c4ccc5c(c4)C(=O)N(C4CCC(=O)NC4=O)C5=O)CC3)C2)CC1] | 5-(4-(1-(2-(4-(4-amino-3-(4-phenoxyphenyl)-1H-pyrazolo[3,4-d]pyrimidin-1-yl)piperidin-1-yl)ethyl)pyrrolidin-3-yl)piperazin-1-yl)-2-(2,6-dioxopiperidin-3-yl)isoindoline-1,3-dione | 823.39 | A | A | A | A |
| 459a | 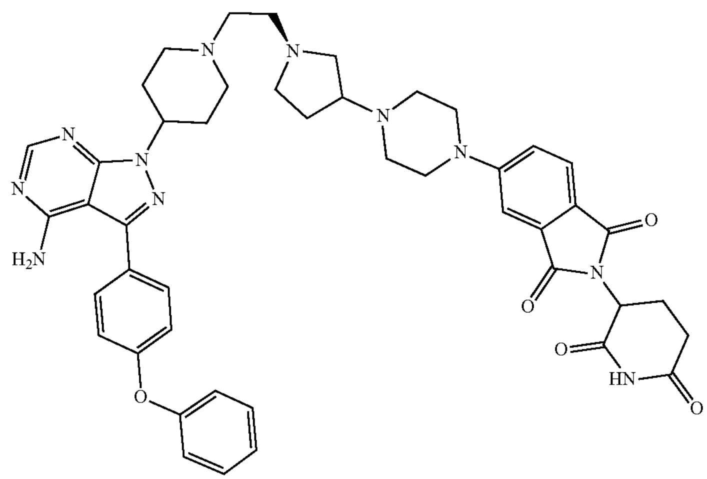 | 5-(4-(1-(2-(4-(4-amino-3-(4-phenoxyphenyl)-1H-pyrazolo[3,4-d]pyrimidin-1-yl)piperidin-1-yl)ethyl)pyrrolidin-3-yl)piperazin-1-yl)-2-(2,6-dioxopiperidin-3-yl)isoindoline-1,3-dione | 823.39 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 459b | 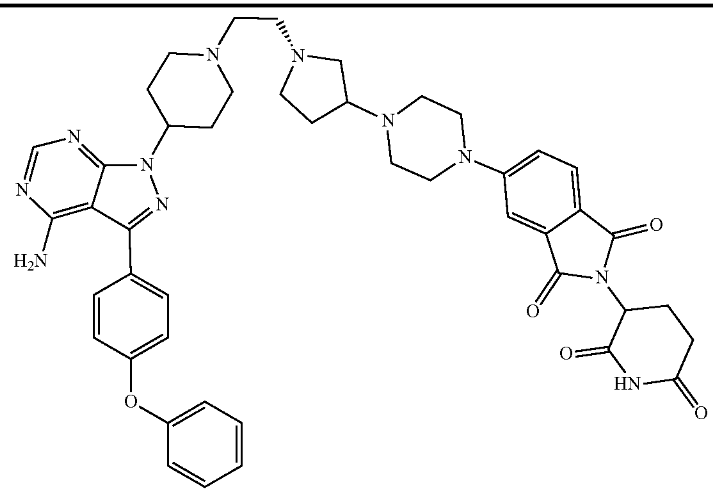 | 5-(4-(1-(2-(4-(4-amino-3-(4-phenoxyphenyl)-1H-pyrazolo[3,4-d]pyrimidin-1-yl)ethyl)pyrrolidin-3-yl)piperazin-1-yl)-2-(2,6-dioxopiperidin-3-yl)isoindoline-1,3-dione | 823.39 | A | A | A | A |
| 460 | 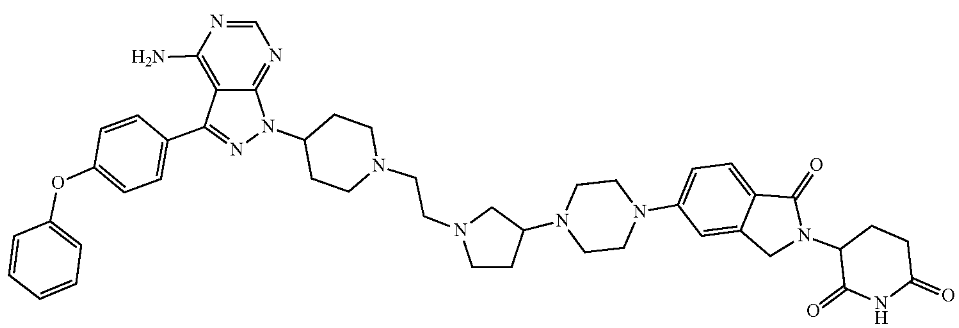 [SMILES: Nc1ncnc2c1c(-c1ccc(Oc3ccccc3)cc1)nn2C1CCN(CCN2CCC(N3CCN(c4ccc5c(c4)CN(C4CCC(=O)NC4=O)C5=O)CC3)C2)CC1] | 3-(5-(4-(1-(2-(4-(4-amino-3-(4-phenoxyphenyl)-1H-pyrazolo[3,4-d]pyrimidin-1-yl)ethyl)pyrrolidin-3-yl)piperazin-1-yl)piperidin-1-yl)-1-oxoisoindolin-2-yl)piperidine-2,6-dione | 809.41 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 461 | 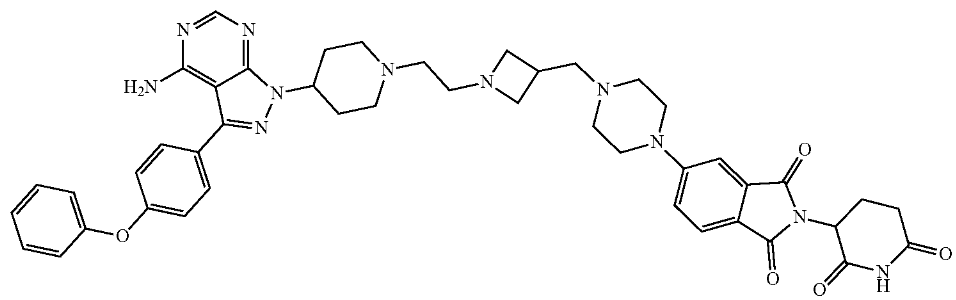 [SMILES: Nc1ncnc2c1c(-c1ccc(Oc3ccccc3)cc1)nn2C1CCN(CCN2CC(CN3CCN(c4ccc5c(c4)C(=O)N(C4CCC(=O)NC4=O)C5=O)CC3)C2)CC1] | 5-(4-((1-(2-(4-(4-amino-3-(4-phenoxyphenyl)-1H-pyrazolo[3,4-d]pyrimidin-1-yl)piperidin-1-yl)ethyl)azetidin-3-yl)methyl)piperazin-1-yl)-2-(2,6-dioxopiperidin-3-yl)isoindoline-1,3-dione | 823.39 | A | A | A | A |
| 462 | 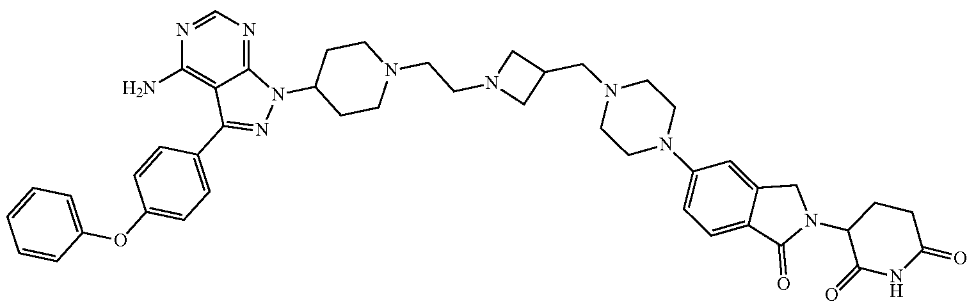 [SMILES: Nc1ncnc2c1c(-c1ccc(Oc3ccccc3)cc1)nn2C1CCN(CCN2CC(CN3CCN(c4ccc5c(c4)CN(C4CCC(=O)NC4=O)C5=O)CC3)C2)CC1] | 3-(5-(4-((1-(2-(4-(4-amino-3-(4-phenoxyphenyl)-1H-pyrazolo[3,4-d]pyrimidin-1-yl)piperidin-1-yl)ethyl)azetidin-3-yl)methyl)piperazin-1-yl)-1-oxoisoindolin-2-yl)piperidine-2,6-dione | 809.41 | B | B | B | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 463 | 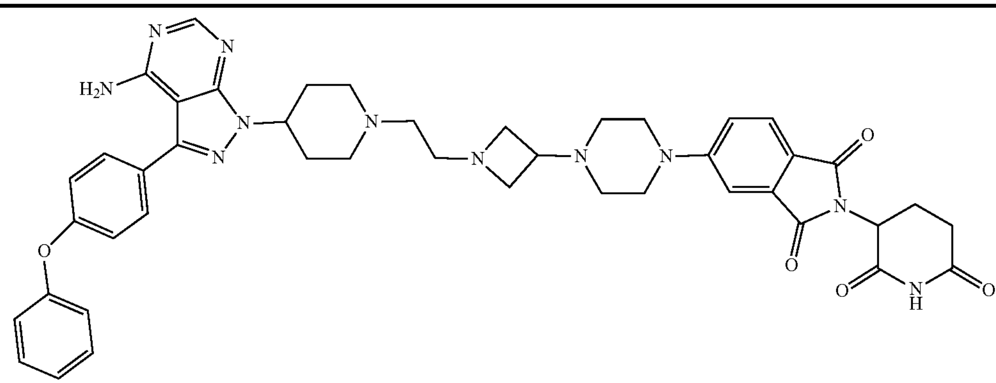 | 5-(4-(1-(2-(4-(4-amino-3-(4-phenoxyphenyl)-1H-pyrazolo[3,4-d]pyrimidin-1-yl)piperidin-1-yl)ethyl)azetidin-3-yl)piperazin-1-yl)-2-(2,6-dioxopiperidin-3-yl)isoindoline-1,3-dione | 809.38 | A | A | B | A |
| 464 | 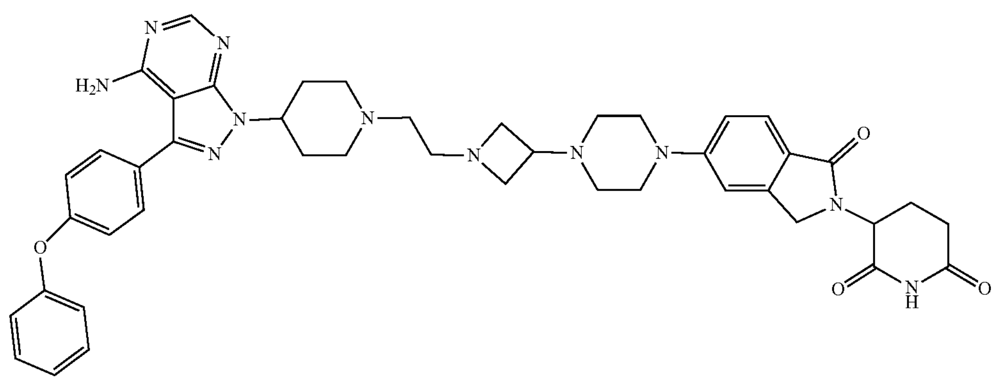 [SMILES: Nc1ncnc2c1c(-c1ccc(Oc3ccccc3)cc1)nn2C1CCN(CCN2CC(N3CCN(c4ccc5c(c4)CN(C4CCC(=O)NC4=O)C5=O)CC3)C2)CC1] | 3-(5-(4-(1-(2-(4-(4-amino-5-(4-phenoxyphenyl)-7H-pyrrolo[2,3-d]pyrimidin-7-yl)piperidin-1-yl)ethyl)azetidin-3-yl)piperazin-1-yl)-1-oxoisoindolin-2-yl)piperidine-2,6-dione | 794.40 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 465 | 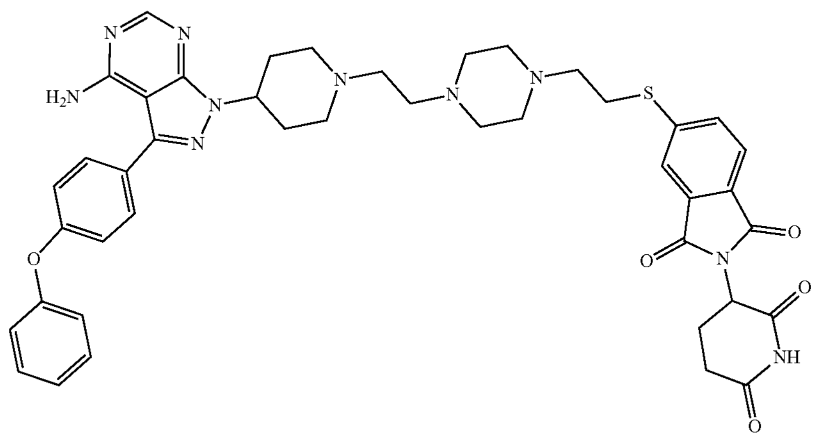 [SMILES: Nc1ncnc2c1c(-c1ccc(Oc3ccccc3)cc1)nn2C1CCN(CCN2CCN(CCSc3ccc4c(c3)C(=O)N(C3CCC(=O)NC3=O)C4=O)CC2)CC1] | 5-((2-(4-(2-(4-(4-amino-3-(4-phenoxyphenyl)-1H-pyrazolo[3,4-d]pyrimidin-1-yl)piperidin-1-yl)ethyl)piperazin-1-yl)ethyl)thio)-2-(2,6-dioxopiperidin-3-yl)isoindoline-1,3-dione | 814.34 | B | B | B | A |
| 466 | 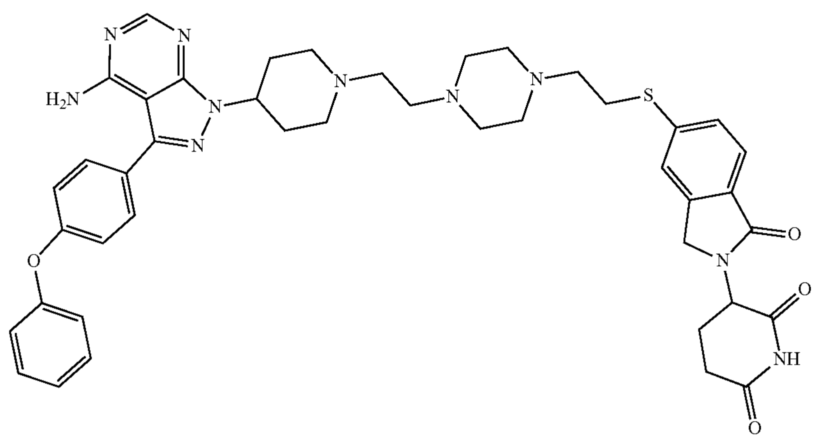 [SMILES: Nc1ncnc2c1c(-c1ccc(Oc3ccccc3)cc1)nn2C1CCN(CCN2CCN(CCSc3ccc4c(c3)CN(C3CCC(=O)NC3=O)C4=O)CC2)CC1] | 3-(5-((2-(4-(2-(4-(4-amino-3-(4-phenoxyphenyl)-1H-pyrazolo[3,4-d]pyrimidin-1-yl)piperidin-1-yl)ethyl)piperazin-1-yl)ethyl)thio)-1-oxoisoindolin-2-yl)piperidine-2,6-dione | 800.36 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 467 | 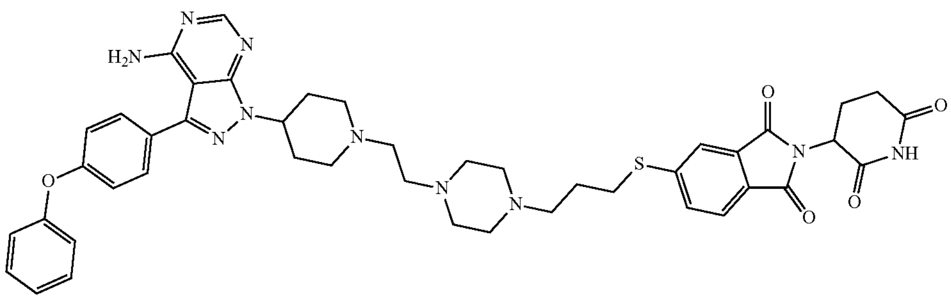 [SMILES: Nc1ncnc2c1c(-c1ccc(Oc3ccccc3)cc1)nn2C1CCN(CCN2CCN(CCCSc3ccc4c(c3)C(=O)N(C3CCC(=O)NC3=O)C4=O)CC2)CC1] | 5-((3-(4-(2-(4-(4-amino-3-(4-phenoxyphenyl)-1H-pyrazolo[3,4-d]pyrimidin-1-yl)piperidin-1-yl)ethyl)piperazin-1-yl)propyl)thio)-2-(2,6-dioxopiperidin-3-yl)isoindoline-1,3-dione | 828.35 | B | B | B | A |
| 468 | 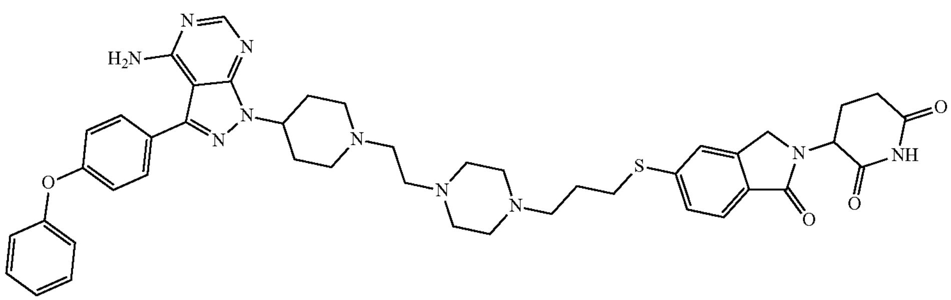 [SMILES: Nc1ncnc2c1c(-c1ccc(Oc3ccccc3)cc1)nn2C1CCN(CCN2CCN(CCCSc3ccc4c(c3)CN(C3CCC(=O)NC3=O)C4=O)CC2)CC1] | 3-(5-((3-(4-(2-(4-(4-amino-3-(4-phenoxyphenyl)-1H-pyrazolo[3,4-d]pyrimidin-1-yl)piperidin-1-yl)ethyl)piperazin-1-yl)propyl)thio)-1-oxoisoindolin-2-yl)piperidine-2,6-dione | 814.37 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 469 | 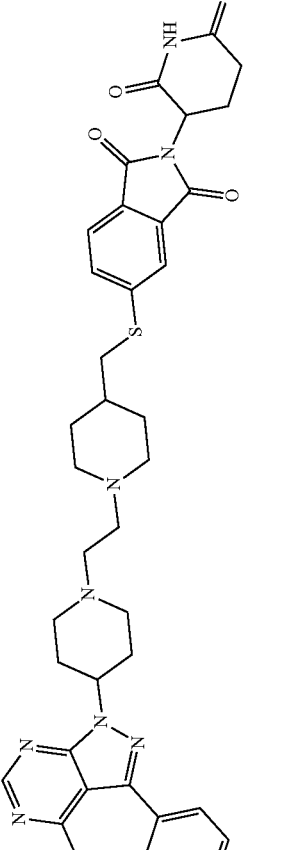 | 5-(((1-(2-(4-(4-amino-3-(4-phenoxyphenyl)-1H-pyrazolo[3,4-d]pyrimidin-1-yl)piperidin-1-yl)ethyl)piperidin-4-yl)methyl)thio)-2-(2,6-dioxopiperidin-3-yl)isoindoline-1,3-dione | 799.33 | B | B | A | A |
| 470 | 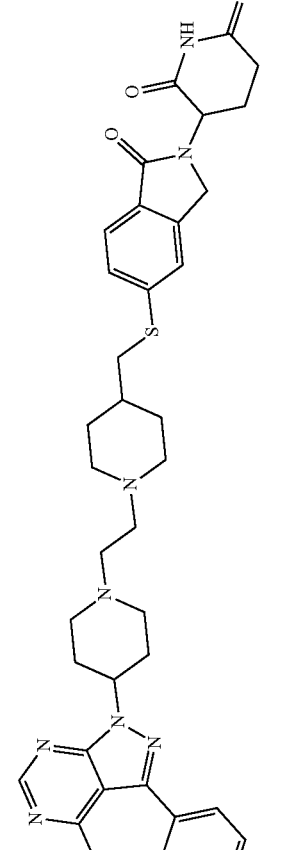 | 3-(5-(((1-(2-(4-(4-amino-3-(4-phenoxyphenyl)-1H-pyrazolo[3,4-d]pyrimidin-1-yl)ethyl)piperidin-4-yl)methyl)thio)-1-oxoisoindolin-2-yl)piperidine-2,6-dione | 784.35 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 471 | 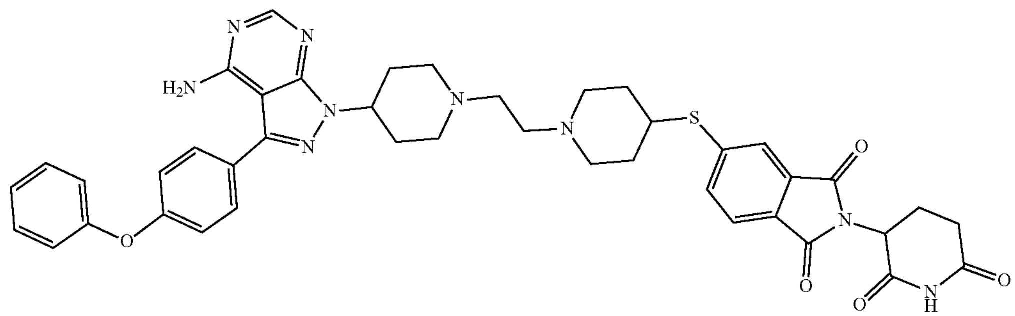 [SMILES: Nc1ncnc2c1c(-c1ccc(Oc3ccccc3)cc1)nn2C1CCN(CCN2CCC(Sc3ccc4c(c3)C(=O)N(C3CCC(=O)NC3=O)C4=O)CC2)CC1] | 5-((1-(2-(4-(4-amino-3-(4-phenoxyphenyl)-1H-pyrazolo[3,4-d]pyrimidin-1-yl)piperidin-1-yl)ethyl)piperidin-4-yl)thio)-2-(2,6-dioxopiperidin-3-yl)isoindoline-1,3-dione | 785.31 | B | B | B | B |
| 472 | 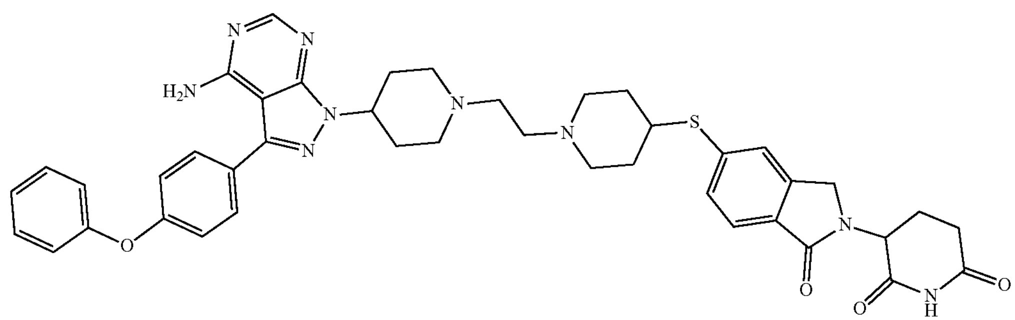 [SMILES: Nc1ncnc2c1c(-c1ccc(Oc3ccccc3)cc1)nn2C1CCN(CCN2CCC(Sc3ccc4c(c3)CN(C3CCC(=O)NC3=O)C4=O)CC2)CC1] | 3-(5-((1-(2-(4-(4-amino-3-(4-phenoxyphenyl)-1H-pyrazolo[3,4-d]pyrimidin-1-yl)piperidin-4-yl)thio)-1-oxoisoindolin-2-yl)piperidine-2,6-dione | 771.33 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 473 | 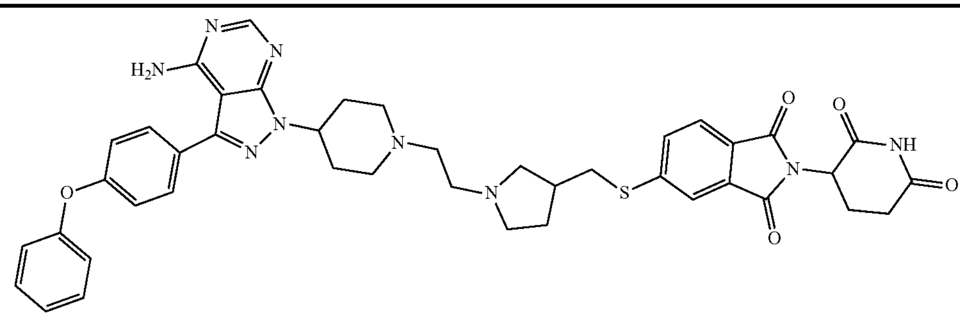 | 5-(((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)thio)-2-(2,6-dioxopiperidin-3-yl)isoindoline-1,3-dione | 785.31 | B | B | B | A |
| 474 | 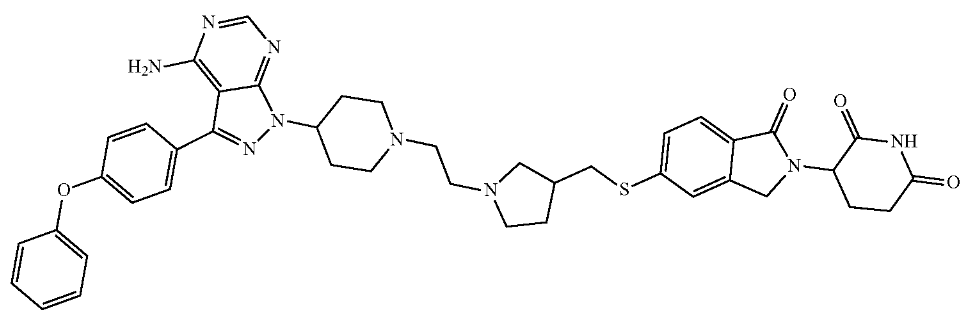 [SMILES: Nc1ncnc2c1c(-c1ccc(Oc3ccccc3)cc1)nn2C1CCN(CCN2CCC(CSc3ccc4c(c3)CN(C3CCC(=O)NC3=O)C4=O)C2)CC1] | 3-(5-(((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)thio)-1-oxoisoindolin-2-yl)piperidine-2,6-dione | 771.33 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 475 | 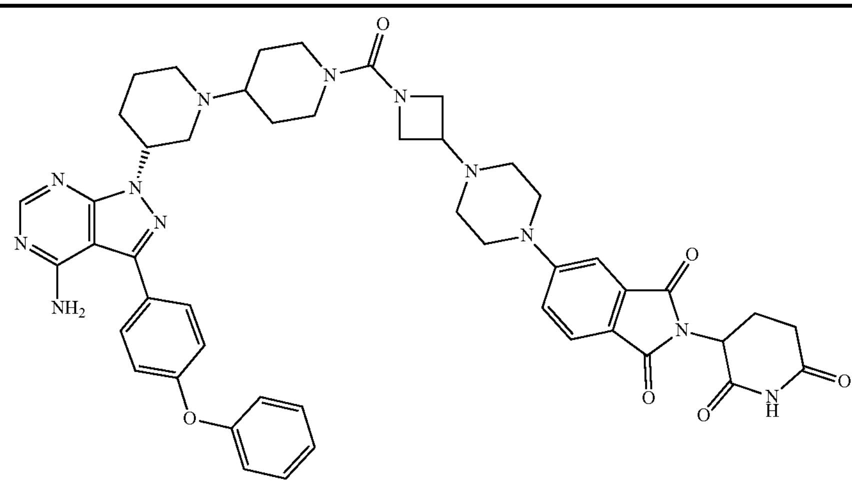 | 5-(4-(1-((R)-3-(4-amino-3-(4-phenoxyphenyl)-1H-pyrazolo[3,4-d]pyrimidin-1-yl)-[1,4'-bipiperidine]-1'-carbonyl)azetidin-3-yl)piperazin-1-yl)-2-(2,6-dioxopiperidin-3-yl)isoindoline-1,3-dione | 892.41 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 476 | 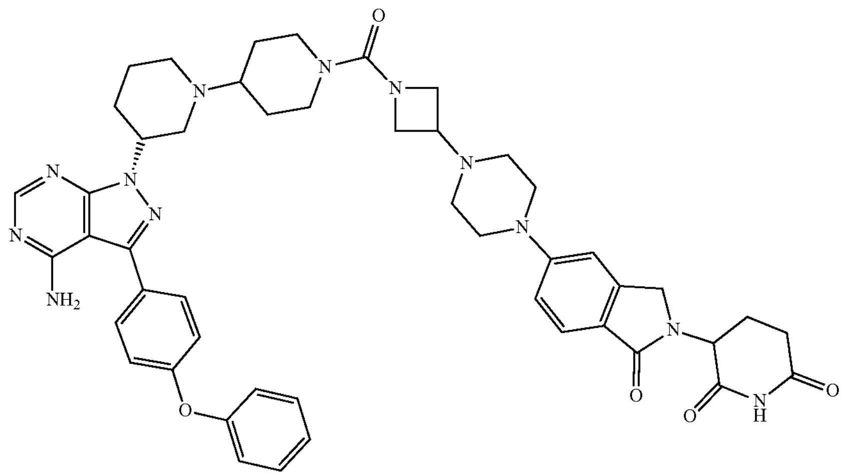 | 3-(5-(4-(1-((R)-3-(4-amino-3-(4-phenoxyphenyl)-1H-pyrazolo[3,4-d]pyrimidin-1-yl)-[1,4'-bipiperidine]-1'-carbonyl)azetidin-3-yl)piperazin-1-yl)-1-oxoisoindolin-2-yl)piperidine-2,6-dione | 878.43 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 477 | 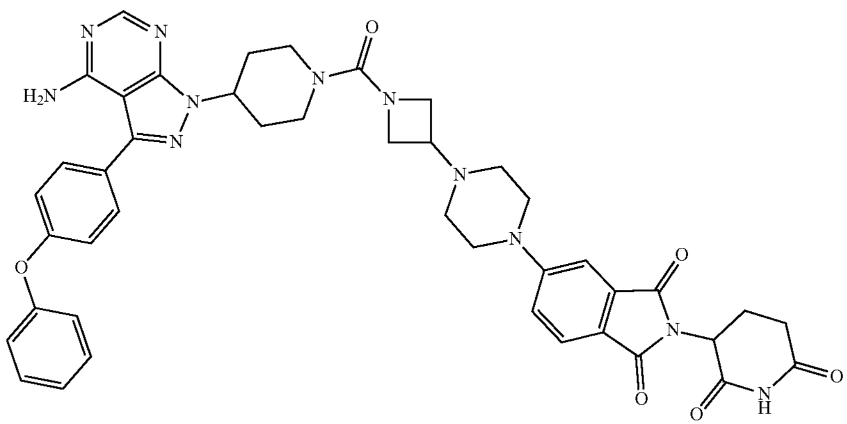 [SMILES: Nc1ncnc2c1c(-c1ccc(Oc3ccccc3)cc1)nn2C1CCN(C(=O)N2CC(N3CCN(c4ccc5c(c4)C(=O)N(C4CCC(=O)NC4=O)C5=O)CC3)C2)CC1] | 5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-2-(2,6-dioxopiperidin-3-yl)isoindoline-1,3-dione | 809.43 | A | A | A | A |
| 478 | 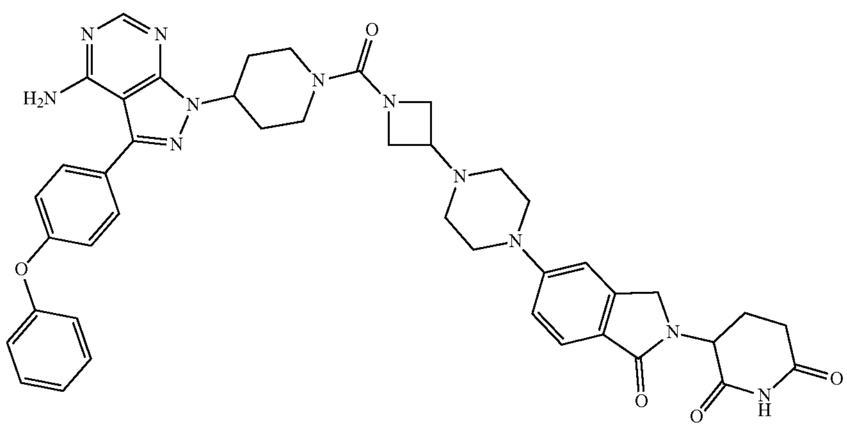 [SMILES: Nc1ncnc2c1c(-c1ccc(Oc3ccccc3)cc1)nn2C1CCN(C(=O)N2CC(N3CCN(c4ccc5c(c4)CN(C4CCC(=O)NC4=O)C5=O)CC3)C2)CC1] | 3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione | 795.36 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | $IC_{50}$ (anti-proliferation) JeKO-1 cells | $IC_{50}$ (anti-proliferation) Mino cells | $DC_{50}$ | $D_{max}$ |
|---|---|---|---|---|---|---|---|
| 479 | 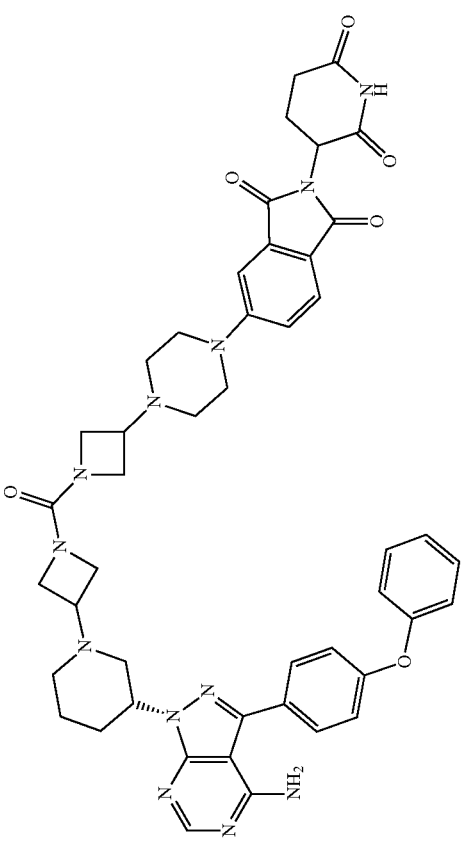 | 5-(4-(1-(3-((R)-3-(4-amino-3-(4-phenoxyphenyl)-1H-pyrazolo[3,4-d]pyrimidin-1-yl)piperidin-1-yl)azetidin-1-yl)piperidin-1-yl)azetidin-1-yl)piperidin-3-yl)piperazin-1-yl)-2-(2,6-dioxopiperidin-3-yl)isoindoline-1,3-dione | 864.38 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 480 | 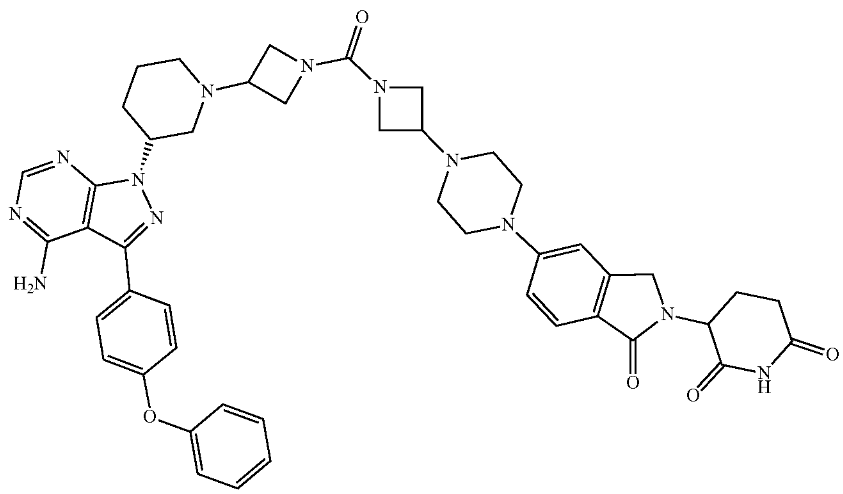 | 3-(5-(4-(1-(3-((R)-3-(4-amino-3-(4-phenoxyphenyl)-1H-pyrazolo[3,4-d]pyrimidin-1-yl)piperidin-1-yl)azetidin-1-carbonyl)azetidin-3-yl)piperazin-1-yl)-1-oxoisoindolin-2-yl)piperidine-2,6-dione | 850.40 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 481 | 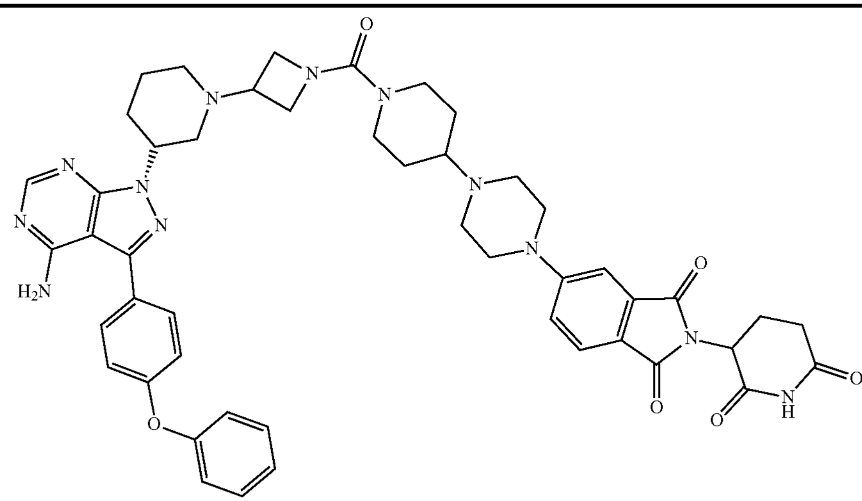 | 5-(4-(1-(3-((R)-3-(4-amino-3-(4-phenoxyphenyl)-1H-pyrazolo[3,4-d]pyrimidin-1-yl)piperidin-1-yl)azetidin-1-carbonyl)piperidin-4-yl)piperazin-1-yl)-2-(2,6-dioxopiperidin-3-yl)isoindoline-1,3-dione | 892.41 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 482 | 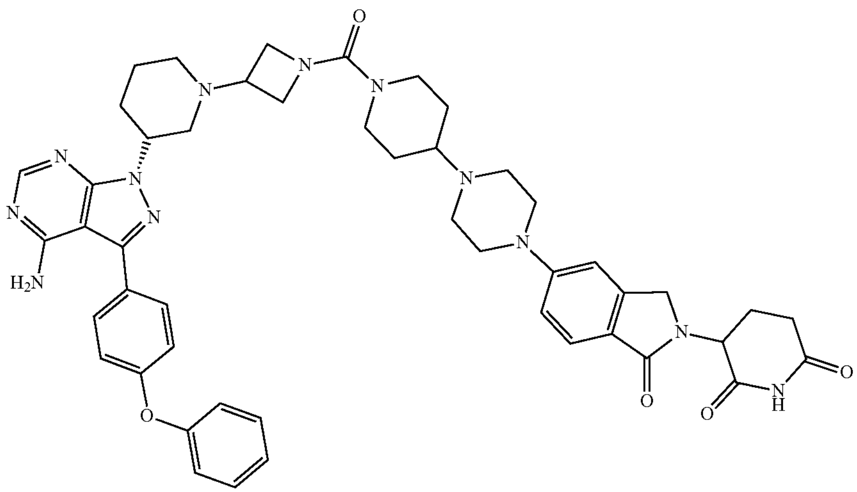 | 3-(5-(4-(1-(3-((R)-3-(4-amino-3-(4-phenoxyphenyl)-1H-pyrazolo[3,4-d]pyrimidin-1-yl)piperidin-1-yl)azetidin-1-carbonyl)piperidin-4-yl)piperazin-1-yl)-1-oxoisoindolin-2-yl)piperidine-2,6-dione | 878.43 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 483 | 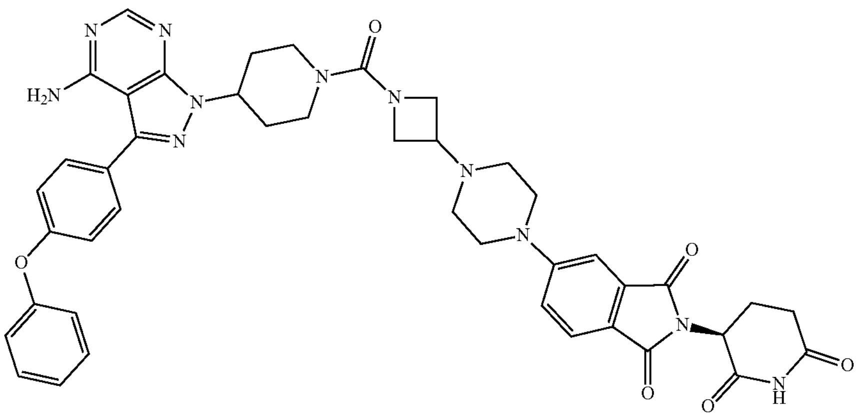 [SMILES: Nc1ncnc2c1c(-c1ccc(Oc3ccccc3)cc1)nn2C1CCN(C(=O)N2CC(N3CCN(c4ccc5c(c4)C(=O)N([C@H]4CCC(=O)NC4=O)C5=O)CC3)C2)CC1] | (S)-5-(4-(1-(4-(4-amino-3-(4-phenoxyphenyl)-1H-pyrazolo[3,4-b]pyrimidin-1-yl)piperidine-1-carbonyl)azetidin-3-yl)piperazin-1-yl)-2-(2,6-dioxopiperidin-3-yl)isoindoline-1,3-dione | 809.34 | B | A | A | A |
| 484 | 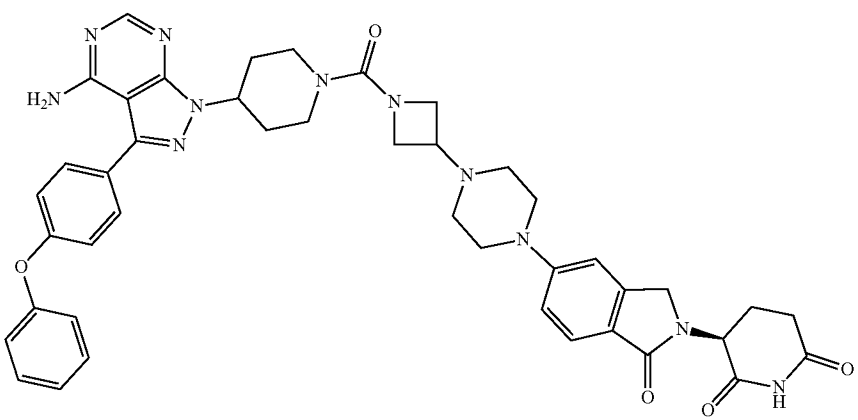 [SMILES: Nc1ncnc2c1c(-c1ccc(Oc3ccccc3)cc1)nn2C1CCN(C(=O)N2CC(N3CCN(c4ccc5c(c4)CN([C@H]4CCC(=O)NC4=O)C5=O)CC3)C2)CC1] | (S)-3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione | 795.36 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 485 | 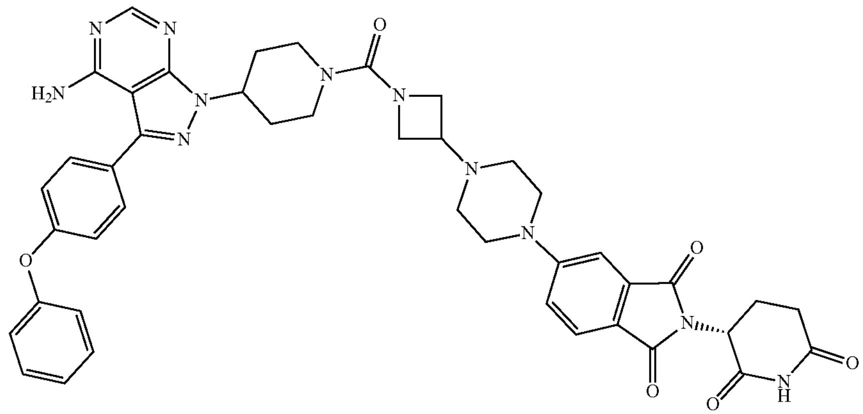 [SMILES: Nc1ncnc2c1c(-c1ccc(Oc3ccccc3)cc1)nn2C1CCN(C(=O)N2CC(N3CCN(c4ccc5c(c4)C(=O)N([C@@H]4CCC(=O)NC4=O)C5=O)CC3)C2)CC1] | (R)-5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-2-(2,6-dioxopiperidin-3-yl)isoindoline-1,3-dione | 809.34 | A | A | A | A |
| 486 | 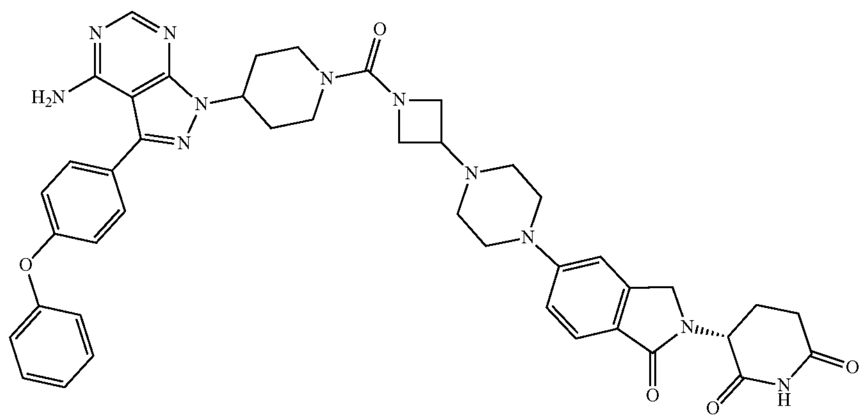 [SMILES: Nc1ncnc2c1c(-c1ccc(Oc3ccccc3)cc1)nn2C1CCN(C(=O)N2CC(N3CCN(c4ccc5c(c4)CN([C@@H]4CCC(=O)NC4=O)C5=O)CC3)C2)CC1] | (R)-3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione | 795.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 487 | 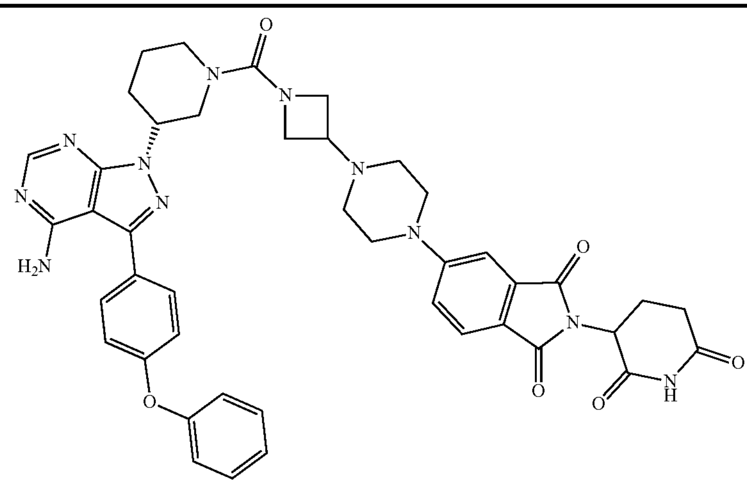 | 5-(4-(1-((R)-3-(4-amino-3-(4-phenoxyphenyl)-1H-pyrazolo[3,4-d]pyrimidin-1-yl)piperidine-1-carbonyl)azetidin-3-yl)piperazin-1-yl)-2-(2,6-dioxopiperidin-3-yl)isoindoline-1,3-dione | 809.34 | A | A | A | A |

TABLE 1-continued

Exemplary compounds of the present invention.
Antiproliferation in mantle cell lymphoma cell (Mino or JeKo-1).

| # | IUPAC Name | Structure | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 488 | 3-(5-(4-(1-((R)-3-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione | 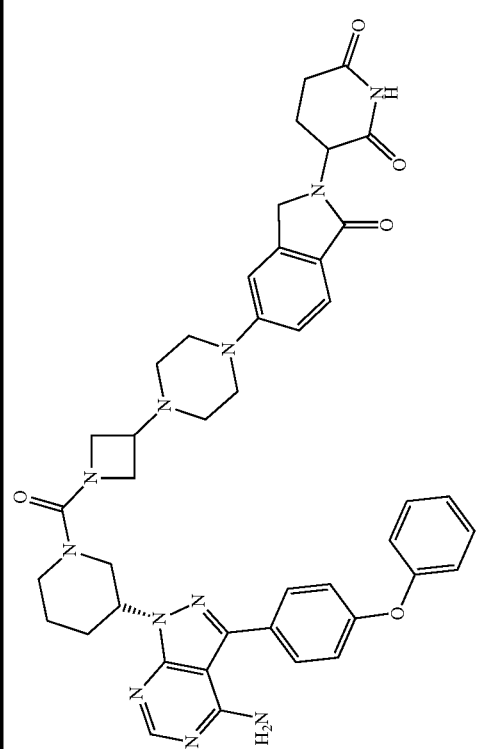 | 795.36 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 489 | 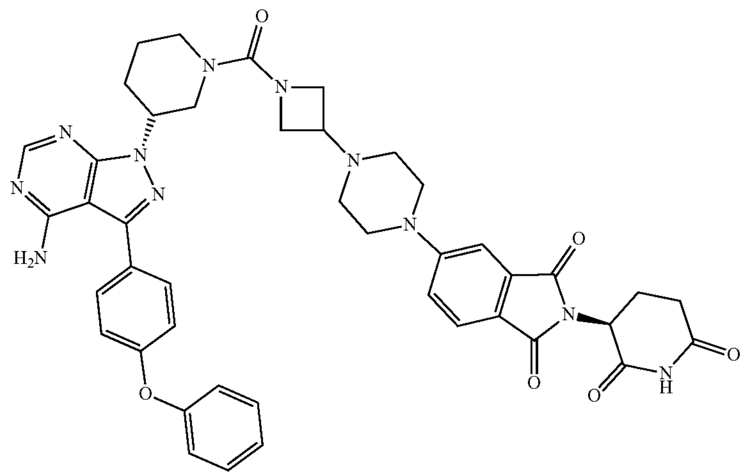 | 5-(4-(1-(R)-3-(4-amino-3-(4-phenoxyphenyl)-1H-pyrazolo[3,4-d]pyrimidin-1-yl)piperidine-1-carbonyl)azetidin-3-yl)piperazin-1-yl)-2-((S)-2,6-dioxopiperidin-3-yl)isoindoline-1,3-dione | 809.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 490 | 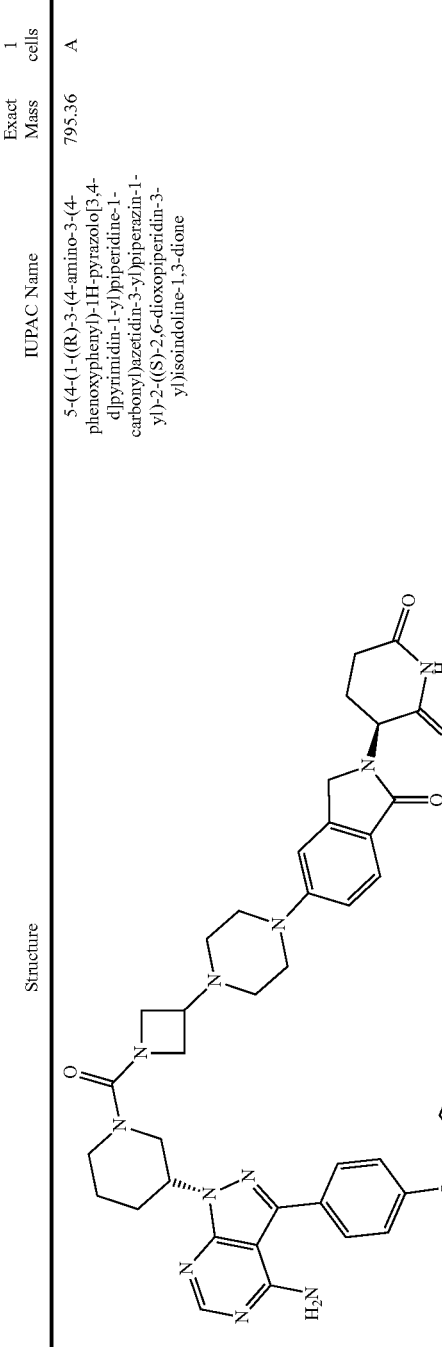 | 5-(4-(1-((R)-3-(4-amino-3-(4-phenoxyphenyl)-1H-pyrazolo[3,4-d]pyrimidin-1-yl)piperidine-1-carbonyl)azetidin-3-yl)piperazin-1-yl)-2-((S)-2,6-dioxopiperidin-3-yl)isoindoline-1,3-dione | 795.36 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 491 | 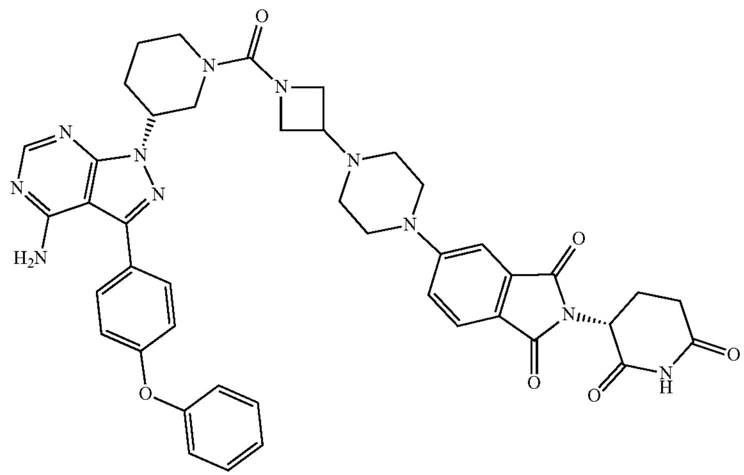 | 5-(4-(1-((R)-3-(4-amino-3-(4-phenoxyphenyl)-1H-pyrazolo[3,4-d]pyrimidin-1-yl)piperidine-1-carbonyl)azetidin-3-yl)piperazin-1-yl)-2-((R)-2,6-dioxopiperidin-3-yl)isoindoline-1,3-dione | 809.34 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 492 | 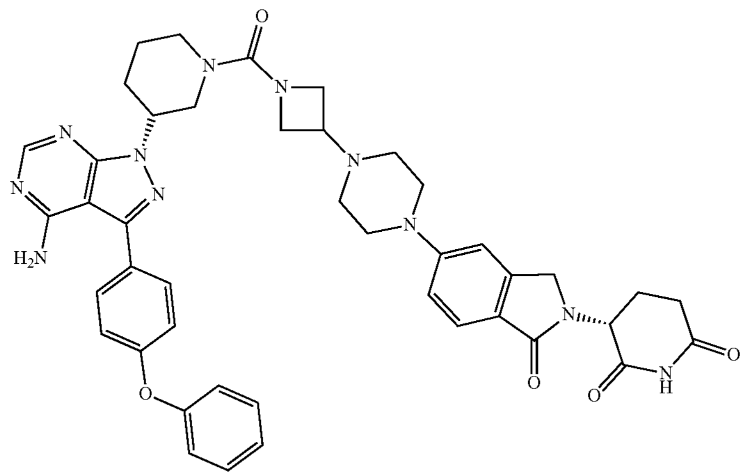 | (R)-3-(5-(4-(1-((R)-3-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione | 795.36 | A | A | A | A |
| 493 | 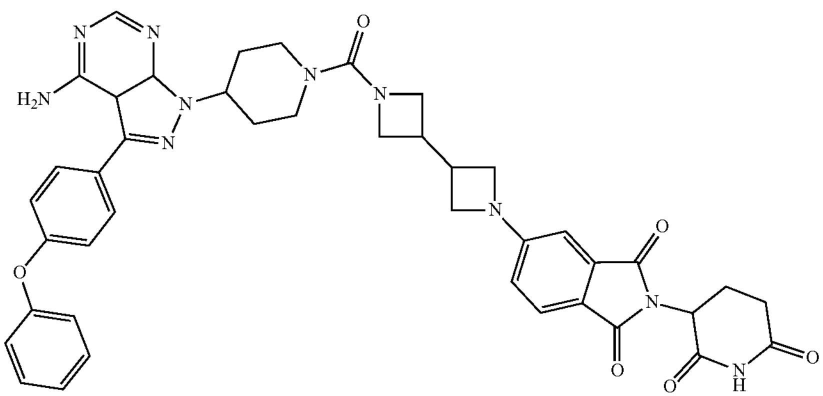 [SMILES: NC1=NC=NC2C1C(c1ccc(Oc3ccccc3)cc1)=NN2C1CCN(C(=O)N2CC(C3CN(c4ccc5c(c4)C(=O)N(C4CCC(=O)NC4=O)C5=O)C3)C2)CC1] | 5-(1'-(4-(4-amino-3-(4-phenoxyphenyl)-3a,7a-dihydro-1H-pyrazolo[3,4-d]pyrimidin-1-yl)piperidine-1-carbonyl)-[3,3'-biazetidin]-1-yl)-2-(2,6-dioxopiperidin-3-yl)isoindoline-1,3-dione | 782.33 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 494 | 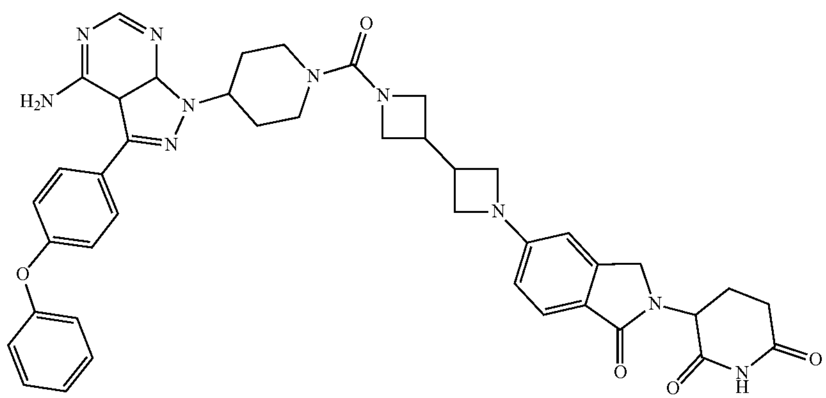 [SMILES: NC1=NC=NC2C1C(c1ccc(Oc3ccccc3)cc1)=NN2C1CCN(C(=O)N2CC(C3CN(c4ccc5c(c4)CN(C4CCC(=O)NC4=O)C5=O)C3)C2)CC1] | 3-(5-(1'-(4-(4-amino-3-(4-phenoxyphenyl)-3a,7a-dihydro-1H-pyrazolo[3,4-d]pyrimidin-1-yl)piperidine-1-carbonyl)-[3,3'-biazetidin]-1-yl)-1-oxoisoindolin-2-yl)piperidine-2,6-dione | 767.39 | A | A | A | A |
| 495 | 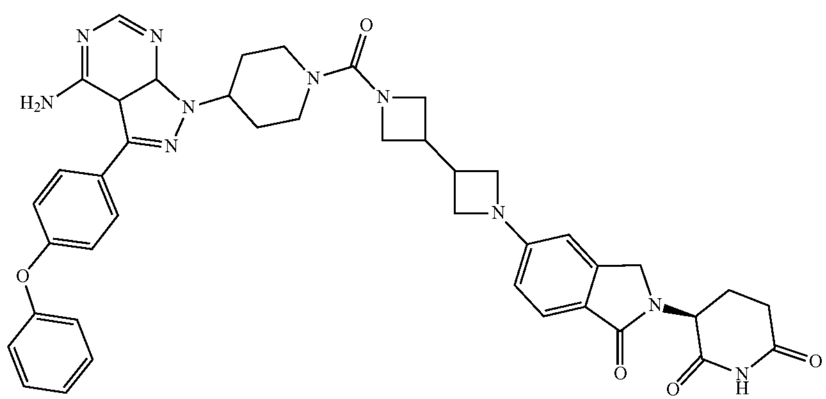 [SMILES: NC1=NC=NC2C1C(c1ccc(Oc3ccccc3)cc1)=NN2C1CCN(C(=O)N2CC(C3CN(c4ccc5c(c4)CN([C@H]4CCC(=O)NC4=O)C5=O)C3)C2)CC1] | (3S)-3-(5-(1'-(4-(4-amino-3-(4-phenoxyphenyl)-3a,7a-dihydro-1H-pyrazolo[3,4-d]pyrimidin-1-yl)piperidine-1-carbonyl)-[3,3'-biazetidin]-1-yl)-1-oxoisoindolin-2-yl)piperidine-2,6-dione | 768.35 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 496 | 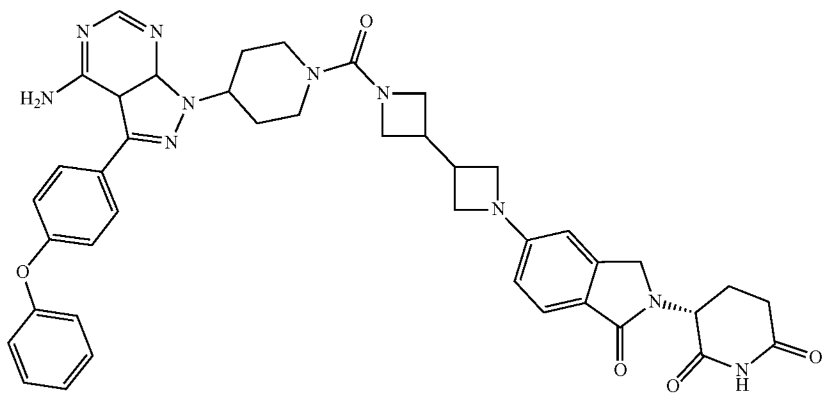 [SMILES: NC1=NC=NC2C1C(c1ccc(Oc3ccccc3)cc1)=NN2C1CCN(C(=O)N2CC(C3CN(c4ccc5c(c4)CN([C@@H]4CCC(=O)NC4=O)C5=O)C3)C2)CC1] | (3R)-3-(5-(1'-(4-(4-amino-3-(4-phenoxyphenyl)-3a,7a-dihydro-1H-pyrazolo[3,4-d]pyrimidin-1-yl)piperidine-1-carbonyl)-[3,3'-biazetidin]-1-yl)-1-oxoisoindolin-2-yl)piperidine-2,6-dione | 768.35 | A | A | A | A |
| 497 | 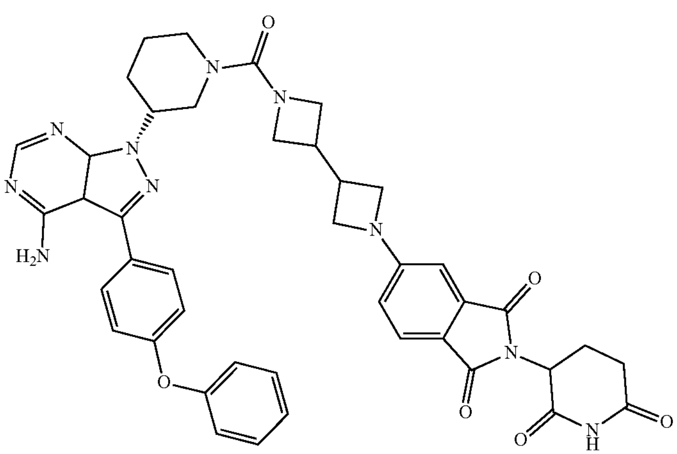 | 5-(1'-((3R)-3-(4-amino-3-(4-phenoxyphenyl)-3a,7a-dihydro-1H-pyrazolo[3,4-d]pyrimidin-1-yl)piperidine-1-carbonyl)-[3,3'-biazetidin]-1-yl)-2-(2,6-dioxopiperidin-3-yl)isoindoline-1,3-dione | 768.35 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 498 | 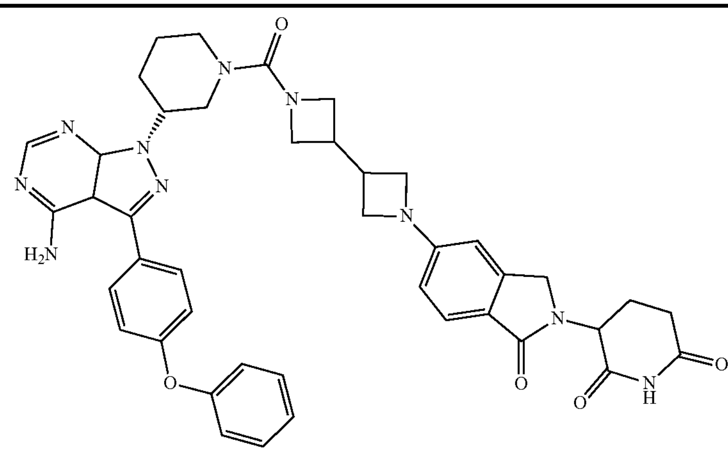 | 3-(5-(1'-((3R)-3-(4-amino-3-(4-phenoxyphenyl)-3a,7a-dihydro-1H-pyrazolo[3,4-d]pyrimidin-1-yl)piperidin-1-carbonyl)-[3,3'-biazetidin]-1-yl)-1-oxoisoindolin-2-yl)piperidine-2,6-dione | 768.35 | A | A | A | A |
| 499 | 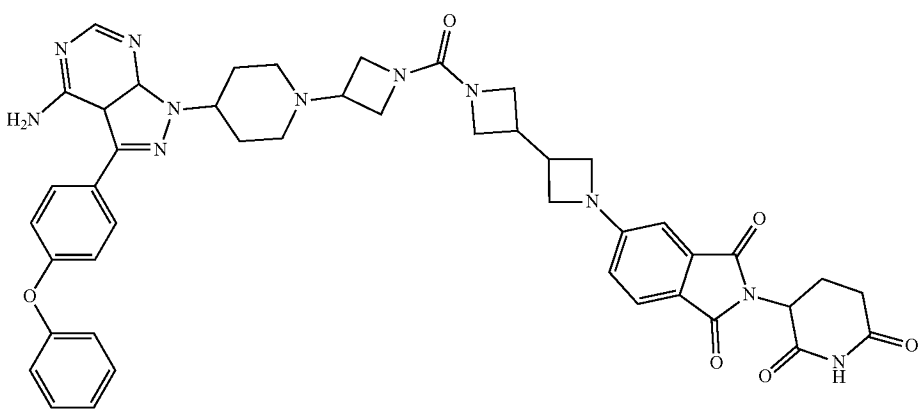 [SMILES: NC1=NC=NC2C1C(c1ccc(Oc3ccccc3)cc1)=NN2C1CCN(C2CN(C(=O)N3CC(C4CN(c5ccc6c(c5)C(=O)N(C5CCC(=O)NC5=O)C6=O)C4)C3)C2)CC1] | 5-(1'-(3-(4-(4-amino-3-(4-phenoxyphenyl)-3a,7a-dihydro-1H-pyrazolo[3,4-d]pyrimidin-1-yl)piperidin-1-yl)azetidine-1-carbonyl)-[3,3'-biazetidin]-1-yl)-2-(2,6-dioxopiperidin-3-yl)isoindoline-1,3-dione | 837.37 | B | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 500 | 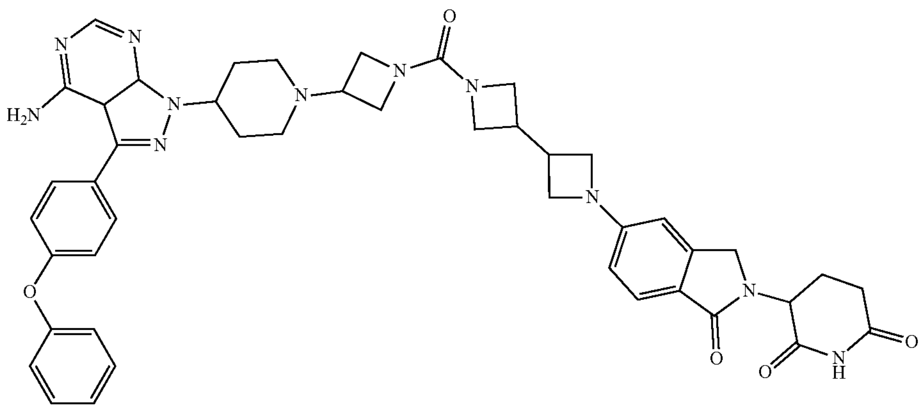 [SMILES: NC1=NC=NC2C1C(c1ccc(Oc3ccccc3)cc1)=NN2C1CCN(C2CN(C(=O)N3CC(C4CN(c5ccc6c(c5)CN(C5CCC(=O)NC5=O)C6=O)C4)C3)C2)CC1] | 3-(5-(1'-(3-(4-(4-amino-3-(4-phenoxyphenyl)-3a,7a-dihydro-1H-pyrazolo[3,4-d]pyrimidin-1-yl)piperidin-1-yl)azetidine-1-carbonyl)-[3,3'-biazetidin]-1-yl)-1-oxoisoindolin-2-yl)piperidine-2,6-dione | 822.39 | B | A | B | A |
| 501 | 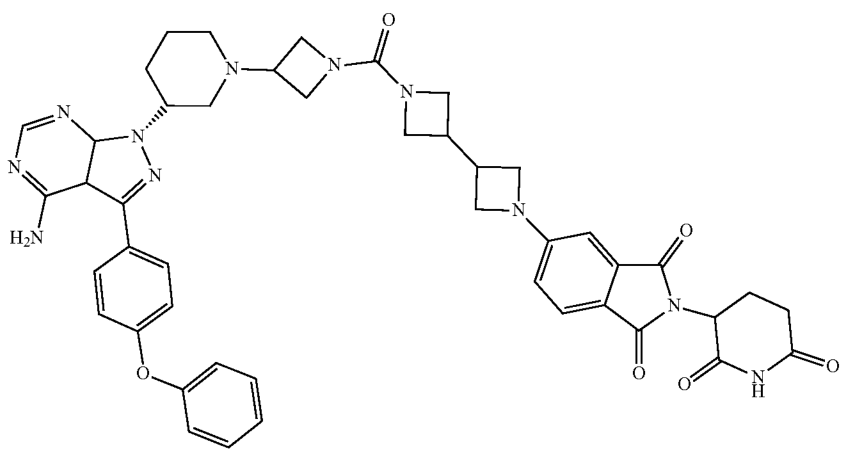 | 3-(5-(1'-(3-((3R)-3-(4-amino-3-(4-phenoxyphenyl)-3a,7a-dihydro-1H-pyrazolo[3,4-d]pyrimidin-1-yl)piperidin-1-yl)azetidine-1-carbonyl)-[3,3'-biazetidin]-1-yl)-1-oxoisoindolin-2-yl)piperidine-2,6-dione | 837.37 | A | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 502 | 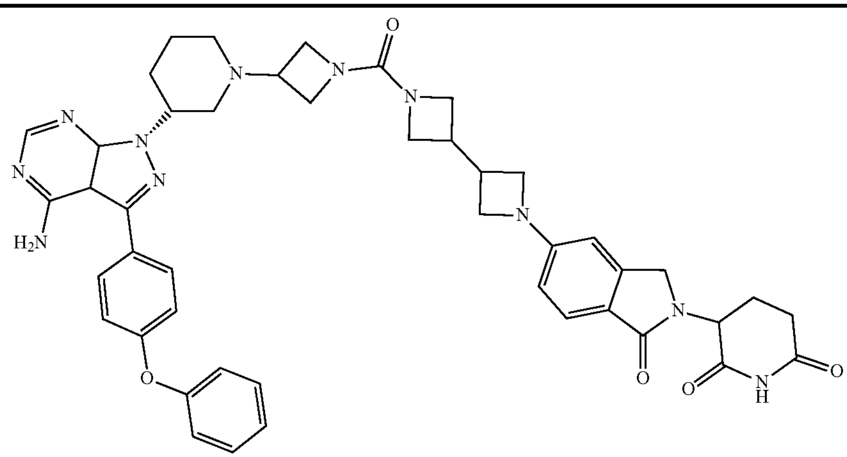 | 5-(1'-(3-((3R)-3-(4-amino-3-(4-phenoxyphenyl)-3a,7a-dihydro-1H-pyrazolo[3,4-d]pyrimidin-1-yl)piperidin-1-yl)azetidine-1-carbonyl)-[3,3'-biazetidin]-1-yl)-2-(2,6-dioxopiperidin-3-yl)isoindoline-1,3-dione | 823.39 | A | A | B | A |
| 503 | 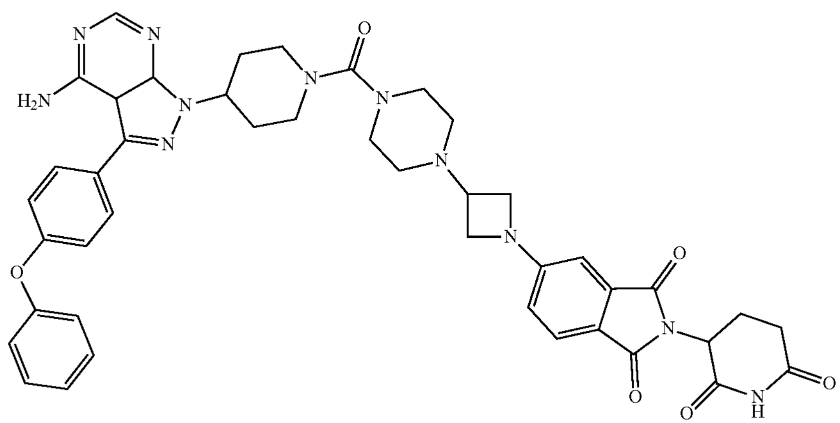 [SMILES: NC1=NC=NC2C1C(c1ccc(Oc3ccccc3)cc1)=NN2C1CCN(C(=O)N2CCN(C3CN(c4ccc5c(c4)C(=O)N(C4CCC(=O)NC4=O)C5=O)C3)CC2)CC1] | 5-(3-(4-(4-(4-amino-3-(4-phenoxyphenyl)-3a,7a-dihydro-1H-pyrazolo[3,4-d]pyrimidin-1-yl)piperidine-1-carbonyl)piperazin-1-yl)azetidin-1-yl)-2-(2,6-dioxopiperidin-3-yl)isoindoline-1,3-dione | 811.36 | A | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 504 | 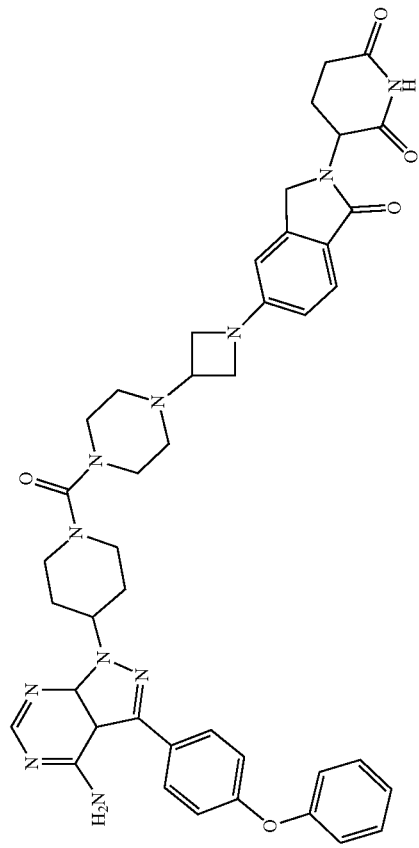 | 3-(5-(3-(4-(4-(4-amino-3-(4-phenoxyphenyl)-3a,7a-dihydro-1H-pyrazolo[3,4-d]pyrimidin-1-yl)piperidine-1-carbonyl)piperazin-1-yl)azetidin-1-yl)-1-oxoisoindolin-2-yl)piperidine-2,6-dione | 797.38 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 505 | 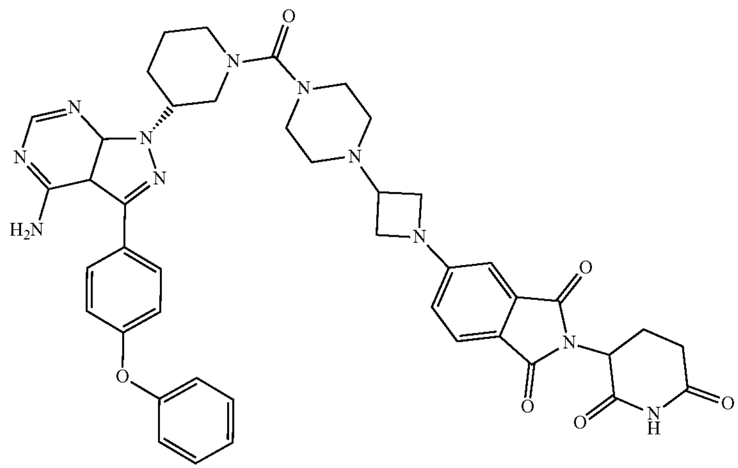 | 5-(3-(4-((3R)-3-(4-amino-3-(4-phenoxyphenyl)-3a,7a-dihydro-1H-pyrazolo[3,4-d]pyrimidin-1-yl)piperidine-1-carbonyl)piperazin-1-yl)azetidin-1-yl)-2-(2,6-dioxopiperidin-3-yl)isoindoline-1,3-dione | 811.36 | A | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 506 | 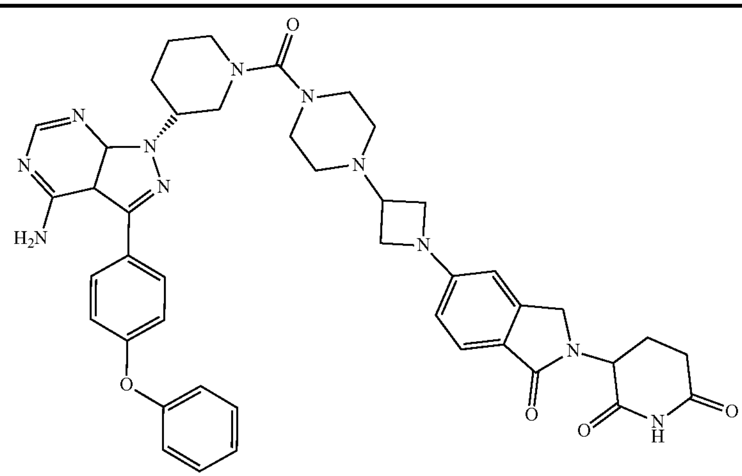 | 3-(5-(3-(4-((3R)-3-(4-amino-3-(4-phenoxyphenyl)-3a,7a-dihydro-1H-pyrazolo[3,4-d]pyrimidin-1-yl)piperidine-1-carbonyl)piperazin-1-yl)azetidin-1-yl)-1-oxoisoindolin-2-yl)piperidine-2,6-dione | 797.38 | A | A | B | A |
| 507 | 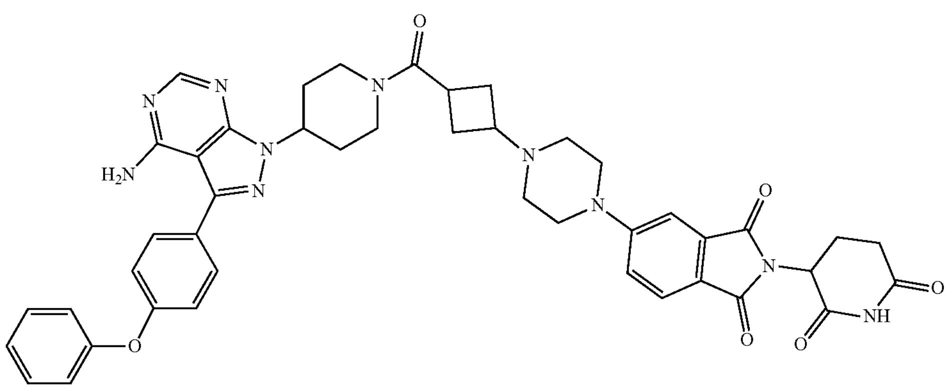 [SMILES: Nc1ncnc2c1c(-c1ccc(Oc3ccccc3)cc1)nn2C1CCN(C(=O)C2CC(N3CCN(c4ccc5c(c4)C(=O)N(C4CCC(=O)NC4=O)C5=O)CC3)C2)CC1] | 5-(4-(3-(4-(4-amino-3-(4-phenoxyphenyl)-1H-pyrazolo[3,4-d]pyrimidin-1-yl)piperidine-1-carbonyl)cyclobutyl)piperazin-1-yl)-2-(2,6-dioxopiperidin-3-yl)isoindoline-1,3-dione | 808.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 508 | 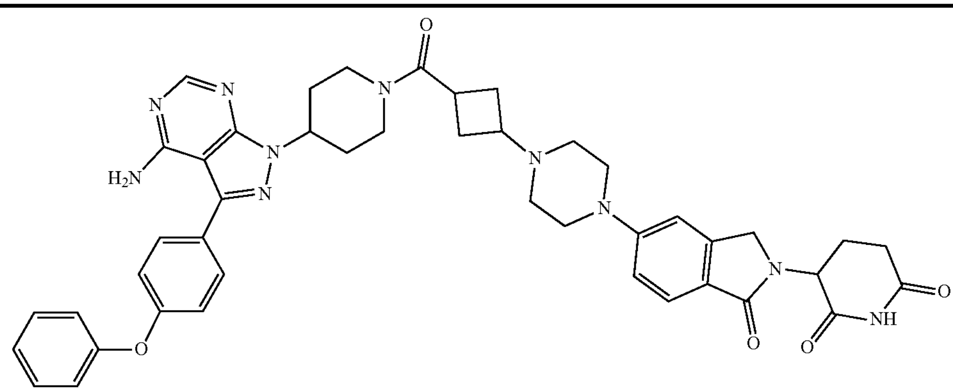 | 3-(5-(4-(3-(4-(4-amino-3-(4-phenoxyphenyl)-1H-pyrazolo[3,4-d]pyrimidin-1-yl)piperidine-1-carbonyl)cyclobutyl)piperazin-1-yl)-1-oxoisoindolin-2-yl)piperidine-2,6-dione | 794.37 | A | A | A | A |
| 509 | 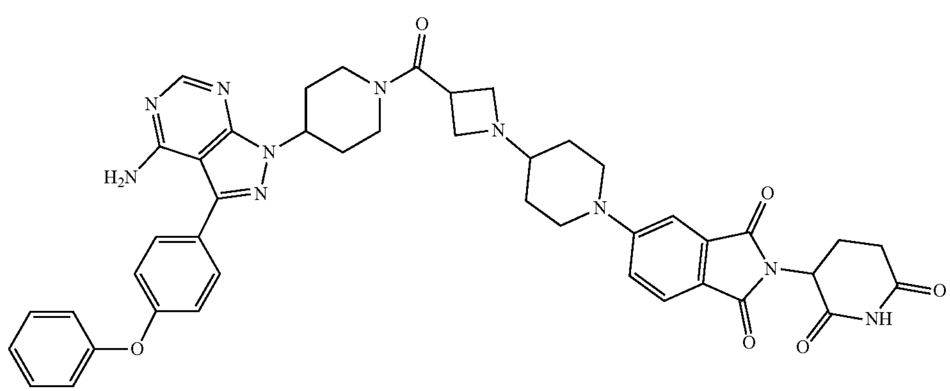 [SMILES: Nc1ncnc2c1c(-c1ccc(Oc3ccccc3)cc1)nn2C1CCN(C(=O)C2CN(C3CCN(c4ccc5c(c4)C(=O)N(C4CCC(=O)NC4=O)C5=O)CC3)C2)CC1] | 5-(4-(3-(4-(4-amino-3-(4-phenoxyphenyl)-1H-pyrazolo[3,4-d]pyrimidin-1-yl)piperidine-1-carbonyl)azetidin-1-yl)piperidin-1-yl)-2-(2,6-dioxopiperidin-3-yl)isoindoline-1,3-dione | 808.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 510 | 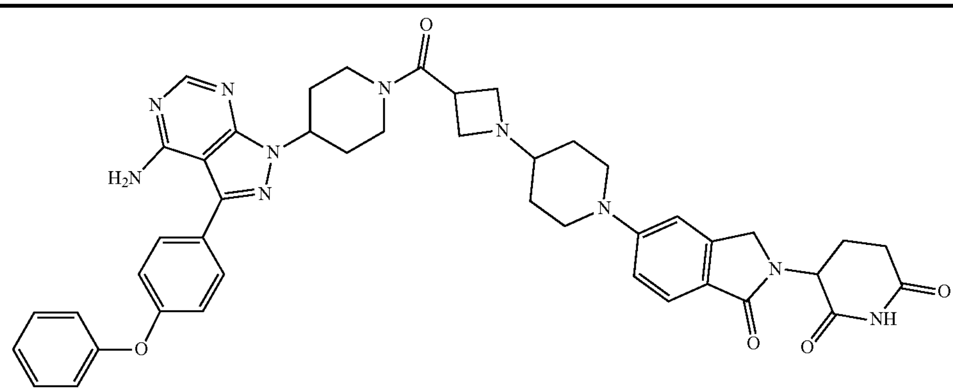 | 3-(5-(4-(3-(4-(4-amino-3-(4-phenoxyphenyl)-1H-pyrazolo[3,4-d]pyrimidin-1-yl)piperidine-1-carbonyl)azetidin-1-yl)piperidin-1-yl)-1-oxoisoindolin-2-yl)piperidine-2,6-dione | 794.37 | A | A | A | A |
| 511 | 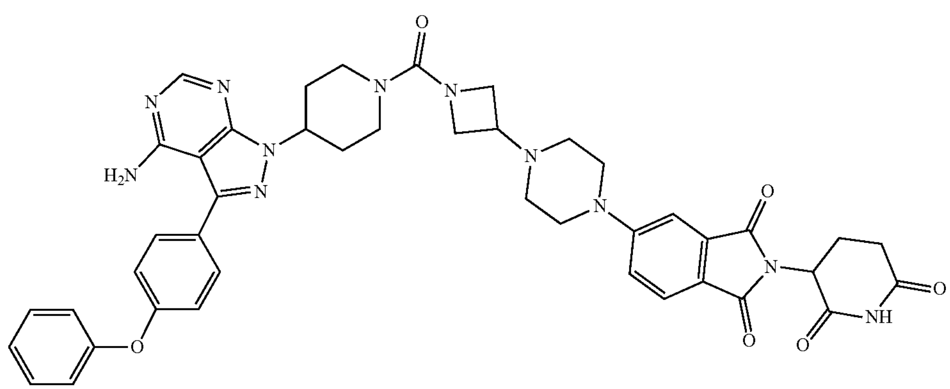 [SMILES: Nc1ncnc2c1c(-c1ccc(Oc3ccccc3)cc1)nn2C1CCN(C(=O)N2CC(N3CCN(c4ccc5c(c4)C(=O)N(C4CCC(=O)NC4=O)C5=O)CC3)C2)CC1] | 5-(4-(1-(4-(4-amino-3-(4-phenoxyphenyl)-1H-pyrazolo[3,4-d]pyrimidin-1-yl)cyclohexane-1-carbonyl)-152-zetidine-3-yl)piperazin-1-yl)-2-(2,6-dioxopiperidin-3-yl)isoindoline-1,3-dione | 808.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 512 | 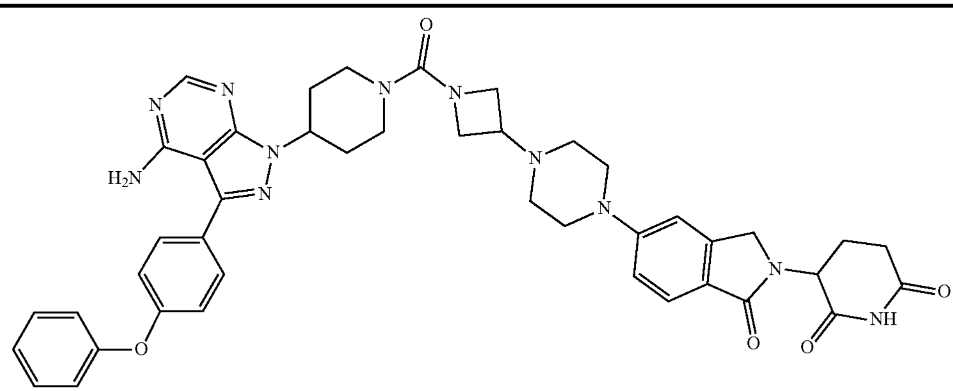 | 3-(5-(4-(1-(4-(4-amino-3-(4-phenoxyphenyl)-1H-pyrazolo[3,4-d]pyrimidin-1-yl)cyclohexane-1-carbonyl)azetidin-3-yl)piperazin-1-yl)-1-oxoisoindolin-2-yl)piperidine-2,6-dione | 794.37 | A | A | A | A |
| 513 | 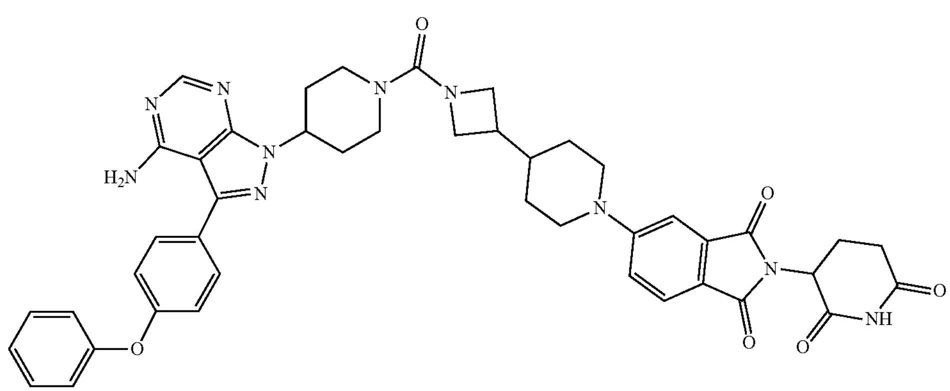 [SMILES: Nc1ncnc2c1c(-c1ccc(Oc3ccccc3)cc1)nn2C1CCN(C(=O)N2CC(C3CCN(c4ccc5c(c4)C(=O)N(C4CCC(=O)NC4=O)C5=O)CC3)C2)CC1] | 5-(4-(1-(4-(4-amino-3-(4-phenoxyphenyl)-1H-pyrazolo[3,4-d]pyrimidin-1-yl)cyclohexane-1-carbonyl)azetidin-3-yl)piperidin-1-yl)-2-(2,6-dioxopiperidin-3-yl)isoindoline-1,3-dione | 807.35 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 514 | 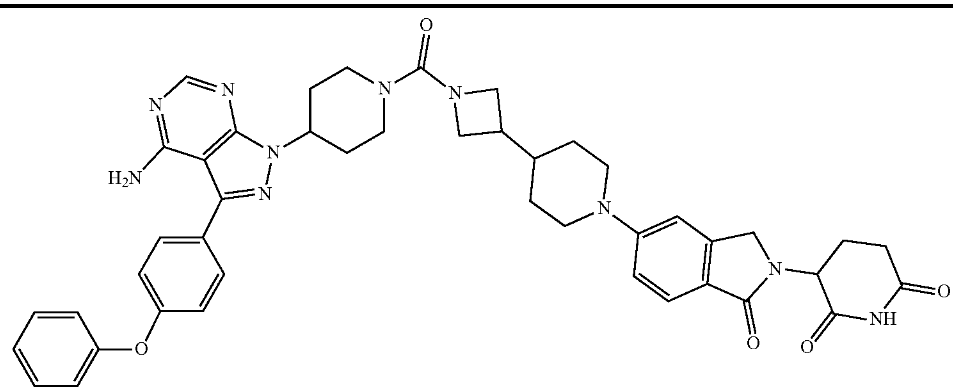 | 3-(5-(4-(1-(4-(4-amino-3-(4-phenoxyphenyl)-1H-pyrazolo[3,4-d]pyrimidin-1-yl)cyclohexane-1-carbonyl)azetidin-3-yl)piperidin-1-yl)-1-oxoisoindolin-2-yl)piperidine-2,6-dione | 793.37 | A | A | A | A |
| 515 | 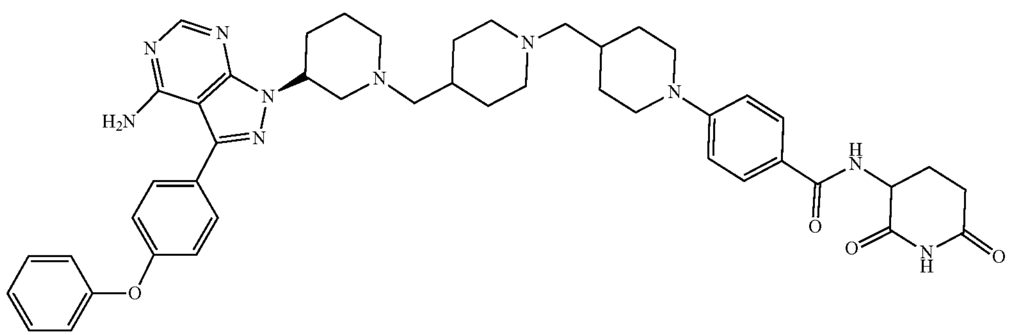 | 4-(4-(4-(((R)-3-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-N-(2,6-dioxopiperidin-3-yl)benzamide | 810.43 | B | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 516 | 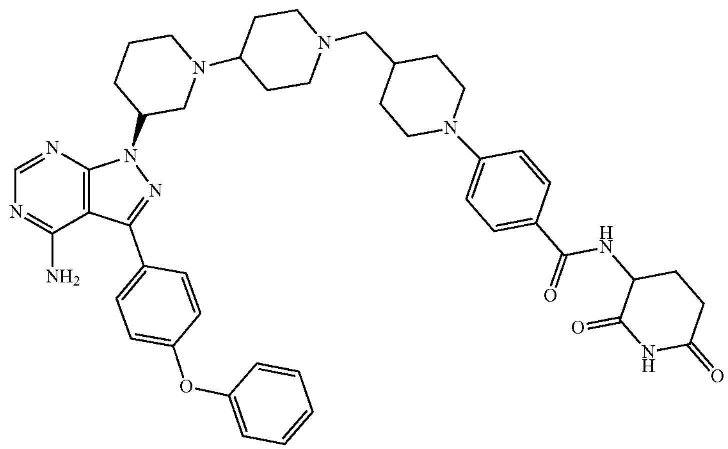 | 4-(4-(((R)-3-(4-amino-3-(4-phenoxyphenyl)-1H-pyrazolo[3,4-d]pyrimidin-1-yl)-[1,4'-bipiperidin]-1'-yl)methyl)piperidin-1-yl)-N-(2,6-dioxopiperidin-3-yl)benzamide | 796.42 | A | B | A | B |
| 517 | 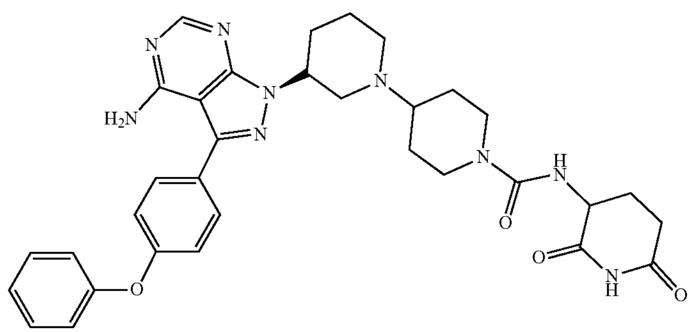 | (3R)-3-(4-amino-3-(4-phenoxyphenyl)-1H-pyrazolo[3,4-d]pyrimidin-1-yl)-N-(2,6-dioxopiperidin-3-yl)-[1,4'-bipiperidine]-1'-carboxamide | 623.30 | B | B | A | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 518 | 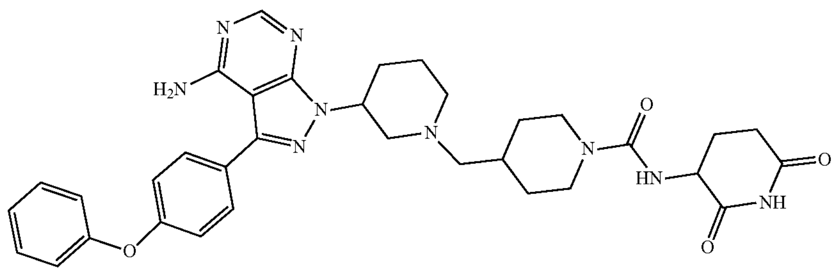 [SMILES: Nc1ncnc2c1c(-c1ccc(Oc3ccccc3)cc1)nn2C1CCCN(CC2CCN(C(=O)NC3CCC(=O)NC3=O)CC2)C1] | 4-((3-(4-amino-3-(4-phenoxyphenyl)-1H-pyrazolo[3,4-d]pyrimidin-1-yl)piperidin-1-yl)methyl)-N-(2,6-dioxopiperidin-3-yl)piperidine-1-carboxamide | 637.31 | B | B | C | B |
| 519 | 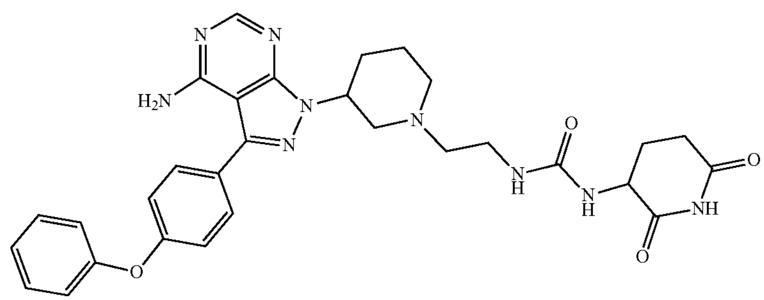 [SMILES: Nc1ncnc2c1c(-c1ccc(Oc3ccccc3)cc1)nn2C1CCCN(CCNC(=O)NC2CCC(=O)NC2=O)C1] | 1-(2-(3-(4-amino-3-(4-phenoxyphenyl)-1H-pyrazolo[3,4-d]pyrimidin-1-yl)piperidin-1-yl)ethyl)-3-(2,6-dioxopiperidin-3-yl)urea | 583.27 | B | C | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 520 | 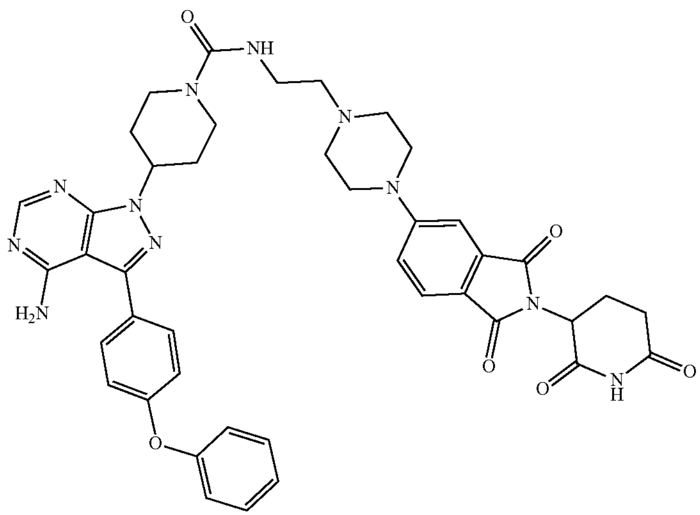 [SMILES: Nc1ncnc2c1c(-c1ccc(Oc3ccccc3)cc1)nn2C1CCN(C(=O)NCCN2CCN(c3ccc4c(c3)C(=O)N(C3CCC(=O)NC3=O)C4=O)CC2)CC1] | 4-(4-amino-3-(4-phenoxyphenyl)-1H-pyrazolo[3,4-d]pyrimidin-1-yl)-N-(2-(4-(2-(2,6-dioxopiperidin-3-yl)-1,3-dioxoisoindolin-5-yl)piperazin-1-yl)ethyl)piperidine-1-carboxamide | 797.34 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 521 | 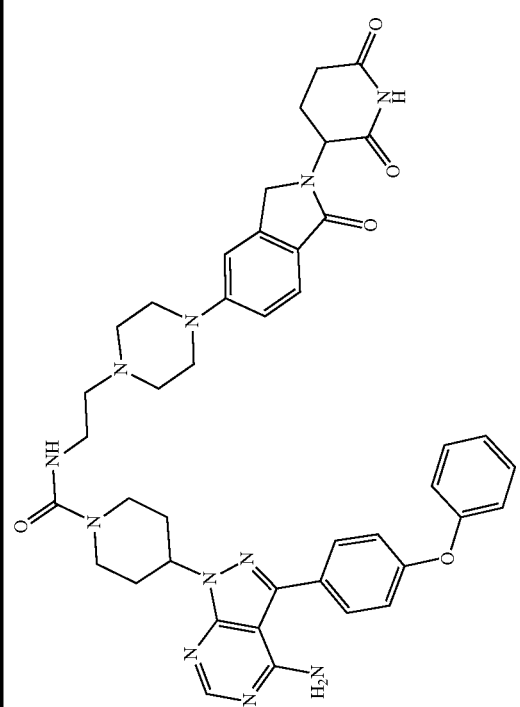 | 4-(4-amino-3-(4-phenoxyphenyl)-1H-pyrazolo[3,4-d]pyrimidin-1-yl)-N-(2-(4-(2-(2,6-dioxopiperidin-3-yl)-1-oxoisoindolin-5-yl)piperazin-1-yl)ethyl)piperidine-1-carboxamide | 783.36 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 522 | 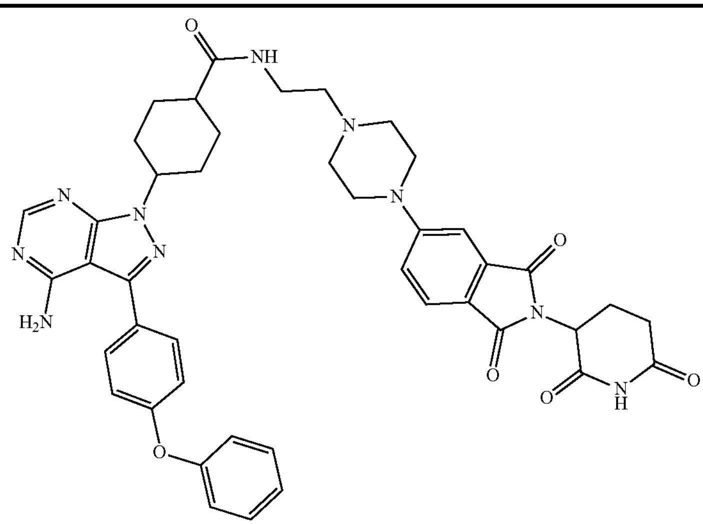 | 4-(4-amino-3-(4-phenoxyphenyl)-1H-pyrazolo[3,4-d]pyrimidin-1-yl)-N-(2-(4-(2-(2,6-dioxopiperidin-3-yl)-1,3-dioxoisoindolin-5-yl)piperazin-1-yl)ethyl)cyclohexane-1-carboxamide | 796.34 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 523 | 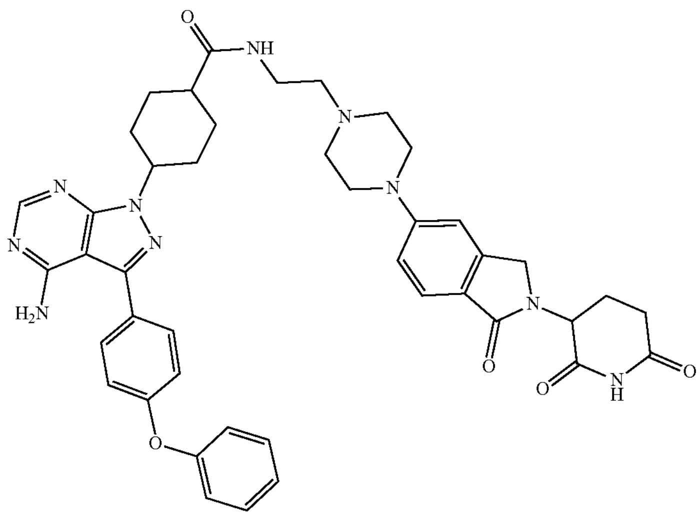 [SMILES: Nc1ncnc2c1c(-c1ccc(Oc3ccccc3)cc1)nn2C1CCC(C(=O)NCCN2CCN(c3ccc4c(c3)CN(C3CCC(=O)NC3=O)C4=O)CC2)CC1] | 4-(4-amino-3-(4-phenoxyphenyl)-1H-pyrazolo[3,4-d]pyrimidin-1-yl)-N-(2-(4-(2-(2,6-dioxopiperidin-3-yl)-1-oxoisoindolin-5-yl)piperazin-1-yl)ethyl)cyclohexane-1-carboxamide | 782.37 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 524 | 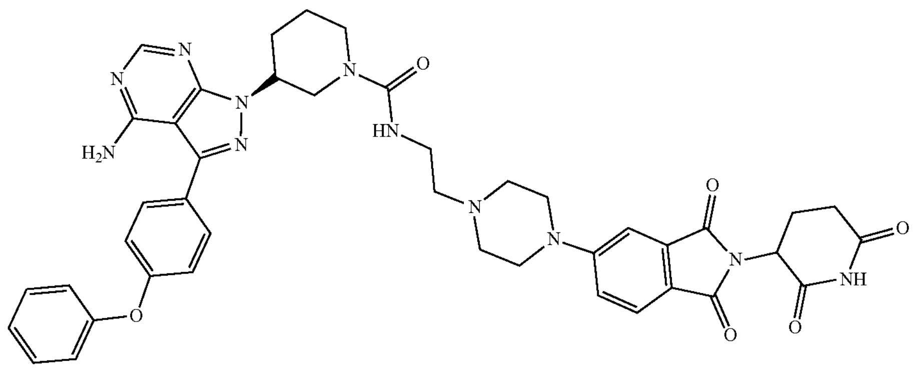 | (3R)-3-(4-amino-3-(4-phenoxyphenyl)-1H-pyrazolo[3,4-d]pyrimidin-1-yl)-N-(2-(4-(2-(2,6-dioxopiperidin-3-yl)-1,3-dioxoisoindolin-5-yl)piperazin-1-yl)ethyl)piperidine-1-carboxamide | 797.34 | B | A | A | A |
| 525 | 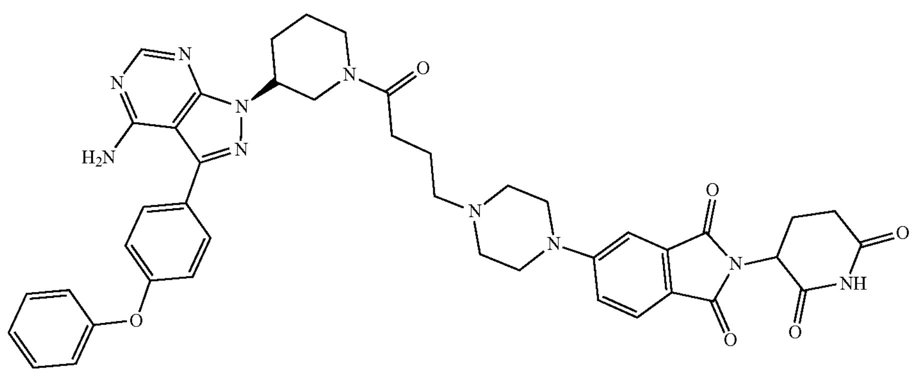 | 5-(4-(4-((R)-3-(4-amino-3-(4-phenoxyphenyl)-1H-pyrazolo[3,4-d]pyrimidin-1-yl)piperidin-1-yl)-4-oxobutyl)piperazin-1-yl)-2-(2,6-dioxopiperidin-3-yl)isoindoline-1,3-dione | 796.34 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 526 | 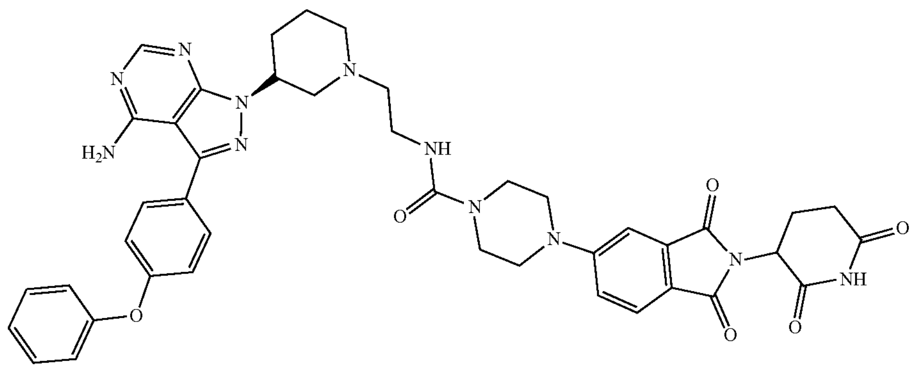 | N-(2-((R)-3-(4-amino-3-(4-phenoxyphenyl)-1H-pyrazolo[3,4-d]pyrimidin-1-yl)piperidin-1-yl)ethyl)-4-(2-(2,6-dioxopiperidin-3-yl)-1,3-dioxoisoindolin-5-yl)piperazine-1-carboxamide | 797.34 | B | B | A | A |
| 527 | 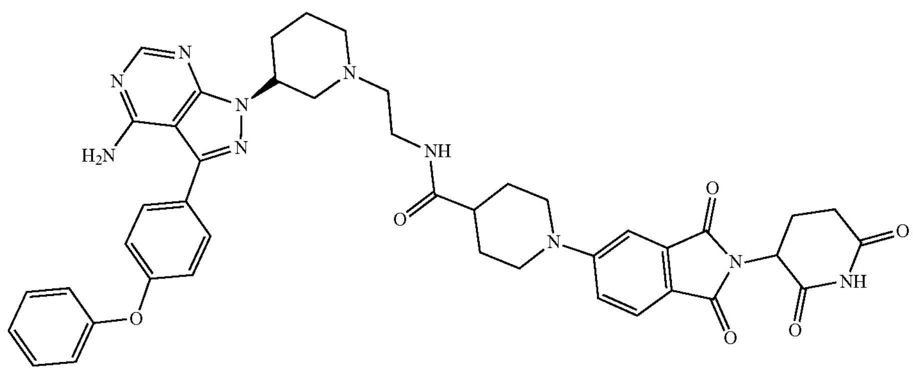 | N-(2-((R)-3-(4-amino-3-(4-phenoxyphenyl)-1H-pyrazolo[3,4-d]pyrimidin-1-yl)piperidin-1-yl)ethyl)-1-(2-(2,6-dioxopiperidin-3-yl)-1,3-dioxoisoindolin-5-yl)piperidine-4-carboxamide | 796.34 | B | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 528 | 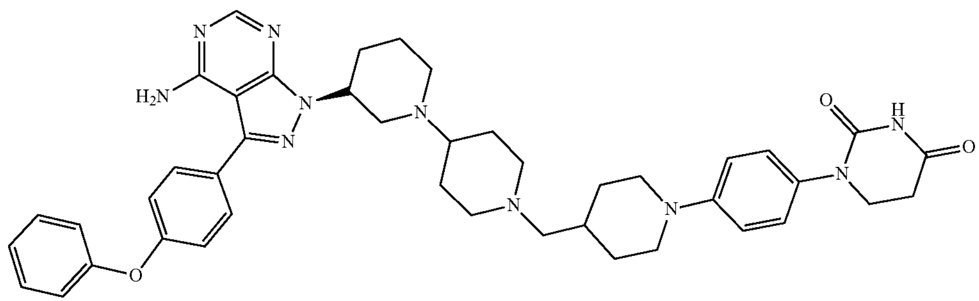 | (R)-1-(4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)phenyl)dihydropyrimidine-2,4(1H,3H)-dione | 754.41 | B | B | B | B |
| 529 | 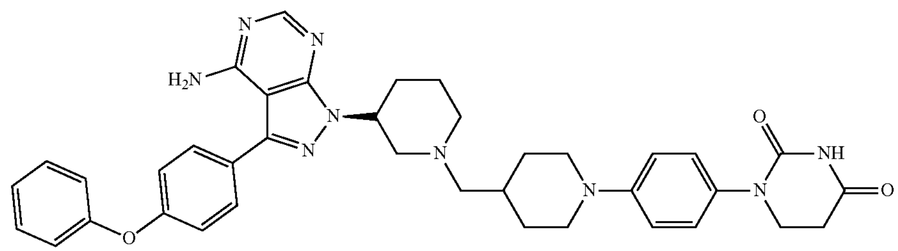 | (R)-1-(4-(4-((3-(4-amino-3-(4-phenoxyphenyl)-1H-pyrazolo[3,4-d]pyrimidin-1-yl)piperidin-1-yl)methyl)piperidin-1-yl)phenyl)dihydropyrimidine-2,4(1H,3H)-dione | 671.33 | C | C | B | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 530 | 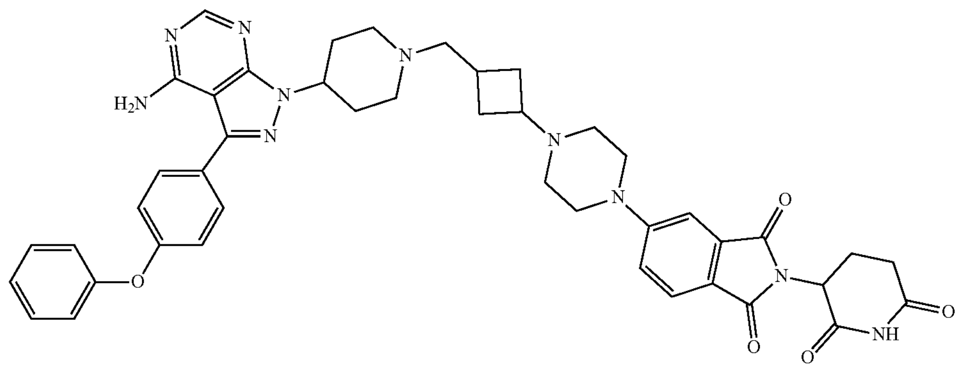 [SMILES: Nc1ncnc2c1c(-c1ccc(Oc3ccccc3)cc1)nn2C1CCN(CC2CC(N3CCN(c4ccc5c(c4)C(=O)N(C4CCC(=O)NC4=O)C5=O)CC3)C2)CC1] | 5-(4-(3-((4-(4-amino-3-(4-phenoxyphenyl)-1H-pyrazolo[3,4-d]pyrimidin-1-yl)piperidin-1-yl)methyl)cyclobutyl)piperazin-1-yl)-2-(2,6-dioxopiperidin-3-yl)isoindoline-1,3-dione | 794.37 | A | A | A | A |
| 531 | 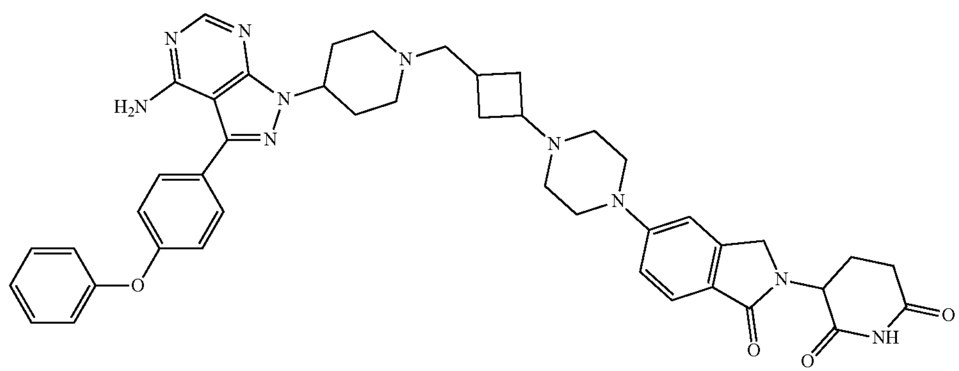 [SMILES: Nc1ncnc2c1c(-c1ccc(Oc3ccccc3)cc1)nn2C1CCN(CC2CC(N3CCN(c4ccc5c(c4)CN(C4CCC(=O)NC4=O)C5=O)CC3)C2)CC1] | 3-(5-(4-(3-((4-(4-amino-3-(4-phenoxyphenyl)-1H-pyrazolo[3,4-d]pyrimidin-1-yl)piperidin-1-yl)methyl)cyclobutyl)piperazin-1-yl)-1-oxoisoindolin-2-yl)piperidine-2,6-dione | 780.39 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 532 | 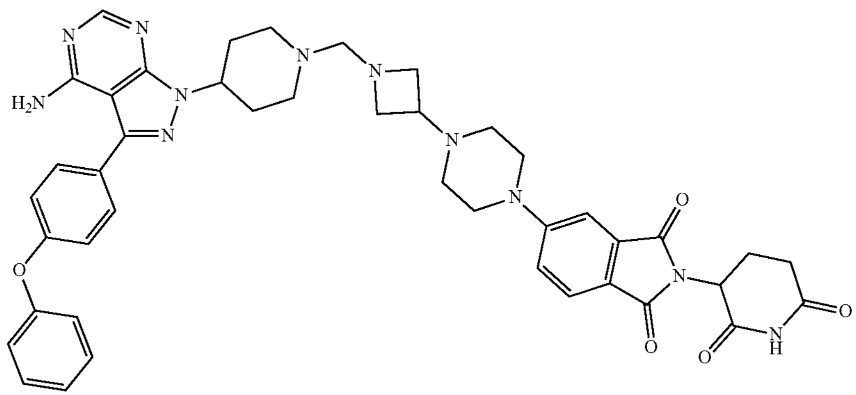 [SMILES: Nc1ncnc2c1c(-c1ccc(Oc3ccccc3)cc1)nn2C1CCN(CN2CC(N3CCN(c4ccc5c(c4)C(=O)N(C4CCC(=O)NC4=O)C5=O)CC3)C2)CC1] | 5-(4-(1-((4-(4-amino-3-(4-phenoxyphenyl)-1H-pyrazolo[3,4-d]pyrimidin-1-yl)cyclohexyl)methyl)azetidin-3-yl)piperazin-1-yl)-2-(2,6-dioxopiperidin-3-yl)isoindoline-1,3-dione | 794.37 | A | A | A | A |
| 533 | 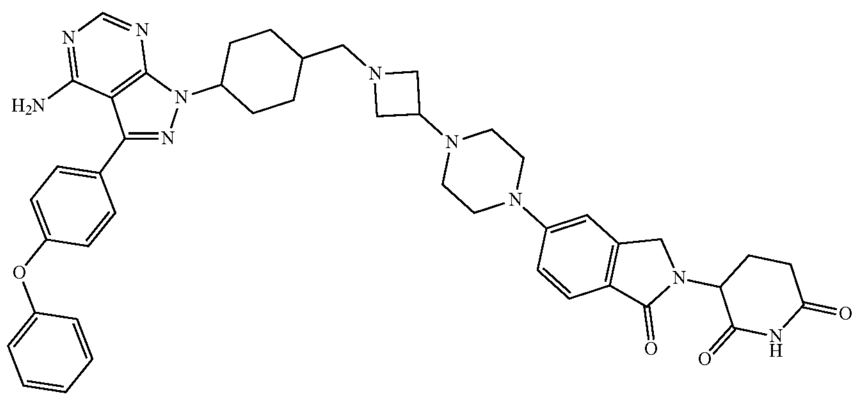 [SMILES: Nc1ncnc2c1c(-c1ccc(Oc3ccccc3)cc1)nn2C1CCC(CN2CC(N3CCN(c4ccc5c(c4)CN(C4CCC(=O)NC4=O)C5=O)CC3)C2)CC1] | 3-(5-(4-(1-((4-(4-amino-3-(4-phenoxyphenyl)-1H-pyrazolo[3,4-d]pyrimidin-1-yl)cyclohexyl)methyl)azetidin-3-yl)piperazin-1-yl)-1-oxoisoindolin-2-yl)piperidine-2,6-dione | 780.39 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 534 | KBR-1196 | 1-(4-(5-(4-(4-amino-3-(4-phenoxyphenyl)-1H-pyrazolo[3,4-d]pyrimidin-1-yl)-[1,4'-bipiperidin]-1'-yl)pent-1-yn-1-yl)phenyl)dihydropyrimidine-2,4(1H,3H)-dione | 723.36 | C | C | C | C |
| 535 | KBR-1190 | 1-(4-(6-(4-(4-amino-3-(4-phenoxyphenyl)-1H-pyrazolo[3,4-d]pyrimidin-1-yl)-[1,4'-bipiperidin]-1'-yl)hex-1-yn-1-yl)phenyl)dihydropyrimidine-2,4(1H,3H)-dione | 737.38 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 536 | KBR-1191 | 1-(4-(6-(3-(4-(4-amino-3-(4-phenoxyphenyl)-1H-pyrazolo[3,4-d]pyrimidin-1-yl)piperidin-1-yl)pyrrolidin-1-yl)hex-1-yn-1-yl)phenyl)dihydropyrimidine-2,4(1H,3H)-dione | 723.36 | C | C | C | C |
| 537 | KBR1311 | 1-(4-(5-(3-(4-(4-amino-3-(4-phenoxyphenyl)-1H-pyrazolo[3,4-d]pyrimidin-1-yl)piperidin-1-yl)pyrrolidin-1-yl)pent-1-yn-1-yl)phenyl)dihydropyrimidine-2,4(1H,3H)-dione | 709.35 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 538 | KB 1243 | 1-(4-(5-(4-(4-amino-3-(4-phenoxyphenyl)-1H-pyrazolo[3,4-d]pyrimidin-1-yl)piperidin-1-yl)pent-1-yn-1-yl)phenyl)dihydropyrimidine-2,4(1H,3H)-dione | 640.29 | C | C | C | C |
| 539 | KBR 1244 | 1-(4-(6-(4-(4-amino-3-(4-phenoxyphenyl)-1H-pyrazolo[3,4-d]pyrimidin-1-yl)piperidin-1-yl)hex-1-yn-1-yl)phenyl)dihydropyrimidine-2,4(1H,3H)-dione | 654.31 | C | C | C | C |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 540 | 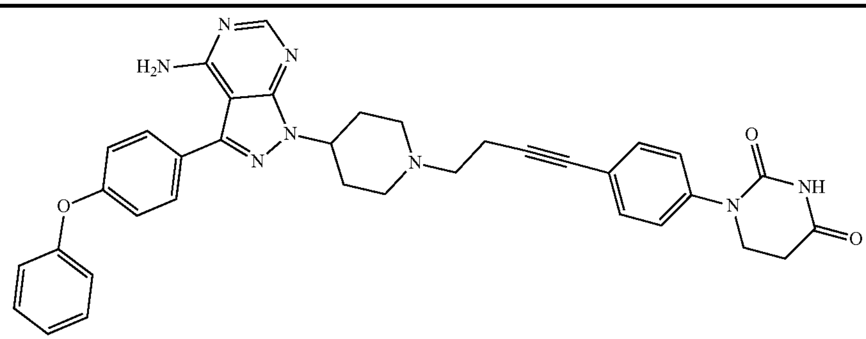 | 1-(4-(4-(4-(4-amino-3-(4-phenoxyphenyl)-1H-pyrazolo[3,4-d]pyrimidin-1-yl)piperidin-1-yl)but-1-yn-1-yl)phenyl)dihydropyrimidine-2,4(1H,3H)-dione | 626.28 | C | C | C | C |
| 541 | KBR 1245 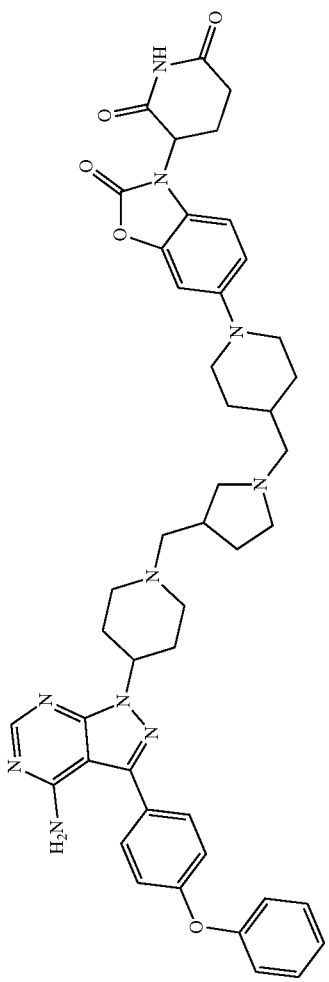 | 3-(6-(4-((3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)-2-oxobenzo[d]oxazol-3(2H)-yl)piperidine-2,6-dione | 810.40 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 542 | 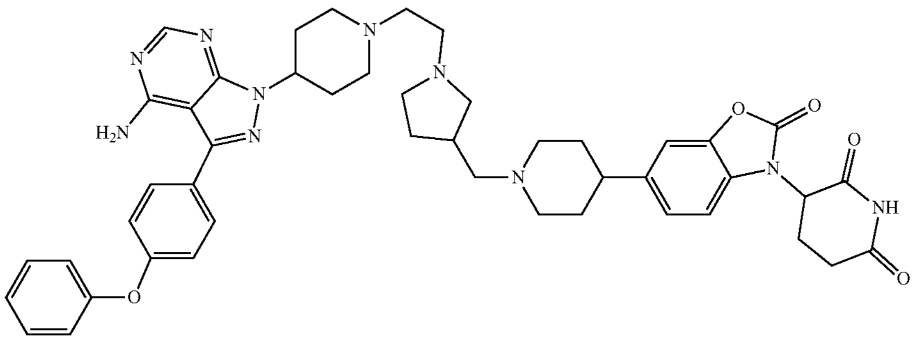 [SMILES: Nc1ncnc2c1c(-c1ccc(Oc3ccccc3)cc1)nn2C1CCN(CCN2CCC(CN3CCC(c4ccc5c(c4)oc(=O)n5C4CCC(=O)NC4=O)CC3)C2)CC1] | 3-(6-(1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperidin-4-yl)-2-oxobenzo[d]oxazol-3(2H)-yl)piperidine-2,6-dione | 824.41 | B | B | B | B |
| 543 | 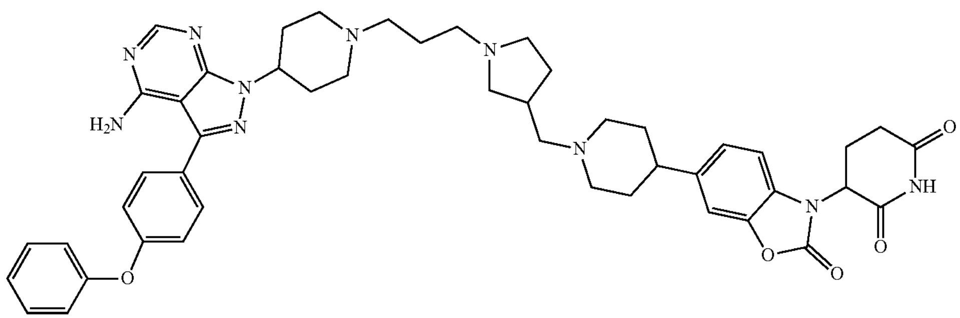 [SMILES: Nc1ncnc2c1c(-c1ccc(Oc3ccccc3)cc1)nn2C1CCN(CCCN2CCC(CN3CCC(c4ccc5c(c4)oc(=O)n5C4CCC(=O)NC4=O)CC3)C2)CC1] | 3-(6-(1-((1-(3-(4-(4-amino-3-(4-phenoxyphenyl)-1H-pyrazolo[3,4-d]pyrimidin-1-yl)piperidin-1-yl)propyl)pyrrolidin-3-yl)methyl)piperidin-4-yl)-2-oxobenzo[d]oxazol-3(2H)-yl)piperidine-2,6-dione | 838.43 | B | B | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 544 | 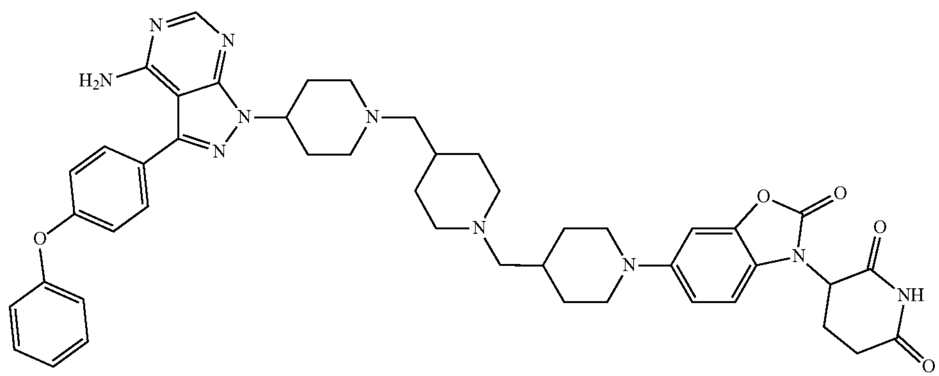 [SMILES: Nc1ncnc2c1c(-c1ccc(Oc3ccccc3)cc1)nn2C1CCN(CC2CCN(CC3CCN(c4ccc5c(c4)oc(=O)n5C4CCC(=O)NC4=O)CC3)CC2)CC1] | 3-(6-(4-((4-((4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-2-oxobenzo[d]oxazol-3(2H)-yl)piperidine-2,6-dione | 824.41 | B | B | B | A |
| 545 | 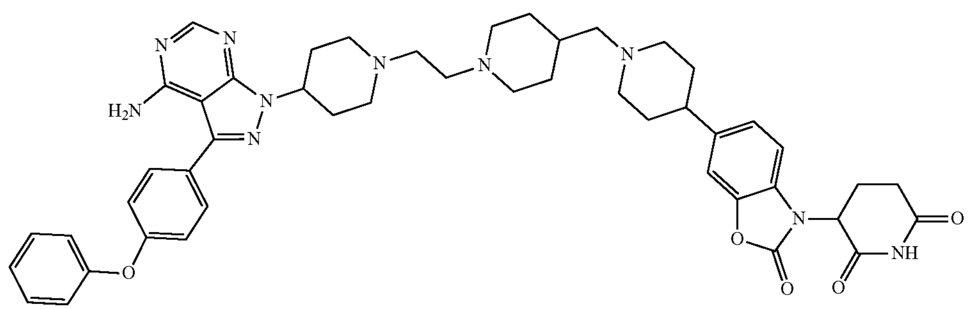 [SMILES: Nc1ncnc2c1c(-c1ccc(Oc3ccccc3)cc1)nn2C1CCN(CCN2CCC(CN3CCC(c4ccc5c(c4)oc(=O)n5C4CCC(=O)NC4=O)CC3)CC2)CC1] | 3-(6-(1-(2-(4-(4-amino-3-(4-phenoxyphenyl)-1H-pyrazolo[3,4-d]pyrimidin-1-yl)piperidin-1-yl)ethyl)piperidin-4-yl)methyl)piperidin-4-yl)-2-oxobenzo[d]oxazol-3(2H)-yl)piperidine-2,6-dione | 838.43 | B | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 546 | 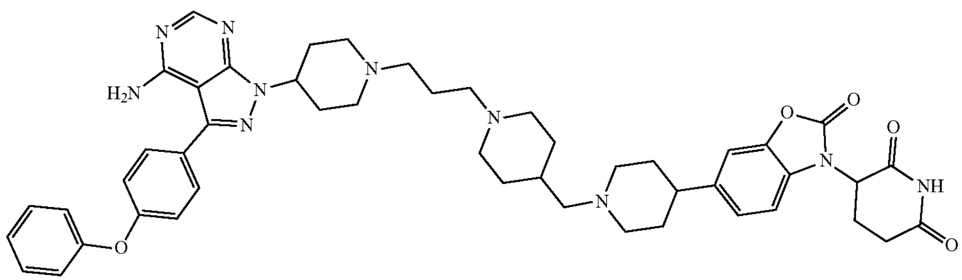 [SMILES: Nc1ncnc2c1c(-c1ccc(Oc3ccccc3)cc1)nn2C1CCN(CCCN2CCC(CN3CCC(c4ccc5c(c4)oc(=O)n5C4CCC(=O)NC4=O)CC3)CC2)CC1] | 3-(6-(1-(1-(3-(4-(4-amino-3-(4-phenoxyphenyl)-1H-pyrazolo[3,4-d]pyrimidin-1-yl)piperidin-1-yl)propyl)piperidin-4-yl)methyl)piperidin-4-yl)-2-oxobenzo[d]oxazol-3(2H)-yl)piperidine-2,6-dione | 852.44 | A | B | A | A |
| 547 | 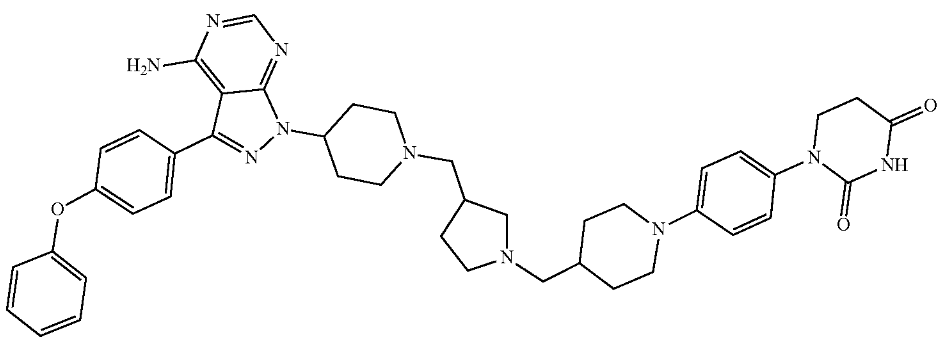 [SMILES: Nc1ncnc2c1c(-c1ccc(Oc3ccccc3)cc1)nn2C1CCN(CC2CCN(CC3CCN(c4ccc(N5CCC(=O)NC5=O)cc4)CC3)C2)CC1] | 1-(4-(4-((3-(4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)phenyl)dihydropyrimidine-2,4(1H,3H)-dione | 754.41 | B | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 548 | 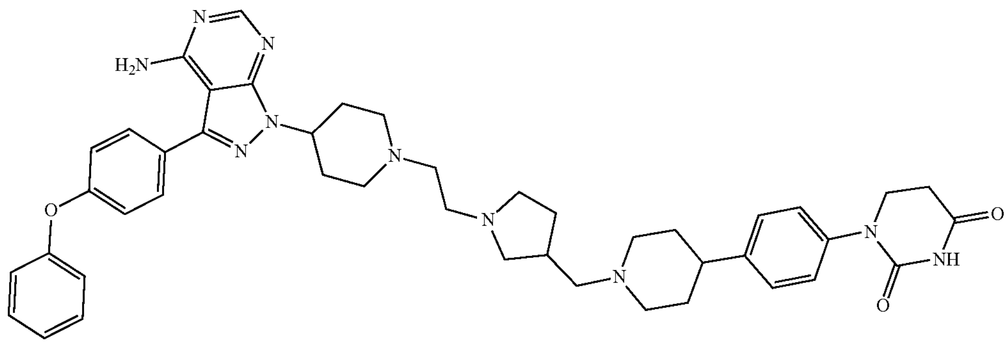 [SMILES: Nc1ncnc2c1c(-c1ccc(Oc3ccccc3)cc1)nn2C1CCN(CCN2CCC(CN3CCC(c4ccc(N5CCC(=O)NC5=O)cc4)CC3)C2)CC1] | 1-(4-(1-(1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperidin-4-yl)phenyl)dihydropyrimidine-2,4(1H,3H)-dione | 768.42 | A | A | A | B |
| 549 | 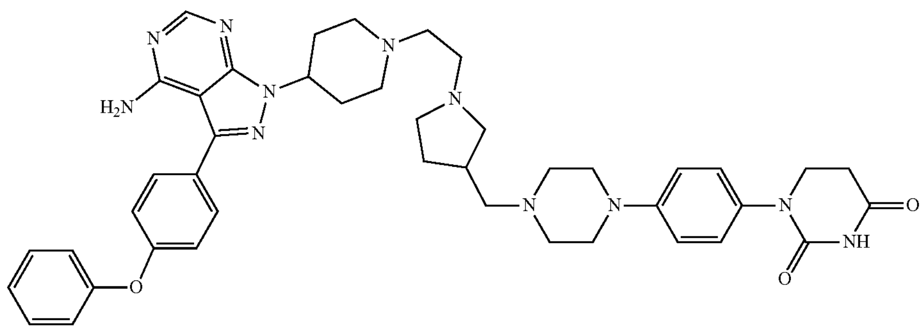 [SMILES: Nc1ncnc2c1c(-c1ccc(Oc3ccccc3)cc1)nn2C1CCN(CCN2CCC(CN3CCN(c4ccc(N5CCC(=O)NC5=O)cc4)CC3)C2)CC1] | 1-(4-(4-((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperazin-1-yl)phenyl)dihydropyrimidine-2,4(1H,3H)-dione | 769.42 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 550 | 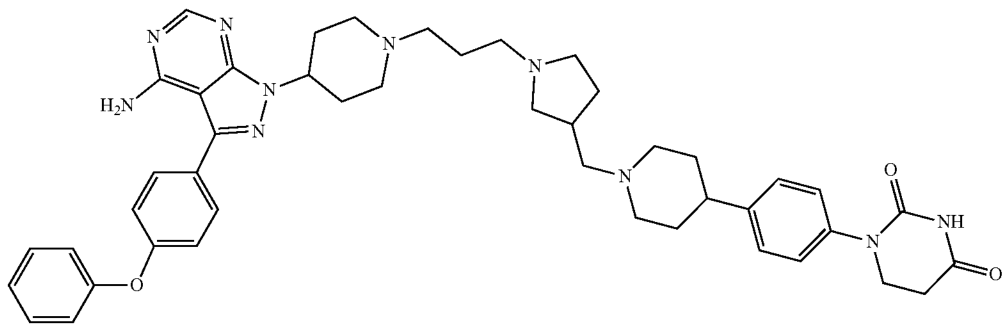 [SMILES: Nc1ncnc2c1c(-c1ccc(Oc3ccccc3)cc1)nn2C1CCN(CCCN2CCC(CN3CCC(c4ccc(N5CCC(=O)NC5=O)cc4)CC3)C2)CC1] | 1-(4-(1-(3-(4-(4-amino-3-(4-phenoxyphenyl)-1H-pyrazolo[3,4-d]pyrimidin-1-yl)piperidin-1-yl)propyl)pyrrolidin-3-yl)methyl)piperidin-4-yl)phenyl)dihydropyrimidine-2,4(1H,3H)-dione | 782.44 | A | A | B | A |
| 551 | 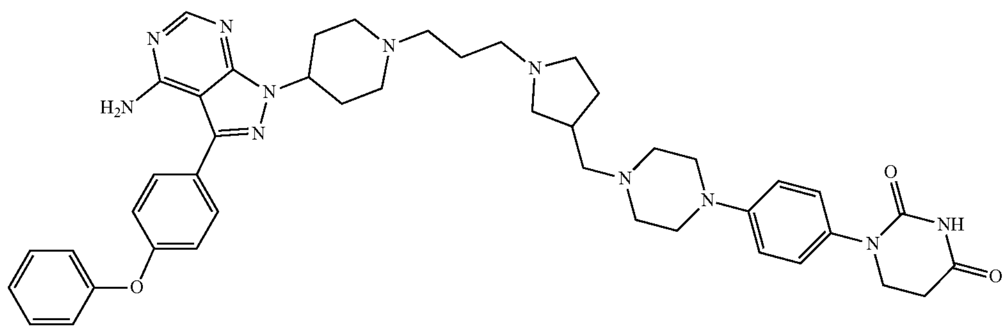 [SMILES: Nc1ncnc2c1c(-c1ccc(Oc3ccccc3)cc1)nn2C1CCN(CCCN2CCC(CN3CCN(c4ccc(N5CCC(=O)NC5=O)cc4)CC3)C2)CC1] | 1-(4-(4-((1-(3-(4-(4-amino-3-(4-phenoxyphenyl)-1H-pyrazolo[3,4-d]pyrimidin-1-yl)piperin-1-yl)propyl)pyrrolidin-3-yl)methyl)piperazin-1-yl)phenyl)dihydropyrimidine-2,4(1H,3H)-dione | 783.43 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 552 | 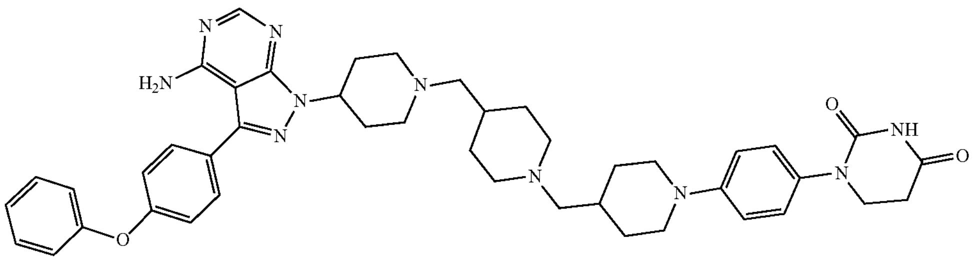 [SMILES: Nc1ncnc2c1c(-c1ccc(Oc3ccccc3)cc1)nn2C1CCN(CC2CCN(CC3CCN(c4ccc(N5CCC(=O)NC5=O)cc4)CC3)CC2)CC1] | 1-(4-(4-((4-(4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)phenyl)dihydropyrimidine-2,4(1H,3H)-dione | 768.42 | A | A | A | A |
| 553 | 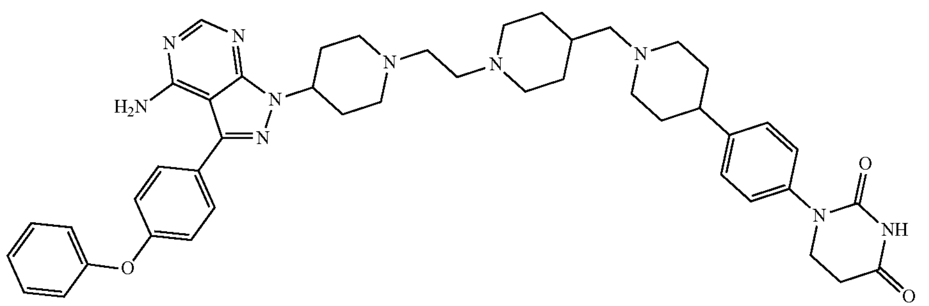 [SMILES: Nc1ncnc2c1c(-c1ccc(Oc3ccccc3)cc1)nn2C1CCN(CCN2CCC(CN3CCC(c4ccc(N5CCC(=O)NC5=O)cc4)CC3)CC2)CC1] | 1-(4-(1-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperidin-4-yl)phenyl)dihydropyrimidine-2,4(1H,3H)-dione | 782.44 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 554 | 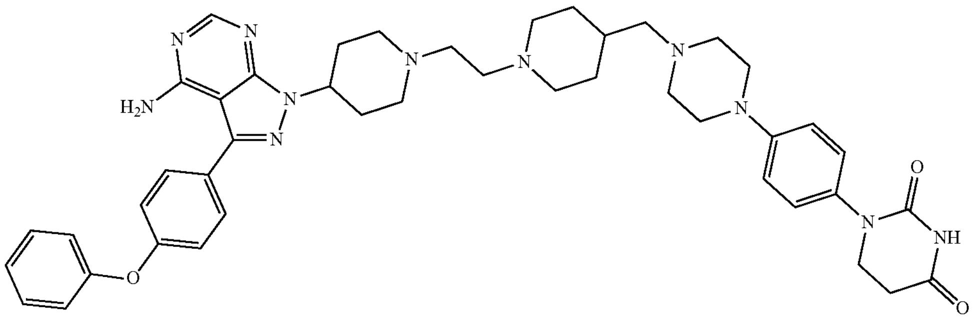 [SMILES: Nc1ncnc2c1c(-c1ccc(Oc3ccccc3)cc1)nn2C1CCN(CCN2CCC(CN3CCN(c4ccc(N5CCC(=O)NC5=O)cc4)CC3)CC2)CC1] | 1-(4-(4-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperazin-1-yl)phenyl)dihydropyrimidine-2,4(1H,3H)-dione | 783.43 | A | A | A | A |
| 555 | 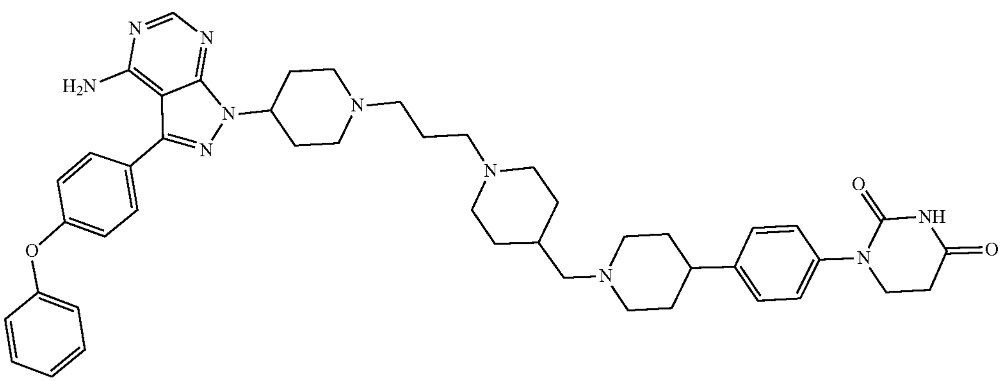 [SMILES: Nc1ncnc2c1c(-c1ccc(Oc3ccccc3)cc1)nn2C1CCN(CCCN2CCC(CN3CCC(c4ccc(N5CCC(=O)NC5=O)cc4)CC3)CC2)CC1] | 1-(4-(1-((1-(3-(4-(4-amino-3-(4-phenoxyphenyl)-1H-pyrazolo[3,4-d]pyrimidin-1-yl)piperidin-1-yl)propyl)piperidin-4-yl)methyl)piperidin-4-yl)phenyl)dihydropyrimidine-2,4(1H,3H)-dione | 796.45 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 556 | 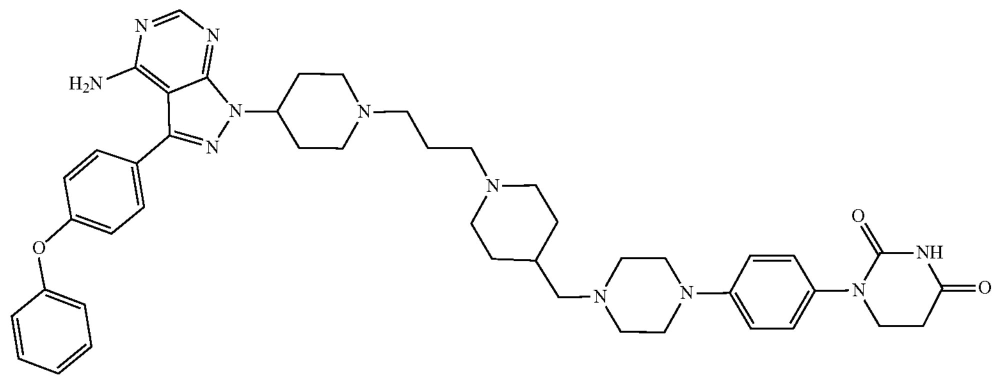 [SMILES: Nc1ncnc2c1c(-c1ccc(Oc3ccccc3)cc1)nn2C1CCN(CCCN2CCC(CN3CCN(c4ccc(N5CCC(=O)NC5=O)cc4)CC3)CC2)CC1] | 1-(4-(4-((1-(3-(4-(4-amino-3-(4-phenoxyphenyl)-1H-pyrazolo[3,4-d]pyrimidin-1-yl)piperidin-1-yl)propyl)piperidin-4-yl)methyl)piperazin-1-yl)phenyl)dihydropyrimidine-2,4(1H,3H)-dione | 797.45 | A | A | A | A |
| 557 | 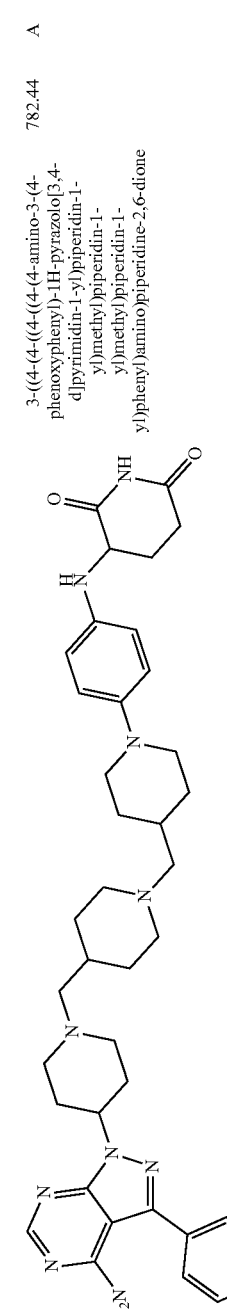 | 3-((4-(4-((4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)phenyl)amino)piperidine-2,6-dione | 782.44 | A | A | A | A |

TABLE 1-continued

Exemplary compounds of the present invention. Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 558 | 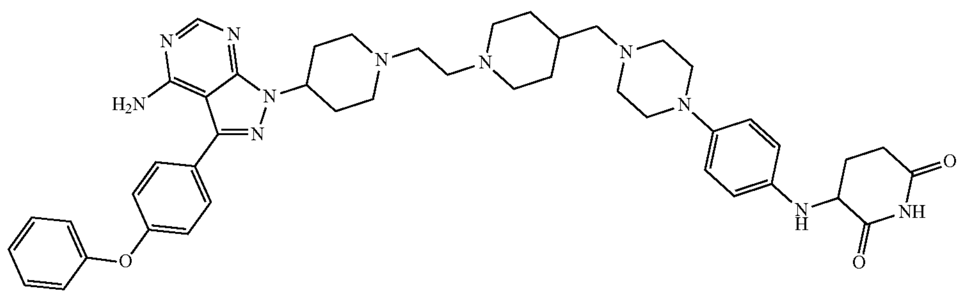 [SMILES: Nc1ncnc2c1c(-c1ccc(Oc3ccccc3)cc1)nn2C1CCN(CCN2CCC(CN3CCN(c4ccc(NC5CCC(=O)NC5=O)cc4)CC3)CC2)CC1] | 3-((4-(4-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperazin-1-yl)phenyl)amino)piperidine-2,6-dione | 797.45 | A | A | A | A |
| 559 | 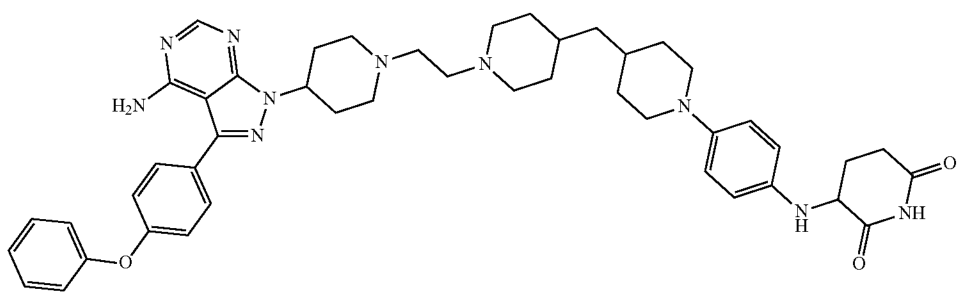 [SMILES: Nc1ncnc2c1c(-c1ccc(Oc3ccccc3)cc1)nn2C1CCN(CCN2CCC(CC3CCN(c4ccc(NC5CCC(=O)NC5=O)cc4)CC3)CC2)CC1] | 3-((4-(4-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperidin-1-yl)phenyl)amino)piperidine-2,6-dione | 796.45 | A | A | | A |
| 560 | 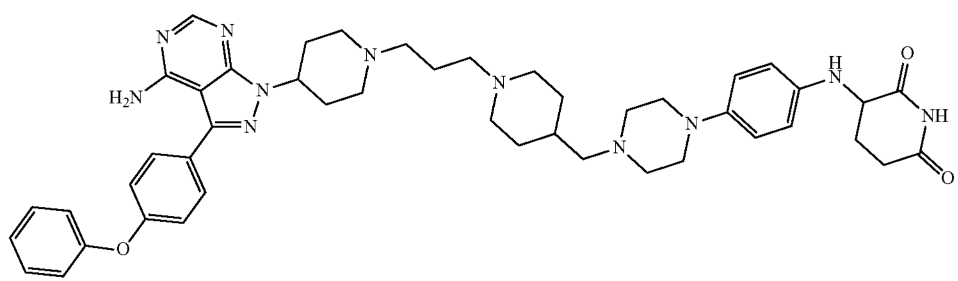 [SMILES: Nc1ncnc2c1c(-c1ccc(Oc3ccccc3)cc1)nn2C1CCN(CCCN2CCC(CN3CCN(c4ccc(NC5CCC(=O)NC5=O)cc4)CC3)CC2)CC1] | 3-((4-(4-((1-(3-(4-(4-amino-3-(4-phenoxyphenyl)-1H-pyrazolo[3,4-d]pyrimidin-1-yl)piperidin-1-yl)propyl)piperidin-4-yl)methyl)piperazin-1-yl)phenyl)amino)piperidine-2,6-dione | 811.46 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 561 | 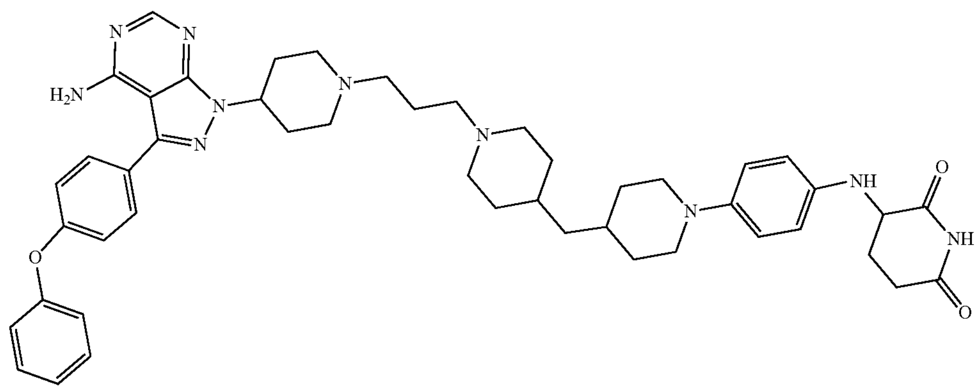 [SMILES: Nc1ncnc2c1c(-c1ccc(Oc3ccccc3)cc1)nn2C1CCN(CCCN2CCC(CC3CCN(c4ccc(NC5CCC(=O)NC5=O)cc4)CC3)CC2)CC1] | 3-((4-((4-(1-(3-(4-(4-amino-3-(4-phenoxyphenyl)-1H-pyrazolo[3,4-d]pyrimidin-1-yl)piperidin-1-yl)propyl)piperidin-4-yl)methyl)piperidin-1-yl)phenyl)amino)piperidine-2,6-dione | 810.47 | A | A | B | A |
| 562 | 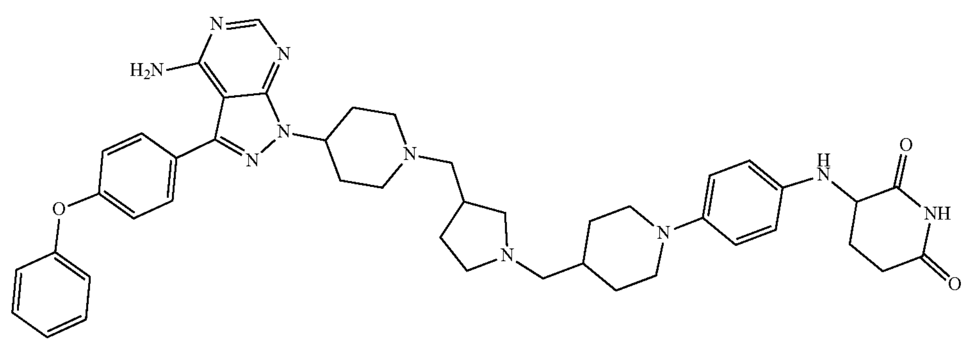 [SMILES: Nc1ncnc2c1c(-c1ccc(Oc3ccccc3)cc1)nn2C1CCN(CC2CCN(CC3CCN(c4ccc(NC5CCC(=O)NC5=O)cc4)CC3)C2)CC1] | 3-((4-((4-((3-((4-(4-amino-3-(4-phenoxyphenyl)-1H-pyrazolo[3,4-d]pyrimidin-1-yl)piperidin-1-yl)methyl)pyrrolidin-1-yl)methyl)piperidin-1-yl)phenyl)amino)piperidine-2,6-dione | 768.42 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 563 | 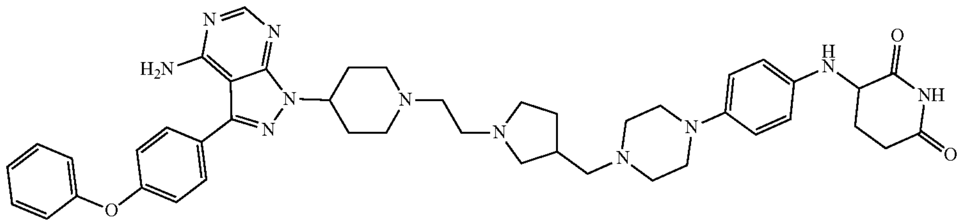 [SMILES: Nc1ncnc2c1c(-c1ccc(Oc3ccccc3)cc1)nn2C1CCN(CCN2CCC(CN3CCN(c4ccc(NC5CCC(=O)NC5=O)cc4)CC3)C2)CC1] | 3-((4-(4-((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperazin-1-yl)phenyl)amino)piperidine-2,6-dione | 783.43 | B | B | B | A |
| 564 | 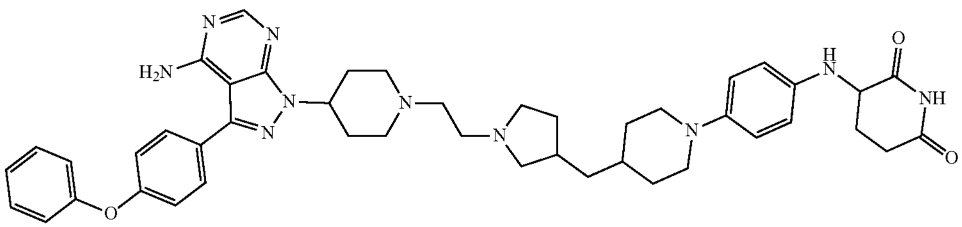 [SMILES: Nc1ncnc2c1c(-c1ccc(Oc3ccccc3)cc1)nn2C1CCN(CCN2CCC(CC3CCN(c4ccc(NC5CCC(=O)NC5=O)cc4)CC3)C2)CC1] | 3-((4-(4-((1-(2-(4-(4-amino-3-(4-phenoxyphenyl)-1H-pyrazolo[3,4-d]pyrimidin-1-yl)piperidin-1-yl)ethyl)pyrrolidin-3-yl)methyl)piperidin-1-yl)phenyl)amino)piperidine-2,6-dione | 782.44 | A | A | B | A |
| 565 | 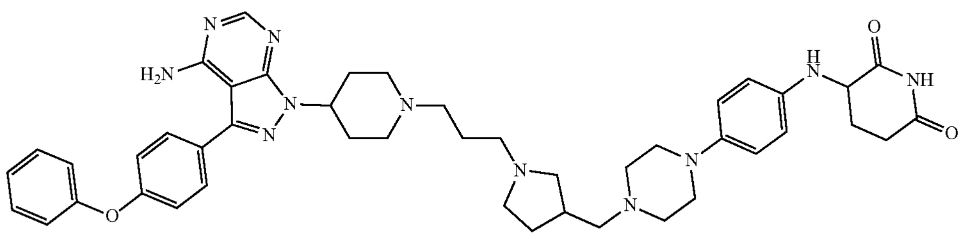 [SMILES: Nc1ncnc2c1c(-c1ccc(Oc3ccccc3)cc1)nn2C1CCN(CCCN2CCC(CN3CCN(c4ccc(NC5CCC(=O)NC5=O)cc4)CC3)C2)CC1] | 3-((4-(4-((1-(3-(4-(4-amino-3-(4-phenoxyphenyl)-1H-pyrazolo[3,4-d]pyrimidin-1-yl)piperidin-1-yl)propyl)pyrrolidin-3-yl)methyl)piperazin-1-yl)phenyl)amino)piperidine-2,6-dione | 797.45 | A | A | B | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 567 | 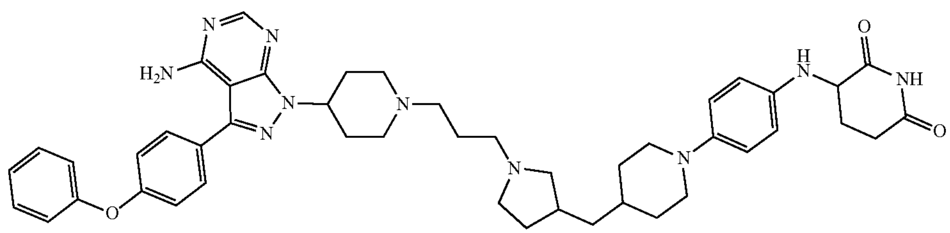 | 3-((4-(4-((1-(3-(4-(4-amino-3-(4-phenoxyphenyl)-1H-pyrazolo[3,4-d]pyrimidin-1-yl)piperidin-1-yl)propyl)pyrrolidin-3-yl)methyl)piperidin-1-yl)phenyl)amino)piperidine-2,6-dione | 796.45 | A | B | B | A |
| 568 | 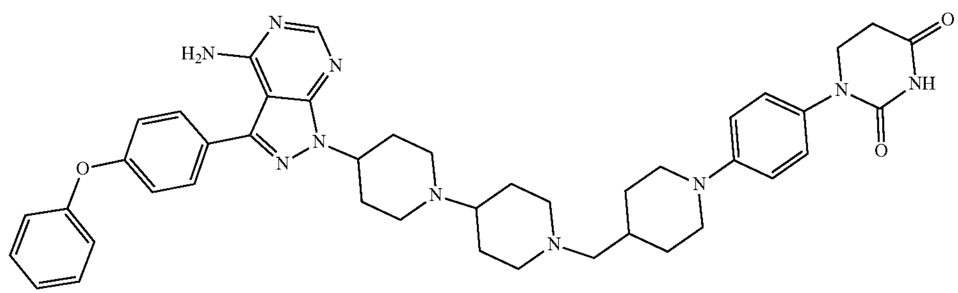 [SMILES: Nc1ncnc2c1c(-c1ccc(Oc3ccccc3)cc1)nn2C1CCN(C2CCN(CC3CCN(c4ccc(N5CCC(=O)NC5=O)cc4)CC3)CC2)CC1] | 1-(4-(4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)phenyl)dihydropyrimidine-2,4(1H,3H)-dione | 754.41 | B | B | C | B |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 569 | 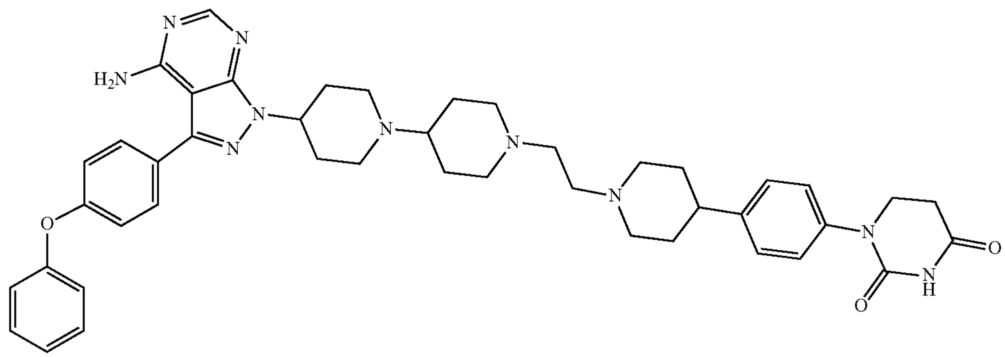 [SMILES: Nc1ncnc2c1c(-c1ccc(Oc3ccccc3)cc1)nn2C1CCN(C2CCN(CCN3CCC(c4ccc(N5CCC(=O)NC5=O)cc4)CC3)CC2)CC1] | 1-(4-(1-(2-(4-(4-amino-3-(4-phenoxyphenyl)-1H-pyrazolo[3,4-d]pyrimidin-1-yl)-[1,4'-bipiperidin]-1'-yl)ethyl)piperidin-4-yl)phenyl)dihydropyrimidine-2,4(1H,3H)-dione | 768.42 | B | B | B | A |
| 570 | 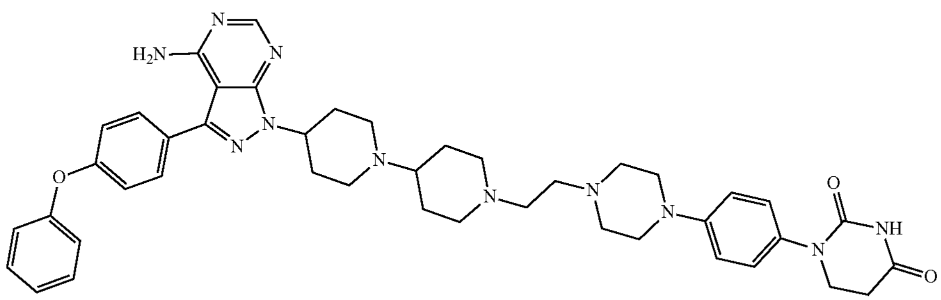 [SMILES: Nc1ncnc2c1c(-c1ccc(Oc3ccccc3)cc1)nn2C1CCN(C2CCN(CCN3CCN(c4ccc(N5CCC(=O)NC5=O)cc4)CC3)CC2)CC1] | 1-(4-(4-(2-(4-(4-amino-3-(4-phenoxyphenyl)-1H-pyrazolo[3,4-d]pyrimidin-1-yl)-[1,4'-bipiperidin]-1'-yl)ethyl)piperazin-1-yl)phenyl)dihydropyrimidine-2,4(1H,3H)-dione | 769.42 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 571 | 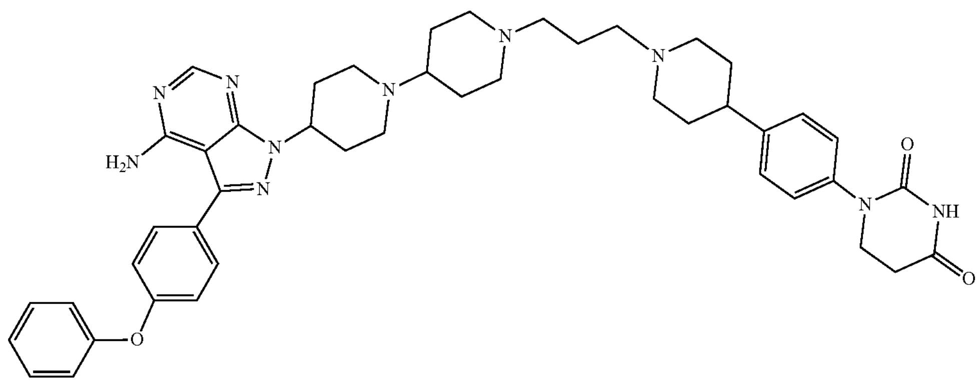 [SMILES: Nc1ncnc2c1c(-c1ccc(Oc3ccccc3)cc1)nn2C1CCN(C2CCN(CCCN3CCC(c4ccc(N5CCC(=O)NC5=O)cc4)CC3)CC2)CC1] | 1-(4-(1-(3-(4-(4-amino-3-(4-phenoxyphenyl)-1H-pyrazolo[3,4-d]pyrimidin-1-yl)-[1,4'-bipiperidin]-1'-yl)propyl)piperidin-4-yl)phenyl)dihydropyrimidine-2,4(1H,3H)-dione | 782.44 | A | A | B | A |
| 572 | 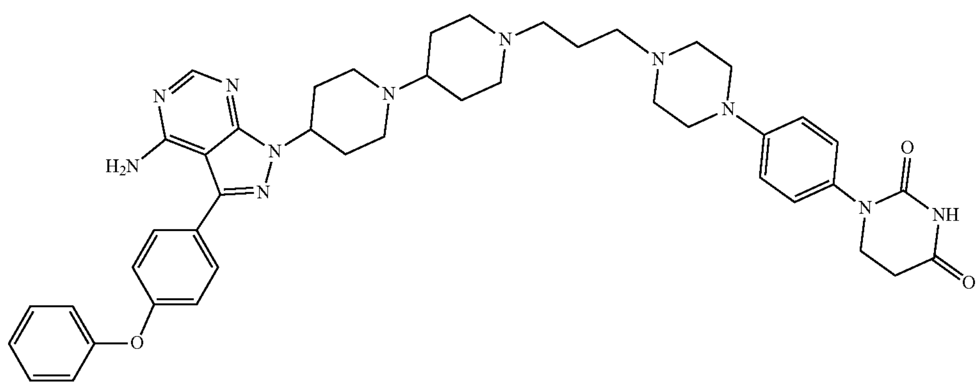 [SMILES: Nc1ncnc2c1c(-c1ccc(Oc3ccccc3)cc1)nn2C1CCN(C2CCN(CCCN3CCN(c4ccc(N5CCC(=O)NC5=O)cc4)CC3)CC2)CC1] | 1-(4-(3-(4-(4-amino-3-(4-phenoxyphenyl)-1H-pyrazolo[3,4-d]pyrimidin-1-yl)-[1,4'-bipiperidin]-1'-yl)propyl)piperazin-1-yl)phenyl)dihydropyrimidine-2,4(1H,3H)-dione | 783.43 | A | A | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 573 | 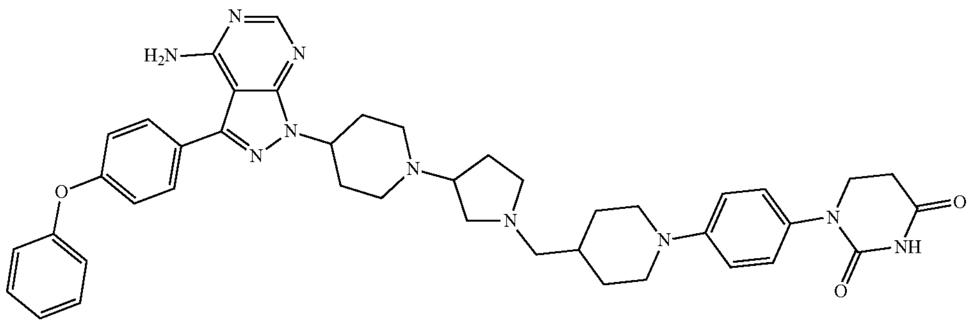 [SMILES: Nc1ncnc2c1c(-c1ccc(Oc3ccccc3)cc1)nn2C1CCN(C2CCN(CC3CCN(c4ccc(N5CCC(=O)NC5=O)cc4)CC3)C2)CC1] | 1-(4-(4-((3-(4-(4-amino-3-(4-phenoxyphenyl)-1H-pyrazolo[3,4-d]pyrimidin-1-yl)piperidin-1-yl)pyrrolidin-1-yl)methyl)piperidin-1-yl)phenyl)dihydropyrimidine-2,4(1H,3H)-dione | 740.39 | A | B | A | B |
| 574 | 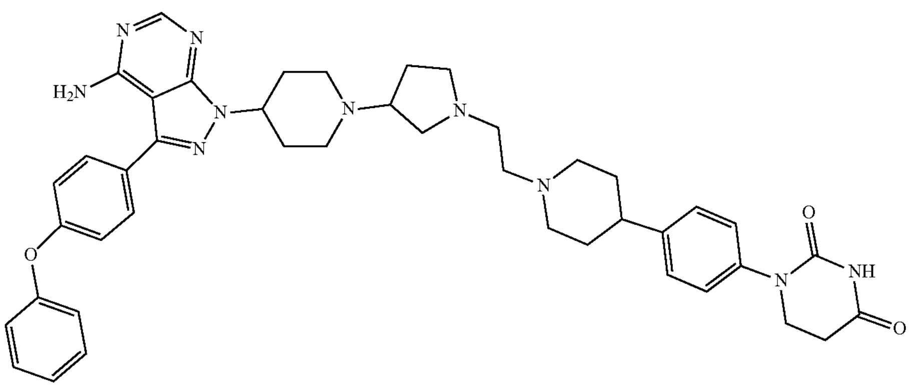 [SMILES: Nc1ncnc2c1c(-c1ccc(Oc3ccccc3)cc1)nn2C1CCN(C2CCN(CCN3CCC(c4ccc(N5CCC(=O)NC5=O)cc4)CC3)C2)CC1] | 1-(4-(1-(2-(3-(4-(4-amino-3-(4-phenoxyphenyl)-1H-pyrazolo[3,4-d]pyrimidin-1-yl)piperidin-1-yl)pyrrolidin-1-yl)ethyl)piperidin-4-yl)phenyl)dihydropyrimidine-2,4(1H,3H)-dione | 754.41 | B | B | B | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 575 | 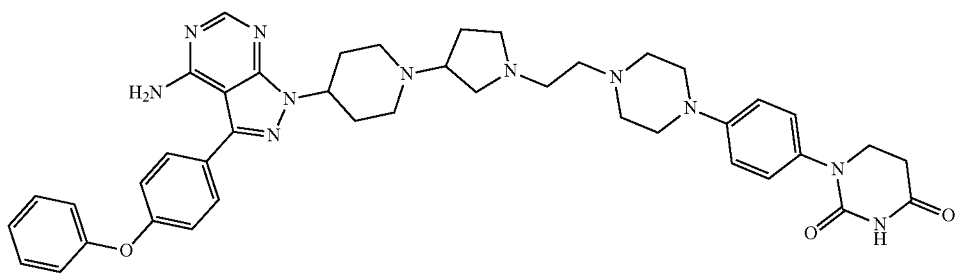 [SMILES: Nc1ncnc2c1c(-c1ccc(Oc3ccccc3)cc1)nn2C1CCN(C2CCN(CCN3CCN(c4ccc(N5CCC(=O)NC5=O)cc4)CC3)C2)CC1] | 1-(4-(4-(2-(3-(4-(4-amino-3-(4-phenoxyphenyl)-1H-pyrazolo[3,4-d]pyrimidin-1-yl)piperidin-1-yl)pyrrolidin-1-yl)ethyl)piperazin-1-yl)phenyl)dihydropyrimidine-2,4(1H,3H)-dione | 755.40 | B | B | A | A |
| 576 | 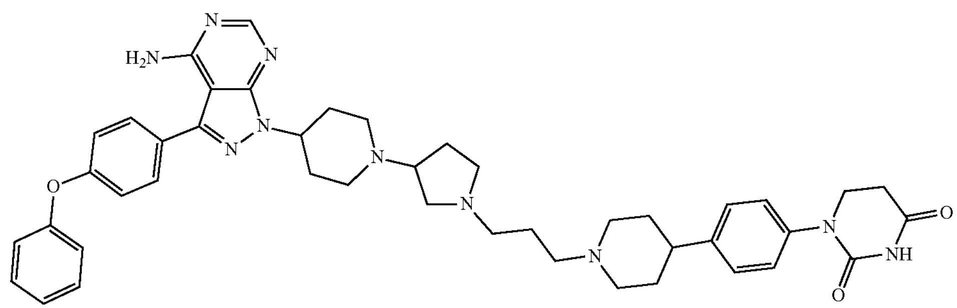 [SMILES: Nc1ncnc2c1c(-c1ccc(Oc3ccccc3)cc1)nn2C1CCN(C2CCN(CCCN3CCC(c4ccc(N5CCC(=O)NC5=O)cc4)CC3)C2)CC1] | 1-(4-(1-(3-(3-(4-(4-amino-3-(4-phenoxyphenyl)-1H-pyrazolo[3,4-d]pyrimidin-1-yl)piperidin-1-yl)pyrrolidin-1-yl)propyl)piperidin-4-yl)phenyl)dihydropyrimidine-2,4(1H,3H)-dione | 768.42 | A | B | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (anti-proliferation) JeKO-1 cells | IC$_{50}$ (anti-proliferation) Mino cells | DC$_{50}$ | D$_{max}$ |
|---|---|---|---|---|---|---|---|
| 577 | 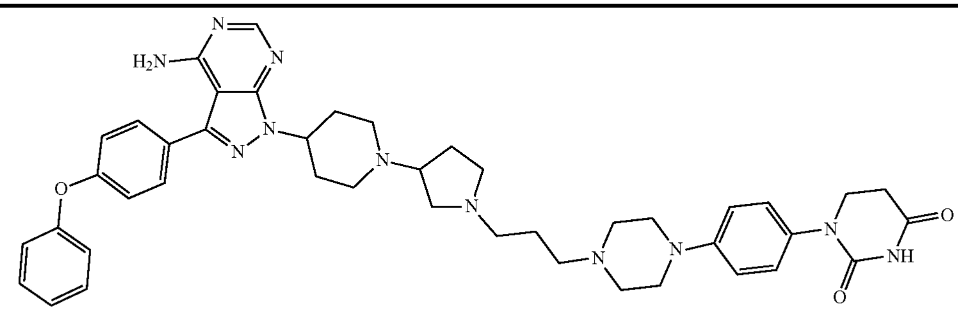 | 1-(4-(4-(3-(3-(4-(4-amino-3-(4-phenoxyphenyl)-1H-pyrazolo[3,4-d]pyrimidin-1-yl)piperidin-1-yl)pyrrolidin-1-yl)propyl)piperazin-1-yl)phenyl)dihydropyrimidine-2,4(1H,3H)-dione | 769.42 | B | B | A | A |
| 578 | 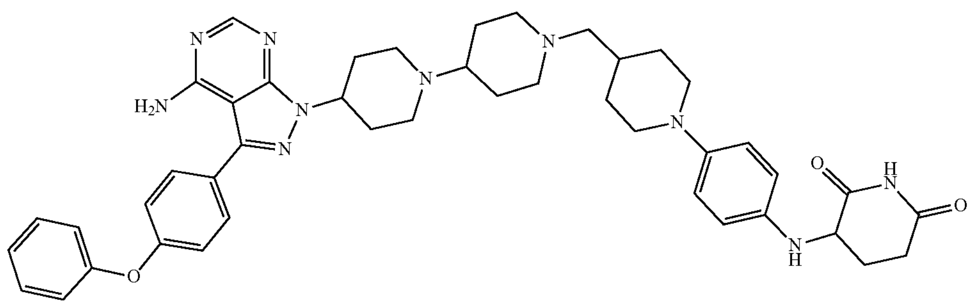 [SMILES: Nc1ncnc2c1c(-c1ccc(Oc3ccccc3)cc1)nn2C1CCN(C2CCN(CC3CCN(c4ccc(NC5CCC(=O)NC5=O)cc4)CC3)CC2)CC1] | 3-((4-((4-(4-amino-3-(4-phenoxyphenyl)-1H-pyrazolo[3,4-d]pyrimidin-1-yl)-[1,4'-bipiperidin]-1'-yl)methyl)piperidin-1-yl)phenyl)amino)piperidine-2,6-dione | 768.42 | B | B | B | A |
| 579 | 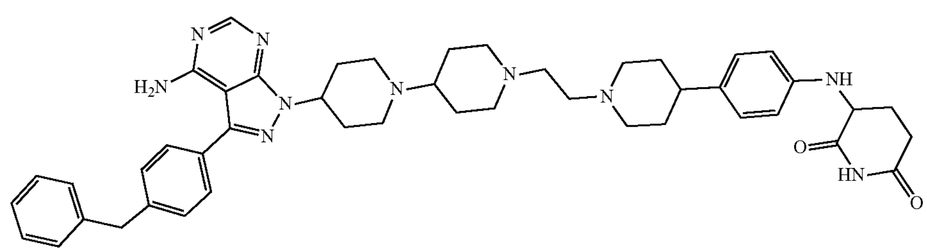 [SMILES: Nc1ncnc2c1c(-c1ccc(Cc3ccccc3)cc1)nn2C1CCN(C2CCN(CCN3CCC(c4ccc(NC5CCC(=O)NC5=O)cc4)CC3)CC2)CC1] | 3-((4-(1-(2-(4-(4-amino-3-(4-phenoxyphenyl)-1H-pyrazolo[3,4-d]pyrimidin-1-yl)-[1,4'-bipiperidin]-1'-yl)ethyl)piperidin-4-yl)phenyl)amino)piperidine-2,6-dione | 782.44 | A | A | B | A |

TABLE 1-continued

Exemplary compounds of the present invention. Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 580 | 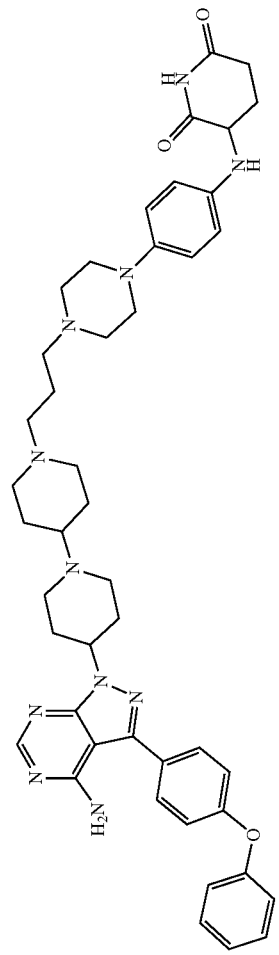 | 3-((4-(1-(3-(4-(4-amino-3-(4-phenoxyphenyl)-1H-pyrazolo[3,4-d]pyrimidin-1-yl)-[1,4'-bipiperidin]-1'-yl)propyl)piperidin-4-yl)phenyl)amino)piperidine-2,6-dione | 796.45 | A | A | A | A |
| 581 | 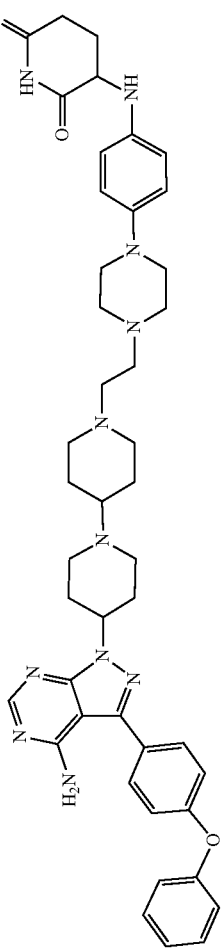 | 3-((4-(4-(2-(4-(4-amino-3-(4-phenoxyphenyl)-1H-pyrazolo[3,4-d]pyrimidin-1-yl)-[1,4'-bipiperidin]-1'-yl)ethyl)piperazin-1-yl)phenyl)amino)piperidine-2,6-dione | 783.43 | A | A | A | A |

TABLE 1-continued

Exemplary compounds of the present invention.
Antiproliferation in mantle cell lymphoma cell (Mino or JeKo-1).

| # | Structure | IUPAC Name | Exact Mass | IC$_{50}$ (antiproliferation) JeKO-1 cells | IC$_{50}$ (antiproliferation) Mino cells | DC$_{50}$ | D$_{max}$ |
|---|---|---|---|---|---|---|---|
| 582 | Exact Mass: 797.45 | 1-(4-(3-(4-((4-(4-amino-3-(4-phenoxyphenyl)-1H-pyrazolo[3,4-d]pyrimidin-1-yl)piperidin-1-yl)methyl)piperidin-1-yl)propyl)piperazin-1-yl)phenyl)dihydropyrimidine-2,4(1H,3H)-dione | 797.45 | B | A | B | A |

A - IC$_{50}$ <1 μM;
B - 1 nM <10 μM;
C - IC$_{50}$ >10 μM.

BTK degradation (DC$_{50}$): A <10 nM; B: 10-50 nM; C: >50 nM.
BTK degradation (D$_{max}$): A >90%; B >75%; C > 50%; D <50%.

Pharmaceutical Compositions

In one aspect, the present invention also provides a composition comprising a compound of Formula (I), or a derivative, tautomer, stereoisomer, mixture of stereoisomers, pharmaceutically acceptable salt, or solvate thereof.

In another aspect, the present invention provides a pharmaceutical composition comprising a compound of Formula (I), or a pharmaceutically acceptable salt thereof, and at least one pharmaceutically acceptable excipient.

In another aspect, the present invention provides a compound of Formula (I), or a pharmaceutically acceptable salt thereof, for use in reducing the level or activity of a target protein (e.g., Bruton's tyrosine kinase (BTK)).

In another aspect, the present invention provides a compound of Formula (I), or a pharmaceutically acceptable salt thereof, for use in inhibiting a target protein (e.g., BTK).

In another aspect, the present invention provides a compound of Formula (I), or a pharmaceutically acceptable salt thereof, for use in therapy.

In another aspect, the present invention provides a compound of Formula (I), or a pharmaceutically acceptable salt thereof, for use in the treatment of cancer.

In some embodiments, the present invention provides a method for treating cancer in a warm-blooded animal in need of such treatment, which comprises administering to the warm-blooded animal a therapeutically effective amount of a compound of Formula (I), or a pharmaceutically acceptable salt thereof.

In one embodiment, the pharmaceutical composition comprises at least one compound of Formula (I) or a pharmaceutically acceptable salt or solvate thereof. In one embodiment, the pharmaceutical compound is for use in treatment of a proliferative disease, such as a cancer, for example, a B-cell malignancy. A further embodiment may provide a method of treating B-cell malignancy comprising administering to a subject in need of treatment or amelioration a compound according to any one of the preceding paragraphs. The B-cell malignancy may be an BTK-dependent lymphoma, for example, mantle cell lymphoma. The subject may express a mutant BTK protein or any variant of BTK, such as BTK C480S. An embodiment may provide proper and effective use of a compound as in the paragraphs above for treating and/or preventing breast cancer. In some embodiments the B-cell malignancy is chronic lymphocytic leukemia. In some embodiments said subject expresses a mutant BTK protein. In some embodiments a compound as presented above is used in the preparation of a medicament for treatment of breast cancer in a patient or subject, such as a human or animal.

The pharmaceutical compositions of the present disclosure can be in any form known to those of skill in the art, and a suitable dosage form of the compound(s) can be administered by an appropriate route. For instance, in some embodiments the pharmaceutical compositions are in a form of a product for oral delivery, said product form being selected from a group consisting of a concentrate, dried powder, liquid, capsule, pellet, and pill. In other embodiments, the pharmaceutical compositions of the disclosure are in the form of a product for parenteral administration including intravenous, intradermal, intramuscular, intraarticular, intra-synovial, intrasternal, intrathecal and subcutaneous administration. The compounds described herein may be administered as a single dose or a divided dose over a period of time. The pharmaceutical compositions disclosed herein may also further comprise carriers, binders, diluents, and excipients. The described carriers, diluents and excipients may include dried corn starch or lactose, the binder may include microcrystalline cellulose, gum tragacanth or gelatin, in addition, the excipients may also include a dispersing agent, a lubricant, a glidant, a sweetening agent or a flavoring agent.

Also, in other aspects, the present disclosure relates to new BTK degrading composition comprising one or more compounds selected from the group consisting of a compound of Formula (I) and pharmaceutically acceptable salts and solvates thereof. In some embodiments, said compound has a purity of ≥75%, ≥80%, ≥85%, ≥90%, ≥95%, ≥96%, ≥97%, or ≥98%, and ≥99%. In some embodiments, the pharmaceutical composition is provided comprising the new BTK degrading composition, either alone or in combination with at least one additional therapeutic agent, with a pharmaceutically acceptable carrier; and uses of the new BTK degrading compositions, either alone or in combination with at least one additional therapeutic agent, in the treatment of proliferative diseases including breast cancer at any stage of the disease diagnosis. The combination with an additional therapeutic agent may take the form of combining the new BTK degrading compounds with any known therapeutic agent.

The disclosed compounds can be used to slow the rate of primary tumor growth. The disclosed compounds can also be used to prevent, abate, minimize, control, and/or lessen tumor metastasis in humans and animals. The disclosed compounds when administered to a subject in need of treatment can be used to stop the spread of cancer cells. As such, the compounds disclosed herein can be administered as part of a combination therapy with one or more drugs or other pharmaceutical agents. When used as part of the combination therapy, the decrease in metastasis and reduction in primary tumor growth afforded by the disclosed compounds allows for a more effective and efficient use of any pharmaceutical or drug therapy being used to treat the patient. In addition, control of metastasis by the disclosed compound affords the subject a greater ability to concentrate the disease in one location.

The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

Methods of Treatment

The methods for treating a clinical indication by the BTK degrading compounds disclosed herein, may be effectuated by administering a therapeutically effective amount of the BTK degrading compounds to a patient in need thereof, this therapeutically effective amount may comprise administration of the prodrug to the patient at 1 mg/kg/day, 2 mg/kg/day, 3 mg/kg/day, 4 mg/kg/day, 5 mg/kg/day, 10 mg/kg/day and 20 mg/kg/day. Alternatively, amounts ranging from about 0.001 mg/kg/day to about 0.01 mg/kg/day, or about 0.01 mg/kg/day to about 0.1 mg/kg/day, or about 0.1 mg/kg/day to about 1 mg/kg/day, or about 1 mg/kg/day to 10 mg/kg/day, or about 10 mg/kg/day to about 100 mg/kg/day are also contemplated.

A further object of the disclosure is a kit, comprising a composition containing at least one BTK degrading compound for treatment and prevention of cancer and cancer related morbidities. The composition of the kit may comprise at least one carrier, at least one binder, at least one diluent, at least one excipient, at least one other therapeutic agent, or mixtures thereof. The kit may be designed, developed, distributed, or sold as a unit for performing the methods of the present invention and to deliver the drugs to the targeted cells for the treatment and prevention of cancer and related diseases. The kits may also include instructions to customers for proper usage of the kit to treat patients exhibiting the symptoms of the desired disease, e.g., B-cell malignancy.

One aspect of the present disclosure is the compounds disclosed herein as well as the intermediates as used for their synthesis, and the synthetic scheme for the preparation of the disclosed final compounds and the intermediates resulted before the final compound is generated.

While certain features of this invention shown and described below are pointed out in the annexed claims, the invention is not intended to be limited to the details specified, since a person of ordinary skill in the relevant art will understand that various omissions, modifications, substitutions, and changes in the forms and details of the invention illustrated and in its operation may be made without departing in any way from the spirit of the present invention. No feature of the invention is critical or essential unless it is specifically stated as being "critical" or "essential".

These and other features, aspects, and advantages of embodiments of the present disclosure will become more evident with regard to the following descriptions, claims, and accompanying drawings explained below.

Another object of the disclosure is to provide a composition, for example a pharmaceutical composition, comprising at least one BTK degrader compound in an amount effective for the indication of proliferative diseases such as cancer, including but not limited to B-cell malignancy. In an embodiment, the cancer is a B-cell malignancy, such as mantle cell lymphoma or chronic lymphocytic leukemia.

In an embodiment, the object of such treatment is to degrade BTK and/or inhibit BTK-dependent proliferation of a cell. In a further embodiment, said object is to inhibit BTK-induced proliferation of a cell by a mechanism selected from BTK inhibitors and PROTAC.

As used herein, "treating" means administering to a subject a pharmaceutical composition to ameliorate, reduce or lessen the symptoms of a disease. As used herein, "treating" or "treat" describes the management and care of a subject for the purpose of combating a disease, condition, or disorder and includes the administration of a compound disclosed herein, or a pharmaceutically acceptable salt, polymorph or solvate thereof, to alleviate the symptoms or complications of a disease, condition or disorder, or to eliminate the disease, condition or disorder. The term "treat" may also include treatment of a cell in vitro or an animal model. As used herein, "subject" or "subjects" refers to any animal, such as mammals including rodents (e.g., mice or rats), dogs, primates, lemurs or humans.

Treating cancer may result in a reduction in size of a tumor. A reduction in size of a tumor may also be referred to as "tumor regression." Preferably, after treatment, tumor size is reduced by about 5% or greater relative to its size prior to treatment; more preferably, tumor size is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75% or greater. Size of a tumor may be measured by any reproducible means of measurement. The size of a tumor may be measured as a diameter of the tumor.

Treating cancer may result in a reduction in tumor volume. Preferably, after treatment, tumor volume is reduced by about 5% or greater relative to its size prior to treatment; more preferably, tumor volume is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by about 75% or greater. Tumor volume may be measured by any reproducible means of measurement.

Treating cancer may result in a decrease in number of tumors. Preferably, after treatment, tumor number is reduced by about 5% or greater relative to number prior to treatment; more preferably, tumor number is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. Number of tumors may be measured by any reproducible means of measurement. The number of tumors may be measured by counting tumors visible to the naked eye or at a specified magnification. Preferably, the specified magnification is about 2×, 3×, 4×, 5×, 10×, or 50×.

Treating cancer may result in a decrease in number of metastatic lesions in other tissues or organs distant from the primary tumor site. Preferably, after treatment, the number of metastatic lesions is reduced by about 5% or greater relative to number prior to treatment; more preferably, the number of metastatic lesions is reduced by about 10% or greater; more preferably, reduced by about 20% or greater; more preferably, reduced by about 30% or greater; more preferably, reduced by about 40% or greater; even more preferably, reduced by about 50% or greater; and most preferably, reduced by greater than about 75%. The number of metastatic lesions may be measured by any reproducible means of measurement. The number of metastatic lesions may be measured by counting metastatic lesions visible to the naked eye or at a specified magnification. Preferably, the specified magnification is about 2×, 3×, 4×, 5×, 10×, or 50×.

Treating cancer may result in an increase in average survival time of a population of treated subjects in comparison to a population receiving carrier alone. Preferably, the average survival time is increased by more than about 30 days; more preferably, by more than about 60 days; more preferably, by more than about 90 days; and most preferably, by more than about 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in an increase in average survival time of a population of treated subjects in comparison to a population of untreated subjects. Preferably, the average survival time is increased by more than about 30 days; more preferably, by more than about 60 days; more preferably, by more than about 90 days; and most preferably, by more than about 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in increase in average survival time of a population of treated subjects in comparison to a population receiving monotherapy with a drug that is not a compound disclosed herein, or a pharmaceutically acceptable salt thereof. Preferably, the average survival time is increased by more than about 30 days; more preferably, by more than about 60 days; more preferably, by more than about 90 days; and most preferably, by more than about 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in a decrease in the mortality rate of a population of treated subjects in comparison to a population receiving carrier alone. Treating cancer may result in a decrease in the mortality rate of a population of treated subjects in comparison to an untreated population. Treating cancer may result in a decrease in the mortality rate of a population of treated subjects in comparison to a population receiving monotherapy with a drug that is not a compound disclosed herein, or a pharmaceutically acceptable salt, prodrug, metabolite, analog or derivative thereof. Preferably, the mortality rate is decreased by more than about 2%; more preferably, by more than about 5%; more preferably, by more than about 10%; and most preferably, by more than about 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in a decrease in tumor growth rate. Preferably, after treatment, tumor growth rate is reduced by at least about 5% relative to number prior to treatment; more preferably, tumor growth rate is reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Tumor growth rate may be measured by any reproducible means of measurement. Tumor growth rate may be measured according to a change in tumor diameter per unit time.

Treating cancer may result in a decrease in tumor regrowth, for example, following attempts to remove it surgically. Preferably, after treatment, tumor regrowth is less than about 5%; more preferably, tumor regrowth is less than about 10%; more preferably, less than about 20%; more preferably, less than about 30%; more preferably, less than about 40%; more preferably, less than about 50%; even more preferably, less than about 60%; and most preferably, less than about 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in a reduction in the rate of cellular proliferation. Preferably, after treatment, the rate of cellular proliferation is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in a reduction in the proportion of proliferating cells. Preferably, after treatment, the proportion of proliferating cells is reduced by at least about 5%; more preferably, by at least about 10%; more preferably, by at least about 20%; more preferably, by at least about 30%; more preferably, by at least about 40%; more preferably, by at least about 50%; even more preferably, by at least about 60%; and most preferably, by at least about 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells may be equivalent to the mitotic index.

Treating or preventing a cell proliferative disorder may result in a decrease in size of an area or zone of cellular proliferation. Preferably, after treatment, size of an area or zone of cellular proliferation is reduced by at least about 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in a decrease in the number or proportion of cells having an abnormal appearance or morphology. Preferably, after treatment, the number of cells having an abnormal morphology is reduced by at least about 5% relative to its size prior to treatment; more preferably, reduced by at least about 10%; more preferably, reduced by at least about 20%; more preferably, reduced by at least about 30%; more preferably, reduced by at least about 40%; more preferably, reduced by at least about 50%; even more preferably, reduced by at least about 60%; and most preferably, reduced by at least about 75%. An abnormal cellular appearance or morphology may be measured by any reproducible means of measurement. An abnormal cellular morphology may be measured by microscopy, e.g., using an inverted tissue culture microscope. An abnormal cellular morphology may take the form of nuclear pleomorphism.

EXAMPLES

Hereby are provided non-limiting examples of embodiments of compounds disclosed herein. The examples and preparations provided below further illustrate and exemplify the compounds as disclosed herein and methods of preparing such compounds. It is to be understood that the scope of the present disclosure is not limited in any way by the scope of the following examples and preparations. Unless stated otherwise, starting materials were commercially available. All solvents and commercial reagents were of laboratory grade and were used as received.

Example 1: General Synthesis

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours. Isolation and purification of the chemical entities and intermediates described herein can be implemented, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, 3rd Ed., 1990 New York: Plenum Press; Mundy et al., Name Reaction and Reagents in Organic Synthesis, 2nd Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, 3rd Ed., John Wiley & Sons). These groups may be removed at a convenient stage of the compound synthesis using methods that are readily apparent to those skilled in the art.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

Example 2: Preparation of Key Intermediate Compounds

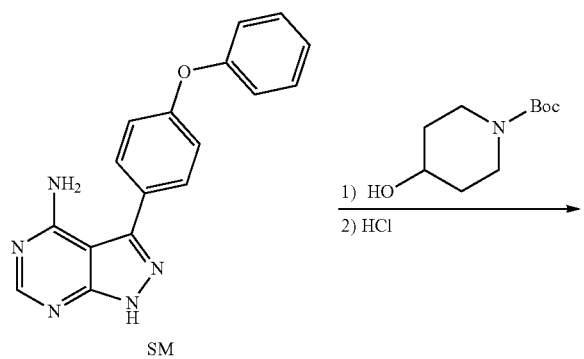

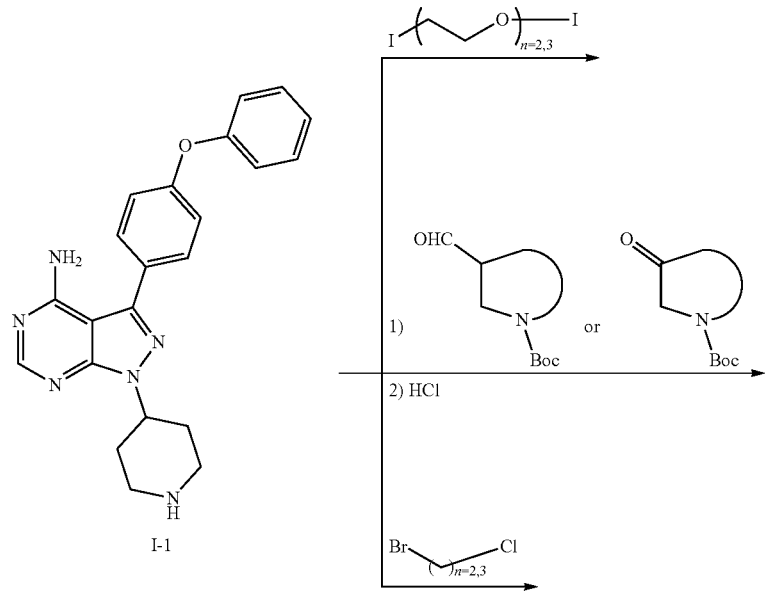

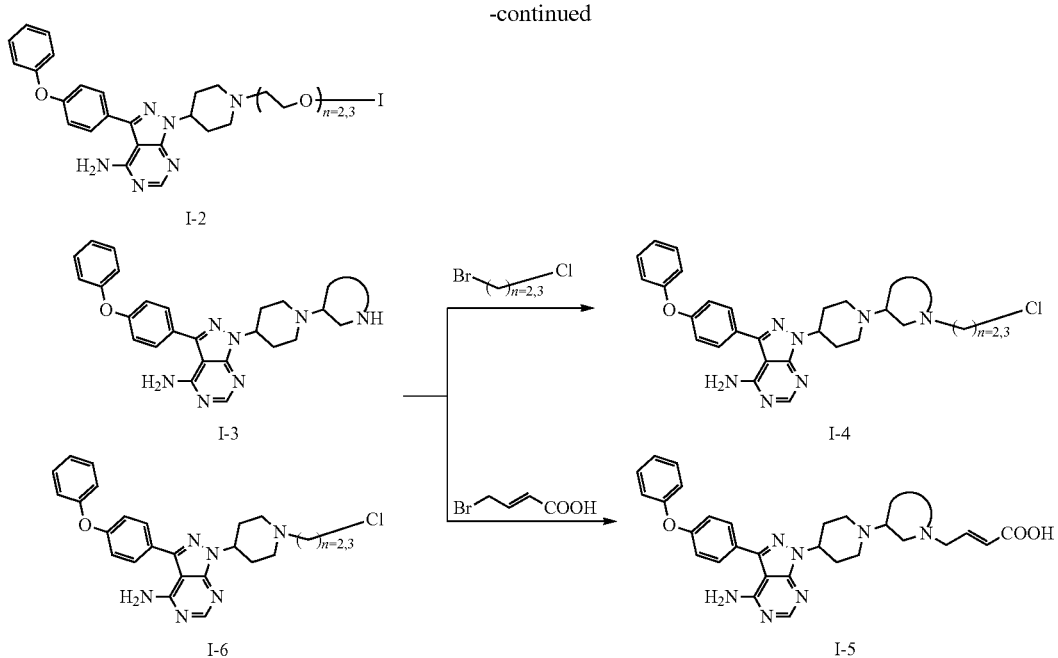

I-2, I-3, I-4, I-5 were key intermediates, including four types of linkers: oxygen-containing aliphatic hydrocarbon linker (OEG-linker), heteroatom ring linker, heteroatom ring-aliphatic hydride liker and heteroatom ring-carbonyl fragment containing linker respectively. Their preparation was illustrated in the synthesis of representative compounds as follows.

Step 1. Preparation of 3-(4-phenoxyphenyl)-1-(piperidin-4-yl)-1H-pyrazolo(3,4-d)pyrimidin-4-amine (I-1)

To the solution of PPh3 (3.44 g, 13.2 mmol) in THF (150 ml) was added DEAD (2.56 ml, 13.2 mmol) dropwise at 0° C. Upon the addition, the mixture was stirred at the same temperature under $N_2$ for 30 min, following by adding the tert-butyl 4-hydroxypiperidine-1-carboxylate (2.64 g, 13.2 mmol). After 30 mins, the SM (2.00 g, 6.60 mmol) was added. Then the reaction mixture was stirred at 50° C. under $N_2$ overnight.

The solvent was removed under vacuum, and the residue was dissolved in EA (100 ml). The organic solution was washed with water (30 mL×3) and sat. NaCl solution (40 ml), dried with $Na_2SO_4$. The crude boc-protected intermediate I-1 was obtained after concentration, used without purification.

To the solution of the boc-protected I-1 was added hydrogen chloride solution (4 M in 1,4-dioxane, 15 ml) at 0° C. After being stirred at r.t. for 3 h, a precipitation was found. The suspension was filtered, the cake was washed with DCM (5 ml×3), dried in drying oven. The desired I-1 hydrochloride was obtained as an off-white solid (2.10 g, 82.7%, two steps). LC-MS (ESI$^+$) m/z=387.2 (M+H)$^+$.

Step 2. 1-(1-(2-(2-(2-iodoethoxy)ethoxy)ethyl)piperidin-4-yl)-3-(4-phenoxyphenyl)-1H-pyrazolo(3,4-d)pyrimidin-4-amine (I-2a)

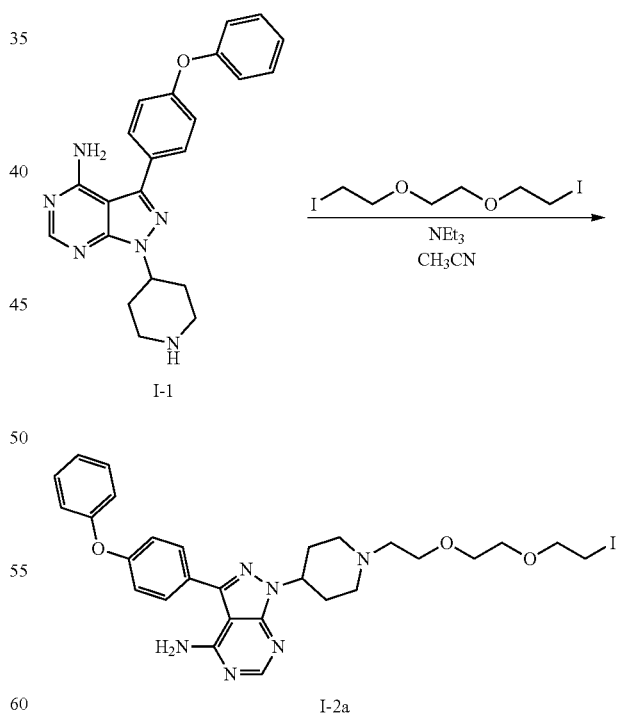

To the mixture of I-1 (0.10 g, 0.26 mmol) and NEt$_3$ (0.40 ml) in CH$_3$CN (10 ml) was added 1,2-bis(2-iodoethoxy) ethane (0.19 g, 0.52 mmol) dropwise at 0° C. under $N_2$. Upon the addition, the reaction mixture was stirred at r.t. under $N_2$ overnight. Then mixture was separated with flash column (SiO$_2$, MeOH in CHCl$_3$=0-15%) to give the I-2a as a white solid (0.15 g, 93.4%). LC-MS (ESI$^+$) m/z=629.2 (M+H)$^+$.

Step 3a. 1-(1-(2-(2-(2-iodoethoxy)ethoxy)ethyl)piperidin-4-yl)-3-(4-phenoxyphenyl)-1H-pyrazolo(3,4-d)pyrimidin-4-amine (I-3a)

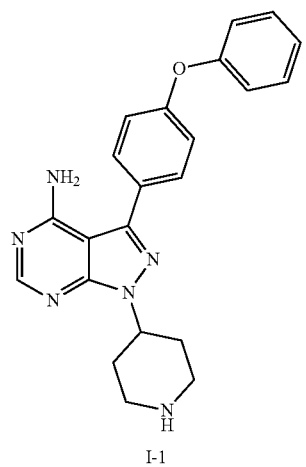

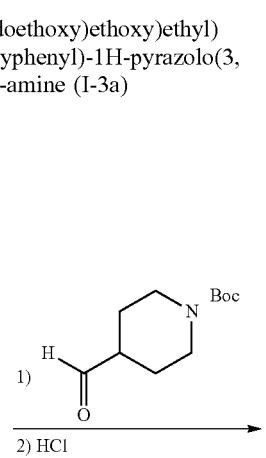

I-3a

The mixture of I-1 (0.80 g, 2.07 mmol), NEt$_3$ (0.45 ml) in DCM (15 ml) was stirred at r.t. for 30 min, following by adding the tert-butyl 4-formylpiperidine-1-carboxylate (1.32 g, 6.22 mmol). The reaction mixture was stirred at r.t. for 6 h. Then the Na(OAc)$_3$BH (0.88 g, 4.14 mmol) was added at 0° C. portionwise. Upon the addition, the reaction mixture was stirred at r.t. for 1 h, and separated with flash column (SiO$_2$, MeOH in DCM=0-30%) to give the boc-protected I-3a as a yellow semi solid.

To the suspension of the boc-protected I-3a in DCM (5 ml) was added the hydrogen chloride solution (4 M in 1,4-dioxane, 5 ml) dropwise at 0° C. Upon the addition, the suspension was stirred at r.t. for 1 h, followed by being concentrated. The crude I-3a hydrochloride was obtained as a yellow solid (1.02 g, 95.0%, two steps). LC-MS (ESI$^+$) m/z=483.3 (M+H)$^+$.

Step 3b. 1-((1,4'-bipiperidin)-4-yl)-3-(4-phenoxyphenyl)-1H-pyrazolo(3,4-d)pyrimidin-4-amine (I-3b)

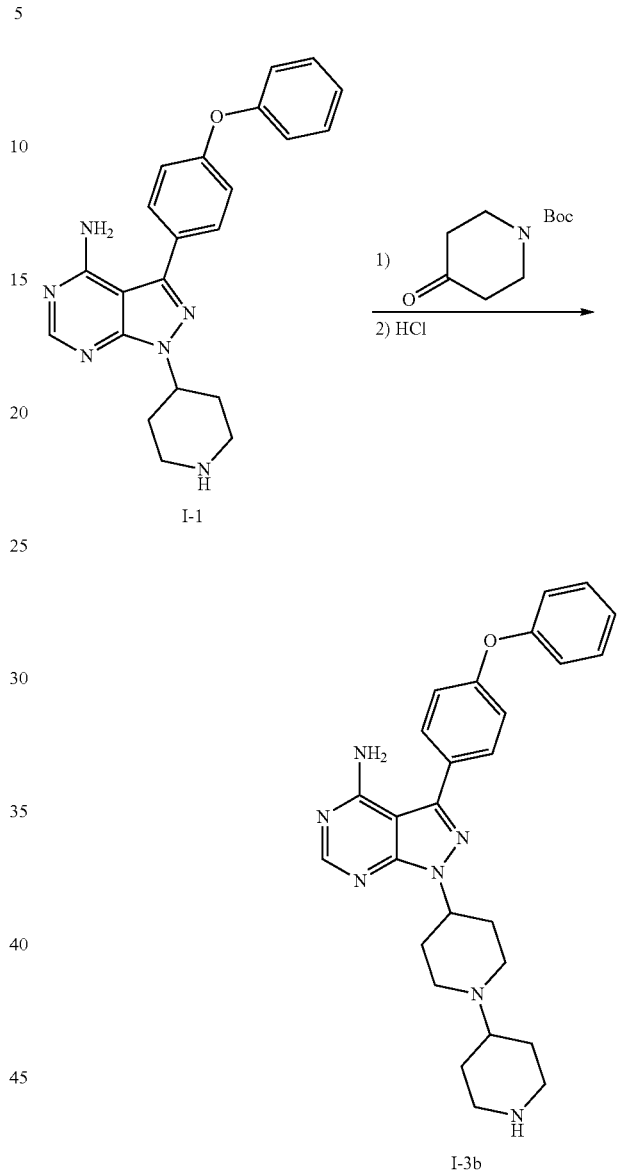

The mixture of I-1 (0.80 g, 2.07 mmol), NEt$_3$ (0.45 ml) in DCM (15 ml) was stirred at r.t. for 30 min, following by adding the tert-butyl 4-oxopiperidine-1-carboxylate (0.83 g, 4.14 mmol). The reaction mixture was stirred at r.t. for 6 h. Then the Na(OAc)$_3$BH (0.88 g, 4.14 mmol) was added at 0° C. portionwise. Upon the addition, the reaction mixture was stirred at r.t. for 1 h, and separated with flash column (SiO$_2$, MeOH in DCM=0-25%) to give the boc-protected I-3b as a yellow semi solid.

To the suspension of the boc-protected I-3b in DCM (5 ml) was added the hydrogen chloride solution (4 M in 1,4-dioxane, 5 ml) dropwise at 0° C. Upon the addition, the suspension was stirred at r.t. for 1 h, followed by being concentrated. The crude I-3b hydrochloride was obtained as a yellow solid (0.97 g, 93.0%, two steps). LC-MS (ESI$^+$) m/z=470.3 (M+H)$^+$.

Step 4. 1-(1-((1-(3-chloropropyl)piperidin-4-yl)methyl)piperidin-4-yl)-3-(4-phenoxyphenyl)-1H-pyrazolo(3,4-d)pyrimidin-4-amine (I-4a)

Step 5. (E)-4-(4-((4-(4-amino-3-(4-phenoxyphenyl)-1H-pyrazolo(3,4-d)pyrimidin-1-yl)piperidin-1-yl)methyl)piperidin-1-yl)but-2-enoic Acid (I-5a)

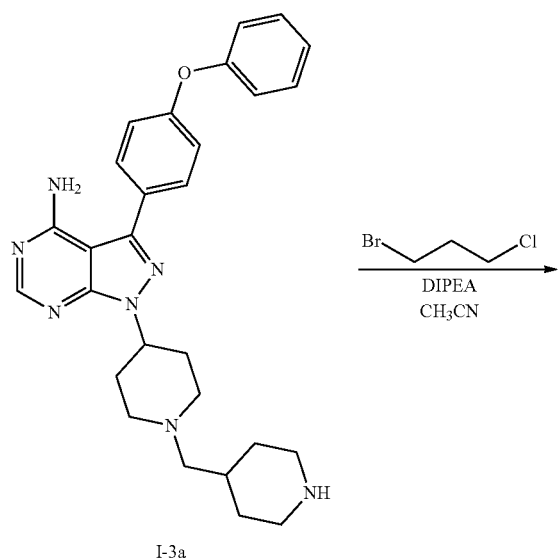

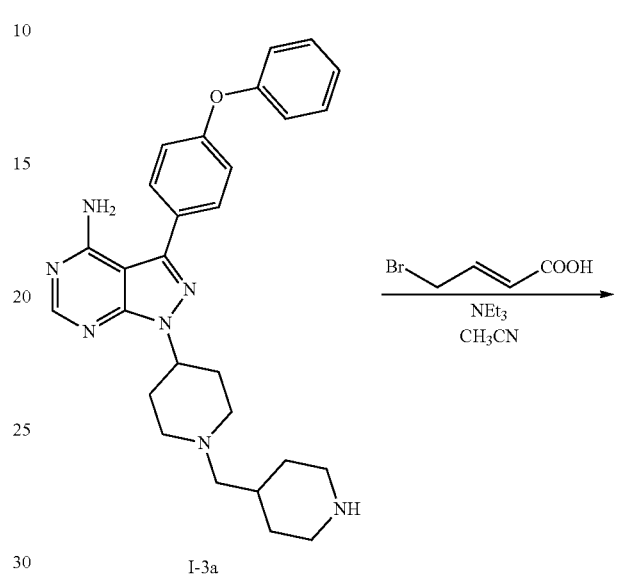

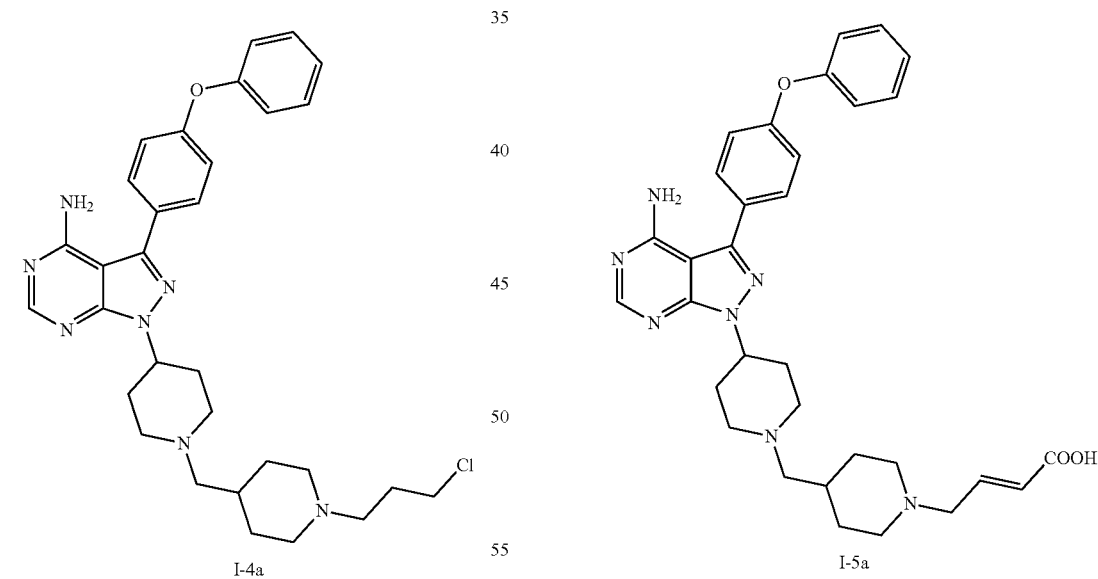

The mixture of I-3a (0.16 g, 0.33 mmol) and DIPEA (0.12 ml, 0.66 mmol) was stirred under $N_2$ for 30 mins, followed by adding 1-bromo-3-chloropropane (0.10 g, 0.66 mmol). The reaction mixture was stirred at r.t. overnight. The mixture was separated with flash column ($SiO_2$, MeOH in $CHCl_3$=0-15%) to give the I-4a yellow semi-solid (0.20 g, >100%). LC-MS ($ESI^+$) m/z=560.3 $(M+H)^+$.

The mixture of I-3a (0.40 g, 0.83 mmol), 4-bromobut-2-enoic acid (0.30 g, 1.83 mmol) and $NEt_3$ (0.11 ml) was stirred at r.t. under $N_2$ for overnight. The suspension was separated with flash column ($SiO_2$, MeOH in $CHCl_3$=0-15%) to give a yellow solid (0.30 g, 63.8%). LC-MS ($ESI^+$) m/z=568.3 $(M+H)^+$.

Step 6. 1-(1-(2-chloroethyl)piperidin-4-yl)-3-(4-phenoxyphenyl)-1H-pyrazolo(3,4-d)pyrimidin-4-amine (I-6a)

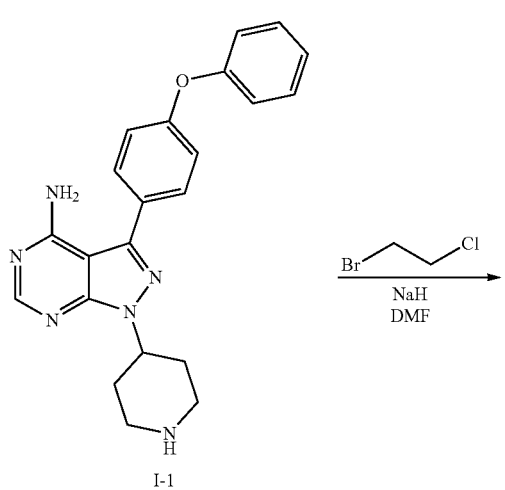

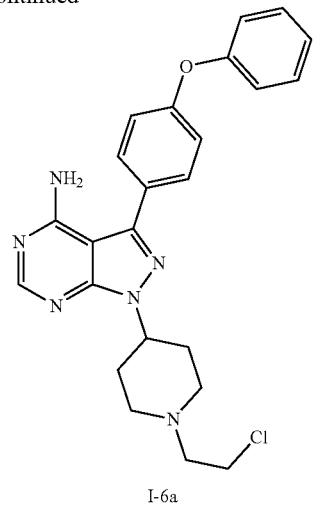

I-6a

To the mixture of I-1 (1.00 g, 2.59 mmol) and 1-bromo-2-chloroethane (0.43 ml, 5.18 mmol) in DMF (10 ml) was added NaH (0.12 g, 5.18 mmol) at 0° C. with stir. Upon the addition, the reaction mixture was stirred at r.t. under $N_2$ for 2.0 h. The suspension was poured to ice-water (50 ml), extracted with EA (20 ml×5). The combined EA layers were washed with sat. NaCl solution (20 ml×2), dried over $Na_2SO_4$.

The crude product was purified with flash column ($SiO_2$, MeOH in $CHCl_3$=0-30%) to give the I-6a as yellow semi-solid (0.70 g, 60.2%). LC-MS (ESI$^+$) m/z=449.2 (M+H)$^+$.

Example 3: Preparation of CRBN-Binding E3 Ligase Ligands

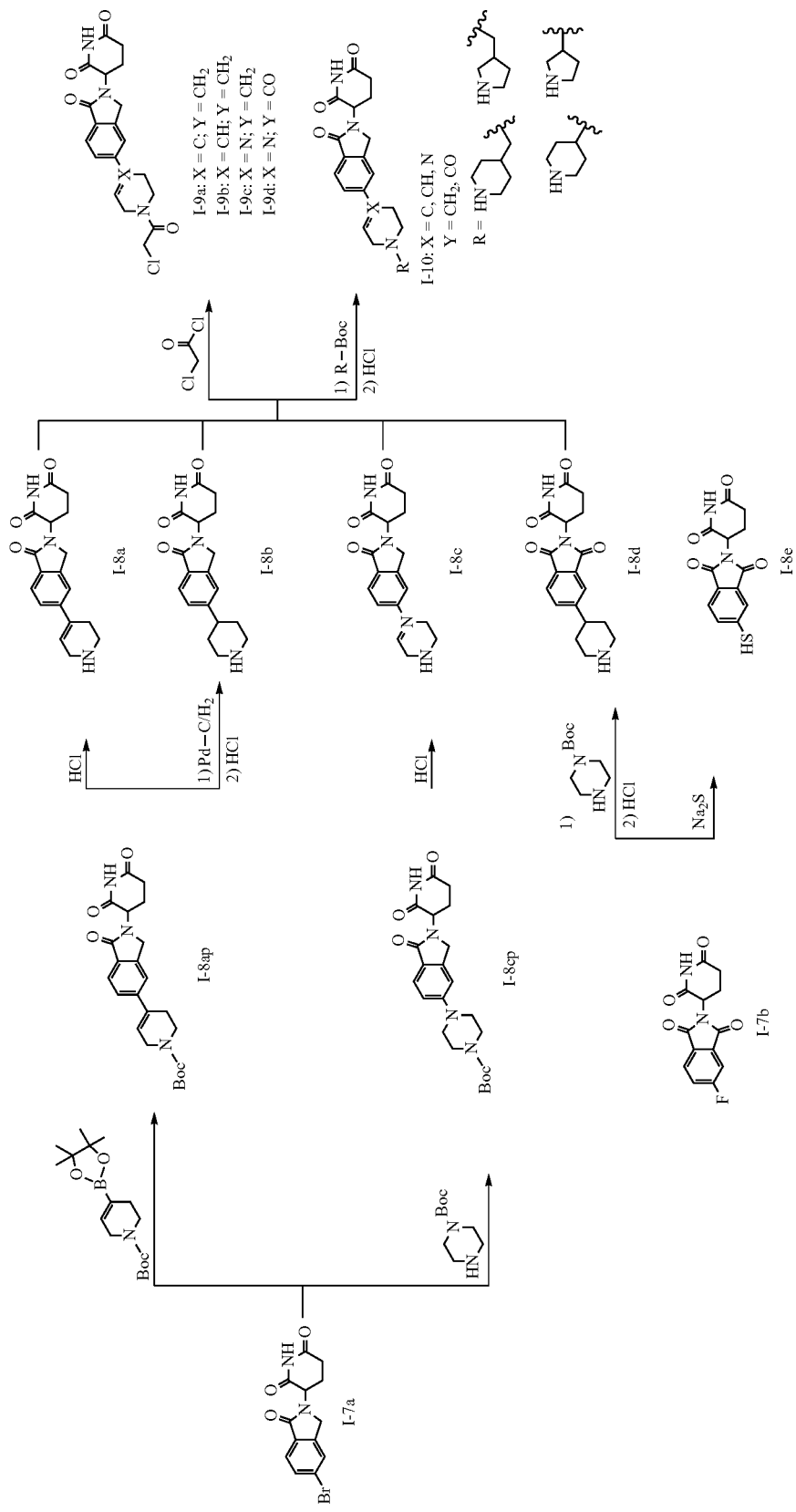

Step 1: Preparation of 3-(1-oxo-5-(1,2,3,6-tetrahydropyridin-4-yl)isoindolin-2-yl)piperidine-2,6-dione (I-8a)

The mixture of I-7a (1.50 g, 4.67 mmol), potassium phosphate (1.20 g, 5.56 mmol) in DMF (15 ml) was degassed for 2 min prior to the addition of 3,6-dihydro-2H-pyridine-I-fer/-butoxycarbonyl-4-boron acid pinacol ester (1.83 g, 5.98 mmol) and Pd(dppf)Cl$_2$ (0.19 g, 0.23 mmol). The reaction mixture was degassed for 2 min and stirred at 90° C. for 16 h. Then the suspension was filtered, and the cake was washed with CHCl$_3$ and MeOH. The combined filtrates were evaporated and redissolved in EA (50 ml), followed by being washed with water (15 ml×3), sat. NaCl solution (15 ml×2), dried over Na$_2$SO$_4$. The crude product was purified with flash column (SiO$_2$, MeOH in CHCl$_3$=0-15%) to give the I-8ap as a brown semi-solid (0.80 g, 40.6%). LC-MS (ESI$^+$) m/z=426.1 (M+H)$^+$, 370.1 (M–C$_4$H$_9$+H)$^+$.

To the solution of I-8ap in DCM (5 ml) was added hydrochloride solution (4 M in 1.40 dioxane, 5 ml) at 0° C. Upon the addition, the suspension was stirred at r.t. for 1 h. The crude I-8a was obtained as its hydrochloride by concentration and used for further reaction without purification (0.68 g, quantitative). LC-MS (ESI$^+$) m/z=326.1 (M+H)$^+$.

Step 2: Preparation of 3-(1-oxo-5-(piperidin-4-yl)isoindolin-2-yl)piperidine-2,6-dione (I-8b)

The suspension of I-8ap (0.50 g, 1.17 mmol) and Pd—C (5%, 0.10 g) in MeOH (20 ml) was degassed for 2 min, then stirred under H$_2$ at 50° C. overnight, followed by being filtered. The cake was washed with hot MeOH and THF. The combined filtrates were concentrated to give the boc-protected I-8b as an off-white solid (0.50 g, quantitative). LC-MS (ESI$^+$) m/z=428.2 (M+H)$^+$, 372.2 (M–C$_4$H$_9$+H)$^+$.

To the solution of boc-protected I-8b in DCM (5 ml) was added hydrochloride solution (4 M in 1.40 dioxane, 5 ml) at 0° C. Upon the addition, the suspension was stirred at r.t. for 1 h. The crude I-8b was obtained as its hydrochloride by concentration and used for further reaction without purification (0.42 g, quantitative). LC-MS (ESI$^+$) m/z=328.2 (M+H)$^+$.

Step 3: Preparation of 3-(1-oxo-5-(piperazin-1-yl)isoindolin-2-yl)piperidine-2,6-dione (I-8c)

The suspension of I-7a (0.50 g, 1.55 mmol), tert-butyl piperazine-1-carboxylate (0.82 g, 1.86 mmol) and Cs$_2$CO$_3$ (1.00 g, 3.09 mmol) in 1,4-dioxane (20 ml) was degassed for 2 min, followed by adding RuPhos (0.15 g, 0.31 mmol), RuPhos G2 Pd (0.24 g, 0.31 mmol). The reaction mixture was stirred under N$_2$ at 100° C. for 16 h, followed by being filtered. The cake was washed with MeOH. The combined filtrates were concentrated and separate by flash column (SiO$_2$, MeOH in CHCl$_3$=0-15%) to give the boc-protected I-8c as brown solid (0.38 g, 57.6%). LC-MS (ESI$^+$) m/z=429.2 (M+H)$^+$, 373.2 (M–C$_4$H$_9$+H)$^+$.

To the solution of boc-protected I-8c in DCM (5 ml) was added hydrochloride solution (4 M in 1.40 dioxane, 5 ml) at 0° C. Upon the addition, the suspension was stirred at r.t. for 1 h. The crude I-8c was obtained as its hydrochloride by concentration and used for further reaction without purification (0.32 g, quantitative). LC-MS (ESI$^+$) m/z=329.2 (M+H)$^+$.

Step 4: Preparation of 2-(2,6-dioxopiperidin-3-yl)-5-(piperazin-1-yl)isoindoline-1,3-dione (I-8d)

The mixture of I-7b (5.00 g, 18.2 mmol), tert-butyl piperazine-1-carboxylate (4.06 g, 21.8 mmol) and DIPEA in NMP (40 ml) was stirred at 90° C. under N$_2$ for 3 h. The reaction mixture was poured to water (200 ml) with stirred, extracted with EA (30 ml×6). The combined organic layers were washed with water (30 ml×4), sat. NaCl sol (30 ml×2), dried with Na$_2$SO$_4$. The crude product was purified with flash column (SiO$_2$, MeOH in DCM=0-10%) to give boc-protected I-8d as a yellow solid (7.45 g, 90.0%). LC-MS (ESI$^+$) m/z=442.1 (M+H)$^+$, 386.1 (M–C$_4$H$_9$+H)$^+$.

To the solution of boc protected I-8d in DCM (10 ml) was added hydrochloride solution (4 M in 1,4-dioxane, 10 ml) at 0° C. Upon the addition, the suspension was stirred at r.t. for 1 h. The crude I-8d was obtained as its hydrochloride by concentration and used for further reaction without purification (6.34 g, quantitative). LC-MS (ESI$^+$) m/z=342.1 (M+H)$^+$.

Step 5: Preparation of 2-(2,6-dioxopiperidin-3-yl)-5-mercaptoisoindoline-1,3-dione (I-8e)

The reaction mixture of I-7b (2.00 g, 7.24 mmol), Na$_2$S (0.85 g, 10.9 mmol) in DMF (20 ml) was stirred at r.t. overnight. The mixture was poured to water (200 ml). An off-white precipitation was found and filtered. The cake was washed with water and dried in oven. The crude I-8e was used for further action without purification (1.50 g, 71.4%). LC-MS (ESI$^+$) m/z=291.0 (M+H)$^+$.

Step 6: Preparation of 5-(4-(2-chloroacetyl)piperazin-1-yl)-2-(2,6-dioxopiperidin-3-yl)isoindoline-1,3-dione (I-9d)

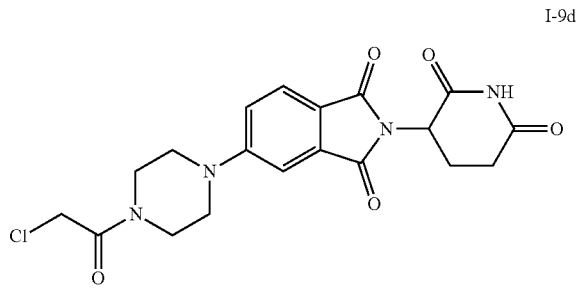 [SMILES: O=C1CCC(N2C(=O)c3ccc(N4CCN(C(=O)CCl)CC4)cc3C2=O)C(=O)N1]

I-9d

The mixture of I-8d (2.00 g, 5.83 mmol), NEt$_3$ (1.89 ml, 10.8 mmol) and in THF (15 ml) was stirred at r.t. for 30 min, flowed by adding the solution of chloroacetyl chloride (0.60 ml, 7.58 mmol) in THF (5 ml) dropwise under N$_2$ at 0° C. Upon the addition, the reaction mixture was stirred at r.t. for 3 h. The solvent was removed, and the residue was dissolved in CHCl$_3$ (50 ml), followed by washing with saturated NaHCO$_3$ solution (15 ml×4), water (15 ml×2) and sat. NaCl solution (15 ml×2), dried with Na$_2$SO$_4$. The crude product was obtained by removing the solvent as yellow semi-solid (2.00 g, 83.3%), and used for further reaction without purification. LC-MS (ESI$^+$) m/z=419.1 (M+H)$^+$.

The I-9 series intermediates were obtained under the same reaction conditions of the preparation of I-9d with their corresponding SMs.

Step 7: Preparation of 2-(2,6-dioxopiperidin-3-yl)-5-(4-(piperidin-4-ylmethyl)piperazin-1-yl)isoindoline-1,3-dione (I-10a)

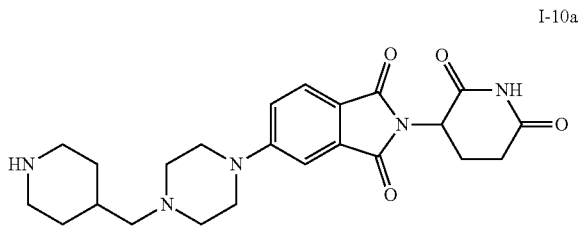 [SMILES: O=C1CCC(N2C(=O)c3ccc(N4CCN(CC5CCNCC5)CC4)cc3C2=O)C(=O)N1]

I-10a

The mixture of I-8d (0.10 g, 0.29 mmol) and NEt₃ (0.12 ml, 0.87 mmol) was stirred at r.t. for 30 min, followed by adding tert-butyl 4-formylpiperidine-1-carboxylate (0.19 g, 0.87 mmol). The reaction mixture was stirred at r.t. overnight. Then the Na(OAc)₃BH (0.10 g, 0.45 mmol) was added at 0° C. The suspension was stirred at r.t. for 1 h, and separated with flash column (SiO₂, MeOH in CHCl₃=0-25%) to give the boc-protected I-10a as a yellow solid (0.14 g, 89.4%).

To the suspension of boc-protected I-10a in DCM (5 ml) was added hydrochloride solution (4 M in 1,4-dioxane, 5 ml) at 0° C. The mixture was stirred at r.t. for 1 h and concentrated to give the crude I-10a as a yellow solid. (0.15 g, quantitative as hydrochloride). LC-MS (ESI⁺) m/z=440.2 (M+H)⁺.

The I-10 series intermediates were prepared under the same reaction conditions of the preparation of I-10a with their corresponding SMs.

Example 4: 3-(5-(4-(2-(2-(2-(4-(4-amino-3-(4-phenoxyphenyl)-1H-pyrazolo(3,4-d)pyrimidin-1-yl)piperidin-1-yl)ethoxy)ethoxy)ethyl)piperazin-1-yl)-1-oxoisoindolin-2-yl)piperidine-2,6-dione (Compound 2)

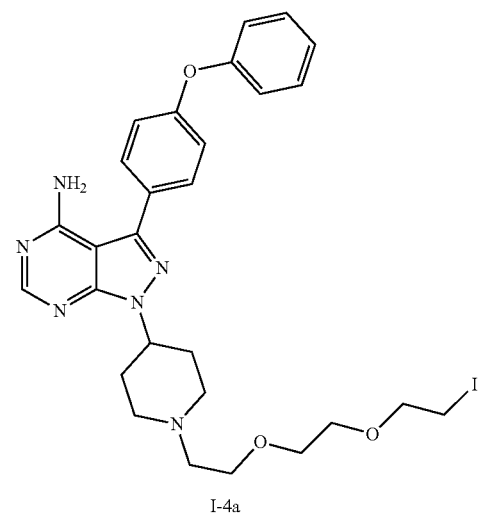

I-4a

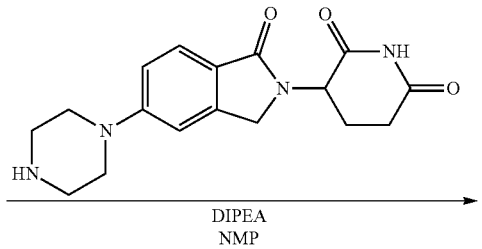

DIPEA
NMP

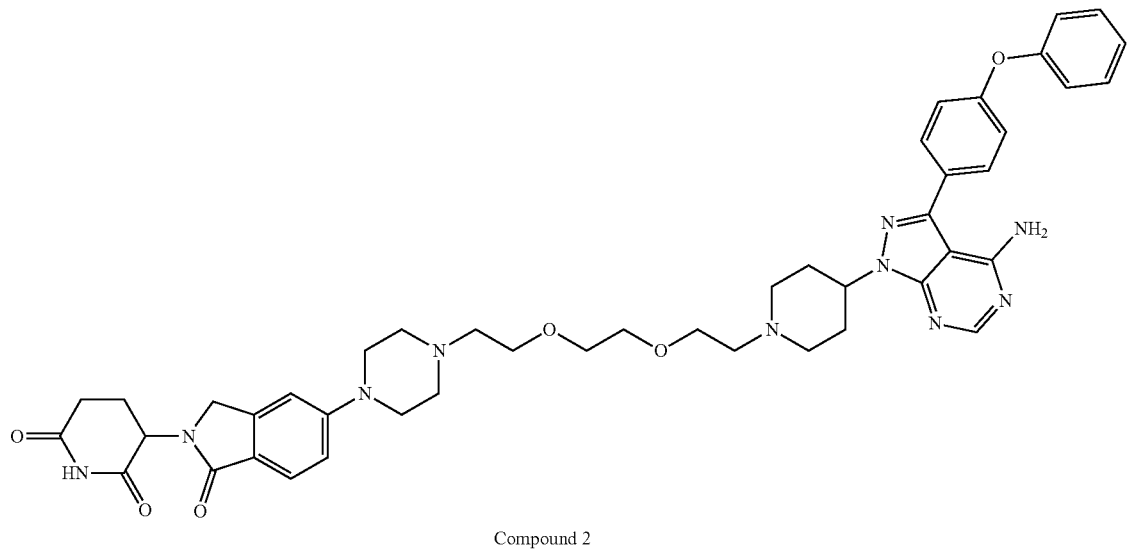

Compound 2

The mixture of I-2a (90 mg, 0.14 mmol) and 3-(1-oxo-5-(piperazin-1-yl)isoindolin-2-yl)piperidine-2,6-dione (45 mg, 0.14 mmol) and DIPEA (0.10 ml) in NMP (6 ml) was stirred at 100° C. under N₂ for 6 h. The reaction mixture was separated with Prep-HPLC (Elute: CH₃CN in H₂O=10-

100%, 15 min) to give Compound 2 as a yellow solid (60 mg, 51.7%). LC-MS (ESI$^+$) m/z=829.4 (M+H)$^+$, 413.2 (M+2H)$^{2+}$.
Example 5: Preparation of Compound 199 (5-(4-((4-((4-(4-amino-3-(4-phenoxyphenyl)-1H-pyrazolo(3,4-d)pyrimidin-1-yl)piperidin-1-yl)methyl)piperidin-1-yl)methyl)piperidin-1-yl)-2-(2,6-dioxopiperidin-3-yl)isoindoline-1,3-dione)
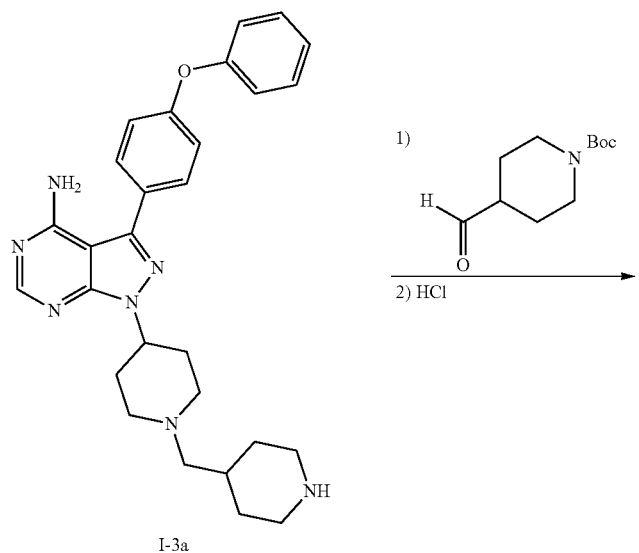
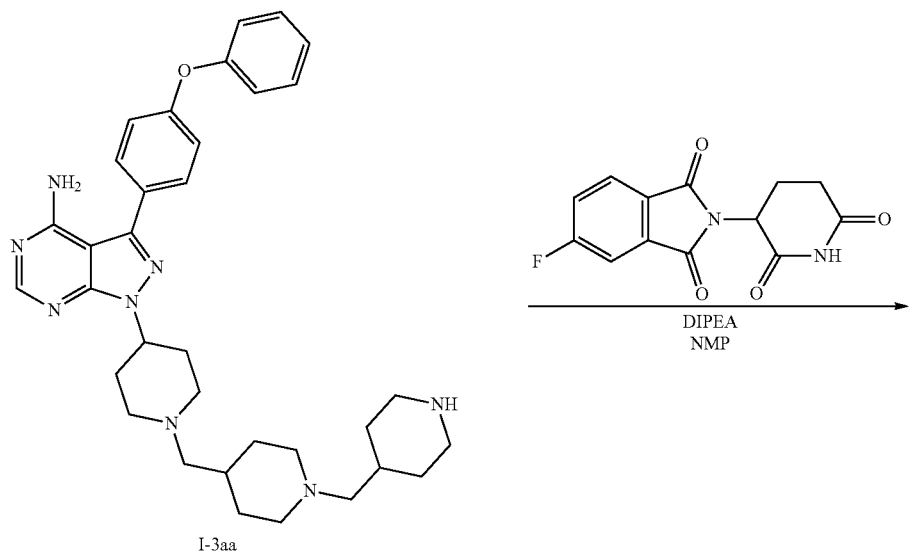

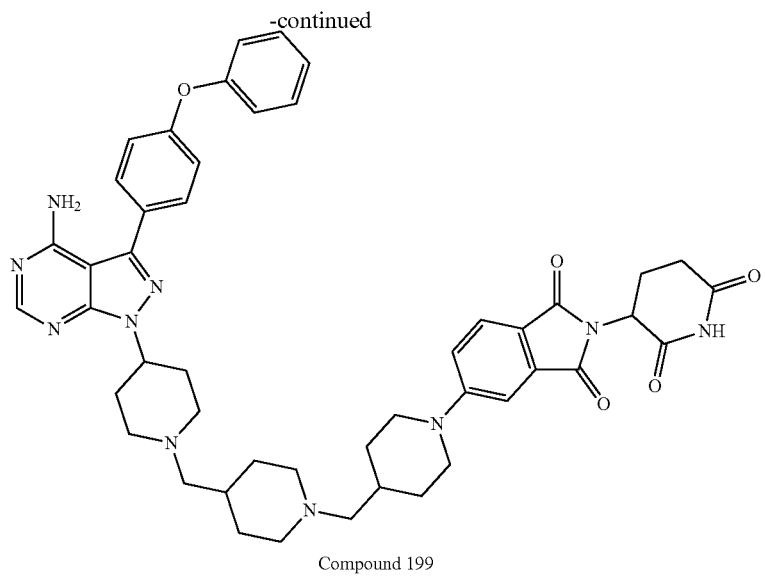

Compound 199

Step 1: Preparation of 3-(4-phenoxyphenyl)-1-(1-((1-(piperidin-4-ylmethyl)piperidin-4-yl)methyl)piperidin-4-yl)-1H-pyrazolo(3,4-d)pyrimidin-4-amine (I-3aa)

This compound was prepared by the procedure identical to the preparation of I-3a with I-3a (0.20 g, 0.41 mmol) as SM. The I-3aa hydrochloride was obtained as a yellow solid (0.21 g, 91.0%, two steps). LC-MS (ESI$^+$) m/z=681.4 (M+H)$^+$.

Step 2: Preparation of 5-(4-((4-((4-(4-amino-3-(4-phenoxyphenyl)-1H-pyrazolo(3,4-d)pyrimidin-1-yl)piperidin-1-yl)methyl)piperidin-1-yl)methyl)piperidin-1-yl)-2-(2,6-dioxopiperidin-3-yl)isoindoline-1,3-dione (Compound 199)

The mixture of I-3aa (0.15 g, 0.26 mmol) and DIPEA (0.11 ml) in NMP (6 ml) was stirred at r.t. for 30 min, followed by adding 2-(2,6-dioxopiperidin-3-yl)-5-fluoroisoindoline-1,3-dione (86 mg, 0.52 mmol). The reaction mixture was stirred at 100° C. under N$_2$ for 6 h.

The mixture was separated with Prep-HPLC (Elute: CH$_3$CN in water=10-100%, 20 min) to give Compound 199 as yellow solid (0.10 g, 46.0%). LC-MS (ESI$^+$) m/z=837.4 (M+H)$^+$, 419.2 (M+2H)$^{2+}$.

Example 6: Preparation of Compound 200 (3-(5-(4-((4-((4-(4-amino-3-(4-phenoxyphenyl)-1H-pyrazolo(3,4-d)pyrimidin-1-yl)piperidin-1-yl)methyl)piperidin-1-yl)methyl)piperidin-1-yl)-1-oxoisoindolin-2-yl)piperidine-2,6-dione)

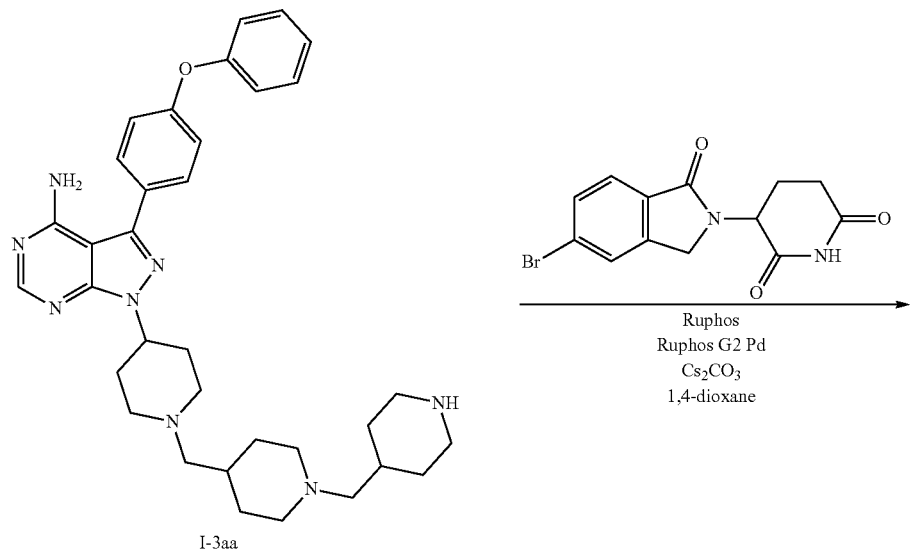

I-3aa

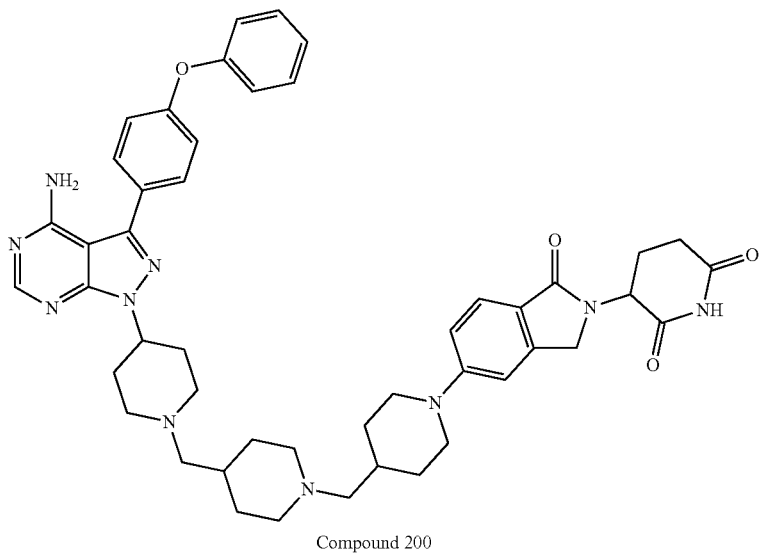

Compound 200

The mixture of I-3aa (0.10 g, 0.17 mmol), $Cs_2CO_3$ (0.11 g, 0.34 mmol) in 1,4-dioxane (10 ml) was degassed for 3 min, stirred at r.t. under $N_2$ for 15 min, followed by adding RuPhos (18 mg, 34 μmol), RuPhos G2 Pd (26 mg, 34 μmol) and 3-(5-bromo-1-oxoisoindolin-2-yl)piperidine-2,6-dione (67 mg, 0.21 mmol). The reaction mixture was stirred at 100° C. under $N_2$ for 8 h.

The suspension was filtered, the cake was washed with $CHCl_3$ (5 ml×3). The combined filtrates were concentrated and separated with pre-HPLC (Elute: $CH_3CN$ in water=10-100%, 15 min) to give Compound 200 as off-white solid (20 mg, 14.3%). LC-MS (ESI$^+$) m/z=823.4 (M+H)$^+$, 412.2 (M+2H)$^{2+}$.

Example 7: Preparation of Compound 207 (3-(5-(1-(4-(4-((4-(4-amino-3-(4-phenoxyphenyl)-1H-pyrazolo(3,4-d)pyrimidin-1-yl)piperidin-1-yl)methyl)piperidin-1-yl)butanoyl)piperidin-4-yl)-1-oxoisoindolin-2-yl)piperidine-2,6-dione)

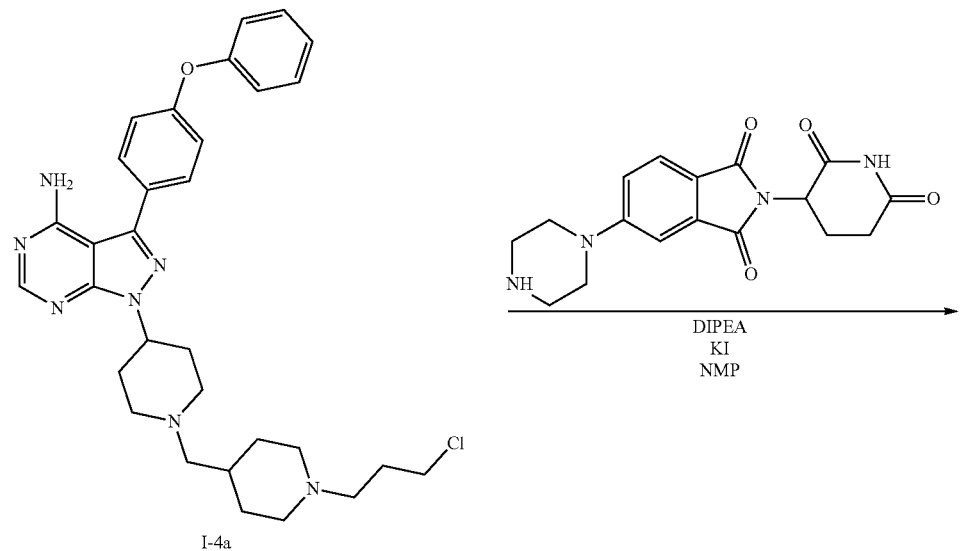

I-4a

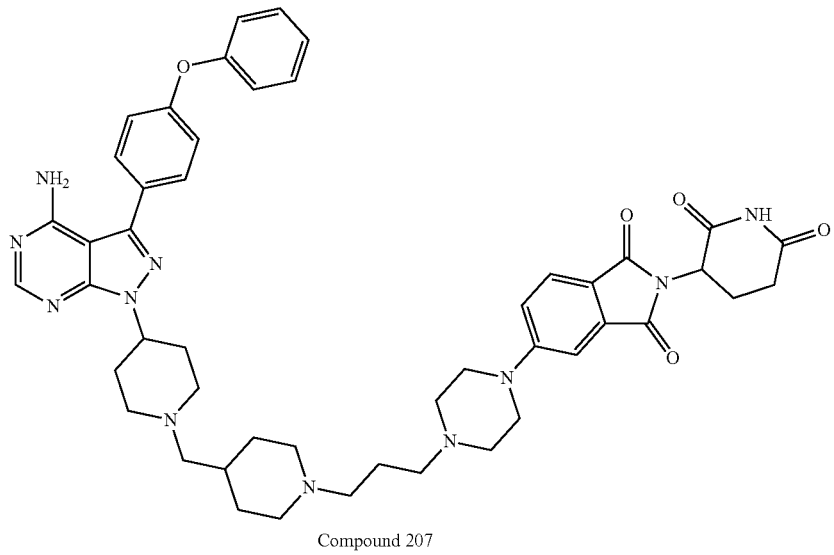

Compound 207

The mixture of 2-(2,6-dioxopiperidin-3-yl)-5-(piperazin-1-yl)isoindoline-1,3-dione (0.14 g, 0.21 mmol) and DIPEA (0.12 ml) in NMP (5 ml) was stirred at r.t. for 30 min, followed by adding I-4a (0.20 g, 0.18 mmol) and KI (0.12 g, 0.36 mmol). The reaction mixture was stirred at 100° C. under $N_2$ for 6 h.

The mixture was separated with Prep-HPLC ($CH_3CN$ in water=0-100%, 20 min) to give the Compound 207 as yellow solid (0.10 g, 64.2%). LC-MS (ESI$^+$) m/z=866.4 (M+H)$^+$, 433.7 (M+2H)$^{2+}$.

Example 8: Preparation of Compound 213 (5-(4-((4-(4-amino-3-(4-phenoxyphenyl)-1H-pyrazolo(3,4-d)pyrimidin-1-yl)-(1,4'-bipiperidin)-1'-yl)methyl)piperidin-1-yl)-2-(2,6-dioxopiperidin-3-yl)isoindoline-1,3-dione)

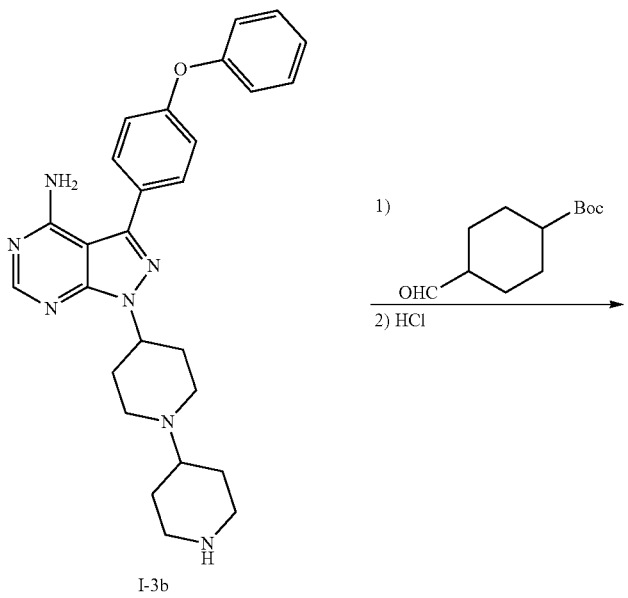

-continued
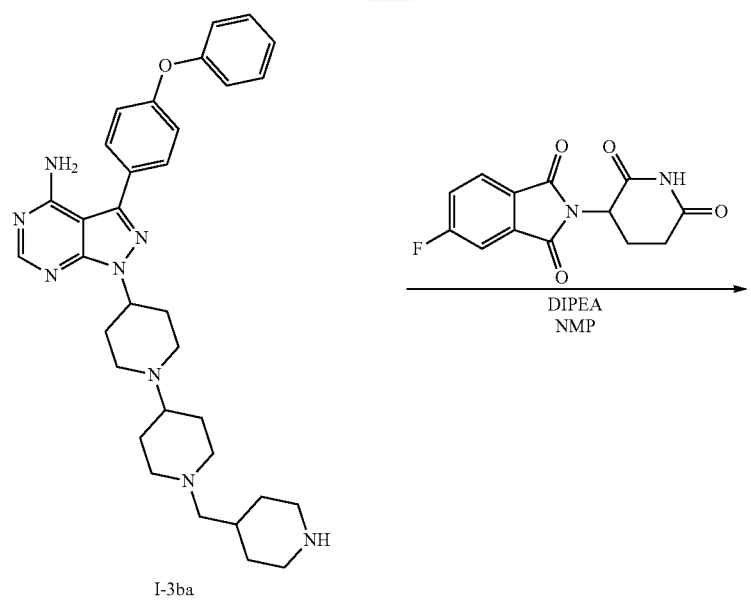
I-3ba
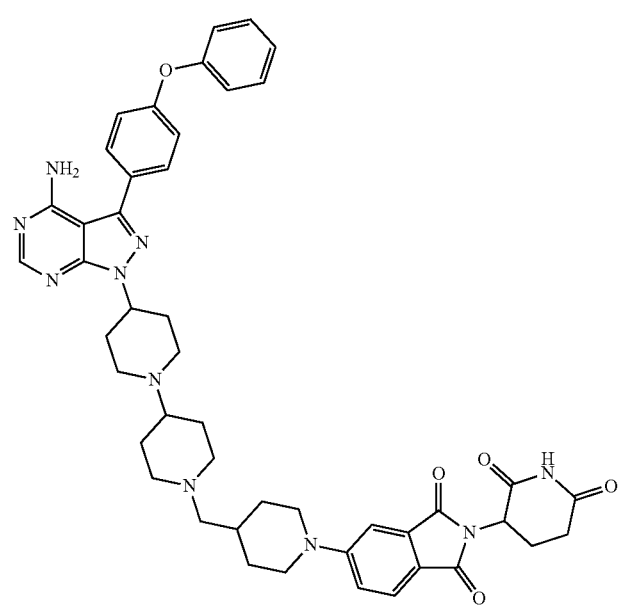
Compound 213

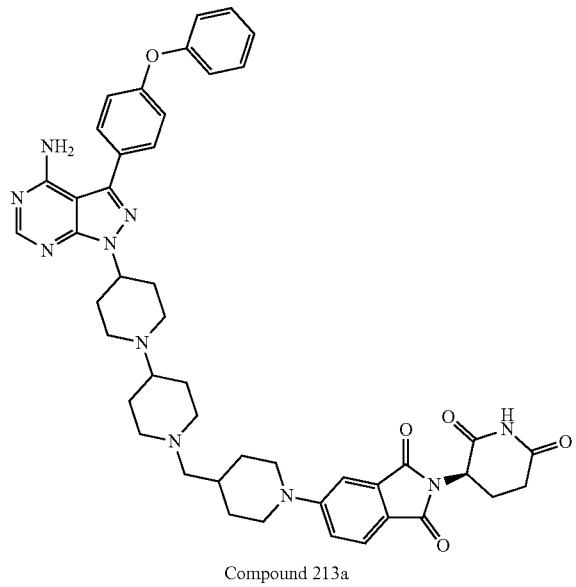

Compound 213a

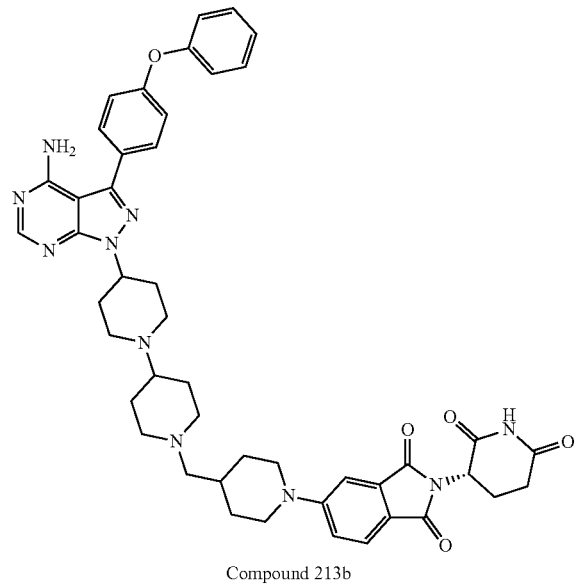

Compound 213b

Step 1: Preparation of 3-(4-phenoxyphenyl)-1-(1'-(piperidin-4-ylmethyl)-(1,4'-bipiperidin)-4-yl)-1H-pyrazolo(3,4-d)pyrimidin-4-amine (I-3ba)

This compound was prepared by the procedure identical to the preparation of I-3a with I-3b (0.20 g, 0.43 mmol) as SM. The I-3ba hydrochloride was obtained as a yellow solid (0.20 g, 78.7%, two steps). LC-MS (ESI$^+$) m/z=567.4 (M+H)$^+$.

Step 2: Preparation of 5-(4-((4-(4-amino-3-(4-phenoxyphenyl)-1H-pyrazolo(3,4-d)pyrimidin-1-yl)-(1,4'-bipiperidin)-1'-yl)methyl)piperidin-1-yl)-2-(2,6-dioxopiperidin-3-yl)isoindoline-1,3-dione (Compound 213)

The mixture of I-3ba (0.15 g, 0.26 mmol) and DIPEA (0.14 ml) in NMP (6 ml) was stirred at r.t. for 30 min, followed by adding 2-(2,6-dioxopiperidin-3-yl)-5-fluoroisoindoline-1,3-dione (86 mg, 0.32 mmol). The reaction mixture was stirred at 100° C. under N$_2$ for 6 h.

The mixture was separated with Prep-HPLC (Elute: CH3CN in water=10-100%, 20 min) to give Compound 213 as yellow solid (0.11 g, 52.4%). LC-MS (ESI$^+$) m/z=823.4 (M+H)$^+$, 412.2 (M+2H)$^{2+}$.

Step 3: Separation of Compound 213a and Compound 213b

The mixture was separated with SFC column to obtain the Compound 213a and Compound 213b.

Example 9: Preparation of Compound 214 (3-(6-(4-((4-(4-amino-3-(4-phenoxyphenyl)-1H-pyrazolo(3,4-d)pyrimidin-1-yl)-(1,4'-bipiperidin)-1'-yl)methyl)piperidin-1-yl)-1-oxoisoindolin-2-yl)piperidine-2,6-dione)

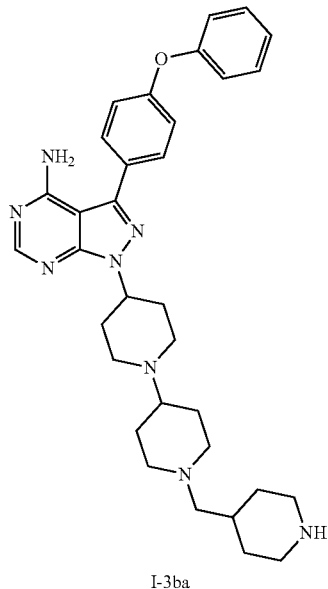

I-3ba

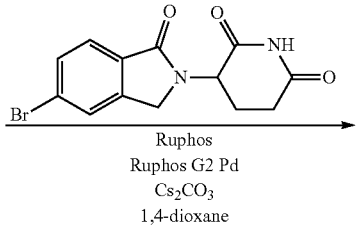

Ruphos
Ruphos G2 Pd
Cs$_2$CO$_3$
1,4-dioxane

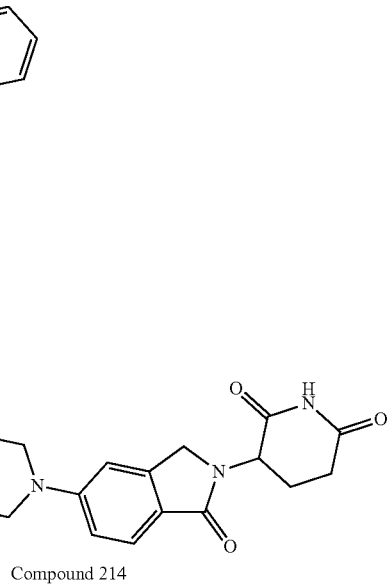

Compound 214

This compound was prepared by the procedure identical to the preparation of Compound 213 with I-3ba (0.10 g, 0.18 mmol) as SM and took the tert-butyl 3-formylazetidine-1-carboxylate as the replacement of tert-butyl 4-formylpiperidine-1-carboxylate. The Compound 214 was obtained as a yellow solid (20 mg, 13.7%). LC-MS (ESI$^+$) m/z=809.4 (M+H)$^+$, 405.2 (M+2H)$^{2+}$.

Example 10: Preparation of Compound 420 and 421 (3-(5-(4-(2-(2-(2-(4-(4-amino-3-(4-phenoxyphenyl)-1H-pyrazolo(3,4-d)pyrimidin-1-yl)piperidin-1-yl)ethoxy)ethoxy)ethyl)piperazin-1-yl)-1-oxoisoindolin-2-yl)piperidine-2,6-dione)

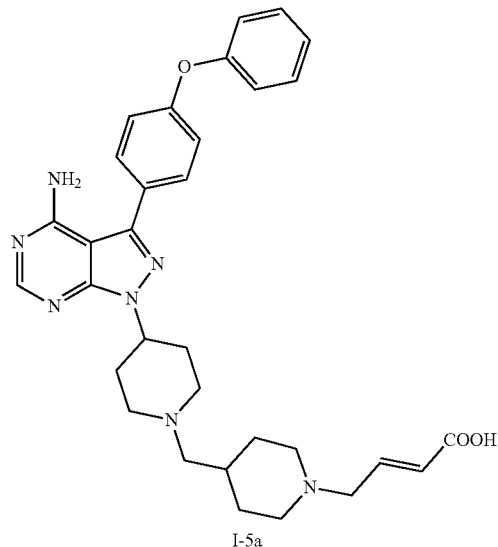

I-5a

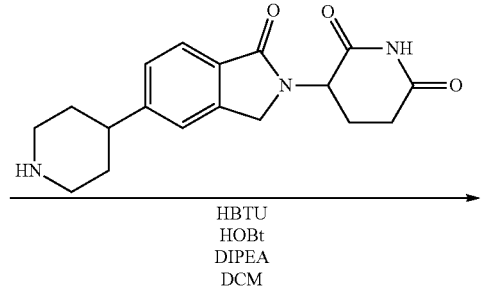

HBTU
HOBt
DIPEA
DCM

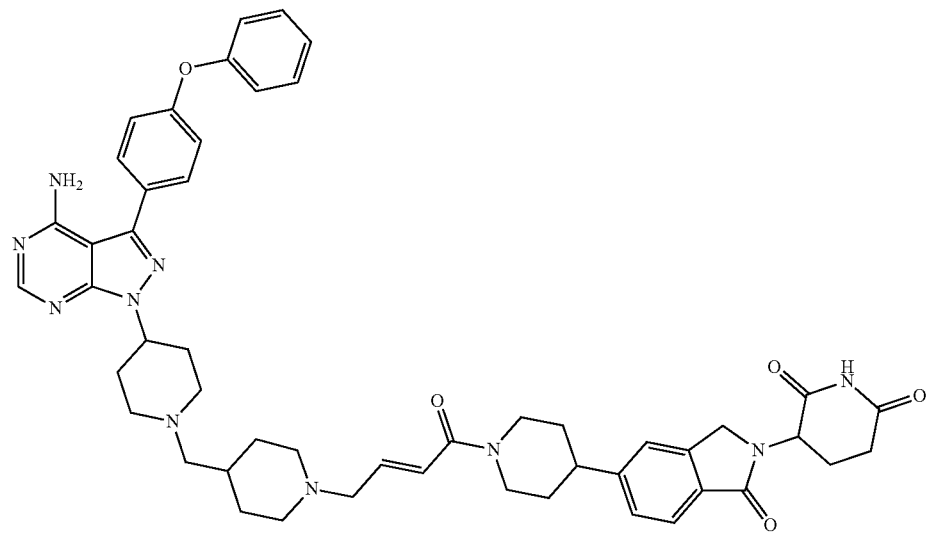

Compound 420 & 421

To the solution of I-5a (0.22 g, 0.39 mmol), 3-(1-oxo-5-(piperidin-4-yl)isoindolin-2-yl)piperidine-2,6-dione (0.14 mmol, 0.43 mmol) and DIPEA (0.14 ml) in DCM was added HBTU (0.30, 0.78 mmol) and HOBt (0.11 g, 0.78 mmol) at 0° C. The mixture was stirred at r.t. under $N_2$ for 3 h. The mixture was separated with Prep-HPLC (Elute: $CH_3CN$ in Water=10-100%, 15 min) to obtain Compound 420 (0.15 g) and Compound 421 (0.10 g) as yellow solids. LC-MS (ESI$^+$) m/z=877.4 (M+H)$^+$, 439.2 (M+2H)$^{2+}$.

Example 11: Preparation of Compound 422 (3-(5-(1-(4-(4-((4-(4-amino-3-(4-phenoxyphenyl)-1H-pyrazolo(3,4-d)pyrimidin-1-yl)piperidin-1-yl)methyl)piperidin-1-yl)butanoyl)piperidin-4-yl)-1-oxoisoindolin-2-yl)piperidine-2,6-dione)

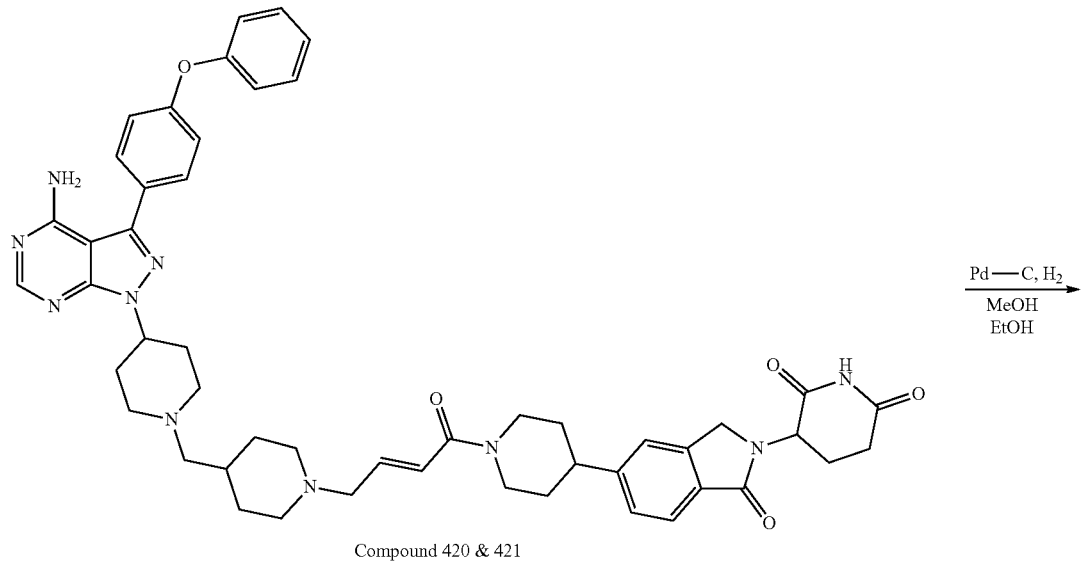

Compound 420 & 421

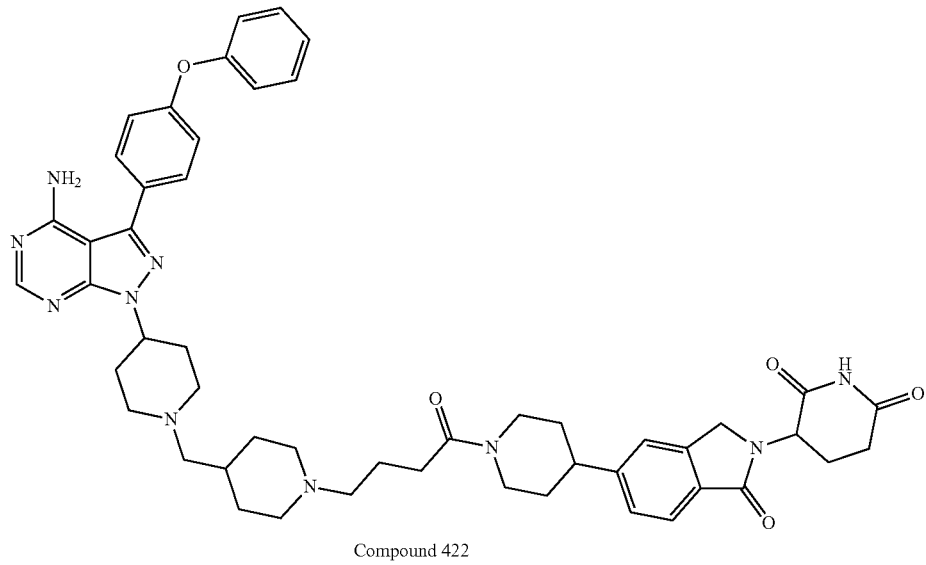

Compound 422

The mixture of Compound 420 and 421 (0.20 g, 0.23 mmol) and Pd—C (10%, 0.05 g) in MeOH and EtOH (1/1, 20 ml) was stirred at r.t. under $H_2$ for 48 h. The suspension was filtered, and the cake was washed with hot MeOH (5 ml×3). The combined filtrates were concentrated and separated with Prep-HPLC (Elute: $CH_3CN$ in $H_2O$=10-100%, 15 min) to give the Compound 422 as an off-white solid (0.20 g, ~100%). LC-MS (ESI$^+$) m/z=879.4 (M+H)$^+$, 440.2 (M+2H)$^{2+}$.

Example 12: Preparation of Compound 423 (5-(3-((3-((4-(4-amino-3-(4-phenoxyphenyl)-1H-pyrazolo(3,4-d)pyrimidin-1-yl)piperidin-1-yl)methyl)pyrrolidin-1-yl)methyl)azetidin-1-yl)-2-(2,6-dioxopiperidin-3-yl)isoindoline-1,3-dione)
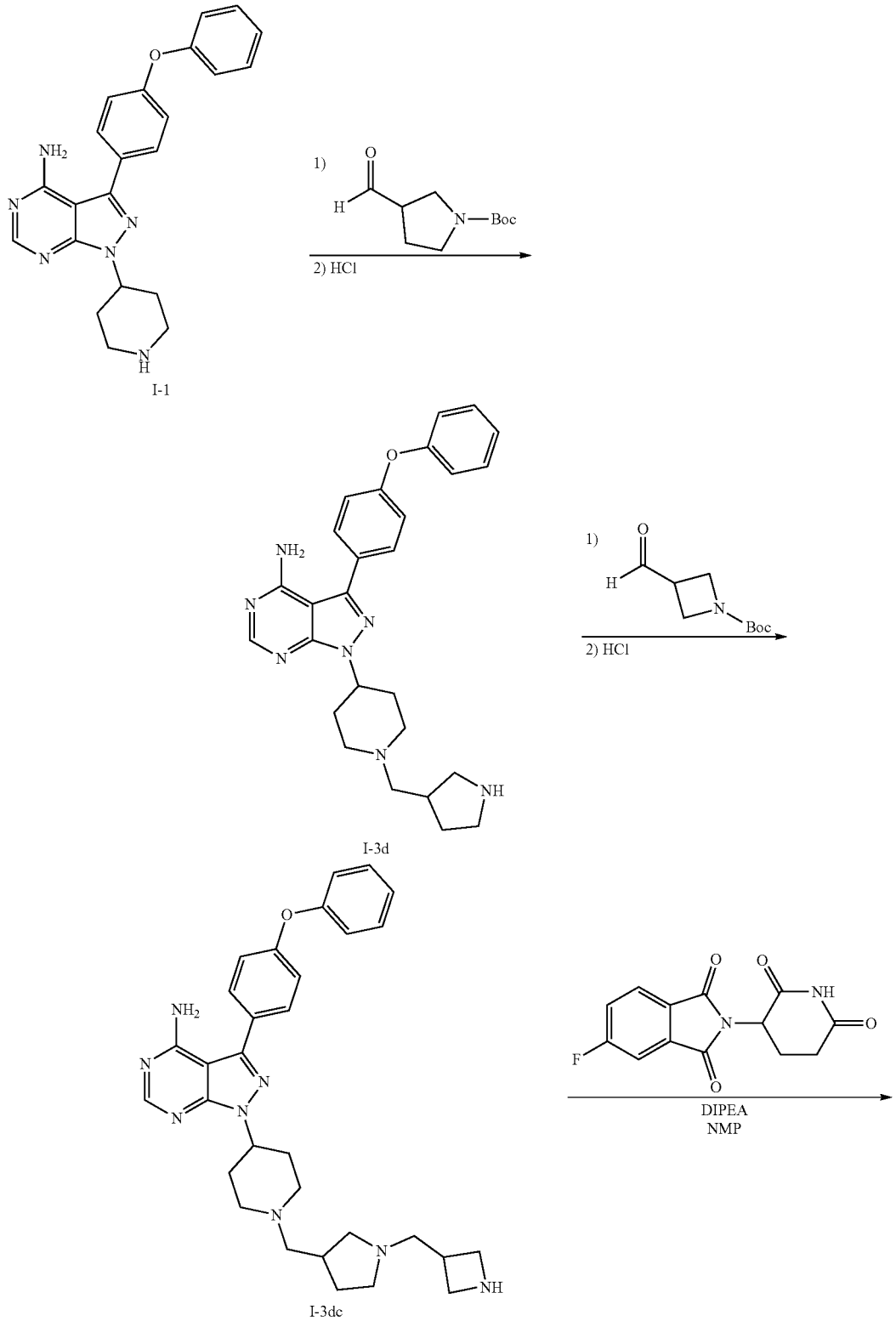

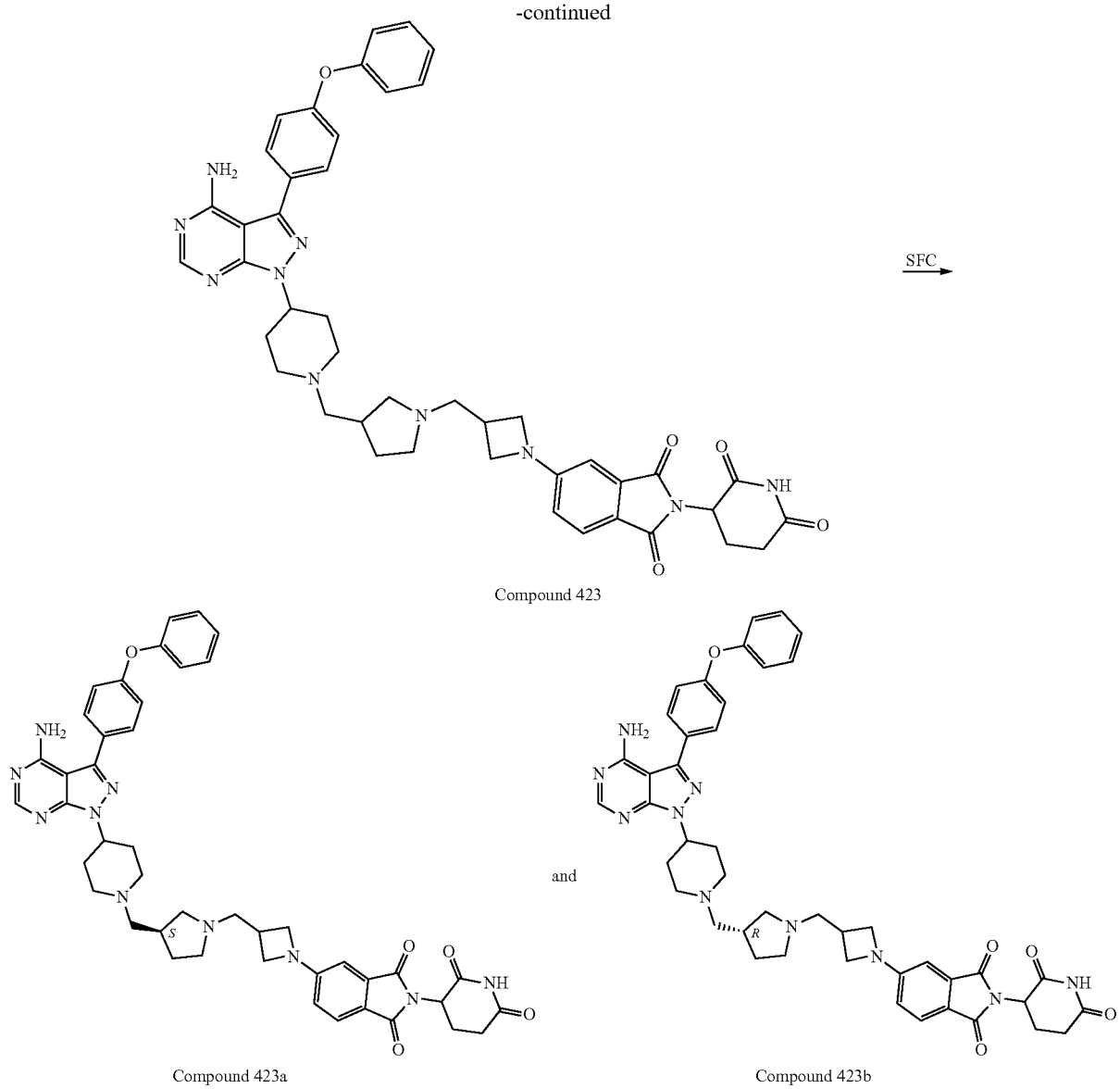

Compound 423

Compound 423a and Compound 423b

Step 1: Preparation of 3-(4-phenoxyphenyl)-1-(1-(pyrrolidin-3-ylmethyl)piperidin-4-yl)-1H-pyrazolo(3,4-d)pyrimidin-4-amine (I-3d)

This compound was prepared by the procedure identical to the preparation of I-3a with tert-butyl 3-formylpyrrolidine-1-carboxylate as the replacement of tert-butyl 4-formylpiperidine-1-carboxylate. The I-3d hydrochloride was obtained as an off-white solid (0.70 g, 89.9%, two steps). LC-MS (ESI$^+$) m/z=470.3 (M+H)$^+$.

Step 2: 1-(1-((1-(azetidin-3-ylmethyl)pyrrolidin-3-yl)methyl)piperidin-4-yl)-3-(4-phenoxy phenyl)-1H-pyrazolo(3,4-d)pyrimidin-4-amine (I-3dc)

This compound was prepared by the procedure identical to the preparation of I-3a with I-3d (0.40 g, 0.85 mmol) as SM and took the tert-butyl 3-formylazetidine-1-carboxylate as the replacement of tert-butyl 4-formylpiperidine-1-carboxylate. The I-3dc hydrochloride was obtained as a yellow solid (0.38 g, 77.8%, two steps). LC-MS (ESI$^+$) m/z=539.3 (M+H)$^+$.

Step 3: 5-(3-((3-((4-(4-amino-3-(4-phenoxyphenyl)-1H-pyrazolo(3,4-d)pyrimidin-1-yl) piperidin-1-yl)methyl)pyrrolidin-1-yl)methyl)azetidin-1-yl)-2-(2,6-dioxopiperidin-3-yl)isoindoline-1,3-dione (Compound 423)

The mixture of I-3dc (0.13 g, 0.24 mmol) and DIPEA (0.16 ml) in NMP (6 ml) was stirred at r.t. for 30 min, followed by adding 2-(2,6-dioxopiperidin-3-yl)-5-fluoroisoindoline-1,3-dione (80 mg, 0.29 mmol). The reaction mixture was stirred at 100° C. under N$_2$ for 6 h.

The mixture was separated with Prep-HPLC (Elute: CH$_3$CN in H$_2$O=10-100%, 20 min) to give the Compound 423 as a yellow solid (50 mg, 26.2%). LC-MS (ESI$^+$) m/z=795.4 (M+H)$^+$, 398.2 (M+2H)$^{2+}$.

Step 4: Separation of Compound 423a and Compound 423b
The mixture was separated with SFC column to obtain the Compound 423a and Compound 423b.
Example 13: Preparation of Compound 425 (5-(3-((3-(4-(4-amino-3-(4-phenoxyphenyl)-1H-pyrazolo (3,4-d)pyrimidin-1-vi)piperidin-1-vi)pyrrolidin-1-yl) methyl)azetidin-1-yl)-2-(2,6-dioxopiperidin-3-yl) isoindoline-1,3-dione)
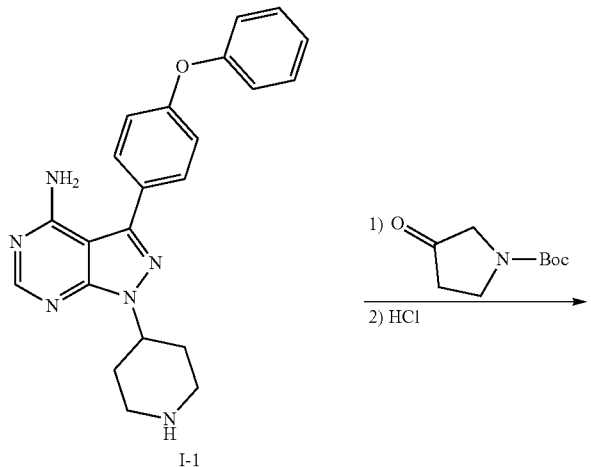
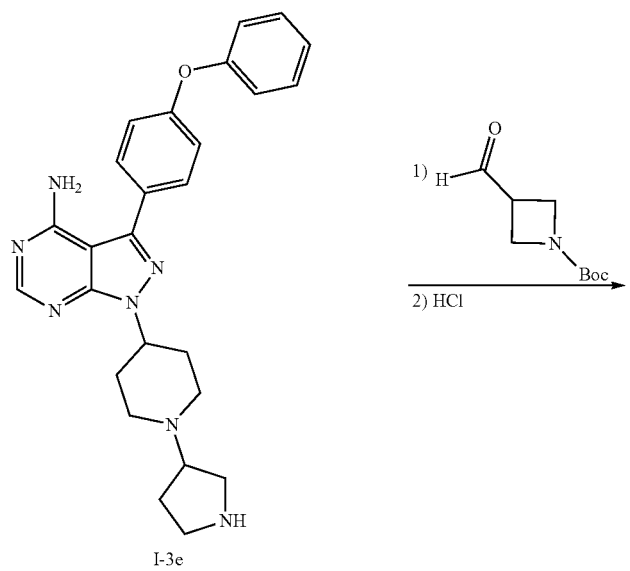

-continued
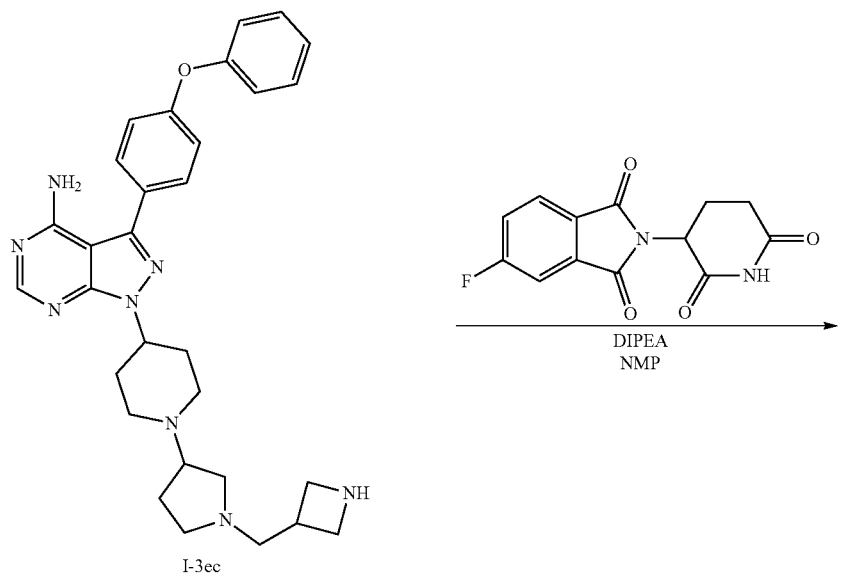
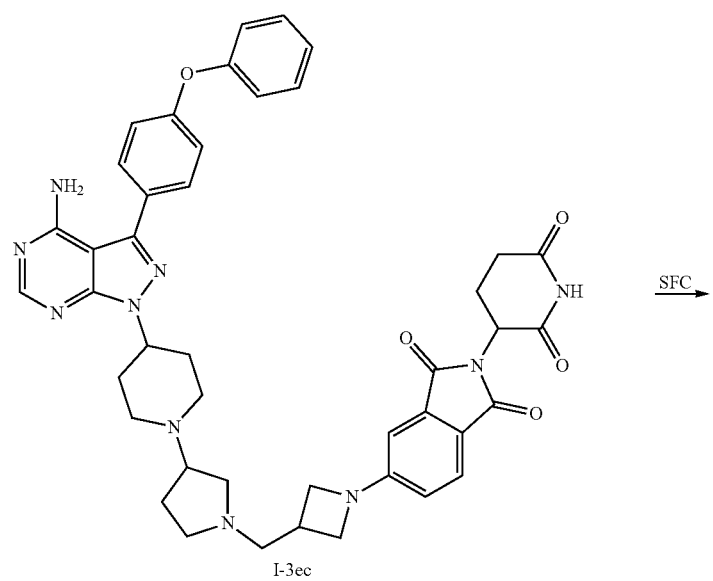
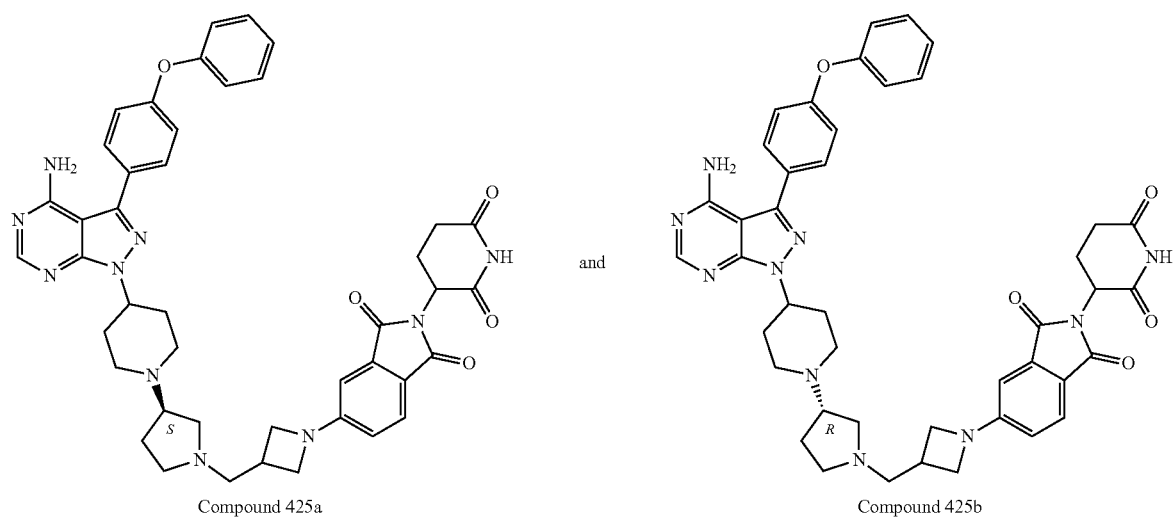

Step 1: Preparation of 3-(4-phenoxyphenyl)-1-(1-(pyrrolidin-3-yl)piperidin-4-yl)-1H-pyrazolo(3,4-d)pyrimidin-4-amine (I-3e)

This compound was prepared by the procedure identical to the preparation of I-3b with tert-butyl 3-oxopyrrolidine-1-carboxylate as the replacement of tert-butyl 4-oxopiperidine-1-carboxylate. The I-3e hydrochloride was obtained as a brown semi-solid (0.70 g, 93.3%, two steps). LC-MS (ESI$^+$) m/z=556.3 (M+H)$^+$.

Step 2: Preparation of 1-(1-(1-(azetidin-3-ylmethyl)pyrrolidin-3-yl)piperidin-4-yl)-3-(4-phenoxyphenyl)-1H-pyrazolo(3,4-d)pyrimidin-4-amine (I-3ec)

This compound was prepared by the procedure identical to the preparation of I-3a with I-3e (0.40 g, 0.88 mmol) as SM and took the tert-butyl 3-formylazetidine-1-carboxylate as the replacement of tert-butyl 4-formylpiperidine-1-carboxylate. The I-3ec hydrochloride was obtained as a yellow solid (0.40 g, 87.0%, two steps). LC-MS (ESI$^+$) m/z=525.3 (M+H)$^+$.

Step 3: Preparation of 5-(3-((3-(4-(4-amino-3-(4-phenoxyphenyl)-1H-pyrazolo(3,4-d)pyrimidin-1-yl)piperidin-1-yl)pyrrolidin-1-yl)methyl)azetidin-1-yl)-2-(2,6-dioxopiperidin-3-yl)isoindoline-1,3-dione (Compound 425)

The mixture of I-3ec (0.13 g, 0.25 mmol) and DIPEA (0.22 ml) in NMP (6 ml) was stirred at r.t. for 30 min, followed by adding 2-(2,6-dioxopiperidin-3-yl)-5-fluoroisoindoline-1,3-dione (80 mg, 0.30 mmol). The reaction mixture was stirred at 100° C. under N$_2$ for 6 h.

The mixture was separated with Prep-HPLC (Elute: CH$_3$CN in water=10-100%, 20 min) to give Compound 425 as yellow solid (0.10 g, 51.3%). LC-MS (ESI$^+$) m/z=781.3 (M+H)$^+$, 391.2 (M+2H)$^{2+}$.

Step 4: Separation of Compound 425a and Compound 425b

The mixture was separated with SFC column to obtain the Compound 425a and Compound 425b.

Example 14: Preparation of Compound 427 (5-(3-((3-((3-((4-(4-amino-3-(4-phenoxyphenyl)-1H-pyrazolo(3,4-d)pyrimidin-1-yl)piperidin-1-yl)methyl)pyrrolidin-1-yl)methyl)azetidin-1-yl)methyl)azetidin-1-yl)-2-(2,6-dioxopiperidin-3-yl)isoindoline-1,3-dione)

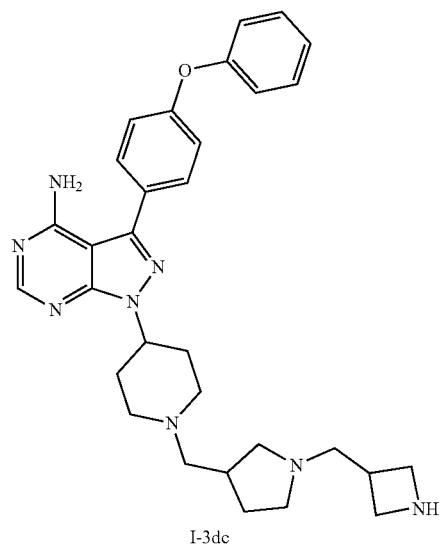

I-3dc

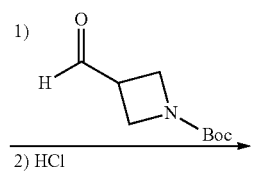

1)
2) HCl

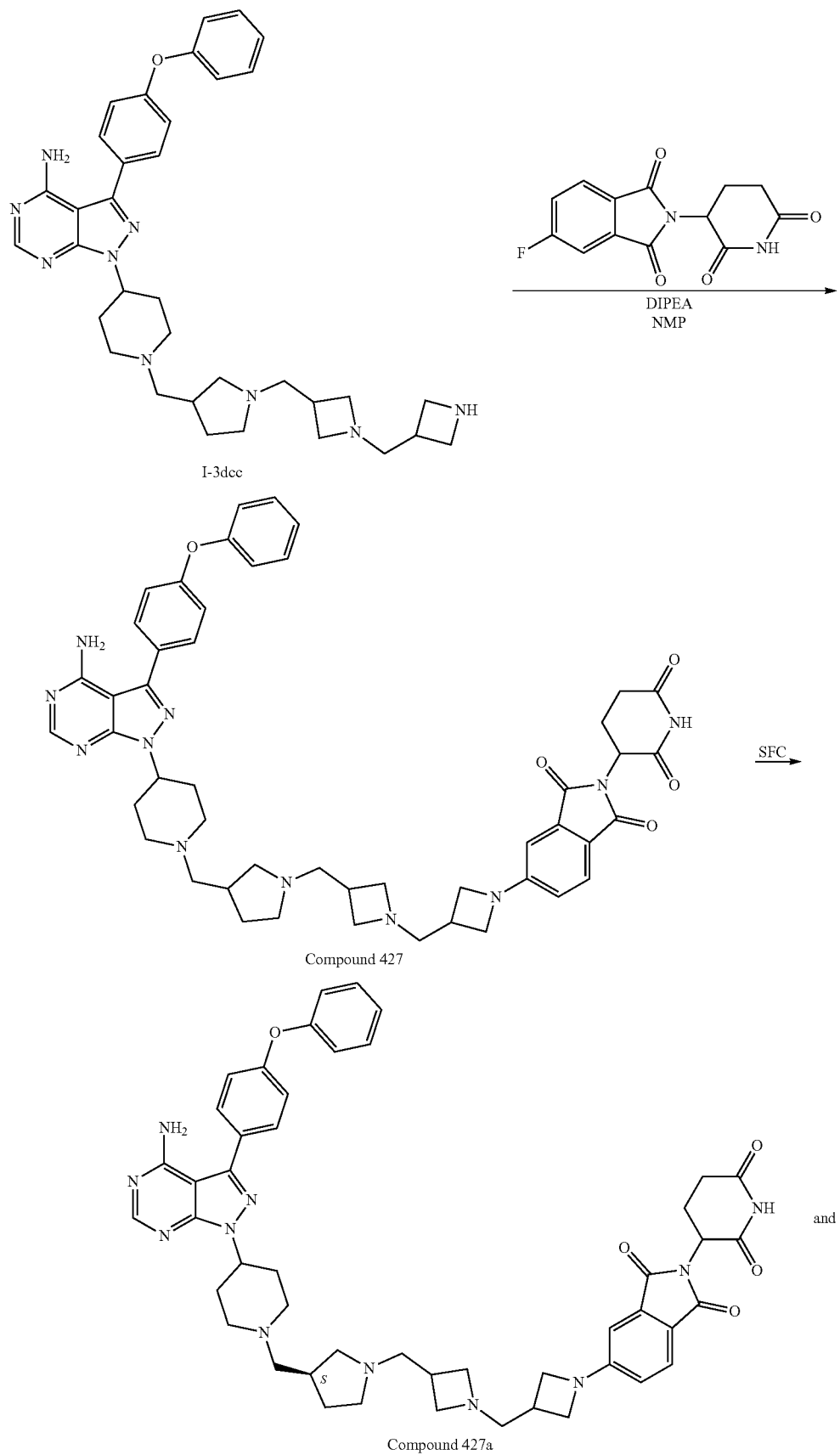

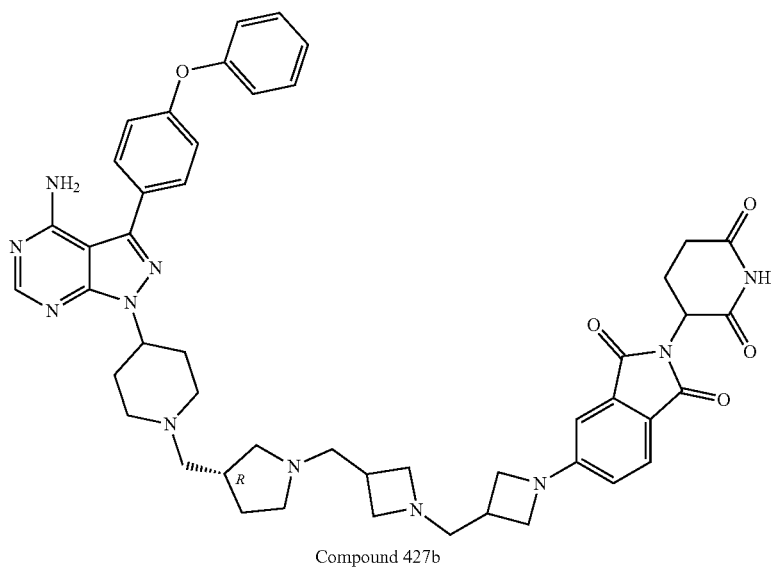

Compound 427b

Step 1: Preparation of 1-(1-(((1-((1-(azetidin-3-ylm-ethyl)azetidin-3-yl)methyl)pyrrolidin-3-yl)methyl)piperidin-4-yl)-3-(4-phenoxyphenyl)-1H-pyrazolo(3,4-d)pyrimidin-4-amine (I-3 dcc)

This compound was prepared by the procedure identical to the preparation of I-3a with I-3dc (0.13 g, 0.24 mmol) as SM and took the tert-butyl 3-formylazetidine-1-carboxylate as the replacement of tert-butyl 4-formylpiperidine-1-carboxylate. The I-3 dcc hydrochloride was obtained as a yellow solid (0.12 g, 83.0%, two steps). LC-MS (ESI$^+$) m/z=608.3 (M+H)$^+$.

Step 2: Preparation of 5-(3-((3-((3-((4-(4-amino-3-(4-phenoxyphenyl)-1H-pyrazolo(3,4-d)pyrimidin-1-yl)piperidin-1-yl)methyl)pyrrolidin-1-yl)methyl)azetidin-1-yl)methyl)azetidin-1-yl)-2-(2,6-dioxopiperidin-3-yl)isoindoline-1,3-dione (Compound 427)

The mixture of I-3 dcc (0.10 g, 0.16 mmol) and DIPEA (0.11 ml) in NMP (6 ml) was stirred at r.t. for 30 min, followed by adding 2-(2,6-dioxopiperidin-3-yl)-5-fluoroisoindoline-1,3-dione (60 mg, 0.20 mmol). The reaction mixture was stirred at 100° C. under N$_2$ for 6 h.

The mixture was separated with Prep-HPLC (Elute: CH$_3$CN in water=10-100%, 20 min) to give Compound 427 as yellow solid (0.10 g, 72.5%). LC-MS (ESI$^+$) m/z=864.4 (M+H)$^+$, 432.7 (M+2H)$^{2+}$.

Step 3: Separation of Compound 427a and Compound 427b
The mixture was separated with SFC column to obtain the Compound 427a and Compound 427b.
Example 15: Preparation of Compound 429 (5-(3-((4-((4-(4-amino-3-(4-phenoxyphenyl)-1H-pyrazolo(3,4-d)pyrimidin-1-yl)piperidin-1-yl)methyl)piperidin-1-yl)methyl)azetidin-1-yl)-2-(2,6-dioxopiperidin-3-yl)isoindoline-1,3-dione)
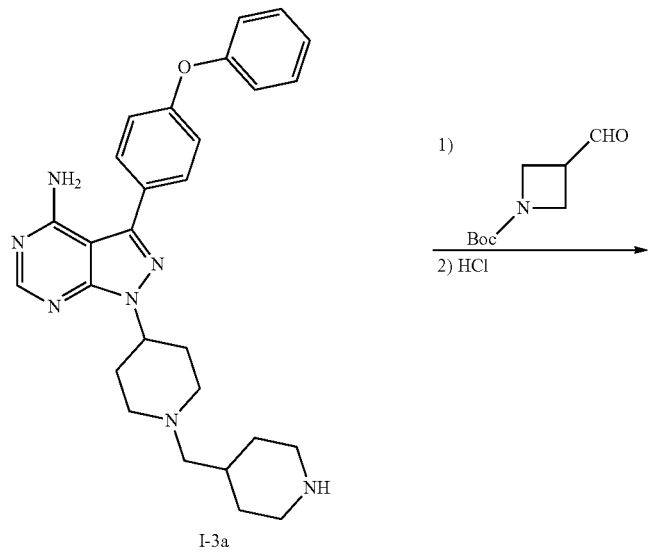
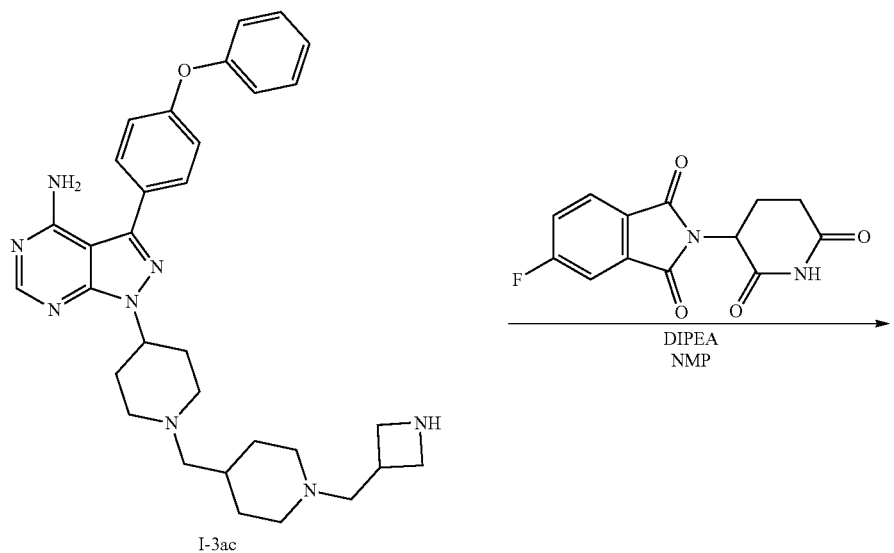

-continued

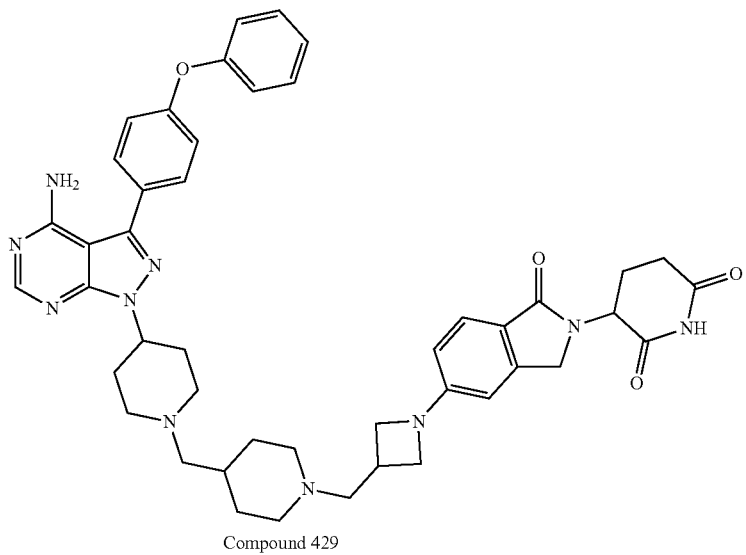

Compound 429

Step 1: Preparation of 1-(1-((1-(azetidin-3-ylmethyl)piperidin-4-yl)methyl)piperidin-4-yl)-3-(4-phenoxyphenyl)-1H-pyrazolo(3,4-d)pyrimidin-4-amine (I-3ac)

This compound was prepared by the procedure identical to the preparation of I-3a with I-3a (0.20 g, 0.41 mmol) as SM and took the tert-butyl 3-formylazetidine-1-carboxylate as the replacement of tert-butyl 4-formylpiperidine-1-carboxylate. The I-3ac hydrochloride was obtained as a yellow solid (0.17 g, 74.9%, two steps). LC-MS (ESI$^+$) m/z=553.4 (M+H)$^+$.

Step 2: Preparation of 5-(3-((4-((4-(4-amino-3-(4-phenoxyphenyl)-1H-pyrazolo(3,4-d)pyrimidin-1-yl)piperidin-1-yl)methyl)piperidin-1-yl)methyl)azetidin-1-yl)-2-(2,6-dioxopiperidin-3-yl)isoindoline-1,3-dione (Compound 429)

The mixture of I-3ac (0.15 g, 0.27 mmol) and DIPEA (0.11 ml) in NMP (6 ml) was stirred at r.t. for 30 min, followed by adding 2-(2,6-dioxopiperidin-3-yl)-5-fluoroisoindoline-1,3-dione (90 mg, 0.33 mmol). The reaction mixture was stirred at 100° C. under N$_2$ for 6 h.

The mixture was separated with Prep-HPLC (Elute: CH$_3$CN in water=10-100%, 20 min) to give Compound 429 as yellow solid (90 mg, 41.2%). LC-MS (ESI$^+$) m/z=809.4 (M+H)$^+$, 405.2 (M+2H)$^{2+}$.

Example 16: Preparation of Compound 431 (5-(3-((4-((4-((4-(4-amino-3-(4-phenoxyphenyl)-1H-pyrazolo(3,4-d)pyrimidin-1-vi)piperidin-1-yl)methyl)piperidin-1-yl)methyl)piperidin-1-yl)methyl)azetidin-1-yl)-2-(2,6-dioxopiperidin-3-yl)isoindoline-1,3-dione)
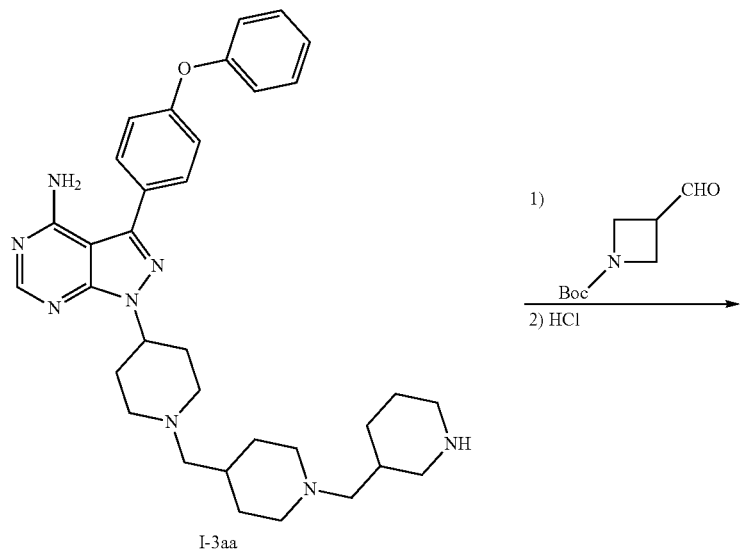
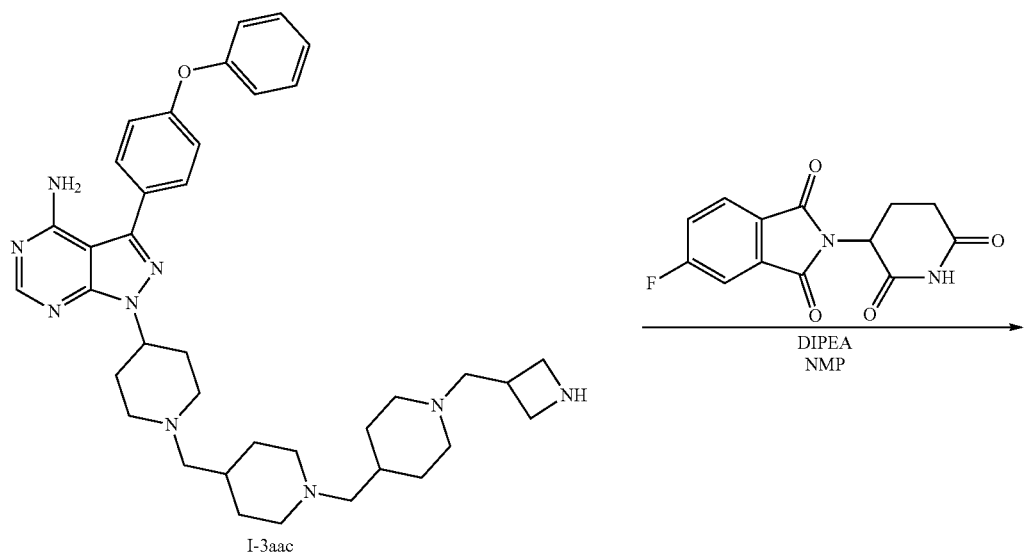

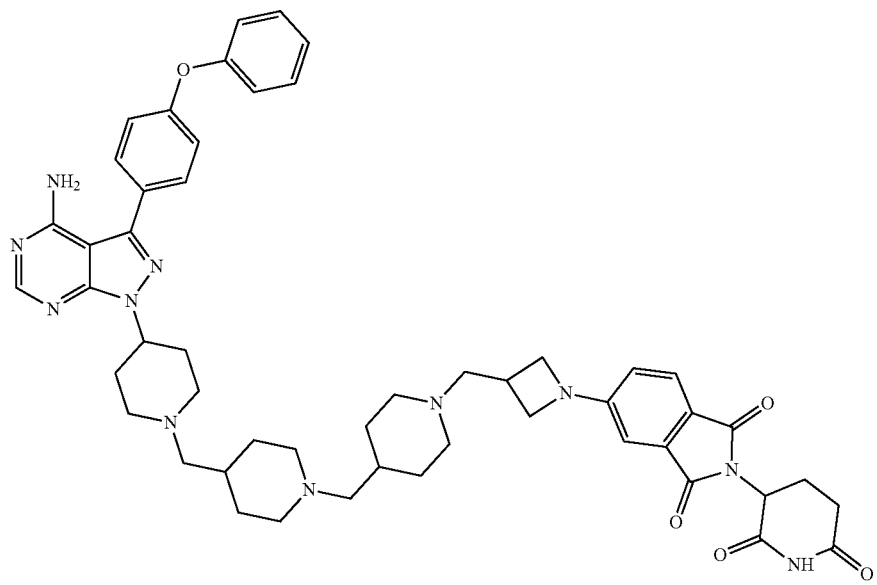

Compound 431

Step 1: Preparation of 1-(1-((1-((1-(azetidin-3-ylmethyl)piperidin-4-yl)methyl)piperidin-4-yl)methyl)piperidin-4-yl)-3-(4-phenoxyphenyl)-1H-pyrazolo(3,4-d)pyrimidin-4-amine (I-3 aac)

This compound was prepared by the procedure identical to the preparation of I-3a with I-3aa (0.15 g, 0.27 mmol) as SM and took the tert-butyl 3-formylazetidine-1-carboxylate as the replacement of tert-butyl 4-formylpiperidine-1-carboxylate. The I-3 aac hydrochloride was obtained as a yellow solid (0.16 g, 90.0%, two steps). LC-MS (ESI$^+$) m/z=650.5 (M+H)$^+$.

Step 2: Preparation of 5-(3-((4-((4-((4-(4-amino-3-(4-phenoxyphenyl)-1H-pyrazolo(3,4-d)pyrimidin-1-yl)piperidin-1-yl)methyl)piperidin-1-yl)methyl)piperidin-1-yl)methyl)azetidin-1-yl)-2-(2,6-dioxopiperidin-3-yl)isoindoline-1,3-dione (Compound 431)

The mixture of I-3 aac (0.15 g, 0.23 mmol) and DIPEA (0.12 ml) in NMP (6 ml) was stirred at r.t. for 30 min, followed by adding 2-(2,6-dioxopiperidin-3-yl)-5-fluoroisoindoline-1,3-dione (76 mg, 0.27 mmol). The reaction mixture was stirred at 100° C. under N$_2$ for 6 h.

The mixture was separated with Prep-HPLC (Elute: CH$_3$CN in water=10-100%, 20 min) to give Compound 431 as yellow solid (0.10 g, 48.0%). LC-MS (ESI$^+$) m/z=906.5 (M+H)$^+$, 453.8 (M+2H)$^{2+}$.

Example 17: Preparation of Compound 433 (5-(3-((4-(4-amino-3-(4-phenoxyphenyl)-1H-pyrazolo(3,4-d)pyrimidin-1-yl)-(1,4'-bipiperidin)-1'-yl)methyl)azetidin-1-yl)-2-(2,6-dioxopiperidin-3-yl)isoindoline-1,3-dione)
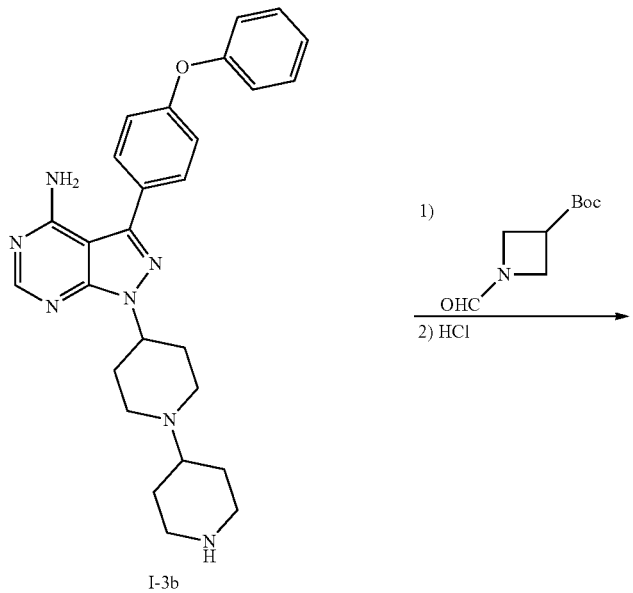
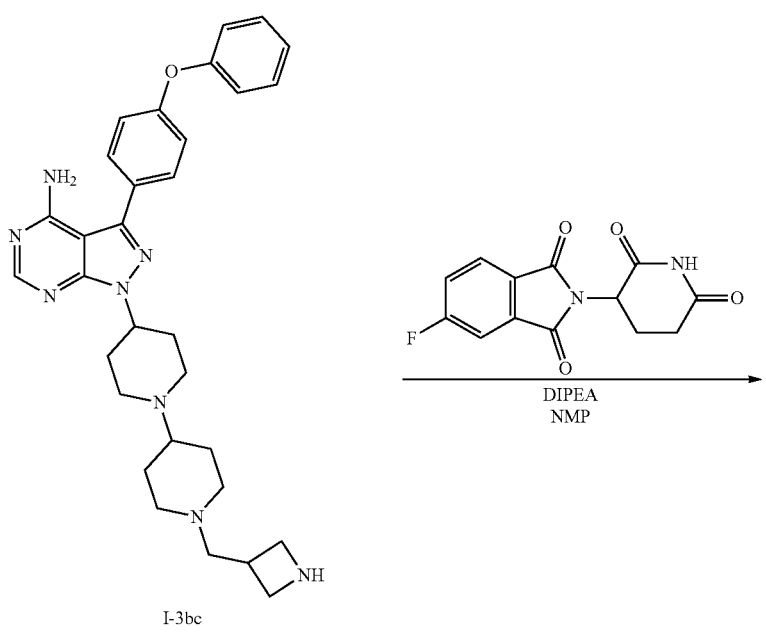

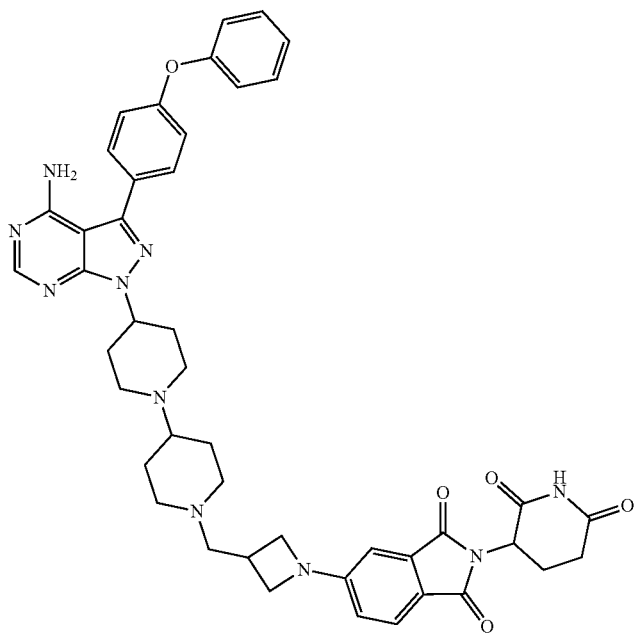

Compound 433

Step 1: Preparation of 1-(1'-(azetidin-3-ylmethyl)-(1,4'-bipiperidin)-4-yl)-3-(4-phenoxyphenyl)-1H-pyrazolo(3,4-d)pyrimidin-4-amine (I-3bc)

This compound was prepared by the procedure identical to the preparation of I-3a with I-3b (0.20 g, 0.43 mmol) as SM and took the tert-butyl 3-formylazetidine-1-carboxylate as the replacement of tert-butyl 4-formylpiperidine-1-carboxylate. The I-3bc hydrochloride was obtained as a yellow solid (0.20 g, 81.7%, two steps). LC-MS (ESI⁺) m/z=539.4 (M+H)⁺.

Step 2: Preparation of 5-(3-((4-(4-amino-3-(4-phenoxyphenyl)-1H-pyrazolo(3,4-d)pyrimidin-1-yl)-(1,4'-bipiperidin)-1'-yl)methyl)azetidin-1-yl)-2-(2,6-dioxopiperidin-3-yl)isoindoline-1,3-dione (Compound 433)

The mixture of I-3bc (0.15 g, 0.28 mmol) and DIPEA (0.15 ml) in NMP (6 ml) was stirred at r.t. for 30 min, followed by adding 2-(2,6-dioxopiperidin-3-yl)-5-fluoroisoindoline-1,3-dione (94 mg, 0.34 mmol). The reaction mixture was stirred at 100° C. under N₂ for 6 h.

The mixture was separated with Prep-HPLC (Elute: CH₃CN in water=10-100%, 20 min) to give Compound 433 as yellow solid (0.12 g, 54.5%). LC-MS (ESI⁺) m/z=795.4 (M+H)⁺, 398.2 (M+2H)²⁺.

Example 18: Preparation of Compound 439 (5-(4-((3-((4-(4-amino-3-(4-phenoxyphenyl)-1H-pyrazolo(3,4-d)pyrimidin-1-yl)piperidin-1-yl)methyl)azetidin-1-yl)methyl)piperidin-1-yl)-2-(2,6-dioxopiperidin-3-yl)isoindoline-1,3-dione)
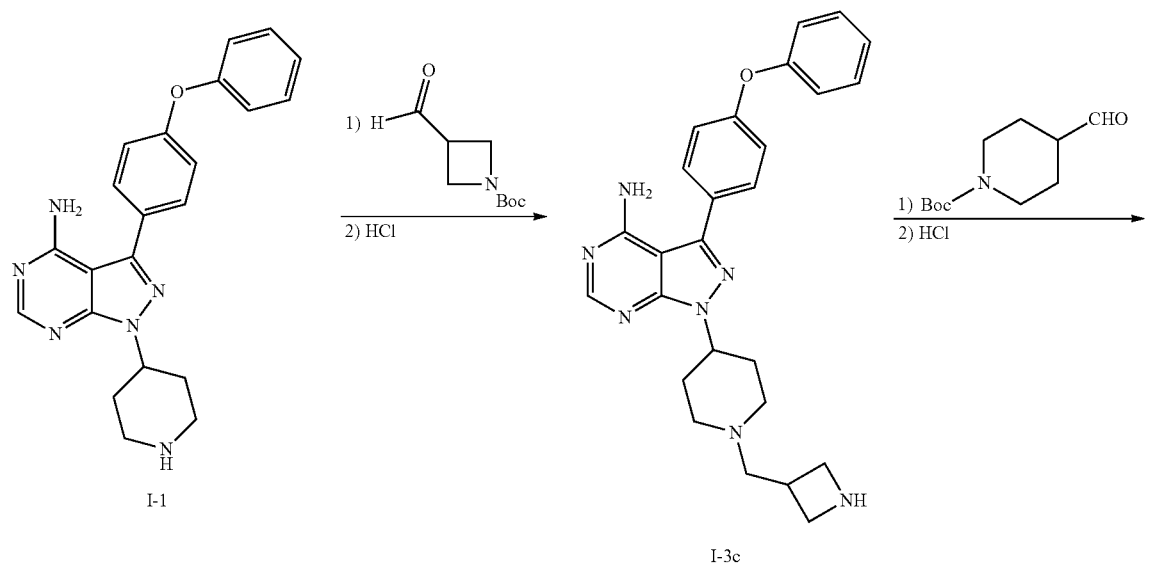
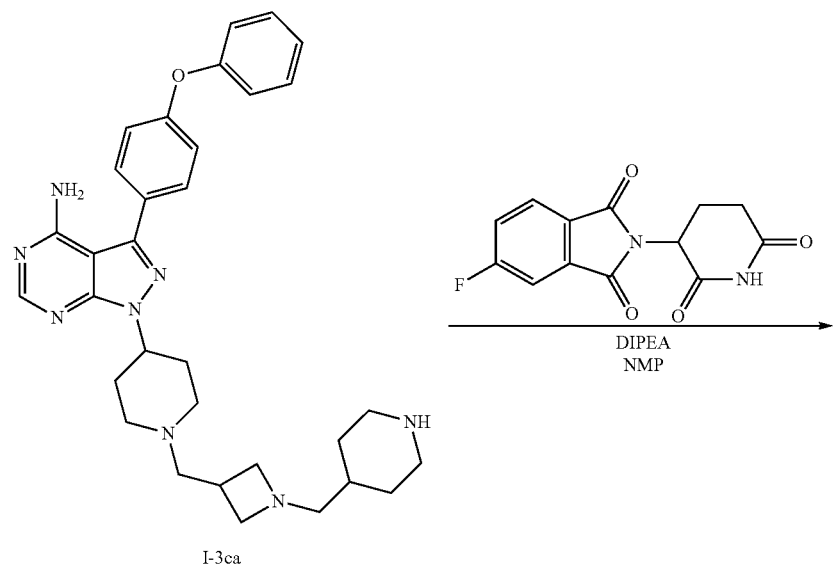

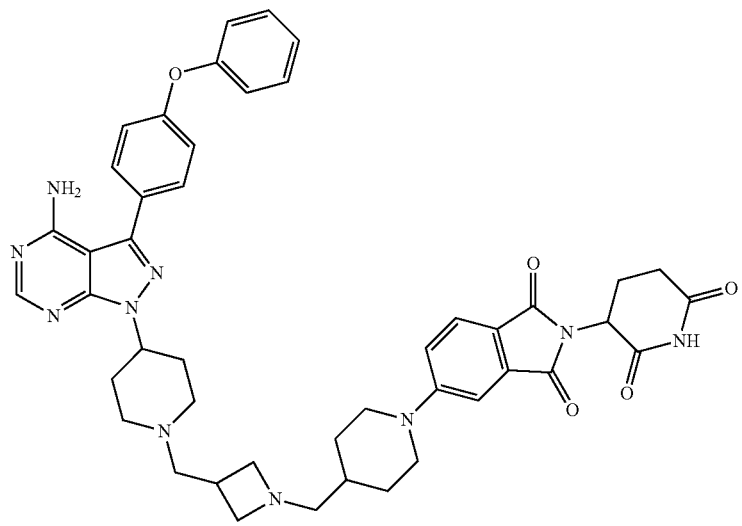

Compound 439

Step 1: Preparation of 1-(1-(azetidin-3-ylmethyl)piperidin-4-yl)-3-(4-phenoxyphenyl)-1H-pyrazolo(3,4-d)pyrimidin-4-amine (I-3c)

The mixture of I-1 (0.80 g, 2.07 mmol), NEt$_3$ (0.56 ml) in DCM (15 ml) was stirred at r.t. for 30 min, following by adding the tert-butyl 3-formylazetidine-1-carboxylate (0.48 ml, 3.11 mmol). The reaction mixture was stirred at r.t. for 6 h. Then the Na(OAc)$_3$BH (0.88 g, 4.14 mmol) was added at 0° C. portionwise. Upon the addition, the reaction mixture was stirred at r.t. for 1 h, and separated with flash column (SiO$_2$, MeOH in DCM=0-40%) to give the boc-protected I-3c as a yellow semi solid.

To the suspension of the boc-protected I-3c in DCM (5 ml) was added the hydrogen chloride solution (4 M in 1,4-dioxane, 5 ml) dropwise at 0° C. Upon the addition, the suspension was stirred at r.t. for 1 h, followed by being concentrated. The crude I-3c hydrochloride was obtained as a yellow solid (0.97 g, 95.8%, two steps). LC-MS (ESI$^+$) m/z=456.3 (M+H)$^+$.

Step 2: Preparation of 3-(4-phenoxyphenyl)-1-(1-((1-(piperidin-4-ylmethyl)azetidin-3-yl)methyl)piperidin-4-yl)-1H-pyrazolo(3,4-d)pyrimidin-4-amine (I-3ca)

This compound was prepared by the procedure identical to the preparation of I-3c with I-3c (0.40 g, 0.89 mmol) as SM and took the tert-butyl 4-formylpiperidine-1-carboxylate as the replacement of tert-butyl 3-formylazetidine-1-carboxylate. The I-3ca hydrochloride was obtained as a yellow solid (0.45 g, 86.2%, two steps). LC-MS (ESI$^+$) m/z=553.4 (M+H)$^+$.

Step 3: Preparation of 5-(4-((3-((4-(4-amino-3-(4-phenoxyphenyl)-1H-pyrazolo(3,4-d)pyrimidin-1-yl)piperidin-1-yl)methyl)azetidin-1-yl)methyl)piperidin-1-yl)-2-(2,6-dioxopiperidin-3-yl)isoindoline-1,3-dione (Compound 439)

The mixture of I-3ca (0.14 g, 0.25 mmol) and DIPEA (0.10 ml) in NMP (6 ml) was stirred at r.t. for 30 min, followed by adding 2-(2,6-dioxopiperidin-3-yl)-5-fluoroisoindoline-1,3-dione (91 mg, 0.33 mmol). The reaction mixture was stirred at 100° C. under N$_2$ for 6 h.

The mixture was separated with Prep-HPLC (Elute: CH$_3$CN in water=10-100%, 15 min) to give Compound 439 as yellow solid (0.12 g, 54.5%). LC-MS (ESI$^+$) m/z=809.4 (M+H)$^+$, 405.2 (M+2H)$^{2+}$.

Example 19: Preparation of Compound 441 (5-(3-((3-((4-(4-amino-3-(4-phenoxyphenyl)-1H-pyrazolo(3,4-d)pyrimidin-1-yl)piperidin-1-yl)methyl)azetidin-1-yl)methyl)azetidin-1-yl)-2-(2,6-dioxopiperidin-3-yl)isoindoline-1,3-dione)
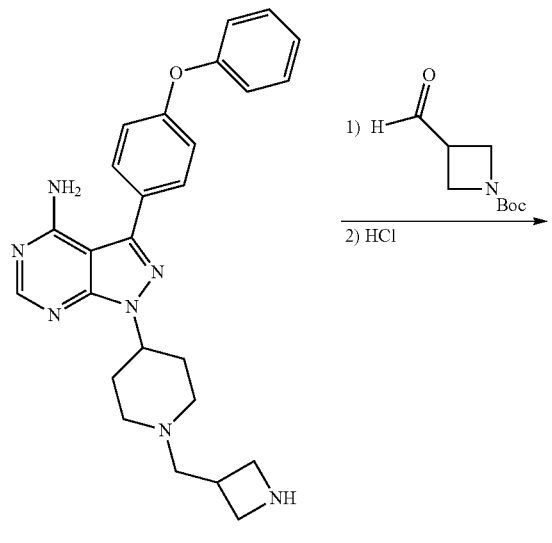
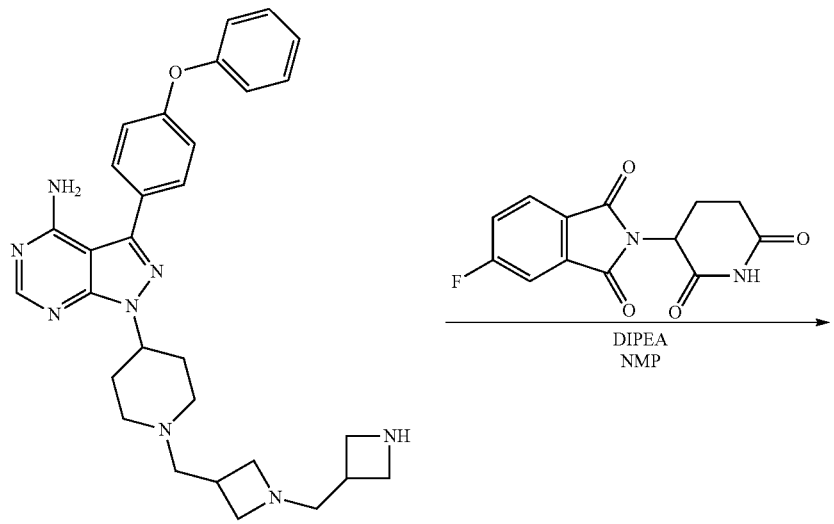

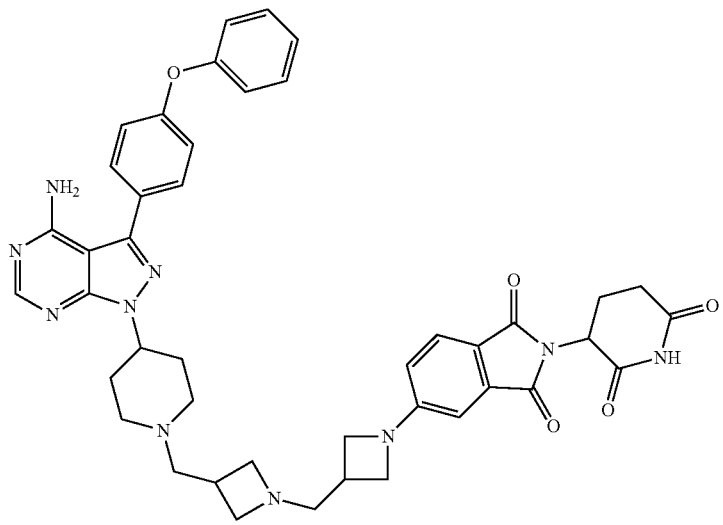

Compound 441

Step 1: Preparation of 1-(1-((1-(azetidin-3-ylm-ethyl)azetidin-3-yl)methyl)piperidin-4-yl)-3-(4-phe-noxyphenyl)-1H-pyrazolo(3,4-d)pyrimidin-4-amine (I-3cc)

This compound was prepared by the procedure identical to the preparation of I-3ca with I-3c (0.40 g, 0.89 mmol) as SM and took the tert-butyl 3-formylazetidine-1-carboxylate as the replacement of tert-butyl 4-formylpiperidine-1-carboxylate. The I-3cc hydrochloride was obtained as a yellow solid (0.45 g, 0.80%, two steps). LC-MS (ESI$^+$) m/z=525.4 (M+H)$^+$.

Step 2: Preparation of 5-(3-((3-((4-(4-amino-3-(4-phenoxyphenyl)-1H-pyrazolo(3,4-d)pyrimidin-1-yl)piperidin-1-yl)methyl)azetidin-1-yl)methyl)azetidin-1-yl)-2-(2,6-dioxopiperidin-3-yl)isoindoline-1,3-dione (Compound 441)

The mixture of I-3cc (0.14 g, 0.26 mmol) and DIPEA (0.10 ml) in NMP (6 ml) was stirred at r.t. for 30 min, followed by adding 2-(2,6-dioxopiperidin-3-yl)-5-fluoroisoindoline-1,3-dione (94 mg, 0.34 mmol). The reaction mixture was stirred at 100° C. under N$_2$ for 6 h.

The mixture was separated with Prep-HPLC (Elute: CH$_3$CN in water=10-100%, 15 min) to give Compound 441 as yellow solid (40 mg, 20.0%). LC-MS (ESI$^+$) m/z=781.4 (M+H)$^+$, 391.2 (M+2H)$^{2+}$.

Example 20: Preparation of Compound 443 (5-(3-((3-((4-(4-amino-3-(4-phenoxyphenyl)-1H-pyrazolo(3,4-d)pyrimidin-1-yl)piperidin-1-yl)methyl)azetidin-1-yl)methyl)pyrrolidin-1-yl)-2-(2,6-dioxopiperidin-3-yl)isoindoline-1,3-dione)
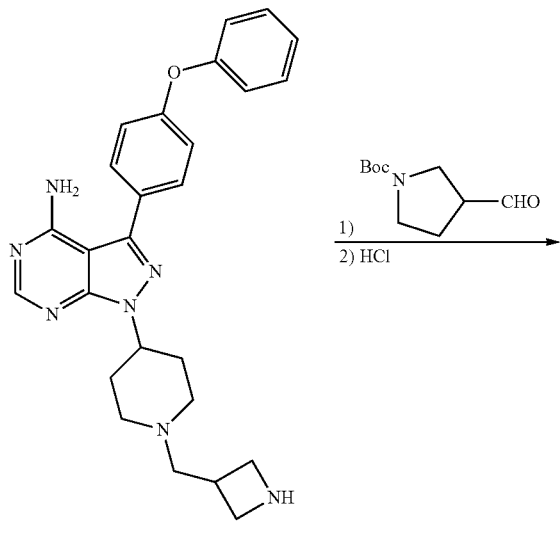
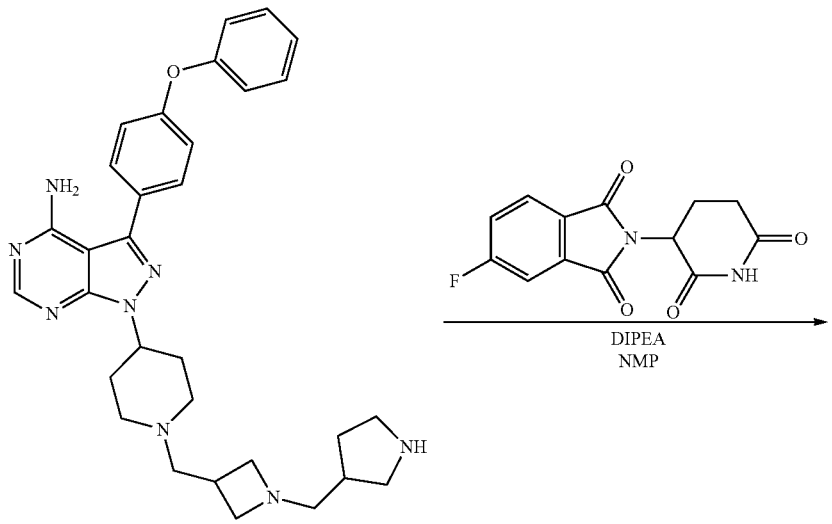

-continued
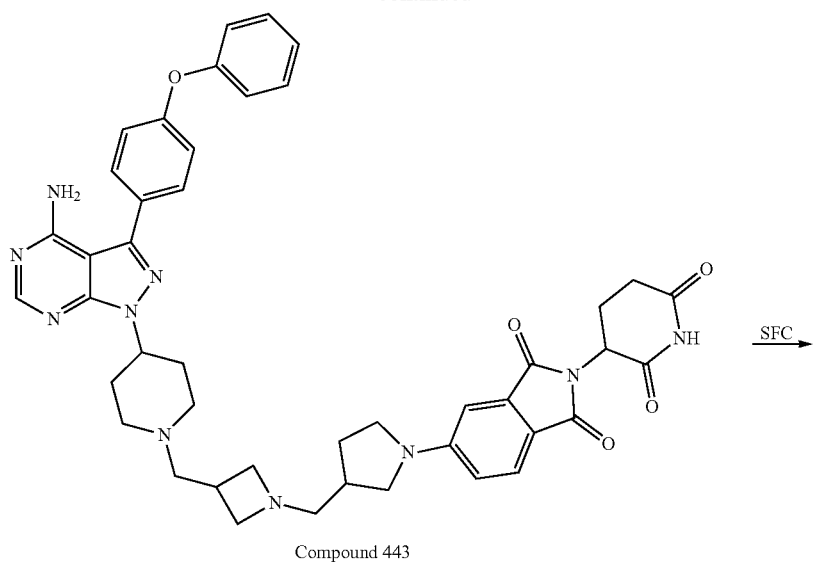
Compound 443
SFC →
Compound 443a
and
Compound 443b

Step 1: 3-(4-phenoxyphenyl)-1-(1-((1-(pyrrolidin-3-ylmethyl)azetidin-3-yl)methyl)piperidin-4-yl)-1H-pyrazolo(3,4-d)pyrimidin-4-amine (I-3cd)

This compound was prepared by the procedure identical to the preparation of I-3ca with I-3c (0.40 g, 0.89 mmol) as SM and took the tert-butyl 3-formylpyrrolidine-1-carboxylate as the replacement of tert-butyl 4-formylpiperidine-1-carboxylate. The I-3cd hydrochloride was obtained as a yellow solid (0.45 g, 0.88%, two steps). LC-MS (ESN) m/z=539.4 (M+H)$^+$.

Step 2: Preparation of 5-(3-((3-((4-(4-amino-3-(4-phenoxyphenyl)-1H-pyrazolo(3,4-d)pyrimidin-1-yl)piperidin-1-yl)methyl)azetidin-1-yl)methyl)pyrrolidin-1-yl)-2-(2,6-dioxopiperidin-3-yl)isoindoline-1,3-dione (Compound 443)

The mixture of I-3cd (0.14 g, 0.26 mmol) and DIPEA (0.10 ml) in NMP (6 ml) was stirred at r.t. for 30 min, followed by adding 2-(2,6-dioxopiperidin-3-yl)-5-fluoroisoindoline-1,3-dione (94 mg, 0.34 mmol). The reaction mixture was stirred at 100° C. under N$_2$ for 6 h.

The mixture was separated with Prep-HPLC (Elute: CH$_3$CN in water=10-100%, 15 mi) to give Compound 443 as yellow solid (50 mg, 24.2%). LC-MS (ESI$^+$) m/z=795.4 (M+H)$^+$, 398.2 (M+2H)$^{2+}$.

Step 3: Separation of Compound 443a and Compound 443b

The mixture was separated with SFC column to obtain the Compound 443a and Compound 443b.

Example 21: Preparation of Compound 445 (5-(4-((3-((4-(4-amino-3-(4-phenoxyphenyl)-1H-pyrazolo(3,4-d)pyrimidin-1-yl)piperidin-1-yl)methyl)pyrrolidin-1-yl)methyl)piperidin-1-yl)-2-(2,6-dioxopiperidin-3-yl)isoindoline-1,3-dione)

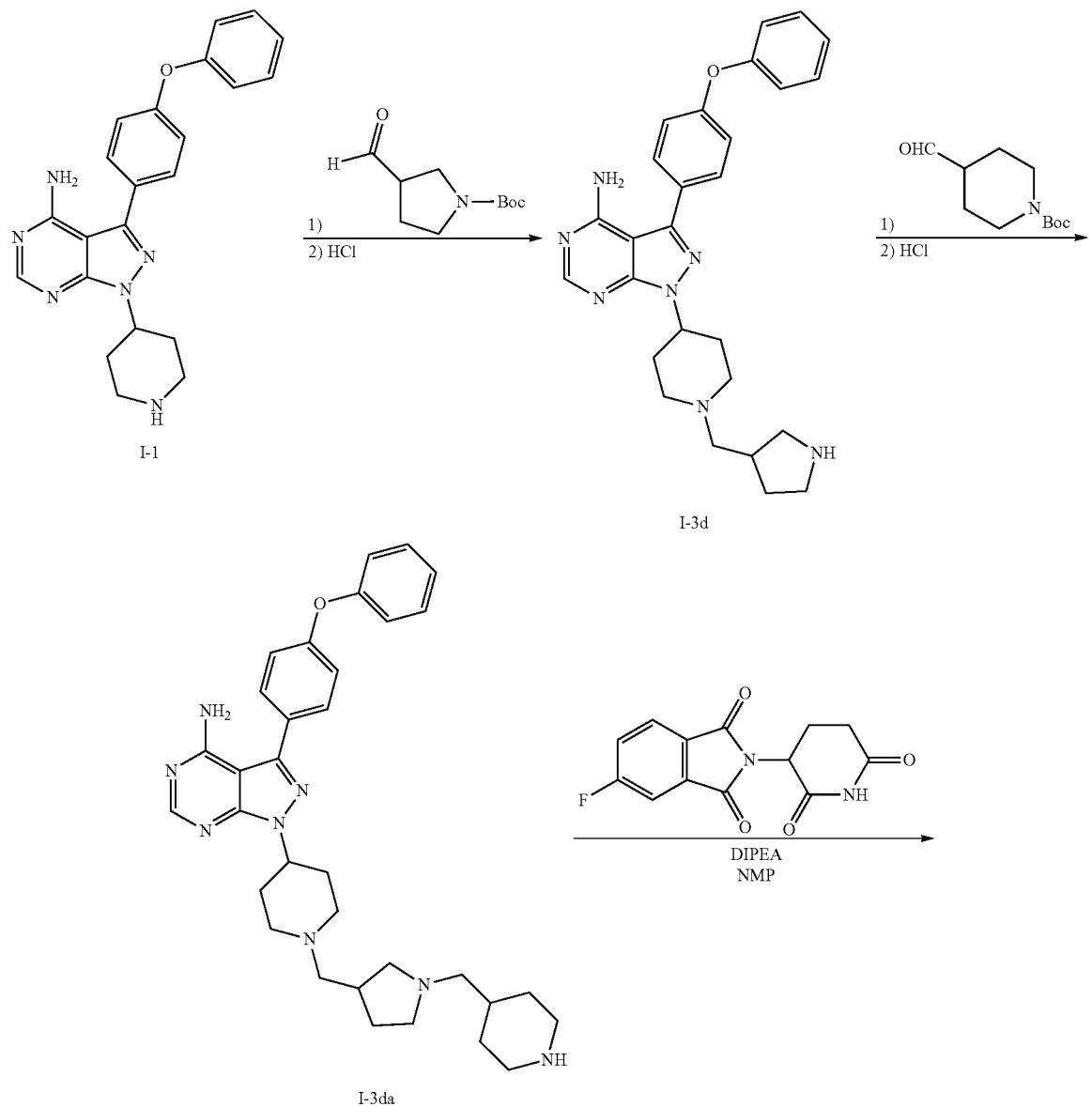

-continued
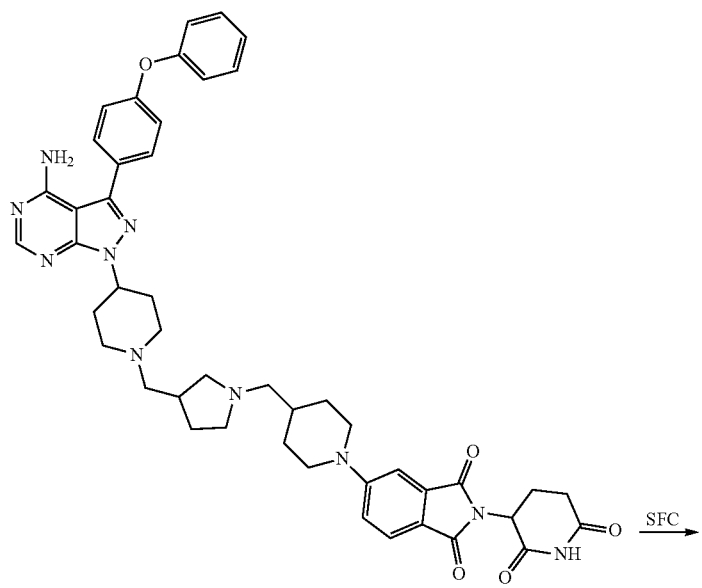
Compound 445
→ SFC →
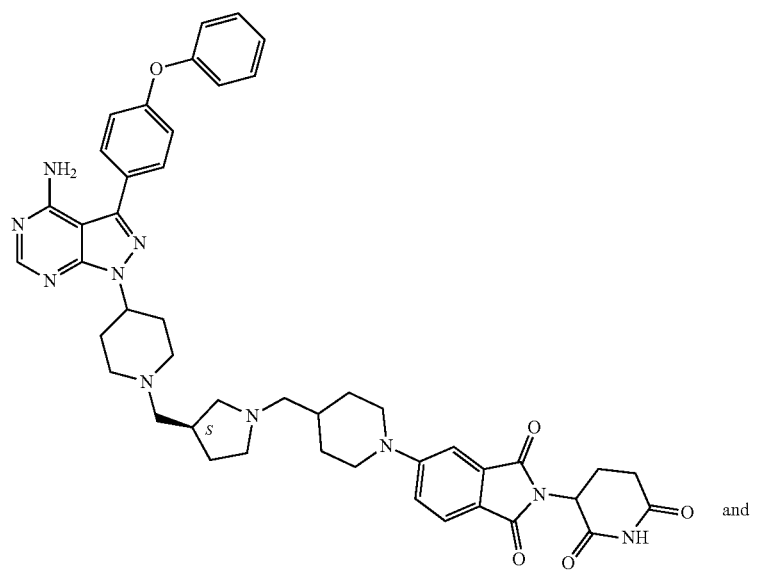
Compound 445a
and

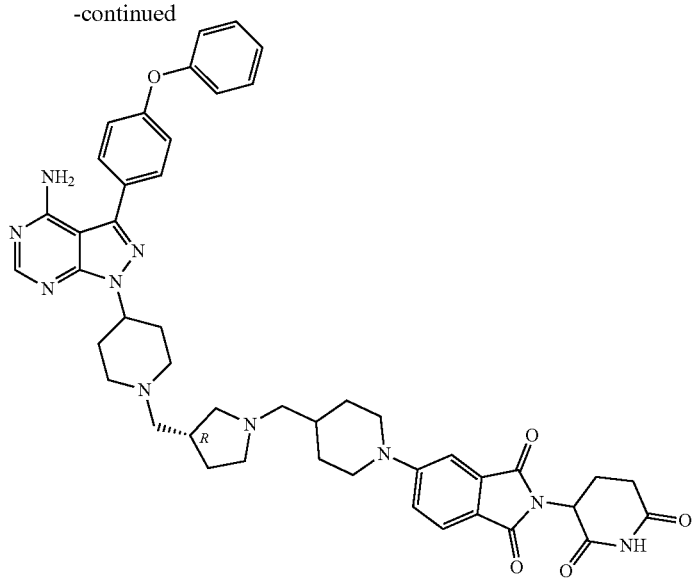

Compound 445b

Step 1: Preparation of 3-(4-phenoxyphenyl)-1-(1-(pyrrolidin-3-ylmethyl)piperidin-4-yl)-1H-pyrazolo(3,4-d)pyrimidin-4-amine (I-3d)

The mixture of I-1 (0.60 g, 1.66 mmol), NEt$_3$ (0.46 ml) in DCM (15 ml) was stirred at r.t. for 30 min, following by adding the tert-butyl 3-formylazetidine-1-carboxylate (0.70 g, 4.00 mmol). The reaction mixture was stirred at r.t. for 6 h. Then the Na(OAc)$_3$BH (0.70 g, 3.32 mmol) was added at 0° C. portionwise. Upon the addition, the reaction mixture was stirred at r.t. for 1 h, and separated with flash column (SiO$_2$, MeOH in DCM=0-35%) to give the boc-protected I-3d as a brown semi solid.

To the suspension of the boc-protected I-3d in DCM (5 ml) was added the hydrogen chloride solution (4 M in 1,4-dioxane, 5 ml) dropwise at 0° C. Upon the addition, the suspension was stirred at r.t. for 1 h, followed by being concentrated. The crude I-3d hydrochloride was obtained as a brown solid (0.74 g, 90.0%, two steps). LC-MS (ESI$^+$) m/z=470.3 (M+H)$^+$.

Step 2: Preparation of 3-(4-phenoxyphenyl)-1-(1-((1-(piperidin-4-ylmethyl)pyrrolidin-3-yl)methyl)piperidin-4-yl)-1H-pyrazolo(3,4-d)pyrimidin-4-amine (I-3da)

This compound was prepared by the procedure identical to the preparation of I-3cc with I-3d (0.30 g, 0.64 mmol) as SM and took the tert-butyl 4-formylpiperidine-1-carboxylate as the replacement of tert-butyl 3-formylazetidine-1-carboxylate. The I-3da hydrochloride was obtained as a yellow solid (0.36 g, 93.9%, two steps). LC-MS (ESI$^+$) m/z=567.4 (M+H)$^+$.

Step 3: Preparation of 5-(4-((3-((4-(4-amino-3-(4-phenoxyphenyl)-1H-pyrazolo(3,4-d)pyrimidin-1-yl)piperidin-1-yl)methyl)pyrrolidin-1-yl)methyl)piperidin-1-yl)-2-(2,6-dioxopiperidin-3-yl)isoindoline-1,3-dione (Compound 445)

The mixture of I-3da (0.20 g, 0.35 mmol) and DIPEA (0.12 ml) in NMP (6 ml) was stirred at r.t. for 30 min, followed by adding 2-(2,6-dioxopiperidin-3-yl)-5-fluoroisoindoline-1,3-dione (0.11 g, 0.34 mmol). The reaction mixture was stirred at 100° C. under N$_2$ for 6 h.

The mixture was separated with Prep-HPLC (Elute: CH$_3$CN in water=10-100%, 15 min) to give Compound 445 as yellow solid (80 mg, 27.8%). LC-MS (ESI$^+$) m/z=823.4 (M+H)$^+$, 412.2 (M+2H)$^{2+}$.

Step 4: Separation of Compound 445a and Compound 445b
The mixture was separated with SFC column to obtain the Compound 445a and Compound 445b.
Example 22: Preparation of Compound 446 (3-(5-(4-((3-((4-(4-amino-3-(4-phenoxyphenyl)-1H-pyrazolo(3,4-d)pyrimidin-1-yl)piperidin-1-yl)methyl)pyrrolidin-1-yl)methyl)piperidin-1-yl)-1-oxoisoindolin-2-yl)piperidine-2,6-dione)
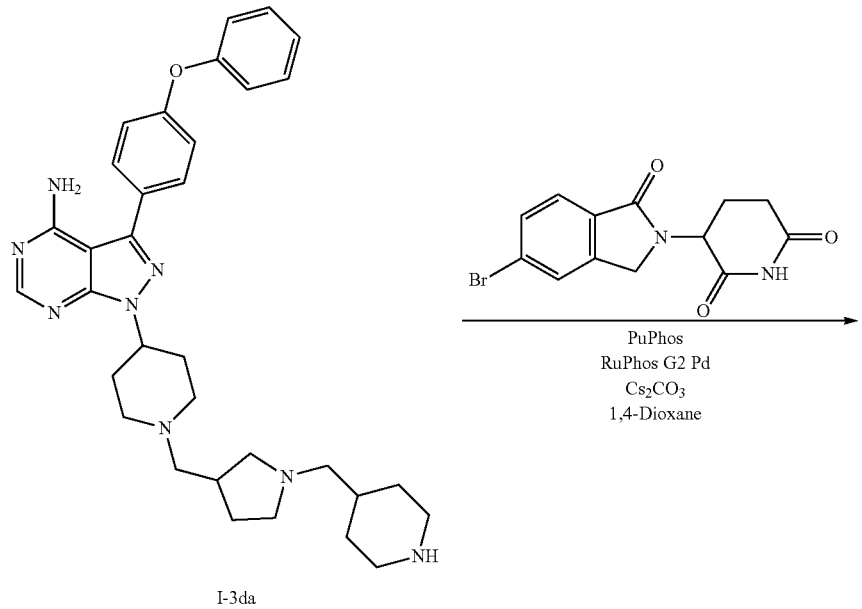
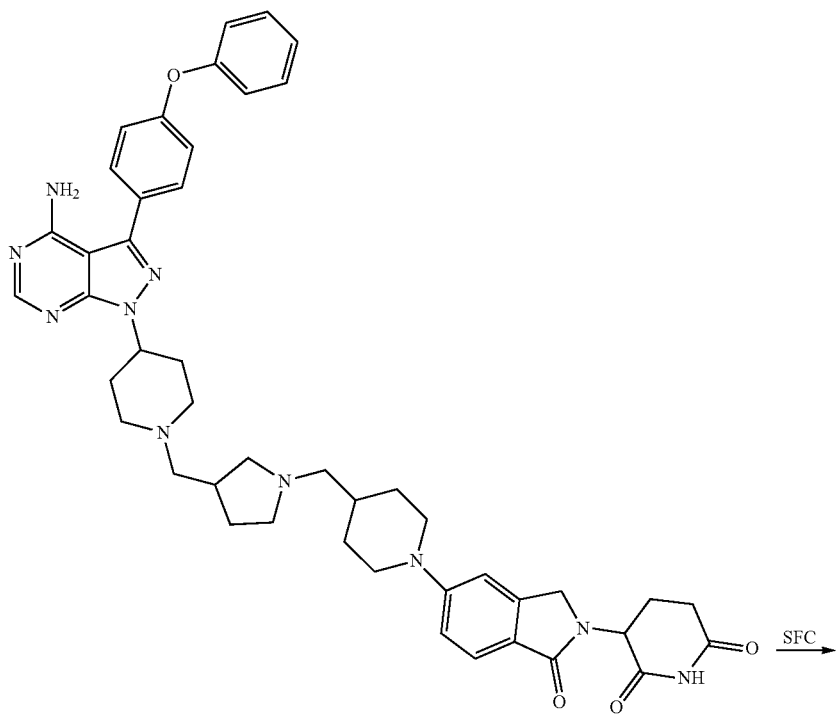

-continued

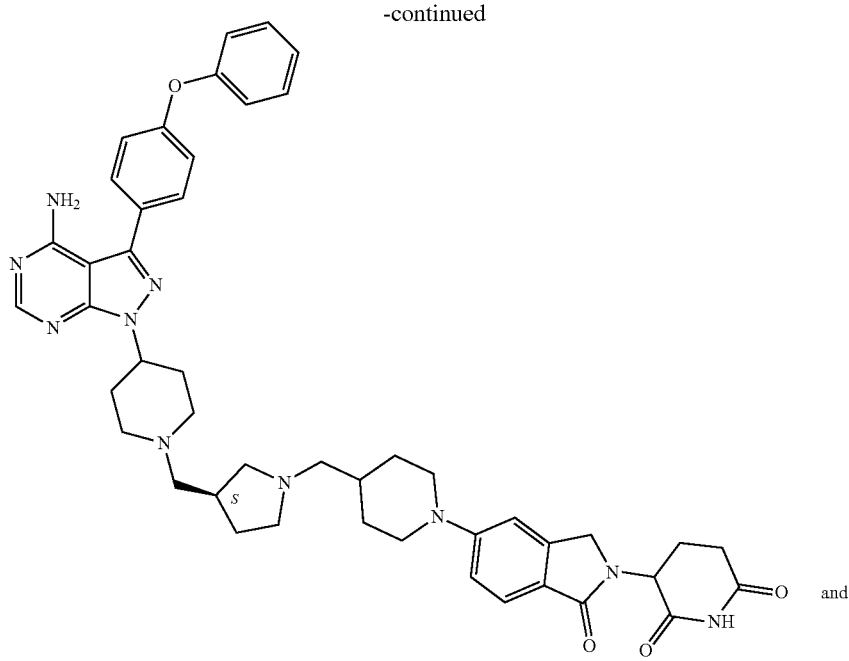

Compound 446a

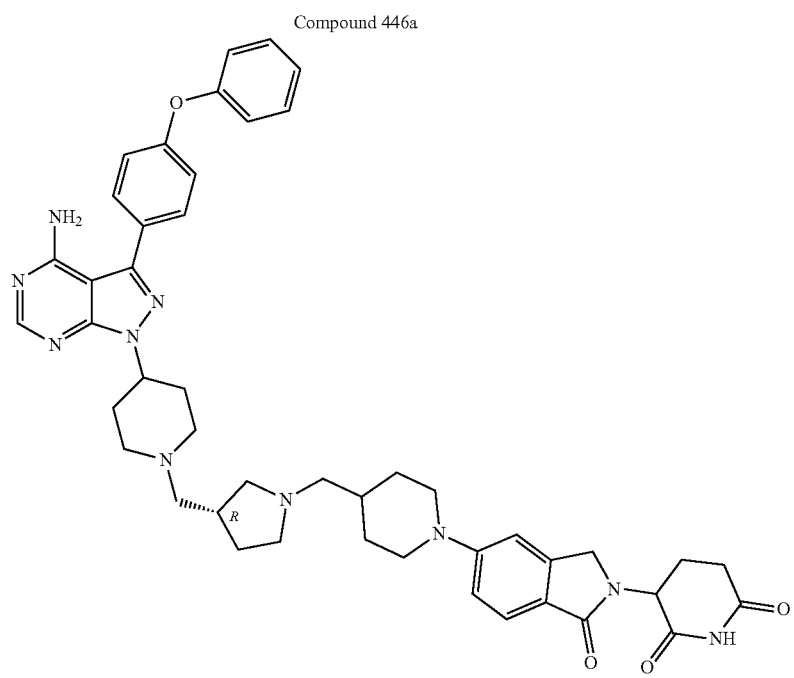

Compound 446b

Step 1: Preparation of Compound 446

The mixture of I-3da (0.10 g, 0.18 mmol), $Cs_2CO_3$ (0.12 g, 0.36 mmol) in 1,4-dioxane (10 ml) was degassed for 3 min, stirred at r.t. under $N_2$ for 15 min, followed by adding RuPhos (17 mg, 36 μmol), RuPhos G2 Pd (28 mg, 36 μmol) and 3-(5-bromo-1-oxoisoindolin-2-yl)piperidine-2,6-dione (74 mg, 0.23 mmol). The reaction mixture was stirred at 100° C. under $N_2$ for 8 h.

The suspension was filtered, the cake was washed with $CHCl_3$ (5 ml×3). The combined filtrates were concentrated and separated with pre-HPLC (Elute: $CH_3CN$ in water=10-100%, 15 min) to give Compound 446 as off-white solid (35 mg, 24.1%). LC-MS (ESI$^+$) m/z=809.4 (M+H)$^+$, 405.2 (M+2H)$^{2+}$.

Step 2: Separation of Compound 446a and Compound 446b

The mixture was separated with SFC column to obtain the Compound 446a and Compound 446b.

Example 23: Preparation of Compound 447 (5-(3-((3-((4-(4-amino-3-(4-phenoxyphenyl)-1H-pyrazolo(3,4-d)pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione)
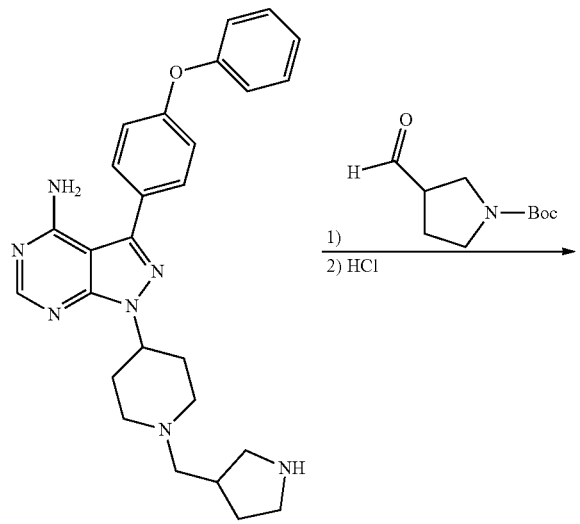
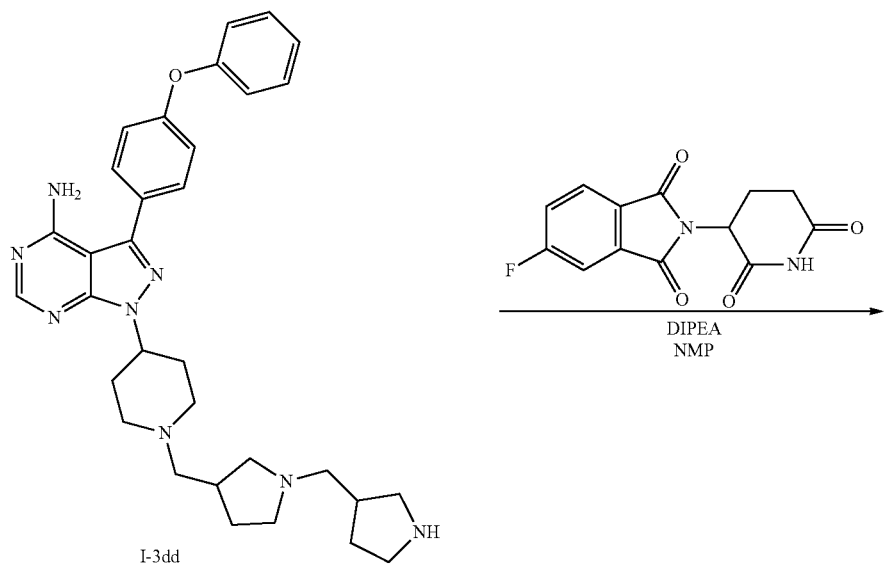

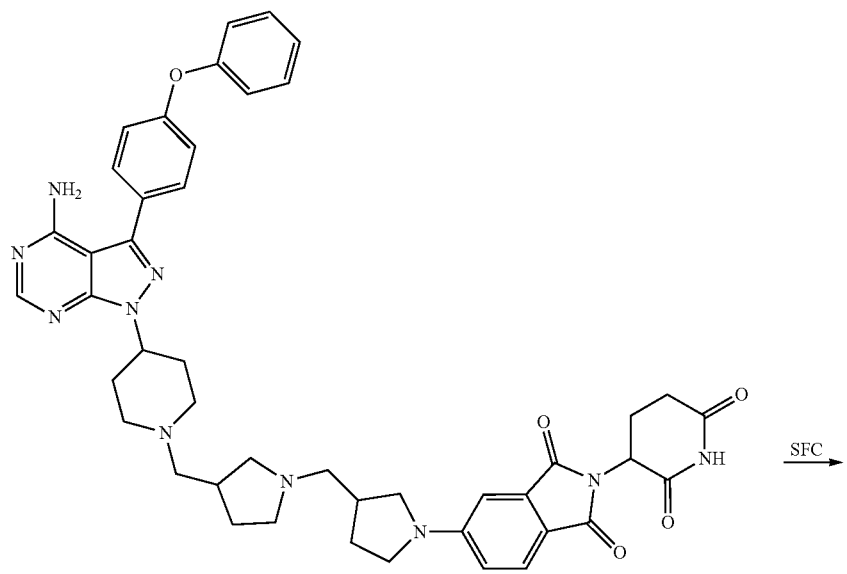
Compound 447
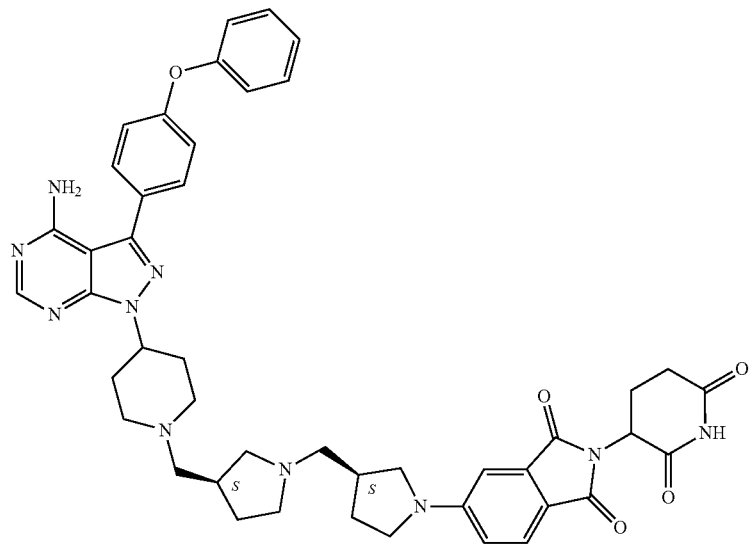
Compound 447a

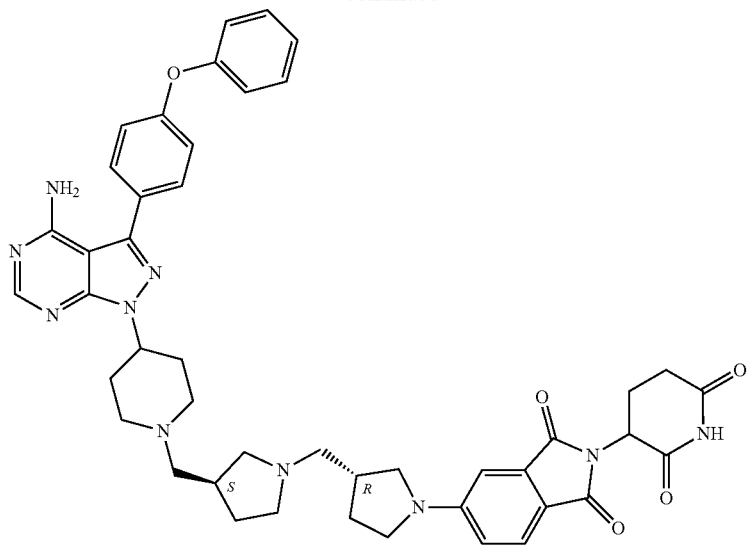
Compound 447b
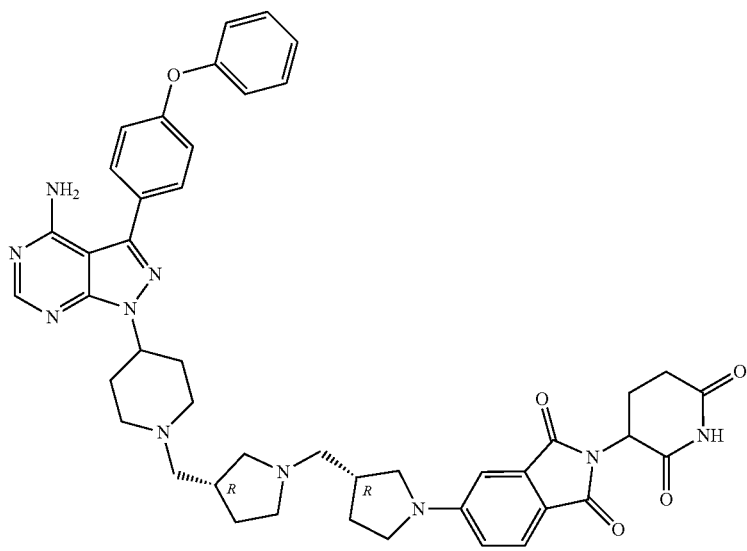
Compound 447c

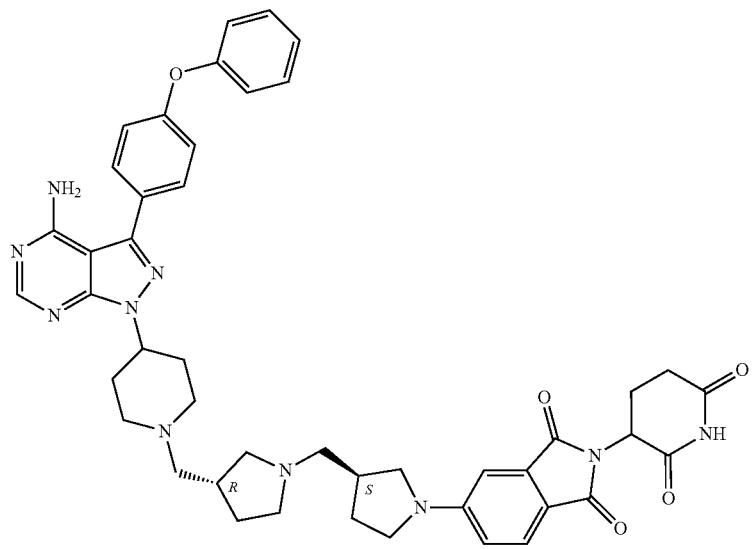

Compound 447d

Step 1: Preparation of 3-(4-phenoxyphenyl)-1-(1-((1-(pyrrolidin-3-ylmethyl)pyrrolidin-3-yl)methyl)piperidin-4-yl)-1H-pyrazolo(3,4-d)pyrimidin-4-amine (I-3dd)

This compound was prepared by the procedure identical to the preparation of I-3cc with I-3d (0.15 g, 0.32 mmol) as SM and took the tert-butyl 3-formylpyrrolidine-1-carboxylate as the replacement of tert-butyl 3-formylazetidine-1-carboxylate. The I-3da hydrochloride was obtained as a yellow solid (0.18 g, 96.2%, two steps). LC-MS (ESI$^+$) m/z=553.4 (M+H)$^+$.

Step 2: Preparation of 5-(3-((3-((4-(4-amino-3-(4-phenoxyphenyl)-1H-pyrazolo(3,4-d)pyrimidin-1-yl)piperidin-1-yl)methyl)pyrrolidin-1-yl)methyl)pyrrolidin-1-yl)-2-(2,6-dioxopiperidin-3-yl)isoindoline-1,3-dione (Compound 447)

The mixture of I-3dd (0.10 g, 0.18 mmol) and DIPEA (0.07 ml) in NMP (6 ml) was stirred at r.t. for 30 min, followed by adding 2-(2,6-dioxopiperidin-3-yl)-5-fluoroisoindoline-1,3-dione (65 mg, 0.24 mmol). The reaction mixture was stirred at 100° C. under $N_2$ for 6 h.

The mixture was separated with Prep-HPLC (Elute: $CH_3CN$ in water=10-100%, 15 min) to give Compound 447 as yellow solid (40 mg, 27.5%). LC-MS (ESI$^+$) m/z=809.4 (M+H)$^+$, 405.2 (M+2H)$^{2+}$.

Step 3: Separation of Compound 447a, Compound 447b, Compound 447c, Compound 447d
The mixture was separated with SFC column to obtain the Compound 447a, Compound 447b, Compound 447c, and Compound 447d.
Example 24: Preparation of Compound 449 (5-(4-((3-(4-(4-amino-3-(4-phenoxyphenyl)-1H-pyrazolo (3,4-d)pyrimidin-1-yl)piperidin-1-yl)pyrrolidin-1-yl) methyl)piperidin-1-yl)-2-(2,6-dioxopiperidin-3-yl) isoindoline-1,3-dione)
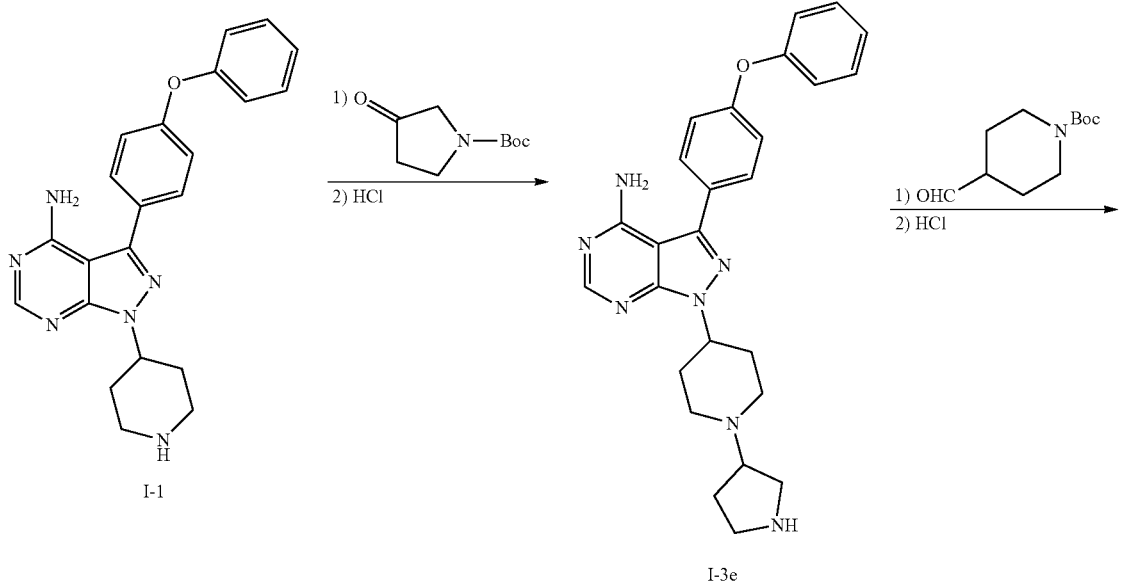
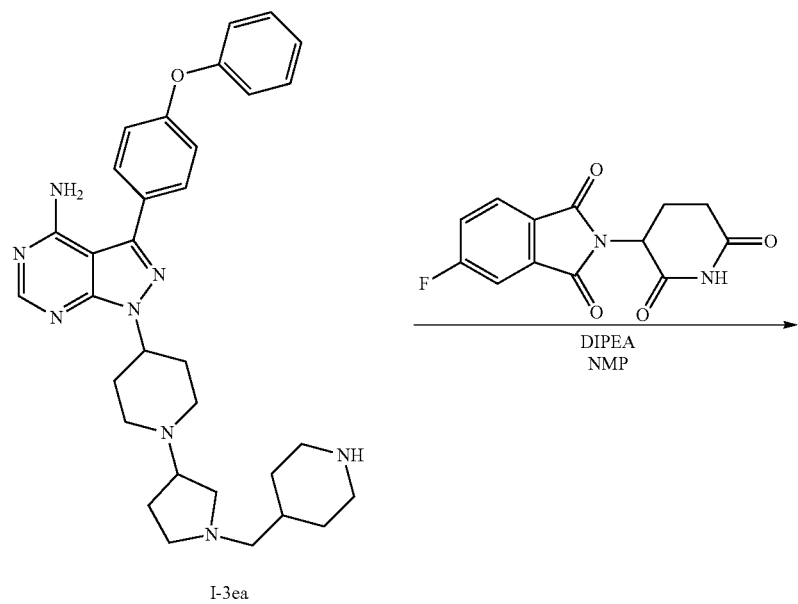

-continued
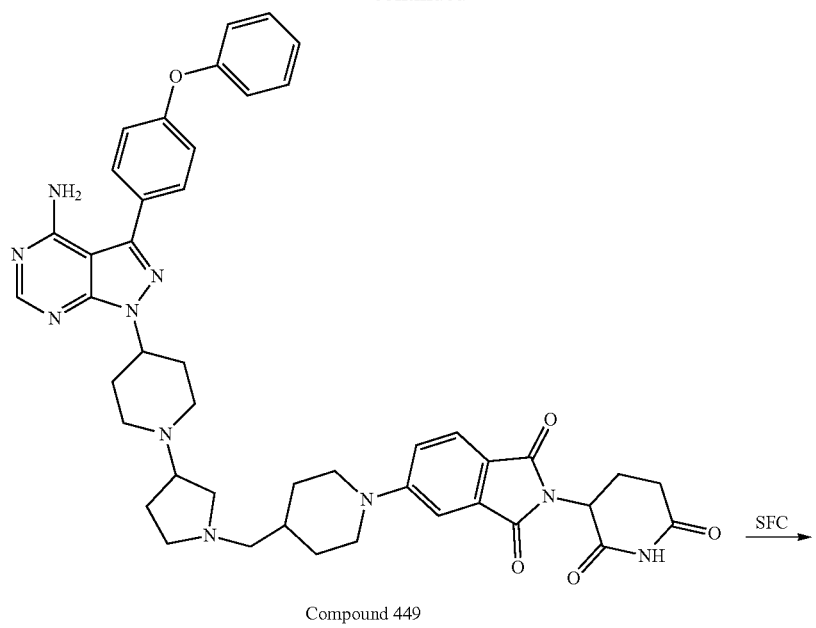
Compound 449
SFC →
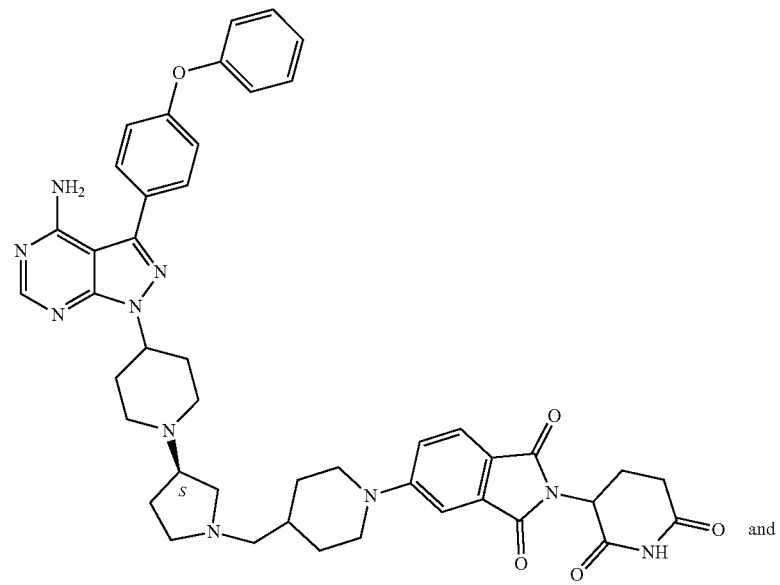
Compound 449a
and

-continued

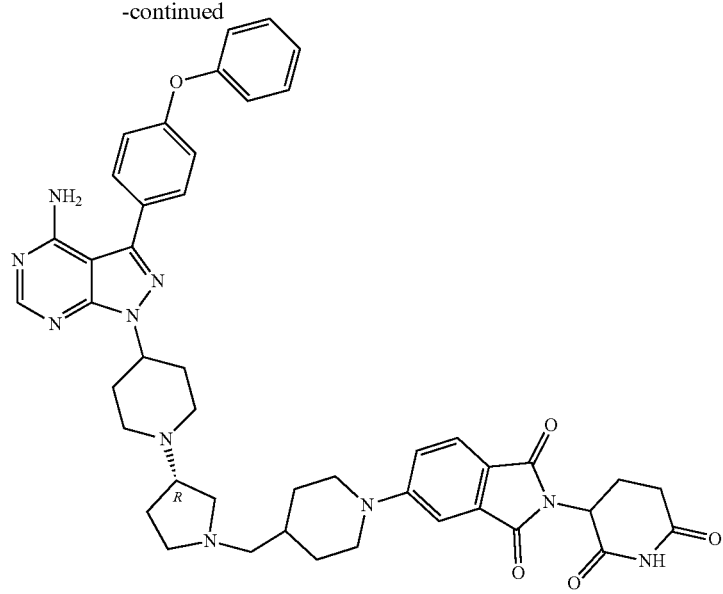

Compound 449b

Step 1: Preparation of 3-(4-phenoxyphenyl)-1-(1-(pyrrolidin-3-yl)piperidin-4-yl)-1H-pyrazolo(3,4-d)pyrimidin-4-amine (I-3e)

The mixture of I-1 (0.60 g, 1.66 mmol), NEt$_3$ (0.46 ml) in DCM (15 ml) was stirred at r.t. for 30 min, following by adding the tert-butyl 3-formylazetidine-1-carboxylate (0.62 g, 3.32 mmol). The reaction mixture was stirred at r.t. for 6 h. Then the Na(OAc)$_3$BH (0.70 g, 3.32 mmol) was added at 0° C. portionwise. Upon the addition, the reaction mixture was stirred at r.t. for 1 h, and separated with flash column (SiO$_2$, MeOH in DCM=0-45%) to give the boc-protected I-3e as a brown semi solid.

To the suspension of the boc-protected I-3e in DCM (5 ml) was added the hydrogen chloride solution (4 M in 1,4-dioxane, 5 ml) dropwise at 0° C. Upon the addition, the suspension was stirred at r.t. for 1 h, followed by being concentrated. The crude I-3e hydrochloride was obtained as a brown solid (0.73 g, 90.0%, two steps). LC-MS (ESI$^+$) m/z=456.3 (M+H)$^+$.

Step 2: Preparation of 3-(4-phenoxyphenyl)-1-(1-(1-(piperidin-4-ylmethyl)pyrrolidin-3-yl)piperidin-4-yl)-1H-pyrazolo(3,4-d)pyrimidin-4-amine (I-3ea)

This compound was prepared by the procedure identical to the preparation of I-3cc with I-3e (0.30 g, 0.66 mmol) as SM and took the tert-butyl 4-formylpiperidine-1-carboxylate as the replacement of tert-butyl 3-formylazetidine-1-carboxylate. The I-3ea hydrochloride was obtained as a yellow solid (0.36 g, 92.9%, two steps). LC-MS (ESI$^+$) m/z=553.4 (M+H)$^+$.

Step 3: Preparation of 5-(4-((3-(4-(4-amino-3-(4-phenoxyphenyl)-1H-pyrazolo(3,4-d)pyrimidin-1-yl)piperidin-1-yl)pyrrolidin-1-yl)methyl)piperidin-1-yl)-2-(2,6-dioxopiperidin-3-yl)isoindoline-1,3-dione (Compound 449)

The mixture of I-3ea (0.20 g, 0.36 mmol) and DIPEA (0.12 ml) in NMP (6 ml) was stirred at r.t. for 30 min, followed by adding 2-(2,6-dioxopiperidin-3-yl)-5-fluoroisoindoline-1,3-dione (0.11 g, 0.40 mmol). The reaction mixture was stirred at 100° C. under N$_2$ for 6 h.

The mixture was separated with Prep-HPLC (Elute: CH$_3$CN in water=10-100%, 15 min) to give Compound 449 as yellow solid (0.10 g, 34.3%). LC-MS (ESI$^+$) m/z=809.4 (M+H)$^+$, 405.2 (M+2H)$^{2+}$.

Step 4: Separation of Compound 449a and Compound 449b

The mixture was separated with SFC column to obtain the Compound 449a and Compound 449b.

Example 25: Preparation of Compound 453 (5-(4-((1-(2-(4-(4-amino-3-(4-phenoxyphenyl)-1H-pyrazolo(3,4-d)pyrimidin-1-yl)piperidin-1-yl)ethyl)piperidin-4-yl)methyl)piperazin-1-yl)-2-(2,6-dioxopiperidin-3-yl)isoindoline-1,3-dione)

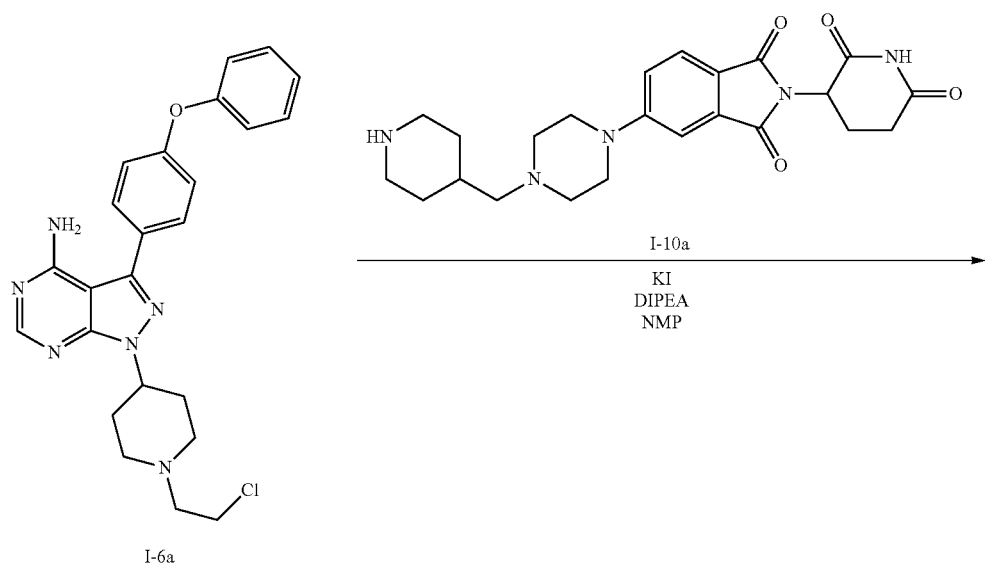

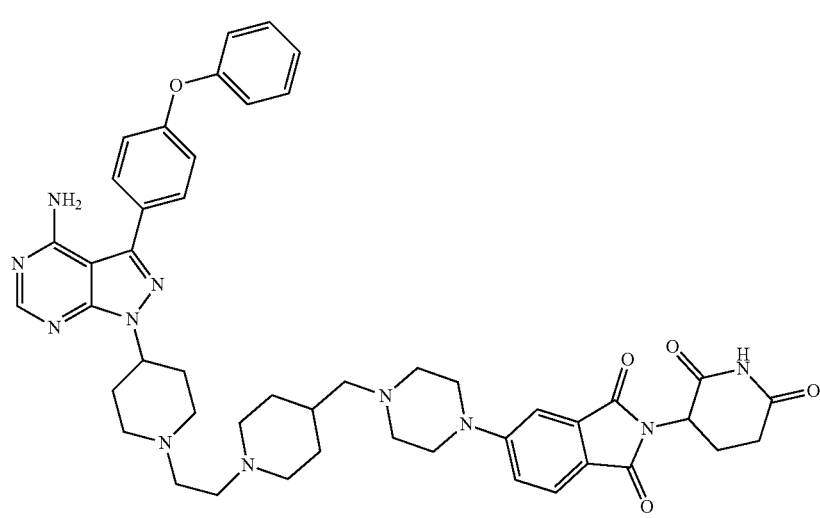

Compound 453

The mixture of I-6a (0.11 g, 0.24 mmol), I-10a (0.10 g, 0.24 mmol), KI (80 mg, 0.48 mmol) and DIPEA (0.13 ml, 0.72 mmol) in NMP (6 ml) was stirred at 100° C. under $N_2$ for 7 h. The mixture was filtered and separated with Prep-HPLC (Elute: $CH_3CN$ in $H_2O$=10-100%, 20 min) to give P1036 as a yellow solid (40 mg, 19.6%). LC-MS (ESI$^+$) m/z=852.4 (M+H)$^+$, 426.7 (M+2H)$^{2+}$.

Example 26: Preparation of Compound 455 (5-(4-((1-(2-(4-(4-amino-3-(4-phenoxyphenyl)-1H-pyrazolo(3,4-d)pyrimidin-1-yl)piperidin-1-yl)ethyl)pyrrolidin-3-yl)methyl)piperazin-1-yl)-2-(2,6-dioxopiperidin-3-yl)isoindoline-1,3-dione)

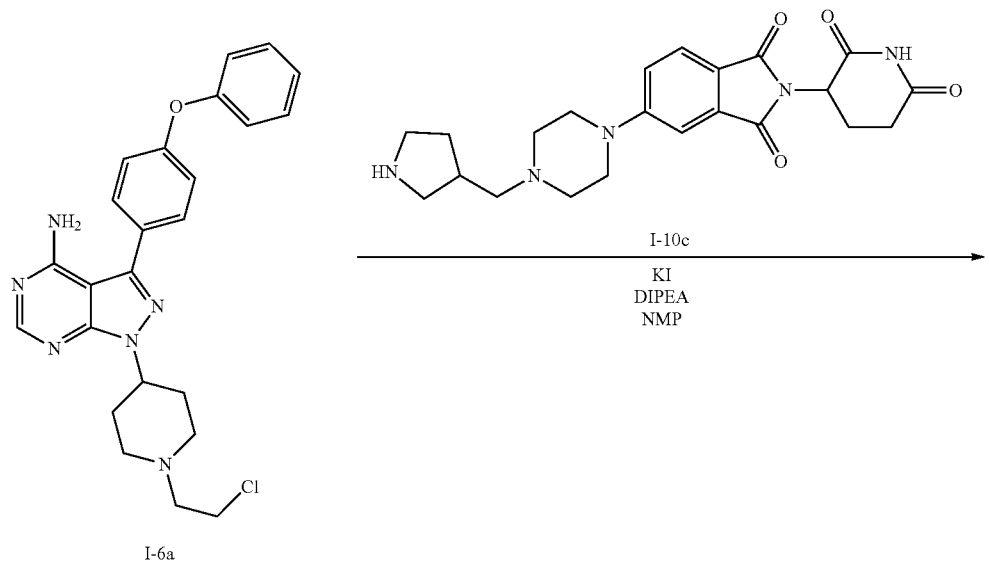

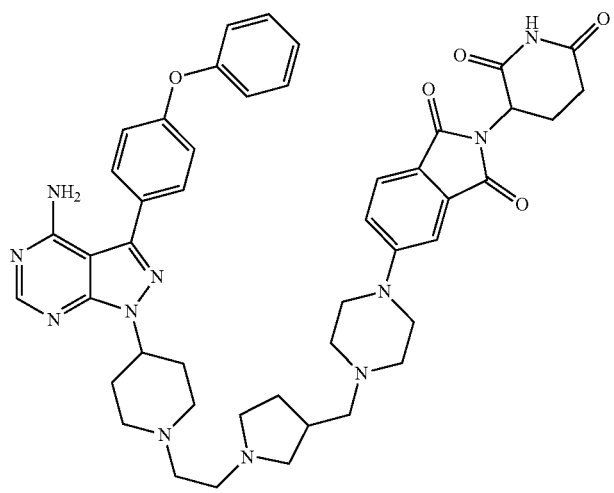

Compound 455

The mixture of I-6a (0.11 g, 0.24 mmol), I-10c (0.10 g, 0.24 mmol), KI (80 mg, 0.48 mmol) and DIPEA (0.13 ml, 0.72 mmol) in NMP (6 ml) was stirred at 100° C. under $N_2$ for 7 h. The mixture was filtered and separated with Prep-HPLC (Elute: $CH_3CN$ in $H_2O$=10-100%, 15 min) to give Compound 455 as a light brown solid (30 mg, 14.9%). LC-MS (ESI+) m/z=838.4 (M+H)+, 419.7 (M+2H)2+.

Example 27: Preparation of Compound 457 (5-(4-(1-(2-(4-(4-amino-3-(4-phenoxyphenyl)-1H-pyrazolo(3,4-d)pyrimidin-1-vi)piperidin-1-yl)ethyl)piperidin-4-yl)piperazin-1-yl)-2-(2,6-dioxopiperidin-3-yl)isoindoline-1,3-dione)

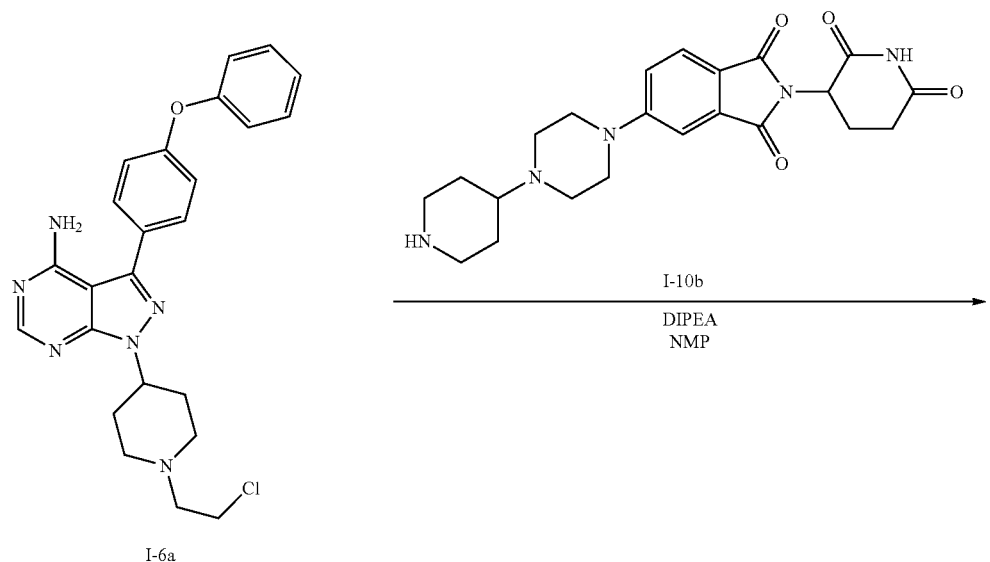

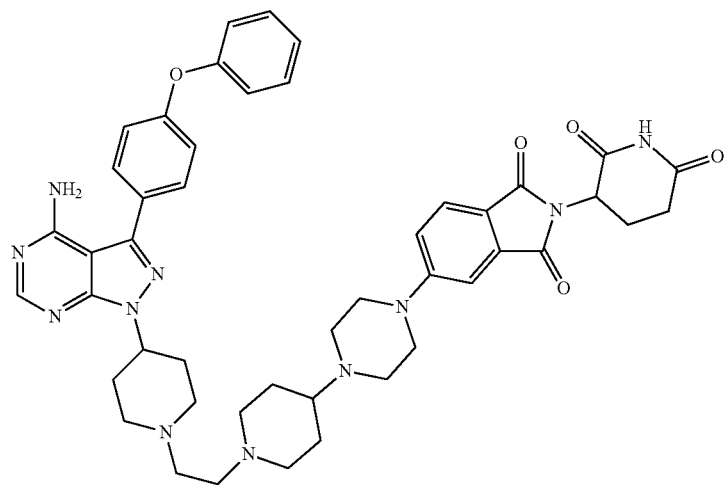

Compound 457

The mixture of I-6a (0.11 g, 0.24 mmol), I-10b (0.20 g, 0.48 mmol), KI (80 mg, 0.48 mmol) and DIPEA (0.13 ml, 0.72 mmol) in NMP (6 ml) was stirred at 100° C. under $N_2$ for 7 h. The mixture was filtered and separated with Prep-HPLC (Elute: $CH_3CN$ in $H_2O$=10-100%, 15 min) to give Compound 457 as a light brown solid (50 mg, 24.9%).

LC-MS (ESI$^+$) m/z=838.4 (M+H)$^+$, 419.7 (M+2H)$^{2+}$.

Example 28: Preparation of Compound 459 (5-(4-(1-(2-(4-(4-amino-3-(4-phenoxyphenyl)-1H-pyrazolo(3,4-d)pyrimidin-1-yl)piperidin-1-yl)ethyl)pyrrolidin-3-yl)piperazin-1-yl)-2-(2,6-dioxopiperidin-3-yl)isoindoline-1,3-dione)
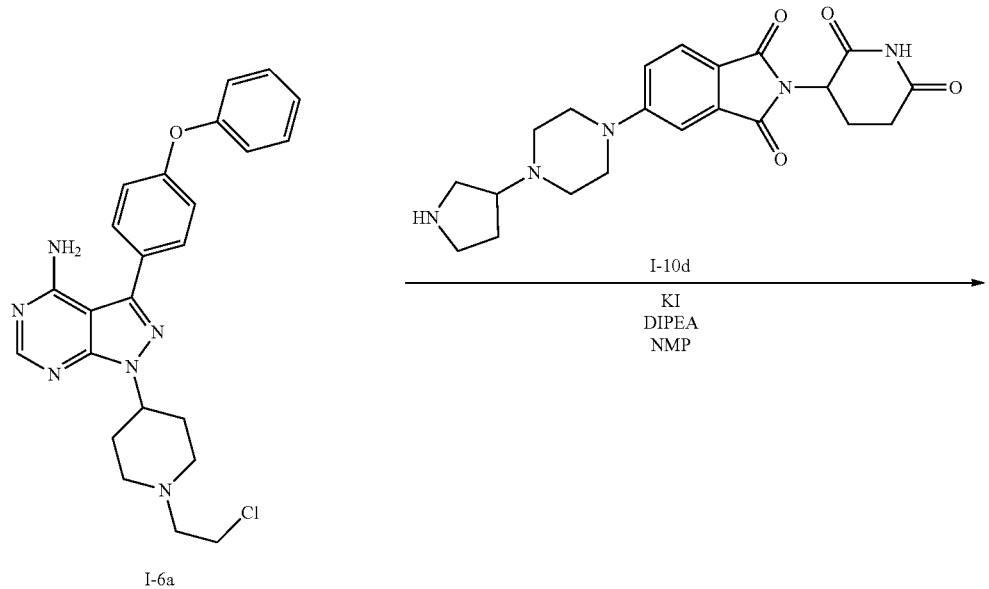
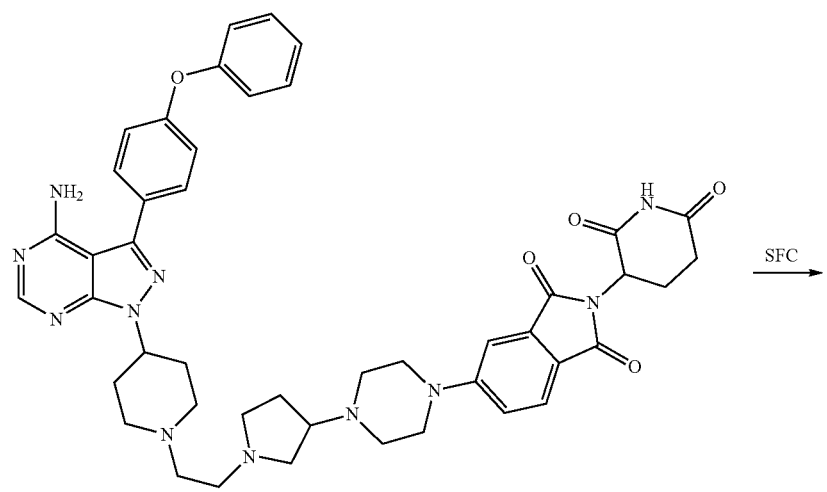
Compound 459

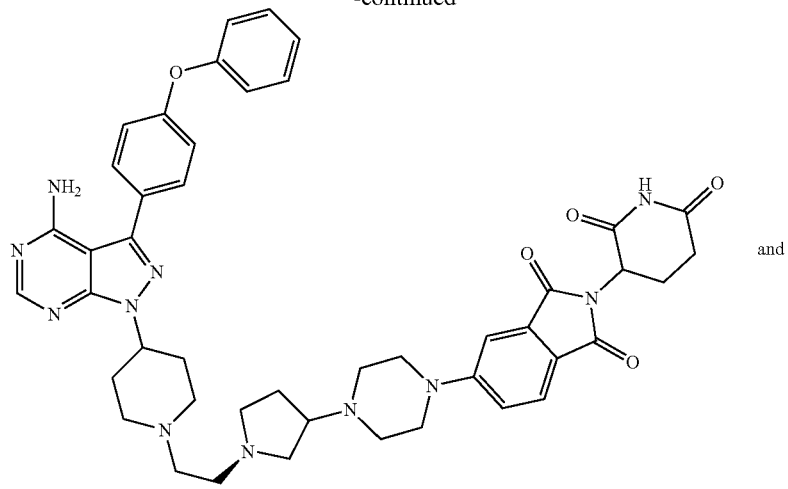
Compound 459a
and
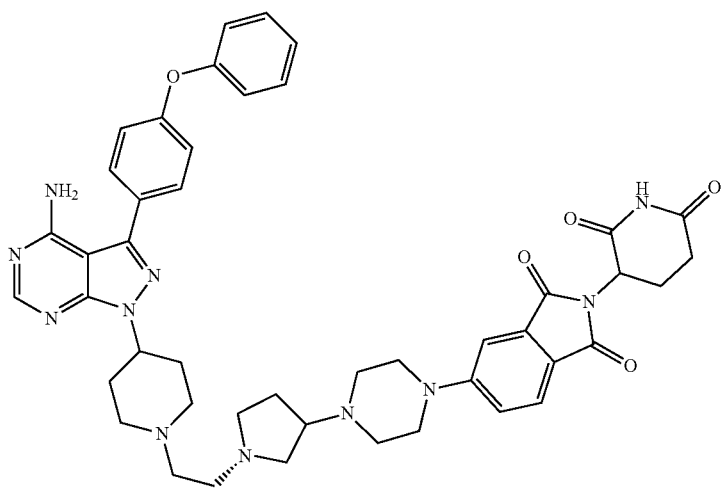
Compound 459b
Step 1: Preparation of Compound 459
The mixture of I-6a (0.11 g, 0.24 mmol), I-10d (0.20 g, 0.48 mmol), KI (80 mg, 0.48 mmol) and DIPEA (0.13 ml, 0.72 mmol) in NMP (6 ml) was stirred at 100° C. under $N_2$ for 7 h. The mixture was filtered and separated with Prep-HPLC (Elute: $CH_3CN$ in $H_2O$=10-100%, 15 min) to give Compound 459 as a light brown solid (20 mg, 9.92%). LC-MS (ESI$^+$) m/z=840.4 (M+H)$^+$, 420.7 (M+2H)$^{2+}$.

Step 2: Separation of Compound 459a and Compound 459b
The mixture was separated with SFC column to obtain the Compound 459a and Compound 459b.
Example 29: Preparation of Compound 465 (5-((2-(4-(2-(4-(4-amino-3-(4-phenoxyphenyl)-1H-pyrazolo(3,4-d)pyrimidin-1-yl)piperidin-1-yl)ethyl)piperazin-1-yl)ethyl)thio)-2-(2,6-dioxopiperidin-3-yl)isoindoline-1,3-dione)
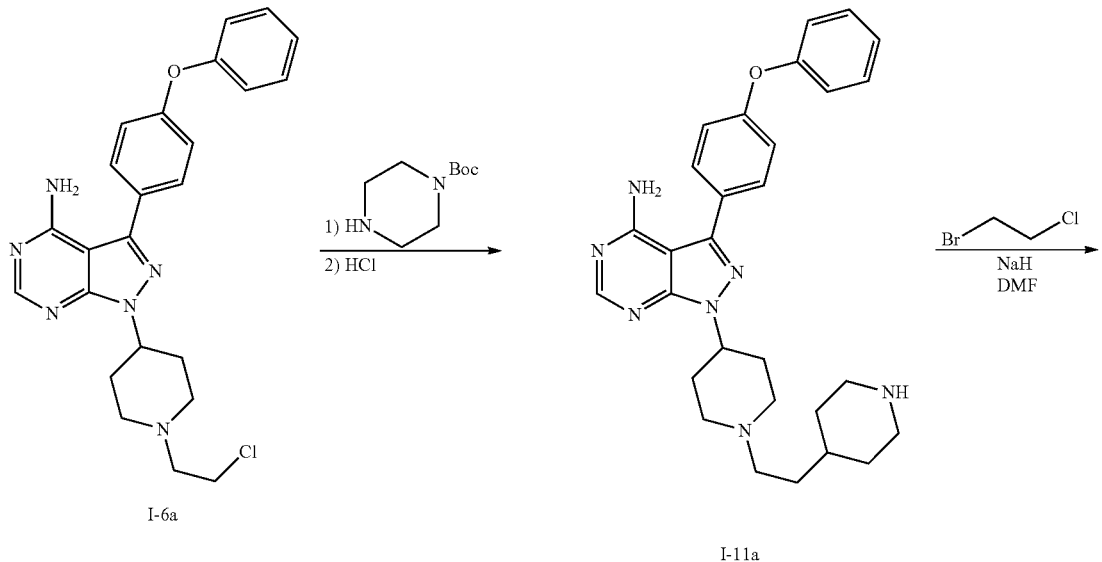
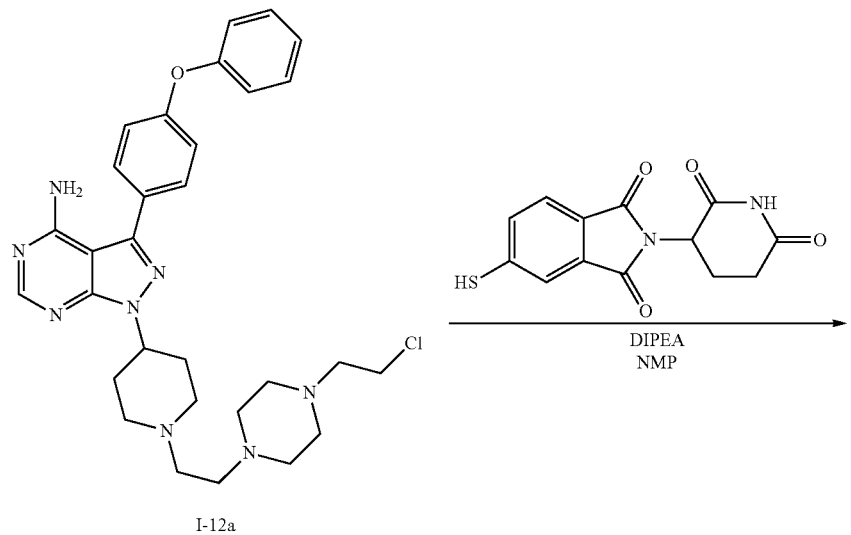

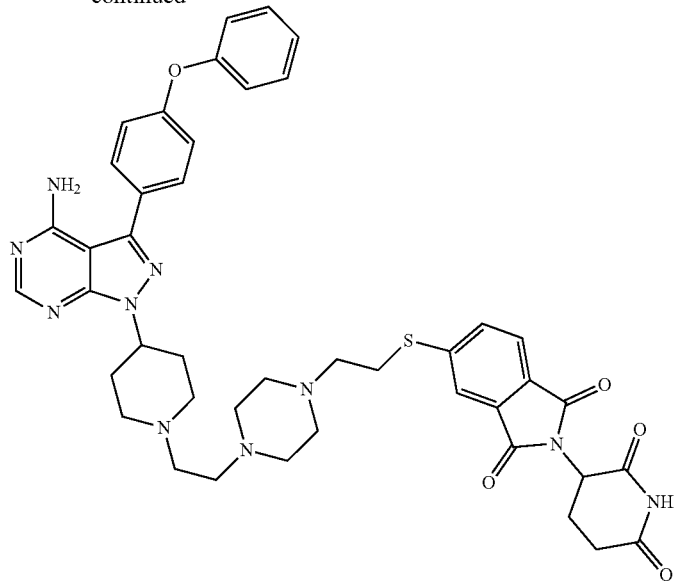

Compound 465

Step 1: Preparation of 3-(4-phenoxyphenyl)-1-(1-(2-(piperazin-1-yl)ethyl)piperidin-4-yl)-1H-pyrazolo(3,4-d)pyrimidin-4-amine (I-11a)

The mixture of I-6a (0.25 g, 0.56 mmol), tert-butyl piperazine-1-carboxylate (0.26 g, 1.38 mmol), KI (0.19 g, 1.12 mmol) and $Cs_2CO_3$ (0.28 g, 0.85 mmol) in DMF (5 ml) was stirred at r.t. under $N_2$ overnight. The suspension was poured to water (50 ml), followed by being extracted with EA (15 ml×4). The combined EA layers were washed sat. NaCl solution (15 ml×2), dried with $Na_2SO_4$. The crude product was purified with flash column to obtain a yellow solid (0.20 g, 59.7%). The LC-MS (ESI$^+$) m/z=599.3 (M+H)$^+$, 543.3 (M−$C_4H_9$+H)$^+$.

To the suspension of boc-protected I-11a in DCM (5 ml) was added hydrochloride solution (4 M in 1,4-dioxane, 5 ml) at 0° C. The reaction mixture was stirred at r.t. for 1 h. The crude I-11a was obtain as hydrochloride by concentration (0.18 g, quantitative). The LC-MS (ESI$^+$) m/z=499.3 (M+H)$^+$.

Step 2: Preparation of 1-(1-(2-(4-(2-chloroethyl)piperazin-1-yl)ethyl)piperidin-4-yl)-3-(4-phenoxyphenyl)-1H-pyrazolo(3,4-d)pyrimidin-4-amine (I-12a)

The I-12a was prepared by the procedure identical to the preparation of I-6a with I-11a (0.15 g, 0.30 mmol) as SM to obtain a yellow semi-solid (0.10 g, 59.5%). The LC-MS (ESI$^+$) m/z=561.3 (M+H)$^+$.

Step 3: Preparation of 5-((2-(4-(2-(4-(4-amino-3-(4-phenoxyphenyl)-1H-pyrazolo(3,4-d)pyrimidin-1-yl)piperidin-1-yl)ethyl)piperazin-1-yl)ethyl)thio)-2-(2,6-dioxopiperidin-3-yl)isoindoline-1,3-dione (Compound 465)

The mixture of I-12a (0.10 g, 0.18 mmol), I-10d (0.10 g, 0.36 mmol), KI (60 mg, 0.36 mmol) and DIPEA (0.10 ml, 0.57 mmol) in NMP (6 ml) was stirred at 100° C. under $N_2$ for 7 h. The mixture was filtered and separated with Prep-HPLC (Elute: $CH_3CN$ in $H_2O$=10-100%, 20 min) to give Compound 465 as a yellow solid (30 mg, 20.4%). LC-MS (ESI$^+$) m/z=815.3 (M+H)$^+$, 408.2 (M+2H)$^{2+}$.

Example 30: Preparation of Compounds 75, 79, 81, 82, 85, 86, 93

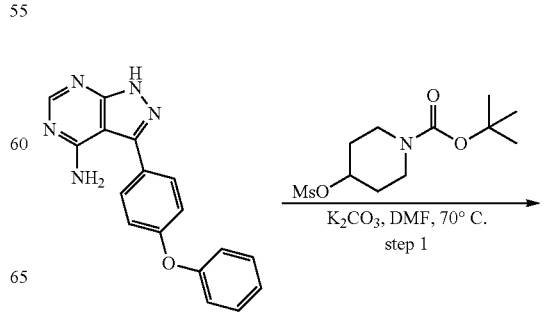

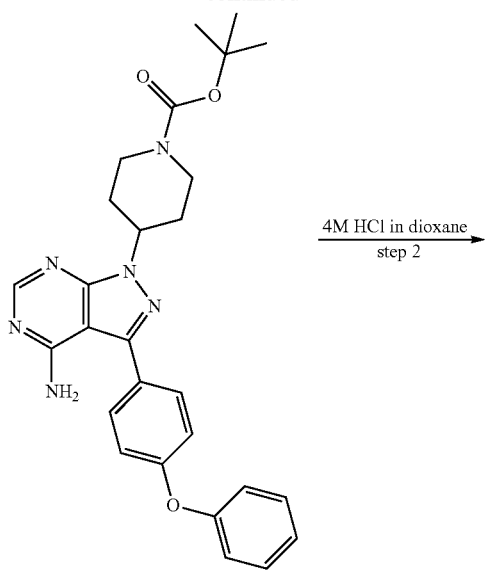
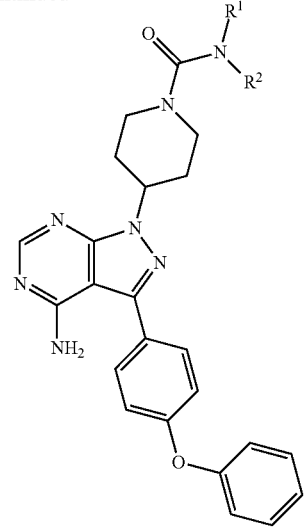
Step 1: tert-butyl 4-(4-amino-3-(4-phenoxyphenyl)-1H-pyrazolo(3,4-d)pyrimidin-1-yl)piperidine-1-carboxylate
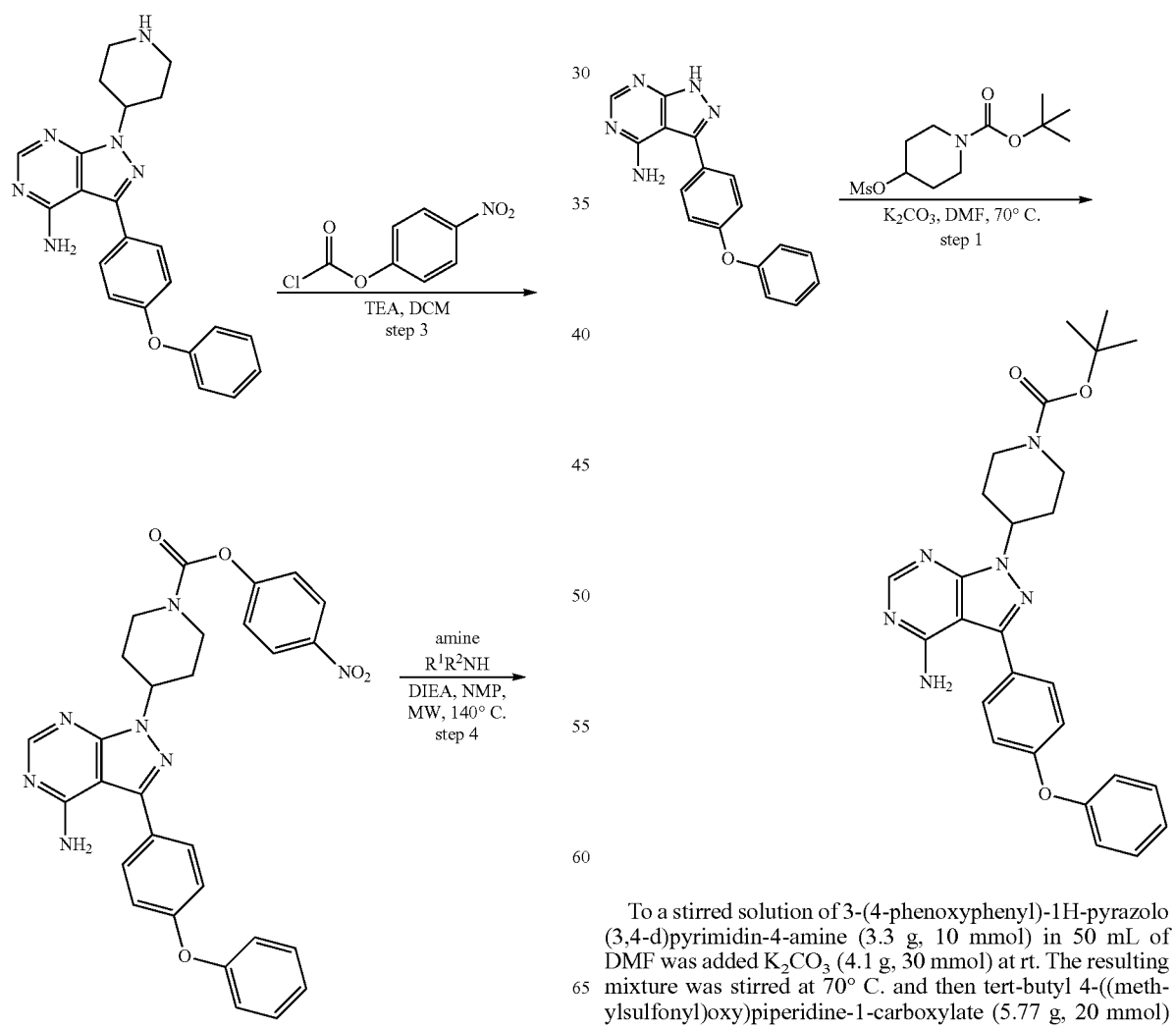
To a stirred solution of 3-(4-phenoxyphenyl)-1H-pyrazolo(3,4-d)pyrimidin-4-amine (3.3 g, 10 mmol) in 50 mL of DMF was added K₂CO₃ (4.1 g, 30 mmol) at rt. The resulting mixture was stirred at 70° C. and then tert-butyl 4-((methylsulfonyl)oxy)piperidine-1-carboxylate (5.77 g, 20 mmol) in 20 mL of DMF was added dropwise for 10 min. The resulting mixture was stirred for additional 12 hours before cooling to rt. EA-ice water was added to extract the product. The organic layers were combined and dried over Na$_2$SO$_4$, filtered, evaporated to dryness. The residue was subjected onto silica gel column chromatography to provide 5.8 g tert-butyl 4-(4-amino-3-(4-phenoxyphenyl)-1H-pyrazolo(3,4-d)pyrimidin-1-yl)piperidine-1-carboxylate as white foam. $^1$H NMR (CDCl3, 300 MHz): δ 1.43 (9H, s), 1.89-2.10 (4H, m), 3.29-3.46 (4H, m), 4.1 (2H, d), 4.91 (1H, m), 6.96 (2H, m), 7.12 (1H, m), 7.28 (2H, m), 7.38 (2H, m), 7.75 (2H, m), 8.25 (1H, s).

Step 2: 3-(4-phenoxyphenyl)-1-(piperidin-4-yl)-1H-pyrazolo(3,4-d)pyrimidin-4-amine Step 3: 4-nitrophenyl 4-(4-amino-3-(4-phenoxyphenyl)-1H-pyrazolo(3,4-d)pyrimidin-1-yl)piperidine-1-carboxylate

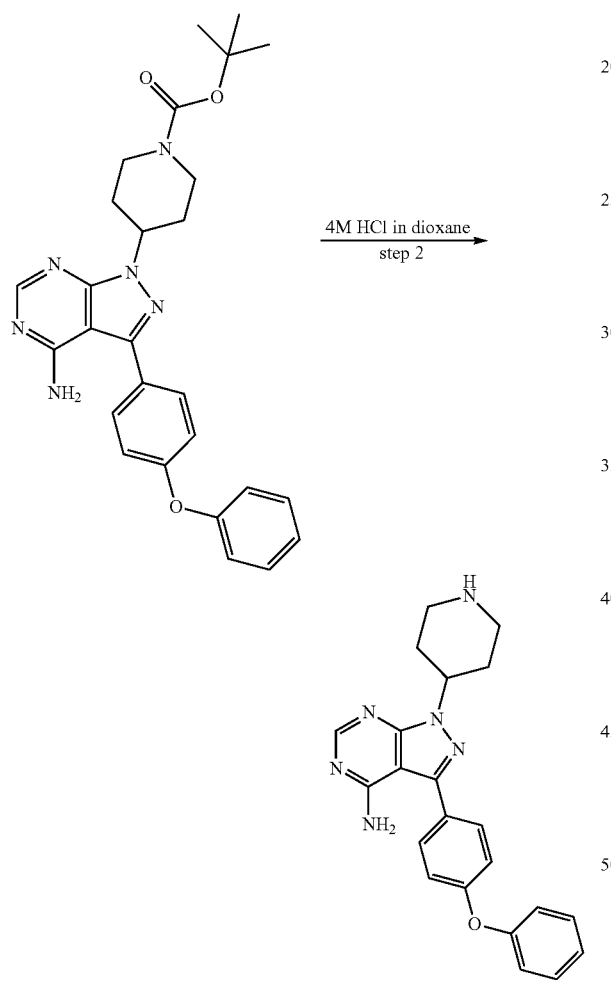

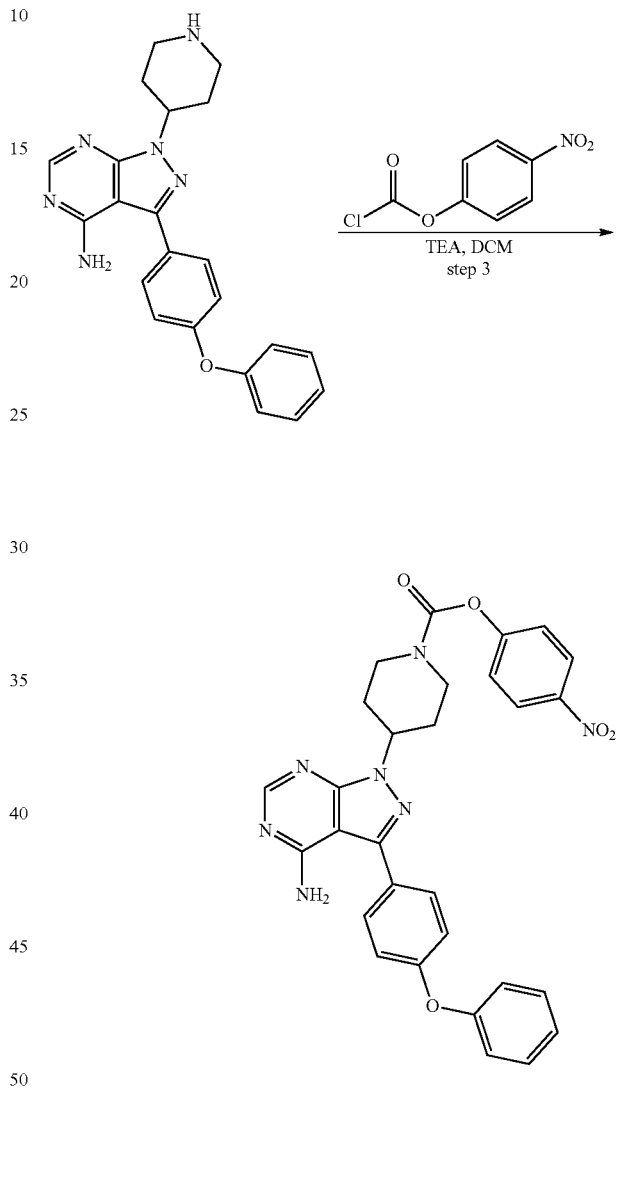

The above obtained tert-butyl 4-(4-amino-3-(4-phenoxyphenyl)-1H-pyrazolo(3,4-d)pyrimidin-1-yl)piperidine-1-carboxylate (5.8 g) was dissolved in 50 mL of EA. 4 M HCl in 1,4-dioxane was added at rt. After stirring for 16 h, the solvent was removed in vacuo to provide 8.0 g 3-(4-phenoxyphenyl)-1-(piperidin-4-yl)-1H-pyrazolo(3,4-d)pyrimidin-4-amine×HCl salt as white solid, which was used in the next step without further purification. $^1$H NMR (DMSO-d6, 300 MHz): δ 2.24-2.43 (4H, m), 2.73 (2H, m), 2.95 (2H, m), 5.13 (1H, m), 7.19 (4H, m), 7.46 (2H, t), 7.68 (2H, dd), 8.58 (1H, s), 9.03 (br, 1H).

To a stirred solution of 3-(4-phenoxyphenyl)-1-(piperidin-4-yl)-1H-pyrazolo(3,4-d)pyrimidin-4-amine×HCl salt (1.94 g, 5 mmol) and TEA (1.0 g, 10 mmol) in 20 ml of DCM was added 4-nitrophenyl carbonochloridate (1.1 g, 5.5 mmol) at rt. The resulting solution was stirred at rt for 2 h. The solvent was evaporated in vacuo. The residue was subjected onto silica gel column chromatography to provide 1.78 g 4-nitrophenyl 4-(4-amino-3-(4-phenoxyphenyl)-1H-pyrazolo(3,4-d)pyrimidin-1-yl)piperidine-1-carboxylate as white solid. $^1$H NMR (DMSO-d6, 300 MHz): δ 2.25-2.45 (4H, m), 3.30-3.47 (4H, m), 5.16 (1H, m), 6.96 (2H, d), 7.12 (1H, t), 7.28 (2H, d), 7.38 (2H, d), 7.56 (2H, d), 7.75 (2H, d), 8.16 (2H, d), 8.58 (1H, s).-

Step 4: 3-(5-(4-((1-(4-(4-amino-3-(4-phenoxyphenyl)-1H-pyrazolo(3,4-d)pyrimidin-1-yl)piperidine-1-carbonyl)piperidin-4-yl)methyl)piperazin-1-yl)-1-oxoisoindolin-2-yl)piperidine-2,6-dione (Compound 86)

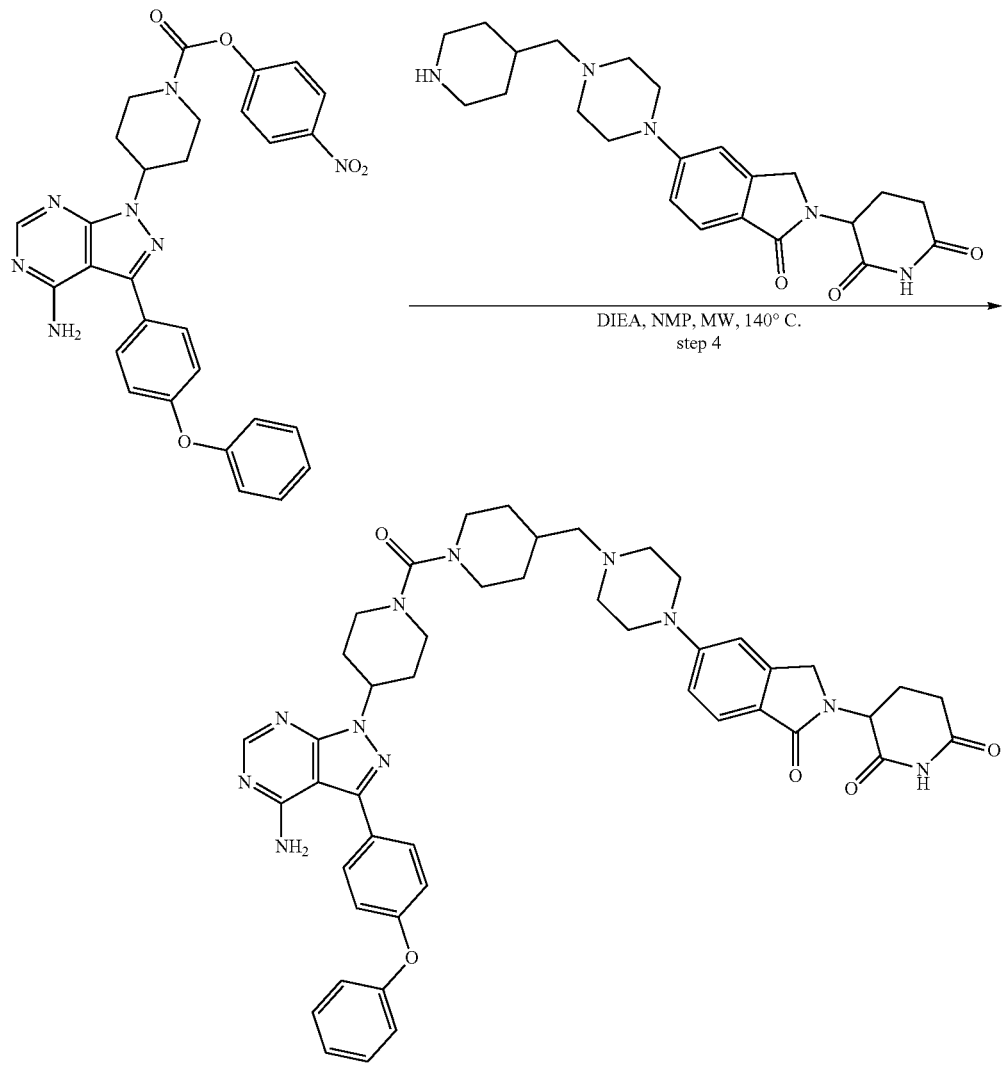

Compound 86

A solution of 4-nitrophenyl 4-(4-amino-3-(4-phenoxyphenyl)-1H-pyrazolo(3,4-d)pyrimidin-1-yl)piperidine-1-carboxylate (200 mg, 0.36 mmol), 3-(1-oxo-5-(4-(piperidin-4-ylmethyl)piperazin-1-yl)isoindolin-2-yl)piperidine-2,6-dione (154 mg, 0.36 mmol) and DIEA (140 mg, 1.1 mmol) in 4 mL of NMP was heated in MW at 140° C. for 1 h. The mixture was subjected onto silica gel column chromatography to provide crude product. The product was further purified by prep-HPLC, C18 column, with 0.5% FA water-MeCN as eluent. 35.5 mg of 3-(5-(4-((1-(4-(4-amino-3-(4-phenoxyphenyl)-1H-pyrazolo(3,4-d)pyrimidin-1-yl)piperidine-1-carbonyl)piperidin-4-yl)methyl)piperazin-1-yl)-1-oxoisoindolin-2-yl)piperidine-2,6-dione was obtained as white solid. $^1$H NMR (DMSO-d6, 300 MHz): δ 1.52-2.40 (11H, m), 2.41-2.73 (8H, m), 2.98-3.12 (4H, m), 3.25-3.45 (8H, m), 4.27 (1H, dd), 4.89-4.93 (1H, m), 5.06 (1H, dd), 6.93-7.01 (3H, m), 7.06 (1H, dd), 7.12 (1H, t), 7.28 (2H, dd), 7.38 (2H, dd), 7.71-7.82 (3H, m), 8.24 (1H, s), 10.95 (1H, s).

5-(4-(4-(4-amino-3-(4-phenoxyphenyl)-1H-pyrazolo(3,4-d)pyrimidin-1-yl)piperidine-1-carbonyl)piperazin-1-yl)-2-(2,6-dioxopiperidin-3-yl)isoindoline-1,3-dione (Compound 75)

Following the procedure of Compound 86, but with corresponding amine, 18 mg of 5-(4-(4-(4-amino-3-(4-phenoxyphenyl)-1H-pyrazolo(3,4-d)pyrimidin-1-yl)piperidine-1-carbonyl)piperazin-1-yl)-2-(2,6-dioxopiperidin-3-yl)isoindoline-1,3-dione was obtained as white solid. $^1$H NMR (DMSO-d6, 300 MHz): δ 1.86-2.55 (8H, m), 3.13-3.44 (8H, m), 3.52-3.67 (4H, m), 4.92 (1H, t), 5.08 (1H, dd), 7.08 (2H, d), 7.08-7.25 (2H, m), 7.28 (2H, d), 7.38 (2H, m), 7.50 (1H, d), 7.75 (3H, d), 8.25 (1H, s).

5-(1'-(4-(4-amino-3-(4-phenoxyphenyl)-1H-pyrazolo (3,4-d)pyrimidin-1-yl)piperidine-1-carbonyl)-(4,4'-bipiperidin)-1-yl)-2-(2,6-dioxopiperidin-3-yl) isoindoline-1,3-dione (Compound 79)

Following the procedure of Compound 86, but with corresponding amine, 22 mg of 5-(1'-(4-(4-amino-3-(4-phenoxyphenyl)-1H-pyrazolo(3,4-d)pyrimidin-1-yl)piperidine-1-carbonyl)-(4,4'-bipiperidin)-1-yl)-2-(2,6-dioxopiperidin-3-yl)isoindoline-1,3-dione was obtained as white solid. 1H NMR (DMSO-d6, 300 MHz): δ 1.52-2.73 (19H, m), 2.99-3.13 (4H, m), 3.25-3.45 (8H, m), 4.87 (1H, t), 5.09 (1H, dd), 6.96 (2H, d), 7.04-7.15 (2H, m), 7.28 (2H, d), 7.38 (2H, d), 7.50 (1H, d), 7.75 (3H, d), 8.25 (1H, s), 11.10 (1H, s).

5-(4-(1-(4-(4-amino-3-(4-phenoxyphenyl)-1H-pyrazolo(3,4-d)pyrimidin-1-yl)piperidine-1-carbonyl) piperidin-4-yl)piperazin-1-yl)-2-(2,6-dioxopiperidin-3-yl)isoindoline-1,3-dione (Compound 81)

Following the procedure of Compound 86, but with corresponding amine, 15 mg of 5-(4-(1-(4-(4-amino-3-(4-phenoxyphenyl)-1H-pyrazolo(3,4-d)pyrimidin-1-yl)piperidine-1-carbonyl)piperidin-4-yl)piperazin-1-yl)-2-(2,6-dioxopiperidin-3-yl)isoindoline-1,3-dione was obtained as white solid. $^1$H NMR (DMSO-d6, 300 MHz): δ 1.71-1.96 (4H, m), 1.96-2.73 (13H, m), 2.99-3.13 (4H, m), 3.28-3.44 (8H, m), 4.89 (1H, t), 5.05 (1H, dd), 6.96 (2H, d), 7.04-7.15 (2H, m), 7.28 (2H, d), 7.38 (2H, d), 7.50 (1H, d), 7.75 (3H, d), 8.25 (1H, s), 11.10 (1H, s).

3-(5-(4-(1-(4-(4-amino-3-(4-phenoxyphenyl)-1H-pyrazolo(3,4-d)pyrimidin-1-yl)piperidine-1-carbonyl)piperidin-4-yl)piperazin-1-yl)-1-oxoisoindolin-2-yl)piperidine-2,6-dione (Compound 82)

Following the procedure of Compound 86, but with corresponding amine, 65 mg of 3-(5-(4-(1-(4-(4-amino-3-(4-phenoxyphenyl)-1H-pyrazolo(3,4-d)pyrimidin-1-yl)piperidine-1-carbonyl)piperidin-4-yl)piperazin-1-yl)-1-oxoisoindolin-2-yl)piperidine-2,6-dione was obtained as white solid. 1H NMR (DMSO-d6, 300 MHz): δ 1.69-2.41 (10H, m), 2.42-2.73 (7H, m), 2.96-3.11 (4H, m), 3.26-3.46 (8H, m), 4.87 (1H, t), 5.09 (1H, dd), 6.90-7.18 (5H, m), 7.21-7.45 (4H, m), 7.68-7.85 (3H, m), 7.79 (dd), 8.25 (1H, s), 11.10 (1H, s).

5-(4-(2-(1-(4-(4-amino-3-(4-phenoxyphenyl)-1H-pyrazolo(3,4-d)pyrimidin-1-yl)piperidine-1-carbonyl)piperidin-4-yl)ethyl)piperazin-1-yl)-2-(2,6-dioxopiperidin-3-yl)isoindoline-1,3-dione (Compound 93)

Following the procedure of Compound 86, but with corresponding amine, 11 mg of 5-(4-(2-(1-(4-(4-amino-3-(4-phenoxyphenyl)-1H-pyrazolo(3,4-d)pyrimidin-1-yl)piperidine-1-carbonyl)piperidin-4-yl)ethyl)piperazin-1-yl)-2-(2,6-dioxopiperidin-3-yl)isoindoline-1,3-dione was obtained as white solid. $^1$H NMR (DMSO-d6, 300 MHz): δ 0.98-1.15 (2H, m), 1.42-1.71 (5H, m), 1.96-2.71 (14H, m), 2.98-3.13 (4H, m), 3.25-3.45 (8H, m), 4.85 (1H, t), 5.05 (1H, dd), 6.96 (2H, d), 7.04-7.15 (2H, m), 7.28 (2H, d), 7.38 (2H, d), 7.50 (1H, d), 7.75 (3H, d), 8.24 (1H, s), 11.09 (1H, s).

5-(4-((1-(4-(4-amino-3-(4-phenoxyphenyl)-1H-pyrazolo(3,4-d)pyrimidin-1-yl)piperidine-1-carbonyl) piperidin-4-yl)methyl)piperazin-1-yl)-2-(2,6-dioxopiperidin-3-yl)isoindoline-1,3-dione (Compound 85)

Following the procedure of Compound 86, but with corresponding amine, 23 mg of 5-(4-((1-(4-(4-amino-3-(4-phenoxyphenyl)-1H-pyrazolo(3,4-d)pyrimidin-1-yl)piperidine-1-carbonyl)piperidin-4-yl)methyl)piperazin-1-yl)-2-(2,6-dioxopiperidin-3-yl)isoindoline-1,3-dione was obtained as white solid. $^1$H NMR (DMSO-d6, 300 MHz): δ 1.27-1.32 (2H, m), 1.42-1.71 (5H, m), 1.96-2.71 (14H, m), 2.98-3.13 (4H, m), 3.25-3.45 (8H, m), 4.82 (1H, t), 5.09 (1H, dd), 6.96 (2H, m), 7.04-7.15 (2H, d), 7.28 (2H, d), 7.38 (2H, d), 7.50 (1H, d), 7.75 (3H, d), 8.25 (1H, s), 11.10 (1H, s).

Example 31: Preparation of Compounds 43, 49, 51, 52, 55, 63

897

-continued

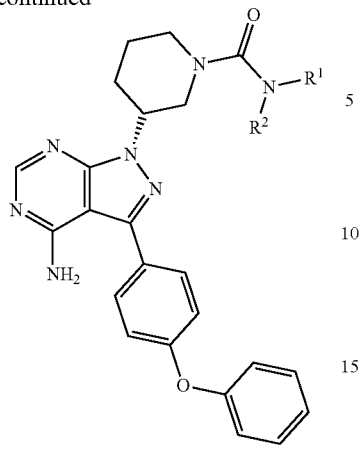

898

-continued

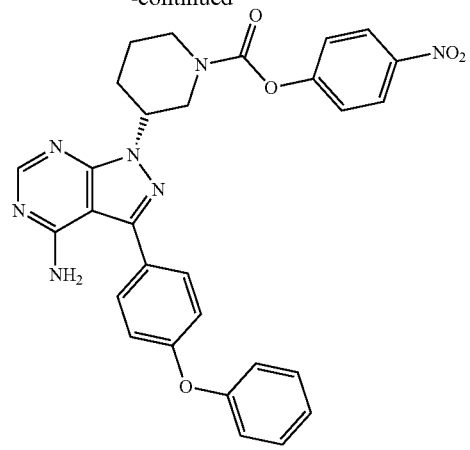

Step 1: 4-nitrophenyl (R)-3-(4-amino-3-(4-phenoxy-phenyl)-1H-pyrazolo(3,4-d)pyrimidin-1-yl)piperi-dine-1-carboxylate

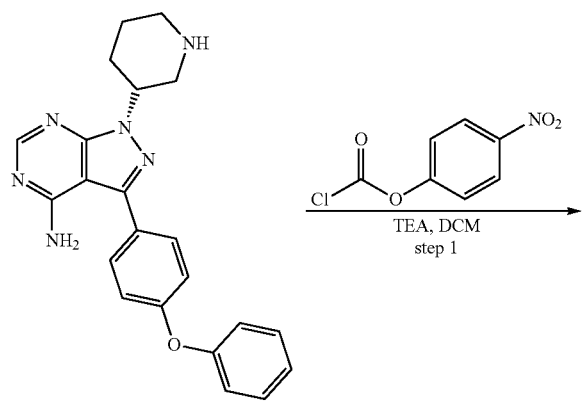

To a stirred solution of (R)-3-(4-phenoxyphenyl)-1-(piperidin-3-yl)-1H-pyrazolo(3,4-d)pyrimidin-4-amine (1.94 g, 5 mmol) and TEA (1.0 g, 10 mmol) in 20 ml of DCM was added 4-nitrophenyl carbonochloridate (1.1 g, 5.5 mmol) at rt. The resulting solution was stirred at rt for 2 h. The solvent was evaporated in vacuo. The residue was subjected onto silica gel column chromatography to provide 2.55 g 4-nitrophenyl (R)-3-(4-amino-3-(4-phenoxyphenyl)-1H-pyrazolo(3,4-d)pyrimidin-1-yl)piperidine-1-carboxylate as white solid. $^1$H NMR (DMSO-d6, 300 MHz): δ 1.46-1.74 (2H, m), 2.19-2.45 (2H, m), 3.21-3.45 (3H, m), 3.81 (1H, dd), 4.99 (1H, m), 6.96 (2H, dd), 7.12 (1H, t), 7.28 (2H, d), 7.38 (2H, d), 7.56 (2H, d), 7.75 (2H, d), 8.16 (2H, d), 8.38 (1H, s).

Step 2: 3-(5-(4-(1-((R)-3-(4-amino-3-(4-phenoxy-phenyl)-1H-pyrazolo(3,4-d)pyrimidin-1-yl)piperi-dine-1-carbonyl)piperidin-4-yl)piperazin-1-yl)-1-oxoisoindolin-2-yl)piperidine-2,6-dione (Compound 52)

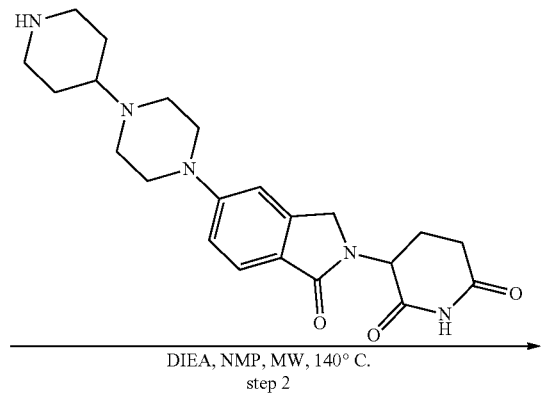

-continued

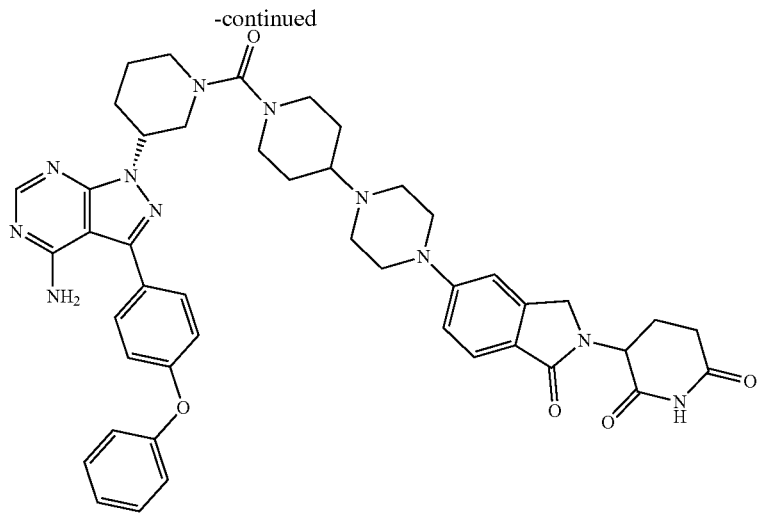

Compound 52

A solution of 4-nitrophenyl (R)-3-(4-amino-3-(4-phenoxyphenyl)-1H-pyrazolo(3,4-d)pyrimidin-1-yl)piperidine-1-carboxylate (200 mg, 0.36 mmol), 3-(1-oxo-5-(4-(piperidin-4-yl)piperazin-1-yl)isoindolin-2-yl)piperidine-2,6-dione (154 mg, 0.36 mmol) and DIEA (140 mg, 1.1 mmol) in 4 mL of NMP was heated in MW at 140° C. for 1 h. The mixture was subjected onto silica gel column chromatography to provide crude product. The product was further purified by prep-HPLC, C18 column, with 0.5% FA water-MeCN as eluent. 67 mg of 3-(5-(4-(1-((R)-3-(4-amino-3-(4-phenoxyphenyl)-1H-pyrazolo(3,4-d)pyrimidin-1-yl)piperidine-1-carbonyl)piperidin-4-yl)piperazin-1-yl)-1-oxoisoindolin-2-yl)piperidine-2,6-dione was obtained as white solid. $^{1}$H NMR (DMSO-d6, 300 MHz): δ 1.47-2.11 (8H, m), 2.18-2.73 (9H, m), 2.97-3.11 (4H, m), 3.18-3.45 (7H, m), 3.75 (1H, dd), 4.93 (1H, dd), 5.15 (1H, dd), 6.93-7.02 (3H, m), 7.06-7.75 (9H, m), 8.25 (1H, s), 10.96 (1H, s).

5-(4-((1-((R)-3-(4-amino-3-(4-phenoxyphenyl)-1H-pyrazolo(3,4-d)pyrimidin-1-yl)piperidine-1-carbonyl)piperidin-4-yl)methyl)piperazin-1-yl)-2-(2,6-dioxopiperidin-3-yl)isoindoline-1,3-dione (Compound 55)

Following the procedure of Compound 52, but with corresponding amine, 12 mg of 5-(4-((1-((R)-3-(4-amino-3-(4-phenoxyphenyl)-1H-pyrazolo(3,4-d)pyrimidin-1-yl)piperidine-1-carbonyl)piperidin-4-yl)methyl)piperazin-1-yl)-2-(2,6-dioxopiperidin-3-yl)isoindoline-1,3-dione was obtained as white solid. $^{1}$H NMR (DMSO-d6, 300 MHz): δ 0.89-2.14 (9H, m), 2.18-2.46 (6H, m), 2.52-2.73 (4H, m), 2.99-3.13 (4H, m), 3.18-3.75 (8H, m), 4.69-4.82 (2H, m), 5.06 (1H, dd), 6.96 (2H, d), 7.04-7.15 (2H, d), 7.28 (2H, dd), 7.38 (2H, dd), 7.50 (1H, d), 7.75 (3H, m), 8.25 (1H, s), 11.09 (1H, s).

5-(4-(2-(1-((R)-3-(4-amino-3-(4-phenoxyphenyl)-1H-pyrazolo(3,4-d)pyrimidin-1-yl)piperidine-1-carbonyl)piperidin-4-yl)ethyl)piperazin-1-yl)-2-(2,6-dioxopiperidin-3-yl)isoindoline-1,3-dione (Compound 63)

Following the procedure of Compound 52, but with corresponding amine, 17 mg of 5-(4-(2-(1-((R)-3-(4-amino-3-(4-phenoxyphenyl)-1H-pyrazolo(3,4-d)pyrimidin-1-yl)piperidine-1-carbonyl)piperidin-4-yl)ethyl)piperazin-1-yl)-2-(2,6-dioxopiperidin-3-yl)isoindoline-1,3-dione was obtained as white solid. $^{1}$H NMR (DMSO-d6, 300 MHz): δ 1.27-1.32 (2H, m), 1.42-1.75 (7H, m), 1.96-2.14 (2H, m), 2.18-2.46 (4H, m), 2.48-2.71 (6H, m), 2.98-3.13 (4H, m), 3.18-3.75 (8H, m), 4.69-4.82 (2H, m), 5.06 (1H, dd), 6.96 (2H, m), 7.04-7.15 (2H, m), 7.28 (2H, dd), 7.38 (2H, dd), 7.50 (1H, dd), 7.75 (3H, dd), 8.25 (1H, s), 11.09 (1H, s).

5-(4-(1-((R)-3-(4-amino-3-(4-phenoxyphenyl)-1H-pyrazolo(3,4-d)pyrimidin-1-yl)piperidine-1-carbonyl)piperidin-4-yl)piperazin-1-yl)-2-(2,6-dioxopiperidin-3-yl)isoindoline-1,3-dione (Compound 51)

Following the procedure of Compound 52, but with corresponding amine, 11 mg of 5-(4-(1-((R)-3-(4-amino-3-(4-phenoxyphenyl)-1H-pyrazolo(3,4-d)pyrimidin-1-yl)piperidine-1-carbonyl)piperidin-4-yl)piperazin-1-yl)-2-(2,6-dioxopiperidin-3-yl)isoindoline-1,3-dione was obtained as white solid. $^{1}$H NMR (DMSO-d6, 300 MHz): δ 1.47-1.93 (6H, m), 1.96-2.14 (2H, m), 2.18-2.46 (4H, m), 2.46-2.73 (5H, m), 2.99-3.13 (4H, m), 3.18-3.75 (8H, m), 4.69-4.83 (2H, m), 5.10 (1H, dd), 6.96 (2H, m), 7.04-7.15 (2H, m), 7.28 (2H, dd), 7.38 (2H, dd), 7.50 (1H, dd), 7.75 (3H, m), 8.26 (1H, s), 11.09 (1H, s).

5-(1'-((R)-3-(4-amino-3-(4-phenoxyphenyl)-1H-pyrazolo(3,4-d)pyrimidin-1-yl)piperidine-1-carbonyl)-(4,4'-bipiperidin)-1-yl)-2-(2,6-dioxopiperidin-3-yl)isoindoline-1,3-dione (Compound 49)

Following the procedure of Compound 52, but with corresponding amine, 8 mg of 5-(1'-((R)-3-(4-amino-3-(4-phenoxyphenyl)-1H-pyrazolo(3,4-d)pyrimidin-1-yl)piperidine-1-carbonyl)-(4,4'-bipiperidin)-1-yl)-2-(2,6-dioxopiperidin-3-yl)isoindoline-1,3-dione was obtained as white solid. $^{1}$H NMR (DMSO-d6, 300 MHz): δ 1.39-1.75 (10H, m), 1.95-2.14 (4H, m), 2.18-2.46 (4H, m), 2.88-2.99 (2H, m), 3.18-3.75 (10H, m), 4.69-4.82 (1H, m), 5.04 (1H, dd), 6.96 (2H, m), 7.12 (1H, t), 7.18 (1H, dd), 7.28 (2H, dd), 7.38 (2H, dd), 7.50 (1H, d), 7.75 (3H, dd), 8.25 (1H, s). 11.09 (1H, s).

5-(4-((R)-3-(4-amino-3-(4-phenoxyphenyl)-1H-pyrazolo(3,4-d)pyrimidin-1-yl)piperidine-1-carbonyl)piperazin-1-yl)-2-(2,6-dioxopiperidin-3-yl)isoindoline-1,3-dione (Compound 43)

Following the procedure of Compound 52, but with corresponding amine, 19 mg of 5-(4-((R)-3-(4-phenoxyphenyl)-1H-pyrazolo(3,4-d)pyrimidin-1-yl)piperidine-1-carbonyl)piperazin-1-yl)-2-(2,6-dioxopiperidin-3-yl)isoindoline-1,3-dione was obtained as white solid. $^1$H NMR (DMSO-d6, 300 MHz): δ 1.47-1.75 (2H, m), 1.96-2.14 (2H, m), 2.18-2.46 (4H, m), 3.13-3.42 (7H, m), 3.52-3.77 (5H, m), 4.69-4.83 (1H, m), 5.10 (1H, dd), 6.96 (2H, d), 7.04-7.15 (2H, dd), 7.28 (2H, dd), 7.38 (2H, dd), 7.50 (1H, dd), 7.75 (3H, dd), 8.26 (1H, s). 11.09 (1H, s).

Example 32: Preparation of Compounds 35, 36, 37, 39, 41, 43

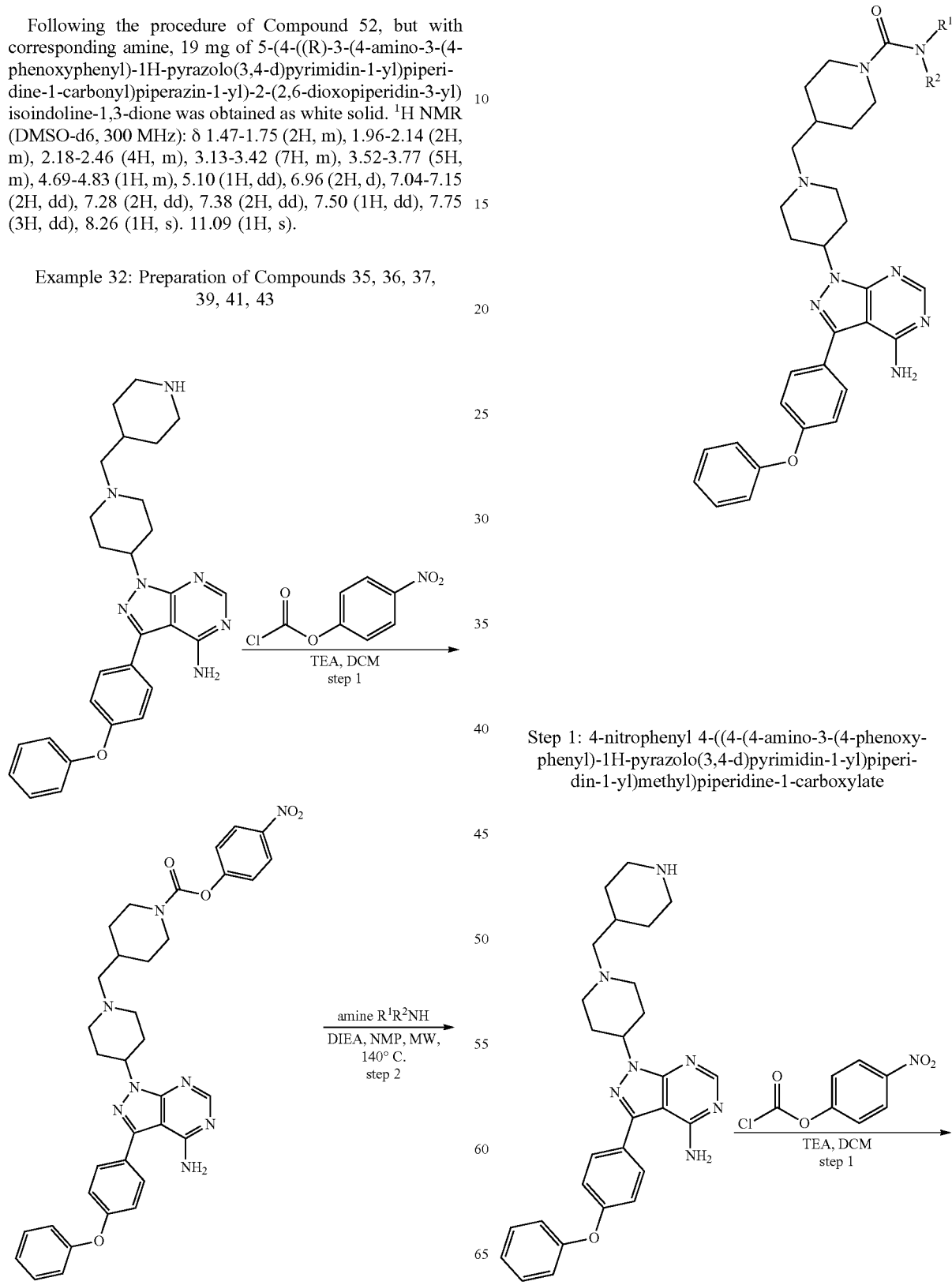

Step 1: 4-nitrophenyl 4-((4-(4-amino-3-(4-phenoxyphenyl)-1H-pyrazolo(3,4-d)pyrimidin-1-yl)piperidin-1-yl)methyl)piperidine-1-carboxylate -continued

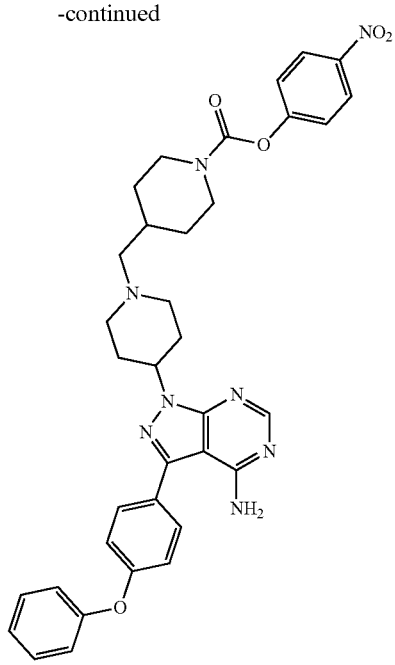

To a stirred solution of 3-(4-phenoxyphenyl)-1-(1-(piperidin-4-ylmethyl)piperidin-4-yl)-1H-pyrazolo(3,4-d)pyrimidin-4-amine (1.57 g, 3 mmol) and TEA (0.91 g, 9 mmol) in 20 ml of DCM was added 4-nitrophenyl carbonochloridate (0.66 g, 3.3 mmol) at rt. The resulting solution was stirred at rt for 2 h. The solvent was evaporated in vacuo. The residue was subjected onto silica gel column chromatography to provide 1.13 g 4-nitrophenyl 4-((4-(4-amino-3-(4-phenoxyphenyl)-1H-pyrazolo(3,4-d)pyrimidin-1-yl)piperidin-1-yl)methyl)piperidine-1-carboxylate as yellow oil. ¹H NMR (DMSO-d6, 300 MHz): δ 1.62-1.81 (4H, m), 1.90 (1H, t), 2.22-2.67 (10H, m), 3.27-3.42 (4H, m), 4.68 (1H, t), 6.96 (2H, d), 7.12 (1H, t), 7.28 (2H, d), 7.38 (2H, dd), 7.56 (2H, dd), 7.75 (2H, dd), 8.16 (2H, dd), 8.298 (1H, s).

Step 2: 3-(5-(4-(4-((4-(4-amino-3-(4-phenoxyphenyl)-1H-pyrazolo(3,4-d)pyrimidin-1-yl)piperidin-1-yl)methyl)piperidine-1-carbonyl)piperazin-1-yl)-1-oxoisoindolin-2-yl)piperidine-2,6-dione (Compound 36)

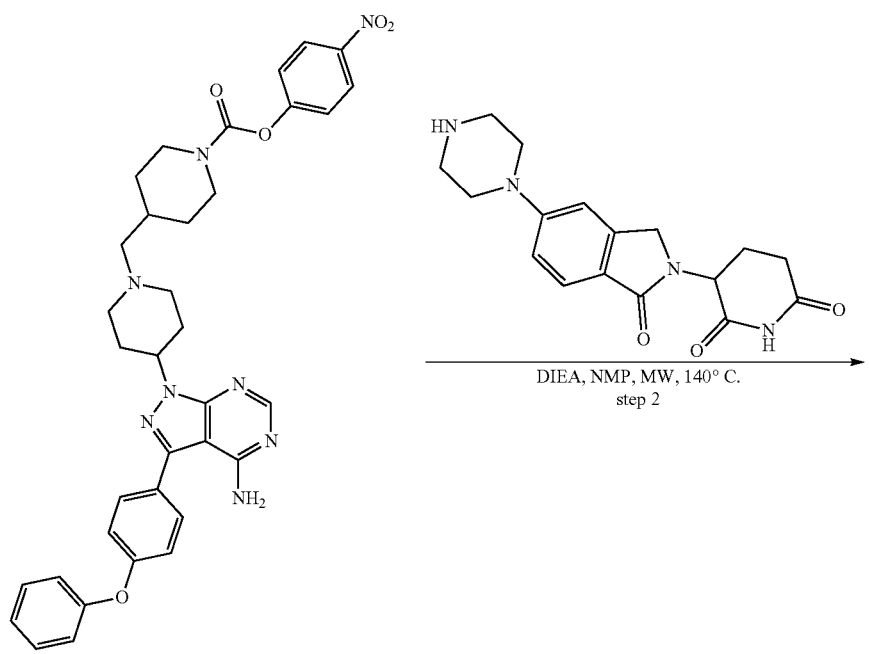

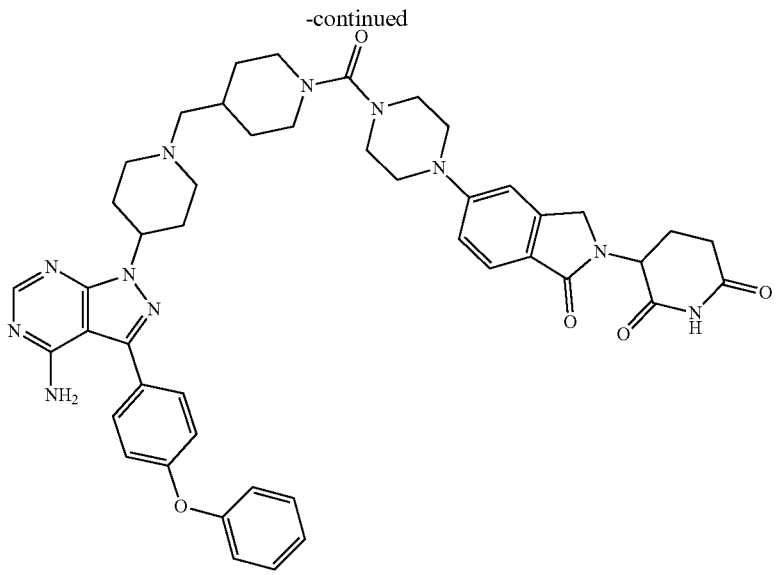

Compound 36

A solution of 4-nitrophenyl 4-nitrophenyl 4-((4-(4-amino-3-(4-phenoxyphenyl)-1H-pyrazolo(3,4-d)pyrimidin-1-yl)piperidin-1-yl)methyl)piperidine-1-carboxylate (200 mg, 0.36 mmol), 3-(1-oxo-5-(piperazin-1-yl)isoindolin-2-yl)piperidine-2,6-dione (154 mg, 0.36 mmol) and DIEA (140 mg, 1.1 mmol) in 4 mL of NMP was heated in MW at 140° C. for 1 h. The mixture was subjected onto silica gel column chromatography to provide crude product. The product was further purified by prep-HPLC, C18 column, with 0.5% FA water-MeCN as eluent. 68 mg of 3-(5-(4-(4-((4-(4-amino-3-(4-phenoxyphenyl)-1H-pyrazolo(3,4-d)pyrimidin-1-yl)piperidin-1-yl)methyl)piperidine-1-carbonyl)piperazin-1-yl)-1-oxoisoindolin-2-yl)piperidine-2,6-dione was obtained as white solid. $^1$H NMR (DMSO-d6, 300 MHz): δ 0.98-1.64 (2H, m), 1.64-2.15 (7H, m), 2.25-2.67 (10H, m), 3.15-3.40 (8H, m), 3.52-3.67 (4H, m), 4.25 (2H, dd), 4.53-4.75 (2H, m), 5.03 (1H, dd), 6.93-7.02 (3H, m), 7.06 (1H, dd), 7.12 (1H, t), 7.28 (2H, dd), 7.38 (2H, dd), 7.71-7.82 (3H, d), 8.23 (1H, s), 10.95 (1H, s).

5-(4-(4-((4-(4-amino-3-(4-phenoxyphenyl)-1H-pyrazolo(3,4-d)pyrimidin-1-yl)piperidin-1-yl)methyl)piperidine-1-carbonyl)piperazin-1-yl)-2-(2,6-dioxopiperidin-3-yl)isoindoline-1,3-dione (Compound 35)

Following the procedure of Compound 36, but with corresponding amine, 8 mg of 5-(4-(4-((4-(4-amino-3-(4-phenoxyphenyl)-1H-pyrazolo(3,4-d)pyrimidin-1-yl)piperidin-1-yl)methyl)piperidine-1-carbonyl)piperazin-1-yl)-2-(2,6-dioxopiperidin-3-yl)isoindoline-1,3-dione was obtained as white solid. $^1$H NMR (DMSO-d6, 300 MHz): δ 0.82-1.64 (2H, m), 1.64-2.15 (7H, m), 2.21-2.67 (10H, m), 3.13-3.40 (8H, m), 3.52-3.67 (4H, m), 4.68 (1H, m), 5.06 (1H, dd), 6.96 (2H, dd), 7.04-7.15 (2H, m), 7.28 (2H, dd), 7.38 (2H, dd), 7.50 (1H, d), 7.75 (3H, d), 8.23 (1H, s), 11.09 (1H, s).

5-(4-(1-(4-((4-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-2-(2,6-dioxopiperidin-3-yl)isoindoline-1,3-dione (Compound 37)

Following the procedure of Compound 36, but with corresponding amine, 21 mg of 5-(4-(1-(4-((4-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-2-(2,6-dioxopiperidin-3-yl)isoindoline-1,3-dione was obtained as white solid. $^1$H NMR (DMSO-d6, 300 MHz): 0.90-1.38 (4H, m), 1.64-2.15 (9H, m), 2.21-2.73 (15H, m), 2.99-3.15 (5H, m), 3.25-3.51 (7H, m), 4.68-4.82 (1H, m), 5.05 (1H, dd), 6.96 (2H, m), 7.04-7.15 (2H, m), 7.28 (2H, d), 7.38 (2H, d), 7.50 (1H, dd), 7.75 (3H, m), 8.23 (1H, s), 11.09 (1H, s).

5-(1'-(4-((4-(4-amino-3-(4-phenoxyphenyl)-1H-pyrazolo(3,4-d)pyrimidin-1-yl)piperidin-1-yl)methyl)piperidine-1-carbonyl)-(4,4'-bipiperidin)-1-yl)-2-(2,6-dioxopiperidin-3-yl)isoindoline-1,3-dione (Compound 39)

Following the procedure of Compound 36, but with corresponding amine, 14 mg of 5-(1'-(4-((4-(4-amino-3-(4-phenoxyphenyl)-1H-pyrazolo(3,4-d)pyrimidin-1-yl)piperidin-1-yl)methyl)piperidine-1-carbonyl)-(4,4'-bipiperidin)-1-yl)-2-(2,6-dioxopiperidin-3-yl)isoindoline-1,3-dione was obtained as white solid. $^1$H NMR (DMSO-d6, 300 MHz): 1.39-1.83 (12H, m), 1.83-2.15 (7H, m), 2.21-2.67 (10H, m), 2.88-2.99 (2H, m), 3.15 (1H, m), 3.22-3.50 (9H, m), 4.68-4.82 (1H, m), 5.05 (1H, dd), 6.96 (2H, dd), 7.12 (1H, t), 7.18 (1H, dd), 7.28 (2H, dd), 7.38 (2H, dd), 7.50 (1H, dd), 7.75 (3H, m), 8.23 (1H, s), 11.08 (1H, s).

5-(4-((1-(4-((4-(4-amino-3-(4-phenoxyphenyl)-1H-pyrazolo(3,4-d)pyrimidin-1-yl)piperidin-1-yl)methyl)piperidine-1-carbonyl)piperidin-4-yl)methyl)piperazin-1-yl)-2-(2,6-dioxopiperidin-3-yl)isoindoline-1,3-dione (Compound 41)

Following the procedure of Compound 36, but with corresponding amine, 18 mg of 5-(4-((1-(4-((4-(4-amino-3-

(4-phenoxyphenyl)-1H-pyrazolo(3,4-d)pyrimidin-1-yl)piperidin-1-yl)methyl)piperidine-1-carbonyl)piperidin-4-yl)methyl)piperazin-1-yl)-2-(2,6-dioxopiperidin-3-yl)isoindoline-1,3-dione was obtained as white solid. ¹H NMR (DMSO-d6, 300 MHz): 1.41-2.15 (14H, m), 2.21-2.73 (16H, m), 2.99-3.20 (5H, m), 3.21-3.47 (7H, m), 4.68-4.82 (1H, m), 5.05 (1H, dd), 6.96 (2H, d), 7.04-7.15 (2H, m), 7.28 (2H, dd), 7.38 (2H, dd), 7.50 (1H, dd), 7.75 (3H, m), 8.23 (1H, s), 11.09 (1H, s).

5-(4-(2-(1-(4-((4-(4-amino-3-(4-phenoxyphenyl)-1H-pyrazolo(3,4-d)pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione (Compound 43)

Following the procedure of Compound 36, but with corresponding amine, 13 mg of 5-(4-(2-(1-(4-((4-(4-amino-3-(4-phenoxyphenyl)-1H-pyrazolo(3,4-d)pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione was obtained as white solid. ¹H NMR (DMSO-d6, 300 MHz): 1.27-1.32 (2H, m), 1.42-2.15 (14H, m), 2.21-2.68 (16H, m), 2.98-3.20 (5H, m), 3.25-3.49 (7H, m), 4.68-4.82 (1H, m), 5.05 (1H, dd), 6.96 (2H, dd), 7.04-7.15 (2H, m), 7.28 (2H, dd), 7.38 (2H, dd), 7.50 (1H, dd), 7.75 (3H, m), 8.23 (1H, s), 11.09 (1H, s).

Example 33: Preparation of Compounds 159, 161, 162, 163, 169, 170, 181

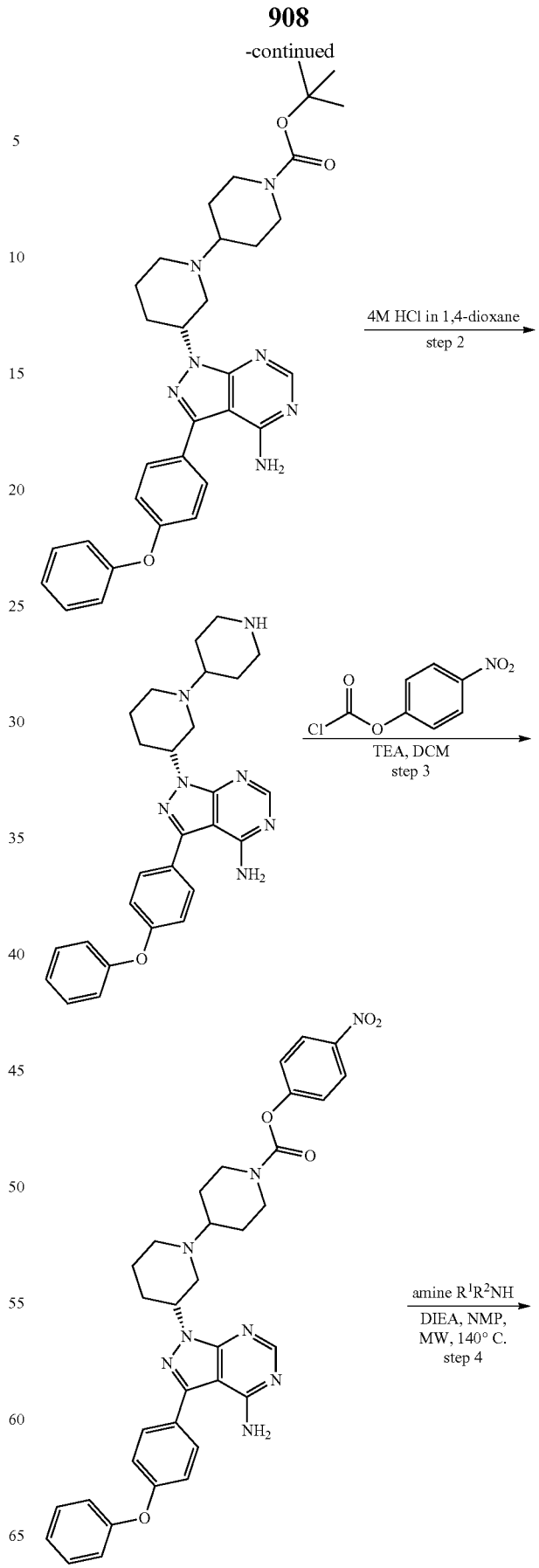

909
-continued

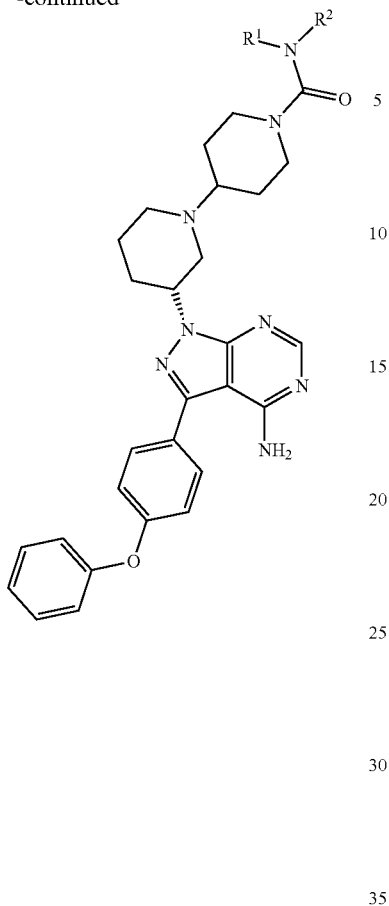

910
-continued

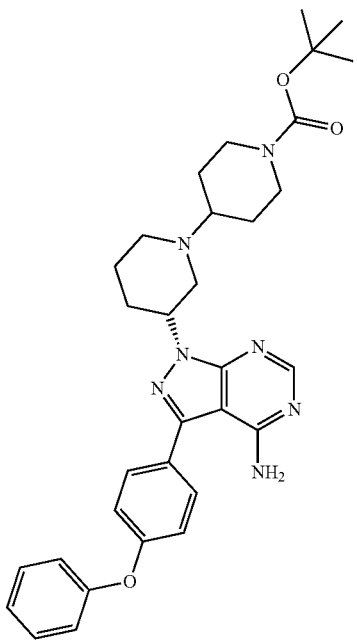

Step 1: tert-butyl (R)-3-(4-amino-3-(4-phenoxyphenyl)-1H-pyrazolo(3,4-d)pyrimidin-1-yl)-(1,4'-bipiperidine)-1'-carboxylate

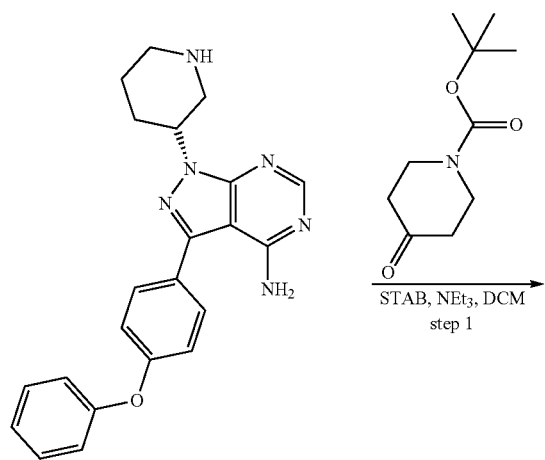

To a stirred solution of (R)-3-(4-phenoxyphenyl)-1-(piperidin-3-yl)-1H-pyrazolo(3,4-d)pyrimidin-4-amine (1.16 g, 3 mmol) and TEA (0.9 g, 9 mmol) in 50 mL of DCM was added tert-butyl 4-oxopiperidine-1-carboxylate (2.0 g, 10 mmol) at rt. The resulting solution was stirred at rt for 2 h. STAB (3.2 g, 15 mmol) was then added portionwise at rt. The mixture was stirred for additional 2 h. The solvent was removed in vacuo. The residue was subjected onto silica gel column chromatography to provide 2.0 g of tert-butyl (R)-3-(4-amino-3-(4-phenoxyphenyl)-1H-pyrazolo(3,4-d)pyrimidin-1-yl)-(1,4'-bipiperidine)-1'-carboxylate as brown oil. 1H NMR (DMSO-d6, 300 MHz): δ 1.42 (9H, s), 1.61-2.14 (7H, m), 2.44-2.73 (4H, m), 2.88-2.99 (2H, m), 3.27-3.45 (4H, m), 4.87 (1H, m), 6.96 (2H, dd), 7.12 (1H, t), 7.28 (2H, dd), 7.38 (2H, dd), 7.75 (2H, dd), 8.24 (1H, s), 11.91 (1H, s).

911

Step 2: (R)-1-((1,4'-bipiperidin)-3-yl)-3-(4-phenoxy-phenyl)-1H-pyrazolo(3,4-d)pyrimidin-4-amine

912

Step 3: 4-nitrophenyl (R)-3-(4-amino-3-(4-phenoxy-phenyl)-1H-pyrazolo(3,4-d)pyrimidin-1-yl)-(1,4'-bipiperidine)-1'-carboxylate

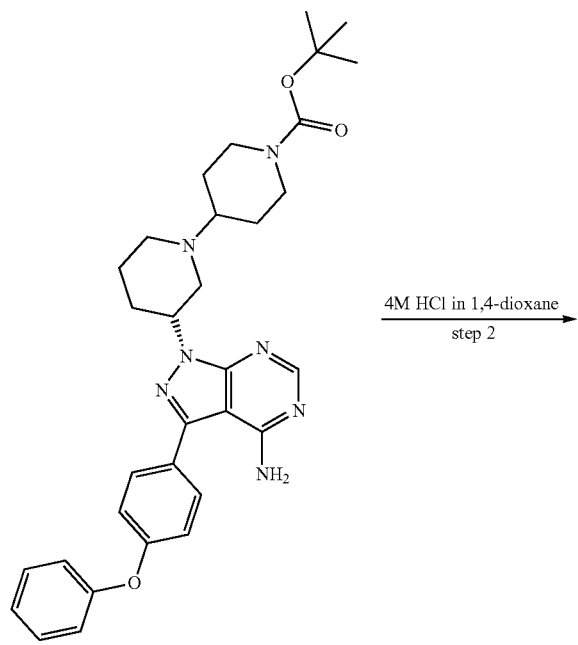

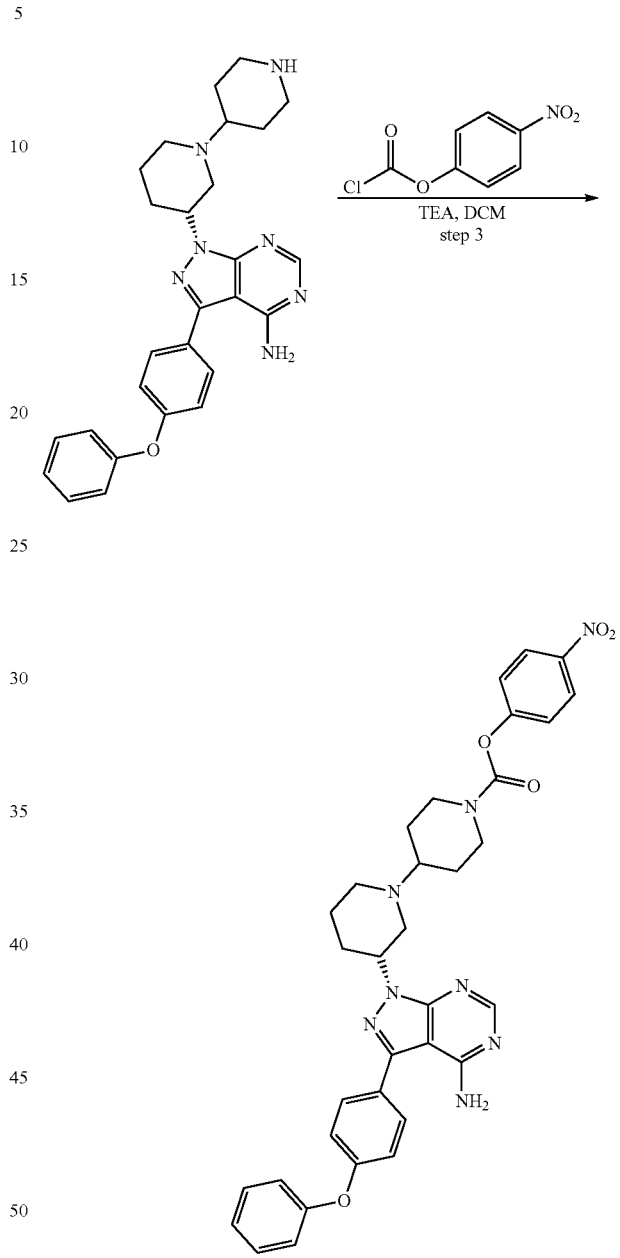

The above obtained tert-butyl (R)-3-(4-amino-3-(4-phenoxyphenyl)-1H-pyrazolo(3,4-d)pyrimidin-1-yl)-(1,4'-bipiperidine)-1'-carboxylate (2.0 g) was dissolved in 50 mL of EA. 5 mL of 4 M HCl in 1,4-dioxane was added at rt. After stirring for 16 h, the solvent was removed in vacuo to provide 1.88 g (R)-1-((1,4'-bipiperidin)-3-yl)-3-(4-phenoxyphenyl)-1H-pyrazolo(3,4-d)pyrimidin-4-amine as white solid, which was used in the next step without further purification. $^1$H NMR (DMSO-d6, 300 MHz): δ $^1$H NMR: δ 1.55-1.83 (5H, m), 1.92-2.14 (2H, m), 2.42-2.68 (6H, m), 2.72-2.79 (2H, m), 2.88-2.99 (2H, m), 5.05 (1H, t), 6.96 (2H, m), 7.12 (1H, t), 7.28 (2H, dd), 7.38 (2H, dd), 7.75 (2H, dd), 8.24 (1H, s).

To a stirred solution of (R)-1-((1,4'-bipiperidin)-3-yl)-3-(4-phenoxyphenyl)-1H-pyrazolo(3,4-d)pyrimidin-4-amine (1.88 g, 3 mmol) and TEA (0.91 g, 9 mmol) in 20 ml of DCM was added 4-nitrophenyl carbonochloridate (0.72 g, 3.6 mmol) at rt. The resulting solution was stirred at rt for 2 h. The solvent was evaporated in vacuo. The residue was subjected onto silica gel column chromatography to provide 1.97 g 4-nitrophenyl (R)-3-(4-amino-3-(4-phenoxyphenyl)-1H-pyrazolo(3,4-d)pyrimidin-1-yl)-(1,4'-bipiperidine)-1'-carboxylate as yellow foam. $^1$H NMR (DMSO-d6, 300 MHz): δ 1.61-2.14 (7H, m), 2.44-2.73 (4H, m), 2.88-2.99 (2H, m), 3.30-3.46 (4H, m), 4.76 (1H, t), 6.96 (2H, dd), 7.12 (1H, t), 7.28 (2H, dd), 7.38 (2H, dd), 7.56 (2H, dd), 7.75 (2H, dd), 8.16 (2H, d), 8.25 (1H, s).

Step 4: 3-(5-(4-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)piperazin-1-yl)-1-oxoisoindolin-2-yl)piperidine-2,6-dione
(Compound 162)

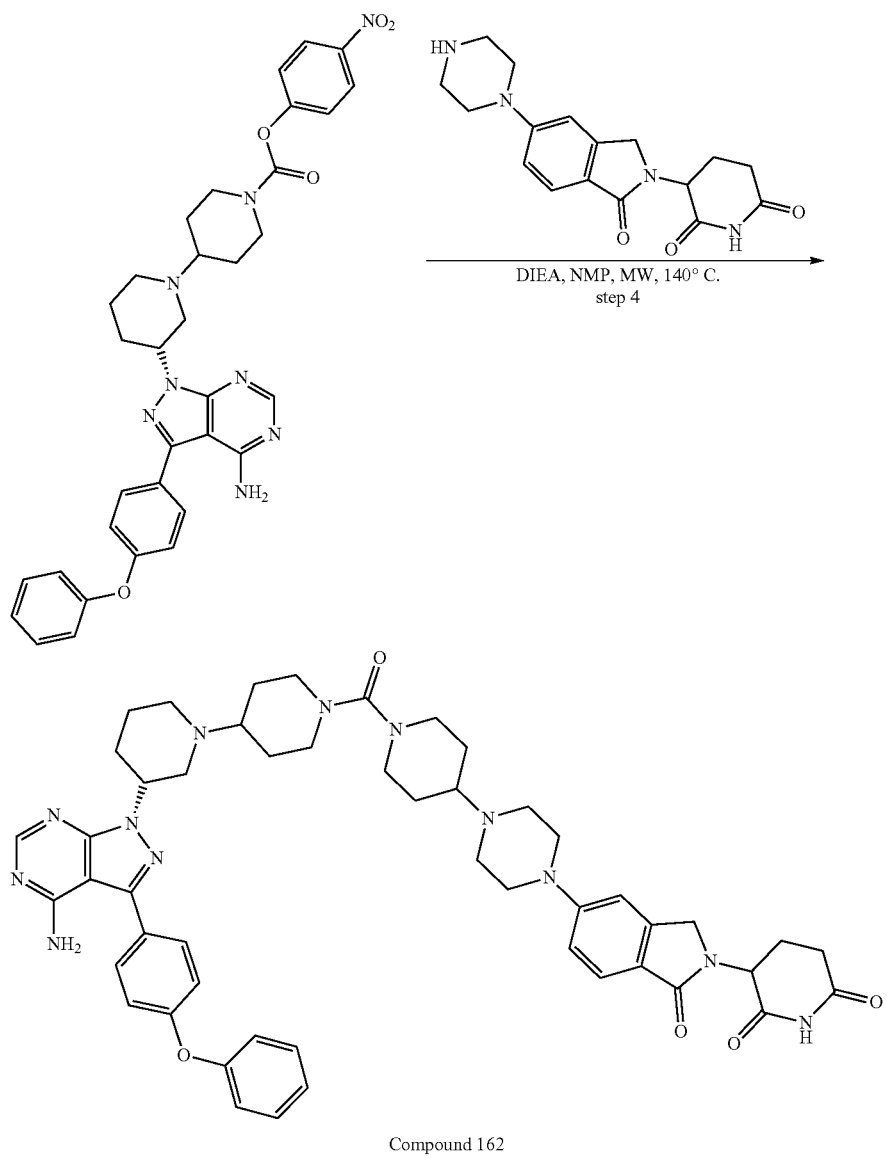

Compound 162

A solution of 4-nitrophenyl (R)-3-(4-amino-3-(4-phenoxyphenyl)-1H-pyrazolo(3,4-d)pyrimidin-1-yl)-(1,4'-bipiperidine)-1'-carboxylate (200 mg, 0.36 mmol), 3-(1-oxo-5-(4-(piperidin-4-yl)piperazin-1-yl)isoindolin-2-yl)piperidine-2,6-dione (154 mg, 0.36 mmol) and DIEA (140 mg, 1.1 mmol) in 4 mL of NMP was heated in MW at 140° C. for 1 h. The mixture was subjected onto silica gel column chromatography to provide crude product. The product was further purified by prep-HPLC, C18 column, with 0.5% FA water-MeCN as eluent. 82 mg of 3-(5-(4-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)piperazin-1-yl)-1-oxoisoindolin-2-yl)piperidine-2,6-dione was obtained as white solid. $^1$H NMR (DMSO-d6, 300 MHz): δ 1.61-2.14 (13H, m), 2.35-2.73 (11H, m), 2.88-3.11 (6H, m), 3.28-3.44 (8H, m), 4.53-4.62 (3H, m), 5.06 (1H, t), 6.93-7.02 (3H, m), 7.06 (1H, d), 7.12 (1H, t), 7.28 (2H, d), 7.38 (2H, dd), 7.71-7.82 (3H, m), 8.25 (1H, s), 10.96 (1H, s).

3-(5-(4-((1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)methyl)piperazin-1-yl)-1-oxoisoindolin-2-yl)piperidine-2,6-dione
(Compound 170)

Following the procedure of Compound 162, but with corresponding amine, 51 mg of 3-(5-(4-((1-((R)-3-(4-amino-3-(4-phenoxyphenyl)-1H-pyrazolo(3,4-d)pyrimidin- 1-yl)-(1,4'-bipiperidine)-1'-carbonyl)piperidin-4-yl)methyl) piperazin-1-yl)-1-oxoisoindolin-2-yl)piperidine-2,6-dione was obtained as white solid. $^1$H NMR (DMSO-d6, 300 MHz): 1.52-2.14 (14H, m), 2.35-2.73 (12H, m), 2.88-3.12 (6H, m), 3.25-3.44 (8H, m), 4.29 (1H, dd), 4.62-4.83 (1H, m), 5.05 (1H, t), 6.93-7.01 (3H, m), 7.06 (1H, dd), 7.12 (1H, t), 7.28 (2H, dd), 7.38 (2H, dd), 7.71-7.82 (3H, d), 8.23 (1H, s), 11.09 (1H, s).

5-(4-((1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)methyl)piperazin-1-yl)-2-(2,6-dioxopiperidin-3-yl)isoindoline-1,3-dione (Compound 169)

Following the procedure of Compound 162, but with corresponding amine, 6 mg of 5-(4-((1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)methyl)piperazin-1-yl)-2-(2,6-dioxopiperidin-3-yl)isoindoline-1,3-dione was obtained as white solid. $^1$H NMR (DMSO-d6, 300 MHz): 1.52-2.14 (14H, m), 2.18-2.73 (12H, m), 2.88-3.13 (6H, m), 3.25-3.44 (8H, m), 4.98-5.12 (2H, m), 6.96 (2H, dd), 7.04-7.15 (2H, d), 7.28 (2H, dd), 7.38 (2H, dd), 7.50 (1H, dd), 7.75 (2H, dd), 8.138 (1H, s), 8.24 (1H, s), 11.09 (1H, s).

5-(4-(2-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)ethyl)piperazin-1-yl)-2-(2,6-dioxopiperidin-3-yl)isoindoline-1,3-dione (Compound 181)

Following the procedure of Compound 162, but with corresponding amine, 9 mg of 5-(4-(2-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)ethyl)piperazin-1-yl)-2-(2,6-dioxopiperidin-3-yl)isoindoline-1,3-dione was obtained as white solid. $^1$H NMR (DMSO-d6, 300 MHz): 1.27-1.32 (2H, m), 1.42-1.71 (6H, m), 1.71-2.14 (8H, m), 2.18-2.42 (2H, m), 2.44-2.73 (10H, m), 2.88-3.13 (6H, m), 3.25-3.44 (8H, m), 4.98-5.12 (2H, m), 6.96 (2H, dd), 7.04-7.15 (2H, d), 7.28 (2H, dd), 7.38 (2H, dd), 7.50 (1H, dd), 7.75 (2H, dd), 8.15 (1H, s), 8.24 (1H, s), 11.08 (1H, s).

5-(4-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)piperazin-1-yl)-2-(2,6-dioxopiperidin-3-yl)isoindoline-1,3-dione (Compound 161)

Following the procedure of Compound 162, but with corresponding amine, 25 mg of 5-(4-(1-((R)-3-(4-amino-3-(4-phenoxyphenyl)-1H-pyrazolo(3,4-d)pyrimidin-1-yl)-(1,4'-bipiperidine)-1'-carbonyl)piperidin-4-yl)piperazin-1-yl)-2-(2,6-dioxopiperidin-3-yl)isoindoline-1,3-dione was obtained as white solid. $^1$H NMR (DMSO-d6, 300 MHz): 1.61-2.14 (13H, m), 2.18-2.42 (2H, m), 2.44-2.73 (9H, m), 2.88-2.99 (2H, m), 2.99-3.13 (4H, m), 3.28-3.44 (8H, m), 4.98-5.12 (2H, m), 6.96 (2H, dd), 7.04-7.15 (2H, d), 7.28 (2H, d), 7.38 (2H, dd), 7.50 (1H, d), 7.75 (2H, dd), 8.14 (1H, s), 8.24 (1H, s), 11.09 (1H, s).

5-(1'-((R)-3-(4-amino-3-(4-phenoxyphenyl)-1H-pyrazolo(3,4-d)pyrimidin-1-yl)-(1,4'-bipiperidine)-1'-carbonyl)-(4,4'-bipiperidin)-1-yl)-2-(2,6-dioxopiperidin-3-yl)isoindoline-1,3-dione (Compound 163)

Following the procedure of Compound 162, but with corresponding amine, 22 mg of 5-(1'-((R)-3-(4-amino-3-(4-phenoxyphenyl)-1H-pyrazolo(3,4-d)pyrimidin-1-yl)-(1,4'-bipiperidine)-1'-carbonyl)-(4,4'-bipiperidin)-1-yl)-2-(2,6-dioxopiperidin-3-yl)isoindoline-1,3-dione was obtained as white solid. $^1$H NMR (DMSO-d6, 300 MHz): 1.39-1.71 (9H, m), 1.71-2.14 (10H, m), 2.38-2.73 (6H, m), 2.88-2.99 (4H, m), 3.26-3.50 (10H, m), 4.98-5.12 (2H, m), 6.96 (2H, dd), 7.12 (1H, t), 7.18 (1H, dd), 7.28 (2H, dd), 7.38 (2H, dd), 7.50 (1H, dd), 7.75 (2H, d), 8.14 (1H, s), 8.24 (1H, s), 11.09 (1H, s).

5-(4-((R)-3-(4-amino-3-(4-phenoxyphenyl)-1H-pyrazolo(3,4-d)pyrimidin-1-yl)-(1,4'-bipiperidine)-1'-carbonyl)piperazin-1-yl)-2-(2,6-dioxopiperidin-3-yl)isoindoline-1,3-dione (Compound 159)

Following the procedure of Compound 162, but with corresponding amine, 32 mg of 5-(4-((R)-3-(4-amino-3-(4-phenoxyphenyl)-1H-pyrazolo(3,4-d)pyrimidin-1-yl)-(1,4'-bipiperidine)-1'-carbonyl)piperazin-1-yl)-2-(2,6-dioxopiperidin-3-yl)isoindoline-1,3-dione was obtained as white solid. $^1$H NMR (DMSO-d6, 300 MHz): δ 1.61-2.14 (9H, m), 2.21-2.44 (2H, m), 2.44-2.73 (4H, m), 2.88-2.99 (2H, m), 3.13-3.44 (8H, m), 3.52-3.67 (4H, m), 4.68-4.82 (1H, m), 5.05 (1H, dd), 6.96 (2H, dd), 7.04-7.15 (2H, d), 7.28 (2H, d), 7.38 (2H, dd), 7.50 (1H, d), 7.75 (2H, dd), 8.20 (1H, d), 8.24 (1H, s), 11.09 (1H, s).

The intermediate amines are synthesized in the following manners:

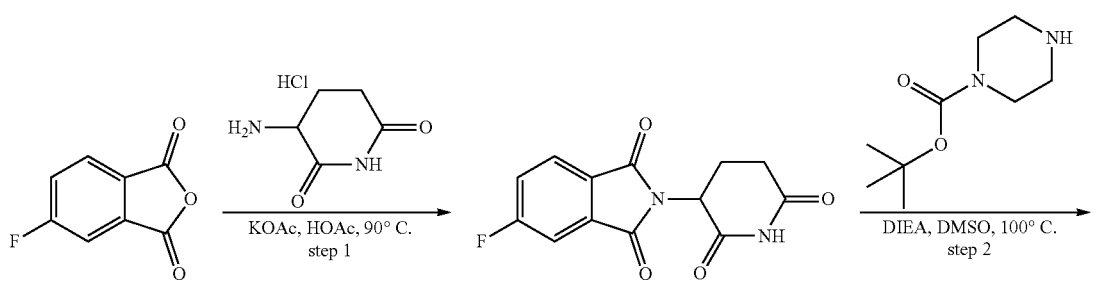

-continued

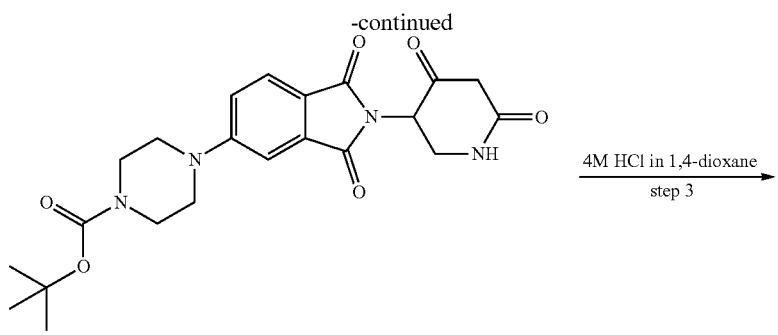

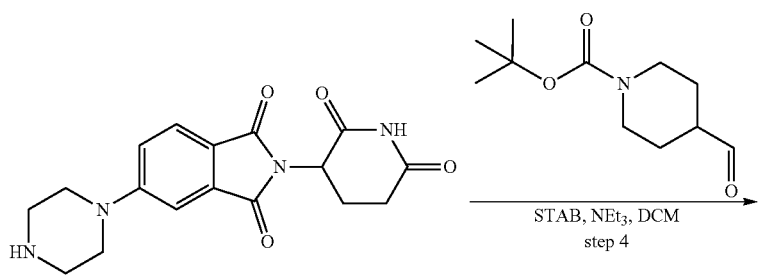

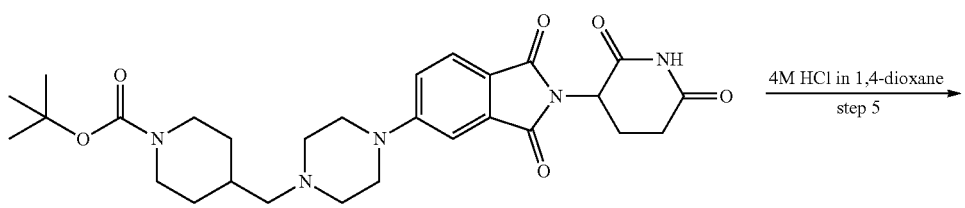

Step 1: 2-(2,6-dioxopiperidin-3-yl)-5-fluoroisoindo-line-1,3-dione

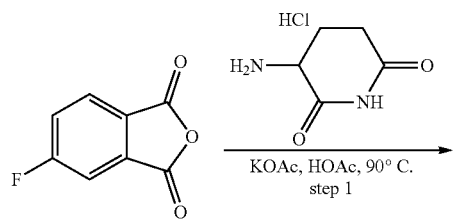

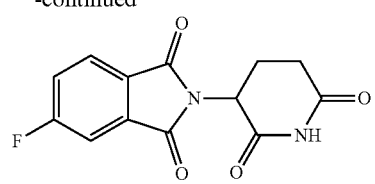

A mixture of 5-fluoroisobenzofuran-1,3-dione (10 g, 61.0 mmol), 3-aminopiperidine-2,6-dione HCl salt (10.0 g, 61.0 mmol) and KOAc (18 g, 18.3 mmol) in 120 mL HOAc was stirred at 90° C. overnight. After cooling to rt, 300 mL of water was added. The solids were collected by filtration, air dried to provide 2-(2,6-dioxopiperidin-3-yl)-5-fluoroisoin-doline-1,3-dione (15.9 g) as pale solid. LCMS (M+H) 277; 1H NMR (DMSO-d6, 400 mHz) δ 11.15 (br, 1H), 8.05 (dd, 1H), 7.84 (dd, 1H), 7.72 (dt, 1H), 5.14 (m, 1H), 2.83-2.91 (m, 1H), 2.50-2.64 (m, 3H), 2.05-2.11 (m, 1H).

Steps 2 and 3: tert-butyl 4-(2-(2,6-dioxopiperidin-3-yl)-1,3-dioxoisoindolin-5-yl)piperazine-1-carboxylate and 2-(2,6-dioxopiperidin-3-yl)-5-(piperazin-1-yl)isoindoline-1,3-dione

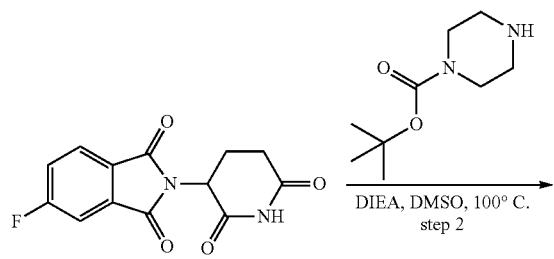

2-(2,6-dioxopiperidin-3-yl)-5-fluoroisoindoline-1,3-dione (I-16) (5.5 g, 20 mmol) reacted with tert-butyl piperazine-1-carboxylate (5.58 g, 30 mmol) in 5 mL DIEA and 50 mL of DMSO to provide tert-butyl 4-(2-(2,6-dioxopiperidin-3-yl)-1,3-dioxoisoindolin-5-yl)piperazine-1-carboxylate (V-1) (7.0 g) as yellow solid. LCMS (M+H) 443; $^1$H NMR (DMSO-d6, 300 MHz): δ 1.42 (9H, s), 1.96-2.14 (2H, m), 2.52-2.98 (10H, m), 5.07 (1H, d), 7.23 (1H, d), 7.35 (1H, d), 7.70 (1H, d), 11.09 (d, 1H).

The obtained solid was suspended in DCM and treated with 4 M HCl in 1,4-dioxane to provide 2-(2,6-dioxopiperidin-3-yl)-5-(piperazin-1-yl)isoindoline-1,3-dione as yellow solid.

Step 4: tert-butyl 4-((4-(2-(2,6-dioxopiperidin-3-yl)-1,3-dioxoisoindolin-5-yl)piperazin-1-yl)methyl)piperidine-1-carboxylate

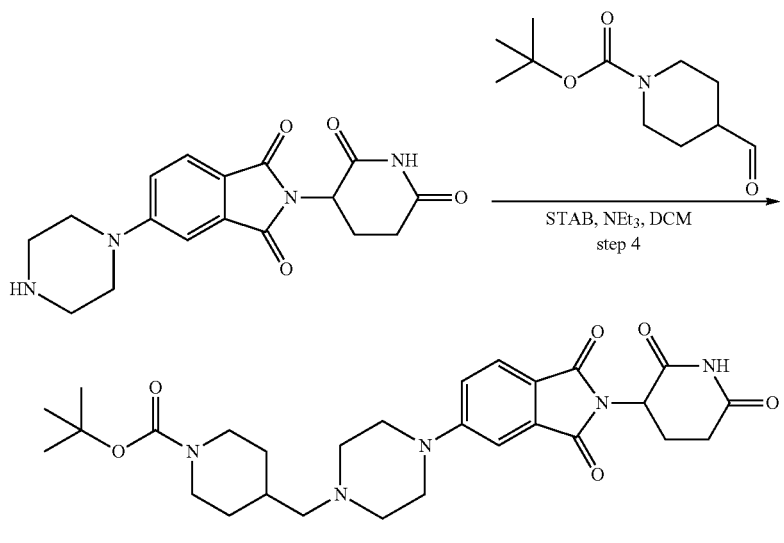

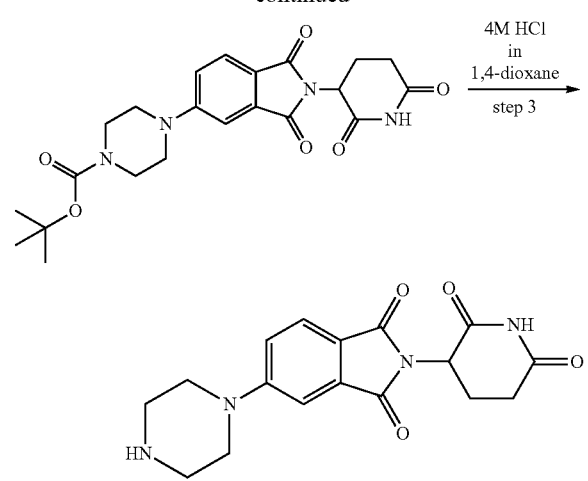

A solution of 2-(2,6-dioxopiperidin-3-yl)-5-(piperazin-1-yl)isoindoline-1,3-dione (1.0 g, 3 mmol), tert-butyl 4-formylpiperidine-1-carboxylate (1.28 g, 6 mmol), triethylamine (910 mg, 9 mmol) in 20 mL of DCM was stirred at room temperature overnight. STAB was added portionwise at 0° C. and the resulting mixture was stirred at room temperature for 2 hours. The solvent was removed in vacuo. The residue was subjected onto silica gel column chromatography with 20% MeOH in EA as eluent to give tert-butyl 4-((4-(2-(2,6-dioxopiperidin-3-yl)-1,3-dioxoisoindolin-5-yl)piperazin-1-yl)methyl)piperidine-1-carboxylate (1.1 g) as yellow solid. LCMS (M+H) 540; $^1$H NMR (DMSO-d6, 300 MHz): δ 1.40 (9H, s), 1.53-1.65 (2H, m), 1.74-2.14 (5H, m), 2.27 (1H, d), 2.29-2.44 (3H, m), 2.50-2.73 (4H, m), 2.99-3.13 (4H, m), 3.89-3.96 (2H, m), 5.08 (1H, d), 7.25 (1H, d), 7.34 (1H, d), 7.67 (1H, d), 11.09 (1H, s).

Step 5: 2-(2,6-dioxopiperidin-3-yl)-5-(4-(piperidin-4-ylmethyl)piperazin-1-yl)isoindoline-1,3-dione

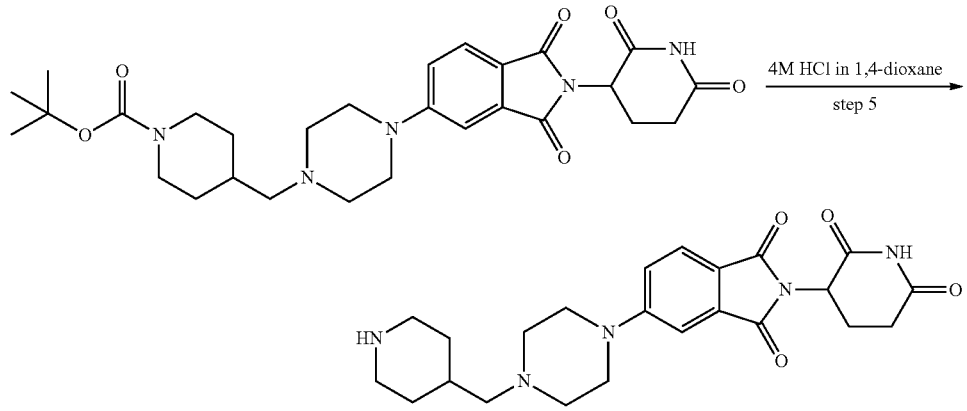

4 M HCl in 1,4-dioxane was added tert-butyl 4-((4-(2-(2,6-dioxopiperidin-3-yl)-1,3-dioxoisoindolin-5-yl)piperazin-1-yl)methyl)piperidine-1-carboxylate (1.1 g) and the mixture was stirred for 1 hour. The solvent was removed in vacuo. 2-(2,6-dioxopiperidin-3-yl)-5-(4-(piperidin-4-ylmethyl)piperazin-1-yl)isoindoline-1,3-dione HCl salt (1.34 g) was obtained as yellow solid and used in the next step without further purification. LCMS (M+H) 440; $^1$H NMR (DMSO-d6, 300 MHz): δ 1.54-1.66 (2H, m), 1.83 (1H, d), 1.74-1.94 (2H, m), 1.96-2.14 (2H, m), 2.21-2.44 (4H, m), 2.50-2.72 (6H, m), 2.85-2.93 (2H, m), 2.99-3.13 (4H, m), 5.07 (1H, dd), 7.34 (1H, dd), 7.50 (1H, dd), 7.77 (1H, dd), 11.11 (1H, s).

3-(1-oxo-5-(4-(piperidin-4-yl)piperazin-1-yl)isoindolin-2-yl)piperidine-2,6-dione; 3-(1-oxo-5-(4-(piperidin-4-ylmethyl)piperazin-1-yl)isoindolin-2-yl)piperidine-2,6-dione; 3-(1-oxo-5-(piperazin-1-yl)isoindolin-2-yl)piperidine-2,6-dione; 2-(2,6-dioxopiperidin-3-yl)-5-(4-(2-(piperidin-4-yl)ethyl)piperazin-1-yl)isoindoline-1,3-dione; 2-(2,6-dioxopiperidin-3-yl)-5-(4-(piperidin-4-yl)piperazin-1-yl)isoindoline-1,3-dione; 5-((4,4'-bipiperidin)-1-yl)-2-(2,6-dioxopiperidin-3-yl)isoindoline-1,3-dione

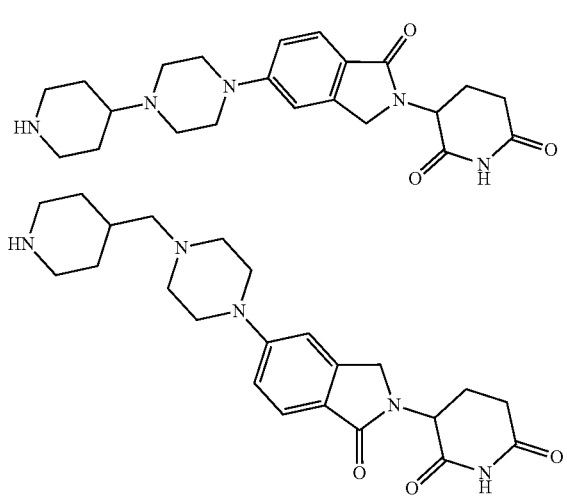

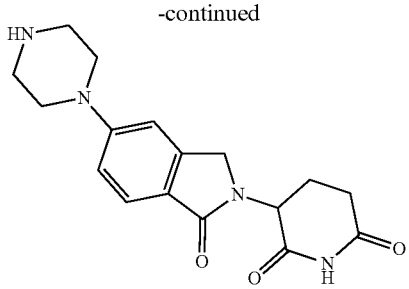

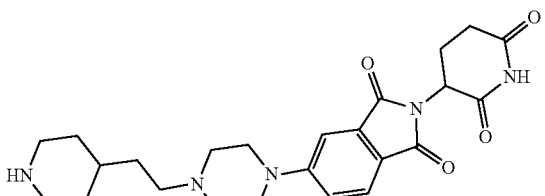

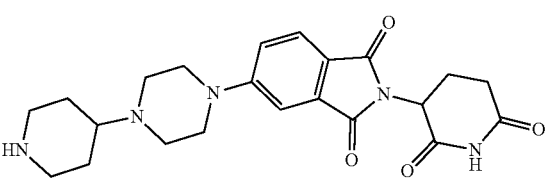

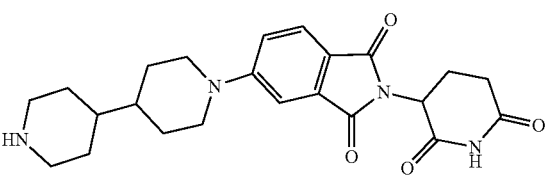

Following the above procedure of step 4 & 5, but with corresponding aldehyde or ketone with amines, 3-(1-oxo-5-(4-(piperidin-4-yl)piperazin-1-yl)isoindolin-2-yl)piperidine-2,6-dione was obtained as white or yellow solid.

Example 34: Preparation of Compounds 25, 27, 28, 29, 31, 33
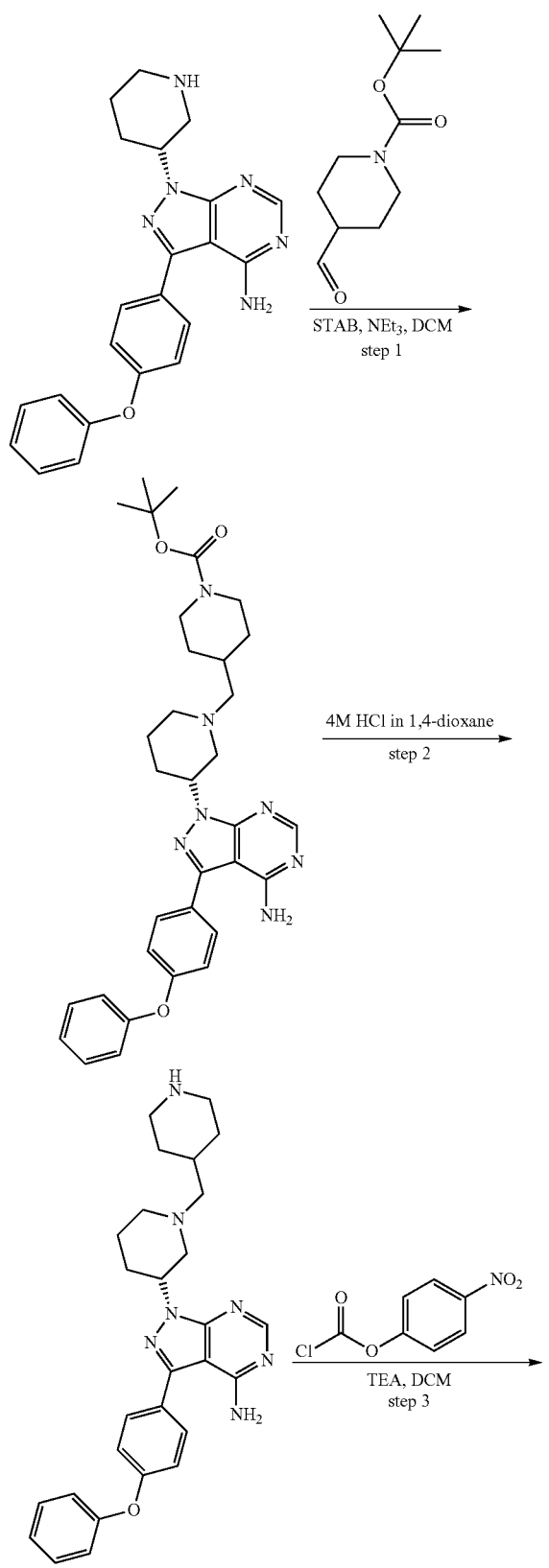
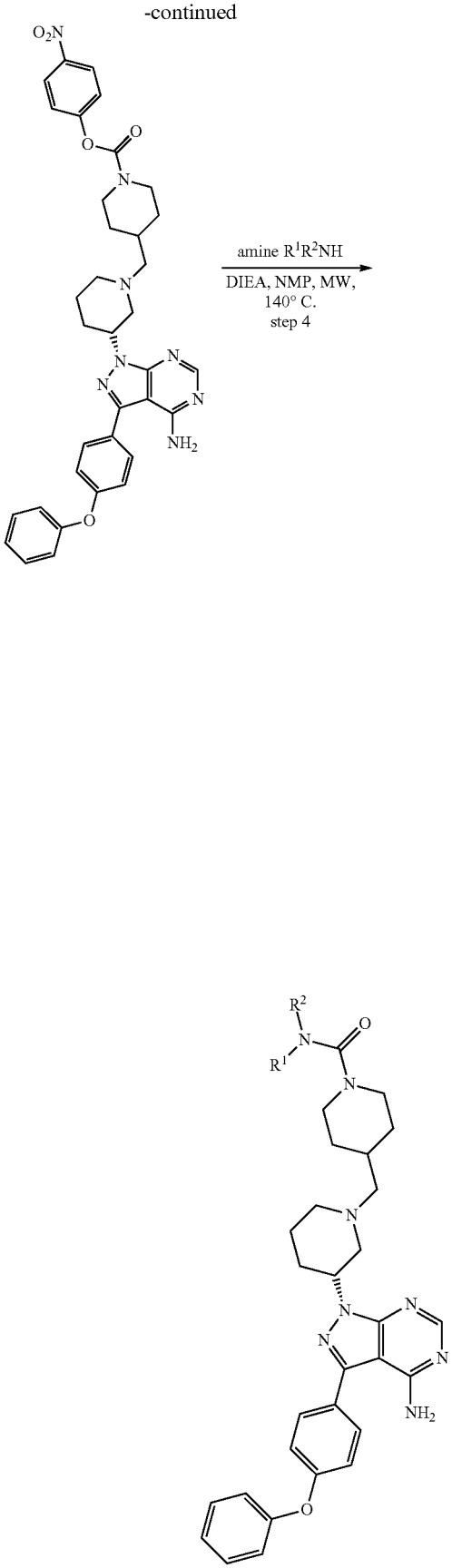

Step 1: tert-butyl (R)-4-((3-(4-amino-3-(4-phenoxyphenyl)-1H-pyrazolo(3,4-d)pyrimidin-1-yl)piperidin-1-yl)methyl)piperidine-1-carboxylate To a stirred solution of (R)-3-(4-phenoxyphenyl)-1-(piperidin-3-yl)-1H-pyrazolo(3,4-d)pyrimidin-4-amine (1.16 g, 3 mmol) and TEA (0.9 g, 9 mmol) in 50 ml of DCM was added tert-butyl 4-formylpiperidine-1-carboxylate (1.3 g, 6 mmol) at rt. The resulting solution was stirred at rt for 2 h. STAB (1.9 g, 9 mmol) was then added portionwise at rt. The mixture was stirred for additional 2 h. The solvent was removed in vacuo. The residue was subjected onto silica gel column chromatography to provide 1.45 g of tert-butyl (R)-4-((3-(4-amino-3-(4-phenoxyphenyl)-1H-pyrazolo(3,4-d)pyrimidin-1-yl)piperidin-1-yl)methyl)piperidine-1-carboxylate as white foam. $^1$H NMR (CDCl3, 300 MHz): δ 1.01-2.14 (8H, m), 2.21-2.44 (2H, m), 2.44-2.73 (4H, m), 2.88-3.12 (12H, m), 3.99-4.13 (2H, m), 4.87-5.02 (1H, m), 6.96 (2H, dd), 7.04-7.15 (2H, d), 7.28 (2H, d), 7.38 (2H, dd), 7.50 (1H, d), 7.75 (3H, d), 8.32 (1H, s).

Step 2: (R)-3-(4-phenoxyphenyl)-1-(1-(piperidin-4-ylmethyl)piperidin-3-yl)-1H-pyrazolo(3,4-d)pyrimidin-4-amine

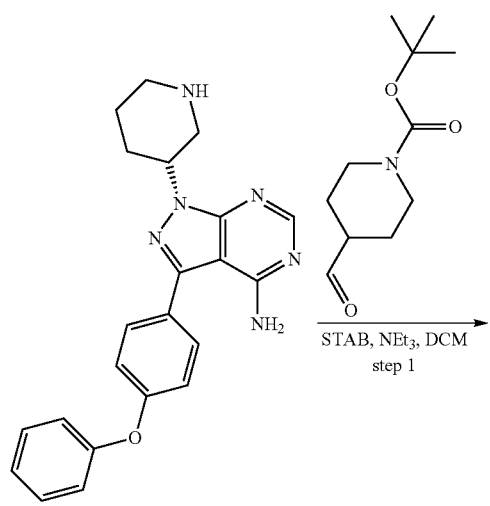
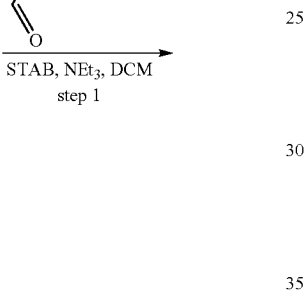
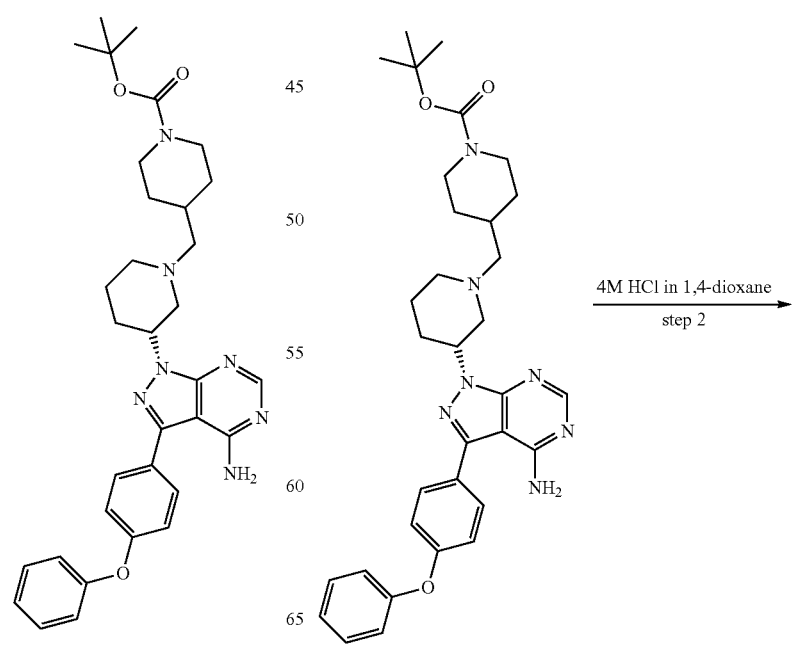

927

-continued

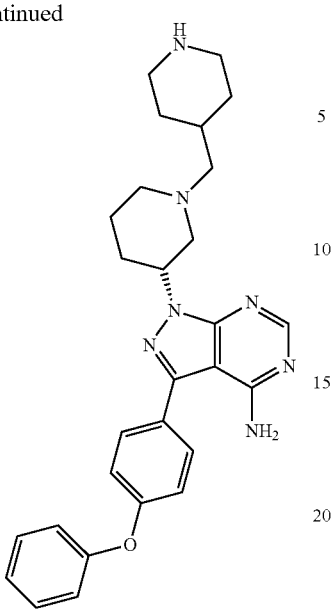

The above obtained tert-butyl tert-butyl (R)-4-((3-(4-amino-3-(4-phenoxyphenyl)-1H-pyrazolo(3,4-d)pyrimidin-1-yl)piperidin-1-yl)methyl)piperidine-1-carboxylate (1.45 g) was dissolved in 50 mL of EA. 5 mL of 4 M HCl in 1,4-dioxane was added at rt. After stirring for 16 h, the solvent was removed in vacuo to provide 1.83 g (R)-3-(4-phenoxyphenyl)-1-(1-(piperidin-4-ylmethyl)piperidin-3-yl)-1H-pyrazolo(3,4-d)pyrimidin-4-amine as yellow solid, which was used in the next step without further purification. $^1$H NMR (DMSO-d6, 300 MHz): δ 1.30-1.52 (2H, m), 1.97-2.44 (8H, m), 2.44-2.73 (4H, m), 2.88-3.12 (12H, m), 3.99-4.13 (2H, m), 4.87-5.02 (1H, m), 6.96 (2H, dd), 7.04-7.15 (2H, d), 7.28 (2H, d), 7.38 (2H, dd), 7.50 (1H, d), 7.75 (3H, d), 8.58 (1H, s).

Step 3: 3-(5-(4-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-1-oxoisoindolin-2-yl)piperidine-2,6-dione

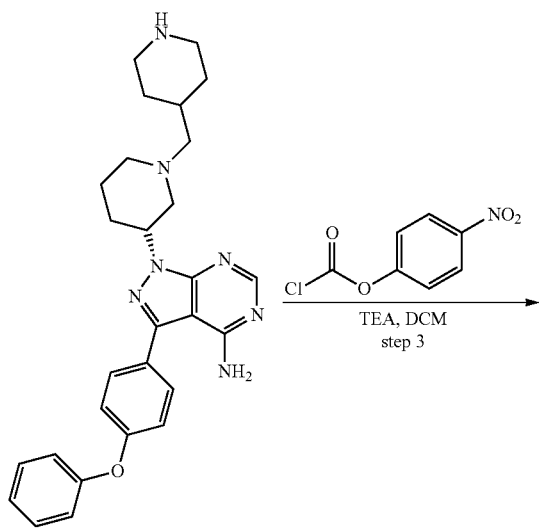

928

-continued

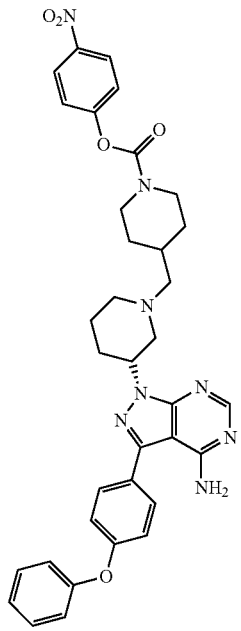

To a stirred solution of (R)-3-(4-phenoxyphenyl)-1-(1-(piperidin-4-ylmethyl)piperidin-3-yl)-1H-pyrazolo(3,4-d)pyrimidin-4-amine (0.48 g, 1 mmol) and TEA (0.3 g, 3 mmol) in 20 ml of DCM was added 4-nitrophenyl carbonochloridate (0.22 g, 1.1 mmol) at rt. The resulting solution was stirred at rt for 2 h. The solvent was evaporated in vacuo. The residue was subjected onto silica gel column chromatography to provide 0.62 g 4-nitrophenyl (R)-4-((3-(4-amino-3-(4-phenoxyphenyl)-1H-pyrazolo(3,4-d)pyrimidin-1-yl)piperidin-1-yl)methyl)piperidine-1-carboxylate as yellow solid, (M+H)$^+$=649.

Step 4: 3-(5-(4-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-1-oxoisoindolin-2-yl)piperidine-2,6-dione (Compound 28)
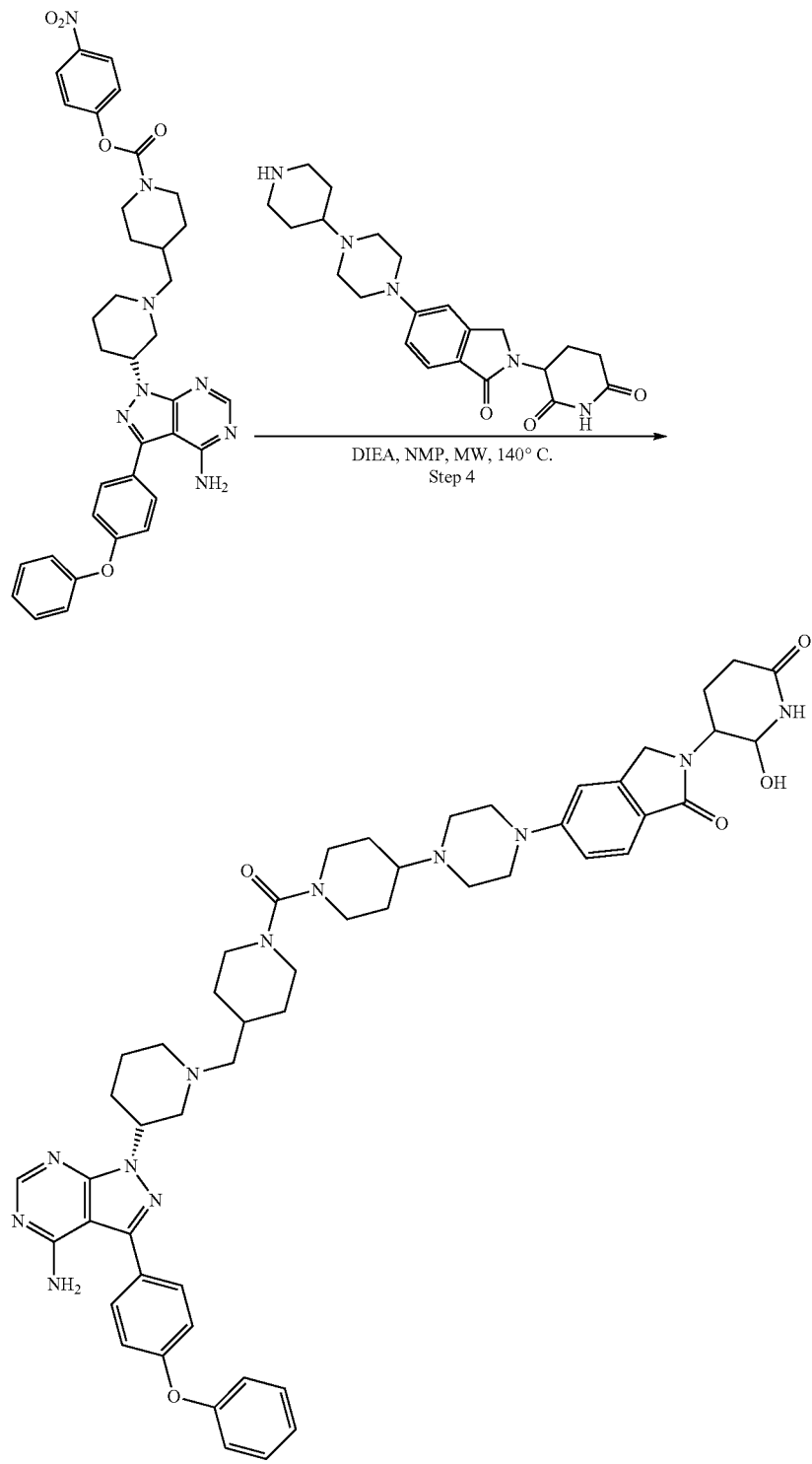
Compound 28

A solution of 4-nitrophenyl 4-nitrophenyl (R)-4-((3-(4-amino-3-(4-phenoxyphenyl)-1H-pyrazolo(3,4-d)pyrimidin-1-yl)piperidin-1-yl)methyl)piperidine-1-carboxylate (200 mg, 0.36 mmol), 3-(1-oxo-5-(4-(piperidin-4-yl)piperazin-1-yl)isoindolin-2-yl)piperidine-2,6-dione (154 mg, 0.36 mmol) and DIEA (140 mg, 1.1 mmol) in 4 mL of NMP was heated in MW at 140° C. for 1 h. The mixture was subjected onto silica gel column chromatography to provide crude product. The product was further purified by prep-HPLC, C18 column, with 0.5% FA water-MeCN as eluent. 66 mg of 3-(5-(4-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-1-oxoisoindolin-2-yl)piperidine-2,6-dione was obtained as white solid. $^1$H NMR (DMSO-d6, 300 MHz): δ 0.88-2.19 (14H, m), 2.40-2.73 (12H, m), 2.87-3.11 (6H, m), 3.25-3.44 (8H, m), 4.22 (1H, dd), 4.65-4.89 (1H, m), 5.05 (1H, dd), 6.93-7.02 (3H, m), 7.06 (1H, d), 7.12 (1H, t), 7.28 (2H, dd), 7.38 (2H, dd), 7.71-7.82 (3H, m), 8.18 (1H, s), 8.24 (1H, s), 10.97 (1H, s).

5-(4-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-2-(2,6-dioxopiperidin-3-yl)isoindoline-1,3-dione (Compound 27)

Following the procedure of Compound 28, but with corresponding amine, 25 mg of 5-(4-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)piperazin-1-yl)-2-(2,6-dioxopiperidin-3-yl)isoindoline-1,3-dione was obtained as white solid. $^1$H NMR (DMSO-d6, 300 MHz): δ 0.96-1.76 (13H, m), 1.82-2.21 (7H, m), 2.40-2.71 (7H, m), 2.87-2.99 (4H, m), 3.25-3.50 (10H, m), 4.67-4.82 (1H, m), 5.02 (1H, dd), 6.96 (2H, dd), 7.12 (1H, t), 7.18 (1H, d), 7.28 (2H, d), 7.38 (2H, dd), 7.50 (1H, d), 7.75 (2H, d), 8.09 (1H, d), 8.25 (1H, s), 11.09 (1H, s)

5-(1'-(4-(((R)-3-(4-amino-3-(4-phenoxyphenyl)-1H-pyrazolo(3,4-d)pyrimidin-1-yl)piperidin-1-yl)methyl)piperidine-1-carbonyl)-(4,4'-bipiperidin)-1-yl)-2-(2,6-dioxopiperidin-3-yl)isoindoline-1,3-dione (Compound 29)

Following the procedure of Compound 28, but with corresponding amine, 43 mg of 5-(1'-(4-(((R)-3-(4-amino-3-(4-phenoxyphenyl)-1H-pyrazolo(3,4-d)pyrimidin-1-yl)piperidin-1-yl)methyl)piperidine-1-carbonyl)-(4,4'-bipiperidin)-1-yl)-2-(2,6-dioxopiperidin-3-yl)isoindoline-1,3-dione was obtained as white solid. $^1$H NMR (DMSO-d6, 300 MHz): δ 0.98-2.20 (14H, m), 2.40-2.73 (12H, m), 2.87-2.98 (2H, m), 2.99-3.13 (4H, m), 3.25-3.44 (8H, m), 4.66-4.82 (1H, m), 5.05 (1H, dd), 6.96 (2H, dd), 7.04-7.15 (2H, d), 7.28 (2H, d), 7.38 (2H, dd), 7.50 (1H, d), 7.75 (2H, d), 8.22 (1H, s), 8.24 (1H, s), 11.09 (1H, s).

5-(4-((1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)methyl)piperazin-1-yl)-2-(2,6-dioxopiperidin-3-yl)isoindoline-1,3-dione (Compound 31)

Following the procedure of Compound 28, but with corresponding amine, 15 mg of 5-(4-((1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)methyl)piperazin-1-yl)-2-(2,6-dioxopiperidin-3-yl)isoindoline-1,3-dione was obtained as white solid. $^1$H NMR (DMSO-d6, 300 MHz): δ 0.87-2.20 (15H, m), 2.40-2.73 (13H, m), 2.87-2.98 (2H, m), 2.99-3.13 (4H, m), 3.25-3.43 (8H, m), 4.66-4.82 (1H, m), 5.05 (1H, dd), 6.96 (2H, dd), 7.04-7.15 (2H, d), 7.28 (2H, d), 7.38 (2H, dd), 7.50 (1H, d), 7.75 (2H, d), 8.21 (1H, s), 8.25 (1H, s), 11.09 (1H, s).

5-(4-(2-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione (Compound 33)

Following the procedure of Compound 28, but with corresponding amine, 17 mg of 5-(4-(2-(1-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperidin-4-yl)ethyl)piperazin-1-yl)-2-(2,6-dioxopiperidin-3-yl)isoindoline-1,3-dione was obtained as white solid. $^1$H NMR (DMSO-d6, 300 MHz): δ 0.89-1.32 (2H, m), 1.42-1.76 (10H, m), 1.82-2.20 (5H, m), 2.40-2.71 (13H, m), 2.98-3.13 (4H, m), 3.25-3.42 (8H, m), 4.66-4.82 (1H, m), 5.05 (1H, dd), 6.96 (2H, dd), 7.04-7.15 (2H, d), 7.28 (2H, d), 7.38 (2H, dd), 7.50 (1H, d), 7.75 (2H, d), 8.25 (1H, s), 8.27 (1H, s), 11.09 (1H, s).

5-(4-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperazin-1-yl)-2-(2,6-dioxopiperidin-3-yl)isoindoline-1,3-dione (Compound 25)

Following the procedure of Compound 28, but with corresponding amine, 13 mg of 5-(4-(4-(((R)-3-(4-amino-3-(4-phenoxyphenyl)-1H-pyrazolo(3,4-d)pyrimidin-1-yl)piperidin-1-yl)methyl)piperidine-1-carbonyl)piperazin-1-yl)-2-(2,6-dioxopiperidin-3-yl)isoindoline-1,3-dione was obtained as white solid. $^1$H NMR (DMSO-d6, 300 MHz): δ 1.52-1.76 (5H, m), 1.84-2.14 (5H, m), 2.21-2.68 (7H, m), 2.87-2.98 (2H, m), 3.13-3.40 (8H, m), 3.52-3.67 (4H, m), 4.66-4.82 (1H, m), 5.05 (1H, dd), 6.96 (2H, dd), 7.04-7.15 (2H, d), 7.28 (2H, d), 7.38 (2H, dd), 7.50 (1H, d), 7.75 (2H, d), 8.25 (1H, s), 11.10 (1H, s).

Example 35: Preparation of Compounds 476, 477, 478, 480, 482, 484
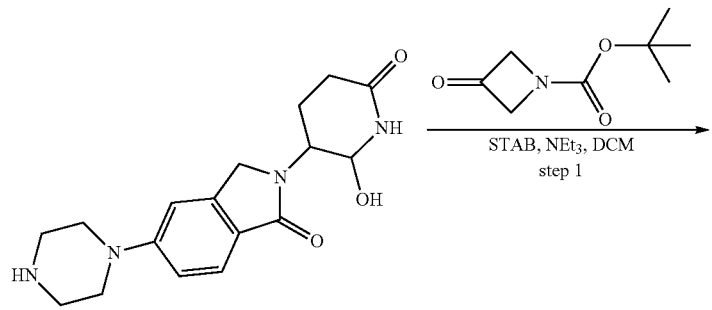
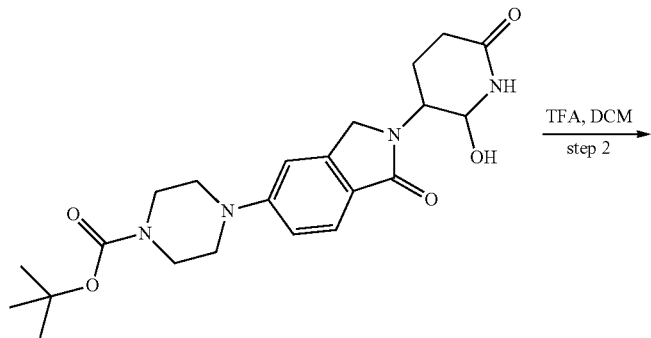
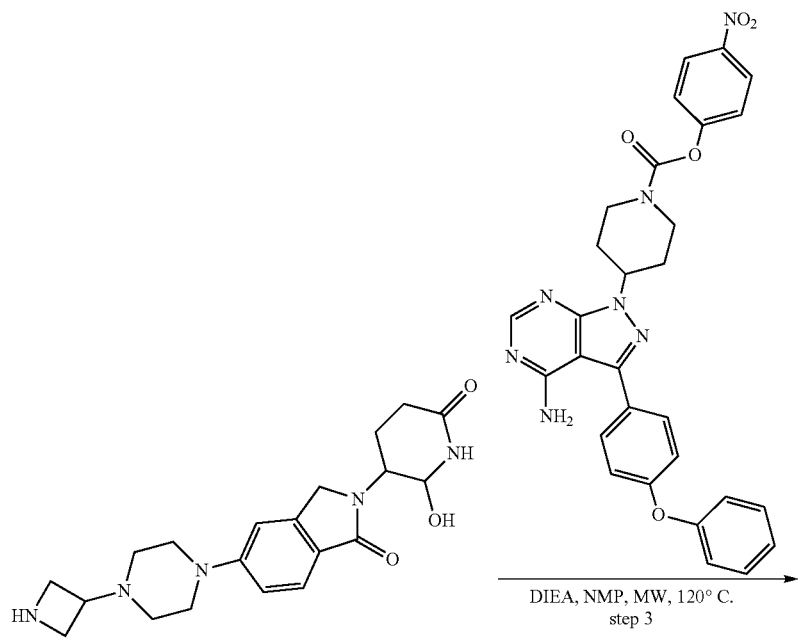

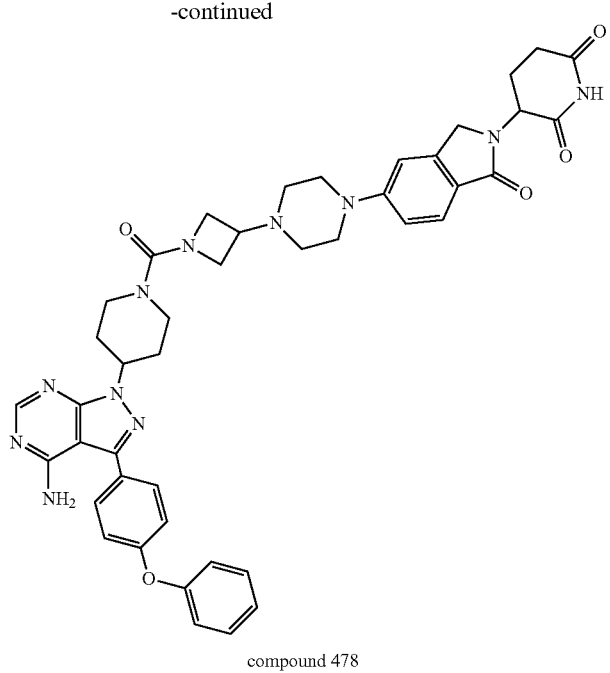

compound 478

Step 1. tert-butyl 3-(4-(2-(2,6-dioxopiperidin-3-yl)-1-oxoisoindolin-5-yl)piperazin-1-yl)azetidine-1-carboxylate

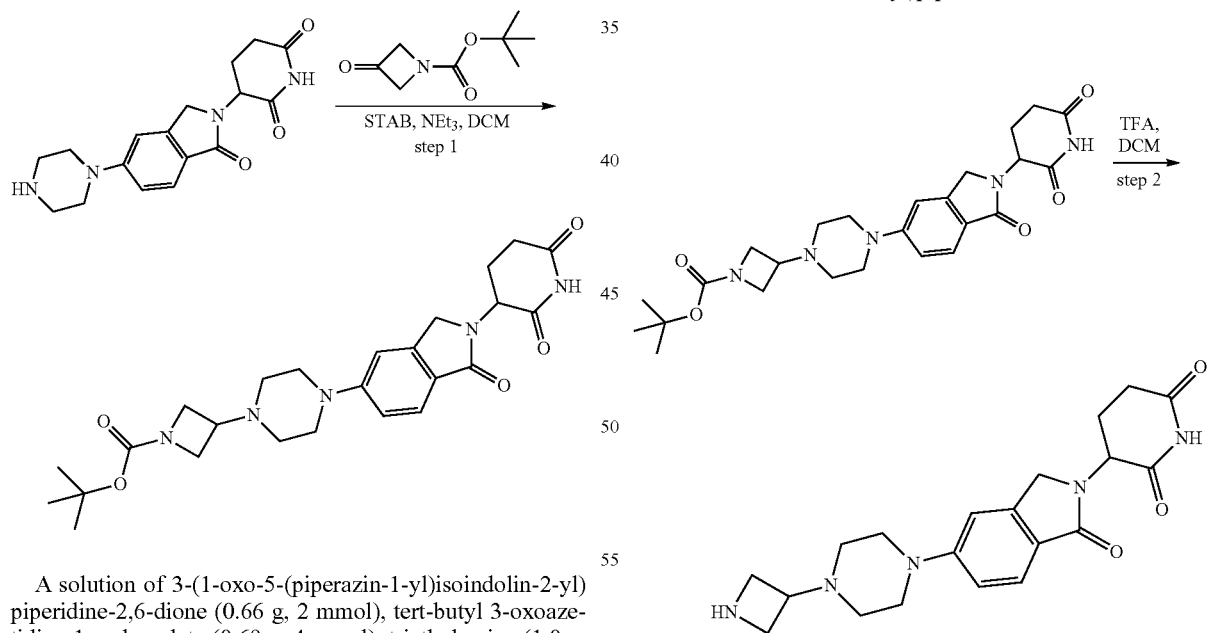

A solution of 3-(1-oxo-5-(piperazin-1-yl)isoindolin-2-yl)piperidine-2,6-dione (0.66 g, 2 mmol), tert-butyl 3-oxoazetidine-1-carboxylate (0.69 g, 4 mmol), triethylamine (1.0 g, 10 mmol) in 20 mL of DCM was stirred at room temperature. STAB was added portionwise at 0° C. and the resulting mixture was stirred at room temperature for 16 hours. The solvent was removed in vacuo. The residue was subjected onto silica gel column chromatography with 20% MeOH in EA as eluent to give tert-butyl 3-(4-(2-(2,6-dioxopiperidin-3-yl)-1-oxoisoindolin-5-yl)piperazin-1-yl)azetidine-1-carboxylate (0.8 g) as white solid. LCMS (M+H) 484; 1H NMR (DMSO-d6, 300 MHz): δ 1H NMR: δ 0.77 (6H, q), 1.38- 1.49 (9H, s), 1.86-2.11 (2H, m), 2.23-2.41 (2H, m), 2.64-3.15 (9H, m), 3.77 (1H, dd), 3.96 (2H, dd), 4.14 (1H, d), 4.46-4.64 (3H, m), 6.92-7.11 (2H, m), 7.79 (1H, d).

Step 2. 3-(5-(4-(azetidin-3-yl)piperazin-1-yl)-1-oxoisoindolin-2-yl)piperidine-2,6-dione The above obtained tert-butyl 3-(4-(2-(2,6-dioxopiperidin-3-yl)-1-oxoisoindolin-5-yl)piperazin-1-yl)azetidine-1-carboxylate (0.8 g) was dissolved in 10 mL of DCM. 2 mL of TFA was added at rt. After stirring for 2 h, the solvent was removed in vacuo to provide crude 3-(5-(4-(azetidin-3-yl)piperazin-1-yl)-1-oxoisoindolin-2-yl)piperidine-2,6-dione as white solid, which was used in the next step without further purification.

Step 3. 3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione

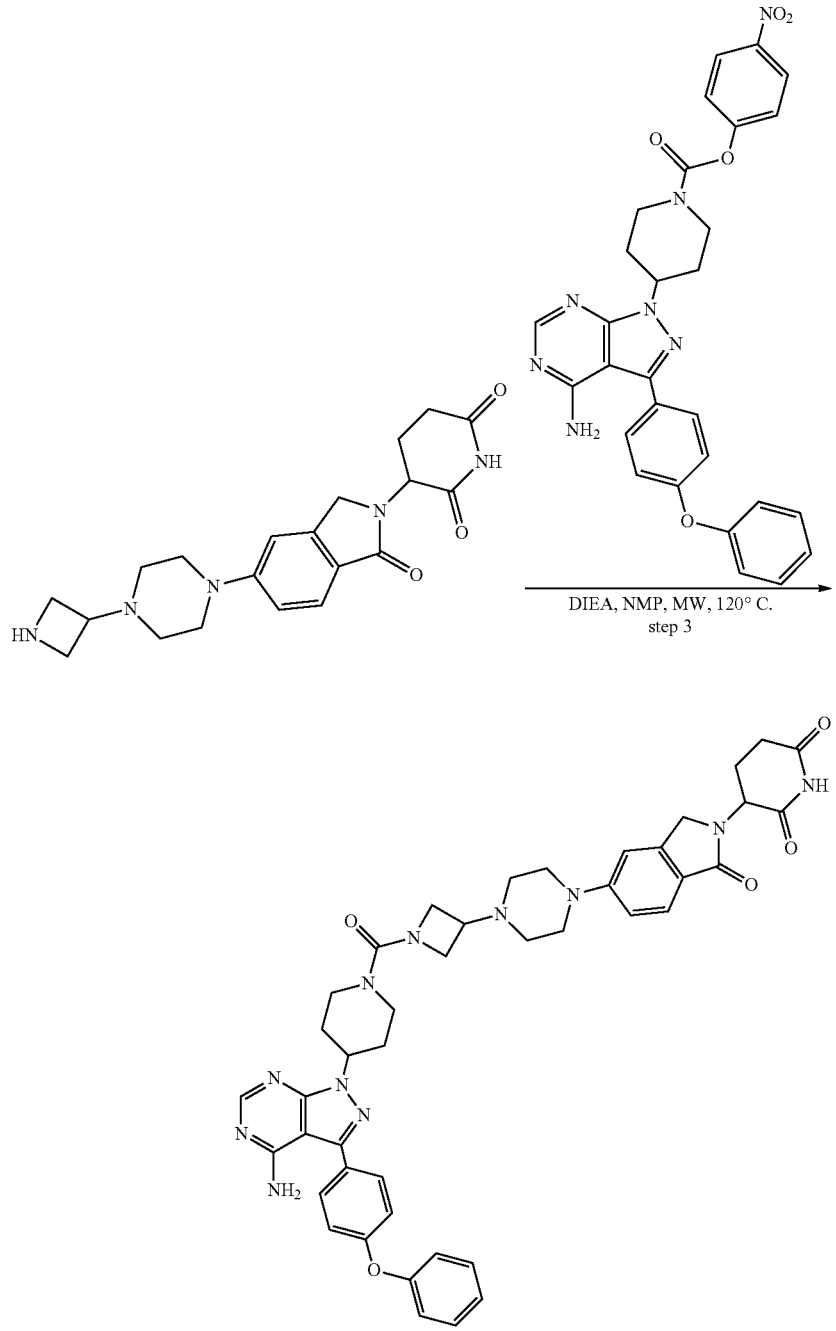

A solution of 4-nitrophenyl 4-(4-amino-3-(4-phenoxyphenyl)-1H-pyrazolo[3,4-d]pyrimidin-1-yl)piperidine-1-carboxylate (200 mg, 0.36 mmol), 3-(5-(4-(azetidin-3-yl)piperazin-1-yl)-1-oxoisoindolin-2-yl)piperidine-2,6-dione and DIEA in 4 mL of NMP was heated in MW at 120° C. for 1 h. The mixture was subjected onto silica gel column chromatography to provide crude product. The product was further purified by prep-HPLC, C18 column, with 0.5% FA water-MeCN as eluent. 88 mg of 3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione (compound 478) was obtained as white solid LCMS (M+H) 796, $^1$H NMR: δ 0.71-0.83 (6H, m), 1.86-2.41 (6H, m), 2.44-2.60 (2H, m), 2.62-3.15 (9H, m), 3.28-3.47 (4H, m), 3.81 (1H, dd), 3.99 (2H, d), 4.17 (1H, d), 4.45-4.64 (4H, m), 6.88-7.59 (12H, m), 7.73-7.90 (2H, m).

3-(5-(4-(1-((R)-3-(4-amino-3-(4-phenoxyphenyl)-1H-pyrazolo[3,4-d]pyrimidin-1-yl)-[1,4'-bipiperidine]-1'-carbonyl)azetidin-3-yl)piperazin-1-yl)-1-oxoisoindolin-2-yl)piperidine-2,6-dione (compound 476); 5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-2-(2,6-dioxopiperidin-3-yl)isoindoline-1,3-dione (compound 477); 3-(5-(4-(1-(3-((R)-3-(4-amino-3-(4-phenoxyphenyl)-1H-pyrazolo[3,4-d]pyrimidin-1-yl)piperidin-1-yl)azetidine-1-carbonyl)azetidin-3-yl)piperazin-1-yl)-1-oxoisoindolin-2-yl)piperidine-2,6-dione (compound 480); 3-(5-(4-(1-(3-((R)-3-(4-amino-3-(4-phenoxyphenyl)-1H-pyrazolo[3,4-d]pyrimidin-1-yl)piperidin-1-yl)azetidine-1-carbonyl)piperidin-4-yl)piperazin-1-yl)-1-oxoisoindolin-2-yl)piperidine-2,6-dione (compound 482); (S)-3-(5-(4-(1-(4-(4-amino-3-(4-phenoxyphenyl)-1H-pyrazolo[3,4-d]pyrimidin-1-yl)piperidine-1-carbonyl)azetidin-3-yl)piperazin-1-yl)-1-oxoisoindolin-2-yl)piperidine-2,6-dione (compound 484)

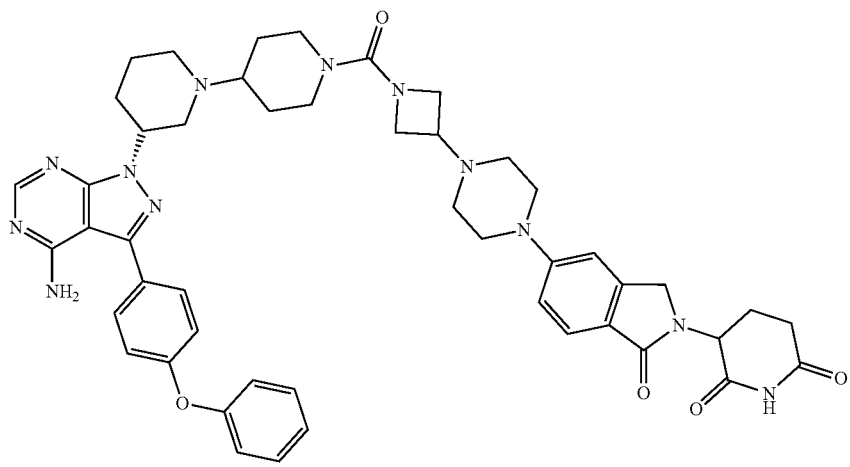

compound 476

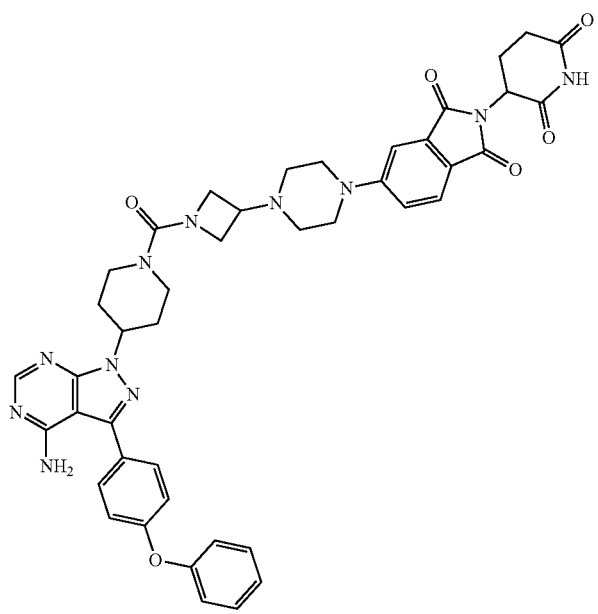

compound 477

-continued
compound 480
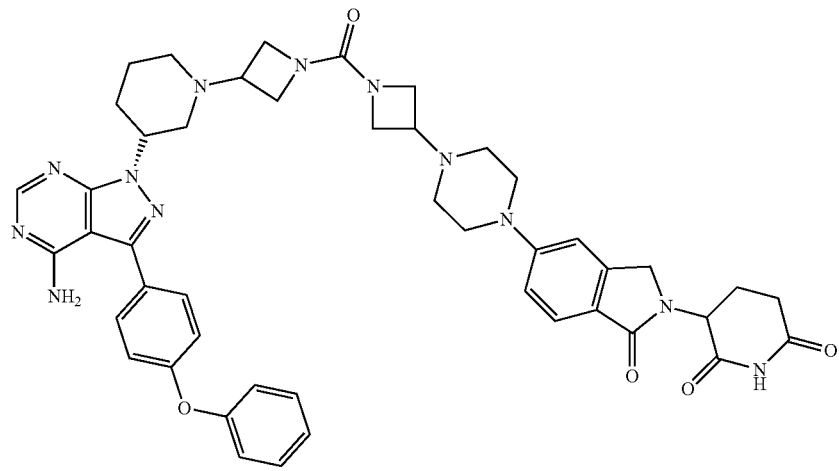
compound 482
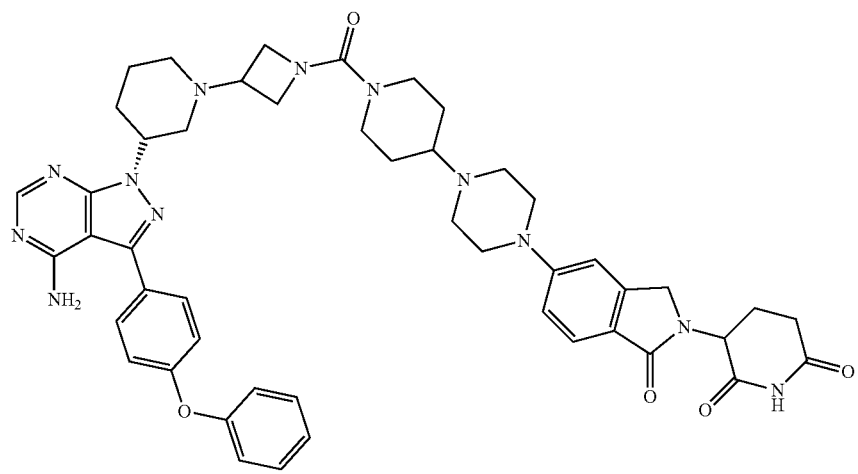
compound 484
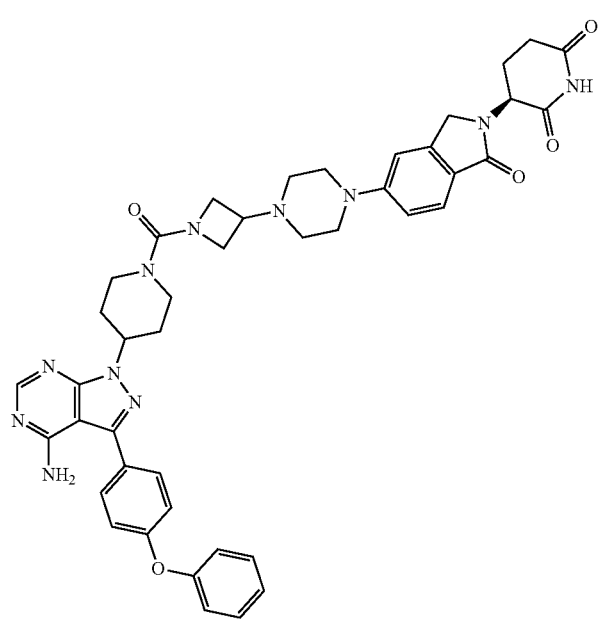
Following the above procedure of step 3, but with corresponding starting materials, compound 476, compound 477, compound 480, compound 482, and compound 484 were obtained as white or pale grey solid.

Example 36: Preparation of Compounds 508
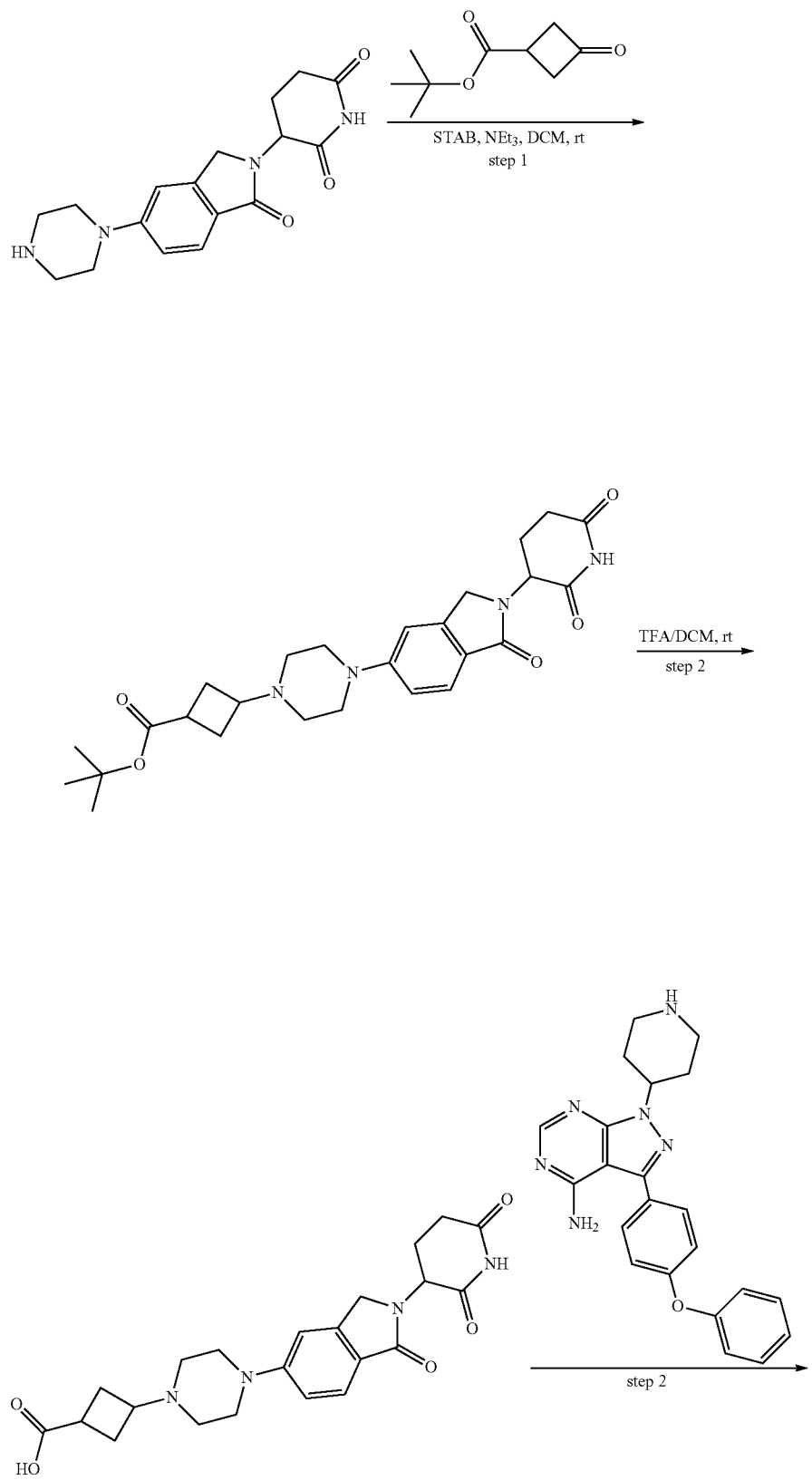

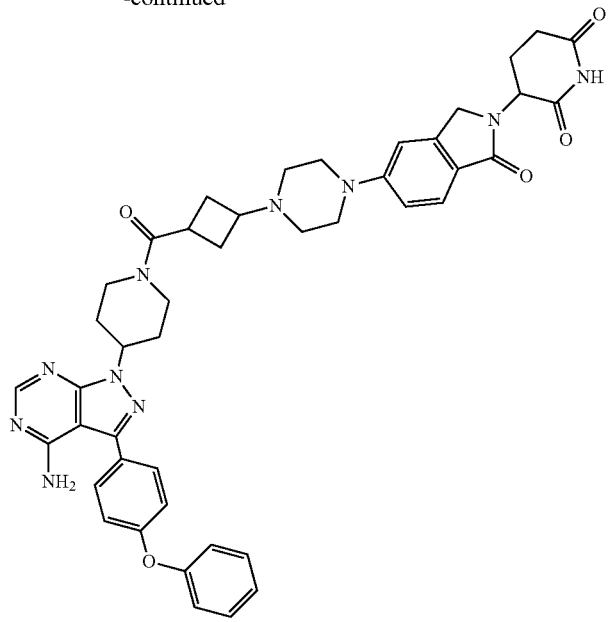

Step 1. tert-butyl 3-(4-(2-(2,6-dioxopiperidin-3-yl)-1-oxoisoindolin-5-yl)piperazin-1-yl)cyclobutane-1-carboxylate Step 2. 3-(4-(2-(2,6-dioxopiperidin-3-yl)-1-oxoisoindolin-5-yl)piperazin-1-yl)cyclobutane-1-carboxylic Acid

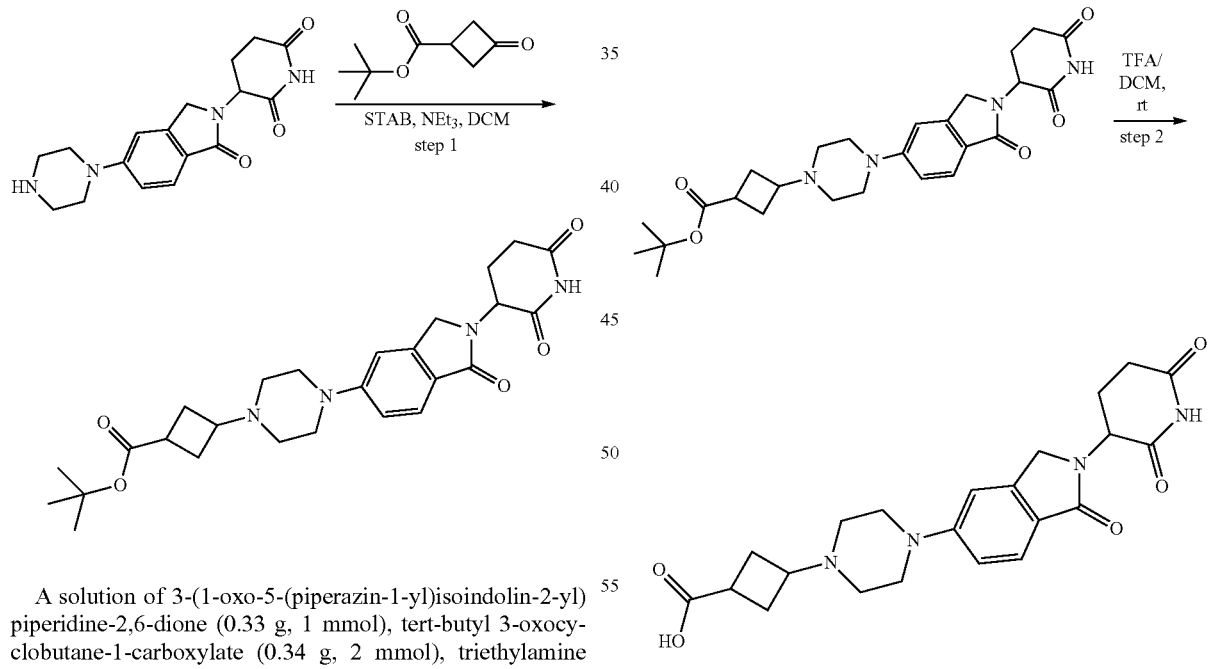

A solution of 3-(1-oxo-5-(piperazin-1-yl)isoindolin-2-yl)piperidine-2,6-dione (0.33 g, 1 mmol), tert-butyl 3-oxocyclobutane-1-carboxylate (0.34 g, 2 mmol), triethylamine (1.0 g, 10 mmol) in 20 mL of DCM was stirred at room temperature. STAB was added portionwise at 0° C. and the resulting mixture was stirred at room temperature for 16 hours. The solvent was removed in vacuo. The residue was subjected onto silica gel column chromatography with 20% MeOH in EA as eluent to give tert-butyl 3-(4-(2-(2,6-dioxopiperidin-3-yl)-1-oxoisoindolin-5-yl)piperazin-1-yl)cyclobutane-1-carboxylate (0.21 g) as white solid. LCMS (M+H) 483.

The above obtained tert-butyl 3-(4-(2-(2,6-dioxopiperidin-3-yl)-1-oxoisoindolin-5-yl)piperazin-1-yl)cyclobutane-1-carboxylate (0.21 g) was dissolved in 10 mL of DCM. 2 mL of TFA was added at rt. After stirring for 2 h, the solvent was removed in vacuo to provide crude 3-(4-(2-(2,6-dioxopiperidin-3-yl)-1-oxoisoindolin-5-yl)piperazin-1-yl)cyclobutane-1-carboxylic acid as white solid, which was used in the next step without further purification.

Step 3. 3-(5-(4-(3-(4-(4-amino-3-(4-phenoxyphenyl)-1H-pyrazolo[3,4-d]pyrimidin-1-yl)piperidine-1-carbonyl)cyclobutyl)piperazin-1-yl)-1-oxoisoindolin-2-yl)piperidine-2,6-dione (compound 508)

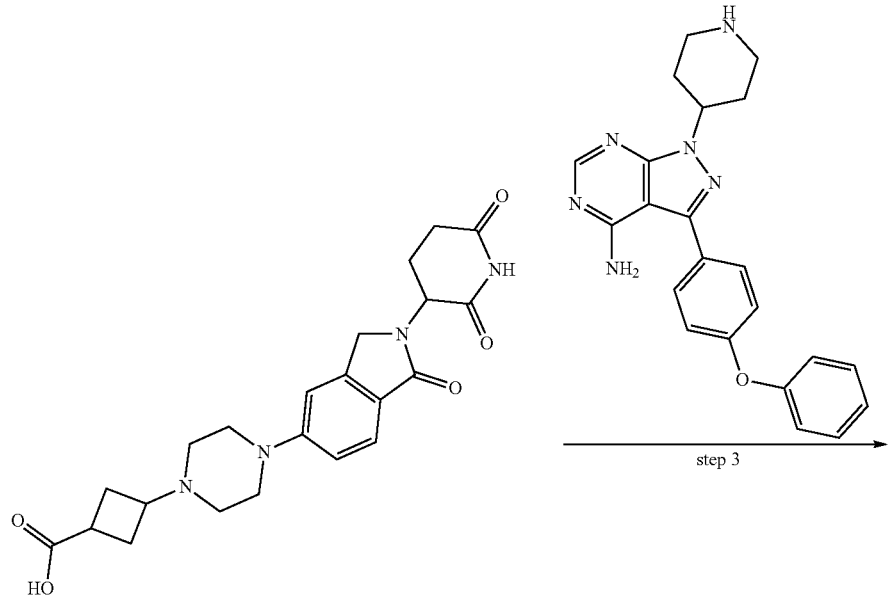

To a solution of 3-(4-phenoxyphenyl)-1-(piperidin-4-yl)-1H-pyrazolo[3,4-d]pyrimidin-4-amine, above obtained 3-(4-(2-(2,6-dioxopiperidin-3-yl)-1-oxoisoindolin-5-yl)piperazin-1-yl)cyclobutane-1-carboxylic acid and DIEA in 5 mL of DMF was added DIEA followed by HBTU at room temperature. After stirring for 1 h, the mixture was subjected onto silica gel column chromatography to provide crude product. The product was further purified by prep-HPLC, C18 column, with 0.5% FA water-MeCN as eluent. 33 mg of 3-(5-(4-(3-(4-(4-amino-3-(4-phenoxyphenyl)-1H-pyrazolo [3,4-d]pyrimidin-1-yl)piperidine-1-carbonyl)cyclobutyl) piperazin-1-yl)-1-oxoisoindolin-2-yl)piperidine-2,6-dione (compound 508) was obtained as white solid LCMS (M+H) 795, $^1$H NMR: δ 1.86-2.41 (10H, m), 2.44-2.63 (6H, m), 2.68-2.88 (2H, m), 2.96-3.11 (4H, m), 3.29-3.48 (4H, m), 3.93 (1H, d), 4.22 (2H, dd), 4.51 (1H, d), 4.91-5.12 (2H, m), 6.90-7.18 (5H, m), 7.21-7.45 (4H, m), 7.68-7.85 (3H, m), 8.25 (1H, s), 10.94 (s, 1H).

Example 37: Preparation of Compounds 512
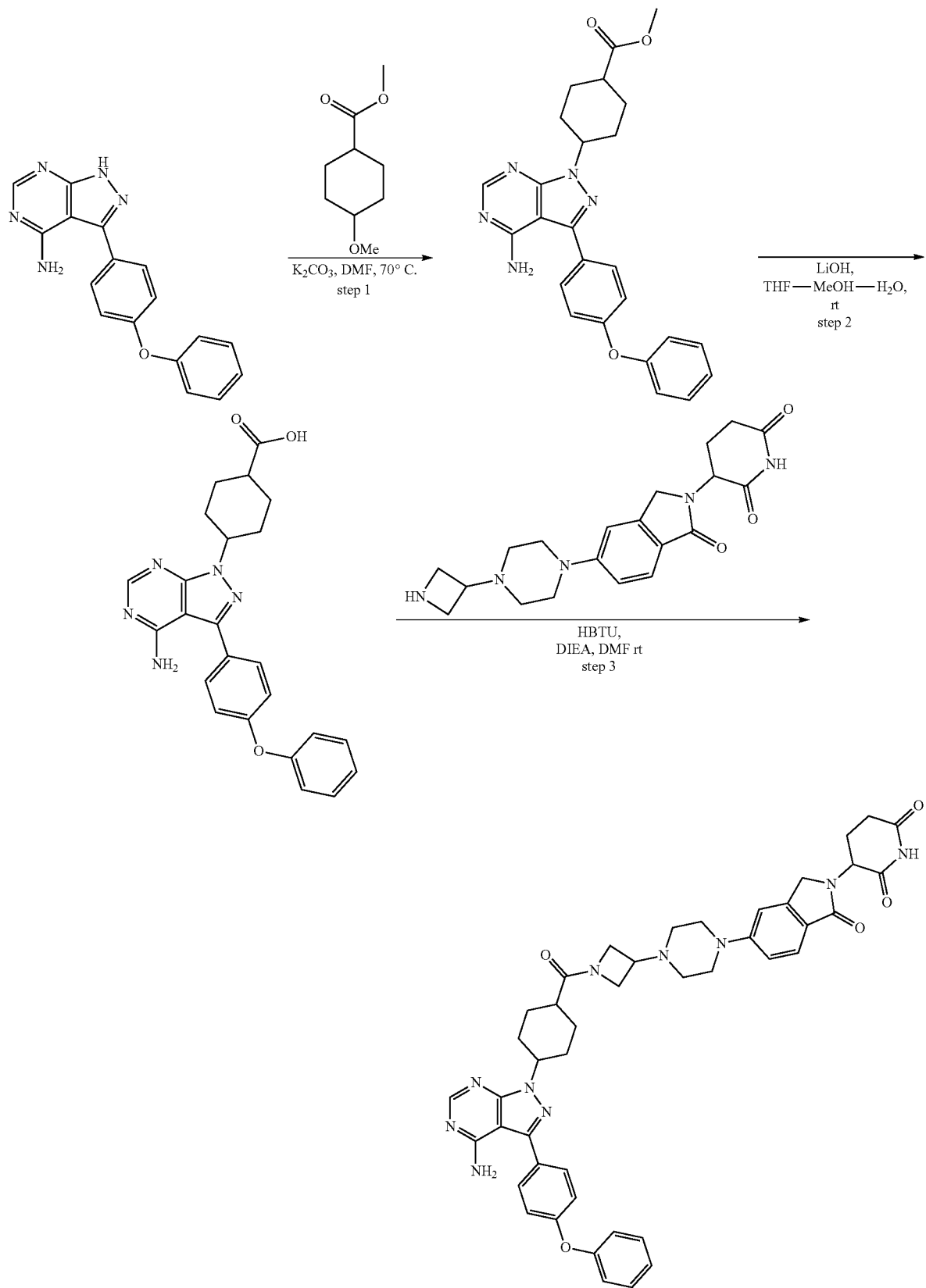

951

Step 1. methyl 4-(4-amino-3-(4-phenoxyphenyl)-1H-pyrazolo[3,4-d]pyrimidin-1-yl)cyclohexane-1-carboxylate

952

Step 2. 4-(4-amino-3-(4-phenoxyphenyl)-1H-pyrazolo[3,4-d]pyrimidin-1-yl)cyclohexane-1-carboxylic Acid

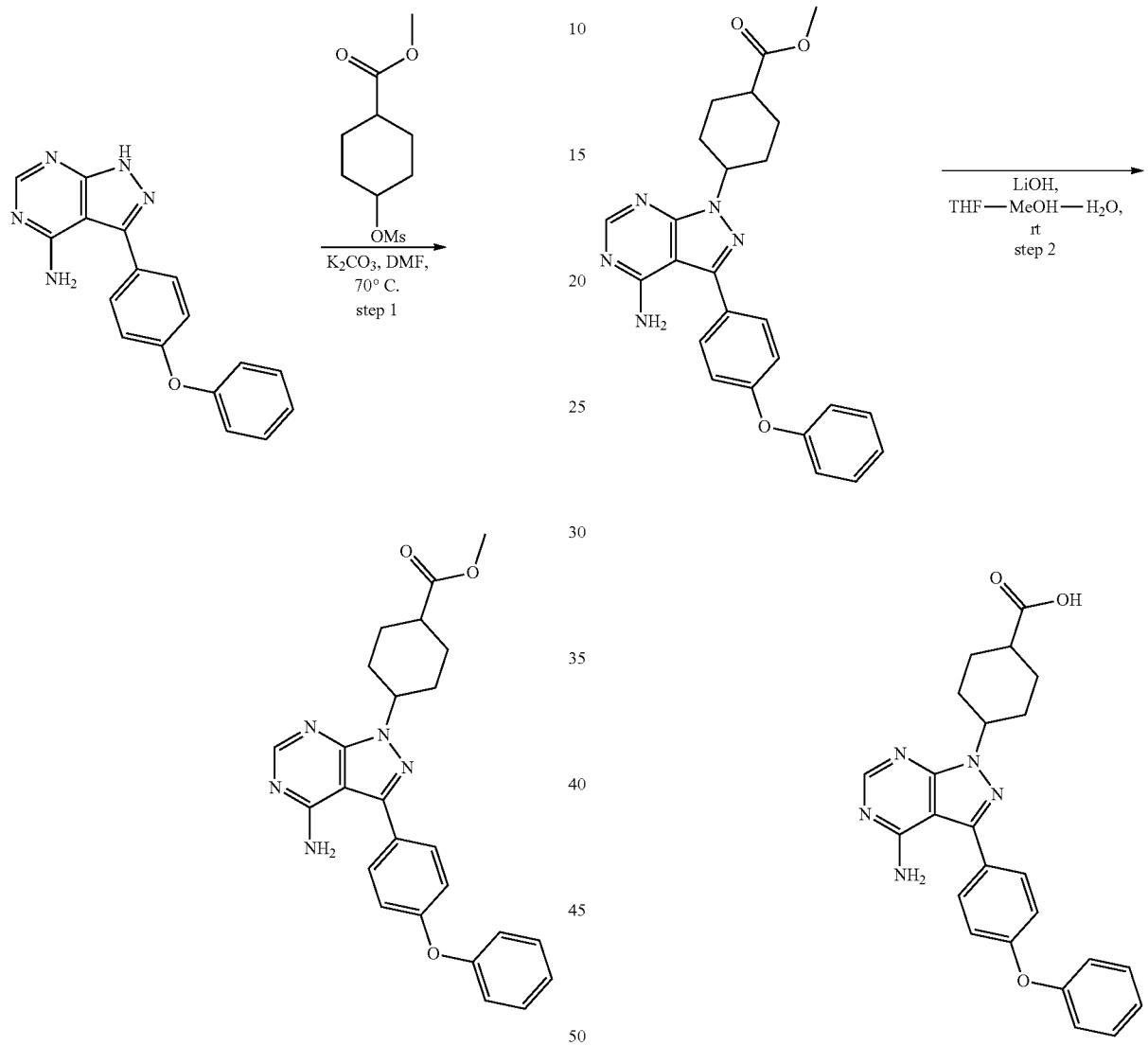

A mixture of 3-(4-phenoxyphenyl)-1H-pyrazolo[3,4-d]pyrimidin-4-amine (3.0 g, 10 mmol), methyl 4-((methylsulfonyl)oxy)cyclohexane-1-carboxylate (2.6 g, 12 mmol) and potassium carbonate (2.7 g, 20 mmol) in 20 mL of DMF was stirred and heated in an oil bath at 70° C. for 16 hours. After cooling to room temperature, 100 mL water and 100 mL ethyl acetate were added to the mixture to quench the reaction. The organic layer was collected and washed with brine, dried over Na2SO4, filtered, evaporated to dryness. The residue was subjected onto silica gel column chromatography to provide 1.6 g of methyl 4-(4-amino-3-(4-phenoxyphenyl)-1H-pyrazolo[3,4-d]pyrimidin-1-yl)cyclohexane-1-carboxylate as light brown oil. LCMS (M+H) 444.

The above obtained methyl 4-(4-amino-3-(4-phenoxyphenyl)-1H-pyrazolo[3,4-d]pyrimidin-1-yl)cyclohexane-1-carboxylate (1.6 g, 3.6 mmol) was dissolved in 20 mL THF and 10 mL of MeOH. LiOH (0.46 g, 13.4 mmol) in 20 mL water was added to the solution. The resulting mixture was stirred at room temperature for 4 hours. After completion, most of the organic solvent was evaporated in vacuo. 2 M HCl aqueous solution was added to the mixture to adjust pH to 4-5. The solids were collected by filtration and dried to provide 1.2 g 4-(4-amino-3-(4-phenoxyphenyl)-1H-pyrazolo[3,4-d]pyrimidin-1-yl)cyclohexane-1-carboxylic acid as white solid. LCMS (M+H) 403.

Step 3. 3-(5-(4-(1-(4-(4-amino-3-(4-phenoxyphenyl)-1H-pyrazolo[3,4-d]pyrimidin-1-yl)cyclohexane-1-carbonyl)azetidin-3-yl)piperazin-1-yl)-1-oxoisoindolin-2-yl)piperidine-2,6-dione (compound 512)

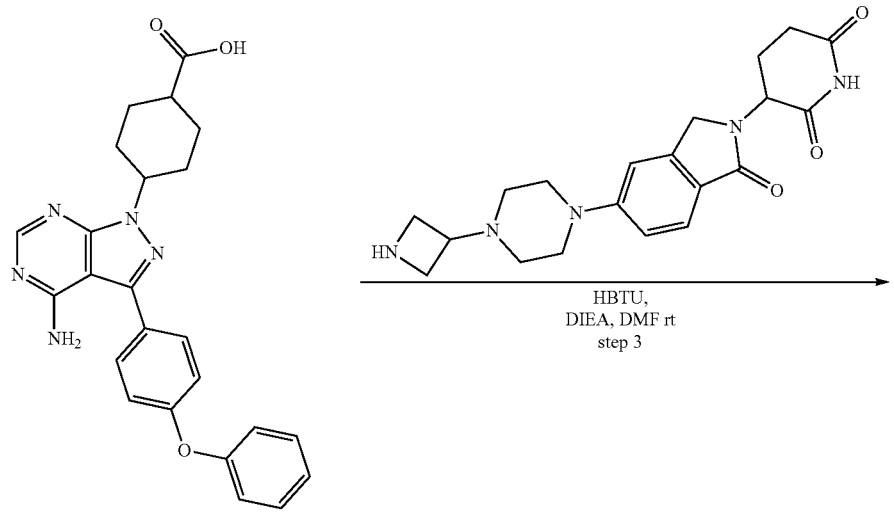

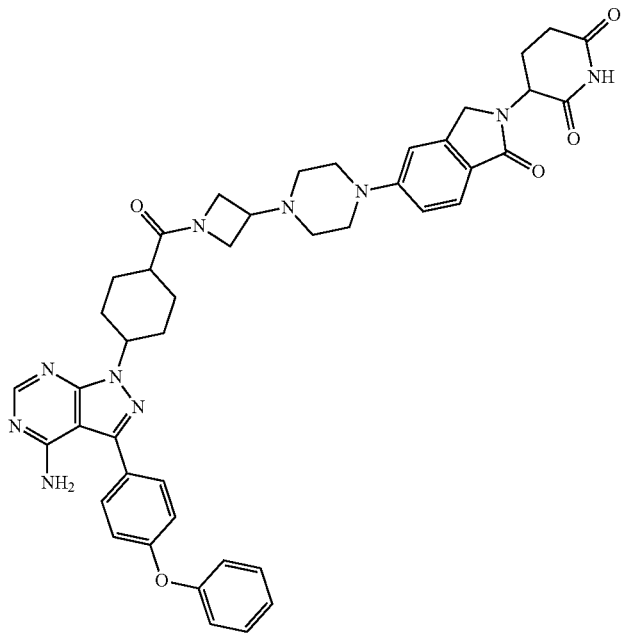

To a solution of 4-(4-amino-3-(4-phenoxyphenyl)-1H-pyrazolo[3,4-d]pyrimidin-1-yl)cyclohexane-1-carboxylic acid (0.2 g, 0.5 mmol), 3-(5-(4-(azetidin-3-yl)piperazin-1-yl)-1-oxoisoindolin-2-yl)piperidine-2,6-dione and DIEA in 5 mL of DMF was added DIEA followed by HBTU at room temperature. After stirring for 1 h, the mixture was subjected onto silica gel column chromatography to provide crude product. The product was further purified by prep-HPLC, C18 column, with 0.5% FA water-MeCN as eluent. 53 mg of 3-(5-(4-(1-(4-(4-amino-3-(4-phenoxyphenyl)-1H-pyrazolo[3,4-d]pyrimidin-1-yl)cyclohexane-1-carbonyl)azetidin-3-yl)piperazin-1-yl)-1-oxoisoindolin-2-yl)piperidine-2,6-dione (compound 512) was obtained as white solid LCMS (M+H) 795, $^1$H NMR: δ 1.58-1.83 (4H, m), 1.86-2.41 (8H, m), 2.63-2.80 (5H, m), 2.88-3.12 (5H, m), 3.80-3.99 (2H, m), 4.36 (2H, d), 4.46-4.64 (3H, m), 5.04 (1H, dd), 6.90-7.18 (5H, m), 7.21-7.45 (4H, m), 7.68-7.85 (3H, m), 8.25 (1H, s), 10.95 (s, 1H).

Example 38: Preparation of Compounds 515 and 516

Step 1. tert-butyl (R)-4-(4-((3-(4-amino-3-(4-phe-noxyphenyl)-1H-pyrazolo[3,4-d]pyrimidin-1-yl)-[1,4'-bipiperidin]-1'-yl)methyl)piperidin-1-yl)benzoate

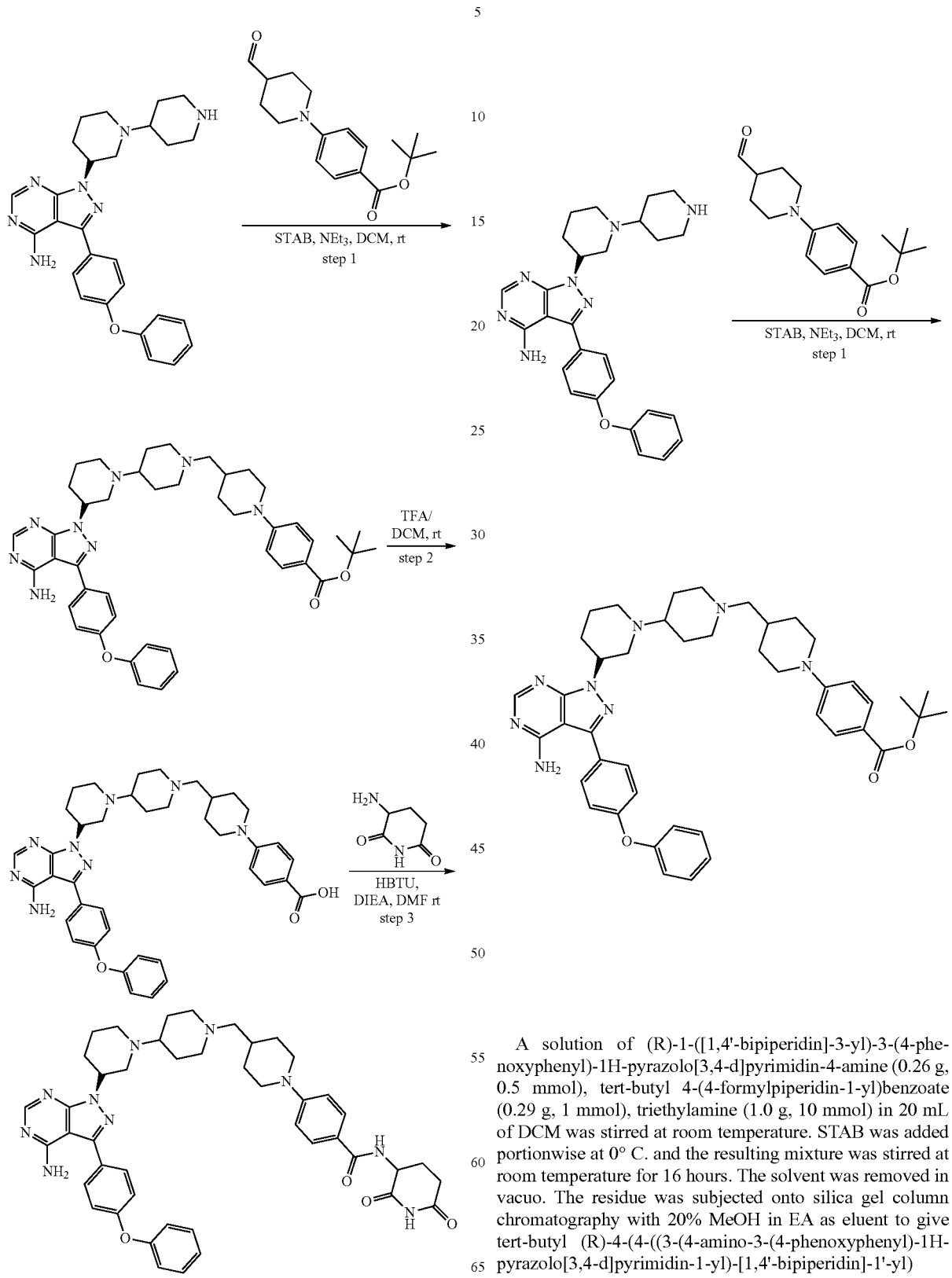

A solution of (R)-1-([1,4'-bipiperidin]-3-yl)-3-(4-phe-noxyphenyl)-1H-pyrazolo[3,4-d]pyrimidin-4-amine (0.26 g, 0.5 mmol), tert-butyl 4-(4-formylpiperidin-1-yl)benzoate (0.29 g, 1 mmol), triethylamine (1.0 g, 10 mmol) in 20 mL of DCM was stirred at room temperature. STAB was added portionwise at 0° C. and the resulting mixture was stirred at room temperature for 16 hours. The solvent was removed in vacuo. The residue was subjected onto silica gel column chromatography with 20% MeOH in EA as eluent to give tert-butyl (R)-4-(4-((3-(4-amino-3-(4-phenoxyphenyl)-1H-pyrazolo[3,4-d]pyrimidin-1-yl)-[1,4'-bipiperidin]-1'-yl) methyl)piperidin-1-yl)benzoate (0.23 g) as white solid. LCMS (M+H) 743.

Step 2. (R)-4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)benzoic Acid

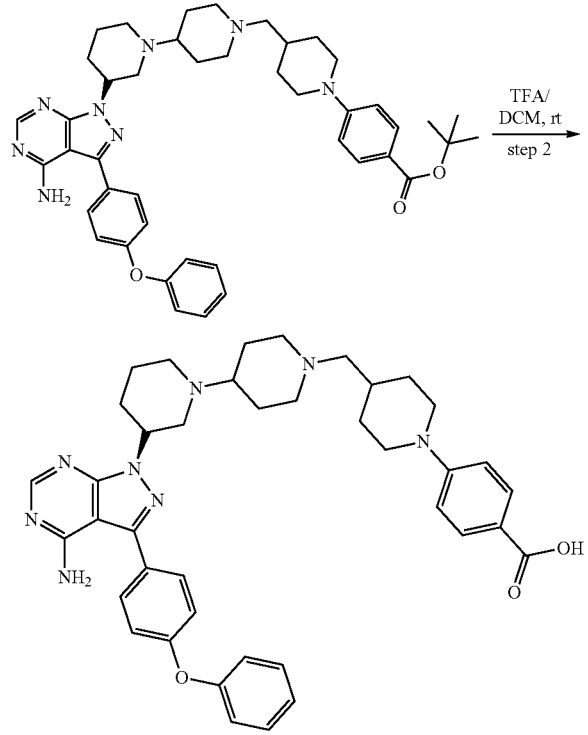

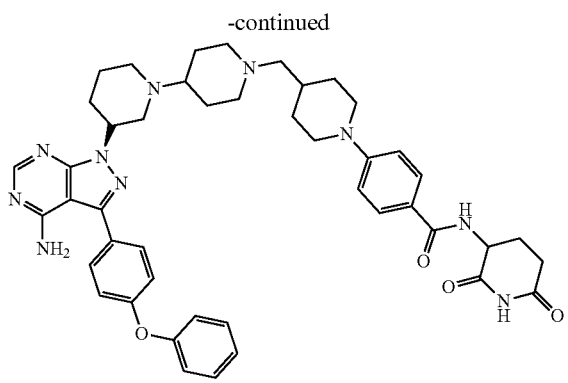

The above obtained tert-butyl (R)-4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)benzoate (0.23 g) was dissolved in 10 mL of DCM. 2 mL of TFA was added at rt. After stirring for 2 h, the solvent was removed in vacuo to provide crude (R)-4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)benzoic acid as brown solid, which was used in the next step without further purification.

Step 3. 4-(4-(((R)-3-(4-amino-3-(4-phenoxyphenyl)-1H-pyrazolo[3,4-d]pyrimidin-1-yl)-[1,4'-bipiperidin]-1'-yl)methyl)piperidin-1-yl)-N-(2,6-dioxopiperidin-3-yl)benzamide (compound 516)

To a solution of (R)-4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)benzoic acid (0.1 g, 0.25 mmol), 3-aminopiperidine-2,6-dione HCl salt and DIEA in 5 mL of DMF was added DIEA followed by HBTU at room temperature. After stirring for 16 h, the mixture was subjected onto silica gel column chromatography to provide crude product. The product was further purified by prep-HPLC, C18 column, with 0.5% FA water-MeCN as eluent. 21 mg of 4-(4-(((R)-3-(4-amino-3-(4-phenoxyphenyl)-1H-pyrazolo[3,4-d]pyrimidin-1-yl)-[1,4'-bipiperidin]-1'-yl)methyl)piperidin-1-yl)-N-(2,6-dioxopiperidin-3-yl)benzamide (compound 516) was obtained as white solid. LCMS (M+H) 797, $^1$H NMR: δ 1.53-2.13 (14H, m), 2.20-2.72 (12H, m), 2.86-3.01 (2H, m), 3.35-3.55 (4H, m), 4.61 (1H, d), 5.05 (1H, d), 6.88-7.03 (4H, m), 7.12 (1H, t), 7.21-7.45 (4H, m), 7.68-7.83 (4H, m), 8.25 (1H, s), 10.83 (1H, s).

Following above procedures, 4-(4-((4-(((R)-3-(4-amino-3-(4-phenoxyphenyl)-1H-pyrazolo[3,4-d]pyrimidin-1-yl)piperidin-1-yl)methyl)piperidin-1-yl)methyl)piperidin-1-yl)-N-(2,6-dioxopiperidin-3-yl)benzamide (compound 515) was obtained as white solid. LCMS (M+H) 811, $^1$H NMR: δ 1.47-1.70 (7H, m), 1.75-2.12 (8H, m), 2.20-2.69 (13H, m), 2.85-3.00 (2H, m), 3.35-3.55 (4H, m), 4.61-4.85 (2H, m), 6.88-7.03 (4H, m), 7.12 (1H, d), 7.21-7.45 (4H, m), 7.68-7.83 (4H, m), 8.25 (1H, s), 8.44 (1H, d), 10.83 (1H, s).

Example 39: Preparation of Compound 517, Compound 512, Compound 513

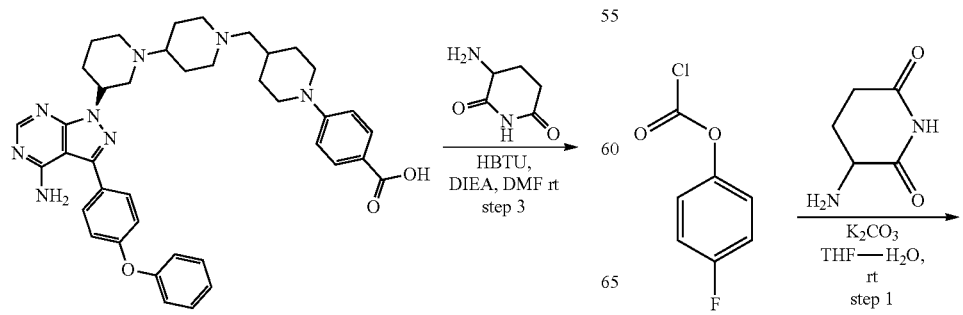

959
-continued

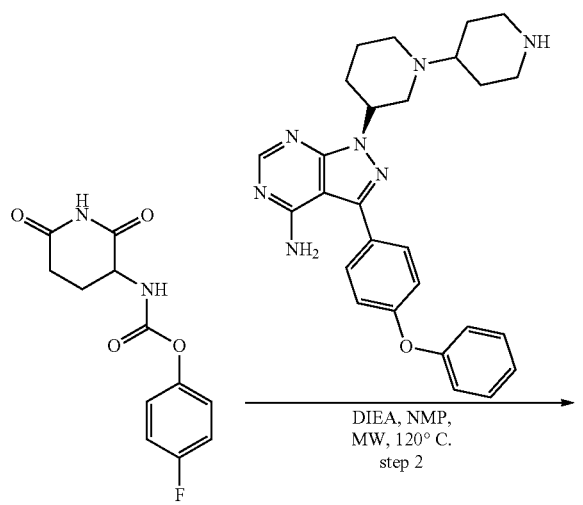

DIEA, NMP,
MW, 120° C.
step 2

960
-continued

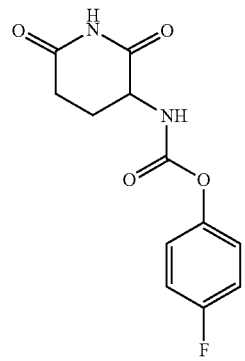

To a solution of 3-aminopiperidine-2,6-dione 2 HCl salt (4.1 g, 25 mmol) and potassium carbonate (10.4 g, 75 mmol) in 75 mL-75 mL of THF-water was added 4-fluorophenyl carbonochloridate (4.4 g, 25 mmol) at room temperature. After stirring for 2 hours, the solids were collected and washed with water. The solids were dried to provide 4.71 g of 4-fluorophenyl(2,6-dioxopiperidin-3-yl)carbamate as white solid.

Step 2. (3R)-3-(4-amino-3-(4-phenoxyphenyl)-1H-pyrazolo[3,4-d]pyrimidin-1-yl)-N-(2,6-dioxopiperidin-3-yl)-[1,4'-bipiperidine]-1'-carboxamide (compound 517)

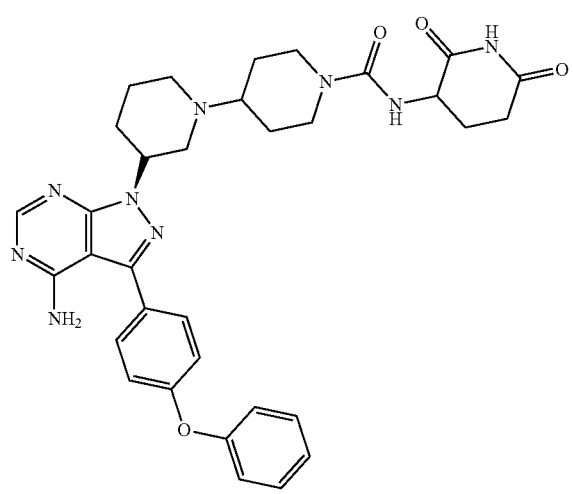

Step 1.
4-fluorophenyl(2,6-dioxopiperidin-3-yl)carbamate

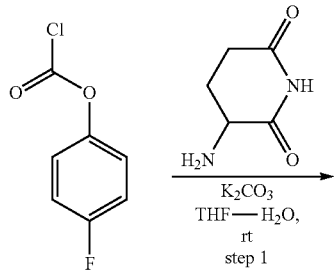

$K_2CO_3$
THF—$H_2O$,
rt
step 1

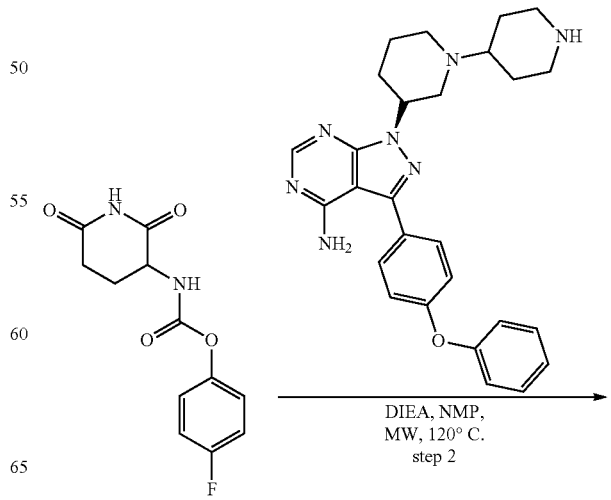

DIEA, NMP,
MW, 120° C.
step 2

-continued

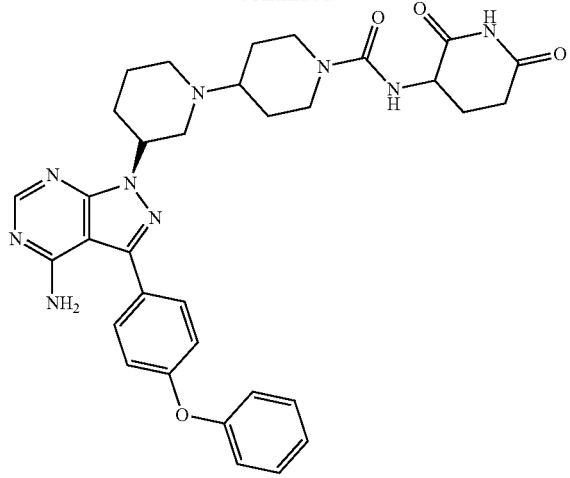

-continued compound 529

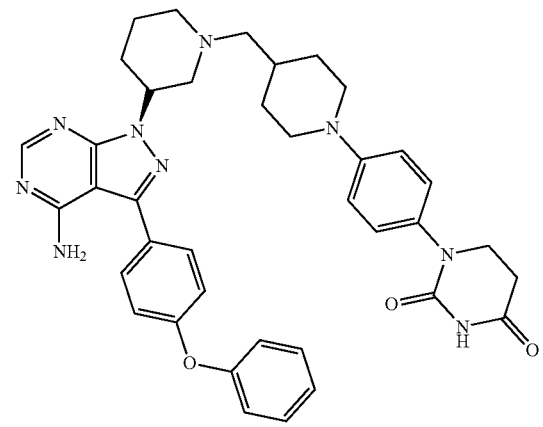

A solution of 4-fluorophenyl (2,6-dioxopiperidin-3-yl) carbamate (0.14 mg, 0.5 mmol), (R)-1-([1,4'-bipiperidin]-3-yl)-3-(4-phenoxyphenyl)-1H-pyrazolo[3,4-d]pyrimidin-4-amine (0.11 g, 0.25 mmol) and DIEA in 4 mL of NMP was heated in MW at 120° C. for 1 h. The mixture was subjected onto silica gel column chromatography to provide crude product. The product was further purified by prep-HPLC, C18 column, with 0.5% FA water-MeCN as eluent. 41 mg of (3R)-3-(4-amino-3-(4-phenoxyphenyl)-1H-pyrazolo[3,4-d] pyrimidin-1-yl)-N-(2,6-dioxopiperidin-3-yl)-[1,4'-bipiperidine]-1'-carboxamide (compound 517) was obtained as white solid LCMS (M+H) 624, $^1$H NMR: δ 1.13-1.42 (2H, m), 1.50-2.13 (8H, m), 2.19-2.39 (2H, m), 2.43-2.73 (4H, m), 2.86-3.01 (2H, m), 3.25-3.44 (4H, m), 4.63 (1H, d), 5.05 (1H, d), 7.05-7.25 (5H, m), 7.43 (2H, t), 7.65 (2H, d), 8.24 (1H, s), 10.67 (1H, s).

Following above procedures, 4-(((R)-3-(4-amino-3-(4-phenoxyphenyl)-1H-pyrazolo[3,4-d]pyrimidin-1-yl)piperidin-1-yl)methyl)-N-(2,6-dioxopiperidin-3-yl)piperidine-1-carboxamide (compound 518) LCMS (M+H) 638 and 1-(2-((R)-3-(4-amino-3-(4-phenoxyphenyl)-1H-pyrazolo[3,4-d] pyrimidin-1-yl)piperidin-1-yl)ethyl)-3-(2,6-dioxopiperidin-3-yl)urea (compound 519) LCMS (M+H) 584 were obtained as white solid.

Example 40: Preparation of Compounds 528 and 529 compound 528

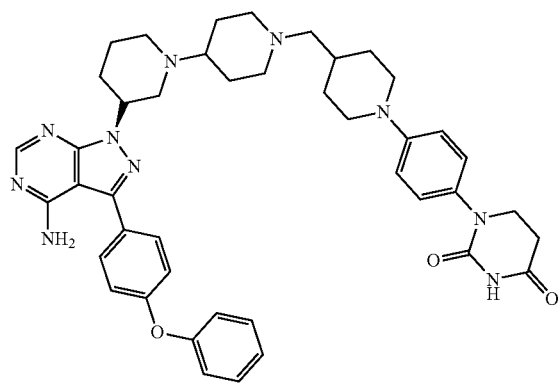

Step 1. (R)-1-(4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)phenyl)dihydropyrimidine-2,4(1H,3H)-dione

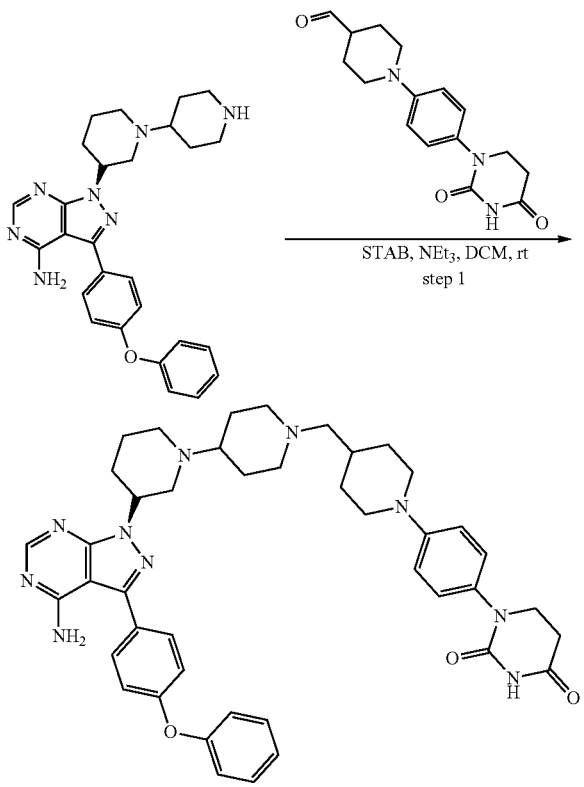

A solution of (R)-1-([1,4'-bipiperidin]-3-yl)-3-(4-phenoxyphenyl)-1H-pyrazolo[3,4-d]pyrimidin-4-amine (0.12 g, 0.25 mmol), 1-(4-(2,4-dioxotetrahydropyrimidin-1(2H)-yl) phenyl)piperidine-4-carbaldehyde (0.15 g, 0.5 mmol), triethylamine (1.0 g, 10 mmol) in 20 mL of DCM was stirred at room temperature. STAB was added portionwise at 0° C. and the resulting mixture was stirred at room temperature for 16 hours. The solvent was removed in vacuo. The residue was subjected onto silica gel column chromatography with 20% MeOH in EA as eluent to provide 22 mg of (R)-1-(4-(4-((3-(4-amino-3-(4-phenoxyphenyl)-1H-pyrazolo[3,4-d]pyrimidin-1-yl)-[1,4'-bipiperidin]-1'-yl)methyl)piperidin-1-yl)phenyl)dihydropyrimidine-2,4(1H,3H)-dione as white solid. LCMS (M+H) 755; 1H NMR (DMSO-d6, 400 MHz): δ 1.03-1.22 (2H, m), 1.42-1.50 (2H, m), 1.53-1.90 (8H, m), 1.94-2.19 (4H, m), 2.34-2.73 (12H, m), 2.86-3.01 (2H, m), 3.06-3.25 (4H, m), 3.54-3.77 (2H, m), 4.68-4.82 (1H, m), 6.83 (2H, d), 7.01-7.23 (6H, m), 7.36-7.45 (2H, t), 7.64 (2H, d), 8.24 (1H, s), 10.25 (1H, s).

Following above procedure, (R)-1-(4-(4-((3-(4-amino-3-(4-phenoxyphenyl)-1H-pyrazolo[3,4-d]pyrimidin-1-yl)piperidin-1-yl)methyl)piperidin-1-yl)phenyl)dihydropyrimidine-2,4(1H,3H)-dione was obtained as white solid. LCMS (M+H) 672; 1H NMR (DMSO-d6, 400 MHz): δ 1.12-1.25 (2H, m), 1.62-1.68 (2H, m), 1.69-1.83 (3H, m), 1.92-2.09 (3H, m), 2.19-2.28 (2H, m), 2.45 (1H, t), 2.57-2.71 (4H, m), 2.83 (1H, d), 3.03 (1H, d), 3.62-3.73 (4H, m), 4.73-4.82 (1H, m), 6.90 (1H, d), 7.09-7.23 (7H, m), 7.43 (2H, t), 7.65 (2H, d), 8.25 (1H, s), 10.25 (1H, s).

Example 41: Preparation of 1-(4-(6-(4-(4-amino-3-(4-phenoxyphenyl)-1H-pyrazolo[3,4-d]pyrimidin-1-yl)-[1,4'-bipiperidin]-1'-yl)hex-1-yn-1-yl)phenyl)dihydropyrimidine-2,4(1H,3H)-dione (Compound 535)

Step 1: Synthesis of 1-(4-(6-hydroxyhex-1-yn-1-yl)phenyl)dihydropyrimidine-2,4(1H,3H)-dione

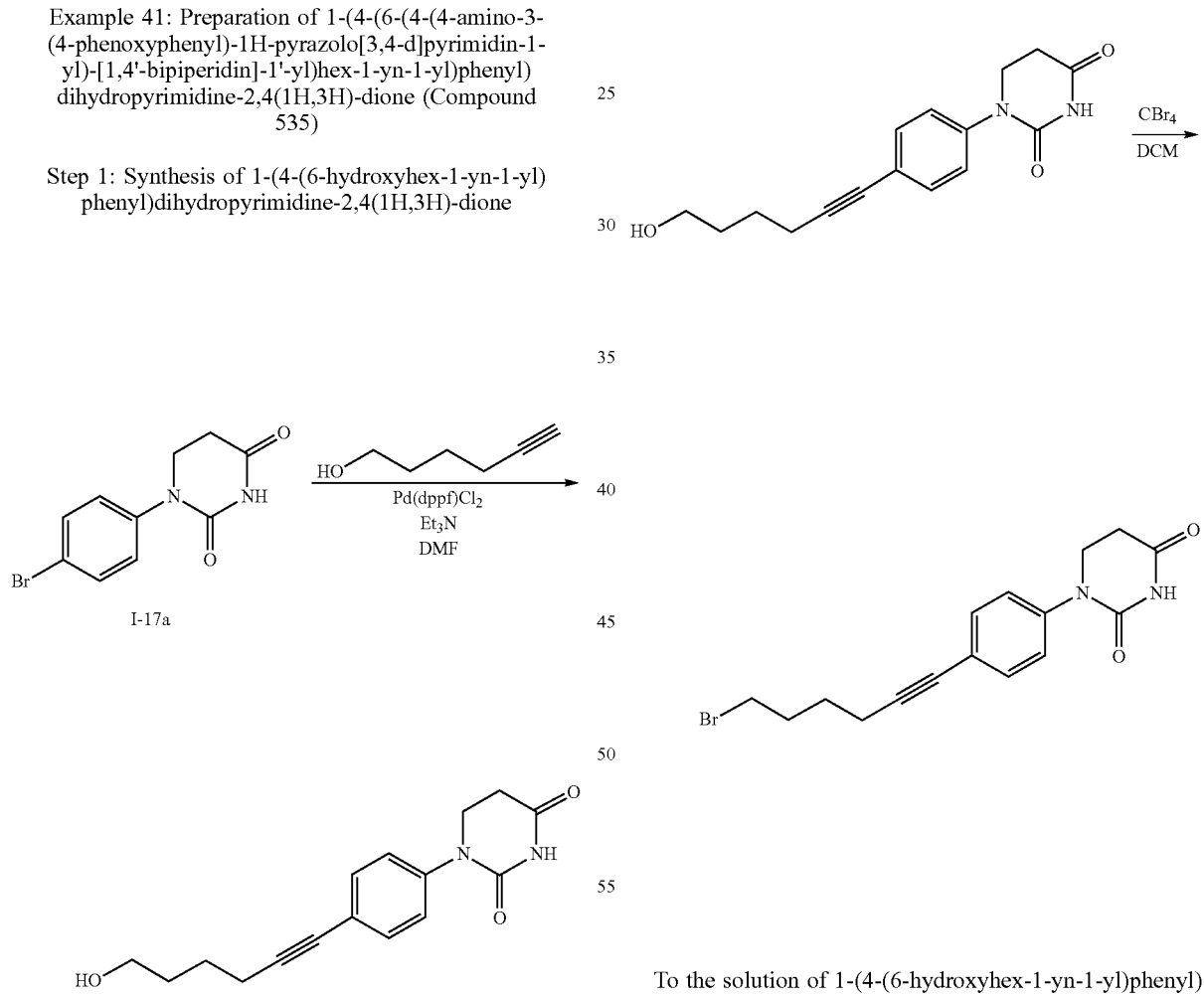

The reaction mixture of I-17a (1.50 g, 5.57 mmol), hex-5-yn-1-ol (0.74 ml, 6.69 mmol), Pd(dppf)₂Cl₂ (0.20 g, 0.28 mmol), CuI (0.11 g, 0.28 mmol) and Et₃N (2.3 ml, 16.7 mmol) in DMF (15 ml) was degassed and stirred at 85° C. in microwave reactor under N₂ for 3 hrs. Then, the mixture was poured to water (200 ml) with stir, followed by filtration.

The cake was soaked in chloroform and methanol (1/1, 20 ml) for 2 hrs, followed by being filtered. The aqueous solution was extracted with chloroform (20 ml×4). Both two organic layers were combined and washed with sat. NaCl solution, dried with Na₂SO₄.

The mixture was purified with flash column (SiO₂, MeOH in Chloroform=0-60%) to give the desired compound as brown semi-solid (1.40 g, 87.9%). LC-MS (ESI) m/z 287⁺ [M+H]⁺.

Step 2: Synthesis of 1-(4-(6-bromohex-1-yn-1-yl)phenyl)dihydropyrimidine-2,4(1H,3H)-dione To the solution of 1-(4-(6-hydroxyhex-1-yn-1-yl)phenyl)dihydropyrimidine-2,4(1H,3H)-dione (1.40 g, 4.89 mmol) and CBr₄ (2.11 g, 6.36 mmol) in DCM (30 ml) was added solution of PPh₃ (1.93 g, 7.34 mmol) in DCM (10 ml) dropwise. Upon the addition, the reaction mixture was stirred at r.t. under N₂ overnight. An off-white participate was found. The suspension was filtered. The crude product was washed with water, dried in oven (1.53 g, 90.1%). LC-MS (ESI) m/z 349⁺ and 351⁺ [M+H]⁺.

Step 3: Synthesis of 1-(4-(6-(4-(4-amino-3-(4-phenoxyphenyl)-1H-pyrazolo[3,4-d]pyrimidin-1-yl)-[1,4'-bipiperidin]-1'-yl)hex-1-yn-1-yl)phenyl)dihydropyrimidine-2,4(1H,3H)-dione

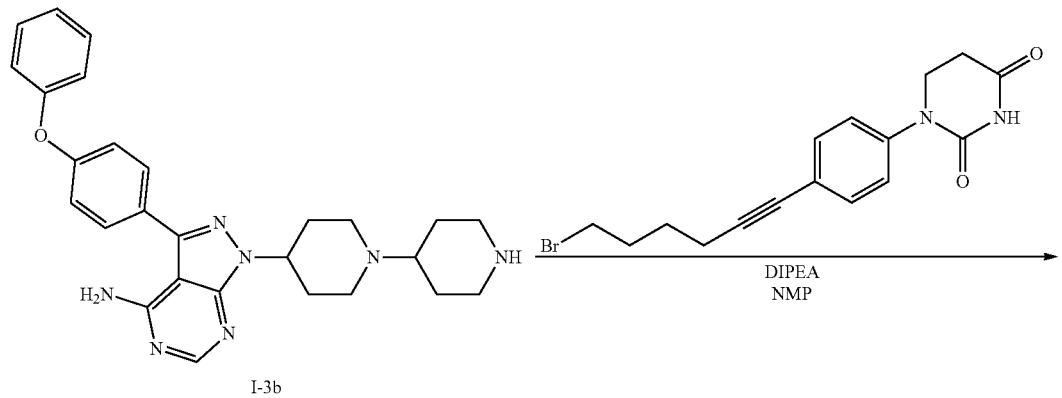

I-3b

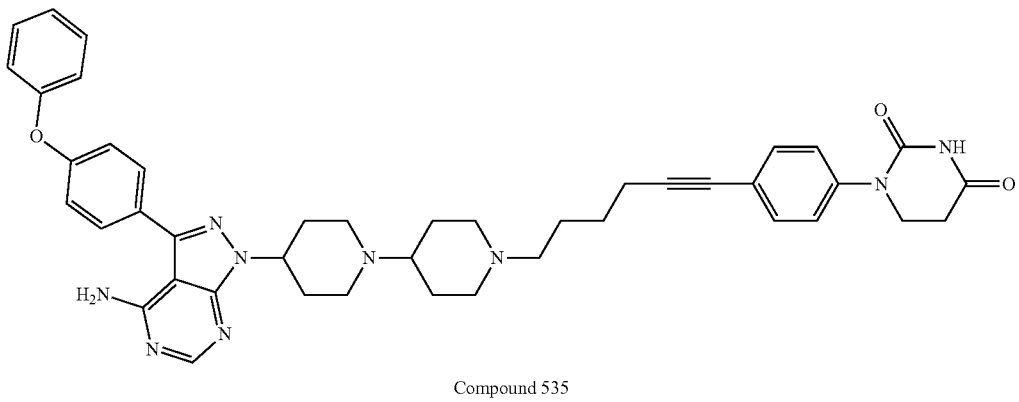

Compound 535

The reaction mixture of I-3b (0.15 g, 0.32 mmol), 1-(4-(6-bromohex-1-yn-1-yl)phenyl)dihydropyrimidine-2,4(1H,3H)-dione (0.15 g, 0.42 mmol) and DIPEA (0.11 ml, 0.64 mmol) in NMP (6 ml) was stirred at 110° C. (oil bath temp. 120±5° C.) under $N_2$ for 6 hrs. The mixture was separated with pre-HPLC (Eluent: MeCN in water=0-100%, 13 min) to obtain the desired compound as dark yellow solid (0.20 g, 85.2%). LC-MS (ESI) m/z 738$^+$[M+H]$^+$.

Example 42: Preparation of CRBN-Binding E3 Ligase Ligands (I-14 and I-16)

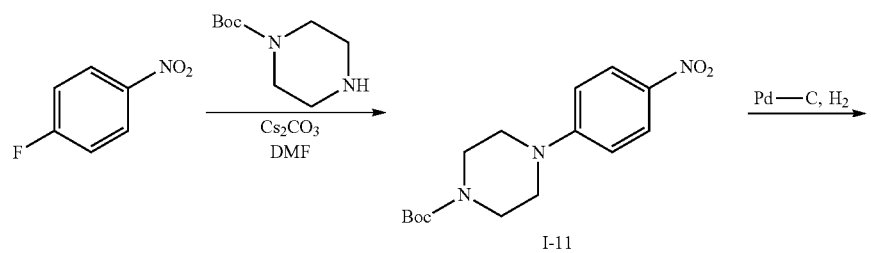

I-11

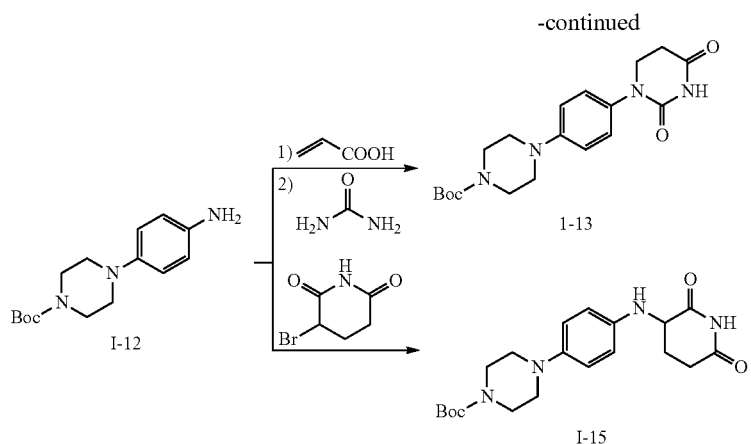
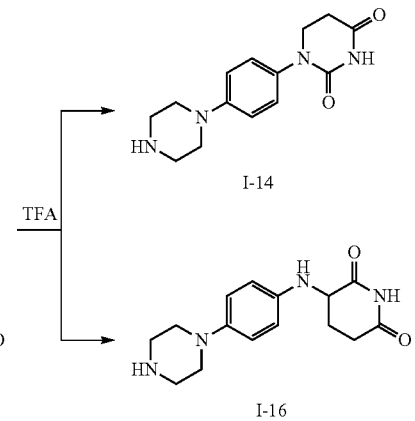

Synthesis of 1-(4-(piperazin-1-yl)phenyl)dihydropyrimidine-2,4(1H,3H)-dione (I-14)

Step 1. Synthesis of tert-butyl 4-(4-nitrophenyl)piperazine-1-carboxylate (I-11)

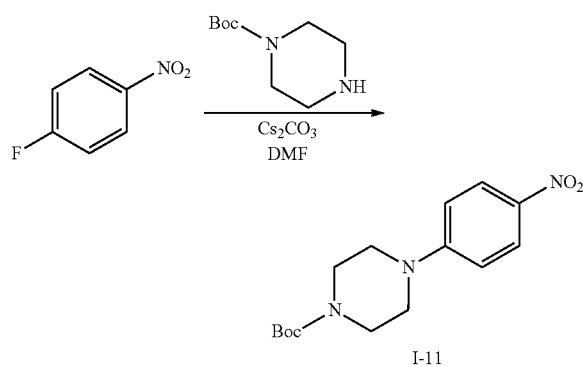

The reaction mixture of 1-fluoro-4-nitrobenzene (3.00 g, 21.7 mmol), tert-butyl piperazine-1-carboxylate (5.14 g, 27.6 mmol) and DIPEA (7.44 ml, 42.6 mmol) in DMF (30 ml) was stirred at 110° C. (oil bath temperature 120±5° C.) under $N_2$ for 5 hrs. After being cooled down, the mixture was poured to water (300 ml) with stir. A yellow participate was found. The suspension was filtered after being stood for 2 hrs. The cake was washed with water and dried in oven, which could be used for next step without further purification (I-11, 6.00 g, 91.7%). LC-MS (ESI) m/z 308$^+$ [M+H]$^+$.

Step 2. Synthesis of tert-butyl 4-(4-aminophenyl)piperazine-1-carboxylate (I-12)

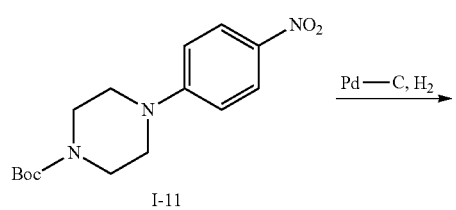

The reaction mixture of I-11 (6.00 g, 19.5 mmol) and Pd—C (10%, 0.60 g) in MeOH (200 ml) was degassed three times and stirred at r.t. under $H_2$ for 72 hrs. The suspension was filtered. The Pd—C cake was washed with hot MeOH. The combined filtrates were concentrated to obtain the desired compound I-12 as colorless semi-solid (5.00 g, 92.6%). LC-MS (ESI) m/z 278$^+$[M+H]$^+$.

Step 3. Synthesis of tert-butyl 4-(4-(2,4-dioxotetrahydropyrimidin-1(2H)-yl)phenyl)piperazine-1-carboxylate (I-13)

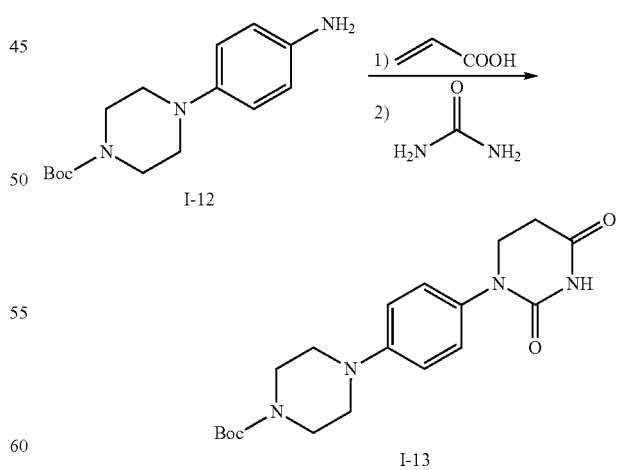

The reaction mixture of I-12 (2.75 g, 9.93 mmol) and acrylic acid (0.65 ml, 9.43 mmol) in water (30 ml) and acetic acid (6 ml) was refluxed for 6 hrs. After being cooled down, the mixture was diluted with water to 200 ml followed by being extracted with EA (50 ml×4). The combined EA layers were washed with brine (50 ml×2), dried over Na$_2$SO$_4$. The solvent was removed to obtain the intermedia as beige solid (3.00 g, 86.5%). LC-MS (ESI) m/z 350$^+$ [M+H]$^+$.

The reaction mixture of previous intermedia (3.00 g, 8.57 mmol) and urine (1.03 g, 17.1 mmol) in acetic acid (30 ml) was relaxed for 12 hrs. After being cooled down, the mixture was poured to water (300 ml) with stir. An off-white participate was found. The suspension was stood for 2 hrs followed by being filtered. The cake was washed with water and dried in oven. The crude product (I-13) was used for next step without further purification (3.00 g, 80.9% two steps). LC-MS (ESI) m/z 375$^+$ [M+H]$^+$.

Step 4. Synthesis of 1-(4-(piperazin-1-yl)phenyl) dihydropyrimidine-2,4(1H,3H)-dione (I-14)

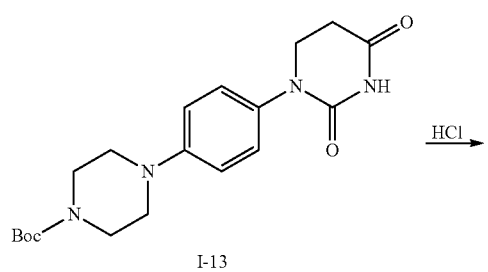

The reaction mixture of I-13 (3.00 g, 8.01 mmol) and hydrochloride solution (3 M in Methanol, 20 ml) in MeOH (10 ml) was stirred at r.t. overnight. A beige participate was found. The suspension was filtered, and the cake was washed with DCM, dried in oven. The crude product was obtained as hydrochloride (I-14, 2.49 g). LC-MS (ESI) m/z 275$^+$ [M+H]$^+$.

Synthesis of 3-((4-(piperazin-1-yl)phenyl)amino) piperidine-2,6-dione (I-16)

Step 1. Synthesis of tert-butyl 4-(4-((2,6-dioxopiperidin-3-yl)amino)phenyl)piperazine-1-carboxylate (I-15)

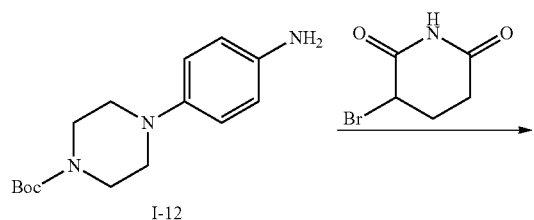

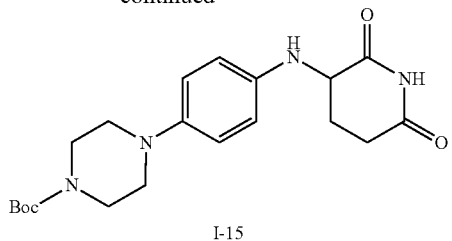

The reaction mixture of I-12 (2.75 g, 9.90 mmol), 3-bromopiperidine-2,6-dione (2.85 g, 14.9 mmol) and DIPEA (3.46 ml, 19.8 mmol) in DMF (20.0 ml) was stirred at 90° C. (oil bath temperature 100±5° C.) under N$_2$ for 16 hrs. After being cooling down to r.t., the mixture was poured to water (300 ml) with stir slowly followed by being extracted with EA (100 ml×5).

The combined organic layers were washed with brine (100 ml×3), dried over Na$_2$SO$_4$. The solvent was removed under vacuum to obtain the desired compound (I-15) as semi-solid, which was used for next step without purification (3.50 g, 91.1%). LC-MS (ESI) m/z 389$^+$ [M+H]$^+$.

Step 2. Synthesis of 1-(4-(piperazin-1-yl)phenyl) dihydropyrimidine-2,4(1H,3H)-dione (I-14)

Synthesis of 3-((4-(piperazin-1-yl)phenyl)amino) piperidine-2,6-dione (I-16)

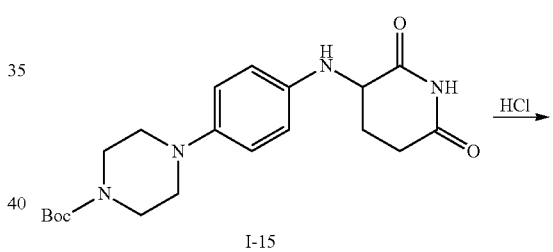

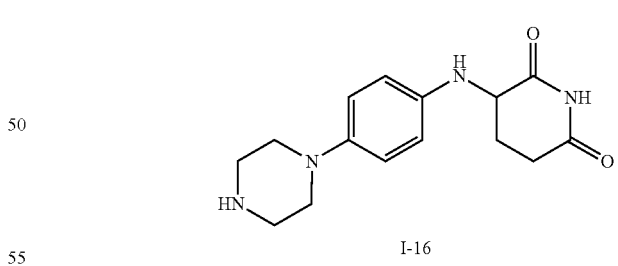

The reaction mixture of I-15 (3.00 g, 7.73 mmol) and hydrochloride solution (3 M in Methanol, 10 ml) in DCM (5 ml) was stirred at r.t. for 2 hrs. The solvent was removed under vacuum to obtain the crude compound as hydrochloride (I-16, 2.50 g). LC-MS (ESI) m/z 289$^+$ [M+H]$^+$.

Example 43: Preparation of CRBN-Binding E3 Ligase Ligands (I-19 and I-22)

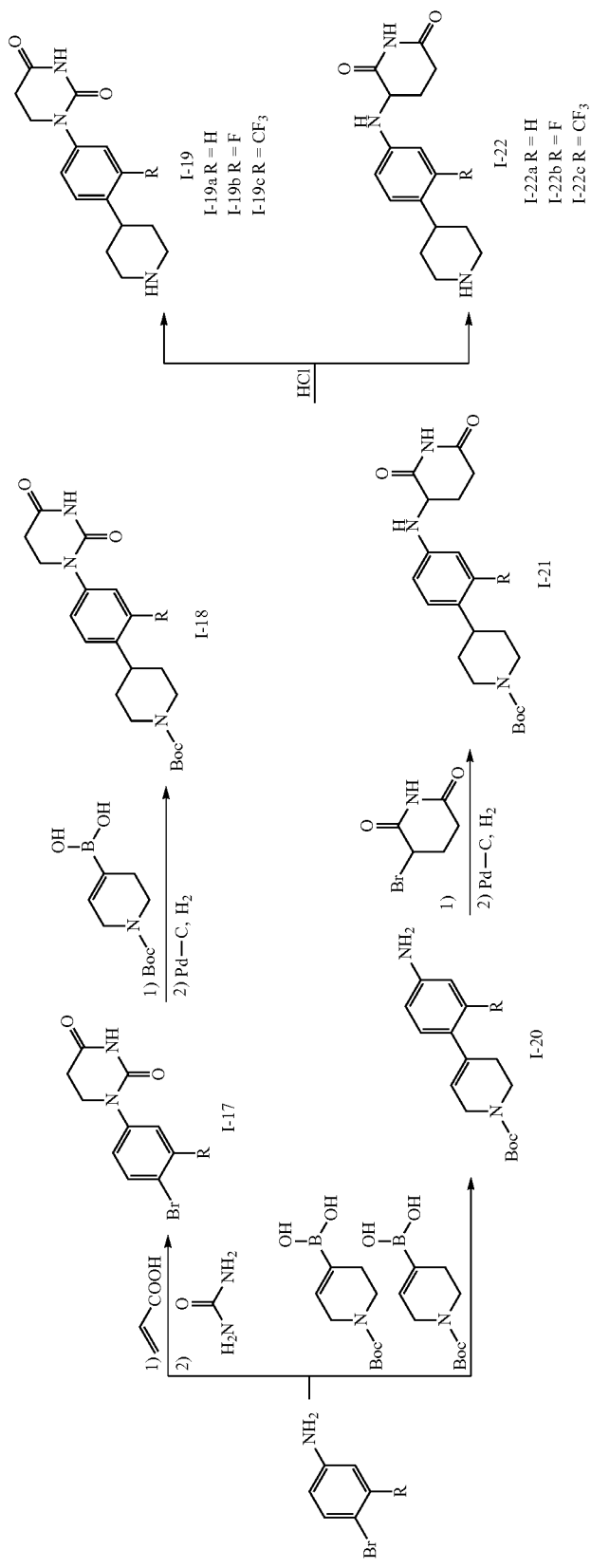

Synthesis of 1-(4-(piperidin-4-yl)phenyl)dihydropyrimidine-2,4(1H,3H)-dione (I-19a)

Step 1. Synthesis of 1-(4-bromophenyl)dihydropyrimidine-2,4(1H,3H)-dione (I-17a)

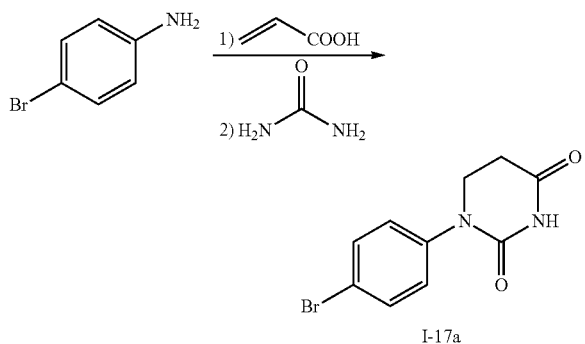

The reaction mixture of 4-bromoaniline (10.0 g, 58.1 mmol) and acrylic acid (3.80 ml, 55.2 mmol) in water (50 ml) and acetic acid (10 ml) was reflexed for 6 hrs. A beige participate was found after being cooled down to r.t. The suspension was filtered after being still for 1 hr, followed by being filtered. The cake was washed with water, dried in oven (11.68 g, 82.3%). LC-MS (ESI) m/z 241- and 243- [M−H]−.

The reaction mixture of intermedia (11.68 g, 48.3 mmol) and urine (5.75 g, 95.8 mmol) in Acetic acid (40 ml) was reflexed for 12 h. An off-white participate was found after being cooled down to r.t. The suspension was filtered after being stood at r.t. for 1 hr. The cake was washed with water and dried in oven. The crude product was obtained as beige solid (12.0 g, 92.4%). LC-MS (ESI) m/z 269+ [M+H]+, 288+ [M+H$_2$O]+.

Step 2. Synthesis of tert-butyl 4-(4-(2,4-dioxotetrahydropyrimidin-1(2H)-yl)phenyl)piperidine-1-carboxylate (I-18a)

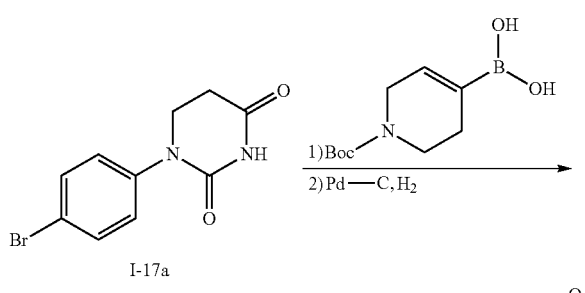

The reaction mixture of I-17a (2.00 g, 7.43 mmol), (1-(tert-butoxycarbonyl)-1,2,3,6-tetrahydropyridin-4-yl)boronic acid (2.02 g, 8.92 mmol) and K$_3$PO$_4$ (1.89 g, 8.92 mmol) in 1,4-dioxane (25 ml) and water (5 ml) was degassed for 1 min with stir. To the suspension was added Pd(dppf)$_2$Cl$_2$ (0.55 g, 0.74 mmol). The reaction mixture was reflexed under N$_2$ for 16 hrs. After being cooled down to r.t., the mixture was poured to water (300 ml) with stir. A pink participation was found. The suspension was filtered after being stood still for 2 hrs. The cake was washed with water and dried in oven. The desired compound was obtained as pink solid (2.60 g, 94.2%). LC-MS (ESI) m/z 372+ [M+H]+.

The reaction mixture of intermedia (2.60 g, 7.00 mmol) and Pd—C (10%, 0.30 g) in MeOH was degassed and stirred under H$_2$ overnight. The suspension was filtered, and the cake was washed with hot MeOH. The combined filtrates were concentrated to obtain the desired compound I-18a as colorless solid (2.60 g, quantitative). LC-MS (ESI) m/z 374+ [M+H]+.

Step 3. Synthesis of 1-(4-(piperidin-4-yl)phenyl)dihydropyrimidine-2,4(1H,3H)-dione (I-19a)

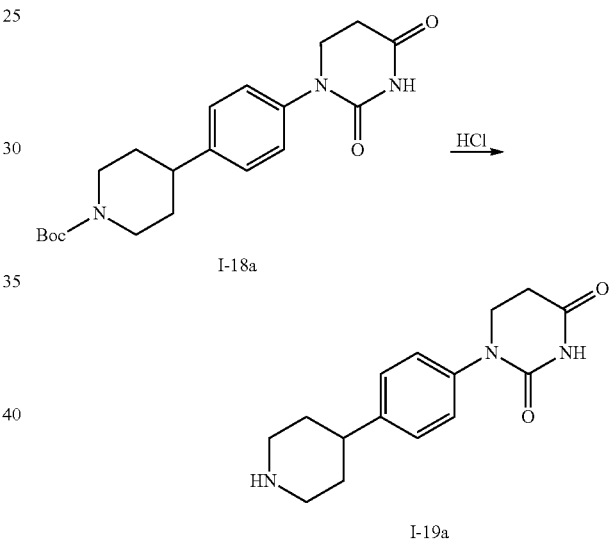

The reaction mixture of I-18a (2.60 g, 7.00 mmol) and hydrochloride solution (3 M in Methanol, 10 ml) in MeOH (5 ml) was stirred at r.t. overnight. The solvent was removed to obtain a yellow solid (hydrochloride, 1.90 g, 98.9%).

Synthesis of 3-((4-(piperidin-4-yl)phenyl)amino)piperidine-2,6-dione (I-22a)

Step 1. Synthesis of tert-butyl 4-(4-aminophenyl)-3,6-dihydropyridine-1(2H)-carboxylate (I-20a)

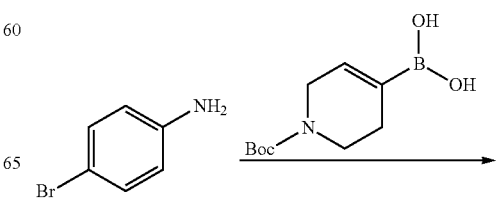

-continued

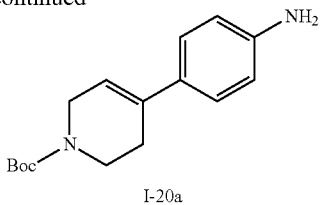
I-20a

The reaction mixture of 4-bromoaniline (2.00 g, 11.6 mmol), (1-(tert-butoxycarbonyl)-1,2,3,6-tetrahydropyridin-4-yl)boronic acid (3.92 g, 17.4 mmol) and $K_3PO_4$ (3.67 g, 17.4 mmol) in 1,4-dioxane (30 ml) and water (6 ml) was degassed for 1 min with stir. To the suspension was added $Pd(dppf)_2Cl_2$ (0.43 g, 0.58 mmol). The reaction mixture was reflexed under $N_2$ for 16 hrs. After being cooled down to r.t., the mixture was poured to water (300 ml) with stir. A pink participation was found. The suspension was filtered after being stood still for 2 hrs. The cake was washed with water and dried in oven. The desired compound was obtained as pink solid (2.90 g, 91.5%). LC-MS (ESI) m/z 275$^+$ [M+H]$^+$.

Step 2. Synthesis of tert-butyl 4-(4-((2,6-dioxopiperidin-3-yl)amino)phenyl)piperidine-1-carboxylate (I-21a)

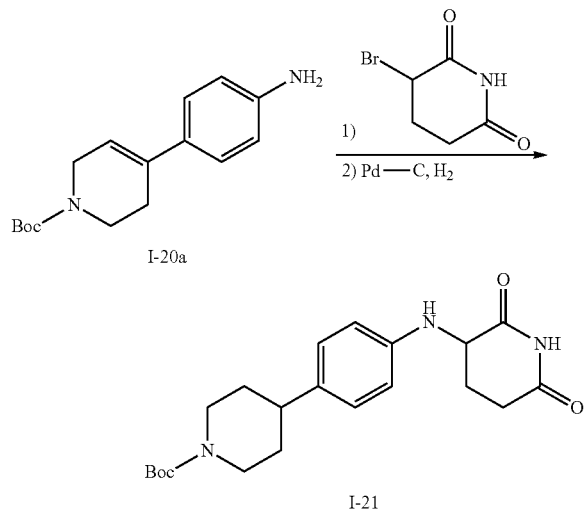

The reaction mixture of I-20 (2.50 g, 9.12 mmol), 3-bromopiperidine-2,6-dione (2.62 g, 13.7 mmol) and DIPEA (2.39 ml, 13.7 mmol) in DMF (20.0 ml) was stirred at 90° C. (oil bath temperature 100±5° C.) under $N_2$ for 16 hrs. After being cooling down to r.t., the mixture was poured to water (200 ml) with stir slowly followed by being extracted with EA (100 ml×5).

The combined organic layers were washed with brine (100 ml×3), dried over $Na_2SO_4$. The solvent was removed, the residue was separated with flash column (MeOH in EA, 0-100%) to give the desired compound as black semi-solid (2.75 g, 78.3%). LC-MS (ESI) m/z 386$^+$ [M+H]$^+$.

The suspension of intermedia (2.75 g, 7.11 mmol) and Pd—C (10%, 0.30 g) in MeOH was stirred at r.t. under $H_2$ for 48 hrs. The mixture was filtered, and the cake was washed with hot MeOH. The combined filtrates were concentrated to obtain the I-21 as black semi-solid (2.70 g). LC-MS (ESI) m/z 388$^+$ [M+H]$^+$.

Step 3. Synthesis of 3-((4-(piperidin-4-yl)phenyl)amino)piperidine-2,6-dione (I-22a)

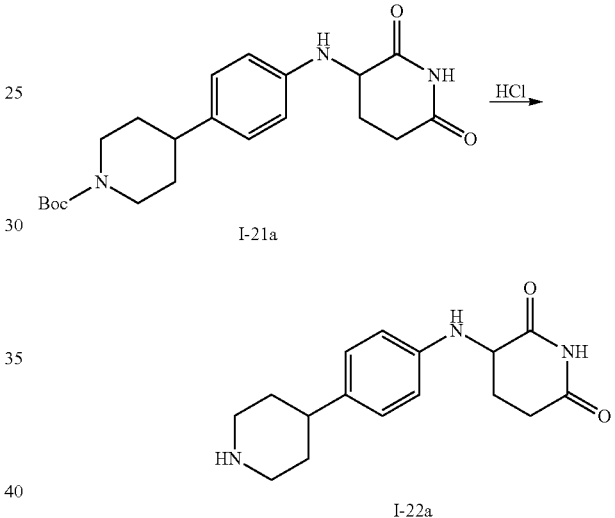

The reaction mixture of I-21a (2.70 g, 6.98 mmol) and hydrochloride solution (3 M in Methanol, 10 ml) in MeOH (5 ml) was stirred at r.t. overnight. The solvent was removed to obtain the desired compound as hydrochloride (off-white solid, 2.20 g). LC-MS (ESI) m/z 288$^+$ [M+H]$^+$.

Example 44: Preparation of CRBN-Binding E3 Ligase Ligands

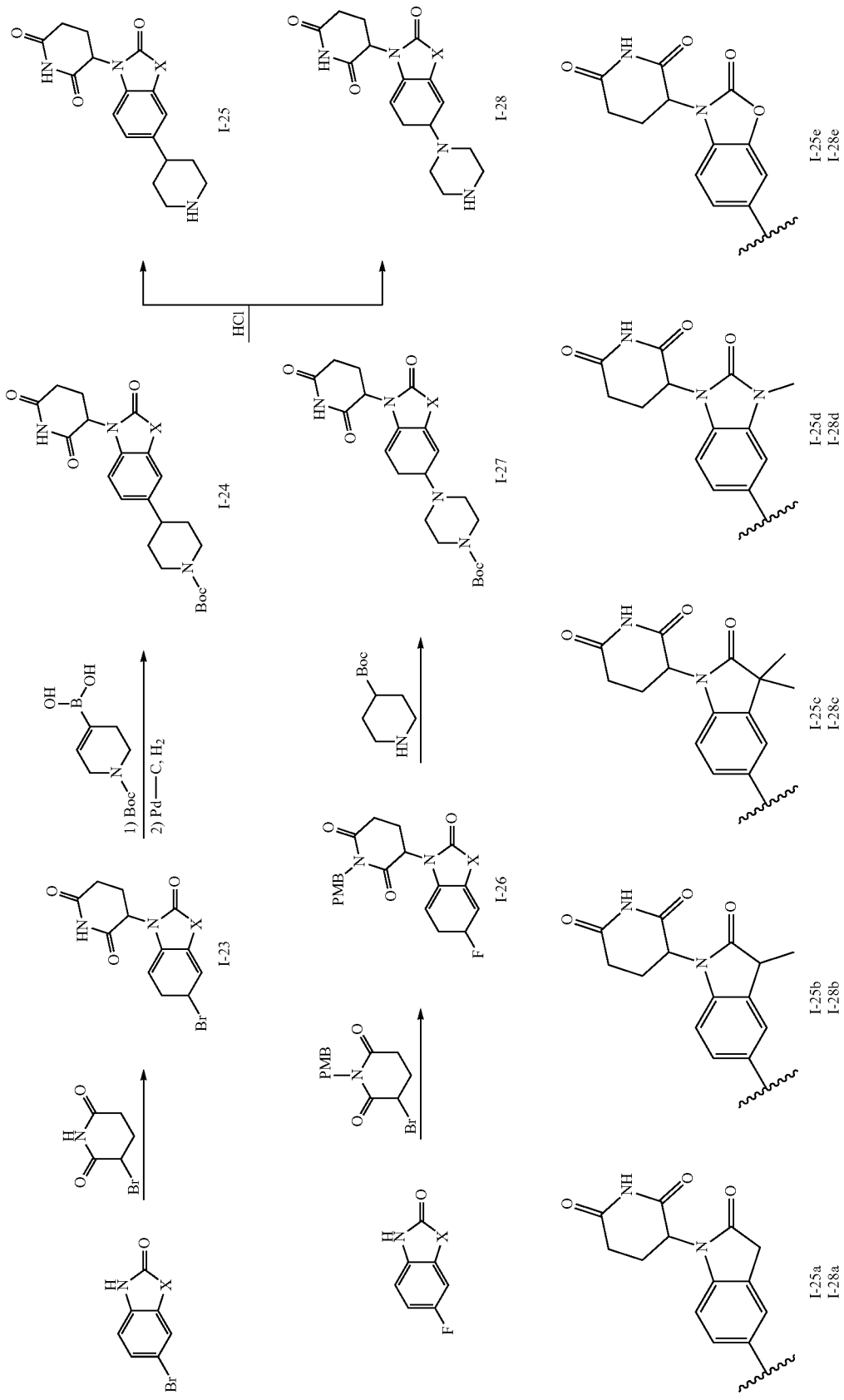

Synthesis of 3-(2-oxo-6-(piperidin-4-yl)benzo[d]oxazol-3(2H)-yl)piperidine-2,6-dione (I-25e)

Step 1. Synthesis of 3-(6-bromo-2-oxobenzo[d]oxazol-3(2H)-yl)piperidine-2,6-dione (I-23e)

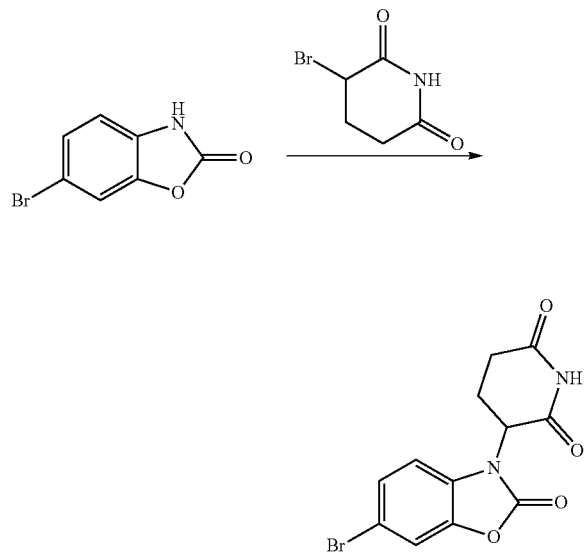 [SMILES: O=c1[nH]c2ccc(Br)cc2o1 ; O=C1CCC(Br)C(=O)N1 ; O=C1CCC(n2c(=O)oc3cc(Br)ccc32)C(=O)N1]

The solution of 6-bromobenzo[d]oxazol-2(3H)-one (1.00 g, 4.67 mmol) and Cs$_2$CO$_3$ (3.04 g, 9.34 mmol) in DMF (10 ml) was stirred at r.t. for 30 min, followed by adding the 3-bromopiperidine-2,6-dione (1.79 g, 9.34 mmol). The RM was stirred at r.t. under N$_2$ for 30 min, at 50° C. for 16 hrs. The reaction mixture was cooled down and poured to water (300 ml) with stir. An off-white participate was found followed by being filtered. The cake was washed with water and dried in oven to obtain a grey powder, which was used for next step without further purification (0.87 g, 57.3%). LC-MS (ESI) m/z 325$^+$, 327$^+$ [M+H]$^+$.

Step 2. Synthesis of tert-butyl 4-(3-(2,6-dioxopiperidin-3-yl)-2-oxo-2,3-dihydrobenzo[d]oxazol-6-yl)-3,6-dihydropyridine-1(2H)-carboxylate (I-24e)

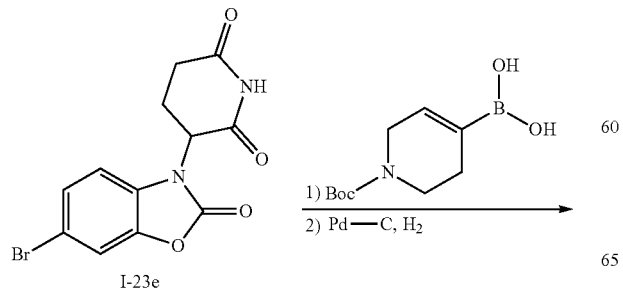

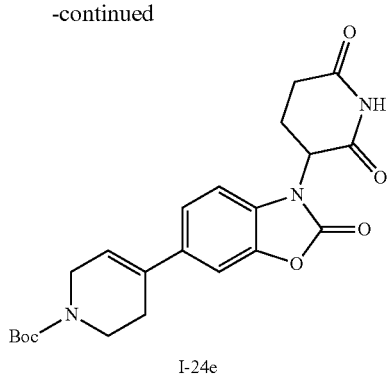

The reaction mixture of I-23e (0.40 g, 1.23 mmol), (1-(tert-butoxycarbonyl)-1,2,3,6-tetrahydropyridin-4-yl)boronic acid (0.34 g, 1.48 mmol) and K$_3$PO$_4$ (0.31 g, 1.48 mmol) in 1,4-dioxane (15 ml) and water (3 ml) was degassed for 1 min with stir. To the suspension was added Pd(dppf)$_2$Cl$_2$ (0.10 g, 0.13 mmol). The reaction mixture was reflexed under N$_2$ for 16 hrs. The mixture was separated with flash column (SiO$_2$, MeOH in EA=0-30%) to give the desired compound as yellow semi-solid (0.40 g, 76.2%). LC-MS (ESI) m/z 426$^+$ [M+H]$^+$.

The mixture of intermedia and Pd—C (0.10 g) in MeOH was stirred at r.t. under H$_2$ for 48 hrs. The suspension was filtered, and the cake was washed with hot MeOH. The combined filtrates were concentrated to obtain am off-white solid (0.40 g). LC-MS (ESI) m/z 428$^+$ [M+H]$^+$.

Step 3. Synthesis of 3-(2-oxo-6-(piperidin-4-yl)benzo[d]oxazol-3(2H)-yl)piperidine-2,6-dione (I-25e)

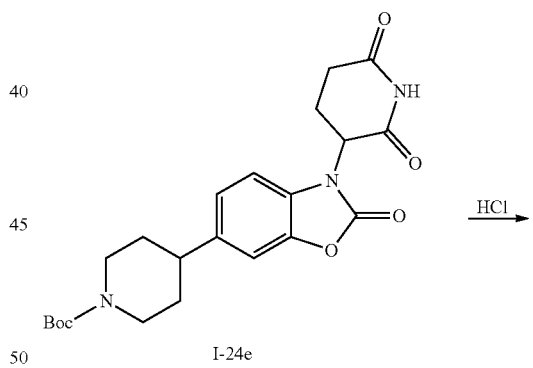

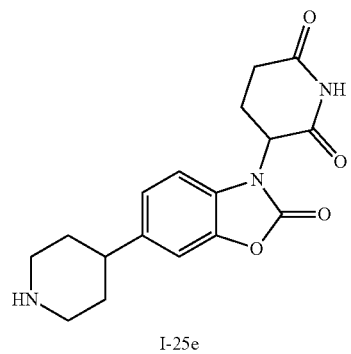

The mixture of I-24e (0.40 g, 0.94 mmol) and hydrochloride solution (3 M in Methanol, 10 ml) in MeOH (5 ml) was stirred at r.t. overnight. The solvent was removed to obtain I-25e as an off-white solid (hydrochloride, 0.32 g). LC-MS (ESI) m/z 328$^+$ [M+H]$^+$.

Example 45: Preparation of 1-(4-(4-((4-((4-(4-amino-3-(4-phenoxyphenyl)-1H-pyrazolo[3,4-d]pyrimidin-1-yl)piperidin-1-yl)methyl)piperidin-1-yl)methyl)piperidin-1-yl)phenyl)dihydropyrimidine-2,4(1H,3H)-dione (Compound 552)

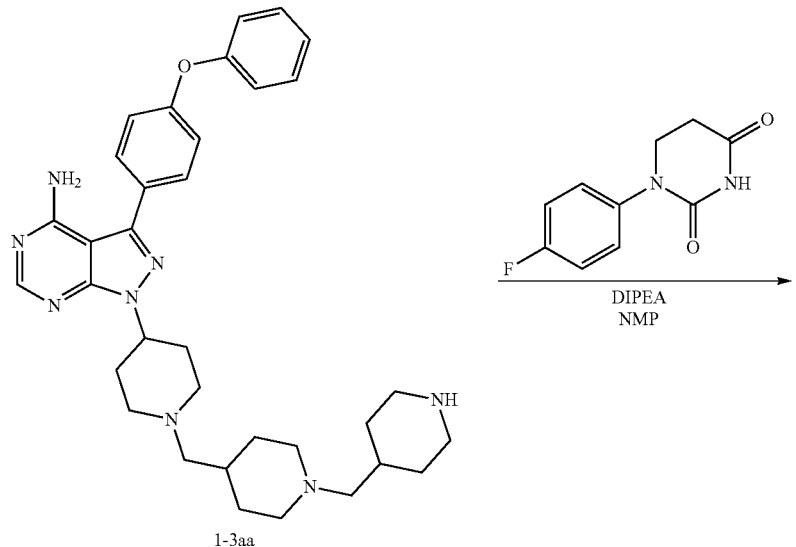

I-3aa

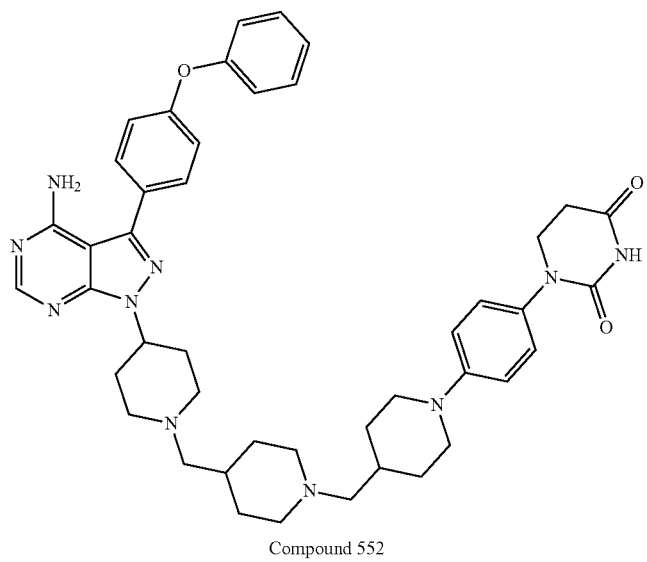

Compound 552

The mixture of I-3aa (0.10 g, 0.17 mmol) and DIPEA (0.10 ml) in NMP (5 ml) was stirred at r.t. for 15 min, followed by adding 1-(4-fluorophenyl)dihydropyrimidine-2,4(1H,3H)-dione (70 mg, 0.34 mmol). The reaction mixture was stirred at 120° C. under $N_2$ for 4 h.

The mixture was separated with Prep-HPLC (Elute: $CH_3CN$ in water=10-100%, 15 min) to give desired compound as an off-white solid (0.11 g, 84.3%). LC-MS (ESI$^+$) m/z=769$^+$ [M+H]$^+$, 385$^+$ [M+2H]$^{2+}$.

Example 46: Preparation of 1-(4-(1-((1-(2-(4-(4-amino-3-(4-phenoxyphenyl)-1H-pyrazolo[3,4-d]pyrimidin-1-yl)piperidin-1-yl)ethyl)piperidin-4-yl)methyl)piperidin-4-yl)phenyl)dihydropyrimidine-2,4(1H,3H)-dione (Compound 553)

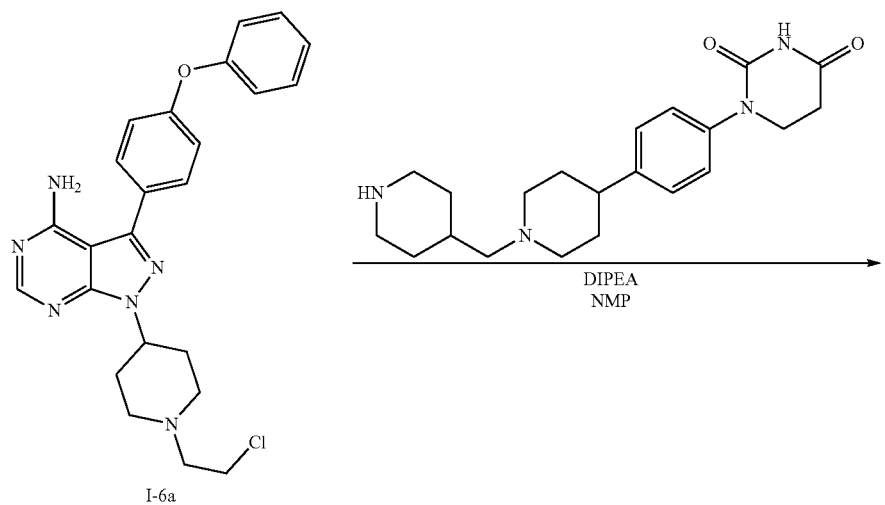

Compound 553

The mixture of I-6a (0.15 g, 0.33 mmol), 1-(4-(1-(piperidin-4-ylmethyl)piperidin-4-yl)phenyl)dihydropyrimidine-2,4(1H,3H)-dione (0.17 g, 0.45 mmol) and DIPEA (0.13 ml, 0.72 mmol) in NMP (6 ml) was stirred at 90° C. under $N_2$ for 8 h. The mixture was filtered and separated with Prep-HPLC (Elute: $CH_3CN$ in $H_2O$=10-100%, 15 min) to give desired compound as an off-white solid (0.18 g, 70.1%). LC-MS (ESI$^+$) m/z=783$^+$ [M+H]$^+$, 393$^+$ [M+2H]$^{2+}$.

Example 47: 1-(4-(4-(3-(4-((4-(4-amino-3-(4-phenoxyphenyl)-1H-pyrazolo[3,4-d]pyrimidin-1-yl)piperidin-1-yl)methyl)piperidin-1-yl)propyl)piperazin-1-yl)phenyl)dihydropyrimidine-2,4(1H,3H)-dione (Compound 582)

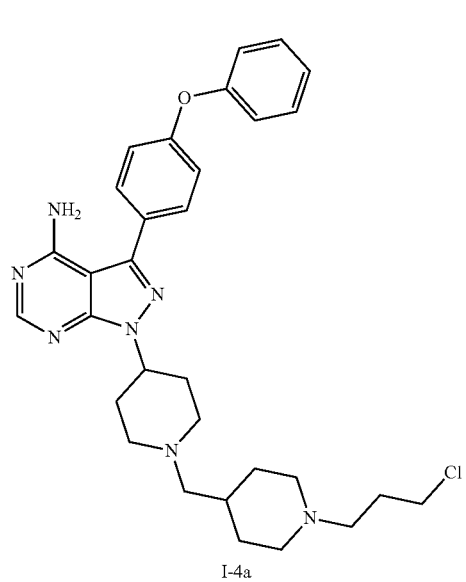

I-4a

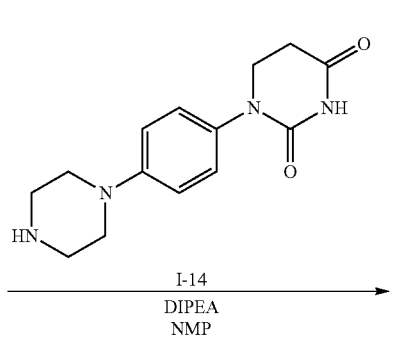

I-14
DIPEA
NMP

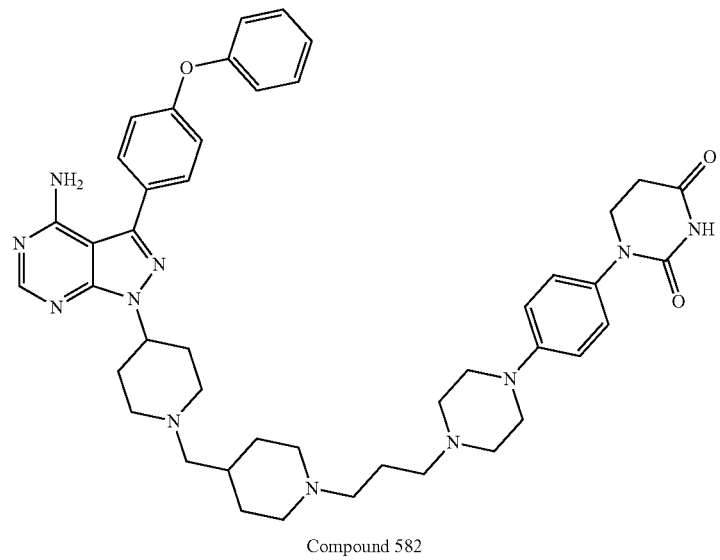

Compound 582

The mixture of I-14 (0.15 g, 0.55 mmol) and DIPEA (0.15 ml) in NMP (6 ml) was stirred at r.t. for 30 min, followed by adding I-4a (0.44 g, 0.40 mmol). The reaction mixture was stirred at 90° C. under $N_2$ for 8 h.

The mixture was separated with Prep-HPLC ($CH_3CN$ in water=0-100%, 15 min) to give the desired compound as an off-white solid (0.20 g, 62.9%). LC-MS ($ESI^+$) m/z=798$^+$ [M+H]$^+$, 400$^+$ [M+2H]$^{2+}$.

Example 48: Degradation of BTK Protein

Degradation of BTK protein by exemplary compounds of the present disclosure was assessed in Namalwa, JeKo-1, and Mino cells.

Namalwa, JeKo-1, or Mino cells were plated in 24-well plates at a density of $10^5$ cells/well. Media containing various drug concentrations were added on the day following plating (day 0) and allowed to incubate for 24 hours for Western blot. Media with the tested compound was changed every other day. Cells were lysed, snapped frozen in liquid nitrogen, and stored at −80° C. until assay for ERα. Media were removed and dishes were washed with 1×DPBS. Lysates were made by adding 150 μL of complete lysis solution and scraping cells into a 1.5 mL microcentrifuge tube. Lysates were placed on a rotisserie at 4° C. for 30 min and then spun at 4° C. at 12000 rcf for 10 min. Supernatants were assayed for protein content, snap-frozen, and stored a −80° C. if not run immediately. Then 50 μg of protein was subjected to Western blot protocol. Membranes were blocked and then incubated with 1:200 dilution of ERα antibody at 4° C. overnight followed by 1:10,000 dilution of secondary antibody for 1 h at room temperature. They were then imaged on a LICOR infrared scanner.

FIGS. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, and 33 show the BTK degradation efficacy of compounds 1, 2, 25, 27, 29, 31, 33, 35, 36, 37, 39, 41, 43, 45, 49, 51, 52, 55, 63, 75, 79, 80, 81, 85, 86, 93, 159, 161, 162, 163, 169, 181, 200, 207, 213, 214, 417, 418, 419, 420, 421, 422, 425, 431, 433, 435, 437, 439, 441, 443, 445, 446, 447, 449, 451, 476, 477, 478, 480, and 484 in Namalwa, JeKo-1, or Mino cells at various concentrations. Degradation of BTK was expressed as an $DC_{50}$ value and was determined for exemplary compounds in Table 1 by calculation of the concentration of compound that was required to give a 50% reduction of BTK expression level. Maximal degradation of BTK was expressed as a $D_{max}$ value by measuring the highest percentage of BTK reduction achieved by exemplary compound in the treatment concentration range. $DC_{50}$ and $D_{max}$ values for each compound are listed in Table 1.

Example 49: Antiproliferative Effect

Antiproliferative effect of the exemplary compounds was assessed in B-cell malignancy models.

To assess the effect of the exemplary compounds on cell viability in B-cell malignancy models by degradation of BTK protein, Mino and JeKo-1 cells were treated with varying concentrations of Ibrutinib (0, 0.001, 0.01, 0.1, 1, 10 µM). Under these conditions, cell viability was determined by an MTS assay. Cytotoxicity was assayed by the determination of reduced tetrazolium (formazan) created by metabolically active cells as detected at 490 nm absorbance using a microplate reader (BMG Labtech, Cary, NC, USA).

The exemplary compounds attenuated the viability of Mino and JeKo-1 cells in a concentration-dependent manner at 72 h post treatment. Results are shown in Table 1 for each exemplary compound.

Example 50: Cell Apoptosis Induced by Exemplary Compounds

Cell apoptosis induced by treatment of exemplary compounds was measured by flow cytometry.

Flow cytometry analysis was performed after staining of the cells with PI and 7-AAD. For PI staining, 0.5×10⁶ cells/mL were centrifuged at 1500 rpm for 5 min, supernatant was removed, and cell pellet was gently suspended with 1 ml Krishan buffer and then incubated at 4° C. in the dark for 60 min. Apoptosis was determined by Cytomic's FC500 Flow Cytometer (Beckman Coulter) and the data were analyzed by Win Cycle Multicycle Software (De Novo Software). For the 7-AAD staining, 0.5×10⁶ cells were washed with PBS and centrifuged at 1500 rpm for 5 min. Supernatant was removed and the cell pellet was suspended in 100 µL PBS. 10 µL 7-AAD was added to each tube and incubated for 20 min at room temperature in the dark. 7-AAD labeled-cells were analyzed by Cytomic's FC500 Flow Cytometry (Beckman Coulter) and FCS Express Flow Cytometry Data Analysis software (DeNovo Software). For morphologic analysis of apoptosis by light microscopy, cells were incubated with Mock or with 0.1, 1, or 10 Ibrutinib for 72 h. Control or drug treated-cells were cytospun on glass slides, stained with Wright-Giemsa, and then examined by light microscopy. Morphological changes associated with apoptosis included cellular shrinkage, nuclear condensation, nuclear fragmentation, and formation of apoptotic bodies.

FIGS. 34, 35, 36, and 37 show the effect of exemplary compounds 1 and 2 on cell apoptosis in Namalwa, JeKo-1, and Mino cells.

Example 51: Ex Vivo Cell Inhibition

Figure 38:
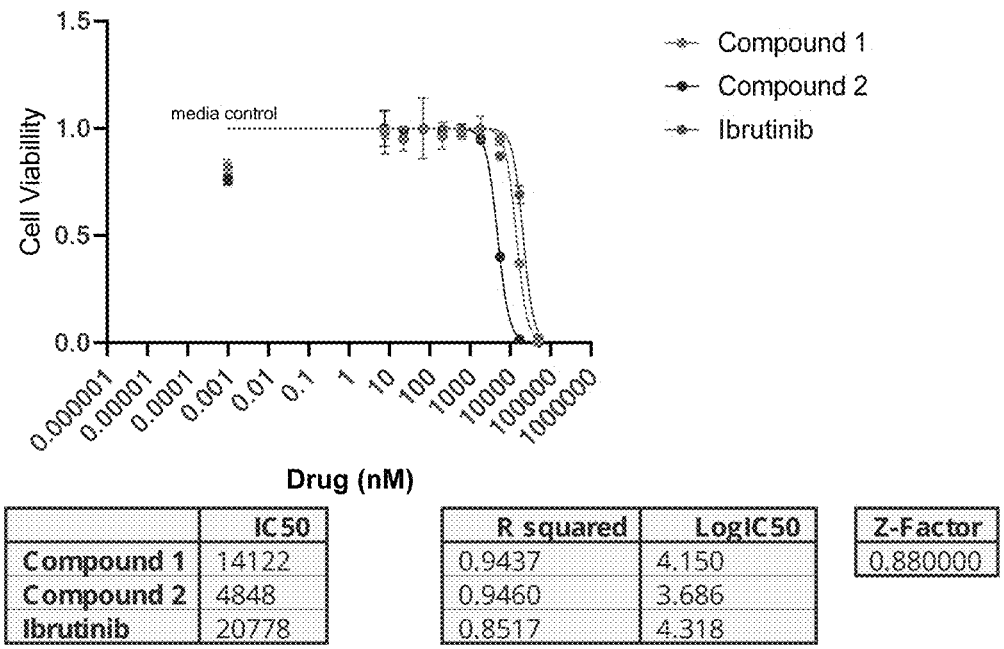
FIG. 38 shows the dose-dependent effect of compound 1 and Compound 2 on primary human CLL cell CTG-3763. The cells were incubated with Compound 1, Compound 2, or ibrutinib at a dose range of 10 nM to 50 µM for 6 days.
Figure 39:
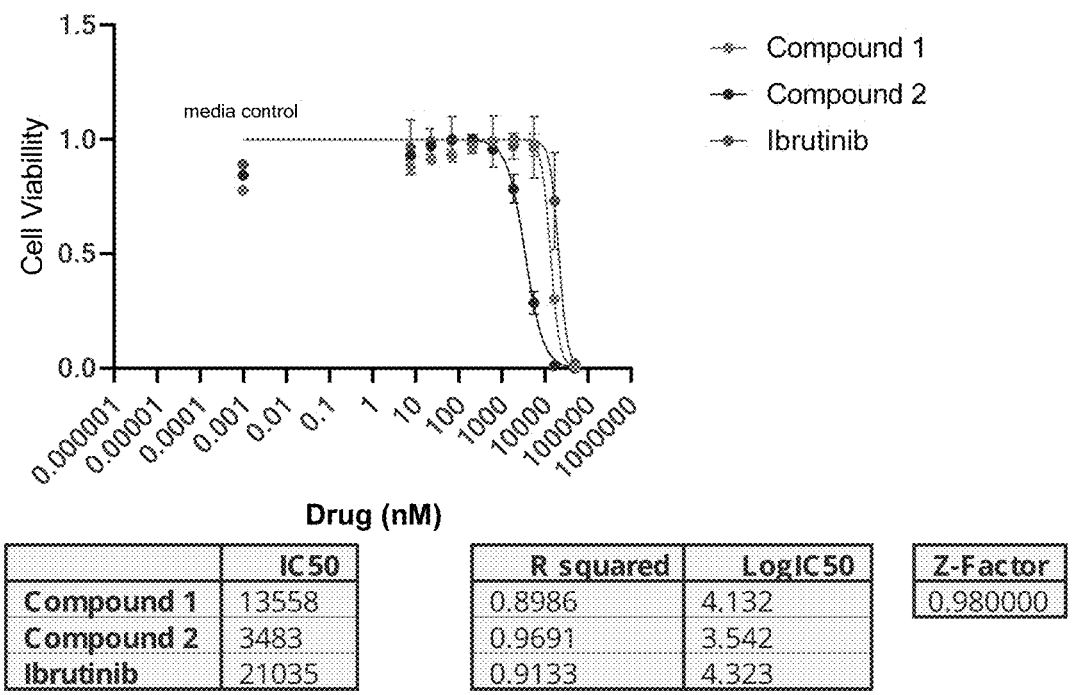
FIG. 39 shows the dose-dependent effect of compound 1 and Compound 2 on primary human CLL cell CTG-3754. The cells were incubated with Compound 1, Compound 2, or ibrutinib at a dose range of 10 nM to 50 µM for 6 days.

Primary human Human Chronic Lymphocytic Leukemia cell lines were used to measure ex vivo cell inhibition by exemplary compounds. The cells were incubated with test compounds at a dose range of 10 nM to 50 µM for 6 days. Cell Titer Glo data were gathered for cell viability evaluation. FIGS. 38 and 39 show the dose-dependent effect of compound 1 and Compound 2 on primary human CLL cell viability.

Example 52: Pharmacokinetic Properties

Pharmacokinetic properties of exemplary compounds 2, 31, and 55 were assessed in Female Sprague Dawley rats Sprague Dawley rats (n=3), weighing between 350 and 400 g (Charles River Laboratories, Portage, MI) were given oral gavage containing compound 2, compound 31, or compound 55 dissolved in propylene glycol (PG):solutol: 40% HP-b-CD in DI water (20:5:75 v:v) at a single dose of 10 mg/kg. After drug administration, blood samples were collected from the tail vein of the rats at various time points into 1.5 mL microcentrifuge tubes containing 0.1 mL of 10% EDTA anticoagulant. Plasma was then separated from cell pellets by centrifugation in a refrigerated centrifuge at 4° C. and transferred to a separate tube. Plasma samples were frozen at −80° C. until analysis.

HPLC-MS/MS Analysis of Plasma Samples. Plasma samples were extracted with chloroform/methanol (2:1) using traditional Folch method for lipid extraction. Methanol (1 mL) and chloroform (2 mL) were added to each plasma sample followed by addition of 5 ng trans-Tamoxifen-13C2, 15N to each sample as the internal standard. The mixtures were stored at −20° C. overnight. Next the samples were sonicated for 5 min and centrifuged with a Thermo Scientific Heraeus Megafuge16 Centrifuge. The top layer was transferred to another test tube. The bottom layer was washed with 1 mL chloroform/methanol (2:1), centrifuged, and the solvent was transferred and combined with previous washings. Eight tenth of a milliliter HPLC grade water was added to the extracts. After vortexing, the mixture was centrifuged. The bottom layer was dried out with nitrogen and re-suspended in 100 µL HPLC grade acetonitrile. An aliquot of 10 µL sample was injected onto a Hypersil Gold column (50×2.1 mm; particle size 1.9 µm, Thermo Scientific) on a Dionex Ultimate 3000 UPLC system equipped with a TSQ Vantage triple quadrupole mass spectrometer for analysis. A binary mobile phase (A: water with 0.05% formic acid, B: acetonitrile with 0.05% formic acid) was used to achieve the gradient of initial 30% B for 1 min and then to 80% B at 8 min, to 100% B at 9 min, and returned to 30% B for 4 min. The flow rate was controlled at 0.6 mL/min. The settings of HESI source were as follows: spray voltage (3200 volt); vaporizer temperature (365° C.); sheath gas pressure (45 psi); auxiliary gas pressure (10 psi); capillary temperature (330° C.). Nitrogen was used as the sheath gas and axillary gas. Argon was used as the collision gas.

Figure 40:
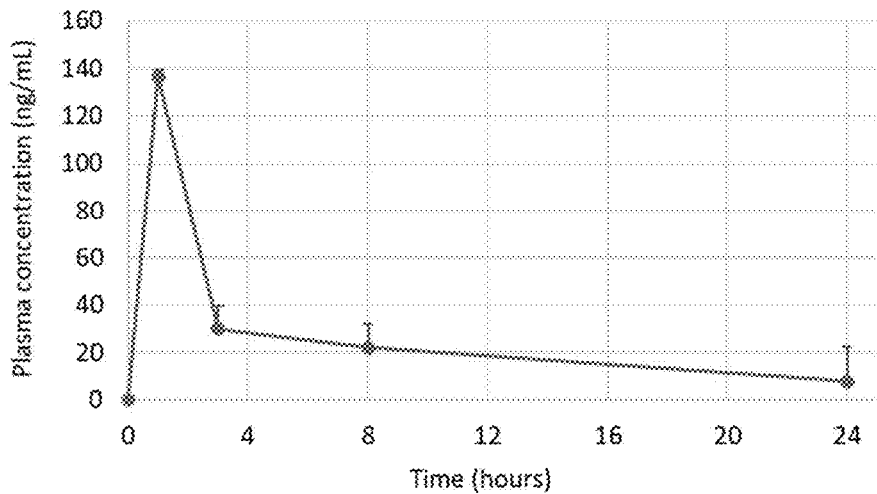
FIG. 40 shows the single dose pharmacokinetics of Compound 2 in Sprague Dawley rat.
Figure 41:
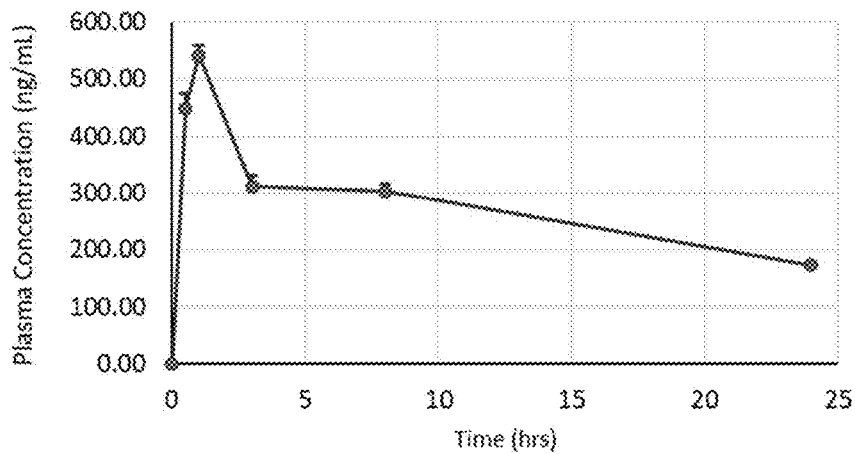
FIG. 41 shows the single dose pharmacokinetics of Compound 31 in Sprague Dawley rat.
Figure 42:
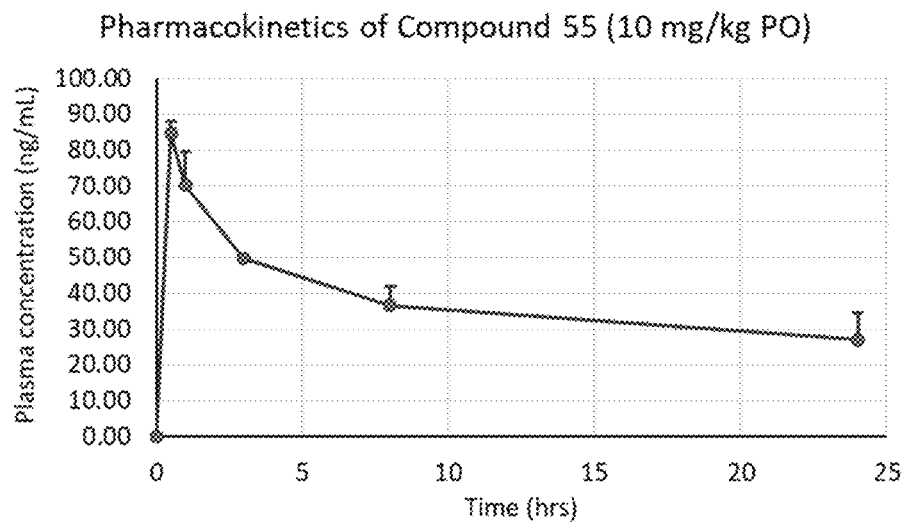
FIG. 42 shows the single dose pharmacokinetics of Compound 55 in Sprague Dawley rat.

FIGS. 40, 41, and 42 show the pharmacokinetic profile of exemplary compounds 2, 31, and 55 in SD rats.

Example 53: In Vivo Tumor Inhibition Efficacy

JeKo-1 cells were obtained from American Type Culture Collection (ATCC, Manassas, VA). cells were maintained in RPMI 1640 (Life Technologies, Grand Island, NY) supplemented with 10% heat-inactivated fetal bovine serum (56° C. for 30 minutes), penicillin (10,000 units/mL; Sigma, St Louis, Mo), streptomycin (10 mg/mL; Sigma), gentamicin (50 mg/mL; Life Technologies), amphotericin B (25 mg/mL; Sigma), and L-glutamine (200 mM, 29.2 mg/mL; Life Technologies). culture, as previously described (29, 30). JeKo-1 cells (10 million) were subcutaneously implanted into the flank of NOD/SCID mice. When the average tumor volume reached approximately 300 mm³, the following treatments were administered in cohorts of 5 mice for each treatment: vehicle alone, 20 mg/kg ibrutinib, 20 mg/kg Compound 2, and 20 mg/kg Compound 161 was administered daily via oral gavage for 3 weeks. Tumor growth was monitored every other day by calipers and tumor volume was calculated using the equation: ($\frac{1}{2}$(length×width²)).

Figure 43:
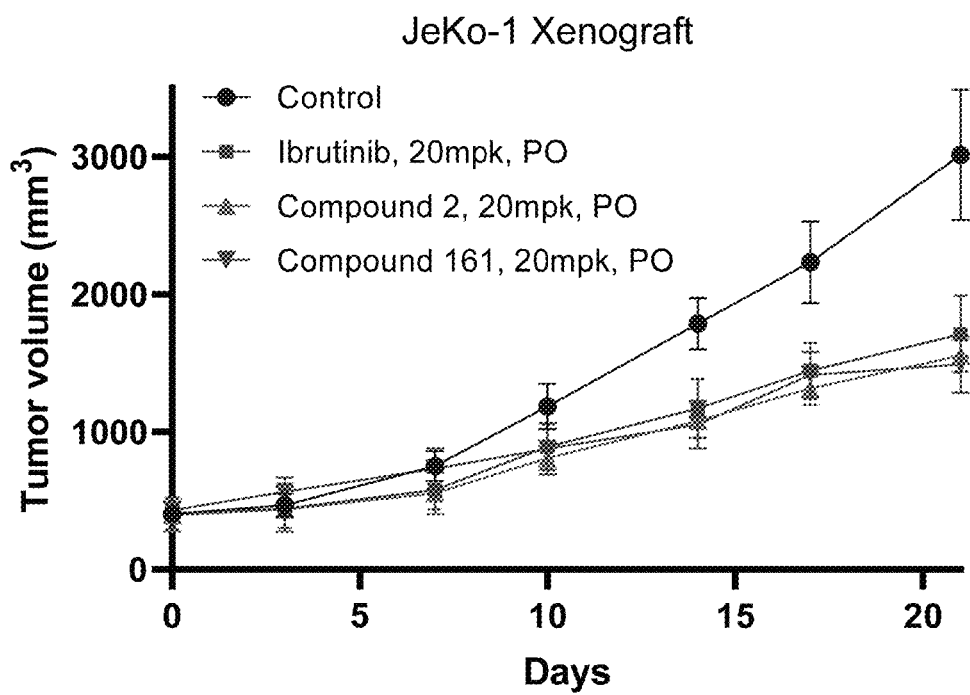
FIG. 43 shows the efficacy of Compound 2 and Compound 161 in inhibiting Jeko-1 xenograft tumor growth in mice.

FIG. 43 shows the efficacy of Compound 2 and Compound 161 in inhibiting Jeko-1 xenograft tumor growth in mice.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or multiple elements together may also find a useful application in other types of methods differing from the type described above, as well as in other types of diseases differing from the type described herein. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is not intended to be limiting only by the following claims.

REFERENCES CITED

Byrd, J. C. et al. Targeting BTK with ibrutinib in relapsed chronic lymphocytic leukemia. N. Engl. J. Med. 369, 32-42 (2013).
Wang, M. L. et al. Targeting BTK with ibrutinib in relapsed or refractory mantle-cell lymphoma. N. Engl. J. Med. 369, 507-516 (2013).
de Claro, R. A.; McGinn, K. M.; Verdun, N.; Lee, S. L.; Chiu, H. J.; Saber, H.; Brower, M. E.; Chang, C. J.; Pfuma, E.; Habtemariam, B.; et al. FDA Approval: Ibrutinib for Patients with Previously Treated Mantle Cell Lymphoma and Previously Treated Chronic Lymphocytic Leukemia. Clin. Cancer Res. 2015, 21, 3586-3590.
Pal Singh, S.; Dammeijer, F.; Hendriks, R. W. Role of Bruton's tyrosine kinase in B cells and malignancies. Mol. Cancer Ther. 2018, 17, 57.
Jolliet-Riant P, Tillement J P. Drug transfer across the blood-brain barrier and improvement of brain delivery. Fundam Clin Pharmacol. 1999; 13(1):16-26. doi: 10.1111/j.1472-8206.1999.tb00316.x. PMID: 10027084.
Emerich D F, Tracy M A, Ward K L, Figueiredo M, Qian R, Henschel C, Bartus R T. Biocompatibility of poly (DL-lactide-co-glycolide) microspheres implanted into the brain. Cell Transplant. 1999 January-February; 8(1):47-58. doi: 10.1177/096368979900800114.
Schroeder U, Sabel B A, Schroeder H. Diffusion enhancement of drugs by loaded nanoparticles in vitro. Prog Neuropsychopharmacol Biol Psychiatry. 1999 July; 23(5):941-9. doi: 10.1016/s0278-5846(99)00037-8
Carey et al. Advanced Organic Chemistry, 3rd Ed., 1990 New York: Plenum Press;
Mundy et al., Name Reaction and Reagents in Organic Synthesis, 2nd Ed., 2005 Hoboken, N.J.: J. Wiley & Sons

What is claimed is:
1. A compound represented by Formula (I):

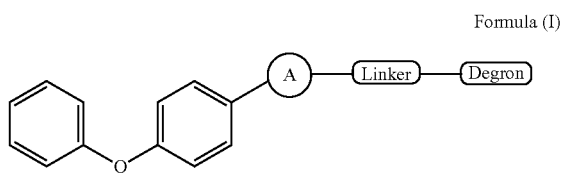

Formula (I)

or a pharmaceutically acceptable salt, stereoisomer, or tautomer thereof,
wherein:
Ring A is:

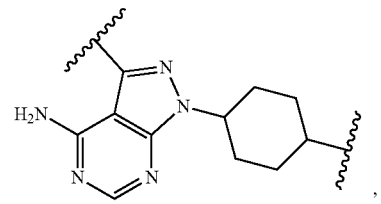 [SMILES: *c1nn(C2CCC(*)CC2)c2ncnc(N)c12]

wherein the carbon atom of the pyrazolo[3,4-d]pyrimidinyl of Ring A is bonded to the 4-phenoxyphenyl moiety and the cyclohexylene ring of Ring A is bonded to —C(O)— of the Linker;
Linker is:

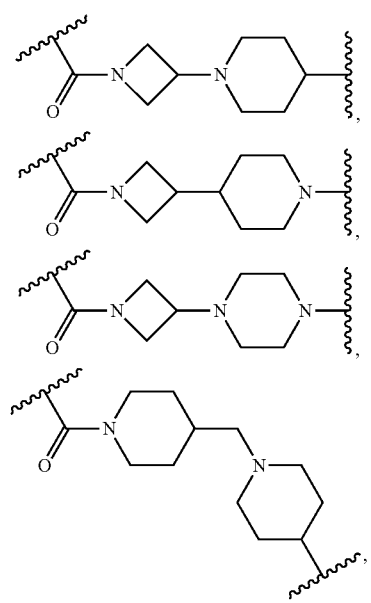

991
-continued
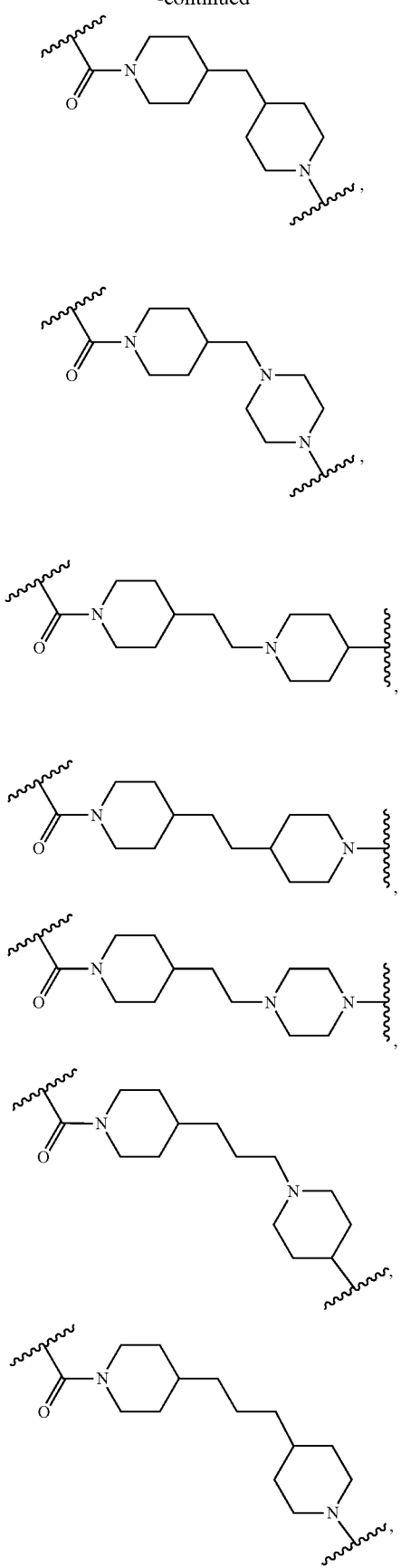
992
-continued
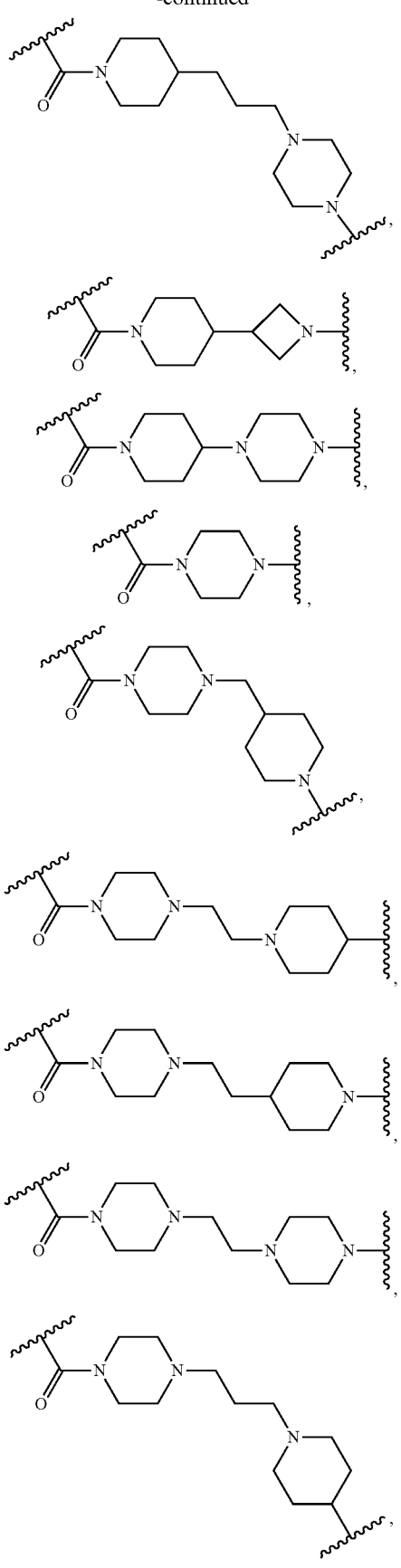

993

-continued

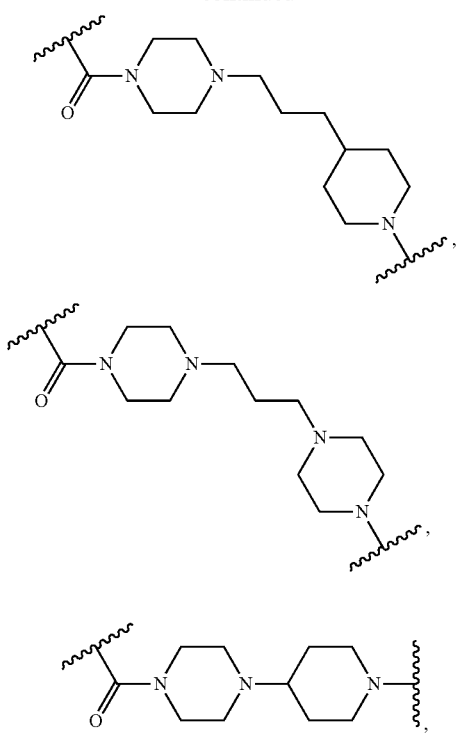

or wherein —C(O)— of the Linker is bonded to the cyclohexylene ring of Ring A and the nitrogen atom of the azetidinylene ring of the Linker or the nitrogen atom of the piperazinylene ring of the Linker is bonded to the Degron; and Degron is:

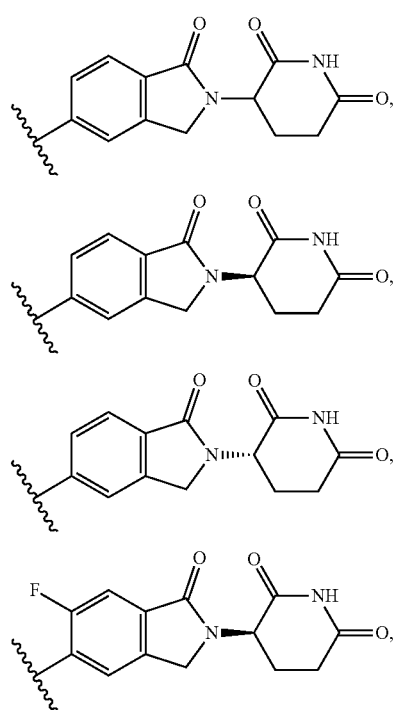

994

-continued

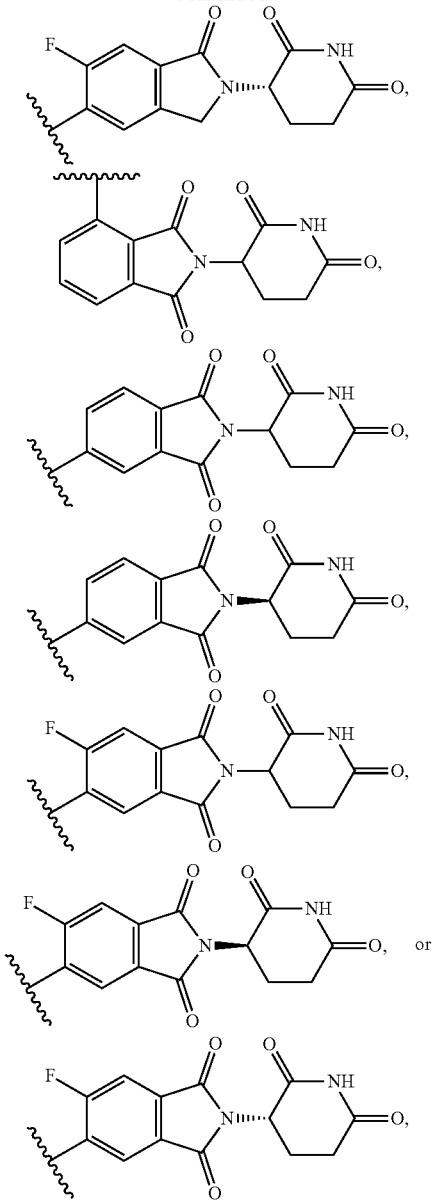

or wherein ⁓ is the point of attachment of the Degron to the nitrogen atom of the azetidinylene ring of the Linker or the nitrogen atom of the piperazinylene ring of the Linker.

2. The compound of claim 1, or a pharmaceutically acceptable salt, stereoisomer, or tautomer thereof, wherein the Linker is:

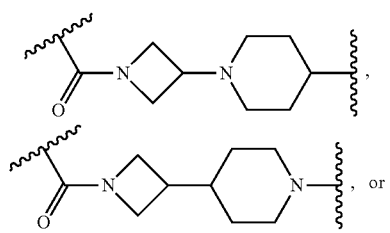

, or

995

-continued

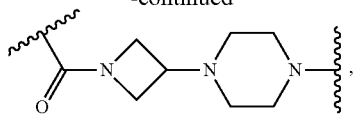

wherein —C(O)— of the Linker is bonded to the cyclohexylene ring of Ring A and the nitrogen atom of the piperazinylene ring of the Linker is bonded to the Degron.

3. The compound of claim 1, or a pharmaceutically acceptable salt, stereoisomer, or tautomer thereof, wherein the Linker is:

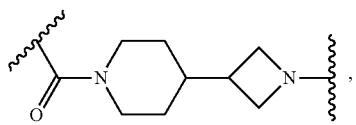

996

-continued

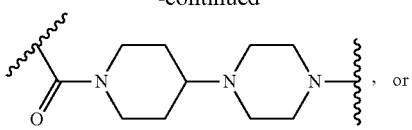, or

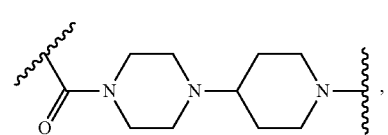, wherein —C(O)— of the Linker is bonded to the cyclohexylene ring of Ring A and the nitrogen atom of the azetidinylene ring of the Linker or the nitrogen atom of the piperazinylene ring of the Linker is bonded to the Degron.

4. The compound of claim 1, wherein the compound is selected from the group consisting of:

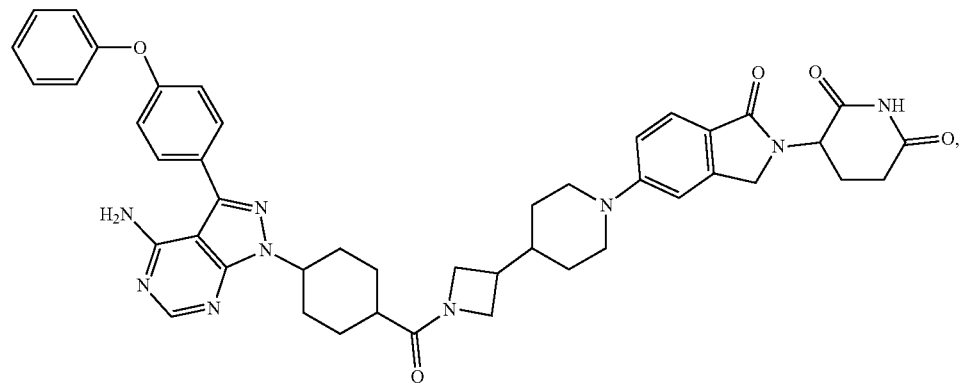

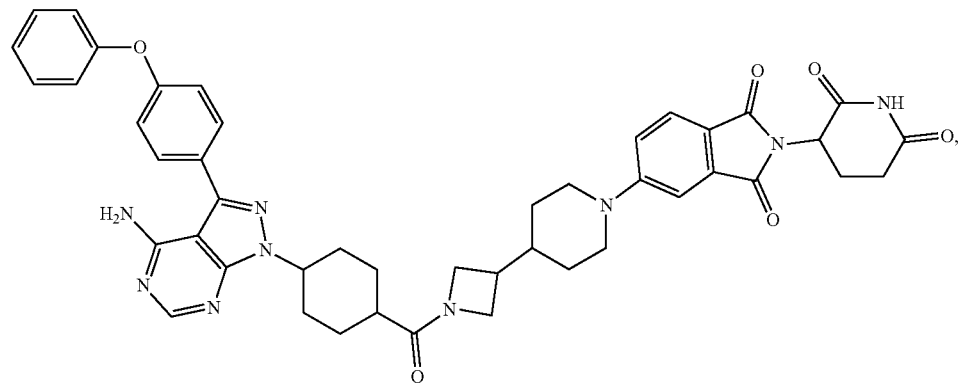

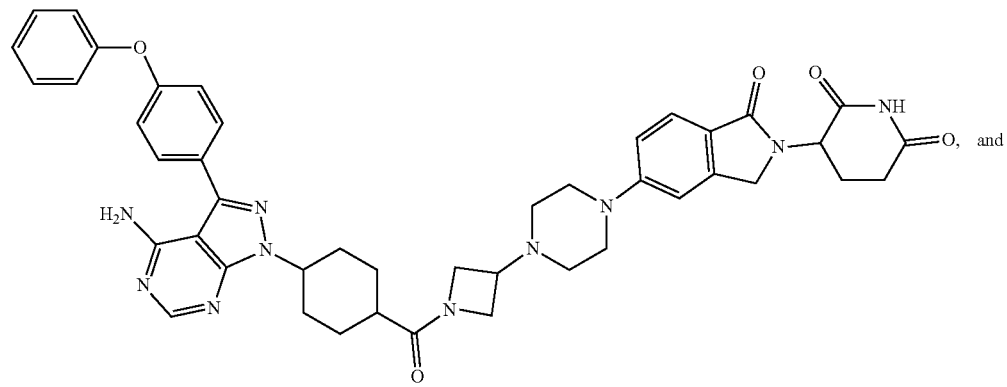

-continued

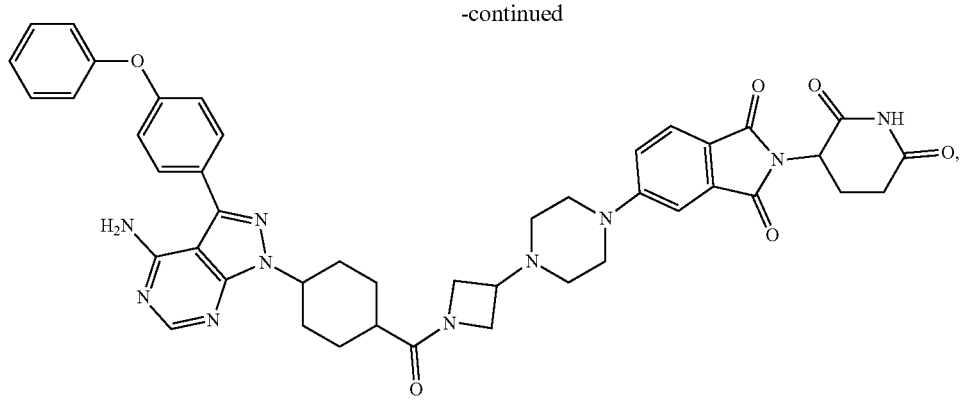

or a pharmaceutically acceptable salt, stereoisomer, or tautomer thereof.

5. A pharmaceutical composition comprising a pharmaceutically acceptable carrier and at least one compound of claim 1, or a pharmaceutically acceptable salt, stereoisomer, or tautomer thereof.

6. The pharmaceutical composition of claim 5, wherein the pharmaceutical composition is an oral pharmaceutical composition.

7. The pharmaceutical composition of claim 5, wherein the pharmaceutical composition is a parenteral pharmaceutical composition.

8. A method for reducing the level of Bruton's tyrosine kinase (BTK) in a subject in need thereof, wherein the method comprises administering to the subject a therapeutically effective amount of at least one compound of claim 1, or a pharmaceutically acceptable salt, stereoisomer, or tautomer thereof.

9. The method of claim 8, wherein the subject has cancer.

10. A method for reducing the level of Bruton's tyrosine kinase (BTK) in a subject in need thereof, wherein the method comprises administering to the subject a therapeutically effective amount of the pharmaceutical composition of claim 5.

11. A method for inhibiting Bruton's tyrosine kinase (BTK) activity in a subject in need thereof, wherein the method comprises administering to the subject a therapeutically effective amount of at least one compound of claim 1, or a pharmaceutically acceptable salt, stereoisomer, or tautomer thereof.

12. The method of claim 11, wherein the subject has cancer.

13. The method of claim 12, wherein the cancer is a B-cell malignancy.

14. The method of claim 12, wherein the subject expresses a mutant Bruton's tyrosine kinase (BTK).

15. A method for inhibiting Bruton's tyrosine kinase (BTK) activity in a subject in need thereof, wherein the method comprises administering to the subject a therapeutically effective amount of the pharmaceutical composition of claim 5.

* * * * *